US00RE47193E

(19) United States
(12) Reissued Patent
Carlson et al.

(10) Patent Number: US RE47,193 E
(45) Date of Reissued Patent: Jan. 8, 2019

(54) SELECTIVELY SUBSTITUTED QUINOLINE COMPOUNDS

(71) Applicant: EISAI R&D MANAGEMENT CO., LTD., Bunkyo-ku (JP)

(72) Inventors: J. Eric Carlson, Merrimack, NH (US); Hans Hansen, Somerville, MA (US); Lynn Hawkins, Concord, MA (US); Sally Ishizaka, Weston, MA (US); Matthew Mackey, Melrose, MA (US); Shawn Schiller, Haverhill, MA (US); Chikako Ogawa, Basel (CH); Heather Davis, Haverhill, MA (US); Atsushi Endo, Andover, MA (US)

(73) Assignee: Eisai R&D Management Co., Ltd., Tokyo (JP)

(21) Appl. No.: 15/668,887

(22) Filed: Aug. 4, 2017

Related U.S. Patent Documents

Reissue of:
(64) Patent No.: 9,428,495
Issued: Aug. 30, 2016
Appl. No.: 14/513,556
Filed: Oct. 14, 2014

U.S. Applications:
(60) Provisional application No. 61/890,718, filed on Oct. 14, 2013.

(51) Int. Cl.

| | |
|---|---|
| ***C07D 413/04*** | (2006.01) |
| ***C07D 401/14*** | (2006.01) |
| ***C07D 403/14*** | (2006.01) |
| ***C07D 401/10*** | (2006.01) |
| ***C07D 413/14*** | (2006.01) |
| ***C07D 417/14*** | (2006.01) |
| ***C07D 215/48*** | (2006.01) |
| ***C07D 471/04*** | (2006.01) |
| ***C07D 471/10*** | (2006.01) |
| ***C07D 487/10*** | (2006.01) |
| ***C12Q 1/6897*** | (2018.01) |
| ***C07D 493/10*** | (2006.01) |
| ***C07D 487/04*** | (2006.01) |
| ***G01N 33/50*** | (2006.01) |
| ***C07D 451/04*** | (2006.01) |

(52) U.S. Cl.
CPC ..... *C07D 417/14* (2013.01); *C07D 215/48* (2013.01); *C07D 401/10* (2013.01); *C07D 401/14* (2013.01); *C07D 403/14* (2013.01); *C07D 413/04* (2013.01); *C07D 413/14* (2013.01); *C07D 451/04* (2013.01); *C07D 471/04* (2013.01); *C07D 471/10* (2013.01); *C07D 487/04* (2013.01); *C07D 487/10* (2013.01); *C07D 493/10* (2013.01); *C12Q 1/6897* (2013.01); *G01N 33/5023* (2013.01); *G01N 33/5047* (2013.01); *C07B 2200/07* (2013.01)

(58) Field of Classification Search
CPC .. C07D 417/14; C07D 493/10; C07D 451/04; C07D 487/04; C07D 403/14; C07D 413/14; C07D 413/04; C07D 401/10; C07D 401/14; C07D 471/10; C07D 487/10; C07D 471/04; C07D 215/48; C12Q 1/6897; G01N 33/5023; G01N 33/5047; C07B 2200/07
See application file for complete search history.

(56) References Cited

U.S. PATENT DOCUMENTS

| | | | |
|---|---|---|---|
| 4,399,134 | A | 8/1983 | Ishikawa et al. |
| 4,552,879 | A | 11/1985 | Ishikawa et al. |
| 4,933,447 | A | 6/1990 | Koono et al. |
| 5,358,949 | A | 10/1994 | Tabusa et al. |
| 6,049,000 | A | 4/2000 | Strohriegl et al. |
| 6,297,283 | B1 | 10/2001 | Ishiwata et al. |
| 6,313,326 | B1 | 11/2001 | Strohriegl et al. |
| 6,423,865 | B1 | 7/2002 | Strohriegl et al. |
| 6,495,565 | B2 | 12/2002 | Duan et al. |
| 6,576,642 | B2 | 6/2003 | Ishiwata et al. |
| 6,605,617 | B2 | 8/2003 | Renhowe et al. |
| 6,635,655 | B1 | 10/2003 | Jayyosi et al. |
| 6,710,205 | B2 | 3/2004 | Tani et al. |
| 6,743,807 | B2 | 6/2004 | Duan et al. |
| 6,762,194 | B2 | 7/2004 | Renhowe et al. |
| 6,774,237 | B2 | 8/2004 | Renhowe et al. |
| 6,800,760 | B2 | 10/2004 | Renhowe et al. |
| 6,897,220 | B2 | 5/2005 | Delorme et al. |
| 6,933,272 | B1 | 8/2005 | Helmerhorst et al. |
| 6,953,857 | B2 | 10/2005 | Nazaré et al. |

(Continued)

FOREIGN PATENT DOCUMENTS

| | | |
|---|---|---|
| AU | 639529 B2 | 7/1993 |
| CN | 1528748 A | 9/2004 |

(Continued)

OTHER PUBLICATIONS

Berge et al., "Pharmaceutical Salts," Journal of Pharmaceutical Sciences, (Jan. 1977), vol. 66, No. 1, pp. 1-19.
Wang et al., "Palladium-Catalyzed Microwave-Assisted Amination of 1-Bromonaphthalenes and 5- and 8-Bromoquinolines," Organic Letters, (Jan. 2003), vol. 5, No. 6, pp. 897-900.
International Search Report (Form PCT/ISA/210) and the Written Opinion of the International Searching Authority (Form PCT/ISA/237) dated Jan. 26, 2015, by the European Patent Office in International Application No. PCT/US2014/0060412. (10 pages).
Non-Final Office Action dated Dec. 21, 2015 in U.S. Appl. No. 14/513,556, "Selectively Substituted Quinoline Compounds".
Notice of Allowance and Fees Due dated Apr. 19, 2016, in U.S. Appl. No. 14/513,556.

(Continued)

*Primary Examiner* — Alan Diamond
(74) *Attorney, Agent, or Firm* — Buchanan Ingersoll & Rooney PC

(57) ABSTRACT

Embodiments of the disclosure relate to selectively substituted quinoline compounds that act as antagonists or inhibitors for Toll-like receptors 7 and/or 8, and their use in pharmaceutical compositions effective for treatment of systemic lupus erythematosus (SLE) and lupus nephritis.

32 Claims, 111 Drawing Sheets

Specification includes a Sequence Listing.

(56) References Cited

U.S. PATENT DOCUMENTS

| | | | |
|---|---|---|---|
| 6,984,648 | B2 | 1/2006 | Lu et al. |
| 7,005,440 | B1 | 2/2006 | Jayyosi et al. |
| 7,041,693 | B2 | 5/2006 | Sheppeck |
| 7,067,665 | B2 | 6/2006 | Nazaré et al. |
| 7,074,810 | B2 | 7/2006 | King et al. |
| 7,196,198 | B2 | 3/2007 | Tani et al. |
| 7,211,671 | B2 | 5/2007 | Sheppeck et al. |
| 7,268,232 | B2 | 9/2007 | Schlienger et al. |
| 7,312,181 | B2 | 12/2007 | Lee et al. |
| 7,317,024 | B2 | 1/2008 | Yang |
| 7,335,774 | B2 | 2/2008 | Renhowe et al. |
| 7,358,249 | B2 | 4/2008 | Murai et al. |
| 7,402,696 | B2 | 7/2008 | Suzuki et al. |
| 7,425,354 | B2 | 9/2008 | Yanai et al. |
| RE40,558 | E | 10/2008 | Jayyosi et al. |
| 7,442,475 | B2 | 10/2008 | Farrand et al. |
| 7,470,709 | B2 | 12/2008 | Barsanti et al. |
| 7,514,450 | B2 | 4/2009 | Peters et al. |
| 7,569,583 | B2 | 8/2009 | Schwink et al. |
| 7,595,343 | B2 | 9/2009 | Delorme et al. |
| 7,598,268 | B2 | 10/2009 | Renhowe et al. |
| 7,683,060 | B2 | 3/2010 | Zhuo et al. |
| 7,776,857 | B2 | 8/2010 | Cee et al. |
| 7,825,132 | B2 | 11/2010 | Cai et al. |
| 7,834,035 | B2 | 11/2010 | Bessis et al. |
| 7,838,547 | B2 | 11/2010 | Schwink et al. |
| 7,868,204 | B2 | 1/2011 | Delorme et al. |
| 7,875,624 | B2 | 1/2011 | Heise et al. |
| 7,880,002 | B2 | 2/2011 | Carson et al. |
| 7,902,363 | B2 | 3/2011 | Facchetti et al. |
| 7,910,595 | B2 | 3/2011 | Betebenner et al. |
| 7,915,408 | B2 | 3/2011 | Zhuo et al. |
| 7,981,891 | B2 | 7/2011 | Deak et al. |
| 7,989,458 | B2 | 8/2011 | Leblanc et al. |
| 7,994,324 | B2 | 8/2011 | Kolczewski et al. |
| 8,013,156 | B2 | 9/2011 | Canne Bannen et al. |
| 8,030,331 | B2 | 10/2011 | Bessis et al. |
| 8,088,385 | B2 | 1/2012 | Chesney et al. |
| 8,088,771 | B2 | 1/2012 | Melvin, Jr. et al. |
| 8,143,251 | B2 | 3/2012 | Zhuo et al. |
| 8,163,741 | B2 | 4/2012 | Schwink et al. |
| 8,163,775 | B2 | 4/2012 | Bessis et al. |
| 8,168,788 | B2 | 5/2012 | Carson et al. |
| 8,173,639 | B2 | 5/2012 | Simonsen et al. |
| 8,198,299 | B2 | 6/2012 | Melvin, Jr. et al. |
| 8,357,686 | B2 | 1/2013 | Schwink et al. |
| 8,362,068 | B2 | 1/2013 | Dousson et al. |
| 8,420,667 | B2 | 4/2013 | Khanzhin et al. |
| 8,436,028 | B2 | 5/2013 | Hunt et al. |
| 8,445,480 | B2 | 5/2013 | Hunt et al. |
| 8,455,528 | B2 | 6/2013 | Lin et al. |
| 9,126,999 | B2 | 9/2015 | Boivin et al. |
| 9,428,495 | B2 | 8/2016 | Carlson et al. |
| 9,446,046 | B2 | 9/2016 | Boivin et al. |
| 9,663,486 | B2 | 5/2017 | Boivin et al. |
| 2003/0028018 | A1 | 2/2003 | Renhowe et al. |
| 2003/0055263 | A1 | 3/2003 | Priepke et al. |
| 2004/0072802 | A1 | 4/2004 | Duan et al. |
| 2004/0116450 | A1 | 6/2004 | Oyama |
| 2004/0235834 | A1 | 11/2004 | Farmer et al. |
| 2005/0137399 | A1 | 6/2005 | Cai et al. |
| 2005/0203101 | A1 | 9/2005 | Barsanti et al. |
| 2005/0203127 | A1 | 9/2005 | Cezanne et al. |
| 2005/0209247 | A1 | 9/2005 | Cai et al. |
| 2005/0256157 | A1 | 11/2005 | Gesner et al. |
| 2006/0019997 | A1 | 1/2006 | Edwards et al. |
| 2006/0247212 | A1 | 11/2006 | Murai et al. |
| 2007/0004679 | A1 | 1/2007 | Schlienger et al. |
| 2007/0185178 | A1 | 8/2007 | Edwards et al. |
| 2007/0254894 | A1 | 11/2007 | Kane, Jr. et al. |
| 2007/0299110 | A1 | 12/2007 | Gagliardi et al. |
| 2008/0009489 | A1 | 1/2008 | Schlienger et al. |
| 2008/0070906 | A1 | 3/2008 | Renhowe et al. |
| 2008/0103162 | A1 | 5/2008 | Oyama et al. |
| 2008/0103163 | A1 | 5/2008 | Oyama et al. |
| 2008/0146576 | A1 | 6/2008 | Braeuer et al. |
| 2008/0227772 | A1 | 9/2008 | Peters et al. |
| 2008/0306055 | A1 | 12/2008 | Egner et al. |
| 2009/0118233 | A1 | 5/2009 | Murai et al. |
| 2009/0181979 | A1 | 7/2009 | Cai et al. |
| 2009/0221824 | A1 | 9/2009 | Briner et al. |
| 2009/0281100 | A1 | 11/2009 | Barsanti et al. |
| 2009/0326020 | A1 | 12/2009 | Miller et al. |
| 2010/0004284 | A1 | 1/2010 | Farina et al. |
| 2010/0041891 | A1 | 2/2010 | Setoh et al. |
| 2010/0130482 | A1 | 5/2010 | Peters et al. |
| 2010/0160355 | A1 | 6/2010 | DeGoey et al. |
| 2010/0168138 | A1 | 7/2010 | DeGoey et al. |
| 2010/0184754 | A1 | 7/2010 | Renhowe et al. |
| 2010/0204234 | A1 | 8/2010 | Hartmann et al. |
| 2010/0222353 | A1 | 9/2010 | Humphrey |
| 2010/0298378 | A1 | 11/2010 | Schwink et al. |
| 2011/0021531 | A1 | 1/2011 | Chobanian et al. |
| 2011/0059958 | A1 | 3/2011 | Nishida et al. |
| 2011/0130381 | A1 | 6/2011 | Bastos et al. |
| 2011/0135650 | A1 | 6/2011 | Chackalamannil et al. |
| 2011/0144056 | A1 | 6/2011 | Lin et al. |
| 2011/0144107 | A1 | 6/2011 | Chatterjee et al. |
| 2011/0144119 | A1 | 6/2011 | Chobanian et al. |
| 2011/0212975 | A1 | 9/2011 | Kao et al. |
| 2011/0230476 | A1 | 9/2011 | Niu et al. |
| 2011/0257196 | A1 | 10/2011 | Lu et al. |
| 2011/0275595 | A1 | 11/2011 | Eckhardt et al. |
| 2011/0312944 | A1 | 12/2011 | Bartolozzi et al. |
| 2011/0319420 | A1 | 12/2011 | Yang et al. |
| 2012/0071524 | A1 | 3/2012 | Lu et al. |
| 2012/0122847 | A1 | 5/2012 | Cee et al. |
| 2012/0142701 | A1 | 6/2012 | Kao et al. |
| 2012/0149715 | A1 | 6/2012 | Kao et al. |
| 2012/0165298 | A1 | 6/2012 | Miller-Moslin et al. |
| 2012/0177749 | A1 | 7/2012 | Tapolsky et al. |
| 2012/0190654 | A1 | 7/2012 | Chen et al. |
| 2012/0202828 | A1 | 8/2012 | Castro Pineiro et al. |
| 2012/0208826 | A1 | 8/2012 | Reddy et al. |
| 2012/0214787 | A1 | 8/2012 | Bartolozzi et al. |
| 2012/0214803 | A1 | 8/2012 | Buhr et al. |
| 2012/0252721 | A1 | 10/2012 | Dousson et al. |
| 2012/0258949 | A1 | 10/2012 | Varasi et al. |
| 2012/0264749 | A1 | 10/2012 | Hadida-Ruah et al. |
| 2012/0277434 | A1 | 11/2012 | Cai et al. |
| 2012/0289495 | A1 | 11/2012 | Baloglu et al. |
| 2012/0322803 | A1 | 12/2012 | Steurer |
| 2013/0012526 | A1 | 1/2013 | Nantermet et al. |
| 2013/0018058 | A1 | 1/2013 | Cai et al. |
| 2013/0030000 | A1 | 1/2013 | Chobanian et al. |
| 2013/0039944 | A1 | 2/2013 | Iadonato et al. |
| 2013/0039945 | A1 | 2/2013 | Iadonato et al. |
| 2013/0059883 | A1 | 3/2013 | Baloglu et al. |
| 2013/0065895 | A1 | 3/2013 | Conn et al. |
| 2013/0096110 | A1 | 4/2013 | Conn et al. |
| 2013/0115311 | A1 | 5/2013 | Charrier et al. |
| 2013/0115312 | A1 | 5/2013 | Charrier et al. |
| 2013/0115313 | A1 | 5/2013 | Charrier et al. |
| 2013/0116231 | A1 | 5/2013 | Wilson et al. |
| 2013/0123270 | A1 | 5/2013 | Carson et al. |
| 2013/0324547 | A1 | 12/2013 | Boivin et al. |
| 2015/0105370 | A1 | 4/2015 | Carlson et al. |
| 2016/0030430 | A1 | 2/2016 | Boivin et al. |
| 2016/0176841 | A1 | 6/2016 | Boivin et al. |
| 2016/0326161 | A1 | 11/2016 | Carlson et al. |

FOREIGN PATENT DOCUMENTS

| | | | |
|---|---|---|---|
| CN | 101440062 | A | 5/2009 |
| CN | 101838264 | A | 9/2010 |
| CN | 102675289 | A | 9/2012 |
| DE | 10222166 | A1 | 12/2003 |
| GB | 2396154 | A | 6/2004 |
| IL | 62783 | A | 1/1987 |
| JP | 58-90511 | | 5/1983 |
| JP | 63-54363 | | 3/1988 |
| JP | 8295690 | | 11/1996 |
| JP | 2005132834 | A | 5/2005 |
| JP | 2007045752 | A | 2/2007 |

(56) References Cited

FOREIGN PATENT DOCUMENTS

| | | | |
|---|---|---|---|
| JP | 2007131765 | A | 5/2007 |
| JP | 2007524615 | A | 8/2007 |
| JP | 2009037104 | A | 2/2009 |
| JP | 2009108152 | A | 5/2009 |
| JP | 2009149754 | A | 7/2009 |
| JP | 2009242540 | A | 10/2009 |
| JP | 2010059131 | A | 3/2010 |
| JP | 2010066630 | A | 3/2010 |
| JP | 2011006360 | A | 1/2011 |
| JP | 2011008205 | A | 1/2011 |
| JP | 2011042606 | A | 3/2011 |
| JP | 2011207765 | A | 10/2011 |
| JP | 2013028588 | A | 2/2013 |
| RU | 2009135621 | A | 4/2011 |
| WO | 9857936 | A1 | 12/1998 |
| WO | 200108488 | A1 | 2/2001 |
| WO | 2002018335 | A1 | 3/2002 |
| WO | 2003024448 | A2 | 3/2003 |
| WO | 2004018419 | A2 | 3/2004 |
| WO | 2004087835 | A1 | 10/2004 |
| WO | 2005/007672 | A2 | 1/2005 |
| WO | 2005028488 | A1 | 3/2005 |
| WO | 2005087217 | A1 | 9/2005 |
| WO | 2005115361 | A2 | 12/2005 |
| WO | 2009058730 | A1 | 5/2009 |
| WO | 2009139438 | A1 | 11/2009 |
| WO | 2010010187 | A | 1/2010 |
| WO | 2010048149 | A2 | 4/2010 |
| WO | 2010065717 | A1 | 6/2010 |
| WO | 2011025565 | A1 | 3/2011 |
| WO | 2011068138 | A1 | 6/2011 |
| WO | 2011109059 | A1 | 9/2011 |
| WO | 2011117381 | A1 | 9/2011 |
| WO | 2011117382 | A1 | 9/2011 |
| WO | 2011133871 | A2 | 10/2011 |
| WO | 2011155623 | A1 | 12/2011 |
| WO | 2012016133 | A2 | 2/2012 |
| WO | 2012033390 | A2 | 3/2012 |
| WO | 2012052540 | A1 | 4/2012 |
| WO | 2012058645 | A1 | 5/2012 |
| WO | 2012084219 | A1 | 6/2012 |
| WO | 2012128582 | A2 | 9/2012 |
| WO | 2013004332 | A | 1/2013 |
| WO | 2013009810 | A1 | 1/2013 |
| WO | 2013009827 | A1 | 1/2013 |
| WO | 2013009830 | A1 | 1/2013 |
| WO | 2013042139 | A1 | 3/2013 |
| WO | 2015057655 | A1 | 4/2015 |
| WO | 2015057659 | A1 | 4/2015 |

OTHER PUBLICATIONS

Excerpt of http://www.sigmaaldrich.com/life-science/cell-culture/classical-media-salts/dmem.html, accessed Dec. 16, 2015, and cited on p. 5 of Dec. 21, 2015 Office Action in U.S. Appl. No. 14/513,556.

Non-Final Office Action dated Feb. 6, 2017, in U.S. Appl. No. 15/220,949, "Selectively Substituted Quinoline Compounds".

Response to Restriction Requirement dated Dec. 23, 2016, in U.S. Appl. No. 15/220,949, "Selectively Substituted Quinoline Compounds".

Restriction Requirement dated Oct. 25, 2016, in U.S. Appl. No. 15/220,949, "Selectively Substituted Quinoline Compounds".

Japanese Office Action for Patent Application No. 2016-523329 dated Jun. 26, 2017.

Costedoat-Chalumeau et al., "Why all Systemic Lupus Erythematosus Patients Should be Given Hydroxychlorquine Treatment?" Joint Bone Spine, (Jan. 2010), vol. 77, pp. 4-5.

Deane et al., "Control of Toll-Like Receptor 7 Expression is Essential to Restrict Autoimmunity and Dendritic Cell Proliferation," Immunity, (Nov. 2007), vol. 27, pp. 801-810, Elsevier Inc.

Gorden et al., "Synthetic TLR Agonists Reveal Functional Differences between Human TLR7 and TLR8," The Journal of Immunology, (2005), vol. 174, No. 3, pp. 1259-1268.

Kono et al., "How dying Cells Alert the Immune System to Danger," Nature Reviews Immunology, (Apr. 2008), vol. 8, pp. 279-289, Nature Publishing Group.

de Montigny et al., "New Route to Unsymmetrical 9,10-Disubstituted Ethynylanthracene Derivatives," Synthesis, (2006), No. 2, pp. 293-298.

Nickerson et al., "TLR9 Regulates TLR7- and MyD88-Dependent Autoantibody Production and Disease in a Murine Model of Lupus," The Journal of Immunology, (Jan. 2010), vol. 184, No. 4, pp. 1840-1848.

Savarese et al., "Requirement of Toll-like Receptor 7 for Pristane-Induced Production of Autoantibodies and Development of Murine Lupus Nephritis," Arthrutis & Rheumatism, (Apr. 2008), vol. 58, No. 4, pp. 1107-1115.

Savarese et al., "U1 Small nuclear Ribonucleoprotein Immune Complexes Induce Type I Interferon in Plasmacytoid Dendritic Cells Through TLR7," Blood Journal, (Apr. 15, 2006), vol. 107, No. 8, pp. 3229-3235.

Tsuzuki et al., "Practical Synthesis of (3S,4S)-3-methoxy-4-methylaminopyrrolidine," Tetrahedron:Asymmetry, (2001), vol. 12, Issue 21, pp. 2989-2997.

Vollmer et al., "Immune Stimulation Mediated by Autoantigen Binding Sites within Small Nuclear RNAs Involves Toll-like Receptors 7 and 8," The Journal of Experimental Medicine, (Dec. 5, 2005), vol. 202, No. 11, pp. 1575-1585, The Rockefeller University Press.

Notification of Transmittal of the International Search Report (Forms PCT/ISA/220 and PCT/ISA/210) and the Written Opinion of the International Searching Authority (Form PCT/ISA/237) Issued on Feb. 23, 2015, by the European Patent Office in International Application No. PCT/US2014/0060418. (10 pages).

Official Action for CL Application No. 2016-00662 dated Jan. 18, 2018. (translation attached).

European Examination Report dated Mar. 5, 2018 for Application No. 14 790 937.8-1116.

Official Action for Russian Application No. 2016118619/04, dated Oct. 14, 2014. English Translation.

Official Action for Russian Application No. 2016118619/04, filed Oct. 14, 2014.

Federal Service on Intellectual Property Federal State Budgetary Enterprise "Federal Institute of Industrial Property", Search Report for RU2016118619/04 (029193) filed Oct. 14, 2014. English Translation.

Federal Service on Intellectual Property Federal State Budgetary Enterprise "Federal Institute of Industrial Property", Search Report for RU2016118619/04 (029193) filed Oct. 14, 2014.

http://www.sigmaaldrich.com/life-science/cell-culture/classical-media-salts/dmem.html, accessed Dec. 16, 2015.*

Banchereau et al., "Type I Interferon in Systemic Lupus Erythematosus and Other Autoimmune Diseases," Immunity, (Sep. 2006), vol. 25, No. 3, pp. 383-392.

Casanova et al., "Human TLRs and IL-1Rs in Host Defense: Natural Insights from Evolutionary, Epidemiological, and Clinical Genetics," Annual Review of Immunology, (2011), vol. 29, pp. 447-491.

Costedoat-Chalumeau et al., "Low Blood Concentration of Hydroxychloroquine Is a Marker for and Predictor of Disease Exacerbations in Patients with Systemic Lupus Erythematosus," Arthritis & Rheumatism, (Oct. 2006), vol. 54, No. 10, pp. 3284-3290.

Deng et al., "MicroRNA-3148 Modulates Allelic Expression of Toll-Like Receptor 7 Variant Associated with Systemic Lupus Erythematosus," PLOS Genetics, (Feb. 2013), vol. 9, issue. 2, e1003336, pp. 1-11.

Fairhurst et al., "Yaa Autoimmune Phenotypes are Conferred by Overexpression of TLR7," European Journal of Immunology, (Jul. 2008), vol. 38, No. 7, pp. 1971-1978.

Kirou et al., "Activation of the Interferon-alpha Pathway Identifies a Subgroup of Systemic Lupus Erythematosus Patients With Distinct Serologic Features and Active Disease," Arthritis & Rheumatism, (May 2005), vol. 52, No. 5, pp. 1491-1503.

Lafyatis et al., "Antimalarial Agents: Closing the Gate on Toll-like Receptors?," Arthritis & Rheumatism, (Oct. 2006), vol. 54, No. 10, pp. 3068-3070.

(56) References Cited

OTHER PUBLICATIONS

Means et al., "Human Lupus Autoantibody-DNA Complexes Activate DCs Through Cooperation of CD32 and TLR9," The Journal of Clinical Investigation, (Feb. 2005), vol. 115, No. 2, pp. 407-417.
Nickerson et al., "TLR9 Regulates TLR7- and MyD88-Dependent Autoantibody Production and Disease in a Murine Model of Lupus," The Journal of Immunology, (Feb. 15, 2010), vol. 184, No. 4. pp. 1840-1848.
Shen et al., "Sex-specific Association of X-linked Toll-like Receptor 7 (TLR7) with Male Systemic Lupus Erythematosus," PNAS, (Sep. 7, 2010), vol. 107, No. 36, pp. 15838-15843.

* cited by examiner

| Treatment | Pre-disease | Veh | -742 | -742 | -742 |
|---|---|---|---|---|---|
| Dose (mpk) | --- | --- | 33 | 100 | 300 |
| Duration (wks) | --- | 21 | 21 | 21 | 21 |
| Age (wks) | 9 | 50 | 50 | 50 | 50 |

FIG. 2B
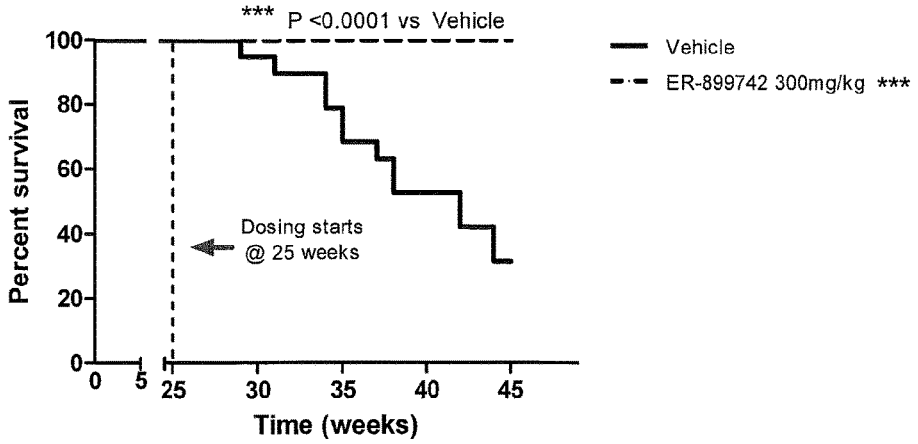
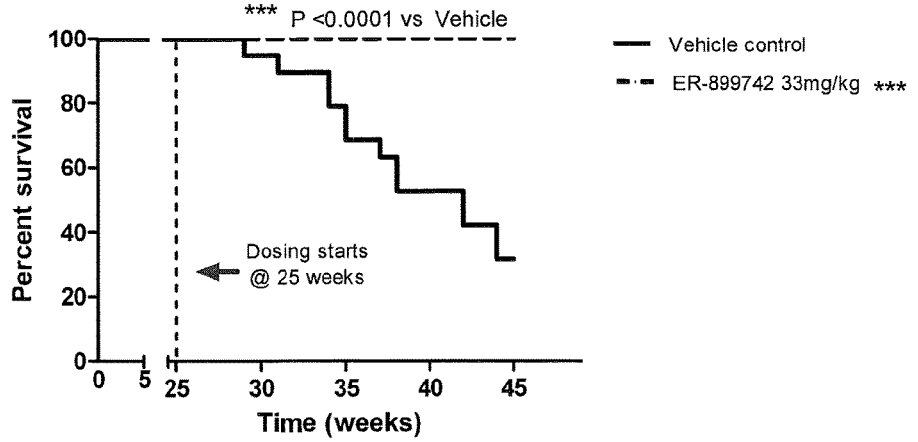

| Treatment | Pre-disease | Pre-dosing | Veh | -742 | -742 | -742 |
|---|---|---|---|---|---|---|
| Dose (mpk) | --- | --- | --- | 33 | 100 | 300 |
| Duration (wks) | --- | -- | 17 | 17 | 17 | 17 |
| Age (wks) | 9 | 27 | 46 | 46 | 46 | 46 |

| Treatment | Normal | Pre-dose | Pris + veh | Pris + -742 | Pris + -742 | Pris + -742 |
|---|---|---|---|---|---|---|
| Dose (mpk) | --- | -- | -- | 33 | 100 | 300 |
| Duration post-pristane (wks) | -- | 9 | 23 | 23 | 23 | 23 |
| Duration of dosing | -- | -- | 13 | 13 | 13 | 13 |
| Age (wks) | 18 | 18 | 32 | 32 | 32 | 32 |

| Treatment | Normal | Pre-dose | Pris + veh | Pris + -742 | Pris + -742 | Pris + -742 |
|---|---|---|---|---|---|---|
| Dose (mpk) | --- | -- | -- | 33 | 100 | 300 |
| Duration post-pristane (wks) | -- | 9 | 23 | 23 | 23 | 23 |
| Duration of dosing | -- | -- | 13 | 13 | 13 | 13 |
| Age (wks) | 18 | 18 | 32 | 32 | 32 | 32 |

| Treatment | Normal | Pre-dose | Pris + veh | Pris + -742 | Pris + -742 | Pris + -742 |
|---|---|---|---|---|---|---|
| Dose (mpk) | --- | -- | -- | 33 | 100 | 300 |
| Duration post-pristane (wks) | -- | 9 | 23 | 23 | 23 | 23 |
| Duration of dosing | -- | -- | 13 | 13 | 13 | 13 |
| Age (wks) | 18 | 18 | 32 | 32 | 32 | 32 |

| Treatment | Normal | Pre-dose | Pris + veh | Pris + -742 | Pris + -742 | Pris + -742 |
|---|---|---|---|---|---|---|
| Dose (mpk) | --- | -- | -- | 33 | 100 | 300 |
| Duration post-pristane (wks) | -- | 9 | 23 | 23 | 23 | 23 |
| Duration of dosing | -- | -- | 13 | 13 | 13 | 13 |
| Age (wks) | 18 | 18 | 32 | 32 | 32 | 32 |

FIG. 3E

| Gene Number | Gene Name |
|---|---|
| 1 | Oas3 |
| 2 | Ifi27l2a |
| 3 | **Ifi44** * |
| 4 | Oasl2 |
| 5 | **Irf7** * |
| 6 | **Ifit1** * |
| 7 | Cmpk2 |
| 8 | Xaf1 |
| 9 | Mx1 |
| 10 | Fcgr1 |
| 11 | Mmp8 |
| 12 | Ddx60 |
| 13 | Ifi204 |
| 14 | **Usp18** * |
| 15 | Ifi202b |
| 16 | **Siglec1** * |
| 17 | **Isg15** * |
| 18 | Herc6 |
| 19 | Ifit3 |
| 20 | Fpr1 |
| 21 | Bst2 |
| 22 | Cxcl10 |
| 23 | Ms4a6c |
| 24 | Mmp9 |
| 25 | Ccr2 |
| 26 | Cd38 |
| 27 | Tlr7 |
| 28 | Prf1 |
| 29 | C1qa |
| | |
| Twenty nine (29) genes significantly altered between Pristane + Vehicle vs. uninduced PBS control (P<0.05, at least 1.5 fold change) | |
| * Significantly reduced by ER-899742 vs. vehicle-treated pristane-induced mice (6 genes) (P<0.05, at least 1.5 fold change) | |

| Treatment | Pre-disease | Veh | -464 | -464 | -464 |
|---|---|---|---|---|---|
| Dose (mpk) | --- | --- | 33 | 100 | 300 |
| Duration (wks) | --- | 21 | 21 | 21 | 21 |
| Age (wks) | 9 | 50 | 50 | 50 | 50 |

FIG. 4B
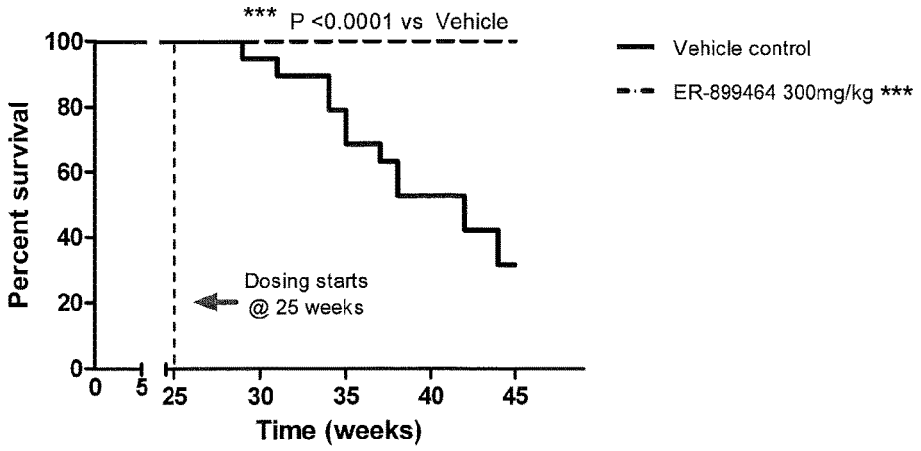
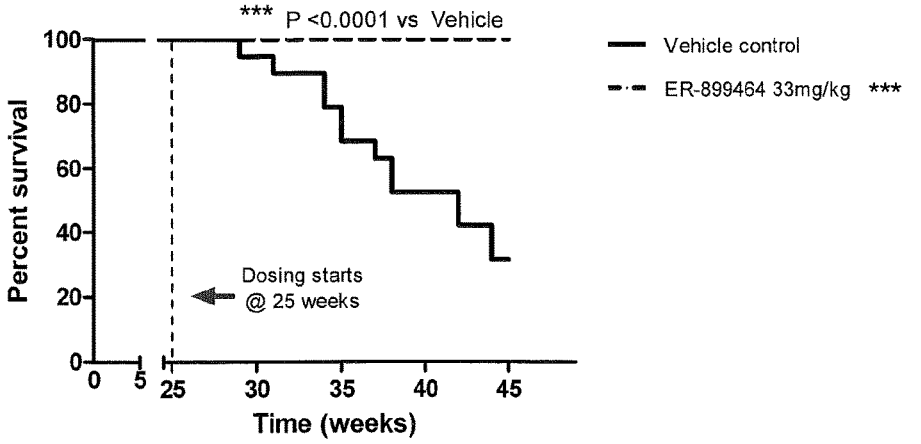

| Treatment | Pre-disease | Pre-dosing | Veh | -464 | -464 | -464 |
|---|---|---|---|---|---|---|
| Dose (mpk) | --- | --- | --- | 33 | 100 | 300 |
| Duration (wks) | --- | -- | 17 | 17 | 17 | 17 |
| Age (wks) | 9 | 27 | 46 | 46 | 46 | 46 |

| Treatment | Normal | Pre-dose | Pris + veh | Pris + -464 | Pris + -464 | Pris + -464 |
|---|---|---|---|---|---|---|
| Dose (mpk) | --- | -- | -- | 33 | 100 | 300 |
| Duration post-pristane (wks) | -- | 9 | 23 | 23 | 23 | 23 |
| Duration of dosing | -- | -- | 13 | 13 | 13 | 13 |
| Age (wks) | 18 | 18 | 32 | 32 | 32 | 32 |

| Treatment | Normal | Pre-dose | Pris + veh | Pris + -464 | Pris + -464 | Pris + -464 |
|---|---|---|---|---|---|---|
| Dose (mpk) | --- | -- | -- | 33 | 100 | 300 |
| Duration post-pristane (wks) | -- | 9 | 23 | 23 | 23 | 23 |
| Duration of dosing | -- | -- | 13 | 13 | 13 | 13 |
| Age (wks) | 18 | 18 | 32 | 32 | 32 | 32 |

| Treatment | Normal | Pre-dose | Pris + veh | Pris + -464 | Pris + -464 | Pris + -464 |
|---|---|---|---|---|---|---|
| Dose (mpk) | --- | -- | -- | 33 | 100 | 300 |
| Duration post-pristane (wks) | -- | 9 | 23 | 23 | 23 | 23 |
| Duration of dosing | -- | -- | 13 | 13 | 13 | 13 |
| Age (wks) | 18 | 18 | 32 | 32 | 32 | 32 |

| Treatment | Normal | Pre-dose | Pris + veh | Pris + -464 | Pris + -464 | Pris + -464 |
|---|---|---|---|---|---|---|
| Dose (mpk) | --- | -- | -- | 33 | 100 | 300 |
| Duration post-pristane (wks) | -- | 9 | 23 | 23 | 23 | 23 |
| Duration of dosing | -- | -- | 13 | 13 | 13 | 13 |
| Age (wks) | 18 | 18 | 32 | 32 | 32 | 32 |

FIG. 6A

| Number | Structure | MW | HEK /hTLR7 IC50 (uM) | HEK/ hTLR9 IC50 (uM) | Chemical Name | 1H-NMR | MS |
|---|---|---|---|---|---|---|---|
| ER-878952 | $C_{16}H_{17}N_3O$ | 267.3 | 0.1136 | >30 | 5-((2R,6S)-2,6-dimethylmorpholino)quinoline-8-carbonitrile | $^1$H NMR (400 MHz, methanol-d4) d ppm 0.93 (6 H, d) 1.97 - 2.12 (2 H, m) 2.31 - 2.45 (2 H, m) 3.35 - 3.47 (2 H, m) 7.09 - 7.22 (1 H, m) 7.53 - 7.62 (1 H, m) 8.01 - 8.10 (1 H, m) 8.46 - 8.56 (1 H, m) 8.86 - 8.95 (1 H, m), | LCMS (ESI+) calcd for $C_{16}H_{17}N_3O$ (M+H$^+$) 268.3, found 268.1 |
| ER-878952-02 | $C_{16}H_{19}Cl_2N_3O$ | 340.3 | 0.0738 | >20 | 5-((2R,6S)-2,6-dimethylmorpholino)quinoline-8-carbonitrile dihydrochloride | 1H NMR (400 MHz, METHANOL-d4) d ppm 0.93 (6 H, d) 1.97 - 2.12 (2 H, m) 2.31 - 2.45 (2 H, m) 3.35 - 3.47 (2 H, m) 7.09 - 7.22 (1 H, m) 7.53 - 7.62 (1 H, m) 8.01 - 8.10 (1 H, m) 8.46 - 8.56 (1 H, m) 8.86 - 8.95 (1 H, m) | LCMS (ESI+) calcd for C16 H17 N3 O (M+H+) 268.3, found 268.1 |
| ER-878952-13 | $C_{17}H_{21}N_3O_4S$ | 363.4 | 0.1410 | >20 | 5-((2R,6S)-2,6-dimethylmorpholino)quinoline-8-carbonitrile methanesulfonate | $^1$H NMR (400 MHz, CHLOROFORM-*d*) d ppm 1.26 (d, *J*=6.34 Hz, 7 H) 2.84 - 2.98 (m, 14 H) 3.40 - 3.54 (m, 2 H) 4.02 - 4.13 (m, 2 H) 7.42 (d, *J*=8.54 Hz, 1 H) 8.22 - 8.35 (m, 2 H) 9.27 (d, *J*=1.22 Hz, 1 H) 9.44 (d, *J*=4.64 Hz, 1 H) 12.42 (br. s., 2 H) | |
| ER-878952-24 | $C_{20}H_{19}F_6N_3O_5$ | 495.4 | 0.0490 | >20 | 5-((2R,6S)-2,6-dimethylmorpholino)quinoline-8-carbonitrile bis(2,2,2-trifluoroacetate) | $^1$H NMR (400 MHz, METHANOL-$d_4$) d ppm 0.94 (d, *J*=6.45 Hz, 9 H) 1.91 (br. s., 1 H) 2.02 (dd, *J*=7.32, 3.81 Hz, 3 H) 2.39 (t, *J*=11.57 Hz, 3 H) 3.38 - 3.43 (m, 3 H) 7.16 (d, *J*=7.91 Hz, 1 H) 7.57 (dd, *J*=8.50, 4.39 Hz, 1 H) 8.07 (d, *J*=8.20 Hz, 1 H) 8.52 (dd, *J*=8.64, 1.61 Hz, 1 H) 8.91 (dd, *J*=4.39, 1.76 Hz, 1 H) | |
| ER-878952-25 | $C_{16}H_{21}N_3O_7S_2$ | 431.5 | 0.1200 | >20 | 5-((2R,6S)-2,6-dimethylmorpholino)quinoline-8-carbonitrile bis(sulfonate) | $^1$H NMR (400 MHz, DMSO-$d_6$) d ppm 1.09 (d, *J*=6.15 Hz, 8 H) 2.52 (t, *J*=11.13 Hz, 3 H) 3.26 - 3.30 (m, 5 H) 3.86 - 3.95 (m, 3 H) 7.16 (d, *J*=8.20 Hz, 1 H) 7.62 (ddd, *J*=8.50, 4.10, 1.17 Hz, 1 H) 8.19 (dd, *J*=7.91, 1.17 Hz, 1 H) 8.51 (dd, *J*=8.64, 1.32 Hz, 1 H) 8.99 (dt, *J*=2.71, 1.43 Hz, 1 H) | |

FIG. 6B

| | | | | | | | |
|---|---|---|---|---|---|---|---|
| ER-878952-26 | $C_{16}H_{19}N_3O_4S$ | 349.4 | 0.0880 | >20 | 5-((2R,6S)-2,6-dimethylmorpholino)quinoline-8-carbonitrile sulfonate | $^1$H NMR (400 MHz, DMSO-$d_6$) d ppm 1.04 - 1.25 (m, 17 H) 2.44 - 2.67 (m, 8 H) 3.30 (s, 3 H) 3.27 (s, 3 H) 3.82 - 4.09 (m, 7 H) 7.12 - 7.31 (m, 3 H) 7.56 - 7.75 (m, 3 H) 8.09 - 8.33 (m, 3 H) 8.49 - 8.74 (m, 4 H) 8.98 (ddd, $J$=4.32, 3.00, 1.76 Hz, 20 H) 9.09 (m, 1 H) | |
| ER-87895227 | $C_{20}H_{23}N_3O_7$ | 417.4 | 0.1250 | >20 | 5-((2S,6R)-2,6-dimethylmorpholino)quinoline-8-carbonitrile 2,3-dihydroxysuccinate | | |
| ER-878952-28 | $C_{18}H_{25}N_3O_7S_2$ | 459.5 | 0.1040 | >20 | 5-((2S,6R)-2,6-dimethylmorpholino)quinoline-8-carbonitrile dimethanesulfonate | | |
| ER-879484 | $C_{15}H_{14}ClN_3O$ | 287.7 | 0.3435 | >20 | 5-(2-(chloromethyl)morpholino)quinoline-8-carbonitrile | $^1$H NMR (400 MHz, METHANOL-$d_4$) d ppm 1.20 (d, $J$=6.15 Hz, 1 H) 3.31 (s, 1 H) 3.64 (dd, $J$=5.57, 0.88 Hz, 2 H) 4.00 - 4.08 (m, 3 H) 7.61 (dd, $J$=8.50, 4.39 Hz, 1 H) 8.09 - 8.14 (m, 2 H) | |
| ER-879570 | $C_{15}H_{14}ClN_3O$ | 287.7 | 0.2230 | >20 | (S)-5-(2-(chloromethyl)morpholino)quinoline-8-carbonitrile | | |

FIG. 6C

| | | | | | | | |
|---|---|---|---|---|---|---|---|
| ER-879689 | 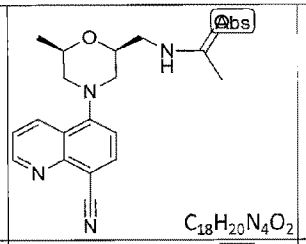 $C_{18}H_{20}N_4O_2$ | 324.4 | 0.3400 | >20 | N-(((2S,6R)-4-(8-cyanoquinolin-5-yl)-6-methylmorpholin-2-yl)methyl)acetamide | $^1$H NMR (400 MHz, CHLOROFORM-*d*) d ppm 0.81 (br. s., 1 H) 1.23 - 1.28 (m, 5 H) 1.54 (s, 4 H) 2.02 - 2.06 (m, 4 H) 2.61 (s, 1 H) 2.63 (s, 1 H) 2.66 (s, 1 H) 2.69 (s, 1 H) 3.17 - 3.24 (m, 2 H) 3.26 - 3.28 (m, 1 H) 3.30 (s, 1 H) 3.60 - 3.66 (m, 1 H) 3.96 - 4.04 (m, 2 H) 5.89 (br. s., 1 H) 7.05 (d, *J*=7.91 Hz, 1 H) 7.24 (d, *J*=0.59 Hz, 4 H) 7.50 (dd, *J*=8.50, 4.39 Hz, 1 H) 8.01 (s, 1 H) 8.03 (s, 1 H) 8.41 (dd, *J*=8.50, 1.76 Hz, 1 H) 9.05 - 9.07 (m, 1 H) | |
| ER-879713 | 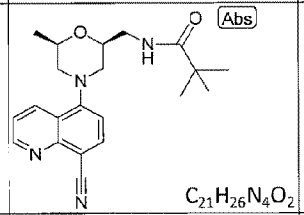 $C_{21}H_{26}N_4O_2$ | 366.5 | 0.0920 | >20 | N-(((2S,6R)-4-(8-cyanoquinolin-5-yl)-6-methylmorpholin-2-yl)methyl)pivalamide | $^1$H NMR (400 MHz, CHLOROFORM-*d*) d ppm 1.21 - 1.28 (m, 13 H) 2.03 - 2.11 (m, 1 H) 2.49 - 2.54 (m, 1 H) 2.60 - 2.67 (m, 2 H) 2.87 - 2.91 (m, 2 H) 3.19 - 3.33 (m, 3 H) 3.43 - 3.47 (m, 1 H) 3.60 - 3.67 (m, 1 H) 3.98 - 4.05 (m, 2 H) 6.27 (br. s., 1 H) 7.05 (d, *J*=7.91 Hz, 1 H) 7.23 - 7.26 (m, 2 H) 7.52 (dd, *J*=8.50, 4.39 Hz, 1 H) 8.03 (d, *J*=7.91 Hz, 1 H) 8.44 (dd, *J*=8.50, 1.46 Hz, 1 H) 9.07 (dd, *J*=4.39, 1.76 Hz, 1 H) | |
| ER-879739 | 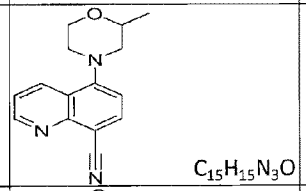 $C_{15}H_{15}N_3O$ | 253.3 | 0.2750 | >20 | 5-(2-methylmorpholino)quinoline-8-carbonitrile | $^1$H NMR (400 MHz, METHANOL-$d_4$) d ppm 1.16 - 1.21 (m, 4 H) 2.67 (dd, *J*=12.01, 9.96 Hz, 1 H) 2.94 - 3.02 (m, 1 H) 3.29 - 3.36 (m, 2 H) 3.93 - 4.01 (m, 4 H) 7.21 (d, *J*=7.91 Hz, 1 H) 7.61 (dd, *J*=8.50, 4.39 Hz, 1 H) 8.11 (d, *J*=7.91 Hz, 1 H) 8.63 (dd, *J*=8.64, 1.61 Hz, 1 H) 8.94 (dd, *J*=4.39, 1.76 Hz, 1 H) | |
| ER-880191 | 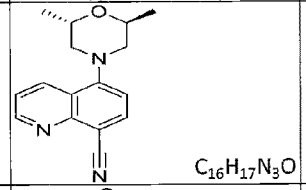 $C_{16}H_{17}N_3O$ | 267.3 | 0.3095 | >20 | 5-((2S,6S)-2,6-dimethylmorpholino)quinoline-8-carbonitrile | $^1$H NMR (400 MHz, METHANOL-$d_4$) d ppm 1.20 (d, *J*=6.15 Hz, 8 H) 1.38 (d, *J*=6.45 Hz, 1 H) 2.55 - 2.64 (m, 3 H) 3.29 - 3.36 (m, 3 H) 3.97 - 4.06 (m, 2 H) 7.18 - 7.22 (m, 1 H) 7.62 (dd, *J*=8.50, 4.39 Hz, 1 H) 8.09 - 8.13 (m, 1 H) 8.64 (dd, *J*=8.64, 1.61 Hz, 1 H) 8.94 (dd, *J*=4.39, 1.46 Hz, 1 H) | |
| ER-880639 | 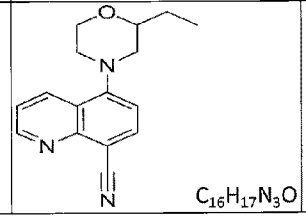 $C_{16}H_{17}N_3O$ | 276.3 | 0.3490 | >20 | 5-(2-ethylmorpholino)quinoline-8-carbonitrile | $^1$H NMR (400 MHz, CHLOROFORM-*d*) d ppm 1.00 (t, *J*=7.47 Hz, 3 H) 1.46 - 1.67 (m, 2 H) 2.05 (br. s., 4 H) 2.70 - 2.74 (m, 1 H) 3.03 (td, *J*=11.57, 3.22 Hz, 1 H) 3.21 - 3.31 (m, 2 H) 3.69 - 3.76 (m, 1 H) 3.96 (td, *J*=11.35, 2.49 Hz, 1 H) 4.04 - 4.09 (m, 1 H) 7.07 (d, *J*=7.91 Hz, 1 H) 7.50 (dd, *J*=8.50, 4.10 Hz, 1 H) 8.03 (d, *J*=7.91 Hz, 1 H) 8.46 (dd, *J*=8.50, 1.76 Hz, 1 H) 9.06 (dd, *J*=4.10, 1.76 Hz, 1 H) | |

FIG. 6D

| | | | | | | | |
|---|---|---|---|---|---|---|---|
| ER-884884 | 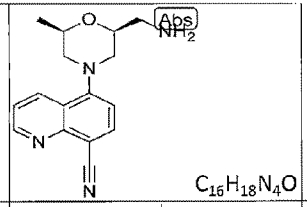 $C_{16}H_{18}N_4O$ | 282.3 | 0.3060 | >20 | 5-((2S,6R)-2-(aminomethyl)-6-methylmorpholino)quinoline-8-carbonitrile | $^1$H NMR (400 MHz, METHANOL-$d_4$) d ppm 1.27 (d, $J$=6.15 Hz, 11 H) 2.63 - 2.67 (m, 2 H) 2.69 - 2.74 (m, 2 H) 2.97 (d, $J$=13.48 Hz, 1 H) 3.15 (s, 1 H) 3.18 (s, 1 H) 3.41 (s, 3 H) 3.37 (s, 3 H) 4.81 - 4.85 (m, 53 H) 7.24 (d, $J$=8.20 Hz, 3 H) 7.60 - 7.63 (m, 2 H) 8.12 (s, 1 H) 8.14 (s, 1 H) 8.60 (d, $J$=1.46 Hz, 1 H) 8.62 (d, $J$=1.46 Hz, 1 H) 8.96 (dd, $J$=4.10, 1.76 Hz, 2 H) | |
| ER-885047 | 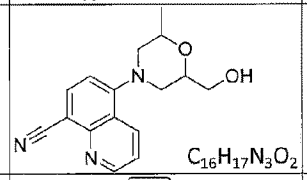 $C_{16}H_{17}N_3O_2$ | 283.3 | 0.9558 | >20 | 5-(2-(hydroxymethyl)-6-methylmorpholino)quinoline-8-carbonitrile | | |
| ER-885113 | 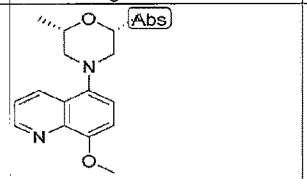 $C_{16}H_{20}N_2O_2$ | 272.4 | 0.5285 | >20 | (2R,6S)-4-(8-methoxyquinolin-5-yl)-2,6-dimethylmorpholine | | |
| ER-885160 | 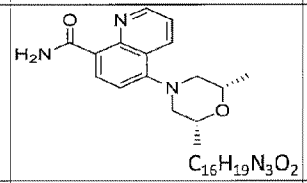 $C_{16}H_{19}N_3O_2$ | 285.3 | 2.1600 | >20 | 5-((2R,6S)-2,6-dimethylmorpholino)quinoline-8-carboxamide | 1H NMR (400 MHz, METHANOL-d4) d ppm 1.21 (6 H, d) 2.63 - 2.81 (2 H, m) 3.34 - 3.48 (2 H, m) 3.95 - 4.12 (2 H, m) 7.34 - 7.48 (1 H, m) 7.91 - 8.02 (1 H, m) 8.49 - 8.67 (1 H, m) 9.08 - 9.18 (1 H, m) 9.18 - 9.27 (1 H, m) | LCMS (ESI+) calcd for C16 H19 N3 O2 (M+H+) 286.3, found 286.3 |
| ER-885211 | 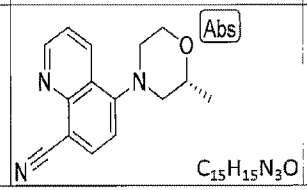 $C_{15}H_{15}N_3O$ | 253.3 | 0.0420 | >20 | (R)-5-(2-methylmorpholino)quinoline-8-carbonitrile | | |

FIG. 6E

| | | | | | | | |
|---|---|---|---|---|---|---|---|
| **ER-885493** | 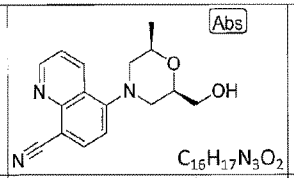 $C_{16}H_{17}N_3O_2$ | 283.3 | 0.1043 | >20 | 5-((2R,6R)-2-(hydroxymethyl)-6-methylmorpholino)quinoline-8-carbonitrile | 1H NMR (400 MHz, METHANOL-d4) d ppm 1.21 (3 H, d) 2.58 - 2.66 (1 H, m) 2.67 - 2.75 (1 H, m) 3.30 - 3.37 (1 H, m) 3.36 - 3.44 (1 H, m) 3.53 (1 H, dd) 3.63 (1 H, dd) 3.91 - 3.98 (1 H, m) 4.00 - 4.08 (1 H, m) 7.15 - 7.25 (1 H, m) 7.56 - 7.65 (1 H, m) 8.07 - 8.15 (1 H, m) 8.56 - 8.68 (1 H, m) 8.88 - 8.96 (1 H, m) | LCMS (ESI+) calcd for C16 H17 N3 O2 (M+H+) 284.3, found 284.3 |
| **ER-885612** | 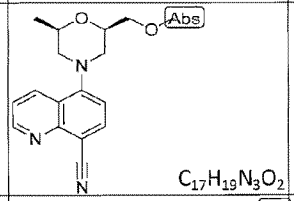 $C_{17}H_{19}N_3O_2$ | 373.5 | 0.2750 | >20 | 5-((2R,6R)-2-(methoxymethyl)-6-methylmorpholino)quinoline-8-carbonitrile | 1H NMR (400 MHz, METHANOL-d4) d ppm 1.22 (3 H, d) 2.62 (1 H, t) 2.82 (1 H, t) 3.30 - 3.41 (2 H, m) 3.99 - 4.27 (2 H, m) 4.41 (1 H, d) 4.53 (1 H, d) 7.18 - 7.32 (1 H, m) 7.62 (1 H, dd) 8.12 (1 H, d) 8.64 (1 H, dd) 8.89 - 8.99 (1 H, m) | LCMS (ESI+) calcd for C16 H16 F N3 O (M+H+) 286.3, found 286.3 |
| **ER-885618** | 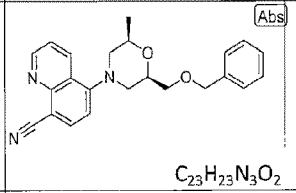 $C_{23}H_{23}N_3O_2$ | 373.5 | 0.0270 | >20 | 5-((2R,6R)-2-((benzyloxy)methyl)-6-methylmorpholino)quinoline-8-carbonitrile | $^1$H NMR (400 MHz, METHANOL-$d_4$) d ppm 1.21 (d, $J$=6.45 Hz, 4 H) 2.59 - 2.63 (m, 1 H) 2.65 (s, 1 H) 2.70 - 2.76 (m, 1 H) 3.30 - 3.43 (m, 3 H) 3.50 - 3.54 (m, 1 H) 3.58 - 3.63 (m, 1 H) 4.01 - 4.06 (m, 1 H) 4.08 - 4.13 (m, 1 H) 4.54 (s, 2 H) 4.82 - 4.87 (m, 7 H) 7.18 - 7.32 (m, 5 H) 7.57 - 7.61 (m, 1 H) 8.11 (d, $J$=7.91 Hz, 1 H) 8.58 - 8.62 (m, 1 H) 8.92 - 8.94 (m, 1 H) | |
| **ER-885621** | 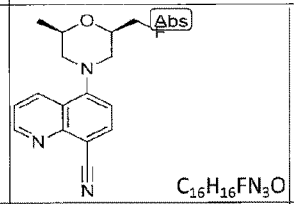 $C_{16}H_{16}FN_3O$ | 285.3 | 0.1800 | >20 | 5-((2R,6R)-2-(fluoromethyl)-6-methylmorpholino)quinoline-8-carbonitrile | | |
| **ER-885807** | 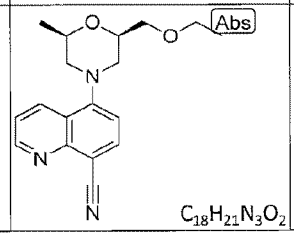 $C_{18}H_{21}N_3O_2$ | 311.4 | 0.1560 | >20 | 5-((2R,6R)-2-(ethoxymethyl)-6-methylmorpholino)quinoline-8-carbonitrile | $^1$H NMR (400 MHz, CHLOROFORM-$d$) d ppm 1.20 (t, $J$=7.03 Hz, 3 H) 1.26 (d, $J$=6.45 Hz, 3 H) 2.00 (s, 1 H) 2.68 (s, 1 H) 2.71 (d, $J$=1.46 Hz, 1 H) 2.74 (s, 1 H) 2.78 (s, 1 H) 2.81 (s, 1 H) 2.84 (s, 1 H) 3.27 (d, $J$=12.01 Hz, 1 H) 3.38 (d, $J$=11.72 Hz, 1 H) 3.49 - 3.64 (m, 4 H) 4.02 - 4.14 (m, 2 H) 5.77 (br. s., 1 H) 7.14 (d, $J$=8.20 Hz, 1 H) 7.24 - 7.25 (m, 2 H) 7.64 (dd, $J$=8.50, 4.39 Hz, 1 H) 8.09 (d, $J$=8.20 Hz, 1 H) 8.61 (dd, $J$=8.50, 1.46 Hz, 1 H) 9.13 - 9.15 (m, 1 H) | |

FIG. 6F

| | | | | | | | |
|---|---|---|---|---|---|---|---|
| ER-885808 | 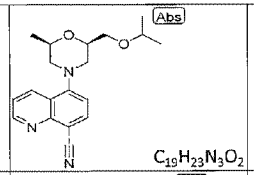 $C_{19}H_{23}N_3O_2$ | 325.4 | 0.0880 | >20 | 5-((2R,6R)-2-(isopropoxymethyl)-6-methylmorpholino)quinoline-8-carbonitrile | $^1$H NMR (400 MHz, CHLOROFORM-*d*) d ppm 1.15 (dd, *J*=7.91, 6.15 Hz, 6 H) 1.25 (d, *J*=6.15 Hz, 3 H) 2.65 (s, 1 H) 2.68 (d, *J*=1.46 Hz, 1 H) 2.70 - 2.73 (m, 1 H) 2.76 (s, 1 H) 3.25 (s, 1 H) 3.28 (s, 1 H) 3.41 - 3.47 (m, 2 H) 3.59 - 3.66 (m, 3 H) 4.01 - 4.08 (m, 1 H) 7.10 (d, *J*=7.91 Hz, 1 H) 7.24 - 7.24 (m, 4 H) 7.54 - 7.57 (m, 1 H) 8.04 (s, 1 H) 8.06 (s, 1 H) 8.52 (dd, *J*=8.50, 1.76 Hz, 1 H) 9.09 (dd, *J*=4.10, 1.76 Hz, 1 H) | |
| ER-885892 | 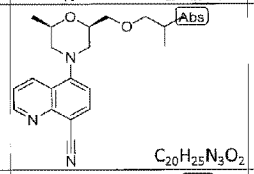 $C_{20}H_{25}N_3O_2$ | 339.4 | 0.0740 | >20 | 5-((2R,6R)-2-(isobutoxymethyl)-6-methylmorpholino)quinoline-8-carbonitrile | $^1$H NMR (400 MHz, CHLOROFORM-*d*) d ppm 0.87 (d, *J*=6.74 Hz, 7 H) 1.25 (d, *J*=6.15 Hz, 4 H) 1.68 (s, 21 H) 1.81 - 1.88 (m, 1 H) 2.63 - 2.66 (m, 1 H) 2.69 - 2.74 (m, 1 H) 3.19 - 3.28 (m, 4 H) 3.41 - 3.48 (m, 3 H) 3.59 (dd, *J*=9.96, 4.98 Hz, 1 H) 7.05 (s, 1 H) 7.07 (s, 1 H) 7.24 (s, 6 H) 7.48 - 7.51 (m, 1 H) 8.02 (s, 1 H) 8.04 (s, 1 H) 8.45 (d, *J*=1.76 Hz, 1 H) 8.47 (d, *J*=1.76 Hz, 1 H) 9.06 (dd, *J*=4.39, 1.76 Hz, 1 H) | |
| ER-885906 | 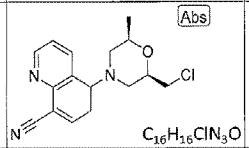 $C_{16}H_{16}ClN_3O$ | 301.8 | 0.1980 | >20 | 5-((2R,6R)-2-(chloromethyl)-6-methylmorpholino)quinoline-8-carbonitrile | $^1$H NMR (400 MHz, CHLOROFORM-*d*) d ppm 1.27 (d, *J*=6.15 Hz, 7 H) 1.60 (s, 83 H) 2.67 - 2.75 (m, 2 H) 3.48 (s, 1 H) 3.51 - 3.53 (m, 2 H) 3.54 (d, *J*=4.69 Hz, 1 H) 7.09 (d, *J*=8.20 Hz, 1 H) 7.24 - 7.24 (m, 31 H) 7.50 - 7.54 (m, 1 H) 8.04 (d, *J*=8.20 Hz, 1 H) 8.44 (d, *J*=7.03 Hz, 1 H) | |
| ER-885929 | 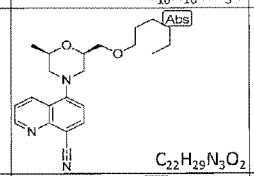 $C_{22}H_{29}N_3O_2$ | 367.5 | 0.2190 | >20 | 5-((2R,6R)-2-((hexyloxy)methyl)-6-methylmorpholino)quinoline-8-carbonitrile | $^1$H NMR (400 MHz, CHLOROFORM-*d*) d ppm 0.81 - 0.87 (m, 3 H) 1.21 - 1.33 (m, 11 H) 1.51 - 1.64 (m, 3 H) 2.62 - 2.76 (m, 3 H) 3.26 (dt, *J*=11.72, 2.05 Hz, 1 H) 3.38 - 3.50 (m, 5 H) 3.58 (dd, *J*=9.96, 5.27 Hz, 1 H) 3.99 - 4.11 (m, 2 H) 7.06 (d, *J*=7.91 Hz, 1 H) 7.24 (s, 1 H) 7.47 - 7.51 (m, 1 H) 8.01 (d, *J*=8.20 Hz, 1 H) 8.45 (dd, *J*=8.50, 1.46 Hz, 1 H) 9.05 (dd, *J*=4.10, 1.47 Hz, 1 H) | |
| ER-885930 | 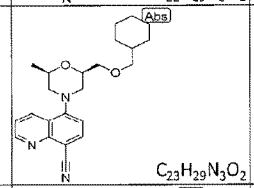 $C_{23}H_{29}N_3O_2$ | 379.5 | 0.0710 | >20 | 5-((2R,6R)-2-((cyclohexylmethoxy)methyl)-6-methylmorpholino)quinoline-8-carbonitrile | $^1$H NMR (400 MHz, CHLOROFORM-*d*) d ppm 0.83 - 0.93 (m, 2 H) 1.10 - 1.27 (m, 6 H) 1.55 - 1.73 (m, 5 H) 2.66 - 2.70 (m, 1 H) 2.73 (d, *J*=7.32 Hz, 1 H) 2.76 (d, *J*=1.17 Hz, 1 H) 2.79 (s, 1 H) 3.24 - 3.32 (m, 3 H) 3.39 - 3.52 (m, 2 H) 3.59 (dd, *J*=9.96, 4.98 Hz, 1 H) 3.80 (br. s., 7 H) 4.01 - 4.12 (m, 2 H) 7.11 (d, *J*=7.91 Hz, 1 H) 7.24 - 7.25 (m, 2 H) 7.58 (dd, *J*=8.79, 4.39 Hz, 1 H) 8.07 (d, *J*=7.91 Hz, 1 H) 8.54 - 8.57 (m, 1 H) 9.11 (dd, *J*=4.39, 1.76 Hz, 1 H) | |
| ER-886131 | 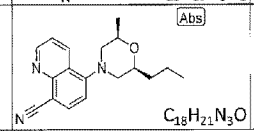 $C_{18}H_{21}N_3O$ | 295.4 | 0.1240 | >20 | 5-((2R,6S)-2-methyl-6-propylmorpholino)quinoline-8-carbonitrile | 1H NMR (400 MHz, CDCl3-d) d ppm 0.93 (3 H, t) 1.25 (3 H, d) 1.35 - 1.66 (4 H, m) 2.57 - 2.74 (2 H, m) 3.26 (2 H, d) 3.79 - 3.91 (1 H, m) 3.92 - 4.05 (1 H, m) 6.99 - 7.14 (1 H, m) 7.49 - 7.59 (1 H, m) 7.98 - 8.12 (1 H, m) 8.43 - 8.53 (1 H, m) 9.02 - 9.14 (1 H, m) | LCMS (ESI+) calcd for C18 H21 N3 O (M+H+) 296.3, found 296.1 |

FIG. 6G

| | | | | | | | |
|---|---|---|---|---|---|---|---|
| ER-886133 | $C_{16}H_{16}FN_3O$ | 285.3 | 0.3410 | >20 | 5-((2S,6S)-2-(fluoromethyl)-6-methylmorpholino)quinoline-8-carbonitrile | | |
| ER-886134 | $C_{16}H_{16}ClN_3O$ | 301.8 | 0.2700 | >20 | 5-((2S,6S)-2-(chloromethyl)-6-methylmorpholino)quinoline-8-carbonitrile | $^1$H NMR (400 MHz, CHLOROFORM-*d*) d ppm 1.27 (d, *J*=6.45 Hz, 4 H) 1.67 (br. s., 9 H) 2.64 (s, 1 H) 2.67 (d, *J*=1.76 Hz, 1 H) 2.69 (s, 1 H) 2.72 (s, 1 H) 2.75 (d, *J*=1.46 Hz, 1 H) 2.78 (s, 1 H) 3.26 (t, *J*=2.05 Hz, 1 H) 3.29 (t, *J*=2.05 Hz, 1 H) 3.48 - 3.55 (m, 3 H) 3.65 (dd, *J*=11.43, 4.98 Hz, 1 H) 4.04 - 4.14 (m, 2 H) 7.09 (d, *J*=8.20 Hz, 1 H) 7.24 (s, 4 H) 7.50 - 7.54 (m, 1 H) 8.03 (s, 1 H) 8.05 (s, 1 H) 8.44 (dd, *J*=8.50, 1.76 Hz, 1 H) 9.07 (dd, *J*=4.10, 1.76 Hz, 1 H) | |
| ER-886137 | $C_{24}H_{25}N_3O_2$ | 387.5 | 0.2500 | >20 | 5-((2R,6R)-2-((2,6-dimethylphenoxy)methyl)-6-methylmorpholino)quinoline-8-carbonitrile | $^1$H NMR (400 MHz, CHLOROFORM-*d*) d ppm 1.23 - 1.29 (m, 6 H) 1.55 (s, 9 H) 2.26 (s, 7 H) 2.68 (d, *J*=11.13 Hz, 1 H) 2.72 (s, 1 H) 2.82 (d, *J*=11.43 Hz, 1 H) 2.86 (s, 1 H) 3.29 (s, 1 H) 3.32 (s, 1 H) 3.47 - 3.53 (m, 1 H) 3.55 (s, 1 H) 3.91 - 3.95 (m, 1 H) 4.07 - 4.16 (m, 2 H) 4.25 - 4.29 (m, 1 H) 6.52 (s, 2 H) 6.60 (s, 1 H) 7.07 (s, 1 H) 7.09 (s, 1 H) 7.24 (d, *J*=0.88 Hz, 5 H) 7.49 - 7.53 (m, 1 H) 8.02 (s, 1 H) 8.04 (s, 1 H) 8.45 - 8.48 (m, 1 H) 9.07 (dd, *J*=4.10, 1.76 Hz, 1 H) | |
| ER-886211 | $C_{18}H_{21}N_3O$ | 295.4 | 2.7795 | >20 | 5-((2R,6S)-2,6-diethylmorpholino)quinoline-8-carbonitrile | $^1$H NMR (400 MHz, CHLOROFORM-*d*) d ppm 0.99 - 1.03 (m, 7 H) 1.47 - 1.57 (m, 2 H) 1.59 - 1.66 (m, 2 H) 2.61 (s, 1 H) 2.64 (s, 1 H) 2.67 (s, 1 H) 3.27 (s, 1 H) 3.30 (s, 1 H) 3.71 - 3.77 (m, 2 H) 7.06 (s, 1 H) 7.08 (s, 1 H) 7.24 - 7.24 (m, 6 H) 7.51 (dd, *J*=8.50, 4.10 Hz, 1 H) 8.02 (s, 1 H) 8.04 (s, 1 H) 8.45 - 8.48 (m, 1 H) 9.07 (dd, *J*=4.39, 1.76 Hz, 1 H) | |
| ER-886212 | $C_{20}H_{25}N_3O$ | 323.4 | 0.2410 | >20 | 5-((2R,6S)-2-methyl-6-pentylmorpholino)quinoline-8-carbonitrile | 1H NMR (400 MHz, CDCl3-d) d ppm 0.88 (3 H, t) 1.25 (3 H, d) 1.28 - 1.35 (3 H, m) 1.39 - 1.53 (2 H, m) 1.54 - 1.65 (1 H, m) 2.60 - 2.69 (2 H, m) 2.73 - 2.83 (2 H, m) 3.19 - 3.33 (2 H, m) 3.76 - 3.88 (1 H, m) 3.93 - 4.06 (1 H, m) 7.00 - 7.14 (1 H, m) 7.48 - 7.61 (1 H, m) 7.98 - 8.10 (1 H, m) 8.38 - 8.56 (1 H, m) 9.00 - 9.13 (1 H, m) | LCMS (ESI+) calcd for C20 H25 N3 O (M+H+) 324.4, found 324.5 |

FIG. 6H

| | | | | | | | |
|---|---|---|---|---|---|---|---|
| ER-886250 | 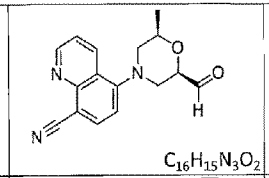 $C_{16}H_{15}N_3O_2$ | 281.3 | 0.1860 | >10.0 | 5-((2R,6R)-2-formyl-6-methylmorpholino)quinoline-8-carbonitrile | 1H NMR (400 MHz, CDCl3-d) 1.35 (3 H, d) 2.65 - 2.85 (2 H, m) 3.24 (1H, d) 3.58 (1 H, d) 4.09 -4.014 (1 H, m) 4.50 (1 H, d) 7.11 (1 H, d) 7.53 (1 H, d) 8.05 (1 H, d) 8.53 (1 H, d) 9.08 (1 H, s) 9.75 (1 H, s) | |
| ER-886250 | 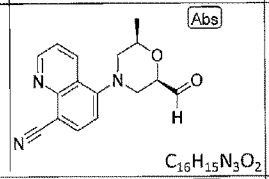 $C_{16}H_{15}N_3O_2$ | 309.4 | 0.1670 | >20 | 5-((2R,6R)-2-formyl-6-methylmorpholino)quinoline-8-carbonitrile | $^1$H NMR (400 MHz, CHLOROFORM-*d*) d ppm 1.37(d, 3 H) 2.64 - 2.88 (m, 2 H) 3.33 (dt, *J*=11.96, 2.14 Hz, 1 H) 3.56 (dt, *J*=11.96, 2.46 Hz, 1 H) 4.06 - 4.22 (m, 1 H) 4.40 (dd, *J*=10.79, 2.88 Hz, 1 H) 7.07 - 7.18 (m, 1 H) 7.50 - 7.61 (m, 1 H) 8.00 - 8.14 (m, 1 H) 8.46 (dd, *J*=8.65, 1.82 Hz, 1 H) 9.05 - 9.15 (m, 1 H) 9.73 (s, 1 H) | |
| ER-886355 | 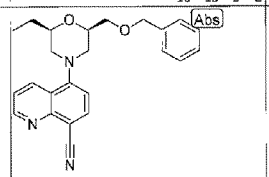 $C_{24}H_{25}N_3O_2$ | 387.5 | 0.0250 | >20 | 5-((2R,6R)-2-((benzyloxy)methyl)-6-ethylmorpholino)quinoline-8-carbonitrile | $^1$H NMR (400 MHz, CHLOROFORM-*d*) d ppm 0.97 - 1.01 (m, 8 H) 1.52 - 1.65 (m, 20 H) 2.62 - 2.66 (m, 1 H) 2.68 - 2.76 (m, 1 H) 3.27 (s, 1 H) 3.30 (s, 1 H) 3.39 (s, 1 H) 3.42 (s, 1 H) 3.51 (dd, *J*=9.96, 5.86 Hz, 2 H) 3.64 (dd, *J*=10.25, 4.98 Hz, 2 H) 4.57 (s, 5 H) 5.28 (s, 3 H) 7.05 (s, 1 H) 7.07 (s, 1 H) 7.23 - 7.27 (m, 19 H) 7.29 - 7.33 (m, 8 H) 7.49 (dd, *J*=8.50, 4.39 Hz, 2 H) 8.01 (s, 1 H) 8.03 (s, 1 H) 8.44 (dd, *J*=8.79, 1.76 Hz, 2 H) 9.05 - 9.06 (m, 1 H) | |
| ER-886360 | 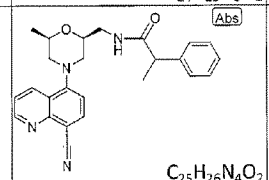 $C_{25}H_{26}N_4O_2$ | 414.5 | 0.3710 | >20 | N-(((2S,6R)-4-(8-cyanoquinolin-5-yl)-6-methylmorpholin-2-yl)methyl)-2-phenylpropanamide | $^1$H NMR (400 MHz, CHLOROFORM-*d*) d ppm 1.15 - 1.18 (m, 4 H) 1.43 (dd, *J*=7.03, 3.81 Hz, 1 H) 1.51 - 1.57 (m, 5 H) 2.42 (s, 1 H) 2.45 (s, 1 H) 2.55 (s, 1 H) 2.58 (s, 1 H) 3.16 - 3.23 (m, 2 H) 3.62 (s, 1 H) 6.94 (s, 1 H) 6.96 (s, 1 H) 7.02 (s, 1 H) 7.04 (s, 1 H) 7.26 - 7.37 (m, 12 H) 7.50 - 7.53 (m, 1 H) 8.02 - 8.05 (m, 1 H) 8.39 - 8.42 (m, 1 H) 9.07 - 9.09 (m, 1 H) | |
| ER-886418 | 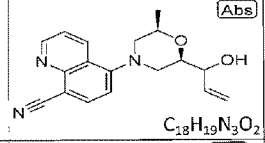 $C_{18}H_{19}N_3O_2$ | 387.5 | 0.2770 | >20 | 5-((2R,6R)-2-(1-hydroxyallyl)-6-methylmorpholino)quinoline-8-carbonitrile | | |
| ER-886431 | 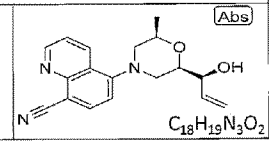 $C_{18}H_{19}N_3O_2$ | 387.5 | 0.2070 | >20 | 5-((2R,6R)-2-((S)-1-hydroxyallyl)-6-methylmorpholino)quinoline-8-carbonitrile | $^1$H NMR (400 MHz, CHLOROFORM-*d*) d ppm 1.30 (d, 3 H) 2.57 - 2.72 (m, 1 H) 2.80 (t, *J*=11.32 Hz, 1 H) 3.30 (d, 2 H) 3.77 - 3.90 (m, 1 H) 4.02 - 4.19 (m, 2 H) 5.23 - 5.34 (m, 1 H) 5.35 - 5.47 (m, 1 H) 5.83 - 5.99 (m, 1 H) 7.09 (d, *J*=7.90 Hz, 1 H) 7.48 - 7.60 (m, 1 H) 8.00 - 8.12 (m, 1 H) 8.43 (dd, *J*=8.55, 1.71 Hz, 1 H) 9.09 (dd, *J*=4.27, 1.71 Hz, 1 H) | LCMS (ESI+) calcd for C18H19N3O2 (M+H+): 310.15, found: 310.16 |

FIG. 6I

| | | | | | | | |
|---|---|---|---|---|---|---|---|
| **ER-886432** | 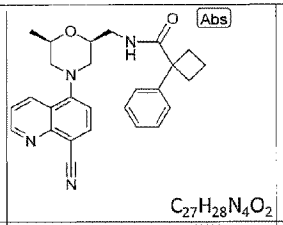 $C_{27}H_{28}N_4O_2$ | 440.5 | 0.3050 | >20 | N-(((2S,6R)-4-(8-cyanoquinolin-5-yl)-6-methylmorpholin-2-yl)methyl)-1-phenylcyclobutanecarboxamide | $^1$H NMR (400 MHz, CHLOROFORM-*d*) d ppm 0.81 - 0.88 (m, 1 H) 1.10 (d, *J*=6.15 Hz, 4 H) 1.22 - 1.29 (m, 2 H) 1.62 (br. s., 1 H) 1.84 - 1.93 (m, 1 H) 2.08 - 2.16 (m, 1 H) 2.31 - 2.38 (m, 2 H) 2.40 - 2.56 (m, 2 H) 2.72 - 2.80 (m, 1 H) 2.83 - 2.90 (m, 1 H) 3.07 - 3.14 (m, 2 H) 3.22 - 3.29 (m, 1 H) 3.37 - 3.44 (m, 1 H) 3.80 - 3.88 (m, 2 H) 5.57 - 5.62 (m, 1 H) 6.90 (d, *J*=7.91 Hz, 1 H) 7.21 - 7.26 (m, 2 H) 7.28 - 7.37 (m, 4 H) 7.47 (dd, *J*=8.50, 4.10 Hz, 1 H) 7.99 (d, *J*=7.91 Hz, 1 H) 8.35 (dd, *J*=8.50, 1.46 Hz, 1 H) 9.04 (dd, *J*=4.10, 1.46 Hz, 1 H) | |
| **ER-886480** | 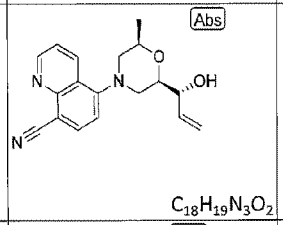 $C_{18}H_{19}N_3O_2$ | 309.4 | 0.2070 | >20 | 5-((2R,6R)-2-((R)-1-hydroxyallyl)-6-methylmorpholino)quinoline-8-carbonitrile | $^1$H NMR (400 MHz, CHLOROFORM-*d*) d ppm 1.29 (d, 3 H) 2.23 (d, *J*=3.85 Hz, 1 H) 2.65 (dd, *J*=11.75, 10.25 Hz, 1 H) 2.91 (dd, *J*=11.96, 10.47 Hz, 1 H) 3.23 - 3.39 (m, 2 H) 3.94 (ddd, *J*=10.47, 4.27, 2.35 Hz, 1 H) 4.02 - 4.13 (m, 1 H) 4.28 - 4.41 (m, 1 H) 5.27 (dt, *J*=10.68, 1.50 Hz, 1 H) 5.41 (dt, *J*=17.09, 1.50 Hz, 1 H) 5.95 (ddd, *J*=17.30, 10.68, 5.77 Hz, 1 H) 7.09 (d, *J*=8.12 Hz, 1 H) 7.48 - 7.58 (m, 1 H) 8.05 (d, *J*=7.90 Hz, 1 H) 8.44 (dd, *J*=8.55, 1.71 Hz, 1 H) 9.08 (dd, *J*=4.27, 1.71 Hz, 1 H) | LCMS (ESI+) calcd for C18H19N3O2 (M+H+): 310.15, found: 310.14 |
| **ER-886507** | 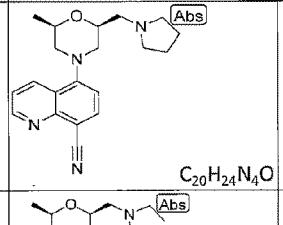 $C_{20}H_{24}N_4O$ | 336.4 | 0.0750 | 13.287 | 5-((2R,6S)-2-methyl-6-(pyrrolidin-1-ylmethyl)morpholino)quinoline-8-carbonitrile | $^1$H NMR (400 MHz, METHANOL-$d_4$) d ppm 1.28 (d, *J*=6.15 Hz, 4 H) 1.99 - 2.07 (m, 2 H) 2.15 (d, *J*=4.10 Hz, 2 H) 2.65 - 2.79 (m, 2 H) 3.12 - 3.25 (m, 3 H) 3.30 - 3.42 (m, 5 H) 3.67 - 3.74 (m, 2 H) 4.11 - 4.17 (m, 1 H) 4.29 - 4.35 (m, 1 H) 4.83 - 4.86 (m, 6 H) 7.24 (d, *J*=7.91 Hz, 1 H) 7.57 - 7.63 (m, 1 H) 8.13 (d, *J*=7.91 Hz, 1 H) 8.63 (dd, *J*=8.50, 1.76 Hz, 1 H) 8.96 (dd, *J*=4.10, 1.76 Hz, 1 H) | |
| **ER-886508** | 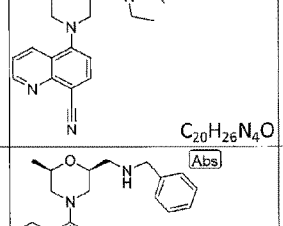 $C_{20}H_{26}N_4O$ | 338.5 | 0.1200 | 14.481 | 5-((2S,6R)-2-((diethylamino)methyl)-6-methylmorpholino)quinoline-8-carbonitrile | $^1$H NMR (400 MHz, METHANOL-$d_4$) d ppm 1.24 1.36 (m, 21 H) 2.65 - 2.75 (m, 3 H) 3.29 - 3.41 (m, 14 H) 4.81 - 4.85 (m, 12 H) 7.25 (d, *J*=8.20 Hz, 2 H) 7.62 (dd, *J*=8.50, 4.10 Hz, 1 H) 8.13 (d, *J*=7.91 Hz, 1 H) 8.62 - 8.65 (m, 1 H) 8.93 - 8.97 (m, 2 H) | |
| **ER-886509** | 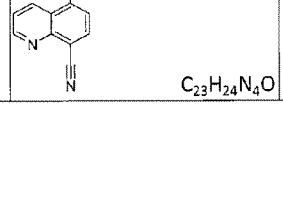 $C_{23}H_{24}N_4O$ | 372.5 | 0.0440 | 3.94 | 5-((2S,6R)-2-((benzylamino)methyl)-6-methylmorpholino)quinoline-8-carbonitrile | $^1$H NMR (400 MHz, METHANOL-$d_4$) d ppm 1.28 (d, *J*=6.45 Hz, 4 H) 2.64 - 2.72 (m, 2 H) 2.74 - 2.79 (m, 1 H) 3.07 - 3.13 (m, 1 H) 3.22 (d, *J*=2.93 Hz, 2 H) 3.34 - 3.41 (m, 2 H) 4.09 - 4.13 (m, 1 H) 4.22 - 4.30 (m, 3 H) 4.82 - 4.85 (m, 9 H) 7.23 (d, *J*=8.20 Hz, 1 H) 7.43 - 7.50 (m, 5 H) 7.61 (dd, *J*=8.50, 4.39 Hz, 1 H) 8.12 (d, *J*=8.20 Hz, 1 H) 8.57 - 8.61 (m, 1 H) 8.94 - 8.96 (m, 1 H) | |

FIG. 6J

| | | | | | | | |
|---|---|---|---|---|---|---|---|
| ER-886514 | 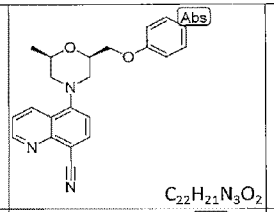 $C_{22}H_{21}N_3O_2$ | 359.4 | 0.0030 | >20 | 5-((2R,6R)-2-methyl-6-(phenoxymethyl)morpholino)quinoline-8-carbonitrile | $^1$H NMR (400 MHz, CHLOROFORM-*d*) d ppm 1.29 (d, *J*=6.15 Hz, 3 H) 1.96 (br. s., 9 H) 2.68 (s, 1 H) 2.71 (d, *J*=1.76 Hz, 1 H) 2.74 (s, 1 H) 2.84 - 2.90 (m, 1 H) 3.29 - 3.30 (m, 1 H) 3.33 (t, *J*=2.05 Hz, 1 H) 3.52 - 3.54 (m, 1 H) 3.56 (s, 1 H) 3.98 (dd, *J*=9.67, 6.74 Hz, 1 H) 4.10 (ddd, *J*=10.25, 6.45, 2.34 Hz, 1 H) 4.17 (dd, *J*=9.67, 4.69 Hz, 1 H) 4.28 - 4.32 (m, 1 H) 6.88 - 6.91 (m, 2 H) 6.93 - 6.98 (m, 1 H) 7.10 (d, *J*=7.91 Hz, 1 H) 7.24 - 7.29 (m, 6 H) 7.53 (dd, *J*=8.50, 4.39 Hz, 1 H) 8.04 (d, *J*=7.91 Hz, 1 H) 8.49 (dd, *J*=8.50, 1.76 Hz, 1 H) 9.08 (dd, *J*=4.39, 1.76 Hz, 1 H) | |
| ER-886515 | 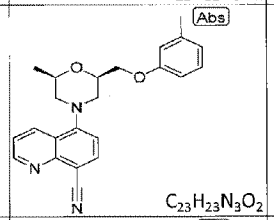 $C_{23}H_{23}N_3O_2$ | 373.5 | 0.0360 | >20 | 5-((2R,6R)-2-methyl-6-((m-tolyloxy)methyl)morpholino)quinoline-8-carbonitrile | $^1$H NMR (400 MHz, CHLOROFORM-*d*) d ppm 1.29 (d, *J*=6.15 Hz, 3 H) 1.90 (br. s., 9 H) 2.30 (s, 3 H) 2.66 (s, 1 H) 2.70 (d, *J*=1.76 Hz, 1 H) 2.73 (s, 1 H) 2.82 - 2.86 (m, 1 H) 2.88 (s, 1 H) 3.29 (t, *J*=2.05 Hz, 1 H) 3.32 (s, 1 H) 3.48 - 3.53 (m, 1 H) 3.55 - 3.58 (m, 1 H) 3.93 - 3.98 (m, 1 H) 4.07 - 4.12 (m, 1 H) 4.16 (dd, *J*=9.67, 4.69 Hz, 1 H) 4.27 - 4.31 (m, 1 H) 6.66 - 6.73 (m, 2 H) 6.77 (d, *J*=7.32 Hz, 1 H) 7.09 (s, 1 H) 7.10 - 7.13 (m, 1 H) 7.15 - 7.17 (m, 1 H) 7.24 (s, 4 H) 7.52 (dd, *J*=8.50, 4.39 Hz, 1 H) 8.03 (s, 1 H) 8.05 (s, 1 H) 8.48 (dd, *J*=8.50, 1.76 Hz, 1 H) 9.08 (dd, *J*=4.39, 1.76 Hz, 1 H) | |
| ER-886516 | 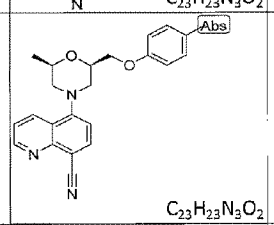 $C_{23}H_{23}N_3O_2$ | 373.5 | 0.0180 | >20 | 5-((2R,6R)-2-methyl-6-((p-tolyloxy)methyl)morpholino)quinoline-8-carbonitrile | $^1$H NMR (400 MHz, CHLOROFORM-*d*) d ppm 1.31 (d, *J*=6.15 Hz, 3 H) 1.58 (s, 6 H) 2.29 (s, 3 H) 2.70 (s, 1 H) 2.73 (d, *J*=1.76 Hz, 1 H) 2.75 (s, 1 H) 2.85 (s, 1 H) 2.87 (d, *J*=1.46 Hz, 1 H) 2.90 (s, 1 H) 3.31 - 3.33 (m, 1 H) 3.34 - 3.35 (m, 1 H) 3.50 (s, 1 H) 3.55 (t, *J*=2.05 Hz, 1 H) 3.57 - 3.59 (m, 1 H) 3.97 (dd, *J*=9.67, 6.74 Hz, 1 H) 4.18 (d, *J*=4.69 Hz, 1 H) 4.18 (d, *J*=4.69 Hz, 1 H) 4.30 (s, 1 H) 6.80 - 6.83 (m, 2 H) 7.07 - 7.11 (m, 2 H) 7.13 (s, 1 H) 7.54 (dd, *J*=8.50, 4.10 Hz, 1 H) 8.05 (s, 1 H) 8.07 (s, 1 H) 8.48 (d, *J*=1.76 Hz, 1 H) 8.50 (d, *J*=1.76 Hz, 1 H) 9.08 (dd, *J*=4.10, 1.76 Hz, 1 H) | |
| ER-886520 | 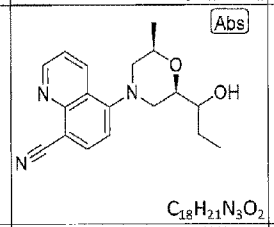 $C_{18}H_{21}N_3O_2$ | 311.4 | 0.2150 | >20 | 5-((2R,6R)-2-(1-hydroxypropyl)-6-methylmorpholino)quinoline-8-carbonitrile | $^1$H NMR (400 MHz, CHLOROFORM-*d*) d ppm 1.04 (t, *J*=7.37 Hz, 3 H) 1.23 - 1.33 (m, 3 H) 1.44 - 1.72 (m, 2 H) 2.02 (d, 1 H) 2.64 (dd, *J*=11.96, 10.25 Hz, 1 H) 2.83 - 3.01 (m, 1 H) 3.24 - 3.43 (m, 2 H) 3.73 (dd, *J*=8.55, 4.27 Hz, 1 H) 3.76 - 3.90 (m, 1 H) 3.97 - 4.15 (m, 1 H) 7.06 - 7.15 (m, 1 H) 7.47 - 7.57 (m, 1 H) 8.00 - 8.11 (m, 1 H) 8.46 (dd, *J*=8.55, 1.71 Hz, 1 H) 9.01 - 9.14 (m, 1 H) | LCMS (ESI+) calcd for C18H21N3O2 (M+H+): 312.17, found: 312.2 |
| ER-886530 | 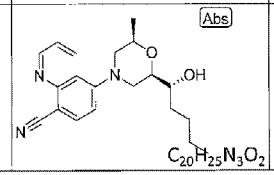 $C_{20}H_{25}N_3O_2$ | 339.4 | 0.0440 | >20 | 5-((2R,6R)-2-((R)-1-hydroxypentyl)-6-methylmorpholino)quinoline-8-carbonitrile | $^1$H NMR (400 MHz, CHLOROFORM-*d*) d ppm 0.83 - 1.01 (m, 3 H) 1.20 - 1.30 (m, 3 H) 1.30 - 1.42 (m, 3 H) 1.44 - 1.60 (m, 3 H) 2.09 (d, *J*=3.42 Hz, 1 H) 2.63 (dd, *J*=11.75, 10.25 Hz, 1 H) 2.94 (dd, *J*=11.86, 10.15 Hz, 1 H) 3.20 - 3.44 (m, 2 H) 3.71 - 3.89 (m, 2 H) 3.99 - 4.14 (m, 1 H) 7.10 (d, *J*=7.90 Hz, 1 H) 7.51 (dd, *J*=8.55, 4.27 Hz, 1 H) 8.04 (d, *J*=7.90 Hz, 1 H) 8.46 (dd, *J*=8.65, 1.82 Hz, 1 H) 9.07 (dd, *J*=4.06, 1.71 Hz, 1 H) | LCMS (ESI+) calcd for C20H25N3O2 (M+H+): 340.20, found: 340.18 |

FIG. 6K

| | | | | | | | |
|---|---|---|---|---|---|---|---|
| ER-886531 | 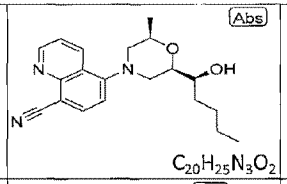 $C_{20}H_{25}N_3O_2$ | 339.4 | 0.1930 | >20 | 5-((2R,6R)-2-((S)-1-hydroxypentyl)-6-methylmorpholino)quinoline-8-carbonitrile | $^1$H NMR (400 MHz, CHLOROFORM-*d*) d ppm 0.82 - 0.97 (m, 3 H) 1.21 - 1.28 (m, 3 H) 1.29 - 1.48 (m, 3 H) 1.50 - 1.55 (m, 3 H) 2.59 - 2.70 (m, 1 H) 2.89 (dd, *J*=11.75, 10.47 Hz, 1 H) 3.21 - 3.34 (m, 2 H) 3.57 (m, 1 H) 3.72 - 3.86 (m, 1 H) 4.00 - 4.13 (m, 1 H) 7.05 - 7.15 (m, 1 H) 7.45 - 7.57 (m, 1 H) 7.99 - 8.10 (m, 1 H) 8.46 (dd, *J*=8.55, 1.71 Hz, 1 H) 9.04 - 9.17 (m, 1 H) | LCMS (ESI+) calcd for C20H25N3O2 (M+H+): 340.20, found: 340.26 |
| ER-886532 | 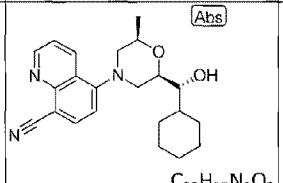 $C_{22}H_{27}N_3O_2$ | 365.5 | 0.0690 | >20 | 5-((2R,6R)-2-((R)-cyclohexyl(hydroxy)methyl)-6-methylmorpholino)quinoline-8-carbonitrile | $^1$H NMR (400 MHz, CHLOROFORM-*d*) d ppm 0.98 - 1.37 (m, 6 H) 1.27 (d, 3 H) 1.47-1.72 (m, 2 H) 1.73 - 1.85 (m, 2 H) 2.02 (m, 1 H) 2.27 (d, 1 H) 2.63 (dd, *J*=11.96, 10.25 Hz, 1 H) 2.91 - 3.03 (m, 1 H) 3.25 - 3.41 (m, 2 H) 3.56 (ddd, *J*=7.42, 4.54, 3.20 Hz, 1 H) 3.95 (ddd, *J*=10.31, 4.75, 2.24 Hz, 1 H) 4.01 - 4.17 (m, 1 H) 7.06 - 7.15 (m, 1 H) 7.46 - 7.56 (m, 1 H) 8.06 (d, *J*=8.12 Hz, 1 H) 8.41 - 8.52 (m, 1 H) 9.01 - 9.13 (m, 1 H) | LCMS (ESI+) calcd for C22H27N3O2 (M+H+): 366.21, found: 366.22 |
| ER-886533 | 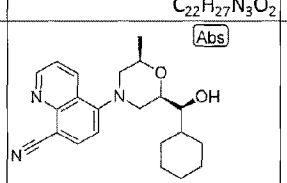 $C_{22}H_{27}N_3O_2$ | 365.5 | 0.0780 | >20 | 5-((2R,6R)-2-((S)-cyclohexyl(hydroxy)methyl)-6-methylmorpholino)quinoline-8-carbonitrile | $^1$H NMR (400 MHz, CHLOROFORM-*d*) d ppm 1.07 - 1.37 (m, 6 H) 1.28 (d, 3H) 1.41 - 1.56 (m, 1 H) 1.62 - 1.74 (m, 2 H) 1.79 (br. s., 2 H) 1.87 (d, *J*=8.33 Hz, 1 H) 2.28 (d, *J*=6.20 Hz, 1 H) 2.63 (dd, *J*=11.96, 10.25 Hz, 1 H) 2.98 (dd, *J*=11.54, 10.47 Hz, 1 H) 3.16 - 3.35 (m, 3 H) 3.96 (ddd, *J*=10.31, 4.65, 2.35 Hz, 1 H) 4.00 - 4.15 (m, 1 H) 7.05 - 7.15 (m, 1 H) 7.47 - 7.56 (m, 1 H) 8.06 (d, *J*=7.90 Hz, 1 H) 8.39 - 8.52 (m, 1 H) 9.00 - 9.15 (m, 1 H) | LCMS (ESI+) calcd for C22H27N3O2 (M+H+): 366.21, found: 366.24 |
| ER-886563 | 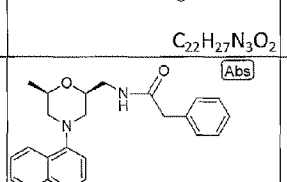 $C_{24}H_{24}N_4O_2$ | 400.5 | 0.2100 | >20 | N-(((2S,6R)-4-(8-cyanoquinolin-5-yl)-6-methylmorpholin-2-yl)methyl)-2-phenylacetamide | $^1$H NMR (400 MHz, CHLOROFORM-*d*) d ppm 1.14 (d, *J*=6.15 Hz, 3 H) 2.40 (br. s., 5 H) 2.48 (s, 1 H) 2.50 (s, 1 H) 2.53 (d, *J*=2.05 Hz, 1 H) 2.57 (d, *J*=11.43 Hz, 1 H) 3.18 - 3.24 (m, 3 H) 3.54 - 3.60 (m, 1 H) 3.64 (s, 2 H) 3.91 - 3.96 (m, 2 H) 5.99 (s, 1 H) 7.00 (s, 1 H) 7.02 (s, 1 H) 7.23 - 7.28 (m, 6 H) 7.31 - 7.38 (m, 2 H) 7.51 (dd, *J*=8.50, 4.39 Hz, 1 H) 8.01 (s, 1 H) 8.03 (s, 1 H) 8.40 (dd, *J*=8.50, 1.76 Hz, 1 H) 9.07 (dd, *J*=4.10, 1.76 Hz, 1 H) | |
| ER-886564 | 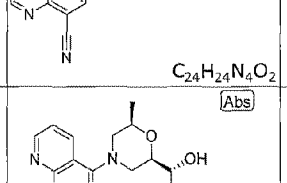 $C_{23}H_{23}N_3O_2$ | 373.5 | 0.1020 | | 5-((2R,6R)-2-((R)-1-hydroxy-2-phenylethyl)-6-methylmorpholino)quinoline-8-carbonitrile | $^1$H NMR (400 MHz, CHLOROFORM-*d*) d ppm 1.30 (d, *J*=6.41 Hz, 3 H) 2.38 (d, *J*=5.77 Hz, 1 H) 2.65 (dd, *J*=11.96, 10.25 Hz, 1 H) 2.84 - 2.94 (m, 1 H) 2.94 - 3.06 (m, 2 H) 3.15 - 3.33 (m, 2 H) 3.73 - 3.93 (m, 2 H) 3.95 - 4.12 (m, 1 H) 7.06 (d, *J*=8.12 Hz, 1 H) 7.23 - 7.29 (m, 3 H) 7.29 - 7.36 (m, 2 H) 7.49 (dd, *J*=8.55, 4.06 Hz, 1 H) 8.02 (d, *J*=7.90 Hz, 1 H) 8.38 (dd, *J*=8.55, 1.71 Hz, 1 H) 9.06 (dd, *J*=4.27, 1.71 Hz, 1 H) | LCMS (ESI+) calcd for C23H23N3O2 (M+H+): 374.18, found: 374.16 |

FIG. 6L

| | | | | | | | |
|---|---|---|---|---|---|---|---|
| ER-886565 | 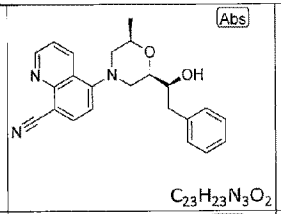 $C_{23}H_{23}N_3O_2$ | 373.5 | 0.0490 | > 2 | 5-((2R,6R)-2-((S)-1-hydroxy-2-phenylethyl)-6-methylmorpholino)quinoline-8-carbonitrile | $^1$H NMR (400 MHz, CHLOROFORM-*d*) d ppm 1.30 (d, *J*=6.41 Hz, 3 H) 2.38 (d, *J*=5.77 Hz, 1 H) 2.65 (dd, *J*=11.96, 10.25 Hz, 1 H) 2.84 - 2.94 (m, 1 H) 2.94 - 3.06 (m, 2 H) 3.15 - 3.33 (m, 2 H) 3.73 - 3.93 (m, 2 H) 3.95 - 4.12 (m, 1 H) 7.06 (d, *J*=8.12 Hz, 1 H) 7.23 - 7.29 (m, 3 H) 7.29 - 7.36 (m, 2 H) 7.49 (dd, *J*=8.55, 4.06 Hz, 1 H) 8.02 (d, *J*=7.90 Hz, 1 H) 8.38 (dd, *J*=8.55, 1.71 Hz, 1 H) 9.06 (dd, *J*=4.27, 1.71 Hz, 1 H) | LCMS (ESI+) calcd for C23H23N3O2 (M+H+): 374.18, found: 374.14 |
| ER-886567 | 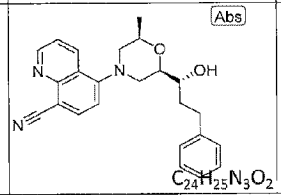 $C_{24}H_{25}N_3O_2$ | 387.5 | 0.0225 | >20 | 5-((2R,6R)-2-((R)-1-hydroxy-3-phenylpropyl)-6-methylmorpholino)quinoline-8-carbonitrile | $^1$H NMR (400 MHz, CHLOROFORM-*d*) d ppm 1.27 (d, 4 H) 1.72 - 1.93 (m, 2 H) 2.07 (d, *J*=3.42 Hz, 1 H) 2.56 - 2.79 (m, 2 H) 2.85 - 2.99 (m, 2 H) 3.21 - 3.39 (m, 2 H) 3.75 - 3.88 (m, 2 H) 4.05 (m, 1 H) 7.09 (d, *J*=8.12 Hz, 1 H) 7.15 - 7.38 (m, 5 H) 7.51 (dd, *J*=8.55, 4.27 Hz, 1 H) 8.05 (d, *J*=7.90 Hz, 1 H) 8.44 (dd, *J*=8.55, 1.71 Hz, 1 H) 9.08 (dd, *J*=4.27, 1.71 Hz, 1 H) | LCMS (ESI+) calcd for C24H25N3O2 (M+H+): 388.20, found: 388.17 |
| ER-886568 | 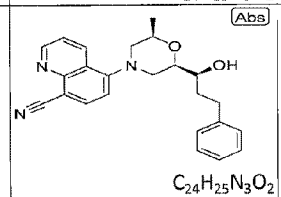 $C_{24}H_{25}N_3O_2$ | 387.5 | 0.0540 | >20 | 5-((2R,6R)-2-((S)-1-hydroxy-3-phenylpropyl)-6-methylmorpholino)quinoline-8-carbonitrile | $^1$H NMR (400 MHz, CHLOROFORM-*d*) d ppm 1.27 (d, 4 H) 1.70 - 1.99 (m, 2 H) 2.46 (d, *J*=5.34 Hz, 1 H) 2.63 (dd, *J*=11.86, 10.15 Hz, 1 H) 2.75 (ddd, *J*=13.62, 9.24, 7.05 Hz, 1 H) 2.82 - 3.00 (m, 2 H) 3.26 (ddt, *J*=18.08, 11.72, 2.08, 2.08 Hz, 2 H) 3.51 - 3.65 (m, 1 H) 3.73 - 3.89 (m, 1 H) 4.05 (ddd, *J*=10.15, 6.20, 2.24 Hz, 1 H) 7.01 - 7.14 (m, 1 H) 7.15 - 7.34 (m, 5 H) 7.47 - 7.59 (m, 1 H) 8.04 (d, *J*=7.90 Hz, 1 H) 8.38 - 8.48 (m, 1 H) 9.03 - 9.14 (m, 1 H) | LCMS (ESI+) calcd for C24H25N3O2 (M+H+): 388.20, found: 388.16 |
| ER-886601 | 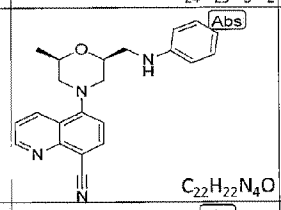 $C_{22}H_{22}N_4O$ | 358.4 | 0.0115 | >20 | 5-((2R,6S)-2-methyl-6-((phenylamino)methyl)morpholino)quinoline-8-carbonitrile | $^1$H NMR (400 MHz, METHANOL-$d_4$) d ppm 1.24 (d, *J*=6.15 Hz, 5 H) 2.62 (s, 1 H) 2.65 (d, *J*=1.76 Hz, 1 H) 2.67 (s, 1 H) 2.72 (s, 1 H) 2.74 (s, 1 H) 2.77 (s, 1 H) 3.24 (d, *J*=5.27 Hz, 3 H) 3.34 (s, 1 H) 3.37 (s, 1 H) 3.46 (s, 1 H) 3.48 (s, 1 H) 4.12 (s, 1 H) 6.59 - 6.67 (m, 3 H) 7.09 (dd, *J*=8.79, 7.32 Hz, 2 H) 7.20 (d, *J*=8.20 Hz, 1 H) 7.53 - 7.57 (m, 1 H) 8.09 (s, 1 H) 8.11 (s, 1 H) 8.52 - 8.55 (m, 1 H) 8.92 (dd, *J*=4.39, 1.76 Hz, 1 H) | |
| ER-886602 | 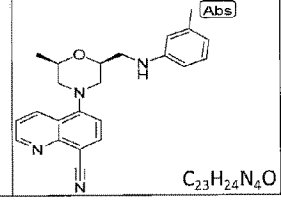 $C_{23}H_{24}N_4O$ | 372.5 | 0.1850 | >20 | 5-((2R,6S)-2-methyl-6-((m-tolylamino)methyl)morpholino)quinoline-8-carbonitrile | $^1$H NMR (400 MHz, METHANOL-$d_4$) d ppm 1.32 (d, *J*=6.15 Hz, 4 H) 2.39 (s, 3 H) 2.66 - 2.80 (m, 2 H) 3.36 - 3.42 (m, 2 H) 3.49 - 3.56 (m, 2 H) 4.06 - 4.18 (m, 2 H) 7.19 - 7.27 (m, 4 H) 7.38 - 7.42 (m, 1 H) 7.56 - 7.60 (m, 1 H) 8.12 (d, *J*=8.20 Hz, 1 H) 8.55 - 8.58 (m, 1 H) 8.94 (dd, *J*=4.39, 1.76 Hz, 1 H) | |

FIG. 6M

| | | | | | | | |
|---|---|---|---|---|---|---|---|
| ER-886603 | 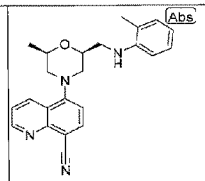 $C_{23}H_{24}N_4O$ | 372.5 | 0.0110 | >20 | 5-((2R,6S)-2-methyl-6-((o-tolylamino)methyl)morpholino)quinoline-8-carbonitrile | $^1$H NMR (400 MHz, METHANOL-$d_4$) d ppm 1.32 (d, $J$=5.57 Hz, 4 H) 2.39 (s, 3 H) 2.68 (d, $J$=12.01 Hz, 1 H) 2.74 (d, $J$=13.48 Hz, 1 H) 2.78 (s, 1 H) 2.81 (s, 1 H) 3.38 - 3.45 (m, 4 H) 3.53 (d, $J$=3.22 Hz, 1 H) 3.57 (d, $J$=3.52 Hz, 1 H) 4.09 (d, $J$=4.69 Hz, 1 H) 4.17 (s, 1 H) 4.85 (s, 9 H) 7.20 - 7.25 (m, 3 H) 7.28 - 7.33 (m, 2 H) 7.57 - 7.60 (m, 1 H) 8.12 (d, $J$=7.32 Hz, 1 H) 8.57 (d, $J$=8.50 Hz, 1 H) 8.94 (d, $J$=4.39 Hz, 1 H) | |
| ER-886604 | 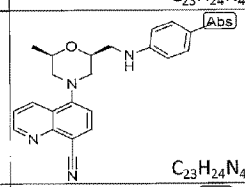 $C_{23}H_{24}N_4O$ | 372.5 | 0.0860 | >20 | 5-((2R,6S)-2-methyl-6-((p-tolylamino)methyl)morpholino)quinoline-8-carbonitrile | $^1$H NMR (400 MHz, METHANOL-$d_4$) d ppm 1.33 (d, $J$=6.15 Hz, 4 H) 2.38 (s, 4 H) 2.66 - 2.80 (m, 3 H) 3.34 - 3.41 (m, 2 H) 3.47 - 3.57 (m, 3 H) 4.04 - 4.16 (m, 2 H) 7.23 (d, $J$=8.20 Hz, 1 H) 7.34 - 7.40 (m, 4 H) 7.56 - 7.60 (m, 1 H) 8.11 (d, $J$=8.20 Hz, 1 H) 8.56 (dd, $J$=8.50, 1.76 Hz, 1 H) 8.92 - 8.94 (m, 1 H) | |
| ER-886605 | 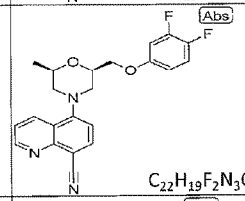 $C_{22}H_{19}F_2N_3O_2$ | 395.4 | 0.0220 | | 5-((2R,6R)-2-((3,4-difluorophenoxy)methyl)-6-methylmorpholino)quinoline-8-carbonitrile | $^1$H NMR (400 MHz, METHANOL-$d_4$) d ppm 1.23 (d, $J$=6.45 Hz, 4 H) 2.66 (dd, $J$=11.72, 10.25 Hz, 1 H) 2.88 (dd, $J$=11.72, 10.55 Hz, 1 H) 3.39 (s, 1 H) 3.36 (s, 1 H) 3.49 (s, 1 H) 3.46 (s, 1 H) 3.99 - 4.13 (m, 4 H) 4.25 - 4.31 (m, 1 H) 4.82 - 4.86 (m, 4 H) 6.68 - 6.74 (m, 1 H) 6.85 - 6.91 (m, 1 H) 7.08 - 7.16 (m, 1 H) 7.24 (d, $J$=8.20 Hz, 1 H) 7.59 - 7.63 (m, 1 H) 8.12 (d, $J$=7.91 Hz, 1 H) 8.61 - 8.65 (m, 1 H) 8.94 (dd, $J$=4.39, 1.76 Hz, 1 H) | |
| ER-886606 | 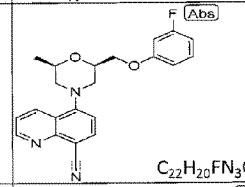 $C_{22}H_{20}FN_3O_2$ | 377.4 | 0.0030 | >20 | 5-((2R,6R)-2-((3-fluorophenoxy)methyl)-6-methylmorpholino)quinoline-8-carbonitrile | 1H NMR (400 MHz, METHANOL-d4) d ppm 1.24 (3 H, d) 2.68 (1 H, t) 2.88 (1 H, t) 3.38 (1 H, d) 3.49 (1 H, d) 3.99 - 4.14 (3 H, m) 4.25 - 4.36 (1 H, m) 6.59 - 6.80 (3 H, m) 7.17 - 7.30 (2 H, m) 7.58 - 7.65 (1 H, m) 8.08 - 8.18 (1 H, m) 8.58 - 8.69 (1 H, m) 8.90 - 8.99 (1 H, m) | LCMS (ESI+) calcd for C22 H20 F N3 O2 (M+H+) 378.4, found 378.5 |
| ER-886608 | 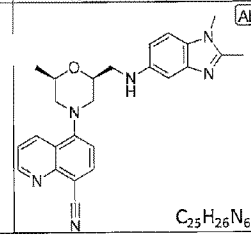 $C_{25}H_{26}N_6O$ | 426.5 | 0.0130 | 3.366 | 5-((2S,6R)-2-(((1,2-dimethyl-1H-benzo[d]imidazol-5-yl)amino)methyl)-6-methylmorpholino)quinoline-8-carbonitrile | $^1$H NMR (400 MHz, METHANOL-$d_4$) d ppm 1.24 (d, $J$=6.15 Hz, 4 H) 2.62 - 2.68 (m, 1 H) 2.72 (s, 3 H) 2.77 - 2.84 (m, 1 H) 3.29 - 3.39 (m, 4 H) 3.46 (d, $J$=12.01 Hz, 1 H) 3.86 (s, 3 H) 4.08 (d, $J$=6.74 Hz, 1 H) 4.16 (d, $J$=7.62 Hz, 1 H) 4.80 (s, 1 H) 6.78 (d, $J$=2.05 Hz, 1 H) 6.95 - 6.98 (m, 1 H) 7.22 (d, $J$=8.20 Hz, 1 H) 7.49 (d, $J$=8.79 Hz, 1 H) 7.55 - 7.58 (m, 1 H) 8.11 (d, $J$=7.91 Hz, 1 H) 8.56 - 8.59 (m, 1 H) 8.92 - 8.94 (m, 1 H) | |

FIG. 6N

| | | | | | | | |
|---|---|---|---|---|---|---|---|
| ER-886609 | 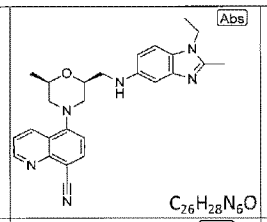 $C_{26}H_{28}N_6O$ | 440.6 | 0.0120 | 6.929 | 5-((2S,6R)-2-(((1-ethyl-2-methyl-1H-benzo[d]imidazol-5-yl)amino)methyl)-6-methylmorpholino)quinoline-8-carbonitrile | | |
| ER-886611 | 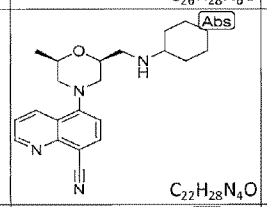 $C_{22}H_{28}N_4O$ | 364.5 | 0.1070 | 8.112 | 5-((2S,6R)-2-((cyclohexylamino)methyl)-6-methylmorpholino)quinoline-8-carbonitrile | $^1$H NMR (400 MHz, METHANOL-$d_4$) d ppm 1.26 - 1.28 (m, 3 H) 1.31 - 1.40 (m, 4 H) 1.70 (d, $J$=12.89 Hz, 1 H) 1.87 (d, $J$=8.20 Hz, 2 H) 2.11 (br. s., 2 H) 2.64 - 2.71 (m, 1 H) 2.73 - 2.77 (m, 1 H) 3.07 - 3.15 (m, 2 H) 3.22 (br. s., 1 H) 3.41 (s, 1 H) 3.38 (s, 1 H) 4.09 - 4.13 (m, 1 H) 4.22 (t, $J$=9.96 Hz, 1 H) 4.84 - 4.85 (m, 8 H) 7.24 (dd, $J$=7.91, 2.34 Hz, 1 H) 7.59 - 7.63 (m, 1 H) 8.12 - 8.15 (m, 1 H) 8.59 - 8.63 (m, 1 H) 8.95 - 8.97 (m, 1 H) | |
| ER-886624 | 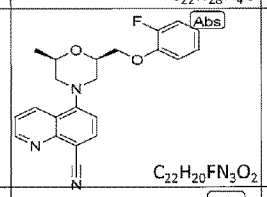 $C_{22}H_{20}FN_3O_2$ | 377.4 | 0.0027 | >20 | 5-((2R,6R)-2-((2-fluorophenoxy)methyl)-6-methylmorpholino)quinoline-8-carbonitrile | $^1$H NMR (400 MHz, METHANOL-$d_4$) d ppm 1.24 (dd, $J$=6.15, 0.88 Hz, 5 H) 2.67 (d, $J$=10.84 Hz, 1 H) 2.87 - 2.90 (m, 1 H) 2.92 (s, 1 H) 3.37 (s, 1 H) 3.40 (s, 1 H) 3.53 (s, 1 H) 3.56 (s, 1 H) 4.06 - 4.10 (m, 1 H) 4.16 - 4.20 (m, 1 H) 4.83 - 4.85 (m, 17 H) 7.03 - 7.11 (m, 3 H) 7.24 (s, 1 H) 7.26 (s, 1 H) 7.60 - 7.63 (m, 1 H) 8.12 (d, $J$=0.88 Hz, 1 H) 8.14 (d, $J$=0.88 Hz, 1 H) 8.63 (s, 1 H) 8.65 (s, 1 H) 8.94 - 8.96 (m, 1 H) | |
| ER-886625 | 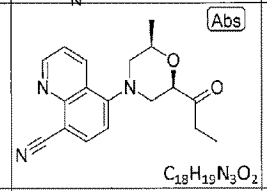 $C_{18}H_{19}N_3O_2$ | 309.4 | 0.1570 | >20 | 5-((2R,6R)-2-methyl-6-propionylmorpholino)quinoline-8-carbonitrile | $^1$H NMR (400 MHz, CHLOROFORM-$d$) d ppm 1.02 - 1.16 (m, 3 H) 1.33 (d, $J$=6.20 Hz, 3 H) 2.58 - 2.86 (m, 5 H) 3.30 (dt, $J$=11.96, 2.14 Hz, 1 H) 3.62 (dt, $J$=12.02, 2.43 Hz, 1 H) 4.01 - 4.16 (m, 1 H) 4.37 (dd, $J$=10.58, 2.67 Hz, 1 H) 7.10 (d, $J$=8.12 Hz, 1 H) 7.53 (dd, $J$=8.65, 4.17 Hz, 1 H) 8.04 (d, $J$=7.90 Hz, 1 H) 8.46 (dd, $J$=8.65, 1.82 Hz, 1 H) 9.08 (dd, $J$=4.06, 1.71 Hz, 1 H) | LCMS (ESI+) calcd for C18H19N3O2 (M+H+): 310.15, found: 310.14 |
| ER-886626 | 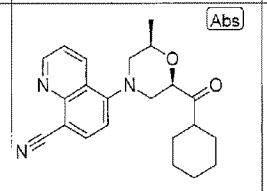 $C_{22}H_{25}N_3O_2$ | 363.5 | 0.0730 | >20 | 5-((2R,6R)-2-(cyclohexanecarbonyl)-6-methylmorpholino)quinoline-8-carbonitrile | $^1$H NMR (400 MHz, CHLOROFORM-$d$) d ppm 1.15 - 1.44 (m, 9 H) 1.71 (d, $J$=11.54 Hz, 1 H) 1.75 - 1.90 (m, 2 H) 1.90 - 2.03 (m, 1 H) 2.68 (dd, $J$=11.96, 10.25 Hz, 1 H) 2.79 (dd, $J$=12.18, 10.68 Hz, 1 H) 2.90 - 3.11 (m, 1 H) 3.31 (dt, $J$=11.91, 2.06 Hz, 1 H) 3.61 (dt, $J$=12.07, 2.30 Hz, 1 H) 4.08 (ddd, $J$=10.15, 6.30, 2.14 Hz, 1 H) 4.44 (dd, $J$=10.58, 2.67 Hz, 1 H) 7.11 (d, $J$=7.90 Hz, 1 H) 7.53 (dd, $J$=8.55, 4.27 Hz, 1 H) 8.06 (d, $J$=7.90 Hz, 1 H) 8.46 (dd, $J$=8.55, 1.71 Hz, 1 H) 9.09 (dd, $J$=4.27, 1.71 Hz, 1 H) | LCMS (ESI+) calcd for C22H25N3O2 (M+H+): 364.20, found: 365.32 |

FIG. 6O

| | | | | | | | |
|---|---|---|---|---|---|---|---|
| ER-886629 | 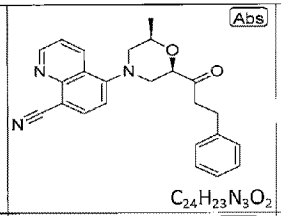 $C_{24}H_{23}N_3O_2$ | 385.5 | 0.1930 | >20 | 5-((2R,6R)-2-methyl-6-(3-phenylpropanoyl)morpholino)quinoline-8-carbonitrile | $^1$H NMR (400 MHz, CHLOROFORM-*d*) d ppm 1.32 (d, *J*=6.41 Hz, 3 H) 2.56 - 2.79 (m, 2 H) 2.88 - 2.98 (m, 2 H) 3.01 - 3.12 (m, 2 H) 3.29 (dt, *J*=11.96, 2.14 Hz, 1 H) 3.58 (dt, *J*=11.96, 2.35 Hz, 1 H) 3.97 - 4.15 (m, 1 H) 4.35 (dd, *J*=10.47, 2.78 Hz, 1 H) 7.07 (d, *J*=7.90 Hz, 1 H) 7.15 - 7.38 (m, 5 H) 7.53 (dd, *J*=8.55, 4.27 Hz, 1 H) 8.05 (d, *J*=7.90 Hz, 1 H) 8.44 (dd, *J*=8.65, 1.82 Hz, 1 H) 9.09 (dd, *J*=4.27, 1.71 Hz, 1 H) | LCMS (ESI+) calcd for C24H23N3O2 (M+H+): 386.18, found: 386.15 |
| ER-886786 | 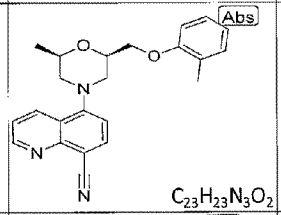 $C_{23}H_{23}N_3O_2$ | 373.5 | 0.0090 | >2.0 | 5-((2R,6R)-2-methyl-6-((o-tolyloxy)methyl)morpholino)quinoline-8-carbonitrile | $^1$H NMR (400 MHz, CHLOROFORM-*d*) d ppm 1.29 (d, *J*=6.15 Hz, 4 H) 1.99 (s, 1 H) 2.03 - 2.13 (m, 2 H) 2.17 (s, 4 H) 2.72 (dd, *J*=11.72, 10.25 Hz, 1 H) 2.82 - 2.88 (m, 1 H) 3.30 - 3.34 (m, 1 H) 3.61 - 3.65 (m, 1 H) 3.93 - 3.98 (m, 1 H) 4.07 - 4.14 (m, 1 H) 4.17 - 4.21 (m, 1 H) 4.30 - 4.37 (m, 1 H) 6.80 - 6.88 (m, 2 H) 7.07 - 7.16 (m, 3 H) 7.24 (s, 1 H) 7.48 - 7.52 (m, 1 H) 8.04 (d, *J*=7.91 Hz, 1 H) 8.48 (dd, *J*=8.50, 1.76 Hz, 1 H) 9.07 (dd, *J*=4.39, 1.76 Hz, 1 H) | |
| ER-886787 | 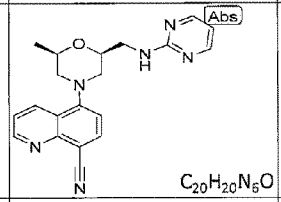 $C_{20}H_{20}N_6O$ | 360.4 | 0.0229 | >2.0 | 5-((2R,6S)-2-methyl-6-((pyrimidin-2-ylamino)methyl)morpholino)quinoline-8-carbonitrile | | |
| ER-886788 | 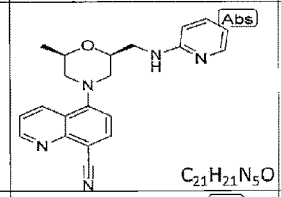 $C_{21}H_{21}N_5O$ | 359.4 | 0.0060 | >2.0 | 5-((2R,6S)-2-methyl-6-((pyridin-2-ylamino)methyl)morpholino)quinoline-8-carbonitrile | | |
| ER-886789 | 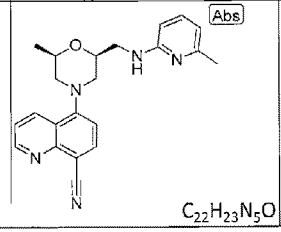 $C_{22}H_{23}N_5O$ | 373.5 | 0.0070 | >2.0 | 5-((2R,6S)-2-methyl-6-(((6-methylpyridin-2-yl)amino)methyl)morpholino)quinoline-8-carbonitrile | $^1$H NMR (400 MHz, METHANOL-$d_4$) d ppm 1.15 (d, *J*=6.15 Hz, 7 H) 2.66 - 2.71 (m, 9 H) 2.94 (d, *J*=11.72 Hz, 1 H) 3.31 (s, 1 H) 4.84 - 4.85 (m, 61 H) 6.83 (d, *J*=6.74 Hz, 1 H) 6.96 (d, *J*=8.20 Hz, 1 H) 7.28 (s, 1 H) 7.30 (s, 1 H) 7.61 - 7.65 (m, 2 H) 7.73 (d, *J*=8.79 Hz, 1 H) 8.15 (s, 1 H) 8.17 (s, 1 H) 8.65 (s, 1 H) 8.67 (s, 1 H) 8.97 (d, *J*=2.64 Hz, 1 H) | |

FIG. 6P

| | | | | | | | |
|---|---|---|---|---|---|---|---|
| ER-886790 | 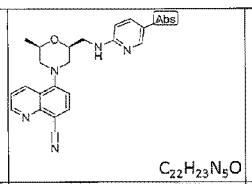 $C_{22}H_{23}N_5O$ | 373.5 | 0.0085 | >2.0 | 5-((2R,6S)-2-methyl-6-(((5-methylpyridin-2-yl)amino)methyl)morpholino)quinoline-8-carbonitrile | | |
| ER-886814 | 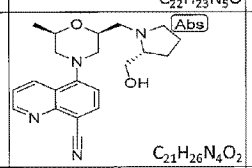 $C_{21}H_{26}N_4O_2$ | 366.5 | 0.0720 | >2.0 | 5-((2S,6R)-2-(((R)-2-(hydroxymethyl)pyrrolidin-1-yl)methyl)-6-methylmorpholino)quinoline-8-carbonitrile | | |
| ER-886815 | 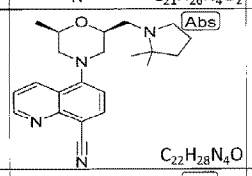 $C_{22}H_{28}N_4O$ | 364.5 | 0.3950 | >2.0 | 5-((2R,6R)-2-((2,2-dimethylpyrrolidin-1-yl)methyl)-6-methylmorpholino)quinoline-8-carbonitrile | | |
| ER-886816 | 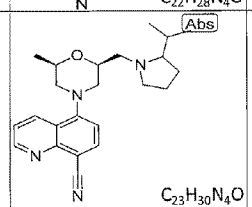 $C_{23}H_{30}N_4O$ | 378.5 | 0.1970 | >2.0 | 5-((2S,6R)-2-((2-isopropylpyrrolidin-1-yl)methyl)-6-methylmorpholino)quinoline-8-carbonitrile | $^1$H NMR (400 MHz, METHANOL-$d_4$) d ppm 1.02 - 1.17 (m, 7 H) 1.28 - 1.34 (m, 4 H) 1.86 - 1.96 (m, 1 H) 2.04 - 2.28 (m, 4 H) 2.68 - 2.80 (m, 2 H) 3.26 - 3.51 (m, 8 H) 3.52 - 3.60 (m, 1 H) 3.73 - 3.81 (m, 1 H) 4.11 - 4.21 (m, 1 H) 4.35 - 4.44 (m, 1 H) 4.85 - 4.91 (m, 8 H) 7.23 - 7.28 (m, 1 H) 7.65 (dd, $J$=8.50, 4.10 Hz, 1 H) 8.15 (d, $J$=7.62 Hz, 1 H) 8.64 - 8.69 (m, 1 H) 8.98 (dd, $J$=4.10, 1.46 Hz, 1 H) | |
| ER-886817 | 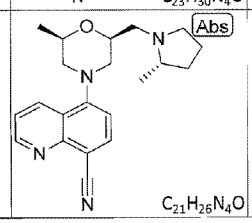 $C_{21}H_{26}N_4O$ | 350.5 | 0.0600 | >2.0 | 5-((2R,6S)-2-methyl-6-(((S)-2-methylpyrrolidin-1-yl)methyl)morpholino)quinoline-8-carbonitrile | $^1$H NMR (400 MHz, METHANOL-$d_4$) d ppm 1.26 - 1.34 (m, 4 H) 1.48 (d, $J$=6.74 Hz, 3 H) 1.71 - 1.77 (m, 1 H) 1.98 - 2.14 (m, 3 H) 2.29 - 2.38 (m, 2 H) 2.67 - 2.81 (m, 4 H) 3.19 - 3.26 (m, 1 H) 3.33 (s, 1 H) 3.38 - 3.46 (m, 4 H) 3.52 (dd, $J$=13.48, 2.34 Hz, 1 H) 3.61 - 3.68 (m, 1 H) 3.81 - 3.88 (m, 1 H) 4.11 - 4.17 (m, 1 H) 4.32 - 4.39 (m, 1 H) 7.26 (d, $J$=7.91 Hz, 1 H) 7.61 - 7.65 (m, 1 H) 8.15 (d, $J$=7.91 Hz, 1 H) 8.63 - 8.67 (m, 1 H) 8.95 - 8.98 (m, 1 H) | |

FIG. 6Q

| | | | | | | | |
|---|---|---|---|---|---|---|---|
| ER-886818 | 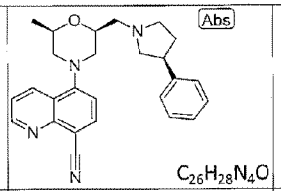 $C_{26}H_{28}N_4O$ | 412.5 | 0.0800 | >2.0 | 5-((2R,6S)-2-methyl-6-(((S)-3-phenylpyrrolidin-1-yl)methyl)morpholino)quinoline-8-carbonitrile | $^1$H NMR (400 MHz, METHANOL-$d_4$) d ppm 1.08 - 1.25 (m, 4 H) 1.30 (d, $J$=6.15 Hz, 4 H) 1.73 - 1.78 (m, 1 H) 2.66 - 2.82 (m, 3 H) 3.32 - 3.48 (m, 6 H) 4.02 - 4.24 (m, 1 H) 4.24 - 4.40 (m, 1 H) 7.26 (d, $J$=8.20 Hz, 1 H) 7.63 (dd, $J$=8.50, 4.39 Hz, 1 H) 8.06 - 8.23 (m, 1 H) 8.57 - 8.73 (m, 1 H) 8.97 (dd, $J$=4.39, 1.76 Hz, 1 H) | |
| ER-886819 | 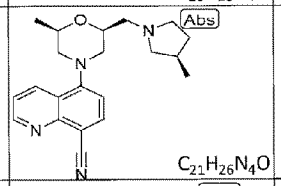 $C_{21}H_{26}N_4O$ | 350.5 | 0.0360 | >2.0 | 5-((2R,6S)-2-methyl-6-(((R)-3-methylpyrrolidin-1-yl)methyl)morpholino)quinoline-8-carbonitrile | | |
| ER-886820 | 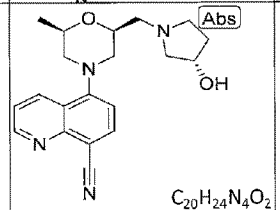 $C_{20}H_{24}N_4O_2$ | 352.4 | 0.0626 | >2.0 | 5-((2S,6R)-2-(((S)-3-hydroxypyrrolidin-1-yl)methyl)-6-methylmorpholino)quinoline-8-carbonitrile | $^1$H NMR (400 MHz, METHANOL-$d_4$) d ppm 1.28 (d, $J$=6.15 Hz, 4 H) 1.96 - 2.07 (m, 1 H) 2.12 (d, $J$=4.39 Hz, 1 H) 2.32 (t, $J$=8.20 Hz, 1 H) 2.64 - 2.79 (m, 4 H) 3.20 (d, $J$=12.31 Hz, 1 H) 3.29 - 3.54 (m, 7 H) 3.58 (d, $J$=11.72 Hz, 1 H) 3.75 - 3.89 (m, 2 H) 4.09 - 4.17 (m, 1 H) 4.35 (br. s., 1 H) 4.55 (d, $J$=15.23 Hz, 1 H) 4.81 - 4.87 (m, 7 H) 7.22 (d, $J$=8.20 Hz, 1 H) 7.57 - 7.62 (m, 1 H) 8.11 (d, $J$=7.91 Hz, 1 H) 8.61 (d, $J$=8.50 Hz, 1 H) 8.91 - 8.95 (m, 1 H) | |
| ER-886853 | 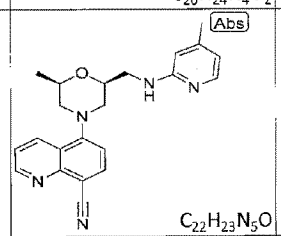 $C_{22}H_{23}N_5O$ | 373.5 | 0.0040 | >2 | 5-((2R,6S)-2-methyl-6-(((4-methylpyridin-2-yl)amino)methyl)morpholino)quinoline-8-carbonitrile | $^1$H NMR (400 MHz, METHANOL-$d_4$) d ppm 1.13 - 1.21 (m, 3 H) 2.34 - 2.39 (m, 3 H) 2.67 (dd, $J$=12.01, 10.25 Hz, 1 H) 2.76 - 2.83 (m, 1 H) 3.36 (d, $J$=12.01 Hz, 1 H) 3.53 (d, $J$=11.72 Hz, 1 H) 3.99 (ddd, $J$=10.25, 6.15, 2.34 Hz, 1 H) 4.21 - 4.37 (m, 3 H) 4.82 - 4.86 (m, 5 H) 6.76 (dd, $J$=7.03, 1.76 Hz, 1 H) 6.86 (s, 1 H) 7.22 - 7.27 (m, 1 H) 7.58 - 7.63 (m, 1 H) 7.79 (d, $J$=7.03 Hz, 1 H) 8.10 - 8.14 (m, 1 H) 8.60 - 8.65 (m, 1 H) 8.92 - 8.96 (m, 1 H) | |
| ER-886854 | 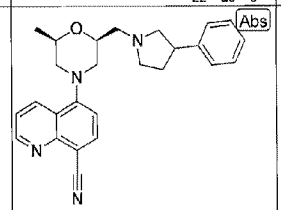 $C_{26}H_{28}N_4O$ | 412.5 | 0.0190 | >2 | 5-((2R,6S)-2-methyl-6-((3-phenylpyrrolidin-1-yl)methyl)morpholino)quinoline-8-carbonitrile | $^1$H NMR (400 MHz, METHANOL-$d_4$) d ppm 1.25 - 1.31 (m, 4 H) 2.50 - 2.53 (m, 1 H) 2.65 - 2.78 (m, 2 H) 3.24 (br. s., 1 H) 3.29 - 3.32 (m, 1 H) 3.41 (s, 1 H) 3.38 (s, 1 H) 3.44 - 3.54 (m, 3 H) 3.54 - 3.64 (m, 1 H) 3.73 (br. s., 1 H) 3.82 - 3.96 (m, 1 H) 3.99 - 4.09 (m, 1 H) 4.15 (br. s., 1 H) 4.37 (br. s., 1 H) 4.81 - 4.85 (m, 5 H) 7.22 - 7.31 (m, 2 H) 7.31 - 7.37 (m, 4 H) 7.61 (d, $J$=4.10 Hz, 1 H) 8.13 (d, $J$=7.91 Hz, 1 H) 8.60 - 8.65 (m, 1 H) 8.95 (br. s., 1 H) | |

FIG. 6R

| | | | | | | | |
|---|---|---|---|---|---|---|---|
| ER-886855 | 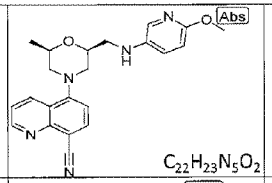 $C_{22}H_{23}N_5O_2$ | 389.5 | 0.0260 | >2 | 5-((2S,6R)-2-(((6-methoxypyridin-3-yl)amino)methyl)-6-methylmorpholino)quinoline-8-carbonitrile | $^1$H NMR (400 MHz, METHANOL-$d_4$) d ppm 1.21 - 1.26 (m, 3 H) 2.60 - 2.67 (m, 1 H) 2.76 - 2.83 (m, 1 H) 3.29 - 3.43 (m, 5 H) 3.99 - 4.17 (m, 5 H) 4.83 - 4.87 (m, 5 H) 7.18 - 7.23 (m, 2 H) 7.59 (dd, $J$=8.50, 4.39 Hz, 1 H) 7.68 (d, $J$=2.64 Hz, 1 H) 7.76 - 7.81 (m, 1 H) 8.08 - 8.12 (m, 1 H) 8.56 - 8.61 (m, 1 H) 8.86 - 8.99 (m, 1 H) | |
| ER-886856 | 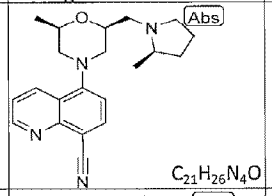 $C_{21}H_{26}N_4O$ | 350.5 | 0.0760 | >2 | 5-((2R,6S)-2-methyl-6-(((R)-2-methylpyrrolidin-1-yl)methyl)morpholino)quinoline-8-carbonitrile | $^1$H NMR (400 MHz, METHANOL-$d_4$) d ppm 1.19 - 1.37 (m, 4 H) 1.37 - 1.53 (m, 3 H) 1.67 - 1.85 (m, 1 H) 2.01 - 2.20 (m, 2 H) 2.20 - 2.39 (m, 1 H) 2.58 - 2.86 (m, 3 H) 3.14 (d, $J$=12.89 Hz, 1 H) 3.33 - 3.59 (m, 5 H) 3.69 - 3.90 (m, 1 H) 4.04 - 4.22 (m, 1 H) 4.34 (t, $J$=10.25 Hz, 1 H) 7.14 - 7.30 (m, 1 H) 7.61 (ddd, $J$=8.50, 4.39, 0.88 Hz, 1 H) 8.12 (dd, $J$=8.20, 0.88 Hz, 1 H) 8.63 (dd, $J$=8.50, 1.46 Hz, 1 H) 8.86 - 9.07 (m, 1 H) | |
| ER-886857 | 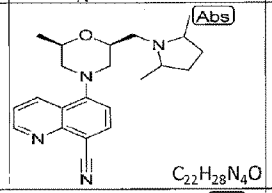 $C_{22}H_{28}N_4O$ | 364.5 | 0.1030 | >2 | 5-((2S,6R)-2-((2,5-dimethylpyrrolidin-1-yl)methyl)-6-methylmorpholino)quinoline-8-carbonitrile | $^1$H NMR (400 MHz, METHANOL-$d_4$) d ppm 1.21 - 1.30 (m, 4 H) 1.34 - 1.37 (m, 1 H) 1.46 - 1.51 (m, 5 H) 1.73 - 1.86 (m, 2 H) 2.23 - 2.32 (m, 2 H) 2.60 - 2.79 (m, 2 H) 3.24 - 3.45 (m, 6 H) 3.54 - 3.66 (m, 1 H) 3.69 - 3.84 (m, 2 H) 4.04 - 4.17 (m, 1 H) 4.33 - 4.41 (m, 1 H) 4.86 (s, 4 H) 7.19 - 7.25 (m, 1 H) 7.58 - 7.63 (m, 1 H) 8.09 - 8.13 (m, 1 H) 8.60 - 8.65 (m, 1 H) 8.92 - 8.96 (m, 1 H) | |
| ER-886858 | 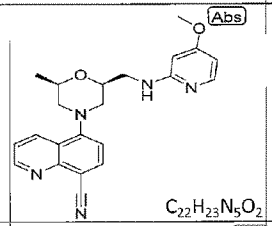 $C_{22}H_{23}N_5O_2$ | 389.5 | 0.0080 | >2 | 5-((2S,6R)-2-(((4-methoxypyridin-2-yl)amino)methyl)-6-methylmorpholino)quinoline-8-carbonitrile | $^1$H NMR (400 MHz, METHANOL-$d_4$) d ppm 1.15 - 1.22 (m, 3 H) 2.65 (d, $J$=10.55 Hz, 1 H) 2.69 (s, 1 H) 2.75 - 2.82 (m, 1 H) 3.37 (s, 1 H) 3.34 (s, 1 H) 3.52 (d, $J$=11.43 Hz, 1 H) 3.92 - 4.02 (m, 4 H) 4.16 - 4.23 (m, 1 H) 4.26 - 4.34 (m, 2 H) 6.42 (d, $J$=2.64 Hz, 1 H) 6.53 - 6.56 (m, 1 H) 7.23 - 7.27 (m, 1 H) 7.59 - 7.70 (m, 1 H) 7.79 (d, $J$=7.62 Hz, 1 H) 8.11 - 8.15 (m, 1 H) 8.61 - 8.65 (m, 1 H) 8.94 - 8.97 (m, 1 H) | |
| ER-886859 | 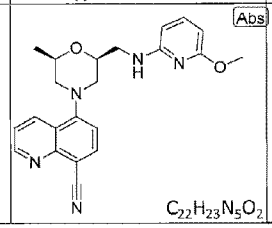 $C_{22}H_{23}N_5O_2$ | 389.5 | 0.0810 | >2 | 5-((2S,6R)-2-(((6-methoxypyridin-2-yl)amino)methyl)-6-methylmorpholino)quinoline-8-carbonitrile | $^1$H NMR (400 MHz, METHANOL-$d_4$) d ppm 1.21 - 1.25 (m, 3 H) 2.66 (dd, $J$=12.01, 10.25 Hz, 1 H) 2.76 - 2.82 (m, 1 H) 3.34 - 3.51 (m, 3 H) 3.56 (d, $J$=3.81 Hz, 1 H) 3.59 (d, $J$=3.81 Hz, 1 H) 3.96 - 3.98 (m, 3 H) 4.07 - 4.12 (m, 1 H) 4.18 (dd, $J$=6.74, 4.39 Hz, 1 H) 4.83 - 4.85 (m, 7 H) 6.27 (d, $J$=7.91 Hz, 1 H) 6.52 (d, $J$=8.50 Hz, 1 H) 7.23 (d, $J$=7.91 Hz, 1 H) 7.58 - 7.62 (m, 1 H) 7.74 - 7.79 (m, 1 H) 8.12 (d, $J$=7.91 Hz, 1 H) 8.61 (dd, $J$=8.50, 1.76 Hz, 1 H) 8.95 (dd, $J$=4.10, 1.76 Hz, 1 H) | |

FIG. 6S

| | | | | | | | |
|---|---|---|---|---|---|---|---|
| ER-886860 | 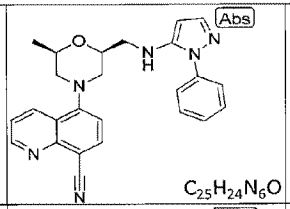 $C_{25}H_{24}N_6O$ | 424.5 | 0.3280 | >2 | 5-((2R,6S)-2-methyl-6-(((1-phenyl-1H-pyrazol-5-yl)amino)methyl)morpholino)quinoline-8-carbonitrile | $^1$H NMR (400 MHz, METHANOL-$d_4$) d ppm 1.23 (d, $J$=6.45 Hz, 3 H) 2.52 - 2.59 (m, 1 H) 3.13 (s, 1 H) 3.16 (s, 1 H) 3.32 - 3.35 (m, 1 H) 3.98 - 4.08 (m, 3 H) 4.85 - 4.87 (m, 12 H) 6.02 (d, $J$=3.52 Hz, 1 H) 7.17 (d, $J$=7.91 Hz, 1 H) 7.58 - 7.63 (m, 2 H) 7.72 - 7.76 (m, 2 H) 8.11 (d, $J$=7.91 Hz, 1 H) 8.19 (d, $J$=3.52 Hz, 1 H) 8.50 (dd, $J$=8.50, 1.76 Hz, 1 H) 8.97 (dd, $J$=4.39, 1.76 Hz, 1 H) | |
| ER-886866 | 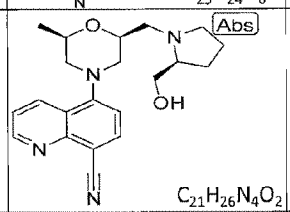 $C_{21}H_{26}N_4O_2$ | 366.5 | 0.1160 | >2 | 5-((2S,6R)-2-(((S)-2-(hydroxymethyl)pyrrolidin-1-yl)methyl)-6-methylmorpholino)quinoline-8-carbonitrile | $^1$H NMR (400 MHz, METHANOL-$d_4$) d ppm 1.25 - 1.29 (m, 3 H) 1.85 - 1.94 (m, 1 H) 2.00 - 2.26 (m, 3 H) 2.64 - 2.77 (m, 2 H) 3.26 - 3.40 (m, 14 H) 3.59 - 3.71 (m, 2 H) 3.74 - 3.83 (m, 2 H) 3.87 - 3.92 (m, 1 H) 4.09 - 4.17 (m, 1 H) 4.32 - 4.39 (m, 1 H) 4.82 (s, 1 H) 4.87 (d, $J$=0.88 Hz, 11 H) 7.20 - 7.24 (m, 1 H) 7.58 - 7.62 (m, 1 H) 8.08 - 8.12 (m, 1 H) 8.60 - 8.64 (m, 1 H) 8.92 - 8.95 (m, 1 H) | |
| ER-886867 | 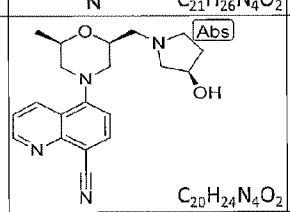 $C_{20}H_{24}N_4O_2$ | 352.4 | 0.0870 | >2 | 5-((2S,6R)-2-(((R)-3-hydroxypyrrolidin-1-yl)methyl)-6-methylmorpholino)quinoline-8-carbonitrile | | |
| ER-886868 | 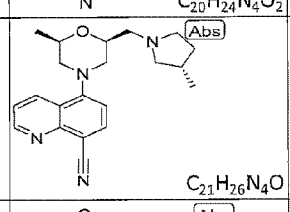 $C_{21}H_{26}N_4O$ | 350.5 | 0.0370 | >2 | 5-((2R,6S)-2-methyl-6-(((S)-3-methylpyrrolidin-1-yl)methyl)morpholino)quinoline-8-carbonitrile | $^1$H NMR (400 MHz, METHANOL-$d_4$) d ppm 1.12 - 1.21 (m, 3 H) 1.28 (d, $J$=6.15 Hz, 3 H) 2.65 - 2.76 (m, 2 H) 3.30 - 3.49 (m, 5 H) 3.75 - 3.81 (m, 1 H) 4.10 - 4.16 (m, 1 H) 4.82 - 4.85 (m, 5 H) 7.24 (d, $J$=7.91 Hz, 1 H) 7.61 (dd, $J$=8.50, 4.39 Hz, 1 H) 8.13 (d, $J$=8.20 Hz, 1 H) 8.62 (d, $J$=8.50 Hz, 1 H) 8.94 - 8.97 (m, 1 H) | |
| ER-886869 | 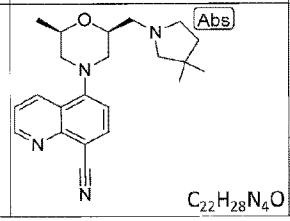 $C_{22}H_{28}N_4O$ | 364.5 | 0.0310 | >2 | 5-((2S,6R)-2-((3,3-dimethylpyrrolidin-1-yl)methyl)-6-methylmorpholino)quinoline-8-carbonitrile | $^1$H NMR (400 MHz, METHANOL-$d_4$) d ppm 1.19 - 1.29 (m, 9 H) 1.86 - 1.93 (m, 1 H) 1.95 - 1.99 (m, 1 H) 2.65 - 2.74 (m, 2 H) 2.96 - 3.05 (m, 1 H) 3.08 (s, 1 H) 3.30 - 3.52 (m, 7 H) 3.75 - 3.81 (m, 1 H) 4.10 - 4.15 (m, 1 H) 4.32 (d, $J$=8.20 Hz, 1 H) 4.83 - 4.85 (m, 5 H) 7.24 (d, $J$=8.20 Hz, 1 H) 7.59 - 7.63 (m, 1 H) 8.11 - 8.14 (m, 1 H) 8.62 (dd, $J$=8.50, 1.76 Hz, 1 H) 8.94 - 8.96 (m, 1 H) | |

FIG. 6T

| | | | | | | | |
|---|---|---|---|---|---|---|---|
| ER-886912 | 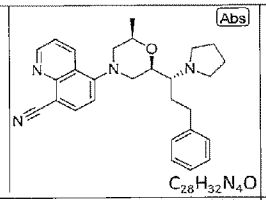 $C_{28}H_{32}N_4O$ | 440.6 | 0.6480 | | 5-((2R,6R)-2-methyl-6-((R)-3-phenyl-1-(pyrrolidin-1-yl)propyl)morpholino)quinoline-8-carbonitrile | | |
| ER-886913 | 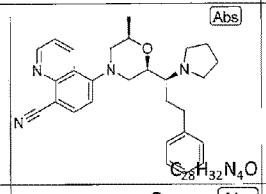 $C_{28}H_{32}N_4O$ | 440.6 | 1.8930 | | 5-((2R,6R)-2-methyl-6-((S)-3-phenyl-1-(pyrrolidin-1-yl)propyl)morpholino)quinoline-8-carbonitrile | $^1$H NMR (400 MHz, CHLOROFORM-*d*) d ppm 1.21 - 1.32 (m, 5 H) 1.72 (d, *J*=5.77 Hz, 4 H) 1.85 - 1.98 (m, 2 H) 2.59 - 2.83 (m, 6 H) 3.28 (d, *J*=12.18 Hz, 1 H) 3.46 - 3.55 (m, 1 H) 3.98 (br. s., 2 H) 7.07 (t, *J*=7.16 Hz, 1 H) 7.14 - 7.34 (m, 5 H) 7.49 (dt, *J*=8.92, 4.62 Hz, 1 H) 8.04 (d, *J*=8.12 Hz, 1 H) 8.45 (d, *J*=8.55 Hz, 1 H) 9.03 - 9.11 (m, 1 H) | LCMS (ESI+) calcd for C28H32N4O (M+H+): 441.26, found: 441.33 |
| ER-886948 | 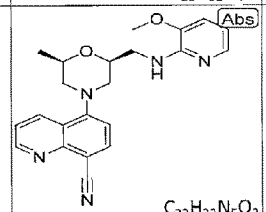 $C_{22}H_{23}N_5O_2$ | 389.5 | 0.0030 | | 5-((2S,6R)-2-(((3-methoxypyridin-2-yl)amino)methyl)-6-methylmorpholino)quinoline-8-carbonitrile | $^1$H NMR (400 MHz, METHANOL-$d_4$) d ppm 1.16 (d, *J*=6.15 Hz, 4 H) 2.67 (dd, *J*=12.01, 10.25 Hz, 1 H) 2.78 - 2.85 (m, 1 H) 3.36 (d, *J*=12.01 Hz, 1 H) 3.54 (d, *J*=11.43 Hz, 1 H) 3.96 - 4.03 (m, 5 H) 4.34 - 4.43 (m, 3 H) 4.82 - 4.86 (m, 7 H) 6.82 - 6.86 (m, 1 H) 7.26 (d, *J*=8.20 Hz, 1 H) 7.36 (d, *J*=7.62 Hz, 1 H) 7.52 - 7.55 (m, 1 H) 7.62 (dd, *J*=8.50, 4.10 Hz, 1 H) 8.14 (d, *J*=8.20 Hz, 1 H) 8.64 (dd, *J*=8.50, 1.76 Hz, 1 H) 8.94 - 8.97 (m, 1 H) | |
| ER-886949 | 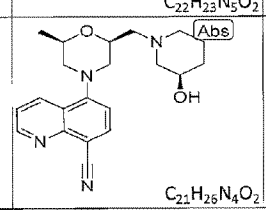 $C_{21}H_{26}N_4O_2$ | 366.5 | 0.1450 | | 5-((2S,6R)-2-(((R)-3-hydroxypiperidin-1-yl)methyl)-6-methylmorpholino)quinoline-8-carbonitrile | $^1$H NMR (400 MHz, METHANOL-$d_4$) d ppm 1.23 - 1.29 (m, 4 H) 1.69 (br. s., 1 H) 1.72 - 1.87 (m, 2 H) 2.63 - 2.76 (m, 2 H) 3.13 (br. s., 1 H) 3.16 - 3.26 (m, 3 H) 3.30 - 3.45 (m, 4 H) 3.70 (d, *J*=12.31 Hz, 1 H) 4.16 (br. s., 1 H) 4.40 (d, *J*=9.96 Hz, 1 H) 4.81 - 4.85 (m, 7 H) 7.24 (d, *J*=7.62 Hz, 1 H) 7.59 - 7.63 (m, 1 H) 8.13 (d, *J*=7.91 Hz, 1 H) 8.59 - 8.64 (m, 1 H) 8.96 (d, *J*=4.39 Hz, 1 H) | |
| ER-886950 | 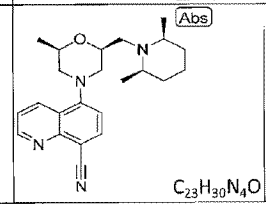 $C_{23}H_{30}N_4O$ | 378.5 | 0.7360 | | 5-((2S,6R)-2-(((2R,6S)-2,6-dimethylpiperidin-1-yl)methyl)-6-methylmorpholino)quinoline-8-carbonitrile | $^1$H NMR (400 MHz, METHANOL-$d_4$) d ppm 1.23 - 1.28 (m, 3 H) 1.34 - 1.36 (m, 2 H) 1.38 - 1.42 (m, 3 H) 1.47 (d, *J*=5.57 Hz, 1 H) 1.61 - 1.68 (m, 1 H) 1.80 (s, 1 H) 2.62 - 2.71 (m, 1 H) 2.74 (s, 1 H) 2.76 - 2.82 (m, 1 H) 3.05 - 3.11 (m, 1 H) 3.34 (d, *J*=14.65 Hz, 1 H) 3.42 (s, 1 H) 3.38 (s, 1 H) 3.46 - 3.56 (m, 1 H) 4.11 (d, *J*=9.67 Hz, 1 H) 4.84 (d, *J*=1.17 Hz, 12 H) 7.25 (d, *J*=7.91 Hz, 1 H) 7.62 (dd, *J*=8.79, 4.39 Hz, 1 H) 8.14 (d, *J*=7.91 Hz, 1 H) 8.60 - 8.64 (m, 1 H) 8.95 - 8.97 (m, 1 H) | |

FIG. 6U

| | | | | | | | |
|---|---|---|---|---|---|---|---|
| ER-886951 | 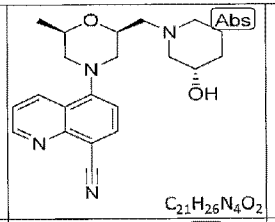 $C_{21}H_{26}N_4O_2$ | 366.5 | 0.6320 | | 5-((2S,6R)-2-(((S)-3-hydroxypiperidin-1-yl)methyl)-6-methylmorpholino)quinoline-8-carbonitrile | $^1$H NMR (400 MHz, METHANOL-$d_4$) d ppm 1.28 (d, $J$=6.45 Hz, 11 H) 3.22 (s, 7 H) 3.38 (s, 1 H) 4.81 - 4.85 (m, 115 H) 7.25 (d, $J$=8.20 Hz, 2 H) 7.62 (dd, $J$=8.50, 4.10 Hz, 2 H) 8.14 (d, $J$=8.20 Hz, 2 H) 8.63 (d, $J$=7.03 Hz, 1 H) 8.95 (s, 1 H) | |
| ER-886953 | 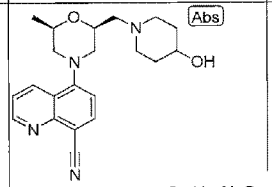 $C_{21}H_{26}N_4O_2$ | 366.5 | 0.0930 | | 5-((2S,6R)-2-((4-hydroxypiperidin-1-yl)methyl)-6-methylmorpholino)quinoline-8-carbonitrile | $^1$H NMR (400 MHz, METHANOL-$d_4$) d ppm 1.27 (d, $J$=6.15 Hz, 3 H) 1.70 - 1.84 (m, 1 H) 1.86 - 2.14 (m, 2 H) 2.63 - 2.75 (m, 2 H) 3.07 - 3.16 (m, 1 H) 3.20 - 3.26 (m, 1 H) 3.29 - 3.40 (m, 5 H) 3.44 - 3.51 (m, 1 H) 3.67 (d, $J$=7.91 Hz, 1 H) 3.80 - 3.86 (m, 1 H) 4.05 - 4.17 (m, 2 H) 4.37 - 4.47 (m, 1 H) 4.86 (s, 1 H) 4.89 - 4.92 (m, 4 H) 7.21 (d, $J$=7.91 Hz, 1 H) 7.56 - 7.61 (m, 1 H) 8.09 (d, $J$=7.91 Hz, 1 H) 8.60 (d, $J$=8.50 Hz, 1 H) 8.93 (d, $J$=4.10 Hz, 1 H) | |
| ER-886955 | 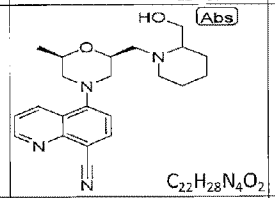 $C_{22}H_{28}N_4O_2$ | 380.5 | 0.1840 | | 5-((2S,6R)-2-((2-(hydroxymethyl)piperidin-1-yl)methyl)-6-methylmorpholino)quinoline-8-carbonitrile | $^1$H NMR (400 MHz, METHANOL-$d_4$) d ppm 1.22 - 1.29 (m, 4 H) 1.58 - 1.72 (m, 2 H) 1.75 - 1.95 (m, 5 H) 2.63 - 2.79 (m, 2 H) 3.20 - 3.25 (m, 1 H) 3.29 - 3.42 (m, 4 H) 3.46 - 3.59 (m, 1 H) 3.61 - 3.74 (m, 2 H) 3.89 - 3.93 (m, 1 H) 4.08 - 4.16 (m, 1 H) 4.43 - 4.49 (m, 1 H) 4.82 - 4.85 (m, 6 H) 7.22 - 7.26 (m, 1 H) 7.59 - 7.63 (m, 1 H) 8.12 (d, $J$=7.91 Hz, 1 H) 8.60 - 8.64 (m, 1 H) 8.95 (d, $J$=4.39 Hz, 1 H) | |
| ER-886957 | 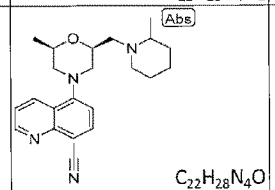 $C_{22}H_{28}N_4O$ | 364.5 | 0.0500 | > 2.0 | 5-((2R,6S)-2-methyl-6-((2-methylpiperidin-1-yl)methyl)morpholino)quinoline-8-carbonitrile | $^1$H NMR (400 MHz, METHANOL-$d_4$) d ppm 1.24 - 1.35 (m, 5 H) 1.39 - 1.45 (m, 2 H) 1.60 - 1.65 (m, 1 H) 1.82 (d, $J$=13.48 Hz, 1 H) 1.93 (br. s., 1 H) 2.63 - 2.79 (m, 2 H) 3.13 - 3.26 (m, 2 H) 3.29 - 3.51 (m, 5 H) 3.76 (d, $J$=12.89 Hz, 1 H) 4.11 - 4.16 (m, 1 H) 4.30 - 4.42 (m, 1 H) 4.85 (s, 5 H) 7.25 (d, $J$=7.91 Hz, 1 H) 7.62 (dd, $J$=8.50, 4.10 Hz, 1 H) 8.13 (d, $J$=7.91 Hz, 1 H) 8.61 - 8.66 (m, 1 H) 8.96 (dd, $J$=4.39, 1.76 Hz, 1 H) | |
| ER-886958 | 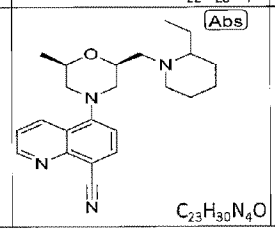 $C_{23}H_{30}N_4O$ | 378.5 | 0.0840 | > 2.0 | 5-((2S,6R)-2-((2-ethylpiperidin-1-yl)methyl)-6-methylmorpholino)quinoline-8-carbonitrile | $^1$H NMR (400 MHz, METHANOL-$d_4$) d ppm 0.98 - 1.04 (m, 3 H) 1.24 - 1.29 (m, 3 H) 1.57 - 1.69 (m, 1 H) 1.73 - 1.96 (m, 3 H) 2.64 - 2.79 (m, 2 H) 3.08 - 3.26 (m, 2 H) 3.29 - 3.49 (m, 3 H) 3.52 - 3.55 (m, 1 H) 3.74 (d, $J$=13.18 Hz, 1 H) 4.10 - 4.17 (m, 1 H) 4.41 (s, 1 H) 4.85 - 4.88 (m, 4 H) 7.24 (d, $J$=7.91 Hz, 1 H) 7.61 (dd, $J$=8.50, 4.39 Hz, 1 H) 8.12 (d, $J$=8.20 Hz, 1 H) 8.60 - 8.66 (m, 1 H) 8.94 - 8.97 (m, 1 H) | |

FIG. 6V

| | | | | | | | |
|---|---|---|---|---|---|---|---|
| ER-887137 | 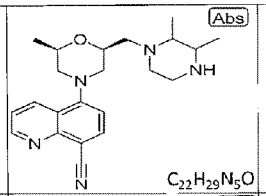 $C_{22}H_{29}N_5O$ | 379.5 | 0.0157 | > 10 < 20.9 | 5-((2S,6R)-2-((2,3-dimethylpiperazin-1-yl)methyl)-6-methylmorpholino)quinoline-8-carbonitrile | $^1$H NMR (400 MHz, METHANOL-$d_4$) d ppm 1.22 - 1.41 (m, 11 H) 2.63 - 2.76 (m, 2 H) 3.05 - 3.11 (m, 1 H) 3.33 - 3.46 (m, 4 H) 3.52 (s, 1 H) 3.72 - 3.77 (m, 1 H) 4.07 - 4.12 (m, 1 H) 7.21 - 7.25 (m, 1 H) 7.59 - 7.63 (m, 1 H) 8.11 - 8.14 (m, 1 H) 8.59 - 8.64 (m, 1 H) 8.95 (dd, $J$=4.39, 1.76 Hz, 1 H) | |
| ER-887138 | 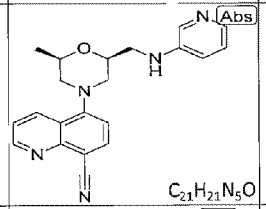 $C_{21}H_{21}N_5O$ | 359.4 | 0.0440 | > 2.0 | 5-((2R,6S)-2-methyl-6-((pyridin-3-ylamino)methyl)morpholino)quinoline-8-carbonitrile | $^1$H NMR (400 MHz, METHANOL-$d_4$) d ppm 1.18 - 1.23 (m, 3 H) 2.63 - 2.69 (m, 1 H) 2.71 - 2.82 (m, 1 H) 3.36 (d, $J$=10.84 Hz, 1 H) 3.53 (d, $J$=10.84 Hz, 1 H) 3.97 - 4.05 (m, 1 H) 4.33 - 4.40 (m, 1 H) 4.43 - 4.49 (m, 1 H) 4.68 (d, $J$=13.48 Hz, 1 H) 4.86 (d, $J$=1.17 Hz, 4 H) 7.25 (dd, $J$=8.20, 1.17 Hz, 1 H) 7.60 - 7.68 (m, 3 H) 8.02 - 8.05 (m, 1 H) 8.07 - 8.15 (m, 2 H) 8.61 - 8.66 (m, 1 H) 8.96 (dt, $J$=4.10, 1.46 Hz, 1 H) | |
| ER-887139 | 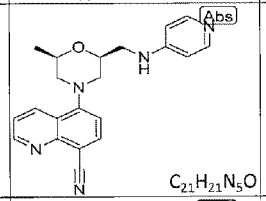 $C_{21}H_{21}N_5O$ | 359.4 | 0.0080 | > 2.0 | 5-((2R,6S)-2-methyl-6-((pyridin-4-ylamino)methyl)morpholino)quinoline-8-carbonitrile | $^1$H NMR (400 MHz, METHANOL-$d_4$) d ppm 1.19 (d, $J$=6.15 Hz, 3 H) 2.60 - 2.72 (m, 2 H) 3.35 (d, $J$=12.01 Hz, 1 H) 3.47 (d, $J$=11.43 Hz, 1 H) 3.96 - 4.03 (m, 1 H) 4.14 - 4.20 (m, 1 H) 4.22 - 4.28 (m, 1 H) 4.34 (d, $J$=2.05 Hz, 1 H) 4.38 (s, 1 H) 4.85 - 4.87 (m, 5 H) 6.80 - 6.83 (m, 2 H) 7.24 (d, $J$=8.20 Hz, 1 H) 7.59 - 7.63 (m, 1 H) 8.05 - 8.09 (m, 2 H) 8.12 (d, $J$=7.91 Hz, 1 H) 8.61 - 8.65 (m, 1 H) 8.95 - 8.97 (m, 1 H) | |
| ER-887140 | 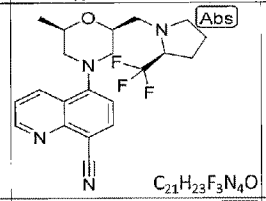 $C_{21}H_{23}F_3N_4O$ | 404.4 | 0.3086 | > 2.0 | 5-((2R,6S)-2-methyl-6-(((S)-2-(trifluoromethyl)pyrrolidin-1-yl)methyl)morpholino)quinoline-8-carbonitrile | $^1$H NMR (400 MHz, METHANOL-$d_4$) d ppm 1.20 - 1.25 (m, 4 H) 2.64 (d, $J$=9.96 Hz, 1 H) 2.75 (d, $J$=10.55 Hz, 1 H) 2.79 (s, 1 H) 3.09 (s, 1 H) 3.15 - 3.19 (m, 1 H) 3.30 - 3.40 (m, 4 H) 4.08 (d, $J$=7.03 Hz, 1 H) 4.80 - 4.86 (m, 9 H) 7.22 (d, $J$=7.91 Hz, 1 H) 7.61 (dd, $J$=8.50, 4.39 Hz, 1 H) 8.13 (d, $J$=8.20 Hz, 1 H) 8.62 (dd, $J$=8.50, 1.76 Hz, 1 H) 8.93 - 8.96 (m, 1 H) | |
| ER-887141 | 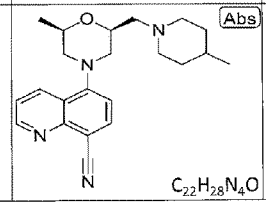 $C_{22}H_{28}N_4O$ | 364.5 | 0.0630 | > 2.0 | 5-((2R,6S)-2-methyl-6-((4-methylpiperidin-1-yl)methyl)morpholino)quinoline-8-carbonitrile | 1H NMR (400 MHz, METHANOL-d4) d ppm 0.99 (3 H, d) 1.27 (3 H, d) 1.40 - 1.60 (2 H, m) 1.63 - 1.76 (1 H, m) 1.83 - 2.03 (2 H, m) 2.60 - 2.77 (2 H, m) 2.96 - 3.09 (2 H, m) 3.23 - 3.26 (2 H, m) 3.32 - 3.46 (2 H, m) 3.60 - 3.72 (2 H, m) 4.08 - 4.24 (1 H, m) 4.33 - 4.49 (1 H, m) 7.19 - 7.26 (1 H, m) 7.56 - 7.66 (1 H, m) 8.08 - 8.17 (1 H, m) 8.56 - 8.66 (1 H, m) 8.90 - 8.99 (1 H, m) | LCMS (ESI+) calcd for C22 H28 N4 O (M+H+) 365.4, found 365.2 |

FIG. 6W

| | | | | | | | |
|---|---|---|---|---|---|---|---|
| ER-887142 | 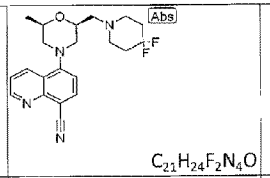 $C_{21}H_{24}F_2N_4O$ | 386.4 | 0.1060 | > 2.0 | 5-((2S,6R)-2-((4,4-difluoropiperidin-1-yl)methyl)-6-methylmorpholino)quinoline-8-carbonitrile | $^1$H NMR (400 MHz, METHANOL-$d_4$) d ppm 1.28 (d, $J$=5.57 Hz, 3 H) 1.33 (s, 1 H) 2.39 (br. s., 3 H) 2.45 (br. s., 1 H) 2.66 - 2.76 (m, 2 H) 3.33 - 3.43 (m, 4 H) 4.11 - 4.19 (m, 1 H) 4.41 - 4.48 (m, 1 H) 7.22 (d, $J$=7.91 Hz, 1 H) 7.58 - 7.62 (m, 1 H) 8.09 - 8.13 (m, 1 H) 8.61 (d, $J$=8.79 Hz, 1 H) 8.93 - 8.95 (m, 1 H) | |
| ER-887143 | 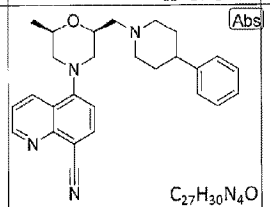 $C_{27}H_{30}N_4O$ | 426.6 | 0.0430 | > 2.0 | 5-((2R,6S)-2-methyl-6-((4-phenylpiperidin-1-yl)methyl)morpholino)quinoline-8-carbonitrile | 1H NMR (400 MHz, METHANOL-d4) d ppm 1.29 (3 H, d) 1.97 - 2.20 (4 H, m) 2.63 - 2.80 (2 H, m) 2.83 - 2.96 (1 H, m) 3.14 - 3.28 (2 H, m) 3.34 - 3.56 (4 H, m) 3.72 - 3.86 (2 H, m) 4.08 - 4.22 (1 H, m) 4.38 - 4.56 (1 H, m) 7.14 - 7.38 (6 H, m) 7.55 - 7.66 (1 H, m) 8.05 - 8.16 (1 H, m) 8.57 - 8.66 (1 H, m) 8.88 - 8.99 (1 H, m) | LCMS (ESI+) calcd forC27 H30 N4 O (M+H+) 427.5, found 427.6 |
| ER-887144 | 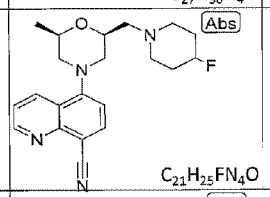 $C_{21}H_{25}FN_4O$ | 368.5 | 0.0760 | > 2.0 | 5-((2S,6R)-2-((4-fluoropiperidin-1-yl)methyl)-6-methylmorpholino)quinoline-8-carbonitrile | 1H NMR (400 MHz, METHANOL-d4) d ppm 1.28 (3 H, d) 1.95 - 2.39 (5 H, m) 2.62 - 2.83 (2 H, m) 3.27 - 3.39 (2 H, m) 3.51 - 3.77 (2 H, m) 4.05 - 4.21 (2 H, m) 4.35 - 4.55 (3 H, m) 4.99 - 5.08 (1 H, m) 7.23 (1 H, d) 7.55 - 7.67 (1 H, m) 8.06 - 8.17 (1 H, m) 8.62 (1 H, d) 8.87 - 8.98 (1 H, m) | LCMS (ESI+) calcd for C21 H25 F N4 O (M+H+) 369.4, found 369.2 |
| ER-887145 | 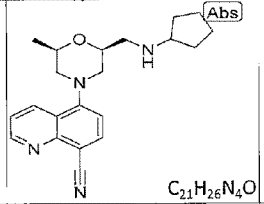 $C_{21}H_{26}N_4O$ | 350.5 | 0.0870 | > 2.0 | 5-((2S,6R)-2-((cyclopentylamino)methyl)-6-methylmorpholino)quinoline-8-carbonitrile | $^1$H NMR (400 MHz, METHANOL-$d_4$) d ppm 1.28 (d, $J$=6.15 Hz, 4 H) 1.61 - 1.71 (m, 4 H) 1.81 (br. s., 2 H) 2.09 - 2.16 (m, 2 H) 2.65 - 2.77 (m, 2 H) 3.07 - 3.14 (m, 1 H) 3.22 - 3.26 (m, 1 H) 3.37 - 3.42 (m, 2 H) 3.58 (t, $J$=7.32 Hz, 1 H) 4.07 - 4.15 (m, 1 H) 4.20 - 4.27 (m, 1 H) 4.85 - 4.87 (m, 5 H) 7.24 (d, $J$=8.20 Hz, 1 H) 7.60 - 7.64 (m, 1 H) 8.13 (d, $J$=8.20 Hz, 1 H) 8.60 - 8.63 (m, 1 H) 8.94 - 8.97 (m, 1 H) | |
| ER-887146 | 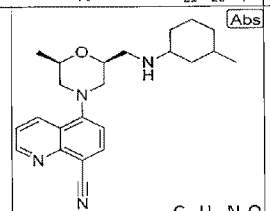 $C_{23}H_{30}N_4O$ | 378.5 | 0.0680 | > 2.0 | 5-((2R,6S)-2-methyl-6-(((3-methylcyclohexyl)amino)methyl)morpholino)quinoline-8-carbonitrile | $^1$H NMR (400 MHz, METHANOL-$d_4$) d ppm 0.86 - 1.10 (m, 5 H) 1.25 - 1.40 (m, 4 H) 1.47 - 1.54 (m, 1 H) 1.62 (s, 1 H) 1.67 - 1.76 (m, 1 H) 1.85 - 1.91 (m, 1 H) 2.09 (d, $J$=5.27 Hz, 2 H) 2.64 - 2.77 (m, 2 H) 3.09 - 3.17 (m, 2 H) 3.22 - 3.26 (m, 1 H) 3.37 - 3.43 (m, 2 H) 4.07 - 4.15 (m, 1 H) 4.20 - 4.27 (m, 1 H) 4.88 (br. s., 1 H) 7.23 (d, $J$=8.20 Hz, 1 H) 7.61 (dd, $J$=8.50, 4.39 Hz, 1 H) 8.12 (d, $J$=7.91 Hz, 1 H) 8.61 (dd, $J$=8.50, 1.76 Hz, 1 H) 8.95 (dd, $J$=4.39, 1.76 Hz, 1 H) | |

FIG. 6X

| | | | | | | | |
|---|---|---|---|---|---|---|---|
| ER-887177 | 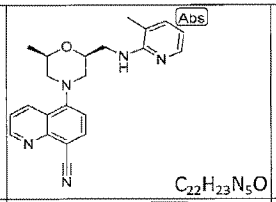 $C_{22}H_{23}N_5O$ | 373.5 | 0.0030 | > 2.0 | 5-((2R,6S)-2-methyl-6-(((3-methylpyridin-2-yl)amino)methyl)morpholino)quinoline-8-carbonitrile | $^1$H NMR (400 MHz, METHANOL-$d_4$) d ppm 1.12 - 1.16 (m, 3 H) 2.24 - 2.28 (m, 3 H) 2.61 - 2.68 (m, 1 H) 2.77 - 2.84 (m, 1 H) 3.24 - 3.26 (m, 1 H) 3.31 - 3.36 (m, 1 H) 3.55 (d, $J$=11.72 Hz, 1 H) 3.94 - 4.01 (m, 1 H) 4.30 - 4.47 (m, 3 H) 4.82 - 4.87 (m, 5 H) 6.80 - 6.85 (m, 1 H) 7.19 - 7.24 (m, 1 H) 7.56 - 7.61 (m, 1 H) 7.74 (d, $J$=7.32 Hz, 1 H) 7.83 (d, $J$=6.74 Hz, 1 H) 8.07 - 8.11 (m, 1 H) 8.57 - 8.62 (m, 1 H) 8.90 - 8.93 (m, 1 H) | |
| ER-887199 | 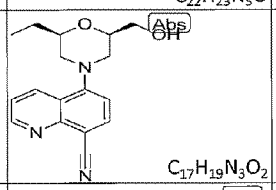 $C_{17}H_{19}N_3O_2$ | 297.4 | 0.1050 | > 2.0 | 5-((2R,6R)-2-ethyl-6-(hydroxymethyl)morpholino)quinoline-8-carbonitrile | 1H NMR (400 MHz, METHANOL-d4) d ppm 0.99 (3 H, t) 1.43 - 1.68 (2 H, m) 2.60 - 2.73 (1 H, m) 2.74 - 2.89 (1 H, m) 3.31 - 3.46 (2 H, m) 3.76 - 3.88 (1 H, m) 4.21 - 4.29 (1 H, m) 4.48 (2 H, br. s.) 7.24 (1 H, s) 7.53 - 7.67 (1 H, m) 7.96 - 8.19 (1 H, m) 8.53 - 8.70 (1 H, m) 8.88 - 9.04 (1 H, m) | LCMS (ESI+) calcd for C17 H19 N3 O2 (M+H+) 298.3, found 298.4 |
| ER-887252 | 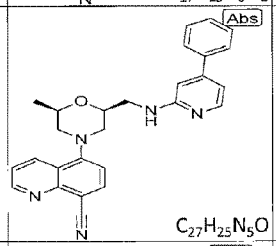 $C_{27}H_{25}N_5O$ | 435.5 | 0.0066 | > 2.0 | 5-((2R,6S)-2-methyl-6-(((4-phenylpyridin-2-yl)amino)methyl)morpholino)quinoline-8-carbonitrile | $^1$H NMR (400 MHz, METHANOL-$d_4$) d ppm 1.16 - 1.22 (m, 4 H) 2.70 (dd, $J$=12.01, 10.25 Hz, 1 H) 2.79 - 2.88 (m, 1 H) 3.31 - 3.39 (m, 1 H) 3.57 (d, $J$=11.43 Hz, 1 H) 4.00 - 4.06 (m, 1 H) 4.29 - 4.44 (m, 3 H) 4.80 - 4.85 (m, 5 H) 7.20 - 7.33 (m, 3 H) 7.52 - 7.64 (m, 4 H) 7.74 - 7.79 (m, 2 H) 7.99 (d, $J$=7.03 Hz, 1 H) 8.11 - 8.15 (m, 1 H) 8.29 (br. s., 1 H) 8.62 - 8.67 (m, 1 H) 8.93 - 8.97 (m, 1 H) | |
| ER-887253 | 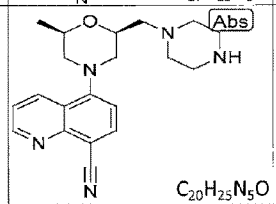 $C_{20}H_{25}N_5O$ | 351.5 | 0.0072 | | 5-((2R,6S)-2-methyl-6-(piperazin-1-ylmethyl)morpholino)quinoline-8-carbonitrile | $^1$H NMR (400 MHz, METHANOL-$d_4$) d ppm 1.25 (d, $J$=6.15 Hz, 4 H) 1.96 - 2.04 (m, 1 H) 2.27 - 2.34 (m, 1 H) 2.64 - 2.79 (m, 3 H) 3.25 (br. s., 1 H) 3.29 - 3.43 (m, 5 H) 3.48 (s, 1 H) 3.52 - 3.63 (m, 9 H) 4.07 - 4.14 (m, 1 H) 4.38 - 4.46 (m, 1 H) 7.16 - 7.24 (m, 1 H) 7.57 - 7.67 (m, 1 H) 8.08 - 8.13 (m, 1 H) 8.58 - 8.62 (m, 1 H) 8.94 (dd, $J$=4.39, 1.76 Hz, 1 H) | |
| ER-887258 | 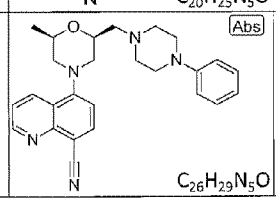 $C_{26}H_{29}N_5O$ | 427.6 | 0.0852 | > 2.0 | 5-((2R,6S)-2-methyl-6-((4-phenylpiperazin-1-yl)methyl)morpholino)quinoline-8-carbonitrile | $^1$H NMR (400 MHz, METHANOL-$d_4$) d ppm 1.29 (d, $J$=6.15 Hz, 3 H) 2.67 - 2.79 (m, 2 H) 3.30 - 3.43 (m, 7 H) 4.13 - 4.19 (m, 1 H) 4.44 - 4.51 (m, 1 H) 4.82 - 4.86 (m, 5 H) 6.88 - 6.93 (m, 1 H) 6.98 - 7.03 (m, 2 H) 7.22 - 7.29 (m, 3 H) 7.59 - 7.64 (m, 1 H) 8.11 - 8.15 (m, 1 H) 8.61 - 8.65 (m, 1 H) 8.94 - 8.97 (m, 1 H) | |

FIG. 6Y

| | | | | | | | |
|---|---|---|---|---|---|---|---|
| ER-887259 | 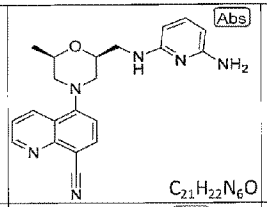 $C_{21}H_{22}N_6O$ | 374.4 | 0.0019 | > 2.0 | 5-((2S,6R)-2-(((6-aminopyridin-2-yl)amino)methyl)-6-methylmorpholino)quinoline-8-carbonitrile | $^1$H NMR (400 MHz, METHANOL-$d_4$) d ppm 1.20 - 1.24 (m, 4 H) 2.61 - 2.68 (m, 1 H) 2.77 - 2.84 (m, 1 H) 3.34 - 3.43 (m, 4 H) 3.47 - 3.52 (m, 1 H) 4.05 - 4.19 (m, 2 H) 4.84 - 4.87 (m, 6 H) 5.96 - 6.04 (m, 2 H) 7.22 (d, $J$=7.91 Hz, 1 H) 7.51 - 7.62 (m, 2 H) 8.11 (d, $J$=7.91 Hz, 1 H) 8.59 - 8.63 (m, 1 H) 8.92 - 8.95 (m, 1 H) | |
| ER-887260 | 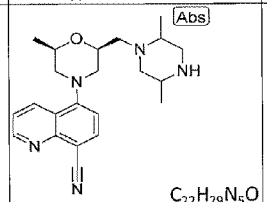 $C_{22}H_{29}N_5O$ | 379.5 | 0.0901 | > 2.0 | 5-((2S,6R)-2-((2,5-dimethylpiperazin-1-yl)methyl)-6-methylmorpholino)quinoline-8-carbonitrile | $^1$H NMR (400 MHz, METHANOL-$d_4$) d ppm 1.28 (d, $J$=6.15 Hz, 4 H) 1.61 - 1.71 (m, 4 H) 1.81 (br. s., 2 H) 2.09 - 2.16 (m, 2 H) 2.65 - 2.77 (m, 2 H) 3.07 - 3.14 (m, 1 H) 3.22 - 3.26 (m, 1 H) 3.37 - 3.42 (m, 2 H) 3.58 (t, $J$=7.32 Hz, 1 H) 4.07 - 4.15 (m, 1 H) 4.20 - 4.27 (m, 1 H) 4.85 - 4.87 (m, 5 H) 7.24 (d, $J$=8.20 Hz, 1 H) 7.60 - 7.64 (m, 1 H) 8.13 (d, $J$=8.20 Hz, 1 H) 8.60 - 8.63 (m, 1 H) 8.94 - 8.97 (m, 1 H) | |
| ER-887261 | 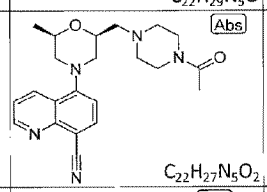 $C_{22}H_{27}N_5O_2$ | 393.5 | 0.0917 | > 2.0 | 5-((2S,6R)-2-((4-acetylpiperazin-1-yl)methyl)-6-methylmorpholino)quinoline-8-carbonitrile | | |
| ER-887262 | 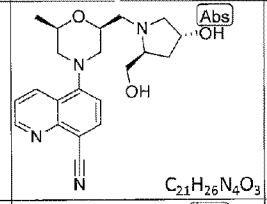 $C_{21}H_{26}N_4O_3$ | 382.5 | 0.2720 | > 2.0 | 5-((2S,6R)-2-(((2S,4R)-4-hydroxy-2-(hydroxymethyl)pyrrolidin-1-yl)methyl)-6-methylmorpholino)quinoline-8-carbonitrile | $^1$H NMR (400 MHz, METHANOL-$d_4$) d ppm 1.25 - 1.34 (m, 3 H) 1.98 - 2.05 (m, 1 H) 2.07 - 2.16 (m, 2 H) 2.30 - 2.34 (m, 1 H) 2.66 - 2.79 (m, 3 H) 3.31 (s, 1 H) 3.36 - 3.44 (m, 5 H) 3.64 - 3.68 (m, 1 H) 3.70 (s, 1 H) 3.74 - 3.84 (m, 2 H) 3.95 (d, $J$=3.81 Hz, 1 H) 3.97 - 4.02 (m, 1 H) 4.11 - 4.15 (m, 1 H) 4.34 - 4.40 (m, 1 H) 4.53 (br. s., 1 H) 7.25 (d, $J$=7.91 Hz, 1 H) 7.62 (dd, $J$=8.50, 4.39 Hz, 1 H) 8.13 (d, $J$=7.91 Hz, 1 H) 8.63 - 8.66 (m, 1 H) 8.96 (dd, $J$=4.10, 1.76 Hz, 1 H) | |
| ER-887268 | 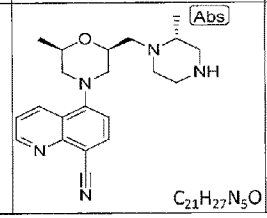 $C_{21}H_{27}N_5O$ | 365.5 | 0.0360 | > 2.0 | 5-((2R,6S)-2-methyl-6-(((R)-2-methylpiperazin-1-yl)methyl)morpholino)quinoline-8-carbonitrile | $^1$H NMR (400 MHz, METHANOL-$d_4$) d ppm 1.23 - 1.27 (m, 3 H) 1.34 - 1.44 (m, 4 H) 1.98 - 2.04 (m, 1 H) 2.30 - 2.34 (m, 1 H) 2.64 - 2.71 (m, 1 H) 2.74 - 2.80 (m, 2 H) 3.10 - 3.25 (m, 2 H) 3.36 - 3.51 (m, 6 H) 3.55 - 3.63 (m, 3 H) 3.81 - 3.86 (m, 1 H) 4.08 - 4.14 (m, 1 H) 4.35 - 4.41 (m, 1 H) 7.22 - 7.25 (m, 1 H) 7.61 (dd, $J$=8.50, 4.39 Hz, 1 H) 8.13 (d, $J$=7.91 Hz, 1 H) 8.61 - 8.64 (m, 1 H) 8.95 (dd, $J$=4.10, 1.76 Hz, 1 H) | |

FIG. 6Z

| | | | | | | | |
|---|---|---|---|---|---|---|---|
| ER-887269 | 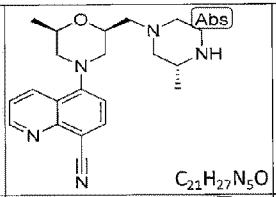 $C_{21}H_{27}N_5O$ | 365.5 | 0.0195 | > 2.0 | 5-((2R,6S)-2-methyl-6-(((R)-3-methylpiperazin-1-yl)methyl)morpholino)quinoline-8-carbonitrile | 1H NMR (400 MHz, METHANOL-d4) d ppm 1.23 (3 H, d) 1.35 (3 H, d) 2.58 - 2.76 (2 H, m) 2.77 - 2.93 (1 H, m) 3.12 (3 H, d) 3.38 (3 H, br. s.) 3.50 - 3.71 (4 H, m) 4.02 - 4.15 (1 H, m) 4.28 - 4.40 (1 H, m) 7.17 - 7.29 (1 H, m) 7.55 - 7.66 (1 H, m) 8.08 - 8.17 (1 H, m) 8.55 - 8.68 (1 H, m) 8.89 - 8.99 (1 H, m) | LCMS (ESI+) calcd for C21 H27 N5 O (M+H+) 366.4, found 366.5 |
| ER-887270 | 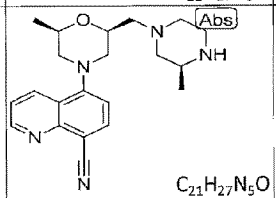 $C_{21}H_{27}N_5O$ | 365.5 | 0.0120 | > 2.0 | 5-((2R,6S)-2-methyl-6-(((S)-3-methylpiperazin-1-yl)methyl)morpholino)quinoline-8-carbonitrile | 1H NMR (400 MHz, METHANOL-d4) d ppm 1.25 (3 H, d) 1.38 (3 H, d) 2.60 - 2.79 (2 H, m) 3.00 - 3.14 (1 H, m) 3.35 - 3.56 (5 H, m) 3.58 - 3.85 (5 H, m) 4.02 - 4.19 (1 H, m) 4.33 - 4.49 (1 H, m) 7.09 - 7.28 (1 H, m) 7.53 - 7.71 (1 H, m) 8.05 - 8.15 (1 H, m) 8.55 - 8.67 (1 H, m) 8.87 - 9.02 (1 H, m) | LCMS (ESI+) calcd for C21 H27 N5 O (M+H+) 366.4, found 366.5 |
| ER-887271 | 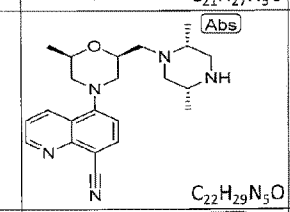 $C_{22}H_{29}N_5O$ | 379.5 | 0.0150 | >2.0 | 5-((2S,6R)-2-(((2R,5R)-2,5-dimethylpiperazin-1-yl)methyl)-6-methylmorpholino)quinoline-8-carbonitrile | 1H NMR (400 MHz, METHANOL-d4) d ppm 1.20 - 1.28 (3 H, d) 1.33-1.40 (6 H, m) 2.62 - 2.77 (2 H, m) 3.03 - 3.18 (4 H, m) 3.31 - 3.50 (4 H, m) 3.55 - 3.70 (2 H, m) 4.02 - 4.14 (1 H, m) 4.23 - 4.34 (1 H, m) 7.19 - 7.29 (1 H, m) 7.57 - 7.64 (1 H, m) 8.08 - 8.18 (1 H, m) 8.58 - 8.65 (1 H, m) 8.92 - 8.99 (1 H, m) | LCMS (ESI+) calcd for C22 H29 N5 O (M+H+) 380.5, found 380.7 |
| ER-887272 | 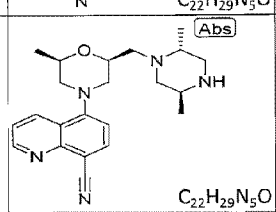 $C_{22}H_{29}N_5O$ | 379.5 | 0.0340 | >2.0 | 5-((2S,6R)-2-(((2R,5S)-2,5-dimethylpiperazin-1-yl)methyl)-6-methylmorpholino)quinoline-8-carbonitrile | | |
| ER-887442 | 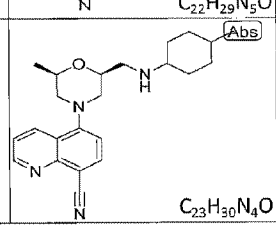 $C_{23}H_{30}N_4O$ | 378.5 | 0.1487 | >2.0 | 5-((2R,6S)-2-methyl-6-(((4-methylcyclohexyl)amino)methyl)morpholino)quinoline-8-carbonitrile | | |

FIG. 6AA

| | | | | | | |
|---|---|---|---|---|---|---|
| ER-887443 | 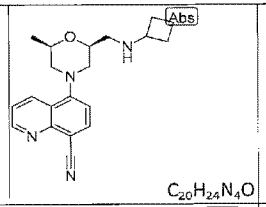 $C_{20}H_{24}N_4O$ | 336.4 | 0.1250 | >2.0 | 5-((2S,6R)-2-((cyclobutylamino)methyl)-6-methylmorpholino)quinoline-8-carbonitrile | $^1$H NMR (400 MHz, METHANOL-$d_4$) d ppm 1.28 (d, $J$=6.15 Hz, 4 H) 1.85 - 1.95 (m, 2 H) 2.13 - 2.26 (m, 2 H) 2.33 (d, $J$=9.38 Hz, 2 H) 2.64 - 2.75 (m, 2 H) 2.95 - 3.01 (m, 1 H) 3.09 - 3.15 (m, 1 H) 3.40 (s, 1 H) 3.37 (s, 1 H) 3.75 - 3.81 (m, 1 H) 4.09 (d, $J$=6.15 Hz, 1 H) 4.16 - 4.23 (m, 1 H) 4.85 - 4.86 (m, 6 H) 7.23 (d, $J$=7.91 Hz, 1 H) 7.61 (dd, $J$=8.50, 4.39 Hz, 1 H) 8.12 (dt, $J$=7.91, 0.88 Hz, 1 H) 8.61 (d, $J$=8.79 Hz, 1 H) 8.94 - 8.97 (m, 1 H) |
| ER-887444 | 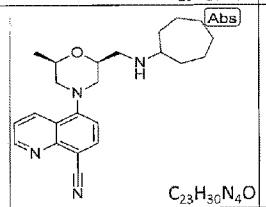 $C_{23}H_{30}N_4O$ | 378.5 | 0.1007 | >2.0 | 5-((2S,6R)-2-((cycloheptylamino)methyl)-6-methylmorpholino)quinoline-8-carbonitrile | $^1$H NMR (400 MHz, METHANOL-$d_4$) d ppm 1.25 - 1.29 (m, 4 H) 1.55 (br. s., 4 H) 1.60 (br. s., 4 H) 1.63 - 1.71 (m, 3 H) 1.78 (br. s., 2 H) 2.08 (d, $J$=5.86 Hz, 2 H) 2.63 - 2.77 (m, 2 H) 3.08 - 3.15 (m, 1 H) 3.23 (d, $J$=14.65 Hz, 1 H) 3.29 (br. s., 1 H) 3.40 (s, 1 H) 3.37 (s, 1 H) 4.11 (d, $J$=7.62 Hz, 1 H) 4.18 - 4.25 (m, 1 H) 4.85 - 4.87 (m, 6 H) 7.21 - 7.25 (m, 1 H) 7.58 - 7.63 (m, 1 H) 8.10 - 8.14 (m, 1 H) 8.58 - 8.63 (m, 1 H) 8.93 - 8.96 (m, 1 H) |
| ER-887526 | 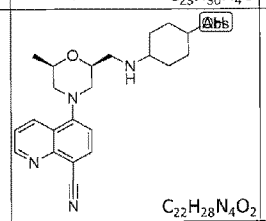 $C_{22}H_{28}N_4O_2$ | 380.5 | 0.1190 | > 2.0 | 5-((2S,6R)-2-(((4-hydroxycyclohexyl)amino)methyl)-6-methylmorpholino)quinoline-8-carbonitrile | $^1$H NMR (400 MHz, METHANOL-$d_4$) d ppm 1.24 - 1.37 (m, 6 H) 1.40 - 1.54 (m, 2 H) 2.04 (s, 1 H) 2.01 (s, 1 H) 2.09 - 2.17 (m, 2 H) 2.64 - 2.76 (m, 2 H) 3.06 - 3.15 (m, 2 H) 3.21 - 3.25 (m, 1 H) 3.40 (s, 1 H) 3.37 (s, 1 H) 3.49 - 3.57 (m, 1 H) 4.07 - 4.14 (m, 1 H) 4.19 - 4.26 (m, 1 H) 4.80 - 4.85 (m, 7 H) 7.23 (d, $J$=7.91 Hz, 1 H) 7.61 (dd, $J$=8.50, 4.39 Hz, 1 H) 8.12 (d, $J$=7.91 Hz, 1 H) 8.60 (dd, $J$=8.79, 1.76 Hz, 1 H) 8.95 (dd, $J$=4.39, 1.76 Hz, 1 H) |
| ER-887528 | 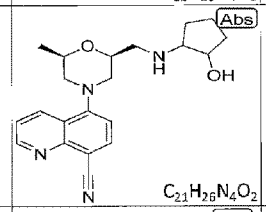 $C_{21}H_{26}N_4O_2$ | 366.5 | >2.0 | >2.0 | 5-((2S,6R)-2-(((2-hydroxycyclopentyl)amino)methyl)-6-methylmorpholino)quinoline-8-carbonitrile | |
| ER-887538 | 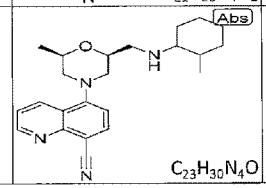 $C_{23}H_{30}N_4O$ | 378.5 | 0.0400 | >2.0 | 5-((2R,6S)-2-methyl-6-(((2-methylcyclohexyl)amino)methyl)morpholino)quinoline-8-carbonitrile | |

FIG. 6BB

| | | | | | | | |
|---|---|---|---|---|---|---|---|
| ER-887539 | 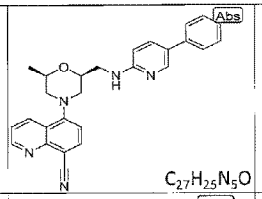 $C_{27}H_{25}N_5O$ | 435.5 | 0.0020 | >2.0 | 5-((2R,6S)-2-methyl-6-(((5-phenylpyridin-2-yl)amino)methyl)morpholino)quinoline-8-carbonitrile | $^1$H NMR (400 MHz, METHANOL-$d_4$) d ppm 1.19 (d, $J$=6.15 Hz, 4 H) 2.72 (dd, $J$=12.01, 10.25 Hz, 1 H) 2.83 - 2.89 (m, 1 H) 3.37 (d, $J$=12.01 Hz, 1 H) 3.59 (d, $J$=11.43 Hz, 1 H) 4.00 - 4.05 (m, 1 H) 4.39 - 4.48 (m, 4 H) 4.80 - 4.86 (m, 17 H) 7.18 (d, $J$=9.38 Hz, 1 H) 7.28 (d, $J$=7.91 Hz, 1 H) 7.39 - 7.50 (m, 3 H) 7.57 - 7.64 (m, 4 H) 8.14 (d, $J$=7.91 Hz, 1 H) 8.19 - 8.26 (m, 2 H) 8.64 - 8.68 (m, 1 H) 8.96 (dd, $J$=4.10, 1.76 Hz, 1 H) | |
| ER-887540 | 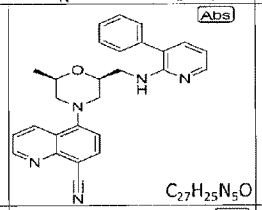 $C_{27}H_{25}N_5O$ | 435.5 | 0.0060 | >2.0 | 5-((2R,6S)-2-methyl-6-(((3-phenylpyridin-2-yl)amino)methyl)morpholino)quinoline-8-carbonitrile | $^1$H NMR (400 MHz, METHANOL-$d_4$) d ppm 1.17 - 1.21 (m, 4 H) 2.67 - 2.73 (m, 1 H) 2.84 - 2.90 (m, 1 H) 3.38 (d, $J$=12.01 Hz, 1 H) 3.59 (d, $J$=12.01 Hz, 1 H) 4.02 - 4.08 (m, 1 H) 4.41 - 4.53 (m, 3 H) 4.83 - 4.87 (m, 14 H) 7.00 - 7.05 (m, 1 H) 7.28 (d, $J$=7.91 Hz, 1 H) 7.44 - 7.64 (m, 6 H) 7.78 (dd, $J$=7.32, 1.17 Hz, 1 H) 7.99 - 8.03 (m, 1 H) 8.14 (d, $J$=7.91 Hz, 1 H) 8.63 - 8.67 (m, 1 H) 8.94 - 8.97 (m, 1 H) | |
| ER-887586 | 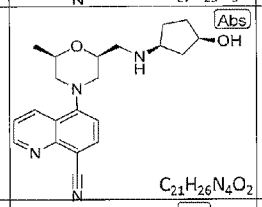 $C_{21}H_{26}N_4O_2$ | 366.5 | 0.0860 | > 2.0 | 5-((2S,6R)-2-((((1S,3R)-3-hydroxycyclopentyl)amino)methyl)-6-methylmorpholino)quinoline-8-carbonitrile | $^1$H NMR (400 MHz, METHANOL-$d_4$) d ppm 1.23 - 1.29 (m, 4 H) 1.80 - 1.87 (m, 3 H) 1.93 - 2.04 (m, 3 H) 2.12 - 2.19 (m, 2 H) 2.29 - 2.34 (m, 2 H) 2.64 - 2.79 (m, 5 H) 3.09 - 3.16 (m, 1 H) 3.24 (d, $J$=2.93 Hz, 1 H) 3.36 - 3.43 (m, 4 H) 3.64 - 3.70 (m, 1 H) 4.08 - 4.13 (m, 1 H) 4.20 - 4.26 (m, 1 H) 4.30 - 4.34 (m, 1 H) 4.82 - 4.86 (m, 7 H) 7.24 (d, $J$=8.20 Hz, 1 H) 7.59 - 7.63 (m, 1 H) 8.13 (d, $J$=7.91 Hz, 1 H) 8.59 - 8.63 (m, 1 H) 8.94 - 8.96 (m, 1 H) | |
| ER-887587 | 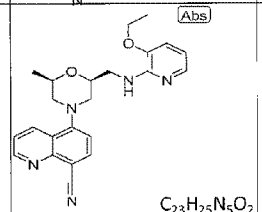 $C_{23}H_{25}N_5O_2$ | 403.5 | 0.0020 | > 2.0 | 5-((2S,6R)-2-(((3-ethoxypyridin-2-yl)amino)methyl)-6-methylmorpholino)quinoline-8-carbonitrile | $^1$H NMR (400 MHz, METHANOL-$d_4$) d ppm 1.14 - 1.18 (m, 4 H) 1.45 - 1.50 (m, 4 H) 2.63 - 2.70 (m, 1 H) 2.80 - 2.87 (m, 1 H) 3.33 - 3.42 (m, 1 H) 3.54 (d, $J$=11.43 Hz, 1 H) 3.97 - 4.03 (m, 1 H) 4.24 (q, $J$=7.03 Hz, 3 H) 4.35 - 4.43 (m, 3 H) 4.81 - 4.86 (m, 7 H) 6.80 - 6.86 (m, 1 H) 7.23 - 7.28 (m, 1 H) 7.32 - 7.41 (m, 1 H) 7.51 - 7.54 (m, 1 H) 7.59 - 7.64 (m, 1 H) 8.12 - 8.15 (m, 1 H) 8.60 - 8.66 (m, 1 H) 8.94 - 8.97 (m, 1 H) | |
| ER-887588 | 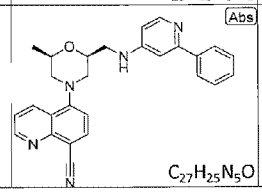 $C_{27}H_{25}N_5O$ | 435.5 | 0.0030 | > 2.0 | 5-((2R,6S)-2-methyl-6-(((2-phenylpyridin-4-yl)amino)methyl)morpholino)quinoline-8-carbonitrile | $^1$H NMR (400 MHz, METHANOL-$d_4$) d ppm 1.18 (d, $J$=6.15 Hz, 3 H) 2.32 (s, 1 H) 2.57 (d, $J$=11.72 Hz, 1 H) 2.79 (s, 1 H) 3.03 (d, $J$=11.72 Hz, 1 H) 3.39 - 3.43 (m, 1 H) 4.05 - 4.10 (m, 1 H) 4.20 - 4.23 (m, 1 H) 4.81 - 4.86 (m, 21 H) 6.73 (d, $J$=2.93 Hz, 1 H) 6.87 - 6.89 (m, 1 H) 7.11 (s, 1 H) 7.13 (s, 1 H) 7.52 - 7.61 (m, 6 H) 8.08 (d, $J$=7.91 Hz, 1 H) 8.21 (s, 1 H) 8.23 (s, 1 H) 8.40 (s, 1 H) 8.41 (s, 1 H) 8.93 - 8.95 (m, 1 H) | |

FIG. 6CC

| | | | | | | | |
|---|---|---|---|---|---|---|---|
| ER-887589 | 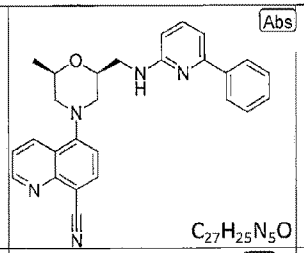 $C_{27}H_{25}N_5O$ | 435.5 | 0.1730 | > 2.0 | 5-((2R,6S)-2-methyl-6-(((6-phenylpyridin-2-yl)amino)methyl)morpholino)quinoline-8-carbonitrile | $^1$H NMR (400 MHz, METHANOL-$d_4$) d ppm 1.06 (br. s., 1 H) 1.97 - 2.02 (m, 1 H) 2.30 - 2.32 (m, 1 H) 2.64 (d, $J$=9.96 Hz, 1 H) 2.79 (s, 1 H) 2.85 - 2.88 (m, 1 H) 3.33 (s, 1 H) 3.36 - 3.41 (m, 1 H) 3.43 (d, $J$=4.98 Hz, 1 H) 3.47 (s, 1 H) 3.75 - 3.79 (m, 1 H) 4.81 - 4.85 (m, 19 H) 7.12 (d, $J$=9.38 Hz, 1 H) 7.19 (d, $J$=7.32 Hz, 1 H) 7.24 (d, $J$=8.20 Hz, 1 H) 7.58 - 7.63 (m, 4 H) 7.78 - 7.82 (m, 2 H) 7.98 - 8.03 (m, 1 H) 8.12 (s, 1 H) 8.13 (s, 1 H) 8.61 - 8.64 (m, 1 H) 8.94 - 8.96 (m, 1 H) | |
| ER-887612 | 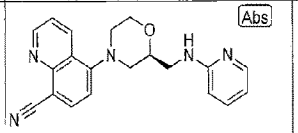 $C_{20}H_{19}N_5O$ | 345.4 | 0.6110 | > 2.0 | (S)-5-(2-((pyridin-2-ylamino)methyl)morpholino)quinoline-8-carbonitrile | $^1$H NMR (400 MHz, CHLOROFORM-$d$) d ppm 2.64 - 2.78 (m, 1 H) 3.04 (td, $J$=11.80, 3.10 Hz, 1 H) 3.25 (d, 1 H) 3.79 - 4.09 (m, 4 H) 4.35 (t, $J$=9.51 Hz, 1 H) 4.80 (d, 1 H) 6.52 (br. s., 1 H) 7.02 - 7.13 (m, 1 H) 7.17 - 7.29 (m, 1 H) 7.37 - 7.56 (m, 3 H) 8.00 (d, $J$=7.90 Hz, 1 H) 8.41 - 8.52 (m, 1 H) 9.01 (dd, $J$=4.27, 1.71 Hz, 1 H) | LCMS (ESI+) calcd for C20H19N5O (M+H+): 346.16, found: 346.33 |
| ER-887722 | 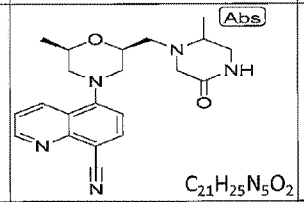 $C_{21}H_{25}N_5O_2$ | 379.5 | 0.0170 | > 2.0 | 5-((2R,6S)-2-methyl-6-((2-methyl-5-oxopiperazin-1-yl)methyl)morpholino)quinoline-8-carbonitrile | | |
| ER-887723 | 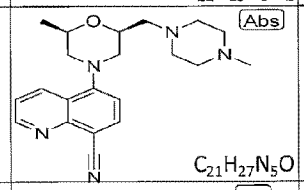 $C_{21}H_{27}N_5O$ | 365.5 | 0.0160 | >10 & < 30 | 5-((2R,6S)-2-methyl-6-((4-methylpiperazin-1-yl)methyl)morpholino)quinoline-8-carbonitrile | 1H NMR (400 MHz, METHANOL-d4) d ppm 1.25 (3 H, d) 2.57 - 2.75 (2 H, m) 2.93 (3 H, s) 3.11 - 3.22 (2 H, m) 3.31 - 3.42 (3 H, m) 3.44 - 3.60 (7 H, m) 4.04 - 4.18 (1 H, m) 4.29 - 4.43 (1 H, m) 7.16 - 7.27 (1 H, m) 7.54 - 7.64 (1 H, m) 8.06 - 8.14 (1 H, m) 8.57 - 8.65 (1 H, m) 8.90 - 8.98 (1 H, m) | LCMS (ESI+) calcd for C21 H27 N5 O (M+H+) 366.4, found 366.6 |
| ER-887724 | 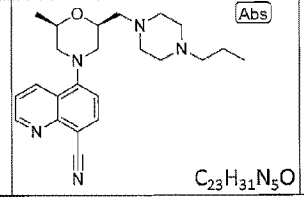 $C_{23}H_{31}N_5O$ | 393.5 | 0.0150 | > 30 | 5-((2R,6S)-2-methyl-6-((4-propylpiperazin-1-yl)methyl)morpholino)quinoline-8-carbonitrile | 1H NMR (400 MHz, METHANOL-d4) d ppm 0.99 (3 H, t) 1.23 (3 H, d) 1.65 - 1.78 (2 H, m) 2.56 - 2.66 (1 H, m) 2.68 - 2.77 (1 H, m) 2.91 - 3.00 (2 H, m) 3.02 - 3.16 (2 H, m) 3.27 (4 H, d) 3.34 - 3.49 (6 H, m) 3.98 - 4.15 (1 H, m) 4.21 - 4.37 (1 H, m) 7.16 - 7.27 (1 H, m) 7.57 - 7.63 (1 H, m) 8.07 - 8.17 (1 H, m) 8.54 - 8.65 (1 H, m) 8.90 - 8.99 (1 H, m) | LCMS (ESI+) calcd for C23 H31 N5 O (M+H+) 394.5, found 394.6 |

FIG. 6DD

| | | | | | | | |
|---|---|---|---|---|---|---|---|
| **ER-887725** | 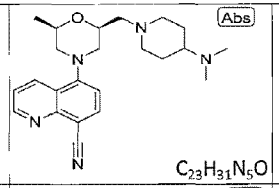 $C_{23}H_{31}N_5O$ | 393.5 | 0.0080 | 0.8 | 5-((2S,6R)-2-((4-(dimethylamino)piperidin-1-yl)methyl)-6-methylmorpholino)quinoline-8-carbonitrile | 1H NMR (400 MHz, METHANOL-d4) d ppm 1.27 (3 H, d) 2.03 - 2.26 (2 H, m) 2.28 - 2.46 (2 H, m) 2.62 - 2.78 (2 H, m) 2.90 (6 H, s) 3.13 - 3.22 (2 H, m) 3.29 - 3.44 (4 H, m) 3.47 - 3.63 (1 H, m) 3.78 - 3.96 (2 H, m) 4.06 - 4.19 (1 H, m) 4.35 - 4.52 (1 H, m) 7.16 - 7.32 (1 H, m) 7.54 - 7.66 (1 H, m) 8.12 (1 H, d) 8.61 (1 H, d) 8.88 - 9.02 (1 H, m) | LCMS (ESI+) calcd for C23 H31 N5 O (M+H+) 394.5, found 394.7 |
| **ER-887927** | 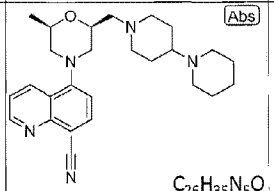 $C_{26}H_{35}N_5O$ | 433.6 | 0.0114 | 0.719 | 5-((2S,6R)-2-([1,4'-bipiperidin]-1'-ylmethyl)-6-methylmorpholino)quinoline-8-carbonitrile | 1H NMR (400 MHz, METHANOL-d4) d ppm 1.26 (3 H, d) 1.43 - 1.60 (1 H, m) 1.71 - 1.86 (3 H, m) 1.90 - 2.04 (2 H, m) 2.08 - 2.28 (2 H, m) 2.38 (2 H, br. s.) 2.63 - 2.79 (2 H, m) 3.00 - 3.05 (3 H, m) 3.30 - 3.42 (4 H, m) 3.52 (4 H, br. s.) 3.77 - 3.94 (2 H, m) 4.12 (1 H, d) 4.43 (1 H, br. s.) 7.23 (1 H, d) 7.49 - 7.71 (1 H, m) 8.11 (1 H, s) 8.50 - 8.66 (1 H, m) 8.85 - 8.99 (1 H, m) | LCMS (ESI+) calcd for C26 H35 N5 O (M+H+) 434.5, found 434.6 |
| **ER-887927** | 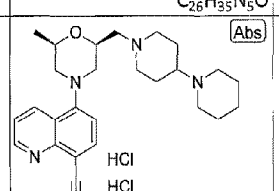 $C_{26}H_{37}Cl_2N_5O$ | 433.6 | 0.0109 | 0.41482 | 5-((2S,6R)-2-([1,4'-bipiperidin]-1'-ylmethyl)-6-methylmorpholino)quinoline-8-carbonitrile dihydrochloride | $^1$H NMR (400 MHz, DMSO-$d_6$) d ppm 1.21 (d, $J$=6.20 Hz, 3 H) 1.31 - 1.51 (m, 1 H) 1.71 (d, $J$=13.03 Hz, 1 H) 1.76 - 2.03 (m, 4 H) 2.11 - 2.30 (m, 2 H) 2.30 - 2.41 (m, 2 H) 2.60 - 2.80 (m, 2 H) 2.80 - 3.01 (m, 2 H) 3.03 - 3.21 (m, 2 H) 3.37 - 3.53 (m, 2 H) 3.63 (d, $J$=11.75 Hz, 1 H) 3.80 (d, $J$=12.60 Hz, 1 H) 3.97 - 4.15 (m, 1 H) 4.50 (t, $J$=9.19 Hz, 1 H) 7.19 - 7.34 (m, 1 H) 7.63 - 7.76 (m, 1 H) 8.29 (d, $J$=8.12 Hz, 1 H) 8.55 - 8.67 (m, 1 H) 9.07 (dd, $J$=4.27, 1.71 Hz, 1 H) 10.84 (br. s., 1 H) 10.94 (br. s., 1 H) | LCMS (ESI+) calcd for C26H37Cl2N5O (M+H+): 434.23, found: 434.55 |
| **ER-887928** | 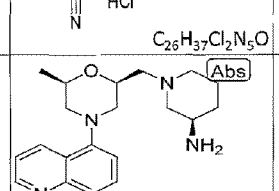 $C_{21}H_{27}N_5O$ | 365.5 | 0.1410 | > 2.0 | 5-((2S,6R)-2-(((R)-3-aminopiperidin-1-yl)methyl)-6-methylmorpholino)quinoline-8-carbonitrile | $^1$H NMR (400 MHz, METHANOL-$d_4$) d ppm 1.26 (d, $J$=6.15 Hz, 3 H) 1.41 (br. s., 1 H) 1.51 - 1.77 (m, 2 H) 1.78 - 2.02 (m, 2 H) 2.03 - 2.29 (m, 2 H) 2.57 - 2.81 (m, 2 H) 3.10 (s, 1 H) 3.05 (s, 1 H) 3.32 (br. s., 1 H) 3.40 (s, 1 H) 3.37 (s, 1 H) 3.59 (br. s., 2 H) 3.73 (br. s., 2 H) 4.12 (dd, $J$=8.20, 6.45 Hz, 2 H) 4.42 (br. s., 1 H) 4.59 - 4.82 (m, 1 H) 7.24 (d, $J$=8.20 Hz, 1 H) 7.44 - 7.65 (m, 1 H) 8.13 (d, $J$=7.91 Hz, 1 H) 8.61 (dd, $J$=8.50, 1.76 Hz, 1 H) 8.92 - 8.99 (m, 1 H) | |
| **ER-887960** | 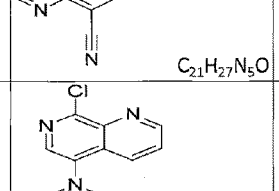 $C_{14}H_{16}ClN_3O$ | 277.8 | 1.1800 | >20 | (2R,6S)-4-(8-chloro-1,7-naphthyridin-5-yl)-2,6-dimethylmorpholine | | |

FIG. 6EE

| | | | | | | | |
|---|---|---|---|---|---|---|---|
| ER-888070 | 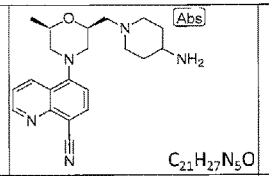 $C_{21}H_{27}N_5O$ | 365.5 | 0.0215 | 0.352 | 5-((2S,6R)-2-((4-aminopiperidin-1-yl)methyl)-6-methylmorpholino)quinoline-8-carbonitrile | 1H NMR (400 MHz, METHANOL-d4) d ppm 1.26 (3 H, d) 1.95 - 2.10 (2 H, m) 2.18 - 2.32 (2 H, m) 2.63 - 2.74 (2 H, m) 3.32 - 3.39 (5 H, m) 3.41 - 3.54 (2H, m) 3.72 - 3.92 (2 H, m) 4.08 - 4.18 (1 H, m) 4.36 - 4.52 (1 H, m) 7.19 - 7.27 (1 H, m) 7.54 - 7.64 (1 H, m) 8.04 - 8.17 (1 H, m) 8.54 - 8.66 (1 H, m) 8.89 - 9.02 (1 H, m) | LCMS (ESI+) calcd for C21 H27 N5 O (M+H+) 366.4, found 366.2 |
| ER-888137 | 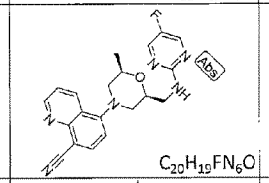 $C_{20}H_{19}FN_6O$ | 378.4 | 0.1860 | > 2.0 | 5-((2S,6R)-2-(((5-fluoropyrimidin-2-yl)amino)methyl)-6-methylmorpholino)quinoline-8-carbonitrile | $^1$H NMR (400 MHz, METHANOL-$d_4$) d ppm 1.20 - 1.27 (m, 7 H) 2.61 (d, $J$=11.72 Hz, 1 H) 2.65 - 2.71 (m, 1 H) 3.33 (s, 1 H) 3.36 (s, 1 H) 3.40 (s, 1 H) 3.43 (s, 1 H) 3.47 - 3.50 (m, 2 H) 4.81 - 4.90 (m, 18 H) 7.19 (d, $J$=8.20 Hz, 1 H) 7.56 - 7.59 (m, 1 H) 8.09 (s, 1 H) 8.11 (s, 1 H) 8.20 (s, 1 H) 8.38 (br. s., 1 H) 8.56 - 8.59 (m, 1 H) 8.92 - 8.94 (m, 1 H) | |
| ER-888200 | 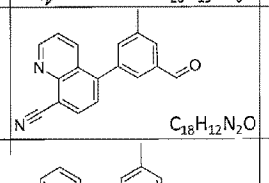 $C_{18}H_{12}N_2O$ | 272.306 | 0.8580 | > 2.0 | 5-(3-formyl-5-methylphenyl)quinoline-8-carbonitrile | $^1$H NMR (400 MHz, CHLOROFORM-$d$) d ppm 2.57 (s, 3 H) 7.50 - 7.57 (m, 2 H) 7.60 (d, $J$=7.48 Hz, 1 H) 7.74 - 7.81 (m, 1 H) 7.85 (d, $J$=0.85 Hz, 1 H) 8.15 - 8.28 (m, 2 H) 9.15 (dd, $J$=4.17, 1.60 Hz, 1 H) 10.10 (s, 1 H) | LCMS (ESI+) calcd for C18H12N2O (M+H+) 273.10, found: 273.26 |
| ER-888201 | 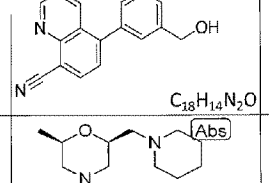 $C_{18}H_{14}N_2O$ | 274.322 | 0.1240 | > 2.0 | 5-(3-(hydroxymethyl)-5-methylphenyl)quinoline-8-carbonitrile | $^1$H NMR (400 MHz, CHLOROFORM-$d$) d ppm 2.47 (d, $J$=0.64 Hz, 3 H) 4.79 (s, 2 H) 7.15 - 7.22 (m, 1 H) 7.27 (m, 1 H) 7.31 - 7.37 (m, 1 H) 7.51 (dd, $J$=8.65, 4.17 Hz, 1 H) 7.56 (d, $J$=7.26 Hz, 1 H) 8.16 (d, $J$=7.48 Hz, 1 H) 8.31 (dd, $J$=8.76, 1.71 Hz, 1 H) 9.10 (dd, $J$=4.27, 1.71 Hz, 1 H) | LCMS (ESI+) calcd for C18H13ClN2 (M+H+) 275.11, found: 275.24 |
| ER-888202 | 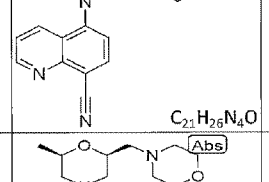 $C_{21}H_{26}N_4O$ | 350.5 | 0.0670 | > 2.0 | 5-((2R,6S)-2-methyl-6-(piperidin-1-ylmethyl)morpholino)quinoline-8-carbonitrile | $^1$H NMR (400 MHz, METHANOL-$d_4$) d ppm 1.27 (d, $J$=6.45 Hz, 4 H) 1.75 - 1.99 (m, 5 H) 2.65 - 2.75 (m, 3 H) 2.98 - 3.07 (m, 3 H) 3.19 - 3.25 (m, 2 H) 3.33 - 3.41 (m, 3 H) 3.62 (s, 1 H) 3.59 (s, 1 H) 4.11 - 4.16 (m, 1 H) 4.37 - 4.44 (m, 1 H) 4.80 - 4.84 (m, 3 H) 7.24 (d, $J$=7.91 Hz, 1 H) 7.59 - 7.63 (m, 1 H) 8.11 - 8.14 (m, 1 H) 8.63 (dd, $J$=8.50, 1.76 Hz, 1 H) 8.96 (dd, $J$=4.10, 1.76 Hz, 1 H) | |
| ER-888203 | 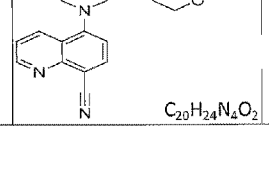 $C_{20}H_{24}N_4O_2$ | 350.5 | 0.2060 | > 2.0 | 5-((2R,6S)-2-methyl-6-(morpholinomethyl)morpholino) quinoline-8-carbonitrile | $^1$H NMR (400 MHz, METHANOL-$d_4$) d ppm 1.24 - 1.29 (m, 4 H) 2.65 - 2.76 (m, 2 H) 3.26 - 3.40 (m, 6 H) 4.09 - 4.16 (m, 1 H) 4.41 - 4.48 (m, 1 H) 4.80 - 4.86 (m, 18 H) 4.90 (s, 1 H) 7.23 (d, $J$=7.91 Hz, 1 H) 7.60 (dd, $J$=8.50, 4.39 Hz, 1 H) 8.11 (d, $J$=7.91 Hz, 1 H) 8.58 - 8.62 (m, 1 H) 8.92 - 8.95 (m, 1 H) | |

FIG. 6FF

| | | | | | | | |
|---|---|---|---|---|---|---|---|
| ER-888204 | 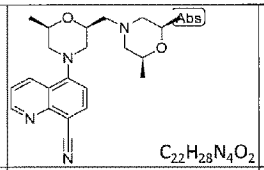 $C_{22}H_{28}N_4O_2$ | 380.5 | 0.3350 | > 2.0 | 5-((2S,6R)-2-(((2S,6R)-2,6-dimethylmorpholino)methyl)-6-methylmorpholino)quinoline-8-carbonitrile | $^1$H NMR (400 MHz, METHANOL-$d_4$) d ppm 1.19 - 1.29 (m, 11 H) 2.66 - 2.80 (m, 5 H) 3.29 - 3.41 (m, 4 H) 3.55 (dd, $J$=18.16, 12.89 Hz, 2 H) 4.12 - 4.18 (m, 1 H) 4.46 (br. s., 1 H) 4.80 - 4.86 (m, 11 H) 7.24 (d, $J$=8.20 Hz, 1 H) 7.62 (dd, $J$=8.50, 4.39 Hz, 1 H) 8.13 (d, $J$=7.91 Hz, 1 H) 8.62 (dd, $J$=8.50, 1.76 Hz, 1 H) 8.94 - 8.97 (m, 1 H) | |
| ER-888205 | 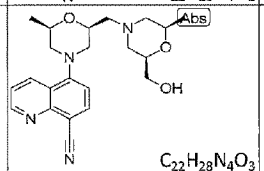 $C_{22}H_{28}N_4O_3$ | 396.5 | 0.3550 | > 2.0 | 5-((2S,6R)-2-(((2R,6R)-2-(hydroxymethyl)-6-methylmorpholino)methyl)-6-methylmorpholino)quinoline-8-carbonitrile | $^1$H NMR (400 MHz, METHANOL-$d_4$) d ppm 1.26 (dd, $J$=12.89, 6.15 Hz, 8 H) 2.66 - 2.84 (m, 4 H) 2.98 (t, $J$=11.72 Hz, 1 H) 3.30 - 3.42 (m, 5 H) 3.56 (d, $J$=12.01 Hz, 1 H) 3.60 - 3.66 (m, 4 H) 3.83 (d, $J$=10.25 Hz, 1 H) 4.13 - 4.18 (m, 1 H) 4.80 - 4.87 (m, 12 H) 7.25 (d, $J$=7.91 Hz, 1 H) 7.60 - 7.64 (m, 1 H) 8.13 (d, $J$=7.91 Hz, 1 H) 8.61 - 8.64 (m, 1 H) 8.94 - 8.97 (m, 1 H) | |
| ER-888285 | 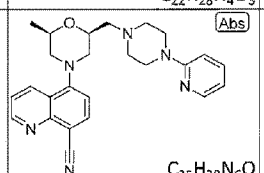 $C_{25}H_{28}N_6O$ | 428.5 | 0.1200 | > 2.0 | 5-((2R,6S)-2-methyl-6-((4-(pyridin-2-yl)piperazin-1-yl)methyl)morpholino)quinoline-8-carbonitrile | $^1$H NMR (400 MHz, METHANOL-$d_4$) d ppm 1.29 (d, $J$=6.15 Hz, 4 H) 2.67 - 2.78 (m, 2 H) 3.35 - 3.43 (m, 5 H) 3.53 (br. s., 2 H) 4.14 - 4.19 (m, 1 H) 4.47 (d, $J$=7.91 Hz, 1 H) 6.86 - 6.90 (m, 1 H) 7.08 (d, $J$=8.79 Hz, 1 H) 7.25 (d, $J$=7.91 Hz, 1 H) 7.62 (dd, $J$=8.50, 4.39 Hz, 1 H) 7.75 - 7.79 (m, 1 H) 8.12 - 8.15 (m, 2 H) 8.61 - 8.65 (m, 1 H) 8.95 - 8.97 (m, 1 H) | |
| ER-888286 | 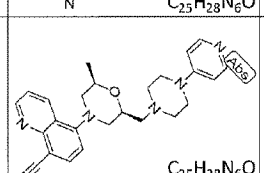 $C_{25}H_{28}N_6O$ | 428.5 | 1.3700 | > 2.0 | 5-((2R,6S)-2-methyl-6-((4-(pyridin-4-yl)piperazin-1-yl)methyl)morpholino)quinoline-8-carbonitrile | $^1$H NMR (400 MHz, METHANOL-$d_4$) d ppm 1.22 (d, $J$=6.15 Hz, 2 H) 2.60 - 2.80 (m, 2 H) 3.29 - 3.49 (m, 5 H) 3.56 (s, 1 H) 3.53 (s, 1 H) 3.94 - 4.13 (m, 2 H) 4.18 - 4.42 (m, 2 H) 4.43 - 4.66 (m, 1 H) 4.83 - 5.07 (m, 5 H) 7.25 - 7.48 (m, 2 H) 7.59 - 7.75 (m, 1 H) 8.18 (d, $J$=7.91 Hz, 1 H) 8.37 (d, $J$=7.62 Hz, 2 H) 8.63 - 8.77 (m, 1 H) 8.99 - 9.03 (m, 1 H) | |
| ER-888288 | 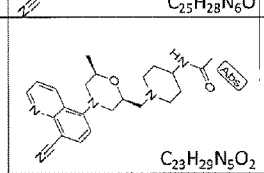 $C_{23}H_{29}N_5O_2$ | 407.5 | 0.0220 | > 10.0 | N-(1-(((2S,6R)-4-(8-cyanoquinolin-5-yl)-6-methylmorpholin-2-yl)methyl)piperidin-4-yl)acetamide | $^1$H NMR (400 MHz, METHANOL-$d_4$) d ppm 1.27 (d, $J$=6.45 Hz, 3 H) 1.72 - 1.85 (m, 1 H) 1.90 - 1.96 (m, 3 H) 2.09 - 2.20 (m, 2 H) 2.64 - 2.75 (m, 2 H) 3.11 - 3.20 (m, 2 H) 3.29 - 3.41 (m, 3 H) 3.73 (s, 1 H) 3.70 (s, 1 H) 3.85 - 3.92 (m, 1 H) 4.09 - 4.16 (m, 1 H) 4.41 (d, $J$=8.20 Hz, 1 H) 4.81 - 4.86 (m, 8 H) 7.23 (d, $J$=7.91 Hz, 1 H) 7.61 (dd, $J$=8.50, 4.39 Hz, 1 H) 8.12 (d, $J$=7.91 Hz, 1 H) 8.61 (dd, $J$=8.50, 1.47 Hz, 1 H) 8.95 (dd, $J$=4.10, 1.76 Hz, 1 H) | |
| ER-888288 | 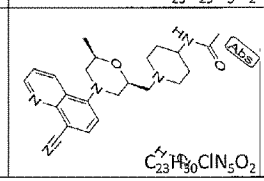 $C_{23}H_{30}ClN_5O_2$ | 407.5 | 0.0050 | > 10.0 | N-(1-(((2S,6R)-4-(8-cyanoquinolin-5-yl)-6-methylmorpholin-2-yl)methyl)piperidin-4-yl)acetamide hydrochloride | 1H NMR (400 MHz, METHANOL-d4) d ppm 1.27 (3 H, d) 1.69 - 1.86 (2 H, m) 1.93 (3 H, s) 2.04 - 2.20 (3 H, m) 2.60 - 2.79 (3 H, m) 3.07 - 3.22 (2 H, m) 3.36 - 3.42 (2 H, m) 3.67 - 3.76 (2 H, m) 3.82 - 3.94 (1 H, m) 4.08 - 4.18 (1 H, m) 4.35 - 4.46 (1 H, m) 7.15 - 7.28 (1 H, m) 7.54 - 7.66 (1 H, m) 8.05 - 8.17 (1 H, m) 8.56 - 8.65 (1 H, m) 8.89 - 8.99 (1 H, m) | LCMS (ESI+) calcd for C23 H29 N5 O2 (M+H+) 408.5, found 408.6 |

FIG. 6GG

| | | | | | | | |
|---|---|---|---|---|---|---|---|
| ER-888289 | 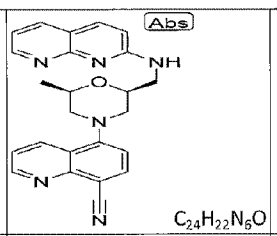 $C_{24}H_{22}N_6O$ | 410.5 | 0.0740 | > 2.0 | 5-((2S,6R)-2-(((1,8-naphthyridin-2-yl)amino)methyl)-6-methylmorpholino)quinoline-8-carbonitrile | $^1$H NMR (400 MHz, METHANOL-$d_4$) d ppm 1.17 (d, $J$=6.15 Hz, 3 H) 1.94 (s, 1 H) 2.64 (dd, $J$=12.01, 10.25 Hz, 2 H) 2.86 - 2.99 (m, 1 H) 3.29 - 3.48 (m, 3 H) 3.64 (s, 1 H) 3.61 (s, 1 H) 3.80 - 4.05 (m, 2 H) 4.37 - 4.57 (m, 1 H) 4.66 (dd, $J$=13.18, 8.20 Hz, 1 H) 4.78 - 4.98 (m, 6 H) 5.37 (dd, $J$=13.18, 2.64 Hz, 1 H) 7.15 (d, $J$=9.08 Hz, 1 H) 7.29 (d, $J$=7.91 Hz, 1 H) 7.42 - 7.59 (m, 1 H) 7.65 (dd, $J$=8.50, 4.10 Hz, 2 H) 8.04 - 8.29 (m, 2 H) 8.56 - 8.75 (m, 2 H) 8.76 - 8.90 (m, 1 H) 8.91 - 9.09 (m, 1 H) | |
| ER-888320 | 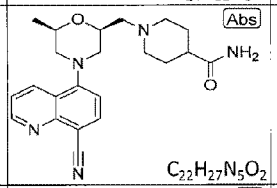 $C_{22}H_{27}N_5O_2$ | 393.5 | 0.0520 | > 2.0 | 1-(((2S,6R)-4-(8-cyanoquinolin-5-yl)-6-methylmorpholin-2-yl)methyl)piperidine-4-carboxamide | 1H NMR (400 MHz, METHANOL-d4) d ppm 1.25 (3 H, d) 2.05 - 2.23 (3 H, m) 2.35 - 2.47 (2 H, m) 2.61 - 2.77 (2 H, m) 3.10 - 3.21 (3 H, m) 3.31 - 3.42 (2 H, m) 3.68 (1 H, br. s.) 3.74 - 3.94 (2 H, m) 4.08 - 4.21 (1 H, m) 4.38 - 4.50 (1 H, m) 7.17 - 7.27 (1 H, m) 7.54 - 7.66 (1 H, m) 8.09 - 8.16 (1 H, m) 8.57 - 8.66 (1 H, m) 8.89 - 8.98 (1 H, m) | LCMS (ESI+) calcd for C22 H27 N5 O2 (M+H+) 394.4, found 394.5 |
| ER-888321 | 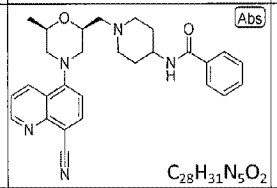 $C_{28}H_{31}N_5O_2$ | 469.6 | 0.0072 | > 2.0 | N-(1-(((2S,6R)-4-(8-cyanoquinolin-5-yl)-6-methylmorpholin-2-yl)methyl)piperidin-4-yl)benzamide | 1H NMR (400 MHz, METHANOL-d4) d ppm 1.27 (3 H, d) 1.85 - 2.08 (2 H, m) 2.10 - 2.35 (3 H, m) 2.59 - 2.82 (2 H, m) 3.24 - 3.31 (2 H, m) 3.33 - 3.43 (3 H, m) 3.72 - 3.82 (2 H, m) 4.09 - 4.21 (2 H, m) 4.35 - 4.50 (1 H, m) 7.21 - 7.27 (1 H, m) 7.39 - 7.48 (2 H, m) 7.49 - 7.54 (1 H, m) 7.58 - 7.66 (1 H, m) 7.72 - 7.86 (2 H, m) 8.08 - 8.19 (1 H, m) 8.57 - 8.69 (1 H, m) 8.90 - 9.02 (1 H, m) | LCMS (ESI+) calcd for C28 H31 N5 O2 (M+H+) 470.5, found 470.6 |
| ER-888322 | 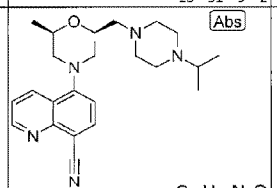 $C_{23}H_{31}N_5O$ | 393.5 | 0.0630 | > 2.0 | 5-((2S,6R)-2-((4-isopropylpiperazin-1-yl)methyl)-6-methylmorpholino)quinoline-8-carbonitrile | $^1$H NMR (400 MHz, METHANOL-$d_4$) d ppm 1.22 (d, $J$=6.15 Hz, 4 H) 1.31 - 1.36 (m, 8 H) 2.63 (dd, $J$=12.31, 10.25 Hz, 1 H) 2.72 (dd, $J$=12.01, 10.25 Hz, 1 H) 2.81 - 2.87 (m, 2 H) 3.29 - 3.41 (m, 6 H) 3.43 - 3.52 (m, 1 H) 4.04 - 4.09 (m, 1 H) 4.19 - 4.25 (m, 1 H) 7.22 (d, $J$=8.20 Hz, 1 H) 7.58 - 7.62 (m, 1 H) 8.12 (d, $J$=7.91 Hz, 1 H) 8.61 (dd, $J$=8.50, 1.76 Hz, 1 H) 8.95 (dd, $J$=4.39, 1.76 Hz, 1 H) | |
| ER-888330 | 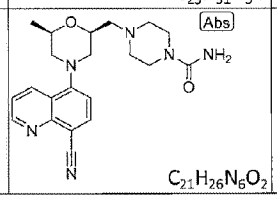 $C_{21}H_{26}N_6O_2$ | 394.5 | 0.4570 | > 2.0 | 4-(((2S,6R)-4-(8-cyanoquinolin-5-yl)-6-methylmorpholin-2-yl)methyl)piperazine-1-carboxamide | $^1$H NMR (400 MHz, METHANOL-$d_4$) d ppm 1.25 (br. s., 1 H) 1.33 (d, $J$=6.15 Hz, 3 H) 2.67 - 2.84 (m, 2 H) 3.23 (br. s., 2 H) 3.27 - 3.49 (m, 6 H) 4.19 (d, $J$=6.15 Hz, 2 H) 4.47 (br. s., 2 H) 4.84 - 5.07 (m, 6 H) 7.30 (d, $J$=8.20 Hz, 1 H) 7.49 - 7.77 (m, 2 H) 8.18 (d, $J$=8.20 Hz, 1 H) 8.67 (dd, $J$=8.50, 1.76 Hz, 1 H) 8.85 - 9.06 (m, 1 H) | |

FIG. 6HH

| | | | | | | | |
|---|---|---|---|---|---|---|---|
| ER-888479 | Abs $C_{27}H_{36}N_4O$ | 432.6 | 0.3220 | > 2.0 | 5-((2S,6R)-2-((4-cyclohexylpiperidin-1-yl)methyl)-6-methylmorpholino)quinoline-8-carbonitrile | 1H NMR (400 MHz, METHANOL-d4) d ppm 0.85 - 1.04 (2 H, m) 1.11 - 1.21 (3 H, m) 1.27 (3 H, d) 1.38 - 1.41 (2 H, m) 1.66 (1 H, d) 1.69 - 1.80 (5 H, m) 1.89 - 2.06 (2 H, m) 2.61 - 2.77 (2 H, m) 2.87 - 3.06 (2 H, m) 3.20 - 3.24 (2 H, m) 3.31 - 3.43 (3 H, m) 3.63 - 3.72 (2 H, m) 4.06 - 4.18 (1 H, m) 4.37 - 4.44 (1 H, m) 7.18 - 7.27 (1 H, m) 7.56 - 7.65 (1 H, m) 8.06 - 8.16 (1 H, m) 8.57 - 8.65 (1 H, m) 8.91 - 8.98 (1 H, m) | LCMS (ESI+) calcd for C27 H36 N4 O (M+H+) 433.6, found 433.2 |
| ER-888480 | Abs $C_{25}H_{33}N_5O$ | 419.6 | 0.0263 | 0.536 | 5-((2R,6S)-2-methyl-6-((4-(pyrrolidin-1-yl)piperidin-1-yl)methyl)morpholino)quinoline-8-carbonitrile | $^1$H NMR (400 MHz, METHANOL-$d_4$) d ppm 1.29 (d, $J$=6.45 Hz, 2 H) 1.98 (s, 2 H) 2.12 (s, 2 H) 2.45 (br. s., 2 H) 2.64 - 2.80 (m, 1 H) 3.19 (br. s., 2 H) 3.24 - 3.51 (m, 4 H) 3.70 (br. s., 1 H) 3.81 (br. s., 1 H) 3.88 (br. s., 1 H) 4.09 - 4.20 (m, 1 H) 4.45 (br. s., 1 H) 4.77 (s, 1 H) 4.81 - 4.88 (m, 16 H) 4.92 (s, 1 H) 7.26 (d, $J$=8.20 Hz, 1 H) 7.64 (dd, $J$=8.50, 4.10 Hz, 1 H) 8.15 (d, $J$=7.91 Hz, 1 H) 8.58 - 8.68 (m, 1 H) 8.90 - 9.06 (m, 1 H) | |
| ER-888603 | Abs $C_{24}H_{28}N_6O$ | 416.5 | 0.4060 | > 2.0 | 5-((2R,6R)-2-((4-cyclohexyl-1H-1,2,3-triazol-1-yl)methyl)-6-methylmorpholino)quinoline-8-carbonitrile | | |
| ER-888604 | Abs $C_{24}H_{22}N_6O$ | 410.5 | 0.1230 | > 2.0 | 5-((2R,6R)-2-methyl-6-((4-phenyl-1H-1,2,3-triazol-1-yl)methyl)morpholino)quinoline-8-carbonitrile | $^1$H NMR (400 MHz, METHANOL-$d_4$) d ppm 1.21 (d, $J$=6.15 Hz, 4 H) 2.58 - 2.73 (m, 2 H) 3.33 (d, $J$=12.01 Hz, 1 H) 3.44 - 3.50 (m, 1 H) 4.01 - 4.09 (m, 1 H) 4.36 - 4.42 (m, 1 H) 4.54 - 4.61 (m, 1 H) 4.63 - 4.69 (m, 1 H) 4.83 - 4.86 (m, 4 H) 7.21 (d, $J$=8.20 Hz, 1 H) 7.29 - 7.34 (m, 1 H) 7.38 - 7.43 (m, 2 H) 7.59 (dd, $J$=8.50, 4.10 Hz, 1 H) 7.77 - 7.81 (m, 2 H) 8.10 (d, $J$=7.91 Hz, 1 H) 8.33 (s, 1 H) 8.58 - 8.62 (m, 1 H) 8.91 - 8.94 (m, 1 H) | |
| ER-888605 | Abs $C_{26}H_{33}N_5O_2$ | 432.6 | 0.0360 | > 2.0 | 5-((2R,6S)-2-methyl-6-((2-oxo-[1,4'-bipiperidin]-1'-yl)methyl)morpholino)quinoline-8-carbonitrile | $^1$H NMR (400 MHz, METHANOL-$d_4$) d ppm 1.24 (d, $J$=6.45 Hz, 3 H) 1.32 (s, 1 H) 1.39 (s, 1 H) 1.57 - 1.82 (m, 4 H) 1.83 - 2.05 (m, 2 H) 2.17 - 2.42 (m, 2 H) 2.48 - 2.74 (m, 3 H) 2.74 - 2.90 (m, 2 H) 3.24 (br. s., 2 H) 3.30 (br. s., 1 H) 3.38 (s, 1 H) 3.35 (s, 1 H) 4.08 (d, $J$=8.20 Hz, 1 H) 4.23 (br. s., 1 H) 4.43 (s, 1 H) 4.40 (s, 1 H) 4.75 (br. s., 1 H) 4.80 (br. s., 1 H) 4.90 (s, 1 H) 7.22 (d, $J$=8.20 Hz, 2 H) 7.61 (dd, $J$=8.50, 4.39 Hz, 1 H) 8.12 (d, $J$=7.91 Hz, 1 H) 8.43 (br. s., 2 H) 8.62 (d, $J$=8.50 Hz, 2 H) 8.95 (d, $J$=4.10 Hz, 1 H) | |

FIG. 6II

| | | | | | | | |
|---|---|---|---|---|---|---|---|
| ER-888644 | 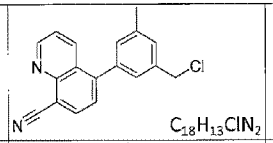 $C_{18}H_{13}ClN_2$ | 292.768 | 1.0940 | > 2.0 | 5-(3-(chloromethyl)-5-methylphenyl)quinoline-8-carbonitrile | $^1$H NMR (400 MHz, CHLOROFORM-*d*) d ppm 2.48 (s, 3 H) 4.65 (s, 2 H) 7.23 (s, 1 H) 7.27 - 7.31 (m, 1 H) 7.37 (s, 1 H) 7.53 (dd, *J*=8.65, 4.17 Hz, 1 H) 7.58 (d, *J*=7.48 Hz, 1 H) 8.18 (d, *J*=7.48 Hz, 1 H) 8.29 (dd, *J*=8.55, 1.71 Hz, 1 H) 9.14 (dd. *J*=4.27, 1.71 Hz, 1 H) | LCMS (ESI+) calcd for C18H14N2O (M+H+) 293.08, found: 293.26 |
| ER-888645 | 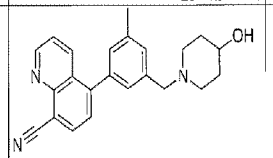 $C_{23}H_{23}N_3O$ | 357.455 | 0.3220 | > 2.0 | 5-(3-((4-hydroxypiperidin-1-yl)methyl)-5-methylphenyl)quinoline-8-carbonitrile | $^1$H NMR (400 MHz, CHLOROFORM-*d*) d ppm 1.52 - 1.78 (m, 2 H) 1.83 - 1.98 (m, 2 H) 2.21 (t, *J*=9.61 Hz, 2 H) 2.45 (s, 3 H) 2.70 - 2.88 (m, 2 H) 3.56 (s, 2 H) 3.65 - 3.85 (m, 1 H) 7.16 (s, 1 H) 7.25 - 7.31 (m, 2 H) 7.51 (dd, *J*=8.55, 4.06 Hz, 1 H) 7.58 (d, *J*=7.48 Hz, 1 H) 8.17 (d, *J*=7.48 Hz, 1 H) 8.33 (dd, *J*=8.55, 1.71 Hz, 1 H) 9.12 (dd, *J*=4.27, 1.71 Hz, 1 H) | LCMS (ESI+) calcd for C23H23N3O (M+H+) 358.19, found: 358.41 |
| ER-888646 | 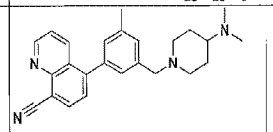 $C_{25}H_{28}N_4$ | 384.524 | 0.1380 | 0.4850 | 5-(3-((4-(dimethylamino)piperidin-1-yl)methyl)-5-methylphenyl)quinoline-8-carbonitrile | $^1$H NMR (400 MHz, CHLOROFORM-*d*) d ppm 1.51 - 1.68 (m, 2 H) 1.70 - 1.97 (m, 2 H) 1.99 - 2.11 (m, 2 H) 2.25 - 2.40 (m, 4 H) 2.45(s, 3 H) 3.00 (d, 2 H) 3.56 (s, 2 H) 7.16 (s, 1 H) 7.21 (s, 1 H) 7.24 - 7.31 (m, 1 H) 7.51 (dd, *J*=8.55, 4.27 Hz, 1 H) 7.57 (d, *J*=7.48 Hz, 1 H) 8.17 (d, *J*=7.48 Hz, 1 H) 8.33 (dd, *J*=8.76, 1.71 Hz, 1 H) 9.12 (dd, *J*=4.27, 1.71 Hz, 1 H) | LCMS (ESI+) calcd for C25H28N4 (M+H+) 385.23, found: 385.46 |
| ER-888647 | 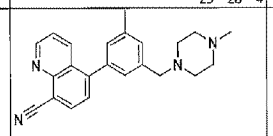 $C_{23}H_{24}N_4$ | 356.471 | 0.2300 | > 2.0 | 5-(3-methyl-5-((4-methylpiperazin-1-yl)methyl)phenyl)quinoline-8-carbonitrile | $^1$H NMR (400 MHz, CHLOROFORM-*d*) d ppm 2.31 (s, 3 H) 2.36 - 2.65 (m, 11 H) 3.59 (s, 2 H) 7.15 (s, 1 H) 7.22 (s, 1 H) 7.25 - 7.31 (m, 1 H) 7.51 (dd, *J*=8.65, 4.17 Hz, 1 H) 7.57 (d, *J*=7.48 Hz, 1 H) 8.17 (d, *J*=7.48 Hz, 1 H) 8.32 (dd, *J*=8.55, 1.71 Hz, 1 H) 9.12 (dd, *J*=4.27, 1.71 Hz, 1 H) | LCMS (ESI+) calcd for C23H24N4 (M+H+) 357.20, found: 357.43 |
| ER-888701 | 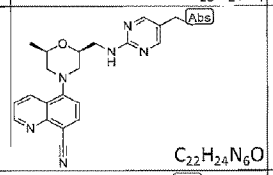 $C_{22}H_{24}N_6O$ | 388.5 | 0.0710 | > 2.0 | 5-((2S,6R)-2-(((5-ethylpyrimidin-2-yl)amino)methyl)-6-methylmorpholino)quinoline-8-carbonitrile | | |
| ER-888838 | 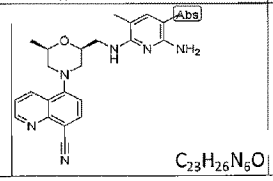 $C_{23}H_{26}N_6O$ | 402.5 | 0.0020 | > 2.0 | 5-((2S,6R)-2-(((6-amino-3,5-dimethylpyridin-2-yl)amino)methyl)-6-methylmorpholino)quinoline-8-carbonitrile | 1H NMR (400 MHz, METHANOL-d4) d ppm 1.22 (3 H, d) 1.96 (3 H, s) 1.98 (3 H, s) 2.57 - 2.69 (1 H, m) 2.72 - 2.85 (1 H, m) 3.30 - 3.44 (2 H, m) 3.45 - 3.63 (2 H, m) 4.03 - 4.10 (1 H, m) 4.13 - 4.25 (1 H, m) 7.13 (1 H, s) 7.16 - 7.24 (1 H, m) 7.51 - 7.63 (1 H, m) 8.03 - 8.15 (1 H, m) 8.52 - 8.61 (1 H, m) 8.86 - 8.96 (1 H, m) | LCMS (ESI+) calcd for C23 H26 N6 O (M+H+) 403.4, found 403.6 |

FIG. 6JJ

| | | | | | | | |
|---|---|---|---|---|---|---|---|
| ER-888896 | 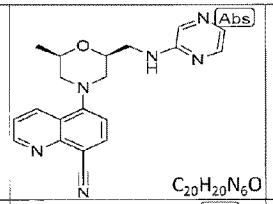 $C_{20}H_{20}N_6O$ | 360.4 | 0.2100 | > 30 | 5-((2R,6S)-2-methyl-6-((pyrazin-2-ylamino)methyl)morpholino)quinoline-8-carbonitrile | | |
| ER-888977 | 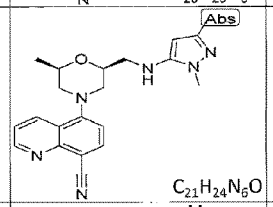 $C_{21}H_{24}N_6O$ | 376.5 | 0.2100 | > 2.0 | 5-((2S,6R)-2-(((1,3-dimethyl-1H-pyrazol-5-yl)amino)methyl)-6-methylmorpholino)quinoline-8-carbonitrile | | |
| ER-889363 | 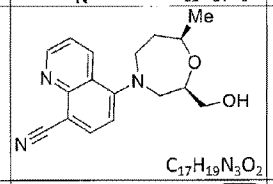 $C_{17}H_{19}N_3O_2$ | 297.4 | | | 5-((2R,7R)-2-(hydroxymethyl)-7-methyl-1,4-oxazepan-4-yl)quinoline-8-carbonitrile | CDCl3/400 MHz: 1.36 (d, 3H, J= 6.4 Hz), 1.96 (m, 1H), 2.18 (dd, 1H, J= 4.4 & 8.4 Hz), 2.27 (m, 1H), 3.39 (dd, 1H, J= 8.8 & 12.8 Hz), 3.45-3.69 (m, 5H), 4.01 (m, 1H), 4.14 (m, 1H), 7.13 (d, 1H, J= 8.0 Hz), 7.51 (dd, 1H, J= 4.4 & 8.4 Hz), 8.02 (d, 1H, J= 8.0 Hz), 8.52 (dd, 1H, J= 1.2 & 8.4 Hz), 9.08 (dd, 1H, J= 1.2 & 4.4 Hz). | |
| ER-889448 | 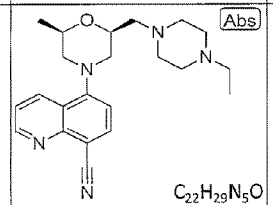 $C_{22}H_{29}N_5O$ | 379.5 | 0.0210 | > 2.0 | 5-((2S,6R)-2-((4-ethylpiperazin-1-yl)methyl)-6-methylmorpholino)quinoline-8-carbonitrile | $^1$H NMR (400 MHz, METHANOL-$d_4$) d ppm 1.17 - 1.38 (m, 4 H) 2.33 (s, 2 H) 2.54 - 2.81 (m, 4 H) 2.88 (br. s., 1 H) 2.97 - 3.13 (m, 3 H) 3.17 (br. s., 2 H) 3.29 - 3.53 (m, 3 H) 3.95 - 4.09 (m, 1 H) 4.13 (br. s., 1 H) 7.15 - 7.40 (m, 2 H) 7.56 - 7.83 (m, 2 H) 8.11 (d, $J$=7.91 Hz, 1 H) 8.28 (br. s., 1 H) 8.60 (d, $J$=8.79 Hz, 1 H) 8.90 - 9.16 (m, 1 H) | |
| ER-889469 | 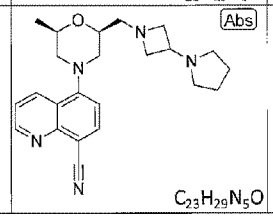 $C_{23}H_{29}N_5O$ | 391.5 | 0.0160 | 4.969 | 5-((2R,6S)-2-methyl-6-((3-(pyrrolidin-1-yl)azetidin-1-yl)methyl)morpholino)quinoline-8-carbonitrile | $^1$H NMR (400 MHz, METHANOL-$d_4$) d ppm 1.22 (d, $J$=6.15 Hz, 2 H) 1.88 - 2.04 (m, 3 H) 2.31 (s, 2 H) 2.53 - 2.75 (m, 2 H) 2.81 - 2.94 (m, 3 H) 2.94 - 3.09 (m, 2 H) 3.29 - 3.50 (m, 2 H) 3.61 - 3.81 (m, 2 H) 3.90 - 4.14 (m, 3 H) 7.07 - 7.29 (m, 2 H) 7.55 - 7.72 (m, 2 H) 7.99 - 8.23 (m, 2 H) 8.52 - 8.72 (m, 1 H) 8.78 - 9.01 (m, 1 H) | |

FIG. 6KK

| | | | | | | | |
|---|---|---|---|---|---|---|---|
| ER-889470 | 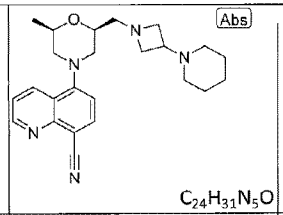 $C_{24}H_{31}N_5O$ | 405.5 | 0.0205 | 6.516 | 5-((2R,6S)-2-methyl-6-((3-(piperidin-1-yl)azetidin-1-yl)methyl)morpholino)quinoline-8-carbonitrile | $^1$H NMR (400 MHz, METHANOL-$d_4$) d ppm 1.23 (d, $J$=6.45 Hz, 2 H) 1.54 (d, $J$=4.39 Hz, 2 H) 1.60 - 1.83 (m, 3 H) 2.02 (d, $J$=16.11 Hz, 1 H) 2.32 (s, 2 H) 2.48 - 2.75 (m, 4 H) 2.88 (s, 1 H) 3.02 (s, 1 H) 3.06 - 3.25 (m, 2 H) 3.29 - 3.39 (m, 2 H) 3.40 - 3.61 (m, 1 H) 3.72 - 3.94 (m, 2 H) 3.99 - 4.26 (m, 3 H) 4.90 (br. s., 1 H) 7.22 (d, $J$=7.91 Hz, 1 H) 7.18 (d, $J$=7.91 Hz, 1 H) 7.51 - 7.75 (m, 2 H) 8.12 (d, $J$=7.91 Hz, 2 H) 8.19 (br. s., 2 H) 8.39 - 8.63 (m, 1 H) 8.95 (dd, $J$=4.39, 1.46 Hz, 1 H) | |
| ER-889504 | 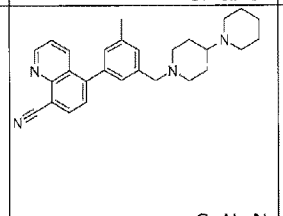 $C_{28}H_{32}N_4$ | 424.589 | 0.4590 | 0.3170 | 5-(3-([1,4'-bipiperidin]-1'-ylmethyl)-5-methylphenyl)quinoline-8-carbonitrile | $^1$H NMR (400 MHz, CHLOROFORM-$d$) d ppm 1.44 (d, $J$=4.91 Hz, 2 H) 1.50 - 1.69 (m, 6 H) 1.79 (d, $J$=11.96 Hz, 2 H) 2.00 (td, $J$=11.75, 2.14 Hz, 2 H) 2.29 (t, $J$=11.43 Hz, 1 H) 2.45 (s, 3 H) 2.51 (br. s., 4 H) 2.99 (d, $J$=11.75 Hz, 2 H) 3.54 (s, 2 H) 7.15 (s, 1 H) 7.21 (s, 1 H) 7.24 - 7.30 (m, 1 H) 7.46 - 7.55 (m, 1 H) 7.57 (m, $J$=7.48 Hz, 1 H) 8.17 (m, $J$=7.48 Hz, 1 H) 8.33 (dd, $J$=8.55, 1.71 Hz, 1 H) 9.12 (dd, $J$=4.27, 1.71 Hz, 1 H) | LCMS (ESI+) calcd for C28H32N4 (M+H+) 425.27, found: 425.48 |
| ER-889556 | 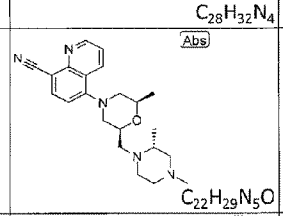 $C_{22}H_{29}N_5O$ | 379.5 | 0.0855 | > 2.0 | 5-((2S,6R)-2-(((R)-2,4-dimethylpiperazin-1-yl)methyl)-6-methylmorpholino)quinoline-8-carbonitrile | $^1$H NMR (400 MHz, METHANOL-$d_4$) d ppm 1.01 - 1.10 (m, 4 H) 1.16 - 1.23 (m, 4 H) 1.87 - 1.97 (m, 1 H) 2.16 - 2.25 (m, 5 H) 2.29 - 2.38 (m, 1 H) 2.46 - 2.70 (m, 7 H) 2.84 - 2.98 (m, 2 H) 3.25 - 3.37 (m, 3 H) 3.96 - 4.12 (m, 2 H) 4.80 - 4.85 (m, 1 H) 7.11 - 7.18 (m, 1 H) 7.52 - 7.59 (m, 1 H) 8.00 - 8.08 (m, 1 H) 8.52 - 8.59 (m, 1 H) 8.86 - 8.92 (m, 1 H) | |
| ER-889557 | 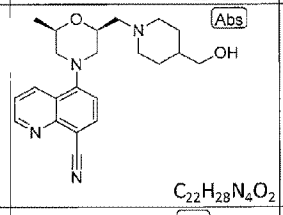 $C_{22}H_{28}N_4O_2$ | 380.5 | 0.4970 | > 2.0 | 5-((2S,6R)-2-((4-(hydroxymethyl)piperidin-1-yl)methyl)-6-methylmorpholino)quinoline-8-carbonitrile | $^1$H NMR (400 MHz, METHANOL-$d_4$) d ppm 1.26 (d, $J$=6.15 Hz, 3 H) 1.47 - 1.69 (m, 2 H) 1.75 (d, $J$=3.22 Hz, 1 H) 1.83 - 2.04 (m, 2 H) 2.29 (s, 1 H) 2.53 - 2.75 (m, 2 H) 2.88 (s, 1 H) 2.94 - 3.10 (m, 2 H) 3.13 - 3.25 (m, 2 H) 3.29 - 3.50 (m, 3 H) 3.53 - 3.71 (m, 2 H) 3.90 - 4.17 (m, 1 H) 4.27 - 4.50 (m, 1 H) 7.09 - 7.29 (m, 1 H) 7.53 - 7.67 (m, 1 H) 7.96 - 8.16 (m, 1 H) 8.38 (br. s., 1 H) 8.49 - 8.76 (m, 1 H) 8.77 - 8.99 (m, 1 H) | |
| ER-889571 | 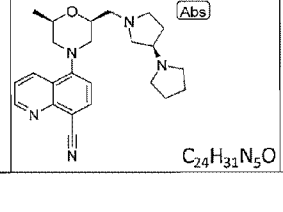 $C_{24}H_{31}N_5O$ | 405.5 | 0.0050 | 5.01 | 5-((2S,6R)-2-((R)-[1,3'-bipyrrolidin]-1'-ylmethyl)-6-methylmorpholino)quinoline-8-carbonitrile | 1H NMR (400 MHz, METHANOL-d4) d ppm 1.18 - 1.25 (3 H, d) 1.94 - 2.01 (3 H, m) 2.29 - 2.36 (4 H, m) 2.60 - 2.73 (4 H, m) 2.91 - 3.00 (1 H, m) 3.09 - 3.19 (3 H, m) 3.32 - 3.40 (2 H, m) 7.15 - 7.26 (3 H, m) 7.58 - 7.63 (1 H, m) 7.64 - 7.71 (2 H, m) 8.08 - 8.16 (1 H, m) 8.43 - 8.49 (2 H, m) 8.57 - 8.66 (1 H, m) 8.91 - 9.01 (1 H, m) | LCMS (ESI+) calcd for C24 H31 N5 O (M+H+) 406.5, found 406.4 |

FIG. 6LL

| | | | | | | | |
|---|---|---|---|---|---|---|---|
| ER-889572 | 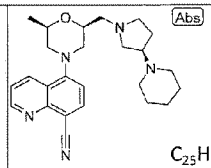 $C_{25}H_{33}N_5O$ | 419.6 | 0.2515 | > 2.0 | 5-((2R,6S)-2-methyl-6-(((R)-3-(piperidin-1-yl)pyrrolidin-1-yl)methyl)morpholino)quinoline-8-carbonitrile | | |
| ER-889601 | 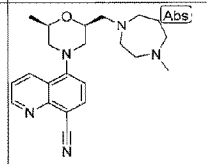 $C_{22}H_{29}N_5O$ | 379.5 | 0.0185 | 9.4 | 5-((2R,6S)-2-methyl-6-((4-methyl-1,4-diazepan-1-yl)methyl)morpholino)quinoline-8-carbonitrile | $^1$H NMR (400 MHz, METHANOL-$d_4$) d ppm 1.23 (d, $J$=6.15 Hz, 3 H) 2.22 (br. s., 2 H) 2.29 (s, 4 H) 2.55 - 2.81 (m, 2 H) 2.93 (s, 2 H) 3.04 - 3.25 (m, 2 H) 3.29 - 3.40 (m, 2 H) 3.45 (br. s., 3 H) 3.66 (br. s., 3 H) 3.90 - 4.18 (m, 2 H) 4.32 (d, $J$=7.91 Hz, 1 H) 7.04 - 7.27 (m, 4 H) 7.38 - 7.61 (m, 1 H) 7.66 (d, $J$=8.20 Hz, 3 H) 7.97 - 8.12 (m, 1 H) 8.59 (d, $J$=7.62 Hz, 1 H) 8.92 (d, $J$=2.64 Hz, 1 H) 8.82 - 9.00 (m, 1 H) | |
| ER-889602 | 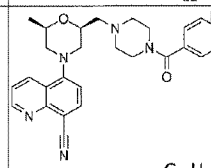 $C_{27}H_{29}N_5O_2$ | 455.6 | 0.0530 | > 2.0 | 5-((2S,6R)-2-((4-benzoylpiperazin-1-yl)methyl)-6-methylmorpholino)quinoline-8-carbonitrile | $^1$H NMR (400 MHz, METHANOL-$d_4$) d ppm 1.22 (dd, $J$=8.15, 0.88 Hz, 4 H) 2.31 (s, 1 H) 2.58 - 2.86 (m, 8 H) 3.30 - 3.46 (m, 3 H) 3.51 (br. s., 2 H) 3.79 (br. s., 3 H) 3.91 - 4.11 (m, 2 H) 4.13 - 4.26 (m, 1 H) 7.04 - 7.30 (m, 2 H) 7.31 - 7.46 (m, 6 H) 7.49 - 7.70 (m, 2 H) 7.76 - 8.00 (m, 2 H) 8.04 - 8.19 (m, 2 H) 8.47 - 8.62 (m, 1 H) 8.78 - 8.95 (m, 1 H) | |
| ER-889728 | 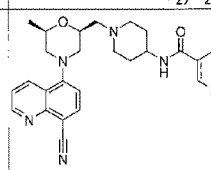 $C_{27}H_{30}N_6O_2$ | 470.6 | 0.0370 | > 2.0 | N-(1-(((2S,6R)-4-(8-cyanoquinolin-5-yl)-6-methylmorpholin-2-yl)methyl)piperidin-4-yl)nicotinamide | $^1$H NMR (400 MHz, METHANOL-$d_4$) d ppm 1.06 (s, 1 H) 1.22 (d, $J$=6.45 Hz, 1 H) 1.30 (s, 1 H) 1.40 (s, 1 H) 1.47 (s, 1 H) 1.69 (br. s., 1 H) 1.92 (br. s., 1 H) 2.26 (s, 1 H) 2.51 (s, 1 H) 2.66 (s, 1 H) 2.62 (s, 1 H) 3.01 (s, 1 H) 3.17 (br. s., 1 H) 3.21 - 3.30 (m, 2 H) 3.34 (br. s., 1 H) 3.39 (br. s., 1 H) 3.87 (s, 1 H) 4.06 (br. s., 1 H) 4.15 (br. s., 1 H) 4.21 (s, 1 H) 4.37 (s, 1 H) 4.84 (s, 2 H) 5.00 (br. s., 1 H) 7.22 (d, $J$=8.20 Hz, 1 H) 7.50 (br. s., 1 H) 7.59 (br. s., 1 H) 7.82 (br. s., 1 H) 8.12 (d, $J$=7.62 Hz, 1 H) 8.21 (br. s., 1 H) 8.35 - 8.56 (m, 1 H) 8.56 - 8.78 (m, 1 H) 8.93 (d, $J$=4.10 Hz, 1 H) | |
| ER-889729 | 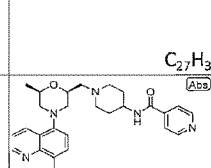 $C_{27}H_{30}N_6O_2$ | 470.6 | 0.0220 | > 2.0 | N-(1-(((2S,6R)-4-(8-cyanoquinolin-5-yl)-6-methylmorpholin-2-yl)methyl)piperidin-4-yl)isonicotinamide | | |

FIG. 6MM

| | | | | | | | |
|---|---|---|---|---|---|---|---|
| ER-889734 | 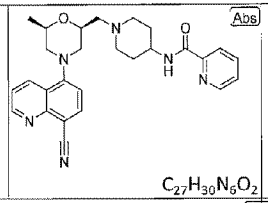 $C_{27}H_{30}N_6O_2$ | 470.6 | 0.2690 | > 2.0 | N-(1-(((2S,6R)-4-(8-cyanoquinolin-5-yl)-6-methylmorpholin-2-yl)methyl)piperidin-4-yl)picolinamide | $^1$H NMR (400 MHz, METHANOL-$d_4$) d ppm 1.28 (d, $J$=6.15 Hz, 3 H) 1.75 - 1.97 (m, 2 H) 2.08 (br. s., 2 H) 2.59 - 2.84 (m, 3 H) 2.84 - 3.09 (m, 2 H) 3.24 - 3.49 (m, 4 H) 3.94 - 4.22 (m, 2 H) 4.30 (br. s., 1 H) 7.26 (d, $J$=8.20 Hz, 1 H) 7.51 - 7.60 (m, 1 H) 7.64 (dd, $J$=8.50, 4.39 Hz, 1 H) 7.91 - 8.02 (m, 1 H) 8.04 - 8.30 (m, 2 H) 8.45 (s, 1 H) 8.55 - 8.82 (m, 2 H) 8.94 - 9.16 (m, 1 H) | |
| ER-889744 | 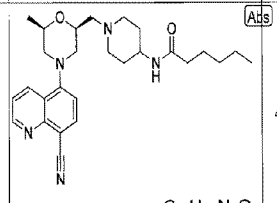 $C_{27}H_{37}N_5O_2$ | 463.6 | 0.0590 | > 2.0 | N-(1-(((2S,6R)-4-(8-cyanoquinolin-5-yl)-6-methylmorpholin-2-yl)methyl)piperidin-4-yl)hexanamide | $^1$H NMR (400 MHz, METHANOL-$d_4$) d ppm 0.72 - 0.96 (m, 2 H) 1.13 - 1.39 (m, 4 H) 1.46 - 1.75 (m, 3 H) 1.77 (s, 1 H) 1.88 (s, 1 H) 2.03 - 2.28 (m, 2 H) 2.40 (br. s., 1 H) 2.51 - 2.80 (m, 2 H) 2.91 (br. s., 1 H) 3.06 (d, $J$=6.45 Hz, 1 H) 3.17 (br. s., 1 H) 3.24 - 3.33 (m, 2 H) 3.33 - 3.55 (m, 2 H) 3.70 (br. s., 1 H) 4.07 (br. s., 1 H) 4.20 (br. s., 1 H) 4.87 (s, 3 H) 7.24 (d, $J$=8.20 Hz, 1 H) 7.63 (dd, $J$=8.50, 4.39 Hz, 1 H) 7.85 (s, 1 H) 8.14 (d, $J$=7.91 Hz, 1 H) 8.50 (s, 1 H) 8.57 - 8.81 (m, 1 H) 8.97 (dd, $J$=4.39, 1.46 Hz, 1 H) | |
| ER-889745 | 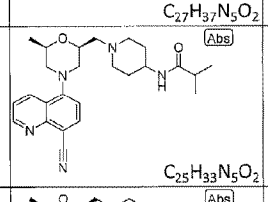 $C_{25}H_{33}N_5O_2$ | 435.6 | 0.0675 | 0.0052? >10.0 | N-(1-(((2S,6R)-4-(8-cyanoquinolin-5-yl)-6-methylmorpholin-2-yl)methyl)piperidin-4-yl)isobutyramide | | |
| ER-889745 | 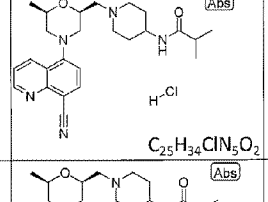 $C_{25}H_{34}ClN_5O_2$ | 472.0 | 0.0062 | > 10.0 | N-(1-(((2S,6R)-4-(8-cyanoquinolin-5-yl)-6-methylmorpholin-2-yl)methyl)piperidin-4-yl)isobutyramide hydrochloride | 1H NMR (400 MHz, METHANOL-d4) d ppm 0.97 - 1.08 (7 H, m) 1.11 - 1.17 (2 H, m) 1.20 - 1.29 (5 H, m) 1.96 - 2.04 (2 H, m) 2.32 - 2.45 (1 H, m) 2.60 - 2.74 (2 H, m) 2.95 - 3.03 (1 H, m) 3.32 - 3.40 (2 H, m) 7.19 - 7.26 (1 H, m) 7.57 - 7.66 (1 H, m) 8.08 - 8.17 (1 H, m) 8.26 - 8.37 (5 H, m) 8.59 - 8.66 (1 H, m) 8.92 - 8.99 (1 H, m) | LCMS (ESI+) calcd for C25 H33 N5 O2 (M+H+) 436.5, found 436.6 |
| ER-889746 | 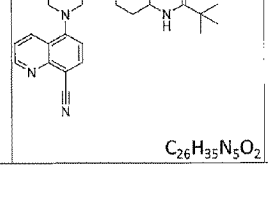 $C_{26}H_{35}N_5O_2$ | 449.6 | 0.1100 | 0.0049 | N-(1-(((2S,6R)-4-(8-cyanoquinolin-5-yl)-6-methylmorpholin-2-yl)methyl)piperidin-4-yl)pivalamide | $^1$H NMR (400 MHz, METHANOL-$d_4$) d ppm 1.18 (s, 2 H) 1.28 (t, $J$=6.15 Hz, 2 H) 1.44 (s, 1 H) 1.72 - 1.90 (m, 2 H) 1.93 (br. s., 1 H) 2.02 (br. s., 1 H) 2.23 (d, $J$=9.96 Hz, 1 H) 2.57 - 2.83 (m, 2 H) 2.92 (d, $J$=7.62 Hz, 1 H) 3.08 (br. s., 1 H) 3.20 - 3.35 (m, 3 H) 3.35 - 3.56 (m, 2 H) 3.89 (br. s., 2 H) 4.13 (br. s., 1 H) 4.29 (br. s., 1 H) 4.34 (br. s., 1 H) 4.88 (s, 3 H) 7.23 - 7.45 (m, 1 H) 7.56 - 7.82 (m, 1 H) 8.11 - 8.24 (m, 1 H) 8.32 (s, 1 H) 8.66 (d, $J$=8.79 Hz, 1 H) 8.95 - 9.11 (m, 1 H) | |

FIG. 6NN

| | | | | | | | |
|---|---|---|---|---|---|---|---|
| ER-889822 | 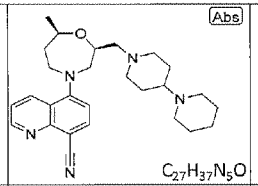 $C_{27}H_{37}N_5O$ | 447.6 | 0.1470 | 0.155 | 5-((2S,7R)-2-([1,4'-bipiperidin]-1'-ylmethyl)-7-methyl-1,4-oxazepan-4-yl)quinoline-8-carbonitrile | 1H NMR (400 MHz, CDCl3) d ppm 1.30 (3 H), 1.58 (5 H), 1.77 (3 H), 1.9 (3 H), 2.02 (2 H), 2.20 (2 H), 2.35 (1 H), 2.49 (2 H), 2.67 (3 H), 2.84 (1 H), 3.04 (1 H), 3.28 (1 H), 3.49 (2 H), 3.63 (1 H), 3.96 (1 H), 4.06 (1 H), 7.12 (1 H), 7.48 (1 H), 7.99 (1 H), 8.50 (1 H), 9.05 (1 H). | LCMS (ESI+) calcd for C27 H37 N5 O (M+H+) 448.6, found 448.5 |
| ER-890093 | 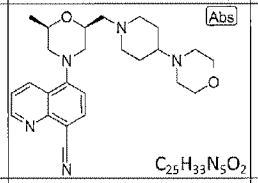 $C_{25}H_{33}N_5O_2$ | 435.6 | 0.0400 | > 2.0 | 5-((2R,6S)-2-methyl-6-((4-morpholinopiperidin-1-yl)methyl)morpholino)quinoline-8-carbonitrile | H NMR (400 MHz, DMSO-d6) d ppm 1.19 (3 H), 1.71 (1 H), 1.99 (1 H), 2.42 (1 H), 2.68 (6 h), 3.06 (1 H), 3.21 (1 H), 3.32 (6 H), 3.40 (2 H), 3.66 (4 H), 4.03 (1 H), 4.36 (1 H), 7.25 (1 H), 7.70 (1 H), 8.28 (1 H), 8.60 (1 H), 9.07 (1 H). | LCMS (ESI+) calcd for C25H33N5O2 (M+H+) 436.27, found: 436.41 |
| ER-890094 | 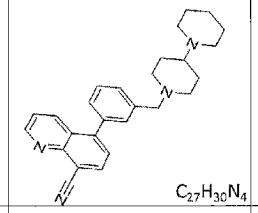 $C_{27}H_{30}N_4$ | 410.562 | 0.7930 | 0.3870 | 5-(3-([1,4'-bipiperidin]-1'-ylmethyl)phenyl)quinoline-8-carbonitrile | H NMR (400 MHz, CHLOROFORM-d1) d ppm 1.56 (2 H), 1.81 (6 H), 2.06 (4 H), 2.78 (4 H), 3.04 (3 H), 3.61 (2 H), 7.35 (1 H), 7.47 (4 H), 7.58 (1 H), 8.18 (1 H), 8.30 (1 H), 9.13 (1 H). | LCMS (ESI+) calcd for C27H30N4 (M+H+) 411.25, found: 411.39 |
| ER-890104 | 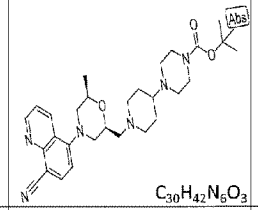 $C_{30}H_{42}N_6O_3$ | 534.7 | 0.2880 | 2.845 | tert-butyl 4-(1-(((2S,6R)-4-(8-cyanoquinolin-5-yl)-6-methylmorpholin-2-yl)methyl)piperidin-4-yl)piperazine-1-carboxylate | | |
| ER-890105 | 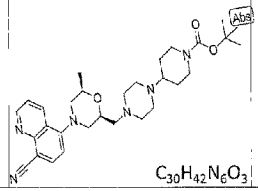 $C_{30}H_{42}N_6O_3$ | 534.7 | 0.1020 | 7.002 | tert-butyl 4-(4-(((2S,6R)-4-(8-cyanoquinolin-5-yl)-6-methylmorpholin-2-yl)methyl)piperazin-1-yl)piperidine-1-carboxylate | $^1$H NMR (400 MHz, CHLOROFORM-*d*) d ppm 1.27 (d, *J*=6.41 Hz, 4 H) 1.40 (m, 1 H) 1.57 (s, 9 H) 1.80 (m, 2 H) 2.35 (m, 1 H) 2.50 - 2.74 (m, 12 H) 3.24 - 3.35 (m, 1 H) 3.41 (d, *J*=11.75 Hz, 1 H) 3.97 - 4.13 (m, 2 H) 7.09 (d, *J*=8.12 Hz, 1 H) 7.47 - 7.55 (m, 1 H) 8.05 (d, *J*=7.90 Hz, 1 H) 8.46 (dd, *J*=8.55, 1.71 Hz, 1 H) 9.08 (dd, *J*=4.06, 1.71 Hz, 1 H) | LCMS (ESI+) calcd for C30H42N6O3 (M+H+) 535.34, found: 535.49 |

FIG. 6OO

| | | | | | | | |
|---|---|---|---|---|---|---|---|
| ER-890106 | 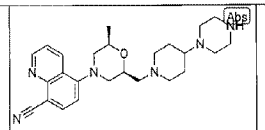 $C_{25}H_{34}N_6O$ | 434.6 | 0.0209 | 0.0973 | 5-((2R,6S)-2-methyl-6-((4-(piperazin-1-yl)piperidin-1-yl)methyl)morpholino)quinoline-8-carbonitrile | $^1$H NMR (400 MHz, CHLOROFORM-*d*) d ppm 1.26 (d, *J*=6.20 Hz, 3 H) 1.44 - 1.62 (m, 2 H) 1.62 - 1.88 (m, 4 H) 1.95 - 2.07 (m, 1 H) 2.08 - 2.26 (m, 2 H) 2.38 - 2.47 (m, 1 H) 2.47 - 2.59 (m, 4 H) 2.59 - 2.72 (m, 2 H) 2.81 - 2.95 (m, 4 H) 3.03 - 3.15 (m, 1 H) 3.23 - 3.33 (m, 1 H) 3.33 - 3.50 (m, 1 H) 3.50 - 3.62 (m, 1 H) 3.94 - 4.11 (m, 2 H) 7.00 - 7.14 (m, 1 H) 7.50 (dd, *J*=8.55, 4.27 Hz, 1 H) 7.97 - 8.08 (m, 1 H) 8.45 (dd, *J*=8.55, 1.71 Hz, 1 H) 9.00 - 9.12 (m, 1 H) | LCMS (ESI+) calcd for C25H34N6O (M+H+) 435.28, found: 435.41 |
| ER-890107 | 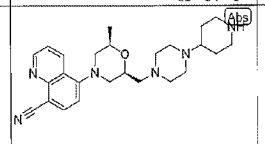 $C_{25}H_{34}N_6O$ | 434.6 | 0.2173 | 0.7285 | 5-((2R,6S)-2-methyl-6-((4-(piperidin-4-yl)piperazin-1-yl)methyl)morpholino)quinoline-8-carbonitrile | $^1$H NMR (400 MHz, CHLOROFORM-*d*) d ppm 1.26 (d, *J*=6.20 Hz, 3 H) 1.39 (qd, *J*=12.03, 4.06 Hz, 2 H) 1.82 (m, 2 H) 2.32 (tt, *J*=11.43, 3.63 Hz, 1 H) 2.48 (d, *J*=6.20 Hz, 1 H) 2.44 - 2.77 (m, 5 H) 3.13 - 3.16 (m, 2 H) 3.29 (dt, *J*=11.70, 1.95 Hz, 1 H) 3.36 - 3.48 (m, 1 H) 3.95 - 4.15 (m, 2 H) 7.09 (d, *J*=7.90 Hz, 1 H) 7.51 (dd, *J*=8.55, 4.27 Hz, 1 H) 8.04 (d, *J*=7.90 Hz, 1 H) 8.46 (dd, *J*=8.55, 1.71 Hz, 1 H) 9.08 (dd, *J*=4.06, 1.71 Hz, 1 H) | LCMS (ESI+) calcd for C25H34N6O (M+H+) 435.28, found: 435.41 |
| ER-890108 | 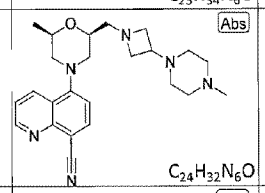 $C_{24}H_{32}N_6O$ | 420.6 | 0.1570 | > 2.0 | 5-((2R,6S)-2-methyl-6-((3-(4-methylpiperazin-1-yl)azetidin-1-yl)methyl)morpholino)quinoline-8-carbonitrile | $^1$H NMR (400 MHz, METHANOL-$d_4$) d ppm 1.11 - 1.30 (m, 3 H) 1.35 - 1.46 (m, 1 H) 2.04 (s, 1 H) 2.45 (br. s., 1 H) 2.55 - 2.81 (m, 3 H) 2.87 - 3.03 (m, 5 H) 3.05 - 3.15 (m, 1 H) 3.20 (br. s., 1 H) 3.29 - 3.41 (m, 3 H) 3.42 - 3.67 (m, 3 H) 4.07 (br. s., 1 H) 4.10 - 4.23 (m, 1 H) 4.90 (br. s., 1 H) 7.23 (d, *J*=8.20 Hz, 2 H) 7.61 (dd, *J*=8.50, 4.10 Hz, 1 H) 8.12 (d, *J*=7.91 Hz, 1 H) 8.34 (br. s., 2 H) 8.55 - 8.78 (m, 1 H) 8.90 - 9.04 (m, 1 H) | |
| ER-890112 | 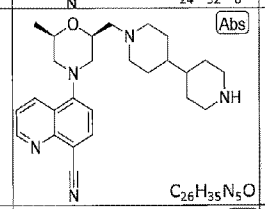 $C_{26}H_{35}N_5O$ | 433.6 | 0.0290 | 0.103 | 5-((2S,6R)-2-([4,4'-bipiperidin]-1-ylmethyl)-6-methylmorpholino)quinoline-8-carbonitrile | $^1$H NMR (400 MHz, DICHLOROMETHANE-$d_2$) d ppm 1.19 - 1.41 (m, 6 H) 1.47 - 1.62 (m, 4 H) 1.76 - 1.89 (m, 5 H) 2.42 - 2.54 (m, 2 H) 2.59 - 2.66 (m, 2 H) 2.71 - 2.82 (m, 3 H) 2.90 - 2.96 (m, 1 H) 3.24 - 3.40 (m, 6 H) 3.61 (d, *J*=12.01 Hz, 1 H) 3.98 - 4.06 (m, 1 H) 4.36 (dd, *J*=9.96, 7.62 Hz, 1 H) 5.30 - 5.31 (m, 1 H) 7.05 (d, *J*=7.91 Hz, 1 H) 7.52 (dd, *J*=8.50, 4.10 Hz, 1 H) 8.01 (d, *J*=7.91 Hz, 1 H) 8.36 (s, 3 H) 8.47 (dd, *J*=8.50, 1.46 Hz, 1 H) 9.00 - 9.02 (m, 1 H) | |
| ER-890113 | 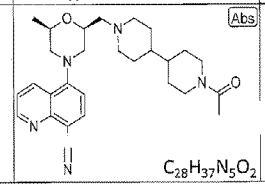 $C_{28}H_{37}N_5O_2$ | 475.6 | 0.1200 | > 2.0 | 5-((2S,6R)-2-((1'-acetyl-[4,4'-bipiperidin]-1-yl)methyl)-6-methylmorpholino)quinoline-8-carbonitrile | | |

FIG. 6PP

| | | | | | | | |
|---|---|---|---|---|---|---|---|
| ER-890114 | 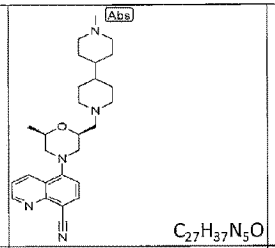 $C_{27}H_{37}N_5O$ | 447.6 | 0.0045 | 0.0665 | 5-((2R,6S)-2-methyl-6-((1'-methyl-[4,4'-bipiperidin]-1-yl)methyl)morpholino)quinoline-8-carbonitrile | $^1$H NMR (400 MHz, METHANOL-$d_4$) d ppm 1.27 (d, $J$=6.15 Hz, 3 H) 1.49 (br. s., 3 H) 1.55 (s, 2 H) 1.59 (s, 1 H) 1.86 (s, 1 H) 1.99 (s, 2 H) 2.33 (s, 3 H) 2.51 - 2.79 (m, 3 H) 2.82 (s, 2 H) 2.90 - 3.08 (m, 3 H) 3.10 - 3.26 (m, 2 H) 3.26 - 3.33 (m, 2 H) 3.39 (d, $J$=12.60 Hz, 2 H) 3.50 (d, $J$=10.84 Hz, 2 H) 3.57 - 3.78 (m, 2 H) 4.12 (d, $J$=6.15 Hz, 1 H) 4.43 (br. s., 2 H) 4.52 - 4.68 (m, 1 H) 4.77 - 5.03 (m, 6 H) 7.16 - 7.42 (m, 3 H) 7.58 - 7.79 (m, 2 H) 8.14 (d, $J$=7.91 Hz, 1 H) 8.30 (br. s., 2 H) 8.64 (dd, $J$=8.50, 1.47 Hz, 2 H) 8.97 (dd, $J$=4.39, 1.46 Hz, 2 H) | |
| ER-890119 | 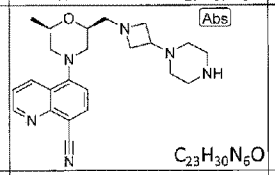 $C_{23}H_{30}N_6O$ | 406.5 | 0.0110 | 0.141 | 5-((2R,6S)-2-methyl-6-((3-(piperazin-1-yl)azetidin-1-yl)methyl)morpholino)quinoline-8-carbonitrile | $^1$H NMR (400 MHz, METHANOL-$d_4$) d ppm 1.25 (d, $J$=6.45 Hz, 3 H) 2.52 - 2.78 (m, 6 H) 3.01 - 3.25 (m, 4 H) 3.29 - 3.53 (m, 5 H) 3.97 - 4.16 (m, 3 H) 4.16 - 4.44 (m, 4 H) 7.23 (d, $J$=8.20 Hz, 1 H) 7.61 (dd, $J$=8.50, 4.39 Hz, 1 H) 8.05 - 8.21 (m, 2 H) 8.60 (dd, $J$=8.50, 1.76 Hz, 2 H) 8.89 - 9.11 (m, 1 H) | |
| ER-890120 | 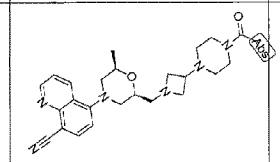 $C_{25}H_{32}N_6O_2$ | 448.6 | 0.1340 | > 2.0 | 5-((2S,6R)-2-((3-(4-acetylpiperazin-1-yl)azetidin-1-yl)methyl)-6-methylmorpholino)quinoline-8-carbonitrile | $^1$H NMR (400 MHz, METHANOL-$d_4$) d ppm 1.24 (d, $J$=6.15 Hz, 3 H) 2.00 (s, 1 H) 2.06 (s, 3 H) 2.31 - 2.41 (m, 4 H) 2.61 - 2.74 (m, 2 H) 3.21 - 3.25 (m, 1 H) 3.29 - 3.39 (m, 3 H) 3.52 - 3.60 (m, 4 H) 3.89 - 3.98 (m, 2 H) 4.04 - 4.09 (m, 1 H) 4.14 - 4.22 (m, 3 H) 4.85 (s, 5 H) 7.23 (d, $J$=7.91 Hz, 1 H) 7.61 (dd, $J$=8.50, 4.39 Hz, 1 H) 8.12 (d, $J$=7.91 Hz, 1 H) 8.32 (s, 2 H) 8.58 - 8.62 (m, 1 H) 8.95 (dd, $J$=4.10, 1.76 Hz, 1 H) | |
| ER-890121 | 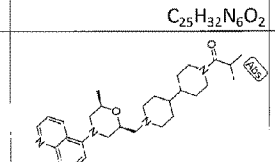 $C_{30}H_{41}N_5O_2$ | 503.7 | 0.2420 | > 2.0 | 5-((2S,6R)-2-((1'-isobutyryl-[4,4'-bipiperidin]-1-yl)methyl)-6-methylmorpholino)quinoline-8-carbonitrile | $^1$H NMR (400 MHz, METHANOL-$d_4$) d ppm 0.98 - 1.24 (m, 6 H) 1.29 (d, $J$=6.15 Hz, 2 H) 1.48 (br. s., 1 H) 1.51 - 1.69 (m, 2 H) 1.70 - 1.95 (m, 2 H) 1.95 - 2.18 (m, 2 H) 2.33 (s, 1 H) 2.43 - 2.63 (m, 1 H) 2.63 - 2.83 (m, 2 H) 2.87 - 3.13 (m, 3 H) 3.17 - 3.34 (m, 3 H) 3.34 - 3.53 (m, 2 H) 3.67 (d, $J$=11.43 Hz, 2 H) 4.04 - 4.26 (m, 2 H) 4.43 (br. s., 1 H) 4.59 (d, $J$=12.31 Hz, 1 H) 4.87 (s, 3 H) 7.15 - 7.42 (m, 2 H) 7.59 - 7.81 (m, 1 H) 8.15 (d, $J$=7.91 Hz, 1 H) 8.25 (s, 1 H) 8.59 - 8.80 (m, 1 H) 8.94 - 9.16 (m, 1 H) | |
| ER-890122 | 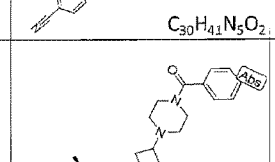 $C_{30}H_{34}N_6O_2$ | 510.6 | 0.0600 | 6.11 | 5-((2S,6R)-2-((3-(4-benzoylpiperazin-1-yl)azetidin-1-yl)methyl)-6-methylmorpholino)quinoline-8-carbonitrile | $^1$H NMR (400 MHz, METHANOL-$d_4$) d ppm 1.26 (d, $J$=6.15 Hz, 3 H) 2.34 (br. s., 2 H) 2.46 (br. s., 2 H) 2.54 - 2.80 (m, 2 H) 2.94 - 3.22 (m, 2 H) 3.23 - 3.44 (m, 4 H) 3.48 (br. s., 2 H) 3.61 - 3.88 (m, 4 H) 4.00 - 4.22 (m, 3 H) 4.82 - 5.05 (m, 3 H) 7.25 (d, $J$=7.91 Hz, 1 H) 7.35 - 7.55 (m, 3 H) 7.55 - 7.79 (m, 2 H) 8.02 - 8.28 (m, 1 H) 8.42 (s, 1 H) 8.52 - 8.80 (m, 2 H) 8.92 - 9.11 (m, 1 H) | |

FIG. 6QQ

| | | | | | | |
|---|---|---|---|---|---|---|
| ER-890142 | 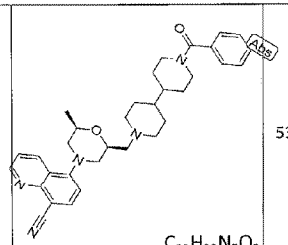 $C_{33}H_{39}N_5O_2$ | 537.7 | 0.0880 | 1.271 | 5-((2S,6R)-2-((1'-benzoyl-[4,4'-bipiperidin]-1-yl)methyl)-6-methylmorpholino)quinoline-8-carbonitrile | $^1$H NMR (400 MHz, METHANOL-$d_4$) d ppm 1.21 (br. s., 2 H) 1.24 - 1.37 (m, 3 H) 1.40 - 1.67 (m, 4 H) 1.71 (d, $J$=13.48 Hz, 1 H) 1.88 (br. s., 1 H) 1.93 - 2.15 (m, 2 H) 2.31 (s, 1 H) 2.62 - 2.89 (m, 3 H) 2.90 - 3.14 (m, 3 H) 3.15 - 3.32 (m, 3 H) 3.33 - 3.53 (m, 2 H) 3.55 - 3.81 (m, 3 H) 4.07 - 4.20 (m, 1 H) 4.29 - 4.56 (m, 1 H) 4.68 (d, $J$=9.67 Hz, 1 H) 4.87 (d, $J$=0.59 Hz, 2 H) 7.09 - 7.31 (m, 2 H) 7.33 - 7.49 (m, 4 H) 7.51 - 7.69 (m, 2 H) 7.84 - 8.06 (m, 1 H) 8.13 (dd, $J$=7.91, 0.88 Hz, 1 H) 8.31 (d, $J$=0.88 Hz, 1 H) 8.49 - 8.70 (m, 1 H) 8.90 - 8.99 (m, 1 H) | |
| ER-890186 | 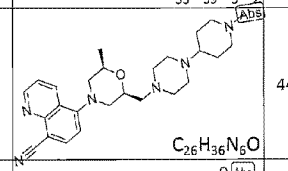 $C_{26}H_{36}N_6O$ | 448.6 | 0.0135 | 1.3615 | 5-((2R,6S)-2-methyl-6-((4-(1-methylpiperidin-4-yl)piperazin-1-yl)methyl)morpholino)quinoline-8-carbonitrile | $^1$H NMR (400 MHz, CHLOROFORM-$d$) d ppm 1.26 (d, $J$=6.20 Hz, 3 H) 1.48 - 1.66 (m, 2 H) 1.66 - 1.85 (m, 4 H) 1.85 - 2.00 (m, 2 H) 2.15 - 2.32 (m, 4 H) 2.37 - 2.74 (m, 12 H) 2.90 (d, 2 H) 3.29 (dt, $J$=11.86, 1.98 Hz, 1 H) 3.35 - 3.48 (m, 1 H) 3.92 - 4.15 (m, 2 H) 7.08 (d, $J$=8.12 Hz, 1 H) 7.50 (dd, $J$=8.55, 4.27 Hz, 1 H) 8.04 (d, $J$=7.90 Hz, 1 H) 8.45 (dd, $J$=8.55, 1.82 Hz, 1 H) 9.08 (dd, $J$=4.06, 1.71 Hz, 1 H) | LCMS (ESI+) calcd for C26H36N6O (M+H+) 449.30, found: 449.4 |
| ER-890187 | 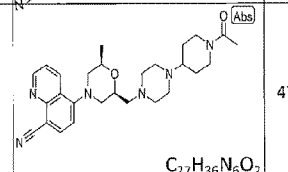 $C_{27}H_{36}N_6O_2$ | 476.6 | 0.0870 | > 2.0 | 5-((2S,6R)-2-((4-(1-acetylpiperidin-4-yl)piperazin-1-yl)methyl)-6-methylmorpholino)quinoline-8-carbonitrile | $^1$H NMR (400 MHz, CHLOROFORM-$d$) d ppm 1.26 (d, $J$=6.20 Hz, 3 H) 1.31 - 1.50 (m, 2 H) 1.79 - 1.95 (m, 2 H) 2.09 (s, 3 H) 2.42 - 2.71 (m, 12 H) 2.95 - 3.12 (m, 1 H) 3.29 (d, $J$=11.75 Hz, 1 H) 3.41 (dd, $J$=11.96, 2.14 Hz, 1 H) 3.78 - 3.90 (m, 1 H) 3.94 - 4.16 (m, 2 H) 4.57 - 4.69 (m, 1 H) 7.09 (d, $J$=7.90 Hz, 1 H) 7.51 (dd, $J$=8.55, 4.27 Hz, 1 H) 8.04 (d, $J$=7.90 Hz, 1 H) 8.45 (dd, $J$=8.55, 1.71 Hz, 1 H) 9.08 (dd, $J$=4.17, 1.60 Hz, 1 H) | LCMS (ESI+) calcd for C27H36N6O2 (M+H+) 477.29, found: 477.39 |
| ER-890188 | 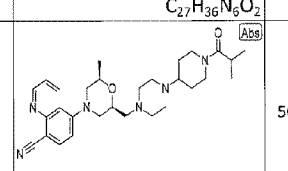 $C_{29}H_{40}N_6O_2$ | 504.7 | 0.0870 | > 2.0 | 5-((2S,6R)-2-((4-(1-isobutyrylpiperidin-4-yl)piperazin-1-yl)methyl)-6-methylmorpholino)quinoline-8-carbonitrile | $^1$H NMR (400 MHz, CHLOROFORM-$d$) d ppm 1.06 - 1.20 (m, 6 H) 1.26 (d, $J$=6.20 Hz, 3 H) 1.32 - 1.52 (m, 2 H) 1.89 (t, $J$=14.31 Hz, 2 H) 2.41 - 2.71 (m, 12 H) 2.74 - 2.88 (m, 1 H) 3.02 (t, $J$=12.39 Hz, 1 H) 3.29 (d, $J$=11.75 Hz, 1 H) 3.41 (d, $J$=11.96 Hz, 1 H) 3.90 - 4.18 (m, 3 H) 4.67 (d, $J$=12.60 Hz, 1 H) 7.09 (d, $J$=8.12 Hz, 1 H) 7.51 (dd, $J$=8.55, 4.06 Hz, 1 H) 8.04 (d, $J$=7.90 Hz, 1 H) 8.45 (dd, $J$=8.55, 1.50 Hz, 1 H) 9.08 (dd, $J$=4.06, 1.50 Hz, 1 H) | LCMS (ESI+) calcd for C29H40N6O2 (M+H+)505.32, found: 505.44 |
| ER-890189 | 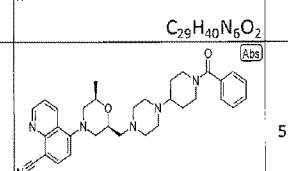 $C_{32}H_{38}N_6O_2$ | 538.7 | 0.1100 | > 2.0 | 5-((2S,6R)-2-((4-(1-benzoylpiperidin-4-yl)piperazin-1-yl)methyl)-6-methylmorpholino)quinoline-8-carbonitrile | $^1$H NMR (400 MHz, CHLOROFORM-$d$) d ppm 1.26 (d, $J$=6.20 Hz, 3 H) 1.32 - 1.53 (m, 2 H) 1.80 -1.96 (m, 2 H) 2.03 (s, 1 H) 2.36 - 2.74 (m, 12 H) 2.79 (m, 1 H) 3.00 (m, 1 H) 3.29 (d, $J$=11.75 Hz, 1 H) 3.41 (d, $J$=11.75 Hz, 1 H) 3.80 (br. s., 1 H) 3.94 - 4.16 (m, 2 H) 4.74 (br. s., 1 H) 7.09 (d, $J$=8.12 Hz, 1 H) 7.34 - 7.45 (m, 5 H) 7.51 (dd, $J$=8.55, 4.27 Hz, 1 H) 8.04 (d, $J$=7.90 Hz, 1 H) 8.46 (dd, $J$=8.55, 1.50 Hz, 1 H) 9.08 (dd, $J$=4.27, 1.50 Hz, 1 H) | LCMS (ESI+) calcd for C32H38N6O2 (M+H+) 539.31, found: 539.42 |

FIG. 6RR

| | | | | | | | |
|---|---|---|---|---|---|---|---|
| ER-890190 | 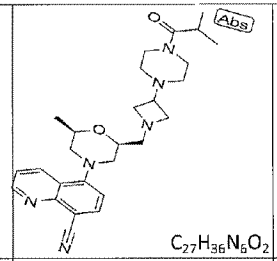 $C_{27}H_{36}N_6O_2$ | 476.6 | 0.2150 | > 30 | 5-((2S,6R)-2-((3-(4-isobutyrylpiperazin-1-yl)azetidin-1-yl)methyl)-6-methylmorpholino)quinoline-8-carbonitrile | | |
| ER-890219 | 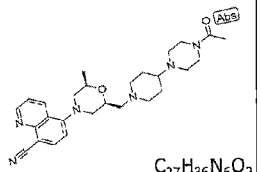 $C_{27}H_{36}N_6O_2$ | 476.6 | 0.1110 | 6.44 | 5-((2S,6R)-2-((4-(4-acetylpiperazin-1-yl)piperidin-1-yl)methyl)-6-methylmorpholino)quinoline-8-carbonitrile | H NMR (400 MHz, CHLOROFORM-d1) d ppm 1.27 (3 H), 1.67 (3 H), 1.86 (3 H), 2.09 (3 H), 2.59 (10 H), 3.28 (2 H), 3.47 (4 H), 3.64 (2 H), 4.07 (1 H), 7.08 (1 H), 7.54 (1 H), 8.03 (1 H), 8.50 (1 H), 9.08 (1 H). | |
| ER-890221 | 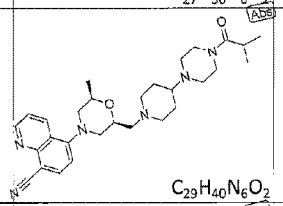 $C_{29}H_{40}N_6O_2$ | 504.7 | 0.1240 | 3.82 | 5-((2S,6R)-2-((4-(4-isobutyrylpiperazin-1-yl)piperidin-1-yl)methyl)-6-methylmorpholino)quinoline-8-carbonitrile | H NMR (400 MHz, CHLOROFORM-d1) d ppm 1.12 (6 H), 1.26 (3 H), 1.72 (2 H), 1.85 (2 H), 2.35 (3 H), 2.55 (4 H), 2.64 (4 H), 2.78 (1 H), 3.06 (1 H), 3.28 (2 H), 3.43 (1 H), 3.53 (2 H), 3.64 (2 H), 4.05 (1 H), 4.25 (1 H), 7.07 (1 H), 7.52 (1 H), 8.03 (1 H), 8.48 (1 H), 9.07 (1 H). | LCMS (ESI+) calcd for C29H40N6O2 (M+H+) 505.32, found: 505.49 |
| ER-890222 | 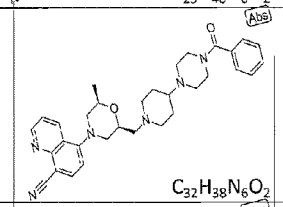 $C_{32}H_{38}N_6O_2$ | 538.7 | 0.1130 | 3.05 | 5-((2S,6R)-2-((4-(4-benzoylpiperazin-1-yl)piperidin-1-yl)methyl)-6-methylmorpholino)quinoline-8-carbonitrile | H NMR (400 MHz, METHANOL-d4) d ppm 1.22 (3 H), 1.57 (2 H), 1.86 (2 H), 2.12 (2 H), 2.31 (1 H), 2.45 (1 H), 2.53 (2 H), 2.64 (4 H), 1.22 (1 H), 3.17 (1 H), 3.33 (4 H), 3.38 (1 H), 3.44 (1 H), 3.76 (1 H), 4.04 (1 H), 4.12 (1 H), 7.22 (1 H), 7.39 (2 H), 7.45 (3 H), 7.62 (1 H), 8.12 (1 H), 8.63 (1 H), 8.96 (1 H). | LCMS (ESI+) calcd for C32H38N6O2 (M+H+) 539.31, found: 539.52 |
| ER-890223 | 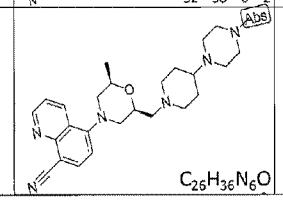 $C_{26}H_{36}N_6O$ | 448.6 | 0.0137 | 0.181 | 5-((2R,6S)-2-methyl-6-((4-(4-methylpiperazin-1-yl)piperidin-1-yl)methyl)morpholino)quinoline-8-carbonitrile | H NMR (400 MHz, CHLOROFORM-d1) d ppm 1.24 (3 H), 1.58 (2 H), 1.83 (2 H), 2.07 (1 H), 2.18 (1 H), 2.36 (4 H), 2.47 (1 H), 2.64 (11 H), 2.95 (1 H), 3.13 (1 H), 3.27 (1 H), 3.41 (1 H), 4.01 (1 H), 4.07 (1 H), 7.06 (1 H), 7.49 (1 H), 8.02 (1 H), 8.44 (1 H), 9.05 (1 H). | LCMS (ESI+) calcd for C26H36N6O (M+H+) 449.30, found: 449.41 |

FIG. 6SS

| | | | | | | | |
|---|---|---|---|---|---|---|---|
| ER-890223 | 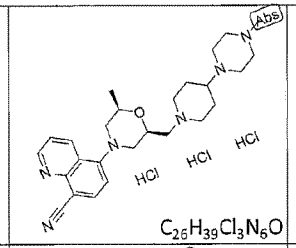 $C_{26}H_{39}Cl_3N_6O$ | 558.0 | 0.0010 | 0.083 | 5-((2R,6S)-2-methyl-6-((4-(4-methylpiperazin-1-yl)piperidin-1-yl)methyl)morpholino)quinoline-8-carbonitrile trihydrochloride | $^1$H NMR (400 MHz, DMSO-$d_6$) d ppm 1.12 - 1.28 (m, 3 H) 2.09 - 2.43 (m, 4 H) 2.60 - 2.77 (m, 2 H) 2.83 (br. s., 3 H) 2.97 - 3.21 (m, 4 H) 3.23 - 3.53 (m, 8 H) 3.67 (br. s., 4 H) 3.74 - 4.01 (m, 6 H) 4.02 - 4.17 (m, 1 H) 4.48 (t, $J$=9.08 Hz, 1 H) 7.27 (m, $J$=8.12 Hz, 1 H) 7.70 (dd, $J$=8.65, 4.17 Hz, 1 H) 8.29 (m, $J$=8.12 Hz, 1 H) 8.62 (dd, $J$=8.55, 1.50 Hz, 1 H) 9.07 (dd, $J$=4.27, 1.50 Hz, 1 H) 10.70 (br. s., 1 H) | LCMS (ESI+) calcd for C26H36N6O (M+H+) 449.30, found: 449.41 |
| ER-890244 | 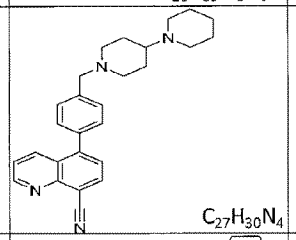 $C_{27}H_{30}N_4$ | 410.562 | 0.0225 | 0.0465 | 5-(4-([1,4'-bipiperidin]-1'-ylmethyl)phenyl)quinoline-8-carbonitrile | H NMR (400 MHz, METHANOL-d4) d ppm 1.50 (2 H), 1.65 (6 H), 1.91 (2 H), 2.08 (2 H), 2.44 (1 H), 2.67 (4 H), 3.04 (2 H), 3.61 (2 H), 7.45 (2 H), 7.52 (2 H), 8.26 (1 H), 8.37 (1 H), 9.01 (1 H). | LCMS (ESI+) calcd for C27H30N4 (M+H+) 411.25, found: 411.35 |
| ER-890250 | 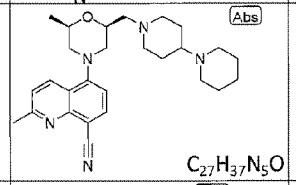 $C_{27}H_{37}N_5O$ | 447.6 | 2.0590 | 0.841 | 5-((2S,6R)-2-([1,4'-bipiperidin]-1'-ylmethyl)-6-methylmorpholino)-2-methylquinoline-8-carbonitrile | H NMR (400 MHz, DMSO-d6) d ppm 1.14 (3 H), 1.35 (4 H), 1.44 (4 H), 1.63 (2 H), 1.94 (3 H), 2.39 (6 H), 2.48 (1 H), 2.55 (1 H), 2.58 (1 H), 2.61 (1 H), 2.71 (3 H), 2.84 (1 H), 3.00 (1 H), 3.98 (2 H), 7.13 (1 H), 7.54 (1 H), 8.17 (1 H), 8.42 (1 H). | LCMS (ESI+) calcd for C27H37N5O (M+H+) 448.30, found: 448.4 |
| ER-890252 | 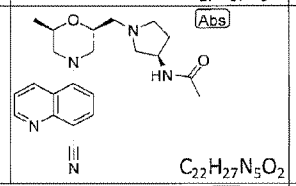 $C_{22}H_{27}N_5O_2$ | 393.5 | 0.0330 | > 10.0 | N-((R)-1-(((2S,6R)-4-(8-cyanoquinolin-5-yl)-6-methylmorpholin-2-yl)methyl)pyrrolidin-3-yl)acetamide | H NMR (400 MHz, CHLOROFORM-d1) d ppm 1.25 (3 H), 1.80 (1 H), 1.94 (2 H), 1.99 (1 H), 2.35 (1 H), 2.65 (3 H), 2.78 (1 H), 2.84 (1 H), 2.92 (1 H), 3.13 (1 H), 3.27 (2 H), 3.37 (1 H), 4.04 (1 H), 4.22 (1 H), 4.59 (1 H), 6.84 (1 H), 7.05 (1 H), 7.50 (1 H), 7.99 (1 H), 8.43 (1 H), 9.03 (1 H). | LCMS (ESI+) calcd for C22H27N5O2 (M+H+) 394.22, found: 394.22 |
| ER-890253 | 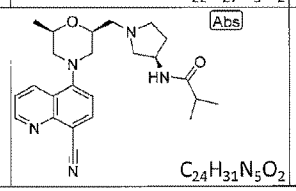 $C_{24}H_{31}N_5O_2$ | 421.5 | 0.1610 | > 10.0 | N-((R)-1-(((2S,6R)-4-(8-cyanoquinolin-5-yl)-6-methylmorpholin-2-yl)methyl)pyrrolidin-3-yl)isobutyramide | H NMR (400 MHz, CHLOROFORM-d1) d ppm 1.09 (6 H), 1.24 (3 H), 1.60 (1 H), 2.28 (2 H), 2.38 (1 H), 2.66 (6 H), 3.01 (1 H), 3.27 (1 H), 3.37 (1 H), 4.03 (2 H), 4.42 (1 H), 6.02 (1 H), 7.05 (1 H), 7.50 (1 H), 7.98 (1 H), 8.43 (1 H), 9.02 (1 H). | LCMS (ESI+) calcd for C24H31N5O2 (M+H+) 422.25, found: 422.31 |

FIG. 6TT

| | | | | | | | |
|---|---|---|---|---|---|---|---|
| ER-890311 | 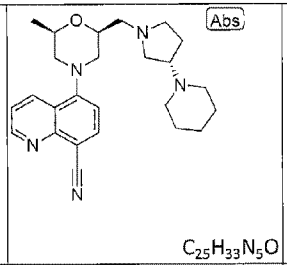 $C_{25}H_{33}N_5O$ | 419.6 | 0.1409 | > 10.0?<br>4.736 | 5-((2R,6S)-2-methyl-6-(((S)-3-(piperidin-1-yl)pyrrolidin-1-yl)methyl)morpholino)quinoline-8-carbonitrile | $^1$H NMR (400 MHz, METHANOL-$d_4$) d ppm 1.21 - 1.49 (m, 3 H) 1.66 (br. s., 2 H) 1.75 - 1.89 (m, 2 H) 1.94 (br. s., 1 H) 2.01 - 2.25 (m, 1 H) 2.36 (s, 3 H) 2.55 - 2.78 (m, 2 H) 2.83 - 2.98 (m, 2 H) 3.06 (s, 1 H) 3.19 (d, $J$=6.45 Hz, 3 H) 3.25 - 3.35 (m, 2 H) 3.37 (s, 1 H) 3.39 (s, 1 H) 3.59 - 3.88 (m, 2 H) 3.94 - 4.15 (m, 1 H) 4.18 (br. s., 1 H) 4.81 - 5.07 (m, 4 H) 7.24 (t, $J$=7.91 Hz, 2 H) 7.56 - 7.80 (m, 2 H) 8.08 (s, 1 H) 8.15 (d, $J$=7.91 Hz, 1 H) 8.42 - 8.67 (m, 1 H) 8.83 - 9.10 (m, 1 H) | |
| ER-890311 | 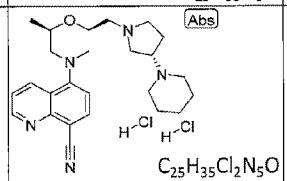 $C_{25}H_{35}Cl_2N_5O$ | 492.6 | 0.0218 | 6.541 | 5-((2R,6S)-2-methyl-6-(((S)-3-(piperidin-1-yl)pyrrolidin-1-yl)methyl)morpholino)quinoline-8-carbonitrile dihydrochloride | | |
| ER-890342 | 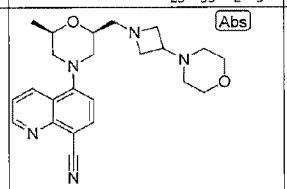 $C_{23}H_{29}N_5O_2$ | 407.5 | 0.0710 | > 2.0 | 5-((2R,6S)-2-methyl-6-((3-morpholinoazetidin-1-yl)methyl)morpholino)quinoline-8-carbonitrile | $^1$H NMR (400 MHz, METHANOL-$d_4$) d ppm 1.25 (d, $J$=6.15 Hz, 4 H) 2.32 (s, 3 H) 2.38 (br. s., 4 H) 2.62 - 2.74 (m, 2 H) 3.29 - 3.39 (m, 5 H) 3.65 - 3.70 (m, 5 H) 3.99 - 4.09 (m, 3 H) 4.20 - 4.27 (m, 2 H) 4.81 - 4.85 (m, 7 H) 7.16 - 7.24 (m, 2 H) 7.59 - 7.63 (m, 1 H) 7.67 (d, $J$=8.20 Hz, 1 H) 8.12 (d, $J$=8.20 Hz, 1 H) 8.19 (br. s., 1 H) 8.61 (dd, $J$=8.50, 1.47 Hz, 1 H) 8.94 - 8.96 (m, 1 H) | |
| ER-890343 | 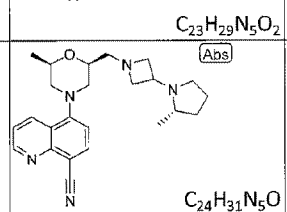 $C_{24}H_{31}N_5O$ | 405.5 | 0.0082 | 5.241 | 5-((2R,6S)-2-methyl-6-((3-((S)-2-methylpyrrolidin-1-yl)azetidin-1-yl)methyl)morpholino)quinoline-8-carbonitrile | | |
| ER-890344 | 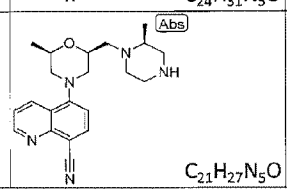 $C_{21}H_{27}N_5O$ | 365.5 | 0.0180 | > 2.0 | 5-((2R,6S)-2-methyl-6-(((S)-2-methylpiperazin-1-yl)methyl)morpholino)quinoline-8-carbonitrile | | |

FIG. 6UU

| | | | | | | | |
|---|---|---|---|---|---|---|---|
| ER-890345 | 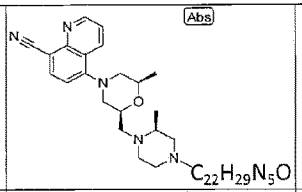 $C_{22}H_{29}N_5O$ | 379.5 | 0.0180 | > 2.0 | 5-((2S,6R)-2-(((S)-2,4-dimethylpiperazin-1-yl)methyl)-6-methylmorpholino)quinoline-8-carbonitrile | | |
| ER-890346 | 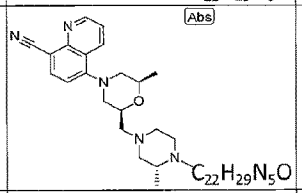 $C_{22}H_{29}N_5O$ | 379.5 | 0.0240 | > 2.0 | 5-((2S,6R)-2-(((R)-3,4-dimethylpiperazin-1-yl)methyl)-6-methylmorpholino)quinoline-8-carbonitrile | | |
| ER-890831 | 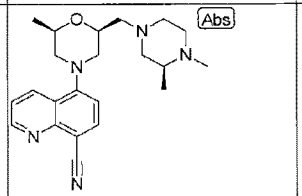 $C_{22}H_{29}N_5O$ | 379.5 | 0.0051 | > 10.0 | 5-((2S,6R)-2-(((S)-3,4-dimethylpiperazin-1-yl)methyl)-6-methylmorpholino)quinoline-8-carbonitrile | 1H NMR (400 MHz, METHANOL-d4) d ppm 1.05 (3 H, d) 1.17 - 1.22 (3 H, m) 1.89 - 1.98 (1 H, m) 2.27 (4 H, s) 2.30 - 2.37 (2 H, m) 2.39 - 2.46 (1 H, m) 2.46 - 2.67 (3 H, m) 2.72 - 2.81 (1 H, m) 2.82 - 2.97 (2 H, m) 3.26 - 3.40 (2 H, m) 3.92 - 4.05 (1 H, m) 4.07 - 4.18 (1 H, m) 7.09 - 7.19 (1 H, m) 7.50 - 7.59 (1 H, m) 7.99 - 8.08 (1 H, m) 8.49 - 8.61 (1 H, m) 8.84 - 8.99 (1 H, m) | LCMS (ESI+) calcd for C22 H29 N5 O (M+H+) 380.5, found 380.3 |
| ER-890963 | 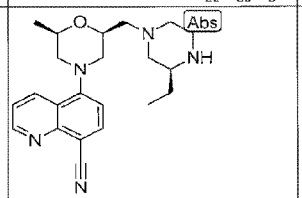 $C_{22}H_{29}N_5O$ | 379.5 | 0.0005 | > 10.0 | 5-((2S,6R)-2-(((S)-3-ethylpiperazin-1-yl)methyl)-6-methylmorpholino)quinoline-8-carbonitrile | 1H NMR (400 MHz, METHANOL-d4) d ppm 0.96 (3 H, t) 1.20 (3 H, d) 1.52 - 1.64 (2 H, m) 2.10 - 2.23 (1 H, m) 2.29 - 2.43 (1 H, m) 2.52 - 2.63 (3 H, m) 2.66 - 2.74 (1 H, m) 3.00 - 3.18 (4 H, m) 3.29 - 3.42 (2 H, m) 3.98 - 4.07 (1 H, m) 4.08 - 4.20 (1 H, m) 7.15 - 7.23 (1 H, m) 7.54 - 7.64 (1 H, m) 8.07 - 8.15 (1 H, m) 8.43 - 8.53 (1 H, m) 8.57 - 8.66 (1 H, m) 8.88 - 8.99 (1 H, m) | LCMS (ESI+) calcd for C22 H29 N5 O (M+H+) 380.5, found 380.2 |
| ER-890963 | 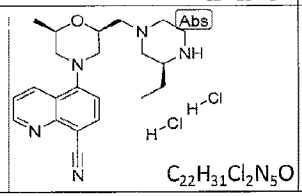 $C_{22}H_{31}Cl_2N_5O$ | 452.4 | 0.0085 | > 10.0 | 5-((2S,6R)-2-(((S)-3-ethylpiperazin-1-yl)methyl)-6-methylmorpholino)quinoline-8-carbonitrile dihydrochloride | | |

FIG. 6VV

| | | | | | | | |
|---|---|---|---|---|---|---|---|
| ER-890964 | 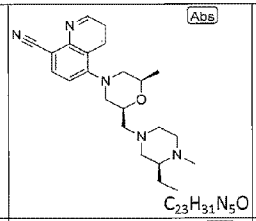 $C_{23}H_{31}N_5O$ | 393.5 | 0.0009 | > 10.0 | 5-((2S,6R)-2-(((S)-3-ethyl-4-methylpiperazin-1-yl)methyl)-6-methylmorpholino)quinoline-8-carbonitrile | $^1$H NMR (400 MHz, CHLOROFORM-*d*) d ppm 0.86 (t, *J*=7.62 Hz, 2 H) 1.18 - 1.40 (m, 4 H) 1.48 - 1.76 (m, 2 H) 1.82 - 2.10 (m, 2 H) 2.15 (s, 1 H) 2.19 - 2.33 (m, 4 H) 2.44 (dd, *J*=12.89, 6.45 Hz, 1 H) 2.54 (dd, *J*=12.89, 5.57 Hz, 1 H) 2.59 - 2.79 (m, 3 H) 2.83 - 3.06 (m, 1 H) 3.26 (dt, *J*=11.72, 2.05 Hz, 1 H) 3.34 - 3.56 (m, 2 H) 3.89 - 4.13 (m, 2 H) 7.06 (d, *J*=7.91 Hz, 1 H) 7.24 (s, 1 H) 7.48 (dd, *J*=8.50, 4.39 Hz, 1 H) 8.02 (d, *J*=8.20 Hz, 1 H) 8.32 - 8.49 (m, 1 H) 9.05 (dd, *J*=4.10, 1.76 Hz, 1 H) | |
| ER-891084 | 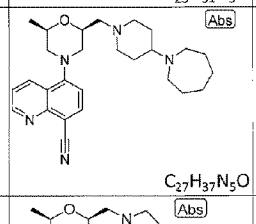 $C_{27}H_{37}N_5O$ | 447.6 | 0.0034 | 0.0362 | 5-((2S,6R)-2-((4-(azepan-1-yl)piperidin-1-yl)methyl)-6-methylmorpholino)quinoline-8-carbonitrile | $^1$H NMR (400 MHz, METHANOL-*d*$_4$) d ppm 1.16 - 1.31 (m, 3 H) 1.71 (br. s., 4 H) 1.74 - 1.85 (m, 2 H) 1.88 (br. s., 3 H) 2.02 (d, *J*=9.38 Hz, 2 H) 2.10 - 2.30 (m, 2 H) 2.35 (s, 1 H) 2.45 - 2.74 (m, 4 H) 3.12 - 3.41 (m, 9 H) 3.99 - 4.23 (m, 2 H) 4.87 (s, 4 H) 7.17 - 7.42 (m, 2 H) 7.57 - 7.84 (m, 2 H) 8.13 (d, *J*=7.91 Hz, 1 H) 8.52 (s, 1 H) 8.57 - 8.79 (m, 2 H) 8.82 - 9.07 (m, 2 H) | |
| ER-891090 | 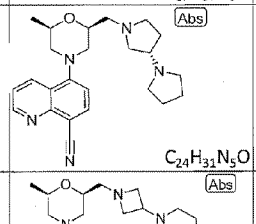 $C_{24}H_{31}N_5O$ | 405.5 | 0.0081 | 1.262 | 5-((2S,6R)-2-((S)-[1,3'-bipyrrolidin]-1'-ylmethyl)-6-methylmorpholino)quinoline-8-carbonitrile | $^1$H NMR (400 MHz, METHANOL-*d*$_4$) d ppm 1.16 - 1.31 (m, 3 H) 1.71 (br. s., 4 H) 1.74 - 1.85 (m, 2 H) 1.88 (br. s., 3 H) 2.02 (d, *J*=9.38 Hz, 2 H) 2.10 - 2.30 (m, 2 H) 2.35 (s, 1 H) 2.45 - 2.74 (m, 4 H) 3.12 - 3.41 (m, 9 H) 3.99 - 4.23 (m, 2 H) 4.87 (s, 4 H) 7.17 - 7.42 (m, 2 H) 7.57 - 7.84 (m, 2 H) 8.13 (d, *J*=7.91 Hz, 1 H) 8.52 (s, 1 H) 8.57 - 8.79 (m, 2 H) 8.82 - 9.07 (m, 2 H) | |
| ER-892253 | 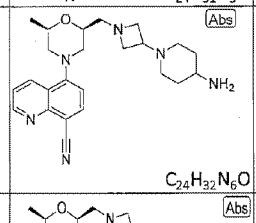 $C_{24}H_{32}N_6O$ | 420.6 | 0.0664 | > 10.0 | 5-((2S,6R)-2-((3-(4-aminopiperidin-1-yl)azetidin-1-yl)methyl)-6-methylmorpholino)quinoline-8-carbonitrile | $^1$H NMR (400 MHz, METHANOL-*d*$_4$) d ppm 1.27 (d, *J*=6.45 Hz, 2 H) 1.57 - 1.77 (m, 2 H) 2.03 (br. s., 3 H) 2.59 - 2.82 (m, 2 H) 2.92 (d, *J*=9.96 Hz, 2 H) 3.12 (d, *J*=12.01 Hz, 1 H) 3.25 - 3.49 (m, 5 H) 4.00 - 4.17 (m, 2 H) 4.17 - 4.30 (m, 1 H) 4.34 (d, *J*=7.03 Hz, 2 H) 7.25 (d, *J*=7.91 Hz, 1 H) 7.58 - 7.84 (m, 1 H) 8.06 (s, 1 H) 8.15 (d, *J*=8.20 Hz, 1 H) 8.63 (dd, *J*=8.50, 1.76 Hz, 1 H) 8.95 - 9.07 (m, 1 H) | |
| ER-892254 | 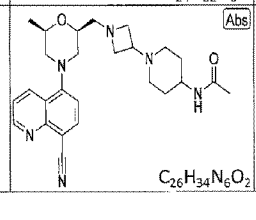 $C_{26}H_{34}N_6O_2$ | 462.6 | 0.0696 | > 10.0 | N-(1-(1-(((2S,6R)-4-(8-cyanoquinolin-5-yl)-6-methylmorpholin-2-yl)methyl)azetidin-3-yl)piperidin-4-yl)acetamide | $^1$H NMR (400 MHz, METHANOL-*d*$_4$) d ppm 1.24 (d, *J*=6.15 Hz, 2 H) 1.35 - 1.58 (m, 2 H) 1.89 (s, 3 H) 1.95 - 2.19 (m, 2 H) 2.51 - 2.76 (m, 2 H) 2.82 (s, 1 H) 2.79 (s, 1 H) 3.22 (br. s., 1 H) 3.29 - 3.48 (m, 3 H) 3.50 - 3.77 (m, 1 H) 3.80 - 4.01 (m, 2 H) 4.01 - 4.12 (m, 1 H) 4.13 - 4.36 (m, 2 H) 7.23 (d, *J*=7.91 Hz, 1 H) 7.56 - 7.76 (m, 1 H) 8.12 (d, *J*=8.20 Hz, 1 H) 8.26 (br. s., 1 H) 8.61 (dd, *J*=8.50, 1.76 Hz, 1 H) 8.95 (dd, *J*=4.10, 1.47 Hz, 1 H) | |

FIG. 6WW

| | | | | | | | |
|---|---|---|---|---|---|---|---|
| ER-892256 | 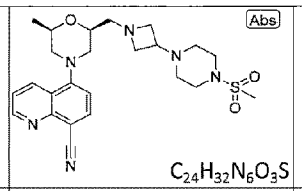 $C_{24}H_{32}N_6O_3S$ | 484.6 | 0.3116 | > 10.0 | 5-((2R,6S)-2-methyl-6-((3-(4-(methylsulfonyl)piperazin-1-yl)azetidin-1-yl)methyl)morpholino)quinoline-8-carbonitrile | | |
| ER-893881 | 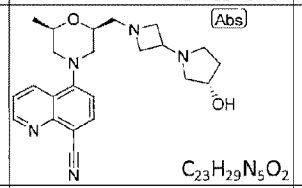 $C_{23}H_{29}N_5O_2$ | 407.5 | 0.0055 | > 10.0 | 5-((2S,6R)-2-((3-((S)-3-hydroxypyrrolidin-1-yl)azetidin-1-yl)methyl)-6-methylmorpholino)quinoline-8-carbonitrile | | |
| ER-893926 | 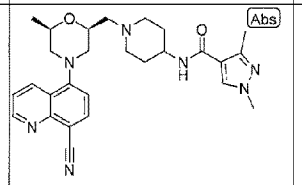 $C_{27}H_{33}N_7O_2$ | 487.6 | 0.0123 | 5.9 | N-(1-(((2S,6R)-4-(8-cyanoquinolin-5-yl)-6-methylmorpholin-2-yl)methyl)piperidin-4-yl)-1,3-dimethyl-1H-pyrazole-4-carboxamide | $^1$H NMR (400 MHz, METHANOL-$d_4$) d ppm 1.27 (d, $J$=6.15 Hz, 3 H) 1.76 - 2.01 (m, 2 H) 2.05 - 2.28 (m, 2 H) 2.36 (s, 3 H) 2.51 - 2.77 (m, 2 H) 3.02 - 3.25 (m, 4 H) 3.29 - 3.47 (m, 2 H) 3.50 - 3.70 (m, 2 H) 3.75 (s, 1 H) 3.80 (s, 2 H) 3.94 - 4.17 (m, 2 H) 4.41 (br. s., 1 H) 7.23 (d, $J$=7.91 Hz, 1 H) 7.55 - 7.72 (m, 1 H) 7.94 (s, 1 H) 8.12 (d, $J$=7.91 Hz, 1 H) 8.24 (s, 2 H) 8.49 - 8.66 (m, 1 H) 8.79 - 9.07 (m, 1 H) | |
| ER-893927 | 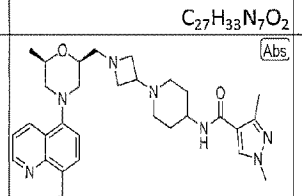 $C_{30}H_{38}N_8O_2$ | 542.7 | 0.0910 | >10.0 | N-(1-(1-(((2S,6R)-4-(8-cyanoquinolin-5-yl)-6-methylmorpholin-2-yl)methyl)azetidin-3-yl)piperidin-4-yl)-1,3-dimethyl-1H-pyrazole-4-carboxamide | $^1$H NMR (400 MHz, METHANOL-$d_4$) d ppm 1.25 (d, $J$=6.15 Hz, 2 H) 1.47 - 1.66 (m, 2 H) 1.96 (s, 1 H) 1.93 (s, 1 H) 2.00 - 2.21 (m, 2 H) 2.35 (s, 3 H) 2.57 - 2.79 (m, 2 H) 2.88 (s, 1 H) 2.85 (s, 1 H) 3.29 - 3.57 (m, 3 H) 3.78 (s, 3 H) 3.86 - 4.04 (m, 2 H) 4.08 (d, $J$=5.57 Hz, 1 H) 4.21 (br. s., 3 H) 7.23 (d, $J$=7.91 Hz, 1 H) 7.42 - 7.69 (m, 2 H) 7.76 (d, $J$=7.62 Hz, 1 H) 7.90 (s, 1 H) 8.13 (d, $J$=8.20 Hz, 1 H) 8.24 (br. s., 2 H) 8.61 (d, $J$=8.79 Hz, 2 H) 8.91 - 9.11 (m, 1 H) | |
| ER-893948 | 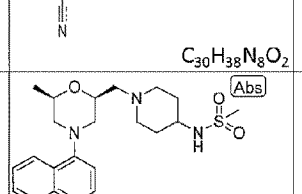 $C_{22}H_{29}N_5O_3S$ | 443.6 | 0.0995 | >10.0 | N-(1-(((2S,6R)-4-(8-cyanoquinolin-5-yl)-6-methylmorpholin-2-yl)methyl)piperidin-4-yl)methanesulfonamide | $^1$H NMR (400 MHz, METHANOL-$d_4$) d ppm 1.25 (d, $J$=6.15 Hz, 3 H) 1.38 (br. s., 1 H) 1.78 (s, 1 H) 1.74 (s, 1 H) 1.83 - 1.96 (m, 1 H) 2.04 (br. s., 1 H) 2.10 (br. s., 2 H) 2.52 - 2.76 (m, 2 H) 2.77 - 2.92 (m, 2 H) 2.92 - 3.06 (m, 3 H) 3.12 (s, 1 H) 3.29 - 3.55 (m, 3 H) 4.09 (br. s., 1 H) 4.28 (br. s., 2 H) 4.74 (br. s., 1 H) 4.85 (s, 6 H) 5.46 (s, 1 H) 7.23 (d, $J$=7.91 Hz, 1 H) 7.61 (dd, $J$=8.50, 4.10 Hz, 1 H) 8.12 (d, $J$=7.91 Hz, 1 H) 8.34 (br. s., 2 H) 8.47 - 8.73 (m, 1 H) 8.80 - 9.00 (m, 1 H) | |

FIG. 6XX

| | | | | | | |
|---|---|---|---|---|---|---|
| **ER-894149** | 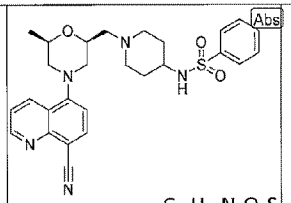 $C_{27}H_{31}N_5O_3S$ | 505.6 | 0.1130 | 9.9 | N-(1-(((2S,6R)-4-(8-cyanoquinolin-5-yl)-6-methylmorpholin-2-yl)methyl)piperidin-4-yl)benzenesulfonamide | $^1$H NMR (400 MHz, METHANOL-$d_4$) d ppm 1.23 (d, $J$=6.15 Hz, 3 H) 1.58 - 1.85 (m, 2 H) 1.85 - 1.98 (m, 2 H) 2.04 (s, 1 H) 2.54 - 2.72 (m, 2 H) 2.88 (s, 1 H) 3.02 (s, 1 H) 2.98 (s, 1 H) 3.05 - 3.25 (m, 2 H) 3.29 - 3.52 (m, 4 H) 3.96 - 4.16 (m, 1 H) 4.31 (br. s., 1 H) 7.21 (d, $J$=7.91 Hz, 1 H) 7.28 - 7.42 (m, 1 H) 7.51 - 7.69 (m, 3 H) 7.70 - 7.82 (m, 1 H) 7.82 - 7.98 (m, 1 H) 8.11 (d, $J$=8.20 Hz, 1 H) 8.23 (br. s., 1 H) 8.59 (dd, $J$=8.50, 1.76 Hz, 1 H) 8.89 - 9.11 (m, 1 H) |
| **ER-894150** | 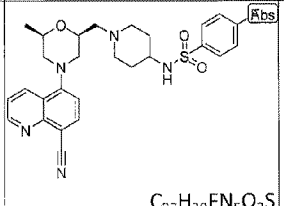 $C_{27}H_{30}FN_5O_3S$ | 523.6 | 0.1275 | >10.0 | N-(1-(((2S,6R)-4-(8-cyanoquinolin-5-yl)-6-methylmorpholin-2-yl)methyl)piperidin-4-yl)-4-fluorobenzenesulfonamide | $^1$H NMR (400 MHz, METHANOL-$d_4$) d ppm 1.26 (d, $J$=6.45 Hz, 2 H) 1.64 - 1.90 (m, 2 H) 1.90 - 2.11 (m, 2 H) 2.54 - 2.74 (m, 2 H) 2.90 (br. s., 1 H) 2.99 - 3.24 (m, 3 H) 3.25 - 3.53 (m, 4 H) 3.96 - 4.22 (m, 1 H) 4.24 - 4.42 (m, 1 H) 7.06 - 7.17 (m, 1 H) 7.23 (d, $J$=7.91 Hz, 1 H) 7.26 - 7.45 (m, 1 H) 7.61 (dd, $J$=8.50, 4.39 Hz, 1 H) 7.73 - 7.88 (m, 1 H) 7.89 - 8.03 (m, 1 H) 8.13 (d, $J$=7.91 Hz, 1 H) 8.23 (br. s., 1 H) 8.62 (dd, $J$=8.79, 1.47 Hz, 1 H) 8.93 - 9.11 (m, 1 H) |
| **ER-894151** | 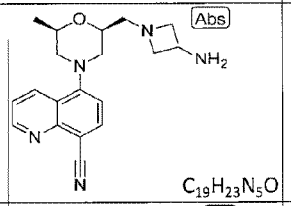 $C_{19}H_{23}N_5O$ | 337.4 | 0.0052 | 11.46 | 5-((2S,6R)-2-((3-aminoazetidin-1-yl)methyl)-6-methylmorpholino)quinoline-8-carbonitrile | $^1$H NMR (400 MHz, METHANOL-$d_4$) d ppm 1.08 - 1.30 (m, 4 H) 2.56 - 2.82 (m, 3 H) 2.83 - 3.00 (m, 2 H) 3.00 - 3.19 (m, 1 H) 3.21 - 3.43 (m, 5 H) 3.44 - 3.59 (m, 2 H) 3.59 - 3.78 (m, 1 H) 3.79 - 3.99 (m, 2 H) 4.00 - 4.11 (m, 2 H) 4.14 (br. s., 1 H) 4.52 - 4.67 (m, 1 H) 4.75 - 4.90 (m, 5 H) 7.17 - 7.31 (m, 1 H) 7.44 - 7.68 (m, 2 H) 8.07 (s, 1 H) 8.15 (d, $J$=8.20 Hz, 1 H) 8.41 (s, 2 H) 8.51 - 8.80 (m, 2 H) 8.81 - 9.04 (m, 1 H) |
| **ER-894152** | 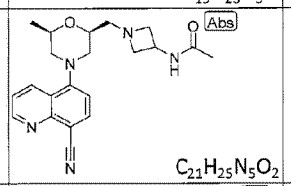 $C_{21}H_{25}N_5O_2$ | 379.5 | 0.0740 | >10.0 | N-(1-(((2S,6R)-4-(8-cyanoquinolin-5-yl)-6-methylmorpholin-2-yl)methyl)azetidin-3-yl)acetamide | $^1$H NMR (400 MHz, METHANOL-$d_4$) d ppm 1.03 - 1.30 (m, 3 H) 1.94 (s, 2 H) 2.57 - 2.79 (m, 2 H) 3.00 - 3.25 (m, 2 H) 3.29 - 3.57 (m, 2 H) 3.79 (br. s., 2 H) 4.05 (br. s., 1 H) 4.17 (d, $J$=8.79 Hz, 2 H) 4.49 (s, 1 H) 4.47 (s, 1 H) 7.22 (d, $J$=8.20 Hz, 1 H) 7.55 - 7.80 (m, 1 H) 8.12 (d, $J$=7.91 Hz, 1 H) 8.39 (br. s., 1 H) 8.60 (d, $J$=8.50 Hz, 2 H) 8.95 (d, $J$=2.64 Hz, 1 H) |
| **ER-894153** | 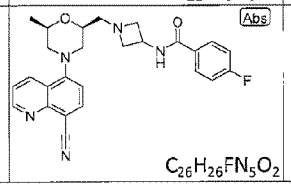 $C_{26}H_{26}FN_5O_2$ | 459.5 | 0.1210 | >10.0 | N-(1-(((2S,6R)-4-(8-cyanoquinolin-5-yl)-6-methylmorpholin-2-yl)methyl)azetidin-3-yl)-4-fluorobenzamide | |

FIG. 6YY

| | | | | | | | |
|---|---|---|---|---|---|---|---|
| ER-894154 | 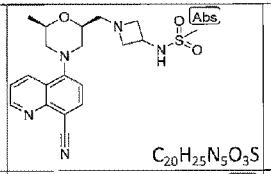 $C_{20}H_{25}N_5O_3S$ | 415.5 | 0.1710 | >10.0 | N-(1-(((2S,6R)-4-(8-cyanoquinolin-5-yl)-6-methylmorpholin-2-yl)methyl)azetidin-3-yl)methanesulfonamide | $^1$H NMR (400 MHz, METHANOL-$d_4$) d ppm 1.27 (d, $J$=6.15 Hz, 3 H) 2.52 - 2.78 (m, 2 H) 2.96 (s, 2 H) 3.01 - 3.21 (m, 2 H) 3.23 - 3.42 (m, 4 H) 3.55 - 3.77 (m, 2 H) 3.91 - 4.17 (m, 2 H) 4.17 - 4.40 (m, 3 H) 4.88 (s, 3 H) 7.25 (d, $J$=7.91 Hz, 1 H) 7.57 - 7.84 (m, 1 H) 8.15 (d, $J$=7.91 Hz, 1 H) 8.30 (br. s., 1 H) 8.64 (dd, $J$=8.50, 1.76 Hz, 1 H) 8.93 - 9.17 (m, 1 H) | |
| ER-894155 | 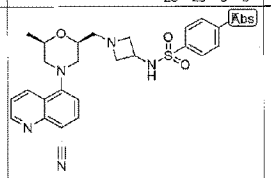 $C_{25}H_{26}FN_5O_3S$ | 495.6 | 0.2820 | >10.0 | N-(1-(((2S,6R)-4-(8-cyanoquinolin-5-yl)-6-methylmorpholin-2-yl)methyl)azetidin-3-yl)-4-fluorobenzenesulfonamide | $^1$H NMR (400 MHz, METHANOL-$d_4$) d ppm 1.09 - 1.33 (m, 2 H) 1.44 (s, 1 H) 2.02 (s, 1 H) 2.54 - 2.76 (m, 1 H) 2.95 - 3.23 (m, 1 H) 3.23 - 3.50 (m, 2 H) 3.62 - 3.80 (m, 1 H) 3.97 - 4.24 (m, 3 H) 6.94 - 7.16 (m, 1 H) 7.20 (d, $J$=8.20 Hz, 1 H) 7.26 - 7.46 (m, 1 H) 7.60 (dd, $J$=8.50, 4.39 Hz, 1 H) 7.73 - 8.01 (m, 1 H) 8.11 (d, $J$=7.91 Hz, 1 H) 8.23 (br. s., 1 H) 8.50 - 8.65 (m, 1 H) 8.95 (dd, $J$=4.39, 1.76 Hz, 1 H) | |
| ER-894159 | 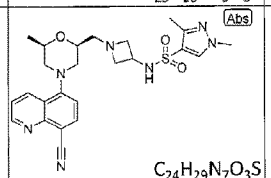 $C_{24}H_{29}N_7O_3S$ | 495.6 | 0.1780 | >10.0 | N-(1-(((2S,6R)-4-(8-cyanoquinolin-5-yl)-6-methylmorpholin-2-yl)methyl)azetidin-3-yl)-1,3-dimethyl-1H-pyrazole-4-sulfonamide | $^1$H NMR (400 MHz, METHANOL-$d_4$) d ppm 1.20 (d, $J$=6.45 Hz, 3 H) 2.32 (s, 3 H) 2.45 (s, 1 H) 2.52 - 2.71 (m, 2 H) 2.93 - 3.14 (m, 2 H) 3.29 - 3.46 (m, 2 H) 3.60 (br. s., 2 H) 3.69 - 3.89 (m, 3 H) 3.91 - 4.12 (m, 4 H) 7.20 (d, $J$=8.20 Hz, 1 H) 7.46 - 7.69 (m, 1 H) 7.98 (s, 1 H) 8.10 (d, $J$=8.20 Hz, 1 H) 8.26 (br. s., 2 H) 8.43 - 8.63 (m, 1 H) 8.77 - 8.97 (m, 1 H) | |
| ER-894160 | 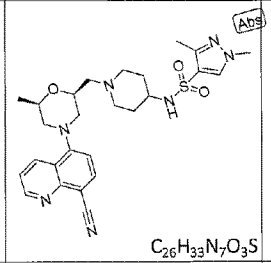 $C_{26}H_{33}N_7O_3S$ | 523.7 | 0.1990 | >10.0 | N-(1-(((2S,6R)-4-(8-cyanoquinolin-5-yl)-6-methylmorpholin-2-yl)methyl)piperidin-4-yl)-1,3-dimethyl-1H-pyrazole-4-sulfonamide | $^1$H NMR (400 MHz, METHANOL-$d_4$) d ppm 1.14 - 1.41 (m, 4 H) 1.73 - 1.95 (m, 2 H) 1.95 - 2.17 (m, 3 H) 2.20 - 2.37 (m, 4 H) 2.44 (d, $J$=18.75 Hz, 1 H) 2.59 - 2.79 (m, 3 H) 2.97 (s, 1 H) 3.06 - 3.25 (m, 4 H) 3.29 - 3.44 (m, 3 H) 3.50 (br. s., 2 H) 3.57 - 3.75 (m, 3 H) 3.77 - 3.88 (m, 3 H) 3.94 (s, 1 H) 3.98 - 4.23 (m, 2 H) 4.24 - 4.45 (m, 2 H) 7.22 (d, $J$=7.91 Hz, 1 H) 7.60 (dd, $J$=8.50, 4.39 Hz, 2 H) 7.68 (s, 1 H) 7.83 - 8.02 (m, 1 H) 8.08 - 8.25 (m, 2 H) 8.37 (s, 1 H) 8.49 - 8.78 (m, 2 H) 8.95 (dd, $J$=4.39, 1.76 Hz, 1 H) | |
| ER-894206 | 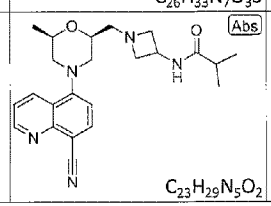 $C_{23}H_{29}N_5O_2$ | 407.5 | 0.0197 | >10.0 | N-(1-(((2S,6R)-4-(8-cyanoquinolin-5-yl)-6-methylmorpholin-2-yl)methyl)azetidin-3-yl)isobutyramide | | |

FIG. 6ZZ

| | | | | | | | |
|---|---|---|---|---|---|---|---|
| **ER-894472** | 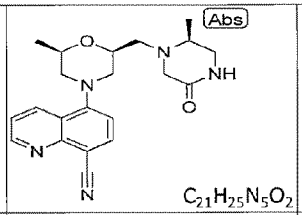 $C_{21}H_{25}N_5O_2$ | 379.5 | 0.1210 | >10.0 | 5-((2R,6S)-2-methyl-6-(((S)-2-methyl-5-oxopiperazin-1-yl)methyl)morpholino)quinoline-8-carbonitrile | | |
| **ER-894473** | 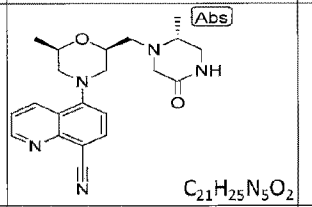 $C_{21}H_{25}N_5O_2$ | 379.5 | 0.4060 | >10.0 | 5-((2R,6S)-2-methyl-6-(((R)-2-methyl-5-oxopiperazin-1-yl)methyl)morpholino)quinoline-8-carbonitrile | | |
| **ER-894483** | 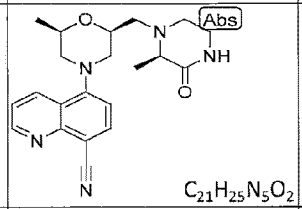 $C_{21}H_{25}N_5O_2$ | 379.5 | 0.1350 | >10.0 | 5-((2R,6S)-2-methyl-6-(((R)-2-methyl-3-oxopiperazin-1-yl)methyl)morpholino)quinoline-8-carbonitrile | 1H NMR (CD3OD) d ppm 8.93 (dd, 1H), 8.61 (dd, 1H), 8.10 (d, 1H), 7.60 (dd, 1H), 7.20 (d, 1H), 4.05 (m, 2H), 3.39-3.07 )overlapping multiplets, 6H), 2.28-2.57 (overlapping multiplets 5H), 1.32 (d, 3H), 1.21 (d, 3H) | LCMS (ESI+) calcd. for: C21H25N5O2 (M+H+): 380.2, found 380.2 |
| **ER-894484** | 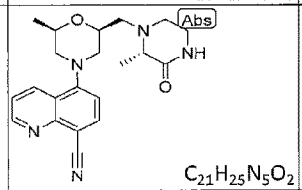 $C_{21}H_{25}N_5O_2$ | 379.5 | 0.1470 | >10.0 | 5-((2R,6S)-2-methyl-6-(((S)-2-methyl-3-oxopiperazin-1-yl)methyl)morpholino)quinoline-8-carbonitrile | 1H NMR (CD3OD) d ppm 8.92 (dd, 1H), 8.59 (dd, 1H), 8.10 (d, 1H), 7.59 (dd, 1H), 7.20 (d, 1H), 4.13-4.01 (m, 2H), 3.45-3.13 (overlapping m, 6H), 2.28-2.57 (overlapping multiplets 5H), 1.30 (d, 3H), 1.21 (d, 3H) | LCMS (ESI+) calcd. for: C21H25N5O2 (M+H+): 380.2, found 380.2 |
| **ER-894504** | 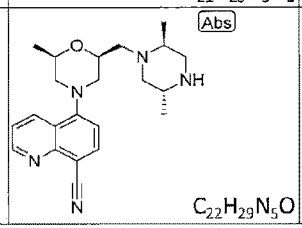 $C_{22}H_{29}N_5O$ | 393.5 | 0.0170 | >10.0 | 5-((2R,6S)-2-methyl-6-((2,4,5-trimethylpiperazin-1-yl)methyl)morpholino)quinoline-8-carbonitrile | 1H NMR (CD3OD) d ppm 8.92 (dd, 1H), 8.58 (m, 1H), 8.07 (d, 1H), 7.58 (m, 1H), 7.17 (m, 1H), 4.11 (m, 1H), 4.02 (m, 1H), 3.40 (m, 1H), 3.31 (m, 1H), 3.27 (m, 1H), 3.00-2.77 (overlapping multiplets (2H, 2.72-2.54 (overlapping multiplets, 2H), 2.44-2.32 (m, 1H), 2.24 (d, 3H), 2.20 (m, 2H) 2.04 (m, 2H), 1.20 (m, 3H), 1.03 (m, 6H) | LCMS (ESI+) calcd. for: C23H31N5O (M+H+): 394.3, found 394.3 |

FIG. 6AAA

| | | | | | | | |
|---|---|---|---|---|---|---|---|
| ER-894505 | 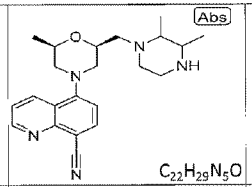 $C_{22}H_{29}N_5O$ | 393.5 | 0.0040 | >10.0 | 5-((2R,6S)-2-methyl-6-((2,3,4-trimethylpiperazin-1-yl)methyl)morpholino)quinoline-8-carbonitrile | 1H NMR (CD3OD) d ppm 8.93 (dd, 1H), 8.59 (m, 1H), 8.10 (d, 1H), 7.59 (m, 1H), 7.20 (dd, 1H), 4.13-4.01 (m, 2H), 3.45-3.31 (overlapping m, 4H), 3.04-2.572.35 (overlapping multiplets 4H), 2.26 (s, 3H), 2.20 (m, 1H), 1.80 (m, 1H), 1.20 (m, 3H), 1.21 (m, 6H) | LCMS (ESI+) calcd. for: C23H31N5O (M+H+): 394.3, found 394.4 |
| ER-894544 | 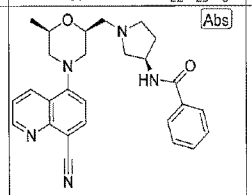 $C_{27}H_{29}N_5O_2$ | 455.6 | 0.0430 | 6.2 | N-((R)-1-(((2S,6R)-4-(8-cyanoquinolin-5-yl)-6-methylmorpholin-2-yl)methyl)pyrrolidin-3-yl)benzamide | H NMR (400 MHz, CHLOROFORM-d1) d ppm 1.26 (3 H), 2.37 (2 H), 2.70 (6 H), 3.07 (1 H), 3.28 (1 H), 3.39 (1 H), 3.46 (1H), 4.04 (2 H), 4.66 (1 H), 6.70 (1 H), 7.07 (1 H), 7.39 (2 H), 7.49 (2 H), 7.75 (2 H), 8.04 (1 H), 8.45 (1 H), 9.03 (1 H). | LCMS (ESI+) calcd for C27H29N5O2 (M+H+) 456.24, found 456.39 |
| ER-894545 | 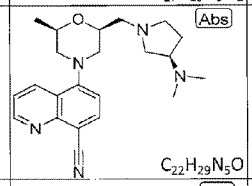 $C_{22}H_{29}N_5O$ | 379.5 | 0.0050 | >10.0 | 5-((2S,6R)-2-(((R)-3-(dimethylamino)pyrrolidin-1-yl)methyl)-6-methylmorpholino)quinoline-8-carbonitrile | H NMR (400 MHz, METHANOL-d4) d ppm 1.25 (3 H), 1.91 (1 H), 2.18 (1 H), 2.57 (6 H), 2.65 (1 H), 2.75 (2 H), 2.85 (1 H), 2.97 (1 H), 3.35 (2 H), 3.4 (3 H), 4.11 (2 H), 7.23 (1 H), 7.63 (1 H), 8.14 (1 H), 8.52 (1 H), 8.64 (1 H), 8.97 (1 H). | LCMS (ESI+) calcd for C22H29N5O (M+H+) 380.24, found 380.25 |
| ER-894546 | 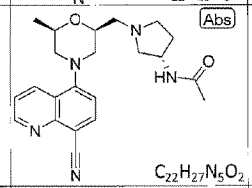 $C_{22}H_{27}N_5O_2$ | 393.5 | 0.0222 | >10.0 | N-((S)-1-(((2S,6R)-4-(8-cyanoquinolin-5-yl)-6-methylmorpholin-2-yl)methyl)pyrrolidin-3-yl)acetamide | H NMR (400 MHz, CHLOROFORM-d1) d ppm 1.25 (3 H), 1.80 (1 H), 1.94 (2 H), 1.99 (1 H), 2.35 (1 H), 2.65 (3 H), 2.78 (1 H), 2.84 (1 H), 2.92 (1 H), 3.13 (1 H), 3.27 (2 H), 3.37 (1 H), 4.04 (1 H), 4.22 (1 H), 4.59 (1 H), 6.84 (1 H), 7.05 (1 H), 7.50 (1 H), 7.99 (1 H), 8.43 (1 H), 9.03 (1 H). | LCMS (ESI+) calcd for C22H27N5O2 (M+H+) 394.22, found 394.27 |
| ER-894547 | 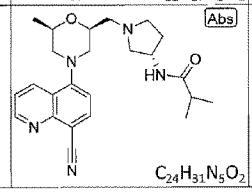 $C_{24}H_{31}N_5O_2$ | 421.5 | 0.0272 | >10.0 | N-((S)-1-(((2S,6R)-4-(8-cyanoquinolin-5-yl)-6-methylmorpholin-2-yl)methyl)pyrrolidin-3-yl)isobutyramide | H NMR (400 MHz, CHLOROFORM-d1) d ppm 1.09 (6 H), 1.24 (3 H), 1.60 (1 H), 2.28 (2 H), 2.38 (1 H), 2.66 (6 H), 3.01 (1 H), 3.27 (1 H), 3.37 (1 H), 4.03 (2 H), 4.42 (1 H), 6.02 (1 H), 7.05 (1 H), 7.50 (1 H), 7.98 (1 H), 8.43 (1 H), 9.02 (1 H). | LCMS (ESI+) calcd for C24H31N5O2 (M+H+) 422.25, found 422.28 |

FIG. 6BBB

| | | | | | | | |
|---|---|---|---|---|---|---|---|
| ER-894548 | 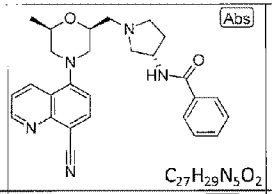 $C_{27}H_{29}N_5O_2$ | 455.6 | 0.0213 | 4.33 | N-((S)-1-(((2S,6R)-4-(8-cyanoquinolin-5-yl)-6-methylmorpholin-2-yl)methyl)pyrrolidin-3-yl)benzamide | H NMR (400 MHz, CHLOROFORM-d1) d ppm 1.26 (3 H), 2.37 (2 H), 2.70 (6 H), 3.07 (1 H), 3.28 (1 H), 3.39 (1 H), 3.46 (1H), 4.04 (2 H), 4.66 (1 H), 6.70 (1 H), 7.07 (1 H), 7.39 (2 H), 7.49 (2 H), 7.75 (2 H), 8.04 (1 H), 8.45 (1 H), 9.03 (1 H). | LCMS (ESI+) calcd for C27H29N5O2 (M+H+) 456.24, found 456.18 |
| ER-894549 | 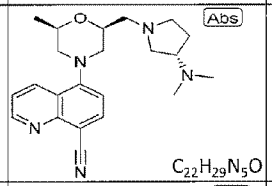 $C_{22}H_{29}N_5O$ | 379.5 | 0.0044 | 3.9 | 5-((2S,6R)-2-(((S)-3-(dimethylamino)pyrrolidin-1-yl)methyl)-6-methylmorpholino)quinoline-8-carbonitrile | H NMR (400 MHz, METHANOL-d4) d ppm 1.25 (3 H), 1.91 (1 H), 2.18 (1 H), 2.57 (6 H), 2.65 (1 H), 2.75 (2 H), 2.85 (1 H), 2.97 (1 H), 3.35 (2 H), 3.4 (3 H), 4.11 (2 H), 7.23 (1 H), 7.63 (1 H), 8.14 (1 H), 8.52 (1 H), 8.64 (1 H), 8.97 (1 H). | LCMS (ESI+) calcd for C22H29N5O (M+H+) 380.24, found 380.26 |
| ER-894550 | 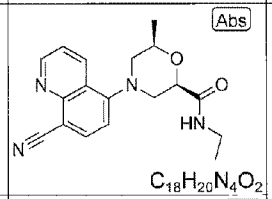 $C_{18}H_{20}N_4O_2$ | 324.38 | 0.0347 | > 10.0 | (2R,6R)-4-(8-cyanoquinolin-5-yl)-N-ethyl-6-methylmorpholine-2-carboxamide | 1H NMR (400 MHz, METHANOL-d4) d ppm 1.10 (2 H), 1.29 (3 H), 2.71 (2 H), 3.23 (3 H), 3.35 (1 H), 3.67 (1 H), 4.11 (1 H), 4.42 (1 H), 7.23 (1 H), 7.62 (1 H), 8.12 (1 H), 8.64 (1 H), 8.95 (1 H). | LCMS (ESI+) calcd for C18H20N4O2 (M+H+): 325.16 ; Found: 325.27 |
| ER-894551 | 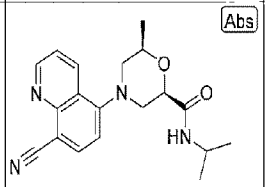 $C_{19}H_{22}N_4O_2$ | 338.41 | 0.0350 | > 10.0 | (2R,6R)-4-(8-cyanoquinolin-5-yl)-N-isopropyl-6-methylmorpholine-2-carboxamide | 1H NMR (400 MHz, METHANOL-d4) d ppm 1.15 (6 H), 1.3 (3 H), 2.71 (2 H), 3.35 (1 H), 3.65 (1 H), 4.07 (2 H), 4.40 (1 H), 7.22 (1 H), 7.47 (1 H), 7.61 (1 H), 8.10 (1 H), 8.62 (1 H), 8.94 (1 H). | LCMS (ESI+) calcd for C19H22N4O (M+H+): 339.18 ; Found: 339.17 |
| ER-894552 | 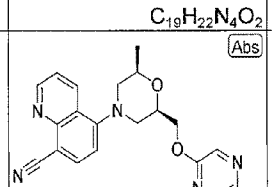 $C_{20}H_{19}N_5O_2$ | 361.4 | 0.1010 | > 10.0 | 5-((2R,6R)-2-methyl-6-((pyrazin-2-yloxy)methyl)morpholino)quinoline-8-carbonitrile | 1H NMR (400 MHz, CDCl3) d ppm 1.31 (3 H), 2.73 (1 H), 2.93 (1 H), 3.33 (1 H), 3.46 (1 H), 4.13 (1 H), 4.34 (1 H), 4.43 (1 H), 4.52 (1 H), 7.13 (1 H), 7.54 (1 H), 8.07 (1 H), 8.09 (1 H), 8.16 (1 H), 8.30 (1 H), 8.49 (1 H), 9.09 (1 H). | LCMS (ESI+) calcd for C20 H19 N5 O2 (M+H+) 362.4, found 362.3 |

FIG. 6CCC

| | | | | | | | |
|---|---|---|---|---|---|---|---|
| ER-894594 | 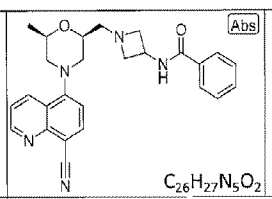 $C_{26}H_{27}N_5O_2$ | 441.5 | 0.0690 | >10.0 | N-(1-(((2S,6R)-4-(8-cyanoquinolin-5-yl)-6-methylmorpholin-2-yl)methyl)azetidin-3-yl)benzamide | | |
| ER-894655 | 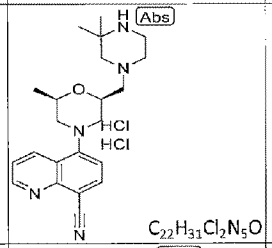 $C_{22}H_{31}Cl_2N_5O$ | 452.4 | 0.0010 | 14.72 | 5-((2S,6R)-2-((3,3-dimethylpiperazin-1-yl)methyl)-6-methylmorpholino)quinoline-8-carbonitrile dihydrochloride | | |
| ER-894656 | 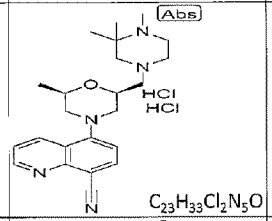 $C_{23}H_{33}Cl_2N_5O$ | 466.5 | 0.0008 | 10.63 | 5-((2R,6S)-2-methyl-6-((3,3,4-trimethylpiperazin-1-yl)methyl)morpholino)quinoline-8-carbonitrile dihydrochloride | 1H NMR (DMSO d6) d PPm 9.007 (m, 1H), 8.56 9 m, 1H), 8.22 9d, 1H), 7.64 (dd, 1H), 7.19 (m, 1H), 4.13 (br s, 8H, 3.39 (m, 1H), 2.62 ( m, 2H, 2.45 (s, 3H), 1.35 (br s, 6H), 1.14 (d, 3H) | LCMS (ESI+) calcd. for: C23H31N5O (M+H+): 393.3; found 393.4 |
| ER-895194 | 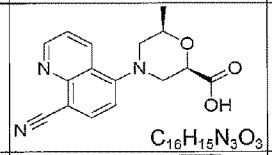 $C_{16}H_{15}N_3O_3$ | 297.30 | > 10.0 | > 10.0 | 5-((2R,6R)-2-formyl-6-methylmorpholino)quinoline-8-carbonitrile | 1H NMR (400 MHz, CDCl3-d) d ppm 1.34 (3 H, d) 2.71 - 2.77 (1 H, m) 2.85 - 2.91 (1 H, m) 3.24 (1H, d) 3.74 (1 H, d) 4.04 - 4.09 (1 H, m) 4.50 (1 H, d) 7.08 (1 H, d) 7.53 (1 H, d) 8.01 (1 H, d) 8.51 (1 H, d) 9.05 (1 H, s) | |
| ER-895200 | 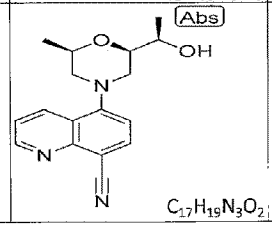 $C_{17}H_{19}N_3O_2$ | 297.4 | 0.1772 | > 10.0 | 5-((2R,6R)-2-((R)-1-hydroxyethyl)-6-methylmorpholino)quinoline-8-carbonitrile | $^1$H NMR (400 MHz, CHLOROFORM-*d*) d ppm 1.21 - 1.28 (m, 9 H) 1.59 (br. s., 4 H) 2.04 (br. s., 1 H) 2.58 - 2.65 (m, 1 H) 2.84 - 2.91 (m, 1 H) 3.28 (s, 1 H) 3.25 (s, 1 H) 3.38 (s, 1 H) 3.35 (s, 1 H) 3.78 (d, *J*=10.55 Hz, 1 H) 3.94 (br. s., 1 H) 4.04 (d, *J*=6.45 Hz, 1 H) 7.08 (d, *J*=7.91 Hz, 1 H) 7.24 (s, 1 H) 7.49 (dd, *J*=8.79, 4.10 Hz, 1 H) 8.02 (d, *J*=7.91 Hz, 1 H) 8.43 (d, *J*=8.50 Hz, 1 H) 9.05 (d, *J*=2.64 Hz, 1 H) | |

FIG. 6DDD

| | | | | | | | |
|---|---|---|---|---|---|---|---|
| ER-895204 | 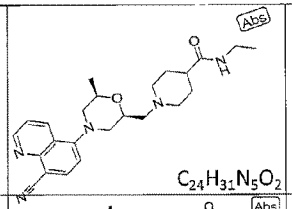 $C_{24}H_{31}N_5O_2$ | 421.5 | 0.0017 | > 10.0 | 1-(((2S,6R)-4-(8-cyanoquinolin-5-yl)-6-methylmorpholin-2-yl)methyl)-N-ethylpiperidine-4-carboxamide | $^1$H NMR (400 MHz, METHANOL-$d_4$) d ppm 1.00 - 1.18 (m, 2 H) 1.26 (d, $J$=6.15 Hz, 3 H) 1.96 (br. s., 3 H) 2.32 (s, 2 H) 2.42 (br. s., 1 H) 2.53 - 2.82 (m, 2 H) 2.93 (br. s., 2 H) 3.03 - 3.25 (m, 3 H) 3.39 (s, 1 H) 3.36 (s, 1 H) 3.57 (s, 1 H) 3.55 (s, 1 H) 4.11 (br. s., 1 H) 4.35 (br. s., 1 H) 4.89 (br. s., 1 H) 7.13 - 7.41 (m, 2 H) 7.56 - 7.72 (m, 2 H) 8.12 (d, $J$=7.91 Hz, 1 H) 8.34 (br. s., 1 H) 8.48 - 8.74 (m, 1 H) 8.95 (dd, $J$=4.10, 1.76 Hz, 1 H) | |
| ER-895204 | 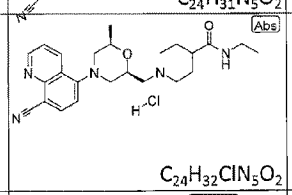 $C_{24}H_{32}ClN_5O_2$ | 458.0 | 0.0270 | > 10.0 | 1-(((2S,6R)-4-(8-cyanoquinolin-5-yl)-6-methylmorpholin-2-yl)methyl)-N-ethylpiperidine-4-carboxamide hydrochloride | | |
| ER-895310 | 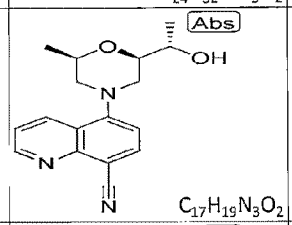 $C_{17}H_{19}N_3O_2$ | 297.4 | 0.3940 | > 10.0 | 5-((2R,6R)-2-((S)-1-hydroxyethyl)-6-methylmorpholino)quinoline-8-carbonitrile | | |
| ER-895324 | 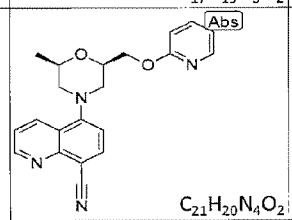 $C_{21}H_{20}N_4O_2$ | 360.4 | 0.0280 | > 10.0 | 5-((2R,6R)-2-methyl-6-((pyridin-2-yloxy)methyl)morpholino)quinoline-8-carbonitrile | 1H NMR (400 MHz, CDCl3-d) d ppm 1.29 (3 H, d) 2.63 - 2.75 (1 H, m) 2.80 - 2.94 (1 H, m) 3.22 - 3.36 (1 H, m) 3.40 - 3.50 (1 H, m) 4.01 - 4.14 (1 H, m) 4.27 - 4.40 (2 H, m) 4.44 - 4.56 (1 H, m) 6.73 - 6.80 (1 H, m) 6.83 - 6.91 (1 H, m) 7.08 (1 H, d) 7.41 - 7.52 (1 H, m) 7.53 - 7.61 (1 H, m) 7.98 - 8.06 (1 H, m) 8.08 - 8.16 (1 H, m) 8.39 - 8.53 (1 H, m) 8.99 - 9.11 (1 H, m) | LCMS (ESI+) calcd for C21 H20 N4 O2 (M+H+) 361.4, found 361.5 |
| ER-895325 | 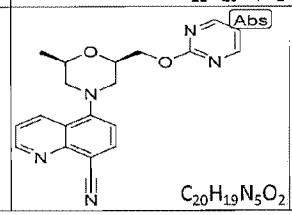 $C_{20}H_{19}N_5O_2$ | 361.4 | 0.0345 | 5.351 | 5-((2R,6R)-2-methyl-6-((pyrimidin-2-yloxy)methyl)morpholino)quinoline-8-carbonitrile | 1H NMR (400 MHz, CDCl3-d) d ppm 1.19 - 1.33 (3 H, d) 2.65 - 2.74 (1 H, m) 2.89 - 2.99 (1 H, m) 3.26 - 3.33 (1 H, m) 3.45 - 3.52 (1 H, m) 4.04 - 4.13 (1 H, m) 4.30 - 4.37 (1 H, m) 4.37 - 4.44 (1 H, m) 4.48 - 4.59 (1 H, m) 6.88 - 7.00 (1 H, m) 7.05 - 7.15 (1 H, m) 7.45 - 7.54 (1 H, m) 7.97 - 8.08 (1 H, m) 8.42 - 8.57 (3 H, m) 8.99 - 9.12 (1 H, m) | LCMS (ESI+) calcd for C20 H19 N5 O2 (M+H+) 362.4, found 362.0 |

FIG. 6EEE

| | | | | | | | |
|---|---|---|---|---|---|---|---|
| ER-895326 | 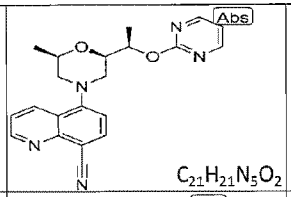 $C_{21}H_{21}N_5O_2$ | 375.4 | 0.0380 | > 10.0 | 5-((2R,6R)-2-methyl-6-((R)-1-(pyrimidin-2-yloxy)ethyl)morpholino)quinoline-8-carbonitrile | 1H NMR (400 MHz, CDCl3-d) d ppm 1.25 (3 H, d) 1.46 (3 H, d) 2.61 - 2.70 (1 H, m) 2.74 - 2.89 (1 H, m) 3.18 - 3.31 (1 H, m) 3.47 - 3.59 (1 H, m) 3.95 - 4.11 (2 H, m) 5.16 - 5.31 (1 H, m) 6.85 - 6.95 (1 H, m) 7.00 - 7.12 (1 H, m) 7.45 - 7.56 (1 H, m) 7.94 - 8.06 (1 H, m) 8.41 - 8.52 (3 H, m) 8.98 - 9.09 (1 H, m) | LCMS (ESI+) calcd for C21 H21 N5 O2 (M+H+) 376.4, found 376.4 |
| ER-895327 | 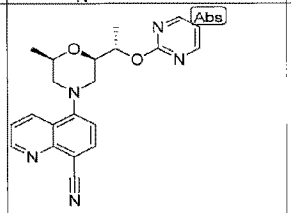 $C_{21}H_{21}N_5O_2$ | 375.4 | 0.1750 | > 10.0 | 5-((2R,6R)-2-methyl-6-((S)-1-(pyrimidin-2-yloxy)ethyl)morpholino)quinoline-8-carbonitrile | $^1$H NMR (400 MHz, CHLOROFORM-*d*) d ppm 0.84 - 0.88 (m, 1 H) 1.24 (d, *J*=6.15 Hz, 4 H) 1.43 (d, *J*=6.45 Hz, 4 H) 1.59 (s, 6 H) 2.62 - 2.69 (m, 1 H) 2.93 - 3.00 (m, 1 H) 3.27 (d, *J*=11.72 Hz, 1 H) 3.37 (d, *J*=11.43 Hz, 1 H) 4.00 - 4.07 (m, 1 H) 4.11 - 4.16 (m, 1 H) 5.34 - 5.40 (m, 1 H) 6.90 - 6.93 (m, 1 H) 7.07 (d, *J*=7.91 Hz, 1 H) 7.24 (s, 2 H) 7.48 (dd, *J*=8.50, 4.10 Hz, 1 H) 8.01 (d, *J*=7.91 Hz, 1 H) 8.40 - 8.44 (m, 1 H) 8.49 (d, *J*=4.98 Hz, 2 H) 9.03 - 9.06 (m, 1 H) | |
| ER-895412 | 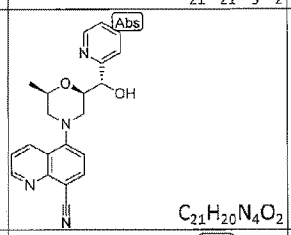 $C_{21}H_{20}N_4O_2$ | 360.4 | 0.0961 | > 10.0 | 5-((2R,6R)-2-((S)-hydroxy(pyridin-2-yl)methyl)-6-methylmorpholino)quinoline-8-carbonitrile | 1H NMR (400 MHz, METHANOL-d4) d ppm 1.10 - 1.20 (3 H, m) 2.59 - 2.70 (1 H, m) 2.81 - 2.91 (1 H, m) 3.37 - 3.45 (1 H, m) 3.93 - 4.03 (1 H, m) 4.16 - 4.28 (1 H, m) 4.56 - 4.62 (1 H, m) 4.70 - 4.78 (1 H, m) 7.13 - 7.22 (1 H, m) 7.25 - 7.34 (1 H, m) 7.49 - 7.59 (2 H, m) 7.75 - 7.85 (1 H, m) 8.03 - 8.14 (1 H, m) 8.44 - 8.57 (2 H, m) 8.86 - 8.94 (1 H, m) | LCMS (ESI+) calcd for C21 H20 N4 O2 (M+H+) 361.4, found 361.4 |
| ER-895415 | 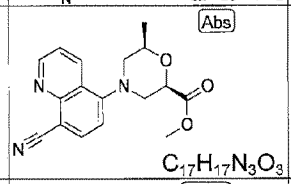 $C_{17}H_{17}N_3O_3$ | 311.34 | 0.2367 | > 10.0 | (2R,6R)-methyl 4-(8-cyanoquinolin-5-yl)-6-methylmorpholine-2-carboxylate | $^1$H NMR (400 MHz, METHANOL-$d_4$) d ppm 0.67 - 0.81 (m, 1 H) 0.86 (d, *J*=6.15 Hz, 4 H) 1.07 (s, 1 H) 2.24 (dd, *J*=12.01, 10.25 Hz, 2 H) 2.40 - 2.61 (m, 1 H) 2.79 (dt, *J*=11.87, 2.27 Hz, 2 H) 3.14 (dt, *J*=11.87, 2.42 Hz, 1 H) 3.45 - 3.67 (m, 1 H) 4.10 (dd, *J*=10.69, 2.49 Hz, 1 H) 6.62 (d, *J*=7.91 Hz, 1 H) 6.76 (s, 1 H) 7.05 (dd, *J*=8.50, 4.39 Hz, 1 H) 7.56 (d, *J*=7.91 Hz, 1 H) 7.97 (dd, *J*=8.50, 1.76 Hz, 1 H) 8.59 (dd, *J*=4.25, 1.61 Hz, 1 H) | |
| ER-895472 | 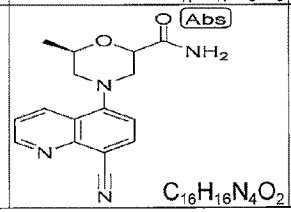 $C_{16}H_{16}N_4O_2$ | 296.33 | 0.0870 | > 10.0 | (6R)-4-(8-cyanoquinolin-5-yl)-6-methylmorpholine-2-carboxamide | 1H NMR (400 MHz, METHANOL-d4) d ppm 1.30 (3 H), 2.74 (2 H), 3.36 (1 H), 3.69 (1 H), 4.11 (2 H), 4.43 (1 H), 7.24 (1 H), 7.63 (1 H), 8.12 (1 H), 8.19 (1H), 8.64 (1 H), 8.95 (1 H). | LCMS (ESI+) calcd for C16H16N4O2 (M+H+): 297.13 ; Found: 297.27 |

FIG. 6FFF

| | | | | | | | |
|---|---|---|---|---|---|---|---|
| **ER-895473** | 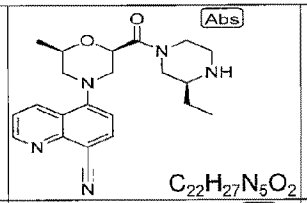 $C_{22}H_{27}N_5O_2$ | 393.49 | 0.0530 | > 10.0 | 5-((2R,6R)-2-((S)-3-ethylpiperazine-1-carbonyl)-6-methylmorpholino)quinoline-8-carbonitrile | 1H NMR (400 MHz, METHANOL-d4) 1.06 (3 H), 1.25 (3 H), 1.64 (2 H), 2.67 (1 H), 2.96 (2 H), 3.11 (2 H), 3.36 (2 H), 3.47 (1 H), 4.18 (2 H), 4.40 (1 H), 4.56 (1 H), 4.80 (1H), 7.26 (1 H), 7.59 (1 H), 8.13 (1 H), 8.35 (1 H), 8.61 (1 H), 8.94 (1 H). | LCMS (ESI+) calcd for C22H27N5O2 (M+H+): 394.22 ; Found: 394.06 |
| **ER-895474** | 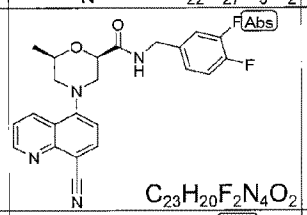 $C_{23}H_{20}F_2N_4O_2$ | 422.43 | 0.1030 | > 10.0 | (2R,6R)-4-(8-cyanoquinolin-5-yl)-N-(3,4-difluorobenzyl)-6-methylmorpholine-2-carboxamide | 1H NMR (400 MHz, METHANOL-d4) d ppm 1.31 (3 H), 2.74 (3 H), 3.36 (1 H), 3.69 (1 H), 4.11 (1 H), 4.36 (2 H), 4.5 (1 H), 7.19 (4 H), 7.62 (1 H), 8.11 (1 H), 8.64 (1 H), 8.95 (1 H). | LCMS (ESI+) calcd for C23H20F2N4O2 (M+H+): 423.16 ; Found: 423.4 |
| **ER-895475** | 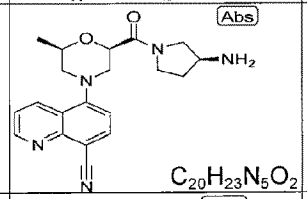 $C_{20}H_{23}N_5O_2$ | 365.43 | 0.0440 | > 10.0 | 5-((2R,6R)-2-((S)-3-aminopyrrolidine-1-carbonyl)-6-methylmorpholino)quinoline-8-carbonitrile | 1H NMR (400 MHz, METHANOL-d4) d ppm 1.25 (1 H), 1.76 (1 H), 2.00 (1 H), 2.09 (2 H), 2.67 (2 H), 3.03 (2 H), 3.16 (1 H), 3.27 (1 H), 3.35 (2 H), 3.46 (2 H). 3.63 (2 H), 3.96 (1 H), 4.11 (1 H), 4.67 (1 H), 7.23 (1 H), 7.59 (1 H), 8.1 (1 H), 8.61 (1 H), 8.93(1 H). | LCMS (ESI+) calcd for C20H23N5O2 (M+H+): 366.19 ; Found: 366.39 |
| **ER-895476** | 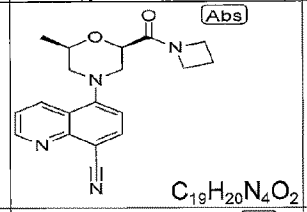 $C_{19}H_{20}N_4O_2$ | 336.39 | 0.0370 | > 10.0 | 5-((2R,6R)-2-(azetidine-1-carbonyl)-6-methylmorpholino)quinoline-8-carbonitrile | 1H NMR (400 MHz, METHANOL-d4) d ppm 1.25 (3 H), 2.31 (2 H), 2.67 (1 H), 2.92 (1 H), 3.35 (1 H), 3.52 (1 H), 4.05 (3 H), 4.51 (3 H), 7.25 (1 H), 7.63 (1 H), 8.13 (1 H), 8.65 (1 H), 8.96 (1 H). | |
| **ER-895477** | 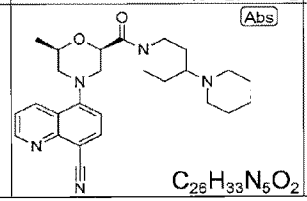 $C_{26}H_{33}N_5O_2$ | 447.58 | 0.1110 | > 10.0 | 5-((2R,6R)-2-([1,4'-bipiperidine]-1'-carbonyl)-6-methylmorpholino)quinoline-8-carbonitrile | 1H NMR (400 MHz, METHANOL-d4) 1.25 (3 H). 1.53 (m, 3 H), 1.75 (m, 4 H), 1.98 (2 H), 2.13 (3 H), 2.69 (2 H), 3.06 (4 H), 3.44 (4 H), 4.14 (1 H), 4.38 (1 H), 4.64 (1 H), 7.27 (1 H), 7.61 (1 H), 8.13 (1 H), 8.63 (1 H), 8.95 (1 H). | LCMS (ESI+) calcd for C26H33N5O2 (M+H+): 448.26 ; Found: 448.5 |

FIG. 6GGG

| | | | | | | | |
|---|---|---|---|---|---|---|---|
| ER-895478 | 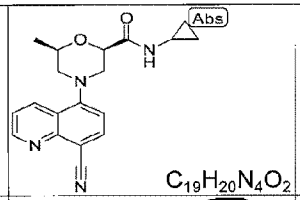 $C_{19}H_{20}N_4O_2$ | 336.39 | 0.0110 | > 10.0 | (2R,6R)-4-(8-cyanoquinolin-5-yl)-N-cyclopropyl-6-methylmorpholine-2-carboxamide | 1H NMR (400 MHz, METHANOL-d4) 0.55 (2 H), 0.72 (2 H), 0.86 (1 H), 1.28 (3 H), 2.71 (2 H), 3.34 (1 H), 3.64 (1 H), 4.08 (1 H), 4.41 (1 H), 7.73 (1 H), 7.62 (1 H), 7.83 (1 H), 8.12 (1 H), 8.63 (1 H), 8.95 (1 H). | LCMS (ESI+) calcd for C19H20N4O2 (M+H+): 337.16 ; Found: 336.98 |
| ER-895479 | 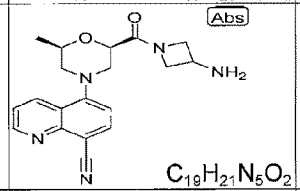 $C_{19}H_{21}N_5O_2$ | 351.41 | 0.0030 | > 10.0 | 5-((2R,6R)-2-(3-aminoazetidine-1-carbonyl)-6-methylmorpholino)quinoline-8-carbonitrile | 1H NMR (400 MHz, METHANOL-d4) 1.25 (3 H), 2.67 (1 H), 2.91 (1 H), 3.35 (1 H), 3.53 (1 H), 3.66 (1 H), 3.79 (1 H), 4.08 (2 H), 4.16 (2 H), 4.57 (3 H), 7.24 (1 H), 7.61 (1 H), 8.12 (1 H), 8.62 (1 H), 8.95 (1 H). | LCMS (ESI+) calcd for C19H21N5O2(M+H+): 352.17 ; Found: 352.34 |
| ER-897383 | 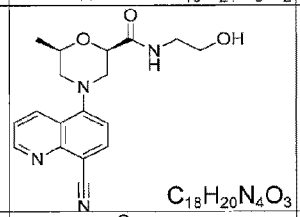 $C_{18}H_{20}N_4O_3$ | 340.38 | 0.2965 | > 10.0 | (2R,6R)-4-(8-cyanoquinolin-5-yl)-N-(2-hydroxyethyl)-6-methylmorpholine-2-carboxamide | 1H NMR (400 MHz, CDCl3-d) d ppm 1.30 (3 H, d) 2.66 (1 H, s) 2.76 (1 H, s) 3.22 - 3.35 (1 H, m) 3.40 - 3.58 (3 H, m) 3.69 - 3.85 (4 H, m) 4.01 - 4.13 (1 H, m) 4.35 - 4.50 (1 H, m) 6.96 - 7.16 (1 H, m) 7.41 - 7.60 (1 H, m) 7.92 - 8.05 (1 H, m) 8.34 - 8.50 (1 H, m) 8.95 - 9.11 (1 H, m) | LCMS (ESI+) calcd for C18 H20 N4 O3 [M+H+] 341.2, found 341.2 |
| ER-897385 | 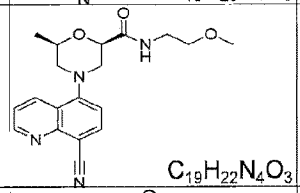 $C_{19}H_{22}N_4O_3$ | 354.41 | 0.0483 | > 10.0 | (2R,6R)-4-(8-cyanoquinolin-5-yl)-N-(2-methoxyethyl)-6-methylmorpholine-2-carboxamide | 1H NMR (400 MHz, METHANOL-d4) d ppm 1.30 (3 H, d) 2.59 - 2.82 (2 H, m) 3.35 - 3.49 (8 H, m) 3.54 - 3.71 (1 H, m) 4.03 - 4.17 (1 H, m) 4.36 - 4.50 (1 H, m) 7.13 - 7.27 (1 H, m) 7.54 - 7.69 (1 H, m) 8.06 - 8.15 (1 H, m) 8.54 - 8.71 (1 H, m) 8.89 - 9.11 (1 H, m) | LCMS (ESI+) calcd for C19 H22 N4 O3 (M+H+) 355.4, found 355.2 |
| ER-897445 | 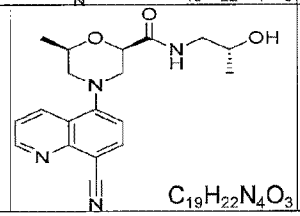 $C_{19}H_{22}N_4O_3$ | 354.41 | 0.0440 | > 10.0 | (2R,6R)-4-(8-cyanoquinolin-5-yl)-N-((R)-2-hydroxypropyl)-6-methylmorpholine-2-carboxamide | 1H NMR (400 MHz, METHANOL-d4) d ppm 1.12 (3 H, d) 1.30 (3 H, d) 2.63 - 2.81 (2 H, m) 3.14 (1 H, dd) 3.24 - 3.31 (1 H, m) 3.36 (1 H, d) 3.68 (1 H, d) 3.74 - 3.88 (1 H, m) 4.00 - 4.18 (1 H, m) 4.47 (1 H, dd) 7.22 (1 H, d) 7.62 (1 H, dd) 8.10 (1 H, d) 8.57 - 8.69 (1 H, m) 8.84 - 9.04 (1 H, m) | LCMS (ESI+) calcd for C19 H22 N4 O3 (M+H+) 355.4, found 355.2 |

FIG. 6HHH

| | | | | | | | |
|---|---|---|---|---|---|---|---|
| ER-897446 | 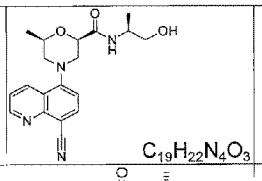 $C_{19}H_{22}N_4O_3$ | 354.41 | 0.0255 | > 10.0 | (2R,6R)-4-(8-cyanoquinolin-5-yl)-N-((S)-1-hydroxypropan-2-yl)-6-methylmorpholine-2-carboxamide | 1H NMR (400 MHz, CDCl3-d) d ppm 1.22 (3 H, d) 1.31 (3 H, d) 1.92 - 2.28 (1 H, brs) 2.61 - 2.71 (1 H, m) 2.72 - 2.84 (1 H, m) 3.22 - 3.31 (1 H, m) 3.50 - 3.61 (1 H, m) 3.64 - 3.72 (1 H, m) 3.73 - 3.84 (1 H, m) 4.03 - 4.17 (2 H, m) 4.35 - 4.46 (1 H, m) 6.69 - 6.85 (1 H, m) 6.98 - 7.13 (1 H, m) 7.45 - 7.57 (1 H, m) 7.94 - 8.07 (1 H, m) 8.37 - 8.50 (1 H, m) 8.93 - 9.16 (1 H, m) | LCMS (ESI+) calcd for C19 H22 N4 O3 (M+H+) 355.4, found 355.2 |
| ER-897447 | 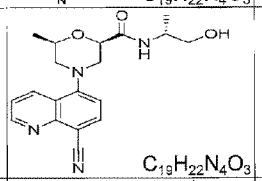 $C_{19}H_{22}N_4O_3$ | 354.41 | 0.0920 | > 10.0 | (2R,6R)-4-(8-cyanoquinolin-5-yl)-N-((R)-1-hydroxypropan-2-yl)-6-methylmorpholine-2-carboxamide | 1H NMR (400 MHz, METHANOL-d4) d ppm 1.12 (3 H, s) 1.30 (3 H, d) 2.62 - 2.82 (3 H, m) 3.34 (1 H, d) 3.61 - 3.72 (1 H, m) 3.92 - 4.17 (3 H, m) 4.44 (1 H, dd) 7.14 - 7.29 (1 H, m) 7.56 - 7.66 (1 H, m) 8.00 - 8.15 (1 H, m) 8.55 - 8.66 (1 H, m) 8.86 - 8.98 (1 H, m) | LCMS (ESI+) calcd for C19 H22 N4 O3 (M+H+) 355.4, found: 355.2 |
| ER-897827 | 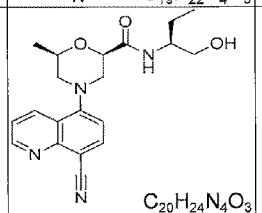 $C_{20}H_{24}N_4O_3$ | 368.43 | 0.0200 | > 10.0 | (2R,6R)-4-(8-cyanoquinolin-5-yl)-N-((S)-1-hydroxybutan-2-yl)-6-methylmorpholine-2-carboxamide | $^1$H NMR (400 MHz, CHLOROFORM-*d*) d ppm 0.99 - 1.12 (m, 1 H) 1.17 (t, *J*=7.47 Hz, 4 H) 1.38 - 1.48 (m, 2 H) 1.52 (d, *J*=6.15 Hz, 4 H) 1.66 - 1.92 (m, 3 H) 2.80 - 3.04 (m, 3 H) 3.48 (dt, *J*=11.94, 2.09 Hz, 1 H) 3.81 (dd, *J*=11.13, 6.15 Hz, 1 H) 3.91 (dd, *J*=11.13, 3.52 Hz, 1 H) 3.98 (dt, *J*=12.01, 2.34 Hz, 1 H) 4.02 - 4.13 (m, 1 H) 4.21 - 4.36 (m, 2 H) 4.63 (dd, *J*=10.84, 2.64 Hz, 1 H) 6.97 (d, *J*=8.20 Hz, 1 H) 7.25 (s, 1 H) 7.71 (dd, *J*=8.64, 4.25 Hz, 1 H) 8.21 (d, *J*=7.91 Hz, 1 H) 8.66 (dd, *J*=8.50, 1.76 Hz, 1 H) 9.24 (dd, *J*=4.25, 1.61 Hz, 1 H) | |
| ER-897828 | 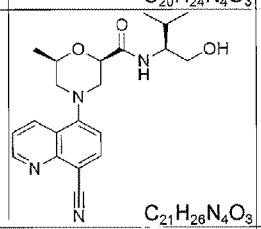 $C_{21}H_{26}N_4O_3$ | 382.46 | 0.0190 | >10.0 | (2R,6R)-4-(8-cyanoquinolin-5-yl)-N-((S)-1-hydroxy-3-methylbutan-2-yl)-6-methylmorpholine-2-carboxamide | $^1$H NMR (400 MHz, CHLOROFORM-*d*) d ppm 0.79 - 0.87 (m, 1 H) 0.95 (dd, *J*=10.40, 6.89 Hz, 7 H) 1.16 - 1.27 (m, 2 H) 1.30 (d, *J*=6.15 Hz, 4 H) 1.85 - 2.03 (m, 2 H) 2.65 (dd, *J*=12.01, 10.25 Hz, 1 H) 2.75 (dd, *J*=12.01, 10.84 Hz, 2 H) 3.25 (dt, *J*=12.01, 2.05 Hz, 1 H) 3.55 - 3.80 (m, 5 H) 3.98 - 4.15 (m, 1 H) 4.43 (dd, *J*=10.55, 2.64 Hz, 1 H) 6.82 (d, *J*=8.50 Hz, 1 H) 7.03 (d, *J*=7.91 Hz, 1 H) 7.49 (dd, *J*=8.64, 4.25 Hz, 1 H) 7.97 (d, *J*=7.91 Hz, 1 H) 8.43 (dd, *J*=8.50, 1.76 Hz, 1 H) 9.01 (dd, *J*=4.39, 1.76 Hz, 1 H) | |
| ER-897829 | 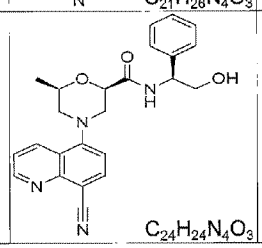 $C_{24}H_{24}N_4O_3$ | 416.48 | 0.0550 | >10.0 | (2R,6R)-4-(8-cyanoquinolin-5-yl)-N-((S)-2-hydroxy-1-phenylethyl)-6-methylmorpholine-2-carboxamide | $^1$H NMR (400 MHz, CHLOROFORM-*d*) d ppm 0.76 - 0.89 (m, 1 H) 1.14 - 1.41 (m, 6 H) 2.68 (dd, *J*=11.87, 10.40 Hz, 1 H) 2.79 - 2.86 (m, 1 H) 3.23 - 3.31 (m, 1 H) 3.76 - 3.82 (m, 1 H) 3.89 (d, *J*=4.98 Hz, 2 H) 4.03 4.13 (m, 1 H) 4.43 (dd, *J*=10.84, 2.64 Hz, 1 H) 5.07 (dt, *J*=7.47, 5.05 Hz, 1 H) 7.05 (d, *J*=7.91 Hz, 1 H) 7.21 - 7.39 (m, 7 H) 7.48 (dd, *J*=8.64, 4.25 Hz, 1 H) 7.99 (d, *J*=8.20 Hz, 1 H) 8.43 (dd, *J*=8.64, 1.61 Hz, 1 H) 9.01 (dd, *J*=4.25, 1.61 Hz, 1 H) | |

FIG. 6III

| | | | | | | | |
|---|---|---|---|---|---|---|---|
| **ER-897830** | $C_{24}H_{24}N_4O_3$ | 416.48 | 0.1050 | >10.0 | (2R,6R)-4-(8-cyanoquinolin-5-yl)-N-((R)-2-hydroxy-1-phenylethyl)-6-methylmorpholine-2-carboxamide | $^1$H NMR (400 MHz, CHLOROFORM-*d*) d ppm 0.79 - 0.88 (m, 1 H) 1.15 - 1.37 (m, 6 H) 2.63 - 2.77 (m, 2 H) 3.28 (dt, *J*=12.01, 2.05 Hz, 1 H) 3.76 (dt, *J*=12.01, 2.20 Hz, 1 H) 3.92 (d, *J*=4.98 Hz, 3 H) 4.06 - 4.15 (m, 1 H) 4.49 (dd, *J*=10.55, 2.64 Hz, 1 H) 5.09 (dt, *J*=7.62, 4.98 Hz, 1 H) 7.04 (d, *J*=8.20 Hz, 1 H) 7.23 - 7.40 (m, 7 H) 7.50 (dd, *J*=8.50, 4.39 Hz, 1 H) 7.99 (d, *J*=7.91 Hz, 1 H) 8.45 (dd, *J*=8.50, 1.76 Hz, 1 H) 9.03 (dd, *J*=4.25, 1.61 Hz, 1 H) | |
| **ER-897922** | $C_{20}H_{24}N_4O_3$ | 368.43 | 0.0280 | > 10.0 | (2R,6R)-4-(8-cyanoquinolin-5-yl)-N-(2-hydroxybutyl)-6-methylmorpholine-2-carboxamide | | LCMS (ESI+) calcd for C20H24N4O3 (M+H+): 369.19, found: 369.18 |
| **ER-897923** | $C_{20}H_{24}N_4O_3$ | 368.43 | 0.0520 | > 10.0 | (2R,6R)-4-(8-cyanoquinolin-5-yl)-N-(2-ethoxyethyl)-6-methylmorpholine-2-carboxamide | | LCMS (ESI+) calcd for C20H24N4O3 (M+H+): 369.19, found: 369.18 |
| **ER-897924** | $C_{20}H_{24}N_4O_3$ | 368.43 | 0.0880 | >10.0 | (2R,6R)-4-(8-cyanoquinolin-5-yl)-N-((R)-1-hydroxybutan-2-yl)-6-methylmorpholine-2-carboxamide | | LCMS (ESI+) calcd for C20H24N4O3(M+H+): 369.19, found: 369.18 |
| **ER-897925** | $C_{19}H_{22}N_4O_4$ | 370.41 | 0.1780 | >10.0 | (2R,6R)-4-(8-cyanoquinolin-5-yl)-N-(1,3-dihydroxypropan-2-yl)-6-methylmorpholine-2-carboxamide | | LCMS (ESI+) calcd for C19H22N4O4 (M+H+): 371.17, found: 371.16 |

FIG. 6JJJ

| | | | | | | | |
|---|---|---|---|---|---|---|---|
| **ER-897926** | $C_{19}H_{22}N_4O_4$ | 370.41 | 0.1710 | >10.0 | (2R,6R)-4-(8-cyanoquinolin-5-yl)-N-(2,3-dihydroxypropyl)-6-methylmorpholine-2-carboxamide | | LCMS (ESI+) calcd for C19H22N4O4 (M+H+): 371.17, found 371.16 |
| **ER-897927** | $C_{21}H_{24}N_4O_3$ | 380.45 | 0.0500 | >10.0 | (2R,6R)-4-(8-cyanoquinolin-5-yl)-6-methyl-N-(((R)-tetrahydrofuran-2-yl)methyl)morpholine-2-carboxamide | | LCMS (ESI+) calcd for C21H24N4O3 (M+H+): 381.19; found: 381.18 |
| **ER-897928** | $C_{21}H_{24}N_4O_3$ | 380.45 | 0.0440 | >10.0 | (2R,6R)-4-(8-cyanoquinolin-5-yl)-6-methyl-N-((tetrahydrofuran-2-yl)methyl)morpholine-2-carboxamide | | LCMS (ESI+) calcd for C21H24N4O3 (M+H+): 381.19; found: 381.18 |
| **ER-897929** | $C_{21}H_{26}N_4O_3$ | 382.46 | 0.0800 | >10.0 | (2R,6R)-4-(8-cyanoquinolin-5-yl)-6-methyl-N-(2-propoxyethyl)morpholine-2-carboxamide | | LCMS (ESI+) calcd for C21H26N4O3 (M+H+): 383.20; found: 383.2 |
| **ER-897930** | $C_{21}H_{26}N_4O_3$ | 382.24 | 0.0810 | >10.0 | (2R,6R)-4-(8-cyanoquinolin-5-yl)-N-((R)-1-hydroxypentan-2-yl)-6-methylmorpholine-2-carboxamide | | LCMS (ESI+) calcd for C21H26N4O3 (M+H+): 383.20; found: 383.2 |

FIG. 6KKK

| | | | | | | | |
|---|---|---|---|---|---|---|---|
| **ER-897931** | $C_{21}H_{26}N_4O_3$ | 382.46 | 0.0750 | >10.0 | (2R,6R)-4-(8-cyanoquinolin-5-yl)-N-(2-isopropoxyethyl)-6-methylmorpholine-2-carboxamide | | LCMS (ESI+) calcd for C21H26N4O3 (M+H+): 383.20; found: 383.2 |
| **ER-897932** | $C_{21}H_{26}N_4O_3$ | 382.46 | 0.0220 | >10.0 | (2R,6R)-4-(8-cyanoquinolin-5-yl)-N-(1-methoxybutan-2-yl)-6-methylmorpholine-2-carboxamide | | LCMS (ESI+) calcd for C21H26N4O3 (M+H+): 383.20; found: 383.2 |
| **ER-897933** | $C_{24}H_{23}FN_4O_3$ | 434.47 | 0.0560 | >10.0 | (2R,6R)-4-(8-cyanoquinolin-5-yl)-N-(2-(2-fluorophenyl)-2-hydroxyethyl)-6-methylmorpholine-2-carboxamide | | LCMS (ESI+) calcd for C24H23FN4O3 (M+H+):435.18; found: 435.18 |
| **ER-897934** | $C_{21}H_{26}N_4O_3$ | 382.46 | 0.1180 | >10.0 | (2R,6R)-4-(8-cyanoquinolin-5-yl)-N-((R)-1-hydroxy-3-methylbutan-2-yl)-6-methylmorpholine-2-carboxamide | | LCMS (ESI+) calcd for C21H26N4O3 (M+H+): 383.20; found: 383.2 |
| **ER-897935** | $C_{20}H_{24}N_4O_4$ | 384.43 | 0.0240 | >10.0 | (2R,6R)-4-(8-cyanoquinolin-5-yl)-N-(2,2-dimethoxyethyl)-6-methylmorpholine-2-carboxamide | | LCMS (ESI+) calcd for C20H24N4O4 (M+H+): 385.18; found: 385.18 |

FIG. 6LLL

| | | | | | | | |
|---|---|---|---|---|---|---|---|
| **ER-897936** | $C_{20}H_{24}N_4O_4$ | 384.43 | 0.0510 | >10.0 | (2R,6R)-4-(8-cyanoquinolin-5-yl)-N-(2-(2-hydroxyethoxy)ethyl)-6-methylmorpholine-2-carboxamide | | LCMS (ESI+) calcd for C20H24N4O4 (M+H+): 385.18; found: 385.18 |
| **ER-897937** | $C_{22}H_{26}N_4O_3$ | 394.47 | 0.0520 | >10.0 | (2R,6R)-4-(8-cyanoquinolin-5-yl)-N-((1S,2S)-2-hydroxycyclohexyl)-6-methylmorpholine-2-carboxamide | | LCMS (ESI+) calcd for C22H26N4O3 (M+H+): 395.20; found: 395.18 |
| **ER-897938** | $C_{22}H_{26}N_4O_3$ | 394.47 | 0.0190 | >10.0 | (2R,6R)-4-(8-cyanoquinolin-5-yl)-N-(2-hydroxycyclohexyl)-6-methylmorpholine-2-carboxamide | | LCMS (ESI+) calcd for C22H26N4O3 (M+H+): 395.20; found: 395.2 |
| **ER-897939** | $C_{22}H_{28}N_4O_3$ | 396.49 | 0.0630 | >10.0 | (2R,6R)-4-(8-cyanoquinolin-5-yl)-N-(1-hydroxyhexan-2-yl)-6-methylmorpholine-2-carboxamide | | LCMS (ESI+) calcd for C22H28N4O3 (M+H+): 397.22; found: 397.22 |
| **ER-897940** | $C_{22}H_{28}N_4O_3$ | 396.49 | 0.0270 | >10.0 | (2R,6R)-4-(8-cyanoquinolin-5-yl)-N-((S)-1-hydroxy-3.3-dimethylbutan-2-yl)-6-methylmorpholine-2-carboxamide | | LCMS (ESI+) calcd for C22H28N4O3 (M+H+): 397.22; found: 397.22 |

FIG. 6MMM

| | | | | | | | |
|---|---|---|---|---|---|---|---|
| **ER-897941** | 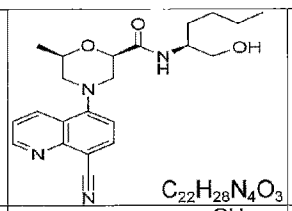 $C_{22}H_{28}N_4O_3$ | 396.49 | 0.0390 | >10.0 | (2R,6R)-4-(8-cyanoquinolin-5-yl)-N-((S)-1-hydroxyhexan-2-yl)-6-methylmorpholine-2-carboxamide | | LCMS (ESI+) calcd for C22H28N4O3 (M+H+): 397.22; found: 397.22 |
| **ER-897942** | 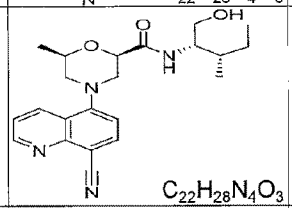 $C_{22}H_{28}N_4O_3$ | 396.49 | 0.0190 | >10.0 | (2R,6R)-4-(8-cyanoquinolin-5-yl)-N-((2S,3S)-1-hydroxy-3-methylpentan-2-yl)-6-methylmorpholine-2-carboxamide | | LCMS (ESI+) calcd for C22H28N4O3 (M+H+): 397.22; found: 397.22 |
| **ER-897943** | 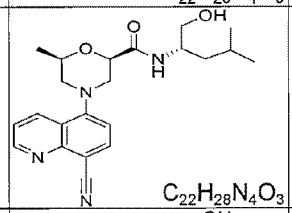 $C_{22}H_{28}N_4O_3$ | 396.49 | 0.0710 | >10.0 | (2R,6R)-4-(8-cyanoquinolin-5-yl)-N-((S)-1-hydroxy-4-methylpentan-2-yl)-6-methylmorpholine-2-carboxamide | | LCMS (ESI+) calcd for C22H28N4O3 (M+H+): 397.22; found: 397.22 |
| **ER-897944** | 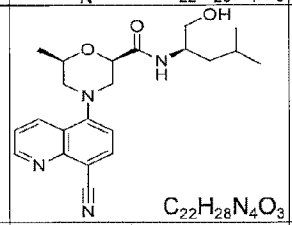 $C_{22}H_{28}N_4O_3$ | 396.49 | 0.1390 | >10.0 | (2R,6R)-4-(8-cyanoquinolin-5-yl)-N-((R)-1-hydroxy-4-methylpentan-2-yl)-6-methylmorpholine-2-carboxamide | | LCMS (ESI+) calcd for C22H28N4O3 (M+H+): 397.22; found: 397.22 |
| **ER-897945** | 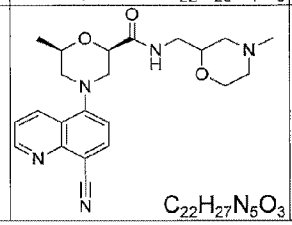 $C_{22}H_{27}N_5O_3$ | 409.49 | 0.0070 | >10.0 | (2R,6R)-4-(8-cyanoquinolin-5-yl)-6-methyl-N-((4-methylmorpholin-2-yl)methyl)morpholine-2-carboxamide | | LCMS (ESI+) calcd for C22H27N5O3 (M+H+): 410.21; found: 410.21 |

FIG. 6NNN

| | | | | | | | |
|---|---|---|---|---|---|---|---|
| **ER-897946** | $C_{21}H_{26}N_4O_3S$ | 414.53 | 0.0540 | >10.0 | (2R,6R)-4-(8-cyanoquinolin-5-yl)-N-((S)-1-hydroxy-4-(methylthio)butan-2-yl)-6-methylmorpholine-2-carboxamide | | LCMS (ESI+) calcd for C21H26N4O3S (M+H+): 415.18; found: 415.17 |
| **ER-897947** | $C_{24}H_{24}N_4O_3$ | 416.48 | 0.3950 | >10.0 | (2R,6R)-4-(8-cyanoquinolin-5-yl)-6-methyl-N-(2-phenoxyethyl)morpholine-2-carboxamide | | LCMS (ESI+) calcd for C21H26N4O3S (M+H+): 415.18; found: 417.18 |
| **ER-897948** | $C_{25}H_{26}N_4O_3$ | 430.51 | 0.0600 | >10.0 | (2R,6R)-4-(8-cyanoquinolin-5-yl)-N-((S)-1-hydroxy-3-phenylpropan-2-yl)-6-methylmorpholine-2-carboxamide | | LCMS (ESI+) calcd for C25H26N4O3 (M+H+): 431.2; found: 431.20 |
| **ER-897949** | $C_{25}H_{26}N_4O_3$ | 430.51 | 0.4830 | >10.0 | (2R,6R)-4-(8-cyanoquinolin-5-yl)-6-methyl-N-(2-phenoxypropyl)morpholine-2-carboxamide | | LCMS (ESI+) calcd for C25H26N4O3 (M+H+): 431.2; found: 431.20 |
| **ER-897950** | $C_{25}H_{26}N_4O_3$ | 430.51 | 0.0700 | >10.0 | (2R,6R)-4-(8-cyanoquinolin-5-yl)-N-(2-hydroxy-3-phenylpropyl)-6-methylmorpholine-2-carboxamide | | LCMS (ESI+) calcd for C25H26N4O3 (M+H+): 431.2; found: 431.20 |

FIG. 6OOO

| | | | | | | | |
|---|---|---|---|---|---|---|---|
| **ER-897952** | 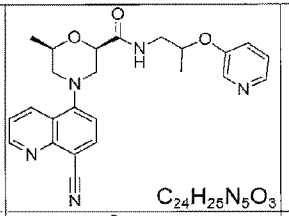 $C_{24}H_{25}N_5O_3$ | 431.49 | 0.0380 | >10.0 | (2R,6R)-4-(8-cyanoquinolin-5-yl)-6-methyl-N-(2-(pyridin-3-yloxy)propyl)morpholine-2-carboxamide | | LCMS (ESI+) calcd for C24H25N5O3 (M+H+): 432.2; found: 432.2 |
| **ER-897955** | 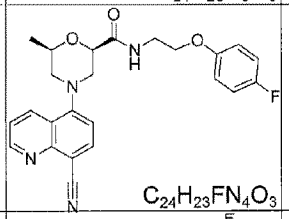 $C_{24}H_{23}FN_4O_3$ | 434.47 | 0.3550 | 9.200 | (2R,6R)-4-(8-cyanoquinolin-5-yl)-N-(2-(4-fluorophenoxy)ethyl)-6-methylmorpholine-2-carboxamide | | LCMS (ESI+) calcd for C24H23FN4O3 (M+H+): 435.18; found: 435.18 |
| **ER-897956** | 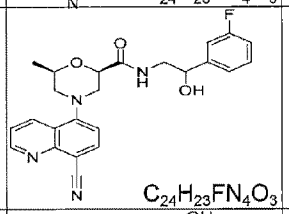 $C_{24}H_{23}FN_4O_3$ | 434.47 | 0.0620 | >10.0 | (2R,6R)-4-(8-cyanoquinolin-5-yl)-N-(2-(3-fluorophenyl)-2-hydroxyethyl)-6-methylmorpholine-2-carboxamide | | LCMS (ESI+) calcd for C24H23FN4O3 (M+H+): 435.18; found: 435.18 |
| **ER-897957** | 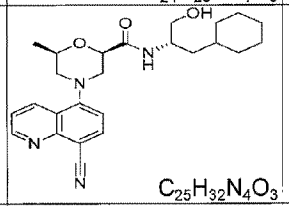 $C_{25}H_{32}N_4O_3$ | 436.55 | 0.0800 | >10.0 | (2R,6R)-4-(8-cyanoquinolin-5-yl)-N-((S)-1-cyclohexyl-3-hydroxypropan-2-yl)-6-methylmorpholine-2-carboxamide | | LCMS (ESI+) calcd for C25H32N4O3 (M+H+): 437.25; found: 437.25 |
| **ER-897958** | 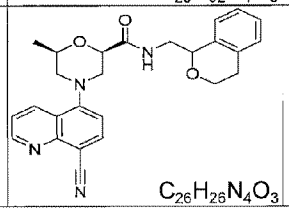 $C_{26}H_{26}N_4O_3$ | 442.52 | 0.1330 | >10.0 | (2R,6R)-4-(8-cyanoquinolin-5-yl)-N-(isochroman-1-ylmethyl)-6-methylmorpholine-2-carboxamide | | LCMS (ESI+) calcd for C26H26N4O3 (M+H+): 443.20; found: 443.20 |

FIG. 6PPP

| | | | | | | | |
|---|---|---|---|---|---|---|---|
| **ER-897960** | 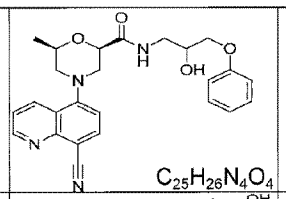 $C_{25}H_{26}N_4O_4$ | 446.50 | 0.1490 | >10.0 | (2R,6R)-4-(8-cyanoquinolin-5-yl)-N-(2-hydroxy-3-phenoxypropyl)-6-methylmorpholine-2-carboxamide | | LCMS (ESI+) calcd for C25H26N4O4 (M+H+): 447.20; found: 447.2 |
| **ER-897961** | 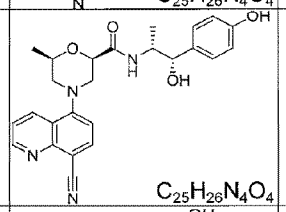 $C_{25}H_{26}N_4O_4$ | 446.50 | 0.0280 | >10.0 | (2R,6R)-4-(8-cyanoquinolin-5-yl)-N-((1S,2R)-1-hydroxy-1-(4-hydroxyphenyl)propan-2-yl)-6-methylmorpholine-2-carboxamide | | LCMS (ESI+) calcd for C25H26N4O4 (M+H+): 447.20; found: 447.2 |
| **ER-897962** | 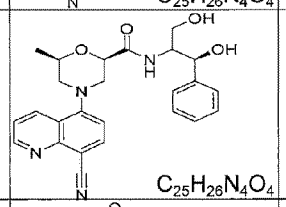 $C_{25}H_{26}N_4O_4$ | 446.50 | 0.0230 | >10.0 | (2R,6R)-4-(8-cyanoquinolin-5-yl)-N-((1S)-1,3-dihydroxy-1-phenylpropan-2-yl)-6-methylmorpholine-2-carboxamide | | LCMS (ESI+) calcd for C25H26N4O4 (M+H+): 447.20; found: 447.2 |
| **ER-897963** | 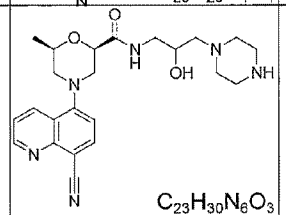 $C_{23}H_{30}N_6O_3$ | 438.53 | 0.0330 | 5.024 | (2R,6R)-4-(8-cyanoquinolin-5-yl)-N-(2-hydroxy-3-(piperazin-1-yl)propyl)-6-methylmorpholine-2-carboxamide | | LCMS (ESI+) calcd for C23H30N6O3 (M+H+): 439.24; found: 439.24 |
| **ER-897964** | 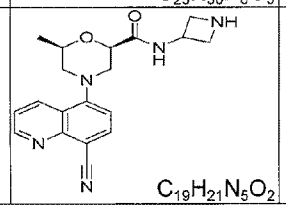 $C_{19}H_{21}N_5O_2$ | 351.41 | 0.0280 | 4.526 | (2R,6R)-N-(azetidin-3-yl)-4-(8-cyanoquinolin-5-yl)-6-methylmorpholine-2-carboxamide | | LCMS (ESI+) calcd for C19H21N5O2 (M+H+): 352.17; found: 352.17 |

FIG. 6QQQ

| | | | | | | | |
|---|---|---|---|---|---|---|---|
| **ER-897965** | 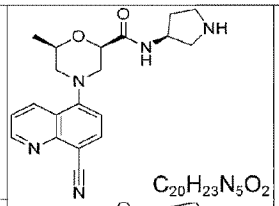 $C_{20}H_{23}N_5O_2$ | 365.43 | 0.0100 | > 10.0 | (2R,6R)-4-(8-cyanoquinolin-5-yl)-6-methyl-N-((S)-pyrrolidin-3-yl)morpholine-2-carboxamide | | LCMS (ESI+) calcd for C20H23N5O2 (M+H+): 366.19; found: 366.19 |
| **ER-897966** | 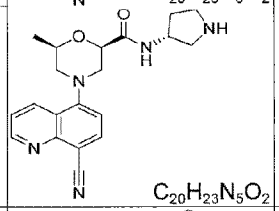 $C_{20}H_{23}N_5O_2$ | 365.43 | 0.0370 | > 10.0 | (2R,6R)-4-(8-cyanoquinolin-5-yl)-6-methyl-N-((R)-pyrrolidin-3-yl)morpholine-2-carboxamide | | LCMS (ESI+) calcd for C20H23N5O2 (M+H+): 366.19; found: 366.19 |
| **ER-897967** | 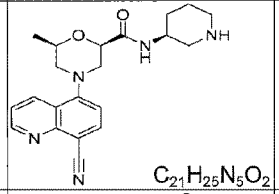 $C_{21}H_{25}N_5O_2$ | 379.46 | 0.0100 | > 10.0 | (2R,6R)-4-(8-cyanoquinolin-5-yl)-6-methyl-N-((S)-piperidin-3-yl)morpholine-2-carboxamide | | LCMS (ESI+) calcd for C21H25N5O2 (M+H+): 380.20; found: 380.2 |
| **ER-897968** | 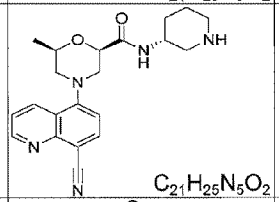 $C_{21}H_{25}N_5O_2$ | 379.46 | 0.0095 | > 10.0 | (2R,6R)-4-(8-cyanoquinolin-5-yl)-6-methyl-N-((R)-piperidin-3-yl)morpholine-2-carboxamide | | LCMS (ESI+) calcd for C21H25N5O2 (M+H+): 380.20; found: 380.2 |
| **ER-897969** | 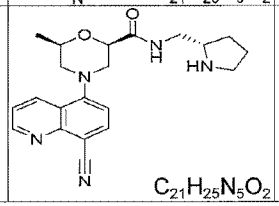 $C_{21}H_{25}N_5O_2$ | 379.46 | 0.0150 | > 10.0 | (2R,6R)-4-(8-cyanoquinolin-5-yl)-6-methyl-N-((S)-pyrrolidin-2-ylmethyl)morpholine-2-carboxamide | | LCMS (ESI+) calcd for C21H25N5O2 (M+H+): 380.20; found: 380.19 |

FIG. 6RRR

| | | | | | | | |
|---|---|---|---|---|---|---|---|
| **ER-897970** | $C_{25}H_{27}N_5O_2$ | 429.52 | 0.0380 | > 10.0 | (2R,6R)-N-(2-(benzylamino)ethyl)-4-(8-cyanoquinolin-5-yl)-6-methylmorpholine-2-carboxamide | | LCMS (ESI+) calcd for C25H27N5O2 (M+H+): 430.22; found: 430.22 |
| **ER-898560** | $C_{21}H_{19}N_5O_2$ | 373.41 | 0.0380 | > 10.0 | (2R,6R)-4-(8-cyanoquinolin-5-yl)-6-methyl-N-(pyridin-2-yl)morpholine-2-carboxamide | 1H NMR (400 MHz, METHANOL-d4) 1.38 (3 H), 2.76 (1 H), 2.91 (1 H), 3.41 (1 H), 3.77 (1 H), 4.24 (1 H), 4.66 (1 H), 7.15 (1 H), 7.28 (1 H), 7.65 (1 H), 7.8 (1 H), 8.14 (2 H), 8.28 (1 H), 8.68 (1 H), 8.97 (1 H). | LCMS (ESI+) calcd for C21H19N5O2 (M+H+): 374.16; found: 374.16 |
| **ER-898561** | $C_{22}H_{21}N_5O2$ | 387.44 | 0.0530 | > 10.0 | (2R,6R)-4-(8-cyanoquinolin-5-yl)-6-methyl-N-(6-methylpyridin-2-yl)morpholine-2-carboxamide | 1H NMR (400 MHz, METHANOL-d4) 1.39 (3 H), 2.44 (1 H), 2.76 (1H), 2.90 (1 H), 3.41 (1 H), 3.76 (1 H), 4.23 (1 H), 4.65 (1 H), 7.02 (1 H), 7.28 (1 H), 7.66 (1 H), 7.96 (2 H), 8.13 (1 H), 8.68 (1 H), 8.97 (1 H). | |
| **ER-898562** | $C_{20}H_{19}N_5O3$ | 377.40 | 0.1570 | > 10.0 | (2R,6R)-4-(8-cyanoquinolin-5-yl)-6-methyl-N-(5-methylisoxazol-3-yl)morpholine-2-carboxamide | 1H NMR (400 MHz, CHLOROFORM-d1) 1.35 (3 H), 2.40 (3 H), 2.71 (1 H), 2.86 (1 H), 3.32 (1 H), 3.80 (1 H), 4.16 (1 H), 4.56 (1 H), 6.68 (1 H), 7.10 (1 H), 7.54 (1 H), 8.04 (1 H), 8.47 (1 H), 8.99 (1 H), 9.09 (1 H). | LCMS (ESI+) calcd for C20H19N5O3 (M+H+): 378.15; found: 378.1 |
| **ER-898563** | $C_{18}H_{16}N_4F_3O_2$ | 378.35 | 0.0180 | > 10.0 | (2R,6R)-4-(8-cyanoquinolin-5-yl)-6-methyl-N-(2,2,2-trifluoroethyl)morpholine-2-carboxamide | 1H NMR (400 MHz, CHLOROFORM-d1) 1.37 (3 H), 2.76 (2 H), 3.33 (1 H), 3.82 (1 H), 3.99 (2 H), 4.15 (1 H), 4.53 (1 H), 7.00 (1 H), 7.12 (1 H), 7.56 (1 H), 8.07 (1 H), 8.49 (1 H), 9.11 (1 H). | LCMS (ESI+) calcd for C18H17F3N4O2 (M+H+): 378.15; found: 380.3 |

FIG. 6SSS

| | | | | | | | |
|---|---|---|---|---|---|---|---|
| **ER-898564** | $C_{18}H_{18}F_2N_4O_2$ | 360.36 | 0.3330 | > 10.0 | (2R,6R)-4-(8-cyanoquinolin-5-yl)-N-(2,2-difluoroethyl)-6-methylmorpholine-2-carboxamide | | LCMS (ESI+) calcd for C18H18F2N4O2 (M+H+): 361.14; found: 361.1 |
| **ER-898565** | $C_{19}H_{19}F_3N_4O_2$ | 392.38 | 0.0340 | > 10.0 | (2R,6R)-4-(8-cyanoquinolin-5-yl)-6-methyl-N-(3,3,3-trifluoropropyl)morpholine-2-carboxamide | 1H NMR (400 MHz, CHLOROFORM-d1) □□ppm 1.31 (3 H), 2.38 (2 H), 2.70 (3 H), 3.28 (1 H), 3.56 (2 H), 3.77 (1 H), 4.09 (1 H), 4.42 (1 H), 7.07 (1 H), 7.52 (1 H), 8.03 (1 H), 8.45 (1 H), 9.07 (1 H). | LCMS (ESI+) calcd for C19H19F3N4O2 (M+H+): 393.15; found: 393.25 |
| **ER-898566** | $C_{22}H_{29}N_5O_2$ | 395.50 | 0.0030 | > 10.0 | (2R,6R)-4-(8-cyanoquinolin-5-yl)-N-(2-(dimethylamino)-2-methylpropyl)-6-methylmorpholine-2-carboxamide | 1H NMR (400 MHz, CHLOROFORM-d1) □□ppm 1.03 (6 H), 1.35 (3H), 2.24 (6 H), 2.75 (2 H), 3.23 (2 H), 3.31 (1 H), 3.77 (1 H), 3.83 (1 H), 4.11 (1 H), 4.45 (1 H), 7.10 (1 H), 7.54 (1 H), 8.05 (1 H), 8.50 (1 H), 9.09 (1 H). | LCMS (ESI+) calcd for C22H29N5O2 (M+H+): 396.24; found: 397.56 |
| **ER-898694** | HCl $C_{21}H_{26}ClN_5O_3$ | 431.92 | 0.0020 | > 10.0 | (2R,6R)-4-(8-cyanoquinolin-5-yl)-6-methyl-N-((S)-morpholin-2-ylmethyl)morpholine-2-carboxamide hydrochloride | 1H NMR (d6 DMSO) d ppm 9.2 (br s 1H), 9.02 (dd, 1H), 8.56 (dd, 1H), 8.21 (d, 1H), 7.97 (d, 1H), 7.65 (dd, 1H), 7.21 (d, 1H), 4.39 (dd, 1H), 4.02 _m, 1H), 3.89 (m,1H), 3.73 (m, 1H), 3.65 (m, 1H), 3.50 (m, 1H), 3.30 (m, 2H), 3.20-3.08 (m, 4H), 2.91 (m, 1H), 2.74 (t, 1H), 2.63 (m, 1H), 1,20 (d, 3H) | (ESI+)calcd. For: C21H25N5O3 395.5 found 396.4 (m+1) |
| **ER-898707** | $CH_3CO_2H$ $C_{24}H_{31}N_5O_5$ | 469.54 | 0.0050 | > 10.0 | (2R,6R)-4-(8-cyanoquinolin-5-yl)-6-methyl-N-(((S)-4-methylmorpholin-2-yl)methyl)morpholine-2-carboxamide acetic acetate | 1H NMR (d4 methanol) d ppm 8.95 (ddd, 1H), 8.62 (dd, 1H), 8.10 (d, 1H), 7.61 (d, 1H), 7.21 (d, 1H), 4.85 (s, 1H), 4.82 (d, 1H) 4.46 (dd, 1H), 4.14 (m,1H), 3.88 (m, 1H), 3.69-3.57 (m, 3H), 3.37-3.29 (m, 3H), 2.83-2.67 (m, 3H), 2.33 (s, 3H), 2.26 (m, 1H), 1.95 (3, 3H), 1.93 (m, 1H) 1,20 (d, 3H) | (ESI+)calcd. For: C22H27N5O3 409.2 found 410.2 (m+1) |

FIG. 6TTT

| | | | | | | | |
|---|---|---|---|---|---|---|---|
| **ER-898914** | 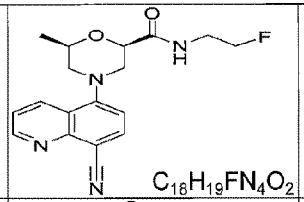 $C_{18}H_{19}FN_4O_2$ | 342.37 | 0.0310 | > 10.0 | (2R,6R)-4-(8-cyanoquinolin-5-yl)-N-(2-fluoroethyl)-6-methylmorpholine-2-carboxamide | 1H NMR (400 MHz, CHLOROFORM-d1) □□ppm 1.33 (3 H), 2.75 (2 H), 3.32 (1 H), 3.65 (2 H), 3.82 (1 H), 4.12 (1 H), 4.48 (2 H), 4.61 (1 H), 7.03 (1 H), 7.10 (1 H), 7.55 (1 H), 8.06 (1 H), 8.49 (1 H), 9.10 (1 H). | LCMS (ESI+) calcd for C18H19FN4O2 (M+H+): 343.15; found: 343.06 |
| **ER-898915** | 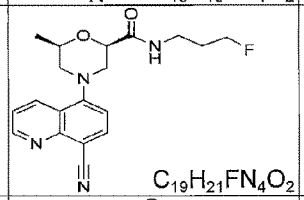 $C_{19}H_{21}FN_4O_2$ | 356.40 | 0.0374 | > 10.0 | (2R,6R)-4-(8-cyanoquinolin-5-yl)-N-(3-fluoropropyl)-6-methylmorpholine-2-carboxamide | 1H NMR (400 MHz, CHLOROFORM-d1) □□ppm 1.33 (3 H), 1.97 (2 H), 2.71 (2 H), 3.30 (1 H), 3.47 (2 H), 3.81 (1 H), 4.10 (1 H), 4.42 (1 H), 4.49 (1 H), 4.61 (1 H), 6.88 (1 H), 7.08 (1 H), 7.53 (1 H), 8.03 (1 H), 8.47 (1 H), 9.07 (1 H). | LCMS (ESI+) calcd for C19H21FN4O2 (M+H+): 357.17; found: 357.26 |
| **ER-898916** | 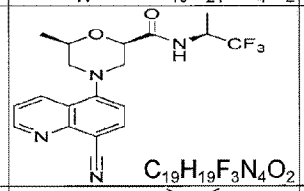 $C_{19}H_{19}F_3N_4O_2$ | 420.43 | 0.0584 | > 10.0 | (2R,6R)-4-(8-cyanoquinolin-5-yl)-6-methyl-N-((S)-1,1,1-trifluoropropan-2-yl)morpholine-2-carboxamide | 1H NMR (400 MHz, CHLOROFORM-d1) □□ppm 1.37 (6 H), 2.73 (2 H), 3.31 (1 H), 3.31 (1 H), 4.12 (1 H), 4.72 (1 H), 6.74 (1 H), 7.10 (1 H), 7.55 (1 H), 8.05 (1 H), 8.47 (1 H), 9.09 (1 H). | LCMS (ESI+) calcd for C19H19F3N4O2 (M+H+): 393.15; found: 393.15 |
| **ER-898917** | 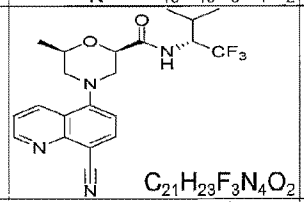 $C_{21}H_{23}F_3N_4O_2$ | 420.43 | 0.4860 | > 10.0 | (2R,6R)-4-(8-cyanoquinolin-5-yl)-6-methyl-N-((R)-1,1,1-trifluoropropan-2-yl)morpholine-2-carboxamide | 1H NMR (400 MHz, CHLOROFORM-d1) □□ppm 1.01 (6 H), 1.35 (3 H), 2.21 (1 H), 2.73 (2 H), 3.32 (1 H), 3.85 (1 H), 4.14 (1 H), 4.51 (2 H), 6.83 (1 H), 7.11 (1 H), 7.54 (1 H), 8.05 (1 H), 8.48 (1 H), 9.09 (1 H) | LCMS (ESI+) calcd for C21H23F3N4O2 (M+H+): 421.18; found: 421.18 |
| **ER-898918** | 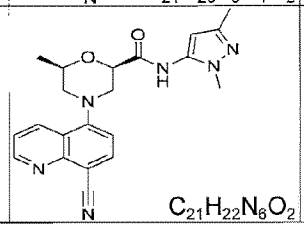 $C_{21}H_{22}N_6O_2$ | 390.45 | 0.0321 | > 10.0 | (2R,6R)-4-(8-cyanoquinolin-5-yl)-N-(1,3-dimethyl-1H-pyrazol-5-yl)-6-methylmorpholine-2-carboxamide | 1H NMR (400 MHz, CHLOROFORM-d1) □□ppm 1.41 (3 H), 2.24 (3 H), 2.76 (1 H), 2.89 (1 H), 3.35 (1 H), 3.70 (3 H), 3.86 (1 H), 4.20 (1 H), 4.62 (1 H), 6.11 (1 H), 7.13 (1 H), 7.56 (1 H), 8.06 (1 H), 8.24 (1 H), 8.49 (1 H), 9.10 (1 H). | LCMS (ESI+) calcd for C21H22N6O2 (M+H+): 391.18; found: 391.27 |

FIG. 6UUU

| | | | | | | | |
|---|---|---|---|---|---|---|---|
| **ER-898919** | 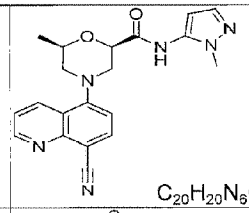 $C_{20}H_{20}N_6O_2$ | 376.42 | 0.0137 | > 10.0 | (2R,6R)-4-(8-cyanoquinolin-5-yl)-6-methyl-N-(1-methyl-1H-pyrazol-5-yl)morpholine-2-carboxamide | H NMR (400 MHz, CHLOROFORM-d1) □□ppm 1.41 (3 H), 2.77 (1 H), 2.91 (1 H), 3.37 (1 H), 3.79 (3 H), 3.88 (1 h), 4.22 (1 H), 4.64 (1 H), 6.32 (1 H), 7.14 (1 H), 7.46 (1 H), 7.57 (1 H), 8.07 (1 H), 8.30 (1 H), 8.50 (1 H), 9.11 (1 H). | LCMS (ESI+) calcd for C20H20N6O2 (M+H+): 377.17; found: 377.28 |
| **ER-898920** | 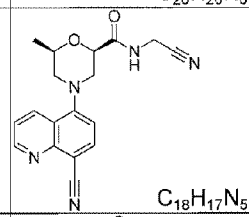 $C_{18}H_{17}N_5O_2$ | 335.37 | 0.0450 | > 10.0 | (2R,6R)-N-(cyanomethyl)-4-(8-cyanoquinolin-5-yl)-6-methylmorpholine-2-carboxamide | H NMR (400 MHz, CHLOROFORM-d1) 1.35 (3 H), 2.70 (1 H), 2.81 (1 H), 3.32 (1 H), 3.79 (1 H), 4.14 (1 H), 4.27 (2 H), 4.52 (1 H), 7.11 (2 H), 7.56 (1 H), 8.06 (1 H), 8.47 (1 H), 9.10 (1 H). | LCMS (ESI+) calcd for C18H17N5O2 (M+H+): 336.14; found: 336.14 |
| **ER-898921** | 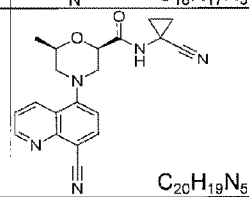 $C_{20}H_{19}N_5O_2$ | 361.40 | 0.0870 | > 10.0 | (2R,6R)-N-(1-cyanocyclopropyl)-4-(8-cyanoquinolin-5-yl)-6-methylmorpholine-2-carboxamide | H NMR (400 MHz, CHLOROFORM-d1) □□ppm 1.34 (5 H), 1.62 (2 H), 2.68 (1 H), 2.80 (1 H), 3.31 (1 H), 3.79 (1 H), 4.11 (1 H), 4.46 (1 H), 7.11 (1 H), 7.16 (1 H), 7.11 (1 H), 8.06 (1 H), 8.46 (1 H), 9.10 (1 H). | LCMS (ESI+) calcd for C20H19N5O2 (M+H+): 362.16; found: 362.15 |
| **ER-898922** | 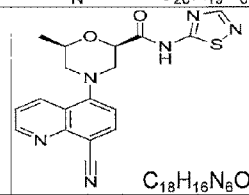 $C_{18}H_{16}N_6O_2S$ | 380.43 | 0.0650 | > 10.0 | (2R,6R)-4-(8-cyanoquinolin-5-yl)-6-methyl-N-(1,2,4-thiadiazol-5-yl)morpholine-2-carboxamide | H NMR (400 MHz, CHLOROFORM-d1) □□ppm 1.42 (3 H), 2.76 (1 H), 2.95 (1 H), 3.39 (1 H), 3.87 (1H), 4.25 (1 H), 4.78 (1 H), 7.14 (1 H), 7.59 (1 H), 8.08 (1 H), 8.39 (1 H), 8.50 (1 H), 9.22 (1 H), 10.17 (1 H). | LCMS (ESI+) calcd for C18H16N6O2S (M+H+): 381.11; found: 381.11 |
| **ER-898923** | 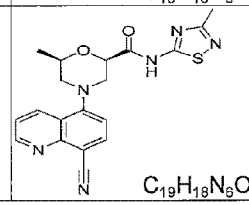 $C_{19}H_{18}N_6O_2S$ | 394.46 | 0.0650 | > 10.0 | (2R,6R)-4-(8-cyanoquinolin-5-yl)-6-methyl-N-(3-methyl-1,2,4-thiadiazol-5-yl)morpholine-2-carboxamide | H NMR (400 MHz, CHLOROFORM-d1) 1.39 (3 H), 2.60 (3 H), 2.75 (1 H), 2.93 (1 H), 3.37 (1 H), 3.86 (1 H), 4.24 (1 H), 4.75 (1 H), 7.13 (1 H), 7.58 (1 H), 8.08 (1 H), 8.49 (1 H), 9.12 (1 H), 10.08 (1 H). | LCMS (ESI+) calcd for C19H18N6O2S (M+H+): 395.12; found: 395.12 |

FIG. 6VVV

| | | | | | | | |
|---|---|---|---|---|---|---|---|
| ER-898946 | $C_{21}H_{25}N_5O_2$ | 379.46 | 0.0030 | 2.110 | (2R,6R)-4-(8-cyanoquinolin-5-yl)-6-methyl-N-(piperidin-4-yl)morpholine-2-carboxamide | 1H NMR (400 MHz, CD3OD) δ ppm: 1.30-1.35 (d, 3H), 1.45-1.58 (m, 2H), 1.79-1.90 (m, 2H), 2.63-2.83 (m, 4H), 3.03-3.11 (m, 2H), 3.35-3.41 (dt, 1H), 3.65-3.71 (dt, 1H), 3.79-3.89 (m, 1H), 4.09-4.19 (m, 1H), 4.43-4.48 (dd, 1H), 7.24-7.28 (d, 1H), 7.63-7.67 (dd, 1H), 8.12-8.16 (d, 1H), 8.64-8.68 (dd, 1H), 8.96-8.99 (dd, 1H). | LCMS (ESI+) calcd for C21H25N5O2 (M+H+): 380.20; found: 380.2 |
| ER-899017 | $C_{22}H_{26}ClN_5O_2$ | 427.93 | 0.0160 | 1.070 | 5-((2R,6R)-2-methyl-6-(2,6-diazaspiro[3.4]octane-2-carbonyl)morpholino)quinoline-8-carbonitrile hydrochloride | δ 1.15, (d, 3H), 1.22, (t, 2H), 2.10, (m, 2H), 2.61, (m, 1H), 2.84, (m, 1H), 3.08, (m, 2H), 3.12, (m, 1H), 3.40, (d, 1H), 3.79, (dd, 1H), 3.89, (dd, 1H), 3.96, (m, 1H), 4.25, (dd, 1H), 4.33, (dd, 1H), 4.49, (t, 1H), 7.21, (d, 1H), 7.65, (dd, 1H), 8.21, (d, 1H), 8.53, (d, 1H), 8.98, (br s, 2H), 9.01, (d, 1H) | LCMS (ESI+) calcd for C22H25N5O2 (M+H+): 392.40; found: 392.33 |
| ER-899018 | $C_{21}H_{26}ClN_5O_2$ | 415.92 | 0.0220 | >10.0 | 5-((2R,6R)-2-methyl-6-(3-((methylamino)methyl)azetidine-1-carbonyl)morpholino)quinoline-8-carbonitrile hydrochloride | δ 1.14 (d, 3H), 2.49, (m, 2H), 2.63, (s, 3H), 2.86, (m, 2H), 3.12, (m, 2H), 3.32, (m, 1H), 3.40, (m, 1H), 3.68, (m, 1H), 3.94, (m, 2H), 4.15, (m, 1H), 4.38, (m, 1H), 4.47, (m, 1H), 7.21, (d, 1H), 7.65, (dd, 1H), 8.21, (d, 1H), 8.53, (d, 1H), 8.62, (br s, 2H), 9.01, (d, 1H) | |
| ER-899019 | $C_{22}H_{27}ClFN_5O_2$ | 447.94 | 0.0300 | >10.0 | (2R,6R)-4-(8-cyanoquinolin-5-yl)-N-((4-fluoropiperidin-4-yl)methyl)-6-methylmorpholine-2-carboxamide hydrochloride | δ 1.17, (d, 3H), 1.62, (m, 2H), 1.74, (m, 2H), 2.60, (m, 1H), 2.89, (m, 3H), 3.18, (m, 1H), 3.32, (m, 3H), 3.42, (d, 1H), 3.75, (t, 1H), 3.97, (m, 2H), 4.17, (dd, 1H), 4.49, (t, 1H), 7.21, (d, 1H), 7.65, (dd, 1H), 8.21, (d, 1H), 8.53, (d, 1H), 8.70, (br s, 2H), 9.01, (d, 1H) | |
| ER-899020 | $C_{20}H_{24}ClN_5O2$ | 401.90 | 0.0290 | >10.0 | (2R,6R)-N-(azetidin-3-ylmethyl)-4-(8-cyanoquinolin-5-yl)-6-methylmorpholine-2-carboxamide hydrochloride | δ 1.21, (d, 3H), 2.63, (t, 1H), 2.76, (t, 1H), 2.87, (m, 1H), 2.99, (m, 1H), 3.28, (m, 2H), 3.33, (d, 1H), 3.54, (m, 1H), 3.68, (m, 2H), 3.85, (m, 1H), 4.01, (m, 1H), 4.38, (m, 2H), 7.23, (d, 1H), 7.65, (dd, 1H), 8.21, (m, 2H), 8.55, (d, 1H), 9.01, (d, 1H) | |
| ER-899021 | $C_{23}H_{28}ClN_5O_2$ | 441.96 | 0.0230 | 11.800 | 5-((2R,6R)-2-methyl-6-(2,6-diazaspiro[3.5]nonane-2-carbonyl)morpholino)quinoline-8-carbonitrile hydrochloride | δ 1.16, (d, 3H), 1.35, (d, 1H), 1.62, (m, 2H), 1.75, (m, 2H), 2.60, (m, 1H), 2.88, (m, 2H), 3.18, (m, 2H), 3.33, (m, 2H), 3.42, (d, 1H), 3.75, (t, 1H), 3.97, (m, 2H), 4.16, (dd, 1H), 4.49, (t, 1H), 7.21, (d, 1H), 7.65, (dd, 1H), 8.21, (d, 1H), 8.53, (d, 1H), 8.70, (br s, 2H), 9.01, (d, 1H) | |
| ER-899023 | $C_{22}H_{28}ClN_5O_2$ | 427.93 | 0.0360 | 11.250 | 5-((2R,6R)-2-methyl-6-(1,6-diazaspiro[3.4]octane-1-carbonyl)morpholino)quinoline-8-carbonitrile hydrochloride | δ 1.15, (d, 3H), 2.08, (m, 1H), 2.30, (m, 1H), 2.44, (m, 1H), 2.61, (t, 1H), 2.87, (m, 1H), 3.19, (m, 2H), 3.33, (m, 2H), 3.41, (m, 2H), 3.81, (m, 1H), 3.96, (m, 1H), 4.18, (m, 2H), 4.46, (dd, 1H), 7.21, (d, 1H), 7.65, (dd, 1H), 8.21, (d, 1H), 8.53, (d, 1H), 8.70, (br s, 2H), 9.01, (d, 1H) | |

FIG. 6WWW

| | | | | | | | |
|---|---|---|---|---|---|---|---|
| ER-899024 | 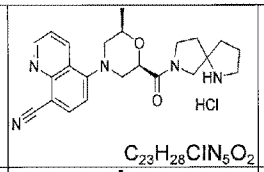 $C_{23}H_{28}ClN_5O_2$ | 441.96 | 0.2050 | 2.190 | 5-((2R,6R)-2-methyl-6-(1,7-diazaspiro[4.4]nonane-7-carbonyl)morpholino)quinoline-8-carbonitrile hydrochloride | δ 1.15, (d, 3H), 1.87, (m, 4H), 2.63, (m, 1H), 2.95, (m, 1H), 3.09, (m, 2H), 3.23, (m, 2H), 3.35, (m, 4H), 3.60, (m, 1H), 4.00, (m, 2H), 4.58, (t, 1H), 7.23, (d, 1H), 7.63, (dd, 1H), 8.21, (d, 1H), 8.55, (d, 1H), 9.01, (d, 1H) | |
| ER-899025 | 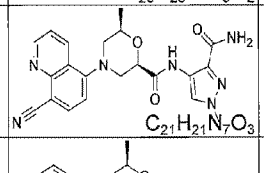 $C_{21}H_{21}N_7O_3$ | 419.44 | 0.0510 | >10.0 | (2R,6R)-N-(3-carbamoyl-1-methyl-1H-pyrazol-4-yl)-4-(8-cyanoquinolin-5-yl)-6-methylmorpholine-2-carboxamide | δ 1.23, (d, 3H), 2.67, (m, 1H), 2.83, (t, 1H), 3.38, (d, 1H), 3.62, (d, 1H), 3.84, (s, 3H), 4.12, (m, 1H), 4.61, (d, 1H), 7.25, (d, 1H), 7.42, (s, 1H), 7.66, (m, 2H), 8.18, (s, 1H), 8.22, (d, 1H), 8.59, (d, 1H), 9.02, (d, 1H), 10.59, (s, 1H) | |
| ER-899121 | 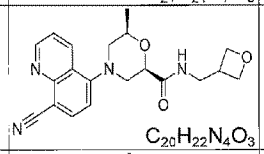 $C_{20}H_{22}N_4O_3$ | 366.42 | 0.0200 | >10.0 | (2R,6R)-4-(8-cyanoquinolin-5-yl)-6-methyl-N-(oxetan-3-ylmethyl)morpholine-2-carboxamide | 1H NMR (400 MHz, CD3OD) δ ppm: 1.28-1.33 (d, 3H), 2.67-2.81 (m, 2H), 3.14-3.23 (m, 1H, overlaping with signal of CD3OD), 3.32-3.39 (m, 1H), 3.48-3.53 (d, 2H), 3.64-3.70 (m, 1H), 4.05-4.15 (m, 1H), 4.38-4.48 (m, 3H), 4.69-4.76 (m, 2H), 7.21-7.25 (d, 1H), 7.60-7.65 (dd, 1H), 8.10-8.14 (d, 1H), 8.61-8.66 (dd, 1H), 8.94-8.97 (dd, 1H). | LCMS (ESI+) calcd for C20H22N4O3 (M+H+): 367.17; found: 367.29 |
| ER-899122 | 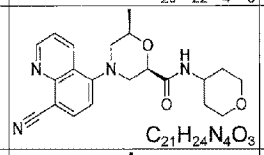 $C_{21}H_{24}N_4O_3$ | 380.45 | 0.0080 | >10.0 | (2R,6R)-4-(8-cyanoquinolin-5-yl)-6-methyl-N-(tetrahydro-2H-pyran-4-yl)morpholine-2-carboxamide | 1H NMR (400 MHz, CD3OD) δ ppm: 1.28-1.35 (d, 3H), 1.55-1.70 (m, 2H), 1.71-1.84 (m, 2H), 2.65-2.83 (m, 2H), 3.32-3.41 (m, 1H), 3.41-3.51 (m, 2H), 3.62-3.72 (m, 1H), 3.88-4.00 (m, 3H), 4.05-4.18 (m, 1H), 4.41-4.48 (dd, 1H), 7.23-7.28 (d, 1H), 7.62-7.67 (dd, 1H), 8.13-8.16 (d, 1H), 8.63-8.68 (dd, 1H), 8.96-9.00 (dd, 1H). | LCMS (ESI+) calcd for C21H24N4O3 (M+H+): 381.19; found: 381.3 |
| ER-899123 | 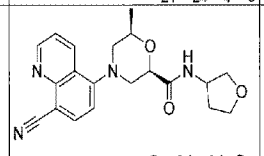 $C_{20}H_{22}N_4O_3$ | 366.42 | 0.0655 | >10.0 | (2R,6R)-4-(8-cyanoquinolin-5-yl)-6-methyl-N-(tetrahydrofuran-3-yl)morpholine-2-carboxamide | 1H NMR (400 MHz, CD3OD) δ ppm: 1.30-1.34 (d, 3H), 1.85-1.96 (m, 1H), 2.17-2.30 (m, 1H), 2.67-2.76 (t, 1H), 2.76-2.85 (t, 1H), 3.34-3.41 (d, 1H), 3.60-3.70 (m, 2H), 3.75-3.82 (q, 1H), 3.82-3.89 (m, 1H), 3.90-3.98 (q, 1H), 4.09-4.18 (m, 1H), 4.40-4.49 (m, 2H), 7.24-7.28 (d, 1H), 7.62-7.67 (dd, 1H), 8.12-8.16 (d, 1H), 8.63-8.68 (dd, 1H), 8.96-8.99 (dd, 1H). | LCMS (ESI+) calcd for C20H22N4O3 (M+H+): 367.17; found: 367.25 |
| ER-899131 | 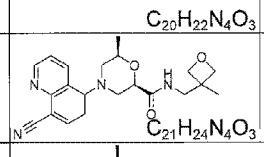 $C_{21}H_{24}N_4O_3$ | 366.42 | 0.0423 | >10.0 | (2R,6R)-4-(8-cyanoquinolin-5-yl)-6-methyl-N-((3-methyloxetan-3-yl)methyl)morpholine-2-carboxamide | δ 1.14, (s, 3H), 1.21, (d, 3H), 2.64, (t, 1H), 2.75, (t, 1H), 3.11, (d, 2H), 3.34, (d, 1H), 3.52, (d, 1H), 4.05, (m, 1H), 4.09, (d, 2H), 4.36, (d, 2H), 4.41, (d, 1H), 7.22, (d, 1H), 7.66, (dd, 1H), 8.00, (t, 1H), 8.20, (d, 1H), 8.56, (d, 1H), 9.01, (d, 1H) | |
| ER-899132 | 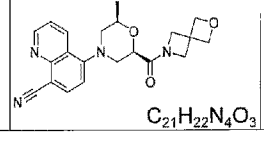 $C_{21}H_{22}N_4O_3$ | 378.43 | 0.1470 | >10.0 | 5-((2R,6R)-2-methyl-6-(2-oxa-6-azaspiro[3.3]heptane-6-carbonyl)morpholino)quinoline-8-carbonitrile | δ 1.16, (d, 3H), 2.59, (t, 1H), 2.83, (t, 1H), 3.31, (d, 1H), 3.39, (d, 1H), 3.95, (m, 1H), 4.01, (s, 2H), 4.44, (m, 1H), 4.46, (s, 2H), 4.62, (m, 4H), 7.21, (d, 1H), 7.64, (dd, 1H), 8.20, (d, 1H), 8.52, (d, 1H), 9.00, (d, 1H) | |

FIG. 6XXX

| | | | | | | | |
|---|---|---|---|---|---|---|---|
| ER-899133 | $C_{19}H_{20}N_4O_3$ | 378.43 | 0.1280 | >10.0 | (2R,6R)-4-(8-cyanoquinolin-5-yl)-6-methyl-N-(oxetan-3-yl)morpholine-2-carboxamide | δ 1.22, (d, 3H), 2.63, (t, 1H), 2.77, (t, 1H), 3.34, (d, 1H), 3.49, (d, 1H), 4.02, (m, 1H), 4.36, (d, 1H), 4.50, (m, 2H), 4.62, (m, 2H), 4.79, (m, 1H), 7.22, (d, 1H), 7.65, (dd, 1H), 8.20, (d, 1H), 8.55, (t, 1H), 9.01, (d, 1H) | |
| ER-899134 | $C_{21}H_{25}N_5O_3$ | 395.46 | 0.0640 | >10.0 | (2R,6R)-N-((3-(aminomethyl)oxetan-3-yl)methyl)-4-(8-cyanoquinolin-5-yl)-6-methylmorpholine-2-carboxamide | δ 1.20, (d, 3H), 2.62, (m, 3H), 2.72, (t, 1H), 3.09, (m, 1H), 3.32, (m, 4H), 3.52, (d, 1H), 4.03, (m, 1H), 4.24, (m, 2H), 4.41, (d, 1H), 7.21, (d, 1H), 7.65, (dd, 1H), 8.12, (t, 1H), 8.20, (d, 1H), 8.56, (d, 1H), 9.01, (d, 1H) | |
| ER-899135 | $C_{20}H_{22}N_4O_3$ | 366.42 | 0.2520 | >10.0 | (2R,6R)-4-(8-cyanoquinolin-5-yl)-6-methyl-N-(oxetan-2-ylmethyl)morpholine-2-carboxamide | δ 1.20, (d, 3H), 2.28, (m, 1H), 2.53, (m, 1H), 2.63, (m, 1H), 2.75, (t, 1H), 3.28, (m, 1H), 3.34, (m, 2H), 3.53, (d, 1H), 4.02, (m, 1H), 4.39, (m, 3H), 4.69, (m, 1H), 7.22, (d, 1H), 7.65, dd, (1H), 7.83, (m, 1H), 8.20, (d, 1H), 8.57, (d, 1H), 9.01, (d, 1H) | |
| ER-899136 | $C_{20}H_{24}ClN_5O_2$ | 378.43 | 0.1080 | >10.0 | 5-((2R,6R)-2-methyl-6-(piperazine-1-carbonyl)morpholino)quinoline-8-carbonitrile hydrochloride | δ 1.14, (d, 3H), 2.63, (t, 1H), 2.98, (m, 5H), 3.33, (m, 3H), 3.45, (m, 2H), 3.54, (m, 1H), 4.02, (m, 1H), 4.69, (d, 1H), 7.21, (d, 1H), 7.63, (dd, 1H), 8.21, (d, 1H), 8.57, (d, 1H), 8.75, (br, s, 2H), 9.00, (d, 1H) | |
| ER-899140 | $C_{19}H_{23}N_5O_2$ | 353.42 | 0.0160 | 3.271 | (2R,6R)-4-(8-cyanoquinolin-5-yl)-6-methyl-N-(2-(methylamino)ethyl)morpholine-2-carboxamide | 1H NMR (400 MHz, CD3OD) δ ppm: 1.30-1.35 (d, 3H), 2.43 (s, 3H), 2.67-2.85 (m, 4H), 3.33-3.48 (m, 3H), 3.67-3.74 (m, 1H), 4.10-4.18 (m, 1H), 4.45-4.51 (dd, 1H), 7.25-7.28 (d, 1H), 7.63-7.68 (dd, 1H), 8.13-8.17 (d, 1H), 8.65-8.69 (dd, 1H), 8.97-9.00 (dd, 1H). Exact mass calculated: 353.4 | LCMS (ESI+) calcd for C19H23N5O2 (M+H+): 354.19; found: 354.3 |
| ER-899151 | $C_{19}H_{19}F_3N_4O_3$ | 408.38 | 0.0330 | > 10.0 | (2R,6R)-4-(8-cyanoquinolin-5-yl)-6-methyl-N-((S)-3,3,3-trifluoro-2-hydroxypropyl)morpholine-2-carboxamide | 1H NMR (400 MHz, CD3OD) δ ppm: 1.30-1.35 (d, 3H), 2.66-2.83 (m, 2H), 3.32-3.42 (m, 2H), 3.58-3.65 (dd, 1H), 3.65-3.73 (m, 1H), 4.05-4.20 (m, 2H), 4.47-4.53 (dd, 1H), 7.24-7.28 (d, 1H), 7.63-7.68 (dd, 1H), 8.13-8.17 (d, 1H), 8.65-8.70 (dd, 1H), 8.96-9.00 (dd, 1H). | LCMS (ESI+) calcd for C19H19F3N4O3 (M+H+): 409.14; found: 409.24 |
| ER-899152 | $C_{19}H_{19}F_3N_4O_3$ | 408.38 | 0.0260 | > 10.0 | (2R,6R)-4-(8-cyanoquinolin-5-yl)-6-methyl-N-((R)-3,3,3-trifluoro-2-hydroxypropyl)morpholine-2-carboxamide | 1H NMR (400 MHz, CD3OD) δ ppm: 1.30-1.35 (d, 3H), 2.66-2.83 (m, 2H), 3.32-3.42 (m, 2H), 3.58-3.65 (dd, 1H), 3.65-3.73 (m, 1H), 4.05-4.20 (m, 2H), 4.47-4.53 (dd, 1H), 7.23-7.28 (d, 1H), 7.62-7.68 (dd, 1H), 8.12-8.17 (d, 1H), 8.64-8.69 (dd, 1H), 8.96-9.00 (dd, 1H). | LCMS (ESI+) calcd for C19H19F3N4O3 (M+H+): 409.14; found: 409.24 |
| ER-899153 | $C_{19}H_{20}N_4O_4$ | 368.39 | 0.0400 | > 10.0 | methyl 2-((2R,6R)-4-(8-cyanoquinolin-5-yl)-6-methylmorpholine-2-carboxamido)acetate | 1H NMR (400 MHz, CD3OD) δ ppm: 1.31-1.36 (d, 3H), 2.68-2.77 (t, 1H), 2.79-2.87 (t, 1H), 3.35-3.43 (m, 1H), 3.66-3.73 (m, 4H), 3.99 (s, 2H), 4.10-4.20 (m, 1H), 4.50-4.56 (dd, 1H), 7.25-7.30 (d, 1H), 7.62-7.68 (dd, 1H), 8.12-8.18 (d, 1H), 8.64-8.70 (dd, 1H), 8.95-9.00 (dd, 1H) | LCMS (ESI+) calcd for C19H20N4O4 (M+H+): 369.15; found: 369.19 |

FIG. 6YYY

| | | | | | | | |
|---|---|---|---|---|---|---|---|
| **ER-899154** | 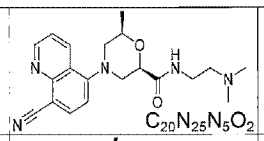 $C_{20}N_{25}N_5O_2$ | 367.45 | 0.0150 | > 10.0 | (2R,6R)-4-(8-cyanoquinolin-5-yl)-N-(2-(dimethylamino)ethyl)-6-methylmorpholine-2-carboxamide | 1H NMR (400 MHz, CD3OD) δ ppm: 1.28-1.35 (d, 3H), 2.65-2.72 (t, 1H), 2.81 (s, 6H), 3.10-3.18 (t, 2H), 3.26-3.30 (m, 1H), 3.35-3.40 (d, 1H), 3.50-3.58 (m, 1H), 3.60-3.72 (m, 2H), 4.08-4.18 (m, 1H), 4.47-4.53 (dd, 1H), 7.20-7.26 (d, 1H), 7.60-7.65 (dd, 1H), 8.08-8.15 (d, 1H), 8.60-8.66 (dd, 1H), 8.94-8.98 (dd, 1H). | LCMS (ESI+) calcd for C20H25N5O4 (M+H+): 368.20; found: 368.27 |
| **ER-899159** | 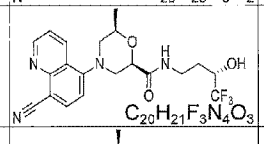 $C_{20}H_{21}F_3N_4O_3$ | 422.40 | 0.0360 | > 10.0 | (2R,6R)-4-(8-cyanoquinolin-5-yl)-6-methyl-N-((S)-4,4,4-trifluoro-3-hydroxybutyl)morpholine-2-carboxamide | 1H NMR (400 MHz, CD3OD) δ ppm: 1.31-1.37 (d, 3H), 1.67-1.78 (m, 1H), 1.87-1.96 (m, 1H), 2.67-2.83 (m, 2H), 3.35-3.54 (m, 3H), 3.68-3.75 (m, 1H), 3.94-4.00 (m, 1H), 4.12-4.20 (m, 1H), 4.45-4.52 (dd, 1H), 7.25-7.30 (d, 1H), 7.64-7.70 (dd, 1H), 8.13-8.19 (d, 1H), 8.66-8.70 (dd, 1H), 8.97-9.01 (dd, 1H). | LCMS (ESI+) calcd for C20H21F3N4O3 (M+H+): 423.16; found: 423.19 |
| **ER-899160** | 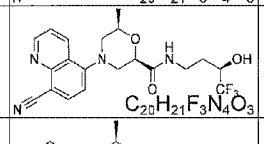 $C_{20}H_{21}F_3N_4O_3$ | 422.40 | 0.0290 | > 10.0 | (2R,6R)-4-(8-cyanoquinolin-5-yl)-6-methyl-N-((R)-4,4,4-trifluoro-3-hydroxybutyl)morpholine-2-carboxamide | 1H NMR (400 MHz, CD3OD) δ ppm: 1.31-1.37 (d, 3H), 1.67-1.78 (m, 1H), 1.87-1.96 (m, 1H), 2.67-2.83 (m, 2H), 3.35-3.53 (m, 3H), 3.68-3.75 (m, 1H), 3.91-4.00 (m, 1H), 4.12-4.19 (m, 1H), 4.45-4.52 (dd, 1H), 7.25-7.30 (d, 1H), 7.63-7.69 (dd, 1H), 8.13-8.18 (d, 1H), 8.65-8.70 (dd, 1H), 8.97-9.01 (dd, 1H). | LCMS (ESI+) calcd for C20H21F3N4O3 (M+H+): 423.16; found: 423.2 |
| **ER-899161** | 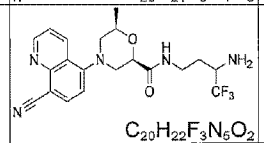 $C_{20}H_{22}F_3N_5O_2$ | 421.42 | 0.0350 | > 10.0 | (2R,6R)-N-(3-amino-4,4,4-trifluorobutyl)-4-(8-cyanoquinolin-5-yl)-6-methylmorpholine-2-carboxamide | 1H NMR (400 MHz, CD3OD) δ ppm: 1.31-1.36 (d, 3H), 1.53-1.63 (m, 1H), 1.90-2.00 (m, 1H), 2.68-2.83 (m, 2H), 3.16-3.23 (m, 1H), 3.35-3.52 (m, 3H), 3.67-3.74 (d, 1H), 4.09-4.19 (m, 1H), 4.46-4.51 (dt, 1H), 7.25-7.29 (dd, 1H), 7.63-7.68 (dd, 1H), 8.13-8.17 (d, 1H), 8.65-8.70 (dd, 1H), 8.97-9.00 (dd, 1H). | LCMS (ESI+) calcd for C20H22F3N5O2 (M+H+): 422.18; found: 422.21 |
| **ER-899162** | 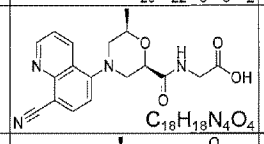 $C_{18}H_{18}N_4O_4$ | 354.36 | 0.4280 | > 10.0 | 2-((2R,6R)-4-(8-cyanoquinolin-5-yl)-6-methylmorpholine-2-carboxamido)acetic acid | 1H NMR (400 MHz, CD3OD) δ ppm: 1.30-1.35 (d, 3H), 2.68-2.76 (dd, 1H), 2.79-2.88 (dd, 1H), 3.35-3.42 (m, 1H), 3.66-3.73 (m, 1H), 3.92-3.97 (m, 2H), 4.11-4.20 (m, 1H), 4.49-4.55 (dd, 1H), 7.23-7.28 (d, 1H), 7.62-7.67 (dd, 1H), 8.12-8.16 (d, 1H), 8.64-8.69 (dd, 1H), 8.95-8.99 (dd, 1H). | LCMS (ESI+) calcd for C18H18N4O4 (M+H+): 355.14; found: 355.22 |
| **ER-899191** | 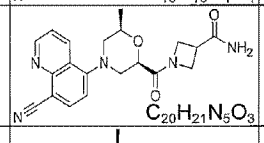 $C_{20}H_{21}N_5O_3$ | 379.42 | 0.0920 | > 10.0 | 1-((2R,6R)-4-(8-cyanoquinolin-5-yl)-6-methylmorpholine-2-carbonyl)azetidine-3-carboxamide | δ 1.15, (d, 3H), 2.60, (t, 1H), 2.84, (t, 1H), 3.29, (m, 1H), 3.41, (d, 1H), 3.83, (m, 1H), 3.94, (m, 2H), 4.29, (m, 1H), 4.39, (m, 1H), 4.49, (m, 1H), 7.02, (s, 1H), 7.21, (d, 1H), 7.44, (s, 1H), 7.64, (dd, 1H), 8.20, (d, 1H), 8.54, (d, 1H), 9.01, (d, 1H) | |
| **ER-899192** | 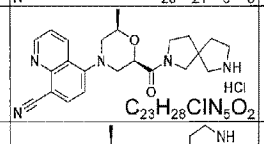 $C_{23}H_{28}ClN_5O_2$ | 379.42 | 0.0780 | 0.365 | 5-((2R,6R)-2-methyl-6-(2,7-diazaspiro[4.4]nonane-2-carbonyl)morpholino)quinoline-8-carbonitrile hydrochloride | δ 1.15, (d, 3H), 1.87, (m, 4H), 2.63, (m, 1H), 2.95, (m, 1H), 3.09, (m, 2H), 3.23, (m, 2H), 3.35, (m, 4H), 3.56, (m, 1H), 3.67, (m, 1H), 3.99, (m, 1H), 4.59, (d, 1H), 7.22, (d, 1H), 7.64, (m, 1H), 8.21, (d, 1H), 8.55, (d, 1H), 9.01, (d, 1H), 9.21, (br s, 2H) | |
| **ER-899193** | 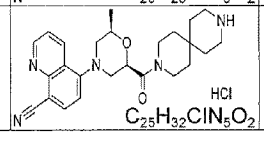 $C_{25}H_{32}ClN_5O_2$ | 470.01 | 0.0192 | 0.087 | 5-((2R,6R)-2-methyl-6-(3,9-diazaspiro[5.5]undecane-3-carbonyl)morpholino)quinoline-8-carbonitrile hydrochloride | δ 1.15, (d, 3H), 2.65, (t, 1H), 2.97, (t, 1H), 3.03, (m, 2H), 3.18, (m, 1H), 3.35, (m, 2H), 3.64, (m, 2H), 3.79, (m, 2H), 4.00, (m, 10H), 4.74, (d, 1H), 7.23, (d, 1H), 7.63, (dd, 1H), 8.22, (d, 1H), 8.55, (d, 1H), 9.01, (d, 1H), 9.22, (br s, 2H) | |

FIG. 6ZZZ

| | | | | | | | |
|---|---|---|---|---|---|---|---|
| ER-899196 | 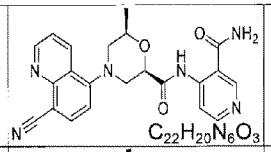 $C_{22}H_{20}N_6O_3$ | 416.44 | 0.0640 | > 10.0 | (2R,6R)-N-(3-carbamoylpyridin-4-yl)-4-(8-cyanoquinolin-5-yl)-6-methylmorpholine-2-carboxamide | δ 1.26, (d, 3H), 2.68, (t, 1H), 2.89, (t, 1H), 3.39, (d, 1H), 3.62, (d, 1H), 4.14, (m, 1H), 4.66, (d, 1H), 7.26, (d, 1H), 7.67, (dd, 1H), 7.96, (s, 1H), 8.22, (d, 1H), 8.39, (m, 1H), 8.49, (ab q, 2H), 8.60, (d, 1H), 8.91, (s, 1H), 9.02, (d, 1H), 12.58, (s, 1H) | |
| ER-899278 | 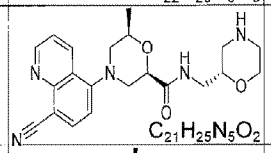 $C_{21}H_{25}N_5O_2$ | 395.46 | 0.0020 | 10.207 | (2R,6R)-4-(8-cyanoquinolin-5-yl)-6-methyl-N-((R)-morpholin-2-ylmethyl)morpholine-2-carboxamide | 1H NMR (400 MHz, CD3OD) δ ppm: 1.31-1.34 (d, 3H), 2.45-2.54 (m, 1H), 2.68-2.90 (m, 5H), 3.25-3.42 (m, 3H) (partially overlapped with CD3OD signal), 3.52-3.75 (m, 3H), 3.83-3.89 (m, 1H), 4.09-4.17 (m, 1H), 4.46-4.51 (dd, 1H), 7.24-7.28 (d, 1H), 7.63-7.68 (dd, 1H), 8.12-8.17 (d, 1H), 8.64-8.69 (dd, 1H), 8.96-9.00 (dd, 1H). | LCMS (ESI+) calcd for C21H25N5O3 (M+H+): 396.20; found: 396.33 |
| ER-899282 | 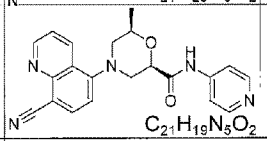 $C_{21}H_{19}N_5O_2$ | 373.41 | 0.0150 | > 10.0 | (2R,6R)-4-(8-cyanoquinolin-5-yl)-6-methyl-N-(pyridin-4-yl)morpholine-2-carboxamide | δ 1.24, (d, 3H), 2.68, (t, 1H), 2.96, (t, 1H), 3.38, (d, 1H), 3.58, (d, 1H), 4.09, (m, 1H), 4.58, (d, 1H), 7.26, (d, 1H), 7.63, (d, 2H), 7.66, (dd, 1H), 8.22, (d, 1H), 8.40, (d, 2H), 8.60, (d, 1H), 9.02, (d, 1H), 10.15, (s, 1H) | |
| ER-899283 | 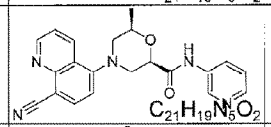 $C_{21}H_{19}N_5O_2$ | 373.41 | 0.0680 | > 10.0 | (2R,6R)-4-(8-cyanoquinolin-5-yl)-6-methyl-N-(pyridin-3-yl)morpholine-2-carboxamide | δ 1.25, (d, 3H), 2.68, (t, 1H), 2.95, (t, 1H), 3.39, (d, 1H), 3.59, (d, 1H), 4.09, (m, 1H), 4.59, (d, 1H), 7.26, (d, 1H), 7.32, (q, 1H), 7.66, (dd, 1H), 8.03, (d, 1H), 8.22, (d, 1H), 8.25, (d, 1H), 8.60, (d, 1H), 8.78, (s, 1H), 9.02, (d, 1H), 9.98, (s, 1H) | |
| ER-899285 | 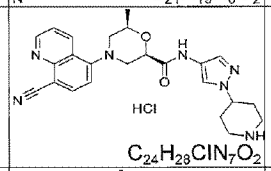 $C_{24}H_{28}ClN_7O_2$ | 481.99 | 0.0110 | 1.264 | (2R,6R)-4-(8-cyanoquinolin-5-yl)-6-methyl-N-(1-(piperidin-4-yl)-1H-pyrazol-4-yl)morpholine-2-carboxamide hydrochloride | δ 1.24, (d, 3H), 2.07, (m, 5H), 2.65, (t, 1H), 2.84, (t, 1H), 2.97, (m, 2H), 3.37, (d, 1H), 3.57, (d, 1H), 4.07, (m, 1H), 4.40, (m, 1H), 4.51, (d, 1H), 7.24, (d, 1H), 7.58, (s, 1H), 7.66, (dd, 1H), 7.93, (s, 1H), 8.21, (d, 1H), 8.58, (d, 1H), 8.69, (br s, 1H), 8.89, (br s, 1H), 9.02, (d, 1H), 9.90, (s, 1H) | |
| ER-899286 | 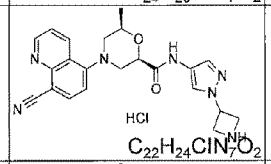 $C_{22}H_{24}ClN_7O_2$ | 453.93 | 0.0480 | 1.071 | (2R,6R)-N-(1-(azetidin-3-yl)-1H-pyrazol-4-yl)-4-(8-cyanoquinolin-5-yl)-6-methylmorpholine-2-carboxamide hydrochloride | δ 1.24, (d, 3H), 2.66, (t, 1H), 2.84, (t, 1H), 3.37, (d, 1H), 3.57, (d, 1H), 4.07, (m, 1H), 4.25, (m, 3H), 4.54, (d, 1H), 5.36, (m, 1H), 7.24, (d, 1H), 7.66, (dd, 1H), 7.75, (s, 1H), 8.10, (s, 1H), 8.22, (d, 1H), 8.59, (d, 1H), 9.02, (d, 1H), 9.13, (br s, 2H), 9.98, (s, 1H) | |
| ER-899287 | 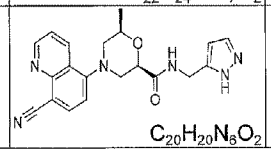 $C_{20}H_{20}N_8O_2$ | 376.42 | 0.0300 | > 10.0 | (2R,6R)-N-((1H-pyrazol-5-yl)methyl)-4-(8-cyanoquinolin-5-yl)-6-methylmorpholine-2-carboxamide | δ 1.19, (d, 3H), 2.63, (t, 1H), 2.77, (t, 1H), 3.34, (d, 1H), 3.54, (d, 1H), 4.01, (m, 1H), 4.26, (m, 2H), 4.40, (d, 1H), 6.06, (s, 1H), 7.22, (d, 1H), 7.66, (dd, 1H), 8.08, (m, 1H), 8.20, (d, 1H), 8.56, (d, 1H), 9.01, (d, 1H), 12.51, (s, 1H) | |

FIG. 6AAAA

| | | | | | | | |
|---|---|---|---|---|---|---|---|
| ER-899288 | $C_{19}H_{18}N_6O_2$ | 376.42 | 0.1460 | > 10.0 | (2R,6R)-N-((1H-pyrazol-4-yl)methyl)-4-(8-cyanoquinolin-5-yl)-6-methylmorpholine-2-carboxamide | δ 1.25, (d, 3H), 2.66, (t, 1H), 2.86, (t, 1H), 3.37, (d, 1H), 3.58, (d, 1H), 4.07, (m, 1H), 4.50, (d, 1H), 7.24, (d, 1H), 7.67, (dd, 1H), 7.72, (m, 1H), 8.21, (d, 1H), 8.58, (d, 1H), 9.01, (d, 1H), 9.80, (s, 1H), 12.55, (s, 1H) | |
| ER-899289 | $C_{23}H_{20}F_3N_5O_2$ | 455.44 | 0.0480 | > 10.0 | (2R,6R)-4-(8-cyanoquinolin-5-yl)-6-methyl-N-((3-(trifluoromethyl)pyridin-2-yl)methyl)morpholine-2-carboxamide | δ 1.23, (d, 3H), 2.67, (t, 1H), 2.80, (t, 1H), 3.37, (d, 1H), 3.56, (d, 1H), 4.07, (m, 1H), 4.49, (d, 1H), 4.57, (m, 2H), 7.23, (d, 1H), 7.51, (m, 1H), 7.66, (dd, 1H), 8.13, (d, 1H), 8.21, (d, 1H), 8.28, (t, 1H), 8.58, (d, 1H), 8.78, (d, 1H), 9.01, (d, 1H) | |
| ER-899290 | $C_{23}H_{23}N_5O_2$ | 401.47 | 0.0550 | > 10.0 | (2R,6R)-4-(8-cyanoquinolin-5-yl)-6-methyl-N-(1-(pyridin-2-yl)ethyl)morpholine-2-carboxamide | δ 1.22, (d, 3H), 1.35, (d, 3H), 2.67, (t, 1H), 2.78, (m, 1H), 3.34, (m, 1H), 3.53, (t, 1H), 4.05, (m, 1H), 4.44, (t, 1H), 4.98, (t, 1H), 7.23, (m, 2H), 7.34, (t, 1H), 7.65, (dd, 1H), 7.73, (t, 1H), 8.15, (m, 1H), 8.20, (t, 1H), 8.49, (d, 1H), 8.56, (d, 1H), 9.01, (d, 1H) | |
| ER-899291 | $C_{20}H_{24}N_4O2$ | 387.44 | 0.0530 | > 10.0 | (2R,6R)-4-(8-cyanoquinolin-5-yl)-6-methyl-N-(pyridin-2-ylmethyl)morpholine-2-carboxamide | δ 1.22, (d, 3H), 2.66, (t, 1H), 2.80, (t, 1H), 3.36, (d, 1H), 3.57, (d, 1H), 4.06, (m, 1H), 4.37, (d, 2H), 4.47, (d, 1H), 7.23, (m, 3H), 7.66, (dd, 1H), 7.71, (t, 1H), 8.21, (d, 1H), 8.40, (t, 1H), 8.45, (d, 1H), 8.57, (d, 1H), 9.01, (d, 1H) | |
| ER-899292 | $C_{23}H_{29}N_5O_2$ | 401.47 | 0.1060 | > 10.0 | (2R,6R)-4-(8-cyanoquinolin-5-yl)-6-methyl-N-((6-methylpyridin-2-yl)methyl)morpholine-2-carboxamide | δ 1.22, (d, 3H), 2.39, (s, 3H), 2.66, (t, 1H), 2.80, (t, 1H), 3.36, (d, 1H), 3.57, (d, 1H), 4.05, (m, 1H), 4.32, (d, 2H), 4.47, (d, 1H), 7.01, (d, 1H), 7.07, (d, 1H), 7.24, (d, 1H), 7.59, (t, 1H), 7.65, (dd, 1H), 8.21, (d, 1H), 8.42, (t, 1H), 8.57, (d, 1H), 9.01, (d, 1H) | |
| ER-899293 | $C_{23}H_{29}N_5O_2$ | 407.52 | 0.0050 | > 10.0 | (2R,6R)-4-(8-cyanoquinolin-5-yl)-6-methyl-N-((1-methylpiperidin-2-yl)methyl)morpholine-2-carboxamide | δ 1.13, (m, 2H), 1.20, (d, 3H), 1.33, (m, 1H), 1.45, (m, 2H), 1.59, (m, 1H), 1.92, (m, 2H), 2.14, (s, 3H), 2.62, (m, 1H), 2.70, (m, 2H), 3.07, (m, 2H), 3.34, (d, 1H), 3.52, (d, 1H), 4.02, (m, 1H), 4.38, (d, 1H), 7.22, (d, 1H), 7.48, (br t, 1H), 7.66, (dd, 1H), 8.20, (d, 1H), 8.56, (d, 1H), 9.01, (d, 1H) | |
| ER-899294 | $C_{23}H_{23}N_5O_2$ | 401.47 | 0.1960 | > 10.0 | (2R,6R)-4-(8-cyanoquinolin-5-yl)-6-methyl-N-((3-methylpyridin-2-yl)methyl)morpholine-2-carboxamide | δ 1.23, (d, 3H), 2.23, (s, 3H), 2.67, (t, 1H), 2.79, (t, 1H), 3.37, (d, 1H), 3.58, (d, 1H), 4.07, (m, 1H), 4.38, (m, 2H), 4.48, (d, 1H), 7.19, (dd, 1H), 7.23, (d, 1H), 7.55, (d, 1H), 7.66, (dd, 1H), 8.21, (d, 1H), 8.28, (t, 1H), 8.33, (d, 1H), 8.58, (d, 1H), 9.01, (d, 1H) | |
| ER-899295 | $C_{20}H_{17}N_7O_2$ | 387.40 | 0.0320 | > 10.0 | (2R,6R)-N-(4-cyano-1H-pyrazol-3-yl)-4-(8-cyanoquinolin-5-yl)-6-methylmorpholine-2-carboxamide | | |

FIG. 6BBBB

| | | | | | | | |
|---|---|---|---|---|---|---|---|
| ER-899332 | 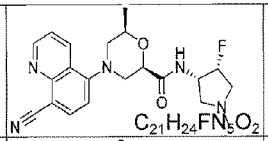 $C_{21}H_{24}FN_5O_2$ | 397.45 | 0.0228 | > 10.0 | (2R,6R)-4-(8-cyanoquinolin-5-yl)-N-((3S,4R)-4-fluoro-1-methylpyrrolidin-3-yl)-6-methylmorpholine-2-carboxamide | H NMR (400 MHz, CHLOROFORM-d1) 1.34 (3 H), 2.41 (3 H), 2.67 (2 H), 2.84 (2 H), 2.97 (1 H), 3.30 (1 H), 3.80 (1 H), 4.10 (1 H), 4.46 (1 H), 4.60 (1 H), 5.02 (1 H), 5.16 (1 H), 7.13 (2 H), 7.54 (1 H), 8.05 (1 H), 8.48 (1 H), 9.09 (1 H). | LCMS (ESI+) calcd for C21H24FN5O3 (M+H+): 398.19; found: 398.4 |
| ER-899333 | 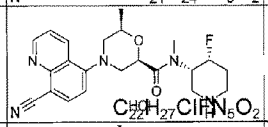 $C_{22}H_{27}ClFN_5O_2$ | 447.94 | 0.0820 | 7.352 | (2R,6R)-4-(8-cyanoquinolin-5-yl)-N-((3S,4R)-4-fluoropiperidin-3-yl)-N,6-dimethylmorpholine-2-carboxamide hydrochloride | H NMR (400 MHz, METHANOL-d4) d ppm 1.25 (4 H), 1.94 (1 H), 2.30 (2 H), 2.75 (2 H), 2.92 (1H), 3.21 (4 H), 3.53 (6 H), 4.15 (1 H), 7.34 (1 H), 7.74 (1 H), 8.23 (1 H), 8.82 (1 H), 9.00 (1 H). | LCMS (ESI+) calcd for C22H26FN5O2 (M+H+): 412.60; found: 412.21 |
| ER-899334 | 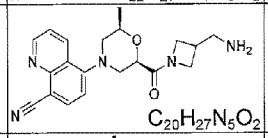 $C_{20}H_{27}N_5O_2$ | 365.43 | 0.1590 | > 10.0 | 5-((2R,6R)-2-(3-(aminomethyl)azetidine-1-carbonyl)-6-methylmorpholino)quinoline-8-carbonitrile | H NMR (400 MHz, CHLOROFORM-d1) 1.29 (3 H), 1.60 (2 H), 2.68 (1 H), 2.81 (2 H), 2.96 (1 H), 3.29 (1 H), 3.38 (1 H), 3.65 (1 H), 3.74 (1 H), 4.02 (1 H), 4.14 (2 H), 4.50 (1 H), 4.69 (1 H), 7.12 (1 H), 7.53 (1 H), 8.06 (1 H), 8.46 (1 H), 9.09 (1 H). | LCMS (ESI+) calcd for C20H23N5O3 (M+H+): 366.19; found: 366.26 |
| ER-899335 | 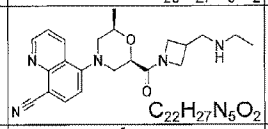 $C_{22}H_{27}N_5O_2$ | 393.49 | 0.0153 | 17.740 | 5-((2R,6R)-2-(3-((ethylamino)methyl)azetidine-1-carbonyl)-6-methylmorpholino)quinoline-8-carbonitrile | H NMR (400 MHz, CHLOROFORM-d1) d ppm 1.15 (4 H), 1.22 (1 H), 1.30 (3 H), 2.70 (2 H), 2.92 (3 H), 3.29 (1 H), 3.39 (1 H), 3.65 (1 H), 3.74 (1 H), 4.02 (1 H), 4.13 (2 H), 4.52 (2 H), 7.11 (1 H), 7.53 (1 H), 8.05 (1 H), 8.45 (1 H), 9.09 (1 H). | LCMS (ESI+) calcd for C22H27N5O2 (M+H+): 394.22; found: 394.22 |
| ER-899336 | 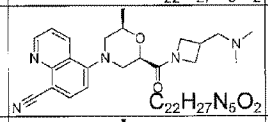 $C_{22}H_{27}N_5O_2$ | 393.49 | 0.0373 | > 10.0 | 5-((2R,6R)-2-(3-((dimethylamino)methyl)azetidine-1-carbonyl)-6-methylmorpholino)quinoline-8-carbonitrile | | LCMS (ESI+) calcd for C22H27N5O2 (M+H+): 394.22; found: 394.22 |
| ER-899337 | 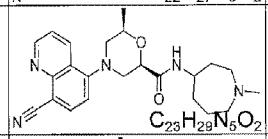 $C_{23}H_{28}N_5O_2$ | 407.52 | 0.0030 | 7.386 | (2R,6R)-4-(8-cyanoquinolin-5-yl)-6-methyl-N-(1-methylazepan-4-yl)morpholine-2-carboxamide | H NMR (400 MHz, CHLOROFORM-d1) 1.30 (3 H), 1.80 (7 H), 2.39 (3 H), 2.54 (2 H), 2.98 (3 H), 3.28 (1 H), 3.79 (1 H), 4.07 (1 H), 4.17 (1 H), 4.37 (1 H), 7.06 (2 H), 7.51 (1 H), 8.02 (1 H), 8.46 (1 H), 9.06 (1 H). | LCMS (ESI+) calcd for C23H29N5O2 (M+H+): 408.24; found: 408.1 |
| ER-899366 | 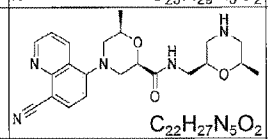 $C_{22}H_{27}N_5O_2$ | 409.49 | 0.0030 | > 10.0 | (2R,6R)-4-(8-cyanoquinolin-5-yl)-6-methyl-N-(((2R,6R)-6-methylmorpholin-2-yl)methyl)morpholine-2-carboxamide | 1H NMR (400 MHz, CD3OD) δ ppm: 1.11-1.14 (d, 3H), 1.32-1.35 (d, 3H), 2.32-2.47 (m, 2H), 2.69-2.88 (m, 4H), 3.20-3.28 (m, 1H), 3.32-3.42 (m, 2H), 3.55-3.75 (m, 3H), 4.11-4.19 (m, 1H), 4.47-4.53 (dd, 1H), 7.25-7.29 (d, 1H), 7.63-7.68 (dd, 1H), 8.13-8.17 (d, 1H), 8.65-8.70 (dd, 1H), 8.97-9.00 (dd, 1H). | LCMS (ESI+) calcd for C22H27N5O3 (M+H+): 410.21; found: 410.3 |
| ER-899367 | 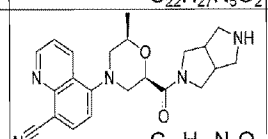 $C_{22}H_{25}N_5O_2$ | 391.47 | 0.1190 | 0.684 | 5-((2R,6R)-2-methyl-6-(octahydropyrrolo[3,4-c]pyrrole-2-carbonyl)morpholino)quinoline-8-carbonitrile | 1H NMR (400 MHz, CD3OD) δ ppm: 1.25-1.30 (dd, 3H), 2.65-2.75 (t, 1H), 2.75-3.10 (m, 5H), 3.15-3.25 (m, 2H), 3.35-3.55 (m, 3H), 3.55-3.70 (m, 2H), 3.80-3.84 (m, 1H), 4.08-4.20 (m, 1H), 4.67-4.74 (d, 1H), 7.25-7.30 (d, 1H), 7.60-7.65 (dd, 1H), 8.13-8.18 (d, 1H), 8.63-8.69 (d, 1H), 8.95-8.99 (d, 1H). | LCMS (ESI+) calcd for C22H25N5O2 (M+H+): 392.20; found: 392.36 |

FIG. 6CCCC

| | | | | | | | |
|---|---|---|---|---|---|---|---|
| ER-899414 | 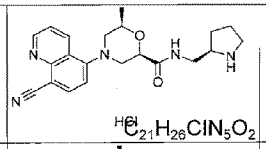 $C_{21}H_{26}ClN_5O_2$ | 415.92 | 0.0130 | > 10.0 | (2R,6R)-4-(8-cyanoquinolin-5-yl)-6-methyl-N-((R)-pyrrolidin-2-ylmethyl)morpholine-2-carboxamide hydrochloride | δ 1.21, (d, 3H), 1.56, (m, 1H), 1.81, (m, 2H), 1.92, (m, 1H), 2.62, (t, 1H), 2.78, (t, 1H), 3.10, (m, 2H), 3.36, (m, 4H), 3.53, (d, 1H), 4.03, (m, 1H), 4.40, (d, 1H), 7.22, (d, 1H), 7.66, (dd, 1H), 8.19, (m, 1H), 8.22, (d, 1H), 8.56, (d, 1H), 8.61, (br s, 1H), 9.02, (d, 1H), 9.20, (br s, 1H) | |
| ER-899415 | 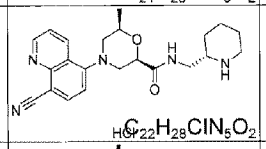 $C_{22}H_{28}ClN_5O_2$ | 429.95 | 0.0050 | > 10.0 | (2R,6R)-4-(8-cyanoquinolin-5-yl)-6-methyl-N-((S)-piperidin-2-ylmethyl)morpholine-2-carboxamide hydrochloride | δ 1.22, (d, 3H), 1.35, (m, 2H), 1.53, (m, 1H), 1.69, (m, 3H), 2.64, (t, 1H), 2.80, (m, 2H), 3.07, (m, 1H), 3.18, (d, 1H), 3.31, (m, 3H), 4.03, (m, 1H), 4.41, (d, 1H), 7.22, (d, 1H), 7.66, (dd, 1H), 8.13, (t, 1H), 8.23, (d, 1H), 8.44, (br s, 1H), 8.57, (d, 1H), 8.66, (br s, 1H), 9.02, (d, 1H) | |
| ER-899416 | 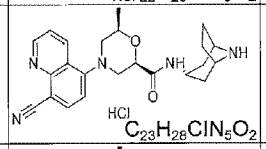 $C_{23}H_{28}ClN_5O_2$ | 441.96 | 0.0040 | > 10.0 | (2R,6R)-N-((1R,3r,5S)-8-azabicyclo[3.2.1]octan-3-yl)-4-(8-cyanoquinolin-5-yl)-6-methylmorpholine-2-carboxamide hydrochloride | δ 1.17, (d, 3H), 1.94, (m, 4H), 2.10, (m, 4H), 2.61, (t, 1H), 2.81, (t, 1H), 3.36, (d, 1H), 3.45, (d, 1H), 3.80, (m, 1H), 3.87, (m, 2H), 4.01, (m, 1H), 4.41, (d, 1H), 7.22, (d, 1H), 7.65, (dd, 1H), 7.71, (d, 1H), 8.21, (d, 1H), 8.58, (d, 1H), 8.71, (br s, 1H), 8.89, (br s, 1H), 9.01, (d, 1H) | |
| ER-899417 | 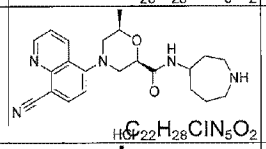 $C_{22}H_{28}ClN_5O_2$ | 429.95 | 0.0002 | | (2R,6R)-N-(azepan-4-yl)-4-(8-cyanoquinolin-5-yl)-6-methylmorpholine-2-carboxamide hydrochloride | δ 1.20, (d, 3H), 1.61, (m, 2H), 1.84, (m, 4H), 2.62, (t, 1H), 2.76, (t, 1H), 2.96, (m, 2H), 3.12, (m, 2H), 3.33, (d, 1H), 3.48, (d, 1H), 3.86, (m, 1H), 4.00, (m, 1H), 4.34, (d, 1H), 7.21, (d, 1H), 7.65, (dd, 1H), 7.80, (d, 1H), 8.21, (d, 1H), 8.56, (d, 1H), 8.78, (br s, 1H), 8.89, (br s, 1H), 9.01, (d, 1H) | |
| ER-899418 | 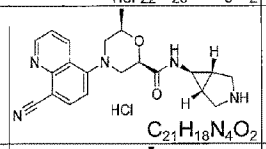 $C_{21}H_{18}N_4O_2$ | 413.91 | 0.0200 | > 10.0 | (2R,6R)-N-((1R,5S,6s)-3-azabicyclo[3.1.0]hexan-6-yl)-4-(8-cyanoquinolin-5-yl)-6-methylmorpholine-2-carboxamide hydrochloride | δ 1.17, (d, 3H), 1.91, (m, 2H), 2.60, (t, 1H), 2.76, (m, 2H), 3.27,(m, 4H), 3.33, (d, 1H), 3.47, (d, 1H), 3.98, (m, 1H), 4.33, (d, 1H), 7.20, (d, 1H), 7.65, (dd, 1H), 8.02, (d, 1H), 8.21, (d, 1H), 8.55, (d, 1H), 8.81, (br s, 1H), 9.01, (d, 1H), 9.38, (br s, 1H) | |
| ER-899431 | 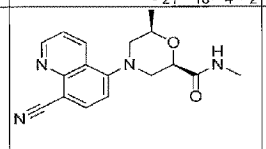 $C_{17}H_{18}N_4O_2$ | 310.36 | 0.0880 | > 10.0 | (2R,6R)-4-(8-cyanoquinolin-5-yl)-N,6-dimethylmorpholine-2-carboxamide | 1H NMR (400 MHz, CHLOROFORM-d) d ppm 1.26 (t, J=7.15 Hz, 1 H) 1.30 - 1.35 (m, 3 H) 1.87 (br. s., 1 H) 2.04 (s, 1 H) 2.67 (dd, J=11.92, 10.32 Hz, 1 H) 2.76 (dd, J=11.94, 10.95 Hz, 1 H) 2.88 (d, J=5.00 Hz, 3 H) 3.30 (dt, J=11.96, 2.01 Hz, 1 H) 3.81 (dt, J=12.09, 2.27 Hz, 1 H) 4.02 - 4.19 (m, 2 H) 4.43 (dd, J=10.74, 2.57 Hz, 1 H) 6.72 (d, J=4.50 Hz, 1 H) 7.08 (d, J=8.01 Hz, 1 H) 7.53 (dd, J=8.56, 4.22 Hz, 1 H) 8.03 (d, J=7.97 Hz, 1 H) 8.48 (dd, J=8.56, 1.66 Hz, 1 H) 9.07 (dd, J=4.20, 1.64 Hz, 1 H) | LCMS (ESI+) calcd for C17H18N4O2 (M+H+): 311.15; found: 310.9 |
| ER-899457 | 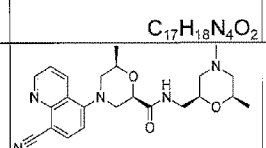 $C_{23}H_{29}N_5O_2$ | 423.51 | 0.0110 | > 10.0 | (2R,6R)-4-(8-cyanoquinolin-5-yl)-N-(((2S,6R)-4,6-dimethylmorpholin-2-yl)methyl)-6-methylmorpholine-2-carboxamide | 1H NMR (400 MHz, CD3OD) δ ppm: 1.14-1.17 (d, 3H), 1.31-1.35 (d, 3H), 1.75-1.88 (m, 2H), 2.28-2.33 (s, 3H), 2.68-2.83 (m, 4H), 3.33-3.41 (m, 2H), 3.60-3.73 (m, 3H), 4.09-4.19 (m, 1H), 4.45-4.52 (dd, 1H), 7.24-7.29 (d, 1H), 7.62-7.68 (dd, 1H), 8.12-8.17 (d, 1H), 8.64-8.69 (dd, 1H), 8.96-9.00 (dd, 1H). | LCMS (ESI+) calcd for C23H29N5O3 (M+H+): 424.23; found: 424.28 |

AMENDED

Fig. 6DDDD

| | | | | | | | |
|---|---|---|---|---|---|---|---|
| ER-899459 | 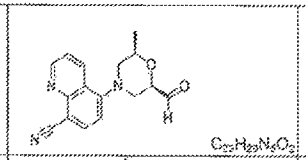 $C_{22}H_{29}N_5O_2$ | 407.52 | 0.0560 | > 10.0 | 5-((2R,6R)-2-(4-(dimethylamino)piperidine-1-carbonyl)-6-methylmorpholino)quinoline-8-carbonitrile | 1H NMR (400 MHz, CD3OD) δ ppm: 1.23-1.65 (m, 5H), 1.90-2.05 (m, 2H), 2.30-2.36 (d, 6H), 2.45-2.75 (m, 3H), 3.04-3.23 (m, 2H), 3.35-3.50 (m, 2H), 4.10-4.21 (m, 1H), 4.21-4.32 (m, 1H), 4.50-4.60 (m, 1H), 4.75-4.85 (m, 1H), 7.26-7.32 (d, 1H), 7.56-7.67 (m, 1H), 8.13-8.18 (d, 1H), 8.63-8.70 (m, 1H), 8.94-9.00 (m, 1H). | LCMS (ESI+) calcd for C23H29N5O2 (M+H+): 408.24; found: 408.37 |
| ER-899464 | 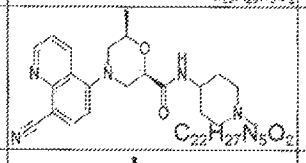 $C_{22}H_{27}N_5O_2$ | 393.49 | 0.0048 | > 10.0 | (2R,6R)-4-(8-cyanoquinolin-5-yl)-6-methyl-N-(1-methylpiperidin-4-yl)morpholine-2-carboxamide | 1H NMR (400 MHz, CD3OD) δ ppm: 1.31-1.36 (d, 3H), 1.57-1.70 (m, 2H), 1.79-1.91 (m, 2H), 2.11-2.22 (m, 2H), 2.30 (s, 3H), 2.68-2.93 (m, 4H), 3.35-3.41 (m, 1H), 3.64-3.80 (m, 2H), 4.09-4.16 (m, 1H), 4.43-4.48 (m, 1H), 7.24-7.26 (d, 1H), 7.62-7.68 (dd, 1H), 8.12-8.16 (d, 1H), 8.64-8.68 (m, 1H), 8.96-8.99 (m, 1H). | LCMS (ESI+) calcd for C22H27N5O2 (M+H+): 394.22; found: 394.3 |
| ER-899476 | 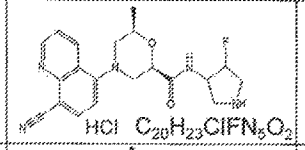 HCl $C_{20}H_{23}ClFN_5O_2$ | 419.89 | 0.0050 | > 10.0 | (2R,6R)-4-(8-cyanoquinolin-5-yl)-N-((3S,4R)-4-fluoropyrrolidin-3-yl)-6-methylmorpholine-2-carboxamide hydrochloride | δ 1.21, (d, 3H), 2.63, (t, 1H), 2.80, (t, 1H), 3.24, (m, 2H), 3.45, (m, 4H), 4.03, (m, 1H), 4.45, (t, 1H), 5.10, (m, 1H), 5.23, (m, 1H), 7.23, (d, 1H), 7.65, (dd, 1H), 8.12, (t, 1H), 8.21, (d, 1H), 8.57, (d, 1H), 9.02, (dd, 1H), 9.26, (br s, 1H), 9.59, (br s, 1H) | |
| ER-899477 | 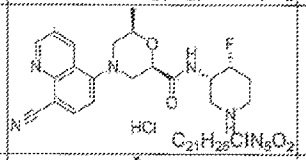 HCl $C_{21}H_{26}ClN_5O_2$ | 433.91 | 0.0160 | > 10.0 | (2R,6R)-4-(8-cyanoquinolin-5-yl)-N-((3S,4R)-4-fluoropiperidin-3-yl)-6-methylmorpholine-2-carboxamide hydrochloride | δ 1.20, (d, 3H), 2.08, (m, 2H), 2.65, (t, 1H), 2.81, (t, 1H), 2.89, (m, 1H), 3.12, (m, 3H), 3.35, (d, 1H), 3.48, (d, 1H), 4.02, (m, 1H), 4.46, (d, 1H), 4.79, (m, 1H), 4.92, (m, 1H), 7.22, (d, 1H), 7.66, (dd, 1H), 7.99, (d, 1H), 8.22, (d, 1H), 8.57, (d, 1H), 8.99, (br s, 1H), 9.02, (d, 1H), 9.07, (br s, 1H) | |
| ER-899479 | 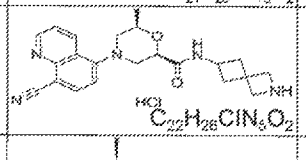 HCl $C_{22}H_{26}ClN_5O_2$ | 427.93 | 0.0070 | > 10.0 | (2R,6R)-4-(8-cyanoquinolin-5-yl)-6-methyl-N-(2-azaspiro[3.3]heptan-6-yl)morpholine-2-carboxamide hydrochloride | δ 1.19,(d, 3H),1.97,(m, 1H), 2.11,(m, 1H), 2.23, (m, 2H), 2.60,(t, 1H), 2.71, (t, 1H), 3.33, (d, 1H), 3.47, (d, 1H), 3.81, (m, 2H), 3.93, (m, 2H), 4.00, (m, 1H), 4.09, (m, 1H), 4.30, (d, 1H), 7.21, (d, 1H), 7.65, (dd, 1H), 7.96, (d, 1H), 8.03, (br s, 1H), 8.21, (d, 1H), 8.55, (d, 1H), 8.77, (br s, 1H), 9.01, (d, 1H) | |
| ER-899481 | 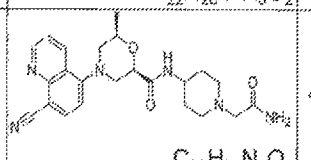 $C_{23}H_{28}N_6O_3$ | 436.51 | 0.0150 | > 10.0 | (2R,6R)-N-(1-(2-amino-2-oxoethyl)piperidin-4-yl)-4-(8-cyanoquinolin-5-yl)-6-methylmorpholine-2-carboxamide | 1H NMR(400 MHz, CDCl3) δ ppm:1.33-1.37(d, 3H),1.65-1.76(m, 2H),1.97-2.10(m, 2H),2.45-2.58(m, 2H),2.65-2.80 (m, 2H),2.98-3.08(m, 2H),3.15-3.22(s, 2H),3.27-3.35(d, 1H),3.76-3.84(d, 1H),3.87-3.95(m, 1H),4.05-4.16(m, 1H), 4.40-4.45 (dd, 1H),5.98-6.05(m, 1H), 6.58-6.65(d, 1H), 7.08-7.13 (d,1H), 7.52-7.58 (dd,1H), 8.03-8.08 (m,2H),8.48-8.51 (d,1H), 9.08-9.12(d,1H) | LCMS (ESI+) calcd for C23H28N6O2 (M+H+): 437.23; found: 437.34 |
| ER-899488 | 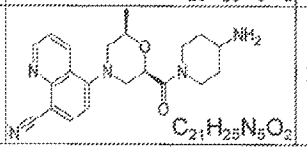 $C_{21}H_{25}N_5O_2$ | 379.46 | 0.1170 | 1.376 | 5-((2R,6R)-2-(4-aminopiperidine-1-carbonyl)-6-methylmorpholino)quinoline-8-carbonitrile | 1H NMR (400 MHz, CD3OD) δ ppm: 1.20-1.60 (m, 5H), 1.86-2.03 (m, 2H), 2.65-2.85 (m, 2H), 2.95-3.25 (m, 2H), 3.35-3.50 (m, 2H), 3.55-3.75 (m, 1H), 4.10-4.25 (m, 2H), 4.35-4.55 (m, 1H), 4.75-4.85 (m, 1H), 7.25-7.32 (d, 1H), 7.60-7.66 (m, 1H), 8.13-8.18 (d, 1H), 8.62-8.70 (m, 1H), 8.96-9.00 (m, 1H). | LCMS (ESI+) calcd for C21H25N5O2 (M+H+): 380.20; found: 380.33 |

FIG. 6EEEE

| | | | | | | | |
|---|---|---|---|---|---|---|---|
| **ER-899608** | $C_{22}H_{27}N_5O_2$ | 393.49 | 0.1041 | 7.040 | 5-((2R,6R)-2-(4-amino-4-methylpiperidine-1-carbonyl)-6-methylmorpholino)quinoline-8-carbonitrile | 1H NMR (400 MHz, CD3OD) δ ppm: 1.22-1.30 (m, 6H), 1.50-1.75 (m, 4H), 2.66-2.75 (t, 1H), 3.06-3.14 (dd, 1H), 3.36-3.50 (m, 2H), 3.50-3.60 (m, 1H), 3.60-3.77 (m, 2H), 3.86-3.96 (m, 1H), 4.11-4.22 (m, 1H), 4.78-4.83 (dd, 1H), 7.27-7.32 (d, 1H), 7.60-7.65 (dd, 1H), 8.14-8.19 (d, 1H), 8.65-8.69 (d, 1H), 8.96-8.99 (dd, 1H). | LCMS (ESI+) calcd for C22H27N5O2 (M+H+): 394.22; found: 394.3 |
| **ER-899616** | HCl $C_{22}H_{28}ClN_5O_2$ | 429.95 | 0.0450 | > 10.0 | (2R,6R)-4-(8-cyanoquinolin-5-yl)-N,6-dimethyl-N-((R)-piperidin-3-yl)morpholine-2-carboxamide hydrochloride | $^1$H NMR (400 MHz, METHANOL-$d_4$) d ppm 1.29 (d, 3 H) 1.80 - 2.11 (m, 4 H) 2.65 - 2.80 (m, 1 H) 2.89 - 3.02 (m, 2 H) 3.19 (s, 3 H) 3.02 - 3.29 (m, 2 H) 3.36 - 3.47 (m, 1 H) 3.47 - 3.58 (m, 1 H) 4.09 - 4.55 (m, 2 H) 4.76 - 4.95 (m, 1 H) 7.27 - 7.37 (m, 1 H) 7.62 - 7.73 (m, 1 H) 8.14 - 8.24 (m, 1 H) 8.67 - 8.79 (m, 1 H) 8.96 - 9.05 (m, 1 H) | LCMS (ESI+) calcd for C22H27N5O2 (M+H+): 394.22; found: 394.32 |
| **ER-899618** | HCl $C_{22}H_{21}ClN_6O_3$ | 452.90 | 0.0438 | > 10.0 | (2R,6R)-N-(2-carbamoylpyridin-4-yl)-4-(8-cyanoquinolin-5-yl)-6-methylmorpholine-2-carboxamide hydrochloride | $^1$H NMR (400 MHz, METHANOL-$d_4$) d ppm 1.41 (d, $J$=6.20 Hz, 3 H) 2.78 (t, $J$=10.25 Hz, 1 H) 2.98 (d, $J$=11.96, 10.68 Hz, 1 H) 3.44 (dt, $J$=12.12, 2.06 Hz, 1 H) 3.76 (d, $J$=12.1,1 H) 4.22-4.25 (m, 1 H) 4.68 (dd, $J$=10.68, 2.56 Hz, 1 H) 7.32 (d, $J$=8.12 Hz, 1 H) 7.68 (dd, $J$=8.76, 4.27 Hz, 1 H) 7.94 - 8.00 (m, 1 H) 8.17 (d, $J$=7.90 Hz, 1 H) 8.36 (s, 1 H) 8.52 (dd, $J$=5.55, 0.64 Hz, 1 H) 8.71 (dd, $J$=8.55, 1.71 Hz, 1 H) 9.00 (dd, $J$=4.27, 1.50 Hz, 1 H) | LCMS (ESI+) calcd for C22H25N6O3 (M+H+): 417.15; found: 417.23 |
| **ER-899619** | HCl $C_{22}H_{28}ClN_5O_2$ | 429.95 | 0.4962 | > 10.0 | (2R,6R)-4-(8-cyanoquinolin-5-yl)-N,6-dimethyl-N-((S)-piperidin-3-yl)morpholine-2-carboxamide hydrochloride | $^1$H NMR (400 MHz, METHANOL-$d_4$) d ppm 1.29 (d, 3 H) 1.76 - 2.12 (m, 4 H) 2.68 - 2.77 (m, 1 H) 2.84 - 3.01 (m, 2 H) 3.06 - 3.29 (m, 5 H) 3.32 - 3.62 (m, 2 H) 4.12 - 4.29 (m, 1 H) 4.46 - 4.62 (m, 1 H) 4.79 - 4.85 (m, 1 H) 7.23 - 7.37 (m, 1 H) 7.61 - 7.73 (m, 1 H) 8.15 - 8.20 (m, 1 H) 8.67 - 8.73 (m, 1 H) 8.99 (dd, $J$=4.27, 1.71 Hz, 1 H) | LCMS (ESI+) calcd for C22H27N5O2 (M+H+): 394.22; found: 394.35 |
| **ER-899626** | $C_{23}H_{29}N_5O_2$ | 407.52 | 0.0027 | > 10.0 | (2R,6R)-4-(8-cyanoquinolin-5-yl)-N-(1-ethylpiperidin-4-yl)-6-methylmorpholine-2-carboxamide | 1H NMR (400 MHz, METHANOL-d4) d ppm 1.30 - 1.38 (m, 6 H) 1.92 (br. s., 2 H) 2.10 (br. s., 2 H) 2.73 (dd, J=12.07, 10.28 Hz, 1 H) 2.81 (dd, J=11.86, 10.83 Hz, 1 H) 3.01 (br. s., 2 H) 3.13 (q, J=7.30 Hz, 2 H) 3.35 (s, 3 H) 3.37 - 3.44 (m, 1 H) 3.54 (d, J=11.33 Hz, 2 H) 3.64 - 3.76 (m, 1 H) 4.01 (s, 1 H) 4.50 (dd, J=10.68, 2.63 Hz, 1 H) 7.27 (d, J=8.05 Hz, 1 H) 7.66 (dd, J=8.58, 4.27 Hz, 1 H) 8.16 (d, J=8.01 Hz, 1 H) 8.42 (s, 1 H) 8.67 (dd, J=8.58, | LCMS (ESI+) calcd for C23H29N5O2 (M+H+): 408.24; found: 408.0 |
| **ER-899680** | $C_{23}H_{29}N_5O_2$ | 407.52 | 0.0148 | 8.784 | (2R,6R)-4-(8-cyanoquinolin-5-yl)-N-(1-ethylpiperidin-3-yl)-6-methylmorpholine-2-carboxamide | 1H NMR (400 MHz, CD3OD) δ ppm: 1.06-1.13 (m, 3H), 1.30-1.35 (d, 3H), 1.42-1.52 (m, 1H), 1.56-1.67 (m, 1H), 1.70-1.83 (m, 2H), 2.44-2.53 (m, 2H), 2.65-2.88 (m, 4H), 3.35-3.41 (m, 1H), 3.66-3.72 (m, 1H), 3.96-4.04 (m, 1H), 4.09-4.18 (m, 1H), 4.43-4.49 (dd, 1H), 7.24-7.29 (d, 1H), 7.62-7.67 (dd, 1H), 8.12-8.16 (d, 1H), 8.64-8.68 (dd, 1H), 8.96-8.99 (dd, 1H). | LCMS (ESI+) calcd for C23H29N5O2 (M+H+): 408.24; found: 408.36. |

Fig. 6FFFF

| | | | | | | | |
|---|---|---|---|---|---|---|---|
| ER-899688 | 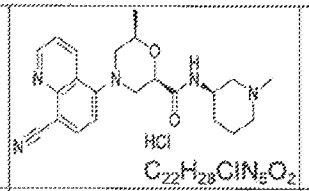 $C_{22}H_{28}ClN_5O_2$ | 393.49 | 0.0082 | > 10.0 | (2R,6R)-4-(8-cyanoquinolin-5-yl)-6-methyl-N-((R)-1-methylpiperidin-3-yl)morpholine-2-carboxamide hydrochloride | 1H NMR (400 MHz, METHANOL-$d_4$) d ppm 1.34 (d, J=6.20 Hz, 3 H) 1.38 - 1.52 (m, 1 H) 1.63 (m, 1 H) 1.89 - 1.85 (m, 2 H) 2.19 (br. s., 2 H) 2.39 (s, 3 H) 2.58 (br. s., 1 H) 2.87 - 2.87 (m, 3 H) 3.40 (d, J=12.07 Hz, 1 H) 3.70 (dt, J=11.98, 3.24 Hz, 1 H) 3.93 - 4.06 (m, 1 H) 4.07 - 4.23 (m, 1 H) 4.47 (dd, J=10.79, 2.87 Hz, 1 H) 7.27 (d, J=7.90 Hz, 1 H) 7.66 (dd, J=8.55, 4.27 Hz, 1 H) 8.15 (d, J=8.12 Hz, 1 H) 8.87 (dd, J=8.55, 1.90 Hz, 1 H) 8.99 (dd, J=4.27, 1.60 Hz, 1 H) | LCMS (ESI+) calcd for C22H27N5O2 (M+H+): 394.22; found: 394.28 |
| ER-899718 | 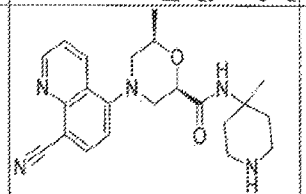 $C_{22}H_{27}N_5O_2$ | 393.49 | 0.0030 | > 10.0 | (2R,6R)-4-(8-cyanoquinolin-5-yl)-6-methyl-N-(4-methylpiperidin-4-yl)morpholine-2-carboxamide | 1H NMR (400 MHz, CHLOROFORM-d) d ppm 1.20 - 1.37 (m, 5 H) 1.40 (s, 3 H) 1.87 - 2.00 (m, 2 H) 2.39 (d, J=12.51 Hz, 2 H) 2.65 - 2.80 (m, 2 H) 2.97 - 3.15 (m, 3 H) 3.17 - 3.33 (m, 3 H) 3.46 (s, 2 H) 3.75 (d, J=12.02 Hz, 1 H) 4.04 - 4.16 (m, 1 H) 4.35 (dd, J=10.72, 2.56 Hz, 1 H) 6.42 (s, 1 H) 7.10 (d, J=8.01 Hz, 1 H) 7.52 (dd, J=8.36, 4.23 Hz, 1 H) 8.03 (d, J=7.97 Hz, 1 H) 8.46 (dd, J=8.56, 1.62 Hz, 1 H) 9.08 (dd, J=4.20, 1.60 Hz, 1 H) | LCMS (ESI+) calcd for C22H27N5O2 (M+H+): 394.22; found: 393.9 |
| ER-899722 | 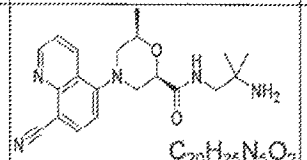 $C_{20}H_{25}N_5O_2$ | 367.46 | 0.0040 | > 10.0 | (2R,6R)-N-(2-amino-2-methylpropyl)-4-(8-cyanoquinolin-5-yl)-6-methylmorpholine-2-carboxamide | 1H NMR (400 MHz, METHANOL-d4) d ppm 1.07 (d, 7 H) 1.25 - 1.36 (m, 3 H) 2.64 - 2.86 (m, 3 H) 3.18 (d, 2 H) 3.38 (dt, 1 H) 3.68 (dt, 1 H) 4.13 (m, 1 H) 4.50 (dd, 1 H) 7.23 (d, 1 H) 7.82 (dd, 1 H) .11 (d, 1 H) 8.63 (dd, 1 H) 8.94 (dd, 1 H) | LCMS (ESI+) calcd for C20H25N5O2 (M+H+): 368.20; found: 368.2 |
| ER-899742 | 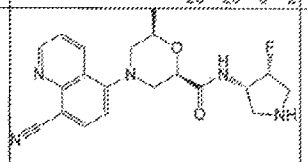 $C_{20}H_{23}ClFN_5O_2$ | 419.89 | 0.0059 | > 10.0 | (2R,6R)-4-(8-cyanoquinolin-5-yl)-N-((3S,4R)-4-fluoropyrrolidin-3-yl)-6-methylmorpholine-2-carboxamide hydrochloride | 1H NMR (400 MHz, METHANOL-d4) d ppm 1.36 (d, 4 H) 2.59 - 2.80 (m, 1 H) 2.88 (t, 1 H) 3.35 (m, 1 H) 3.38 - 3.48 (m, 1 H) 3.48 - 3.65 (m, 1 H) 3.65 - 3.86 (m, 5 H) 4.18 - 4.21 (m, 1 H) 4.58 (dd, 1 H) 5.23 (t, 1 H) 5.37 (t, 1 H) 7.29 (d, 1 H) 7.68 (dd, 1 H) 8.11 (d, 1 H) 8.17 (d, 1 H) 8.69 (dd, 1 H) 9.01 (dd, 1 H) | LCMS (ESI+) calcd for C20H23FN5O2 (M+H+): 384.15; found: 384.03 |
| ER-899745 | 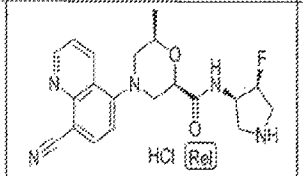 $C_{20}H_{23}ClFN_5O_2$ | 419.89 | 0.0081 | > 10.0 | (2R,6R)-4-(8-cyanoquinolin-5-yl)-N-((3R,4S)-4-fluoropyrrolidin-3-yl)-6-methylmorpholine-2-carboxamide hydrochloride | 1H NMR (400 MHz, METHANOL-d4) d ppm 1.35 (d, 4 H) 2.75 (t, 1 H) 2.86 (t, 1 H) 3.43 (d, 2H) 3.59 (t, 1 H) 3.67 - 3.79 (m, 6 H) 4.05 - 4.29 (m, 1 H) 4.59 (dd, 1 H) 7.29 (d, 1 H) 7.70 (dd, 1 H) 8.12 (d, 1 H) 8.18 (d, 1 H) 8.73 (d, 1 H) 9.01 (dd, 1 H) | LCMS (ESI+) calcd for C20H23FN5O2 (M+H+): 384.15; found: 384.06 |

AMENDED

FIG. 6GGGG

| | | | | | | | |
|---|---|---|---|---|---|---|---|
| **ER-899819** | $C_{22}H_{28}ClN_5O_2$ | 429.95 | 0.0053 | 7.490 | (2R,6R)-N-(azepan-3-yl)-4-(8-cyanoquinolin-5-yl)-6-methylmorpholine-2-carboxamide hydrochloride | | |
| **ER-899820** | $C_{23}H_{30}ClN_5O_2$ | 443.98 | 0.0083 | > 10.0 | (2R,6R)-4-(8-cyanoquinolin-5-yl)-6-methyl-N-(1-methylazepan-3-yl)morpholine-2-carboxamide hydrochloride | | |
| **ER-899835** | $C_{23}H_{29}N_5O_2$ | 407.52 | 0.0661 | > 10.0 | (2R,6R)-4-(8-cyanoquinolin-5-yl)-N-(1,4-dimethylpiperidin-4-yl)-6-methylmorpholine-2-carboxamide | 1H NMR (400 MHz, CHLOROFORM-d) d ppm 0.84 - 0.91 (m, 1 H) 1.21 - 1.28 (m, 5 H) 1.34 (d, J=6.22 Hz, 3 H) 1.42 (s, 3 H) 1.67 - 1.90 (m, 4 H) 2.05 - 2.17 (m, 2 H) 2.21 (d, J=8.09 Hz, 1 H) 2.31 (s, 3 H) 2.54 - 2.65 (m, 1 H) 2.66 - 2.78 (m, 2 H) 3.30 (d, J=11.90 Hz, 1 H) 3.81 (d, J=12.09 Hz, 1 H) 4.03 - 4.16 (m, 1 H) 4.34 (dd, J=10.72, 2.52 Hz, 1 H) 4.85 - 4.93 (m, 1 H) 6.42 (s, 1 H) 7.09 (d, J=7.97 Hz, 1 H) 7.52 (dd, J=8.55, 4.20 Hz, 1 H) 8.04 (d, J=7.93 Hz, 1 H) 8.47 (dd, J=8.54, 1.37 Hz, 1 H) 9.07 (dd, J=4.04, 1.41 Hz, 1 H) | LCMS (ESI+) calcd for C23H29N5O2 (M+H+): 408.24; found: 408 |
| **ER-899836** | $C_{22}H_{27}ClFN_5O_2$ | 447.93 | 0.3190 | > 10.0 | (2R,6R)-4-(8-cyanoquinolin-5-yl)-N-(4-fluoro-1-methylpiperidin-3-yl)-6-methylmorpholine-2-carboxamide hydrochloride | $^1$H NMR (400 MHz, METHANOL-$d_4$) d ppm 1.34 (d, $J$=6.41 Hz, 3 H) 1.92 - 2.14 (m, 2 H) 2.22 - 2.43 (m, 5 H) 2.58 (br, 1 H) 2.64 - 2.89 (m, 3 H) 3.40 (d, $J$=12.07 Hz, 1 H) 3.70 (dd, $J$=11.96, 2.14 Hz, 1 H) 4.09 - 4.28 (m, 2 H) 4.53 (ddd, $J$=10.74, 3.90, 2.67 Hz, 1 H) 4.65 - 4.86 (m, 1 H) 7.28 (d, $J$=8.12 Hz, 1 H) 7.66 (dd, $J$=8.55, 4.27 Hz, 1 H) 8.16 (d, $J$=8.12 Hz, 1 H) 8.68 (dd, $J$=8.65, 1.60 Hz, 1 H) 8.99 (dd, $J$=4.27, 1.71 Hz, 1 H) | LCMS (ESI+) calcd for C22H26FN5O2 (M+H+): 412.18; found: 412.23 |

| Treatment | Pre-bleed | Veh | -742 | -742 |
|---|---|---|---|---|
| Dose (mpk) | --- | --- | 300 | 33 |
| Duration (wks) | --- | 14 | 14 | 14 |
| Age (wks) | 19 | 34 | 34 | 34 |

| Treatment | Pre-bleed | Veh | -742 | -742 |
|---|---|---|---|---|
| Dose (mpk) | --- | --- | 300 | 33 |
| Duration (wks) | --- | 14 | 14 | 14 |
| Age (wks) | 19 | 34 | 34 | 34 |

| Treatment | Pre-bleed | Veh | -742 | -742 |
|---|---|---|---|---|
| Dose (mpk) | --- | --- | 300 | 33 |
| Duration (wks) | --- | 14 | 14 | 14 |
| Age (wks) | 19 | 34 | 34 | 34 |

| Treatment | Pre-bleed | Veh | -742 | -742 |
|---|---|---|---|---|
| Dose (mpk) | --- | --- | 300 | 33 |
| Duration (wks) | --- | 14 | 14 | 14 |
| Age (wks) | 19 | 34 | 34 | 34 |

| Treatment | Pre-bleed | Veh | -742 | -742 |
|---|---|---|---|---|
| Dose (mpk) | --- | --- | 300 | 33 |
| Duration (wks) | --- | 14 | 14 | 14 |
| Age (wks) | 19 | 34 | 34 | 34 |

FIG. 7G

| Gene Number | Gene Name |
|---|---|
| 1 | **Irf7*** |
| 2 | **Isg15*** |
| 3 | Fcgr1 |
| 4 | **Usp18*** |
| 5 | **Oasl2*** |
| 6 | Cmpk2 |
| 7 | Herc6 |
| 8 | **Ifit1*** |
| 9 | Oas3 |
| 10 | Ifi202b |
| 11 | Ifit3 |
| 12 | Ifi27l2a |
| 13 | Ddx60 |
| 14 | Ifi44 |
| 15 | Xaf1 |
| 16 | Mx1 |
| 17 | Ifi204 |
| 18 | Elane |
| 19 | Fpr1 |
| 20 | Mmp8 |
| 21 | Ccl2 |
| 22 | Ms4a6c |
| 23 | Cxcl10 |
| 24 | Ccr2 |
| | |
| 24 genes were significantly upregulated between Pristane + Vehicle vs. uninduced PBS control (P.adj "FDR" <0.05, at least 1.5 Fold Change) | |
| * Significantly reduced by 300 mg/kg ER899742 vs. vehicle-treated pristane-induced mice (5 genes) (P.adj "FDR"<0.05, at least 1.5 fold change) | |

FIG. 8
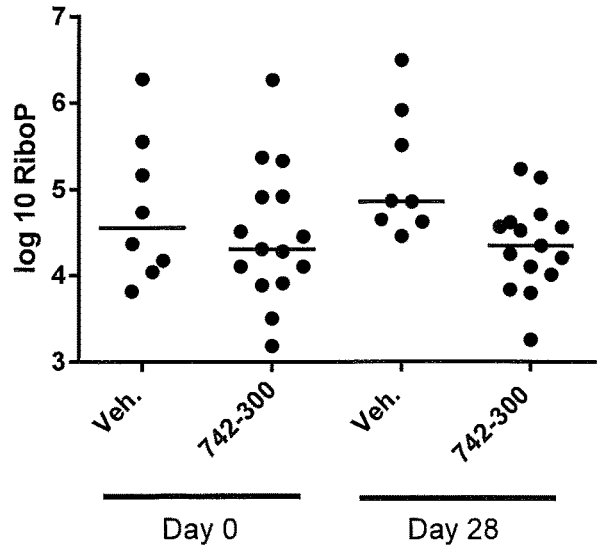
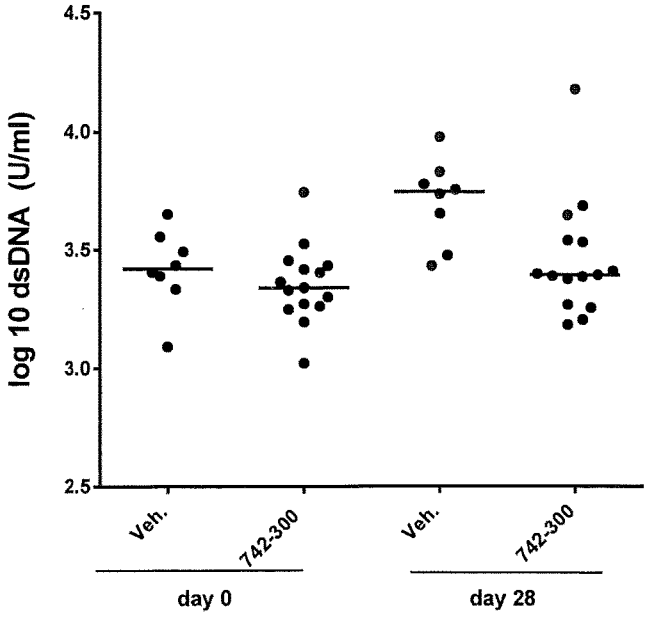
No statistically significant change in titer seen in dosed groups over time.

FIG. 9 ORTEP plot of the crystal structure of ER-899742-HCl.
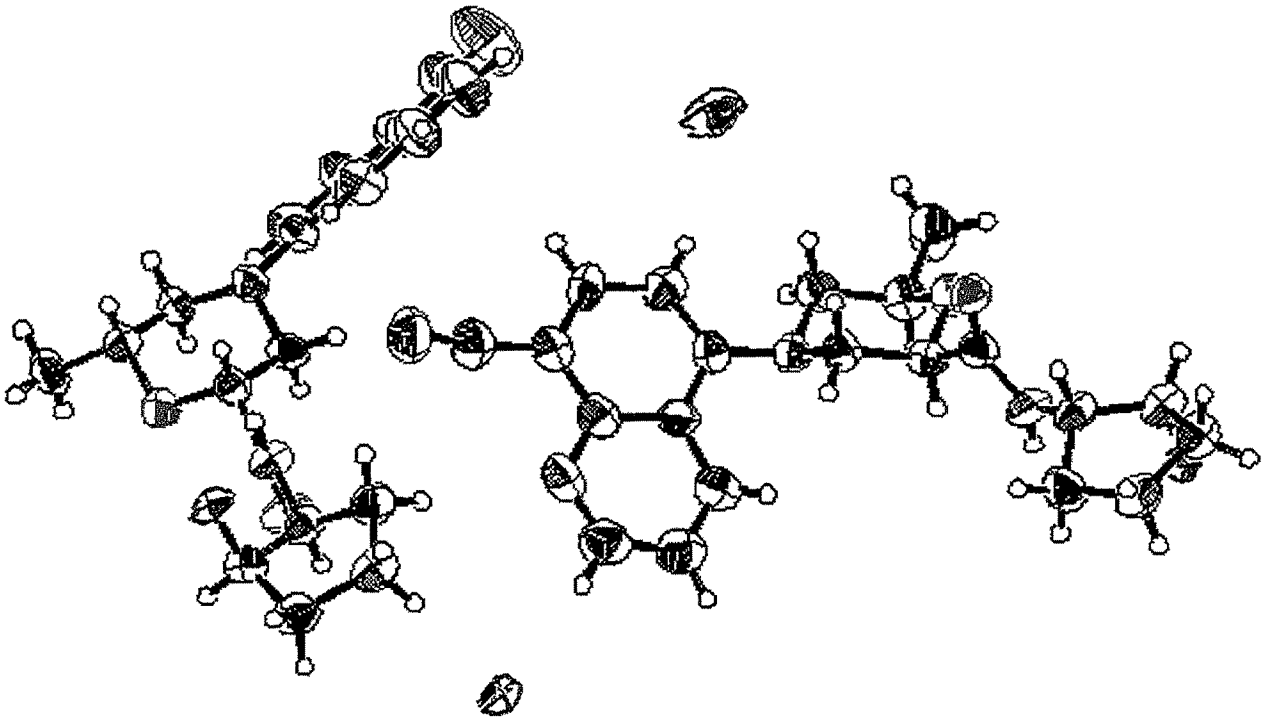

SELECTIVELY SUBSTITUTED QUINOLINE COMPOUNDS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application claims priority to U.S. provisional patent application No. 61/890,718, filed on Oct. 14, 2013. That application is incorporated by reference herein.

BACKGROUND

1. Field of the Disclosure

Embodiments of the disclosure relate to selectively substituted quinoline compounds and pharmaceutical agents comprising one or more of those compounds as active ingredient(s). More particularly, embodiments of the disclosure relate to those compounds that act as an antagonist or inhibitor for Toll-like receptors (TLR) 7 and 8, and their use in a pharmaceutical composition effective for treatment of systemic lupus erythematosus (SLE) and lupus nephritis.

2. Description of Related Art

Systemic lupus erythematosus (SLE) and lupus nephritis are autoimmune diseases characterized by inflammation and tissue damage. For example, SLE may cause damage to the skin, liver, kidneys, joints, lungs, and central nervous system. SLE sufferers may experience general symptoms such as extreme fatigue, painful and swollen joints, unexplained fever, skin rash, and kidney dysfunction. Because organ involvement differs amongst patients, symptoms may vary. SLE is predominantly a disease of younger women, with peak onset between 15-40 years of age and an approximate 10-fold higher prevalence in women vs. men.

Current treatments for SLE typically involve immunomodulatory drugs such as belimumab, hydroxychloroquine, prednisone, and cyclophosphamide. All of these drugs may have dose-limiting side effects, and many patients still have poorly controlled disease.

BRIEF SUMMARY OF THE DISCLOSURE

Embodiments of the disclosure provide compounds and methods of use for preventing or treating diseases or conditions characterized by Toll-like receptor 7 or 8 activation in patients. One embodiment features a compound of formula (I):

(I)

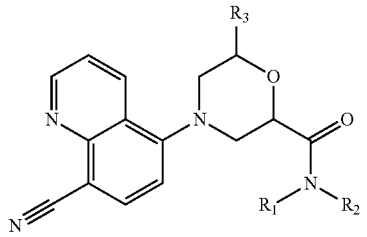

wherein at least one of $R_1$ and $R_2$ is —H, methyl, or ethyl, and the other is —H; or the other is $C_1$-$C_6$ alkyl that is optionally substituted with:

—OH, methoxy, ethoxy, —$OCH(CH_3)_2$, —$O(CH_2)_2CH_3$, phenyl, furanyl, —$O(CH_2)_2OH$, phenoxy, methylthio, —F, —$N(CH_3)_2$, cyano, pyridinyloxy, fluorophenoxy, isochromanyl, phenol, benzylamino, —$NHCH_3$, oxo-, amino, carboxyl, 7-member spiroaminyl, a three to six member cycloalkyl, saturated or unsaturated and optionally including one or more heteroatoms selected from O and N, and optionally substituted at one or more C or N atoms by methyl, cyano, fluoro, methylamino, or trifluoromethyl; or the other is $C_3$-$C_7$ cycloalkane, saturated or unsaturated, optionally bridged, optionally including one or more heteroatoms selected from O, S, and N, and optionally substituted at one or more C or N atoms by methyl, ethyl, pyridinyl, azetidinyl, acetamidyl, carboxamidyl, cyano, fluoro, methylamino, or trifluoromethyl; or $R_1$ and $R_2$, together with the nitrogen atom to which they are attached, form an 8 to 11 member spirodiamine, an 8 member bicyclodiamine, a 7 member spiroxamine, a piperidinyl optionally substituted with ethyl, or a four to six member cycloalkyl, optionally substituted with at least one of carboxamidyl, aminomethyl, methyl, (ethylamino)methyl, (dimethylamino)methyl, dimethylamino, (methylamino)methyl, and amino; and wherein $R_3$ is —H or methyl.

In a further embodiment the compound is a compound of Formula (I), having the stereochemistry set forth in one of Formula (Ia), (Ib), (Ic), or (Id), having the same substituent options as set forth above for Formula (Ia):

(Ia)

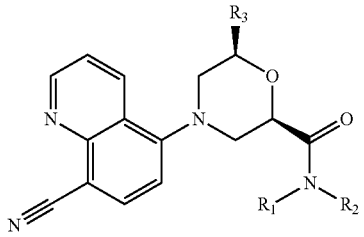

(Ib)

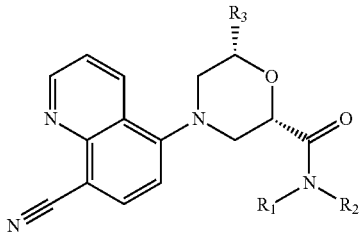

(Ic)

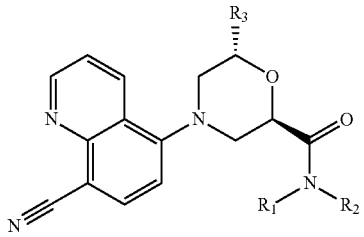

-continued (Id)

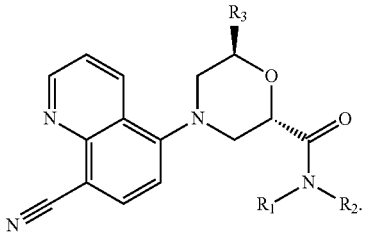

A further embodiment provides a compound of Formula (Ie) (relative stereochemistry indicated):

(Ie)

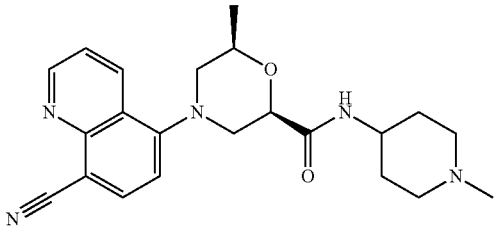

In a further embodiment the compound is a compound of Formula (II):

(II)

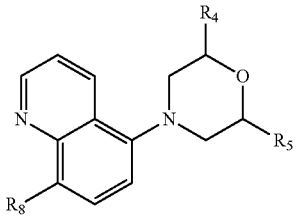

wherein $R_4$ is —H or methyl;

$R_5$ is $C_1$-$C_5$ alkyl that is saturated, partially saturated, or unsaturated, and that is optionally substituted with:

—H, —Cl, —F, —OH, —$NH_2$, oxo-, —$N(CH_2CH_3)_2$, phenyl, cyclohexyl, phenyltriazolyl, cyclohexyltriazolyl, pyridinyl, pyrrolidinyl, morpholinyl optionally substituted with methyl or hydroxymethyl, —O—, substituted with:

$C_1$-$C_6$ alkyl, methylphenyl, methylcyclohexyl, pyridinyl, diazinyl, or phenyl optionally substituted with —F or methyl, —NH—, substituted with:

$C_2$-$C_7$ alkyl that is linear, branched, or cyclic, saturated or unsaturated, and optionally substituted with oxo-, phenyl, methyl, or —OH, pyridinyl optionally substituted with methyl, methoxy, phenyl, or amino, diazinyl optionally substituted with ethyl, benzoimidazolyl, methylphenyl, phenylpyrazolyl, naphthyridyl, phenyl optionally substituted with —F, methyl, ethyl, or ethoxy, imidazolidinyl optionally substituted with methyl or $R_5$ is

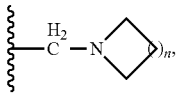

wherein n is 1-3, and wherein the cyclic amine is optionally substituted with $C_1$-$C_3$ alkyl optionally substituted with —OH, —F, phenyl, —$NH_2$, cyclohexyl, —$N(CH_3)_2$, —$C(O)NH_2$, methylsulfonamidyl, benzenesulfonamidyl, methylbenzenesulfonamidyl, or pyrrolidinyl optionally substituted with methyl or hydroxyl, or —$NHC(O)R_6$, wherein $R_6$ is $C_1$-$C_5$ alkyl, phenyl, pyridinyl, fluorophenyl, methylsulfonyl, fluorobenzenesulfonyl, dimethyl pyrazole sulfonyl, or pyrazolyl optionally substituted with methyl;

piperidinyl optionally substituted with —$C(O)CH_3$, —$C(O)CH_2CH_3$, methyl, oxo-, C(O)Ph, —$NH_2$, —NH—$C(O)CH_3$, or

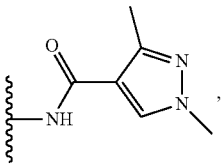

piperazinyl optionally substituted with —$C(O)OC(CH_3)_3$, methyl, —$C(O)CH_3$, —C(O)Ph, $C(O)CH(CH_3)_2$, —$C(O)CH_3$, or methylsulfonyl; or $R_5$ is

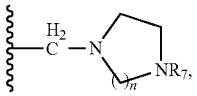

where n is 1 or 2, and wherein the cyclic diamine is optionally substituted on at least one carbon atom with methyl, oxo-, —$N(CH_3)_2$, amino, —$CH_2CH_3$, or piperidinyl optionally substituted with methyl, —$C(O)CH_3$, —$C(O)CH(CH_3)_2$, —C(O)Ph, or —$C(O)OC(CH_3)_3$, and wherein $R_7$ is —H, phenyl, —$C(O)CH_3$, $C_1$-$C_3$ alkyl, —$C(O)NH_2$, or —C(O)Ph; and $R_8$ is methoxy or cyano.

A further embodiment provides a compound of Formula (III):

(III)

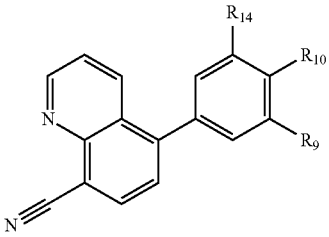

wherein $R_{11}$ is H or methyl;

$R_{10}$ is H or, when both $R_{14}$ and $R_9$ are H, is methyl-1,4'-bipiperidinyl;

$R_9$ is —H or is —$CH_2$— substituted by 1,4'-bipiperidinyl, oxo-, hydroxyl, methylpyridinyl, or piperidinyl optionally substituted with hydroxyl, —$N(CH_3)_2$, or piperidinyl.

In a further embodiment the compound is selected from rel-(2R,6R)-4-(8-cyanoquinolin-5-yl)-N-((3R,4S)-4-fluoropyrrolidin-3-yl)-6-methylmorpholine-2-carboxamide hydrochloride, (2R,6R)-4-(8-cyanoquinolin-5-yl)-6-methyl-N-(1-methylpiperidin-4-yl)morpholine-2-carboxamide, 5-((2S,6R)-2-([1,4'-bipiperidin]-1'-ylmethyl)-6-methylmorpholino)quinoline-8-carbonitrile, and 5-((2R,7R)-2-(hydroxymethyl)-7-methyl-1,4-oxazepan-4-yl)quinoline-8-carbonitrile.

In a further embodiment the compound or pharmaceutically effective salt thereof of the preceding paragraph has an IC50 less than or equal to 20 nM against human TLR7 receptors expressed in a HEK-293 cell line. In a further embodiment the compound or pharmaceutically effective salt thereof of the preceding paragraph of this disclosure has an IC50 less than or equal to 100 nM against human TLR7 receptors expressed in a HEK-293 cell line. In a further embodiment the IC50 against human TLR7 receptors expressed in a HEK-293 cell line is measured by (1) plating cells of the HEK-293 cell line stably expressing TLR7 in Dulbecco's modified Eagle's medium containing 10% fetal bovine serum at a density of 2.22×105 cells/ml into a 384-well plate and incubating for 2 days at 37° C., 5% $CO_2$; (2) adding the compound or pharmaceutically acceptable salt thereof and incubating the cells for 30 minutes; (3) adding CL097 (InvivoGen) at 3 ug/ml and incubating the cells for approximately 20 hours; and (4) quantifying NF-kappaB dependent reporter activation by measuring luminescence.

In further embodiments of the disclosure, compounds have an IC50 against human TLR7 receptors expressed in a HEK-293 cell line less than or equal to 200 nM, less than or equal to 180 nM, less than or equal to 160 nM, less than or equal to 140 nM, less than or equal to 120 nM, less than or equal to 100 nM, less than or equal to 80 nM, less than or equal to 60 nM, less than or equal to 40 nM, or less than or equal to 20 nM. In further embodiments of the disclosure, compounds have an IC50 against human TLR7 receptors expressed in a HEK-293 cell line from 10 nM to 30 nM, from 10 nM to 50 nM, from 10 nM to 100 nM, from 30 nM to 50 nM, from 30 nM to 100 nM, or from 50 nM to 100 nM. In further embodiments the IC50 against human TLR7 receptors expressed in a HEK-293 cell line is measured by (1) plating cells of the HEK-293 cell line stably expressing TLR7 in Dulbecco's modified Eagle's medium containing 10% fetal bovine serum at a density of 2.22×105 cells/ml into a 384-well plate and incubating for 2 days at 37° C., 5% $CO_2$; (2) adding the compound or pharmaceutically acceptable salt thereof and incubating the cells for 30 minutes; (3) adding CL097 (InvivoGen) at 3 ug/ml and incubating the cells for approximately 20 hours; and (4) quantifying NF-kappaB dependent reporter activation by measuring luminescence.

Further embodiments provide methods for treatment of lupus, including but not limited to treatment of systemic lupus erythematosus, cutaneous lupus, neuropsychiatric lupus, fetal heart block, and antiphospholipid syndrome, including administering a pharmaceutically effective amount of a compound or pharmaceutically acceptable salt of the disclosure.

Further embodiments provide methods for antagonizing TLR7, including administering a pharmaceutically effective amount of a compound or pharmaceutically acceptable salt of the disclosure.

Further embodiments provide methods for antagonizing TLR8, including administering a pharmaceutically effective amount of a compound or pharmaceutically acceptable salt of the disclosure.

Further embodiments provide pharmaceutical compositions comprising at least one compound or pharmaceutically acceptable salt of the disclosure and at least one pharmaceutically acceptable carrier.

Further embodiments provide methods for treatment of systemic lupus erythematosus or lupus, including administering a pharmaceutically effective amount of a compound or pharmaceutically acceptable salt of the disclosure.

Further embodiments provide methods for antagonizing TLR7, including administering a pharmaceutically effective amount of a compound or pharmaceutically acceptable salt of the disclosure.

Further embodiments provide methods for antagonizing TLR8, including administering a pharmaceutically effective amount of a compound or pharmaceutically acceptable salt of the disclosure.

Further embodiments provide pharmaceutical compositions comprising at least one compound or pharmaceutically acceptable salt of the disclosure and at least one pharmaceutically acceptable carrier.

The term "optionally substituted," as used herein, means that the subject structure may include, but is not required to include, one or more substituents independently selected from lower alkyl, methoxy-, —OH, —$NH_2$, —$CH_2$—NH—$CH_2$, —$OCH_2CH_2CH_3$, or —$OCH(CH_3)_2$. If the optionally substituted moiety is cyclic, then the optional substitution may be a methyl bridge between two atoms in the ring.

The symbol "C(O)" as used herein refers to a carbonyl group having the formula C═O.

Unless otherwise specified, "a" and "an" as used in this disclosure, including the claims, mean "one or more."

As used herein, "lower alkyl" refers to straight, or, in the case of three- and four-carbon groups, straight, branched, or cyclic saturated hydrocarbons having between one and four carbon atoms.

As used herein, the term "attached through a nitrogen" when referring to a heterocyclic moiety including nitrogen, means that a point of attachment of the moiety to another structure is through a nitrogen that is part of the heterocycle.

As used herein, the term "TLR7/8" means "TLR7 and TLR8" or "TLR7 or TLR8" or "TLR7 and/or TLR8." The particular meaning can be understood by a person skilled in the art based upon the context in which "TLR7/8" appears.

Heterocyclic moieties recited herein include azetidinyl, pyrrolidinyl, piperidinyl, methylazetidinyl, pyrazolyl, piperazinyl, morpholinyl, thiazolyl, pyrrolopyrrolyl, imidazolidinyl, and isothiazolyl. Where a heterocyclic group is mentioned, unless otherwise indicated it will be understood that the heterocyclic atom(s) in the group may be at any position in the group. It will further be understood that imidazolyl, pyrazolyl, thiazolyl, and pyrrolyl may be unsaturated or partially unsaturated. An embodiment of the disclosure may include a pharmaceutical composition that includes one or more compounds of the disclosure with a pharmaceutically acceptable excipient. These pharmaceutical compositions may be used to treat or prevent a disease or condition characterized by TLR7/8 activation in a patient, typically a human patient, who has or is predisposed to have such a condition or disease. Examples of diseases or conditions characterized by TLR7/8 activation include systemic lupus erythematosus (SLE) and lupus nephritis.

As used herein, "effective amount" of a compound of an embodiment of the disclosure is effective amount of the above-identified compounds in an amount sufficient to treat or prevent SLE and lupus nephritis.

Embodiments presented herein may include asymmetric or chiral centers. Embodiments include the various stereoisomers and mixtures thereof. Individual stereoisomers of compounds of embodiments of the disclosure may be prepared synthetically from commercially available starting materials that contain asymmetric or chiral centers, or by preparation of mixtures of enantiomeric compounds followed by resolution of those compounds. Suitable methods of resolution include attachment of a racemic mixture of enantiomers, designated (+/−), to a chiral auxiliary, separation of the resulting diastereomer by chromatography or recrystallization and separation of the optically pure product from the auxiliary; or direct separation of the mixture of optical enantiomers on chiral chromatographic columns.

Embodiments of the disclosure also include a pharmaceutical composition including any compound of the disclosure as well as a pharmaceutically acceptable excipient. The pharmaceutical compositions can be used to treat or prevent SLE and lupus nephritis. Therefore, embodiments of the disclosure may also feature a method for treating or preventing SLE or lupus nephritis in a human patient having or predisposed to having lupus nephritis or SLE.

Embodiments of the disclosure include pharmaceutically acceptable salts of the compounds presented herein. The term "pharmaceutically acceptable salt" refers to those salts that are, within the scope of sound medical judgment, suitable for use in contact with the tissues of humans and animals without undue toxicity, irritation, or allergic response. Pharmaceutically acceptable salts are well known in the art. For example, S. M. Berge, et al., describes pharmaceutically acceptable salts in detail in J. Pharmaceutical Sciences 66:1-19, 1977. Salts can be prepared in situ during final isolation and purification of a compound or separately by reacting a free base group with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, monomaleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, trifluoroacetate, undecanoate, valerate salts, and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The term "pharmaceutically acceptable ester," as used herein, represents esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic, and alkanedioic acids, in which each alkyl or alkenyl group typically has not more than 6 carbon atoms. Examples of particular esters include formates, acetates, propionates, butyates, acrylates, and ethylsuccinates.

In this application enantiomers are designated by the symbols "R" or "S" or are drawn by conventional means with a bolded line defining a substituent above the plane of the page in three-dimensional space and a hashed or dashed line defining a substituent beneath the plane of the printed page in three-dimensional space. If no stereochemical designation is made, then the structure definition includes both stereochemical options. If a structure or chemical name includes "REL" or "rel" then that structure is understood to show relative stereochemistry.

BRIEF SUMMARY OF THE FIGURES

(FIG. 1A). ER-899742 and ER-899464 were tested side by side in a single experiment. (FIG. 1B) A repeat experiment was done with ER-899742 examining all three doses at all three timepoints.

FIG. 2A through FIG. 2C show results of testing ER-899742 in the NZBxNZW strain (abbreviated hereafter as NZBWF1/J or NZB/W) lupus disease model. Figure Legend: Female NZBWF1/J mice were received at 5 weeks of age, baseline bleeds were performed, and mice were monitored for disease progression by following anti-dsDNA titers. At 27 weeks of age, mice were randomized into groups with equivalent median anti-dsDNA titers and treated at 29 weeks of age with Vehicle (Veh; 0.5% methyl-cellulose) alone or 33, 100, or 300 mg/kg once-a-day orally (QD PO). At 46 weeks of age after 17 weeks of treatment mice were bled and tested for anti-dsDNA titers. All mice were sacrificed at 50 weeks of age (21 weeks of compound treatment). (FIG. 2A) Just prior to termination at 50 weeks of age (following 21 weeks of treatment), urine was collected from individual mice, and the Urinary Albumin Creatinine Ratio (UACR, proteinuria) was determined for each animal as an indirect measure of kidney function. (FIG. 2B) Timecourse of mortality observed in this study for the highest and lowest dose groups. No mortality was seen with compound treatment. Further, no mortality was observed in the middle dose group (not shown). (FIG. 2C) Impact of treatment on anti-dsDNA titers after 17 weeks of dosing, at 46 weeks of age. No statistically significant effect was observed.

FIG. 3A through FIG. 3E show results of testing compound ER-899742 in the Pristane: DBA/1 strain lupus disease model. Figure Legend: Female DBA/1 mice at 9 weeks of age were given an intraperitoneal injection of 0.5 ml pristane or PBS. At 9 weeks post-pristane animals were bled for auto-antibody titers. Once-a-day oral dosing with Vehicle (Veh; 0.5% methyl-cellulose) or 33 mg/kg, 100 mg/kg, or 300 mg/kg of ER-899742 was begun 10 weeks after pristane injection and continued for 13 weeks of treatment. Mice were euthanized after 13 weeks of compound treatment, and anti-dsDNA (FIG. 3A), anti-Sm/nRNP (FIG. 3B), anti-histone (FIG. 3C) and anti-RiboP (FIG. 3D) titers were measured in blood plasma samples by ELISA (statistical significance of treatment versus vehicle determined by ANOVA with Dunnett's post-test). (FIG. 3E) The expression of IFN-regulated genes in whole blood was measured by a qPCR panel after 13 weeks of treatment with 300 mg/kg of ER-899742, and an IFN gene signature score was calculated (see Pharmacology Materials and Methods section for details regarding IFN score calculation). The table shows the full list of genes significantly upregulated by pristane treatment vs. PBS controls. When interferon scores were calculated, no significant difference was seen between treated and vehicle-treated animals. However six genes were significantly reduced by compound treatment vs. vehicle treatment (Student's t-test) and are marked in the table.

FIG. 4A through FIG. 4C show results of testing ER-899464 in the NZB/W disease model in the same experiment as FIG. 2A. Figure Legend: (FIG. 4A) Just prior to termination at 50 weeks of age (following 21 weeks of treatment), urine was collected from individual mice, and the Urinary Albumin Creatinine Ratio (UACR, proteinuria) was determined for each animal as an indirect measure of kidney function. (FIG. 4B) Summary of mortality observed in this study for the highest and lowest dose groups. No mortality was seen in the middle dose group (not shown).

FIG. 5A through FIG. 5D show results of testing ER-899464 in the Pristane disease model in the same experiment as that shown in FIG. 3A through FIG. 3E. Figure Legend: Mice were euthanized after 13 weeks of compound treatment, and anti-dsDNA (FIG. 5A), anti-Sm/nRNP (FIG. 5B), anti-histone (FIG. 5C), and anti-RiboP (FIG. 5D) titers were measured in blood plasma samples by ELISA (statistical significance of treatment versus vehicle determined by ANOVA with Dunnett's post-test). As was done for ER-899742, interferon-driven gene expression was tested, but none of the disease up-regulated genes shown in FIG. 3B were affected by treatment with ER-899464.

FIG. 6A through FIG. 6GGGG show structures and corresponding chemical names according to various embodiments presented herein. "ER-Number" is a reference number assigned to each compound. Where available, activity against a HEK cell line stably expressing human TLR7, activity against a HEK cell line stably expressing human TLR9, 1H NMR data, and mass spectrometry data are also included.

FIG. 7A through FIG. 7G show the effect of dosing with ER-899742 in Pristane-induced disease in DBA/1J mice. Figure Legend: Female DBA/1 mice at 9 weeks of age were given an intraperitoneal injection of 0.5 ml pristane or PBS. At 10 weeks post-pristane animals were bled for autoantibody titers. Once-a-day oral dosing with Vehicle (Veh; 0.5% methyl-cellulose) or 33 mg/kg, or 300 mg/kg of ER-899742 was begun 11 weeks after pristane injection and continued for 14 weeks of treatment. Mice were euthanized after 14 weeks of compound treatment, and anti-dsDNA (FIG. 7A), anti-RiboP (FIG. 7B), anti-Sm/nRNP (FIG. 7C), and anti-histone (FIG. 7D) titers were measured in blood plasma samples by ELISA (statistical significance of treatment versus vehicle determined by ANOVA with Dunnett's post-test). The same plasma was used to measure total IgG titers by ELISA at the end of dosing (FIG. 7E). Control of autoantibody against dsDNA and RiboP was seen in the presence of minimal changes in overall IgG level. Pristane-treated mice in this experiment developed arthritis, with swollen joints in the rear paws. Arthritis scores were assigned according to severity, each paw was scored on a scale of 0-4 based on signs of swelling and inflammation. Scores were summed for the two hind paws assessed on each animal, and graphed in FIG. 7F with statistical assessment as for ELISA titers above. Dose-dependent statistically significant suppression was observed. When interferon scores were calculated, no significant difference was seen between treated and vehicle-treated animals. However FIG. 7G demonstrates the downregulation of five out of 28 disease-related interferon-modulated genes upon treatment with ER-899742.

FIG. 8 contains the result of treating for a month with ER-899742 in Pristane-induced disease in DBA/1J mice with advanced disease, after development of high levels of autoantibody. Figure Legend: DBA/1J mice were injected i.p. with pristane at 10 weeks of age. Three months later anti-RiboP and anti-dsDNA titers were taken, and animals randomized into groups with matching mean titers. Groups were sacrificed after one, two or four weeks of oral dosing with ER-899742, and RiboP titers measured in serum. FIG. 8 demonstrates no statistically significant reversal of anti-RiboP or DNA titers after 28 days of dosing, although dosing was associated with lack of increase in titers.

FIG. 9 is an ORTEP plot of the crystal structure of ER-899742 as a HCl salt.

DETAILED DESCRIPTION OF THE DISCLOSURE

I. TLRs and Lupus

Figure 1A:
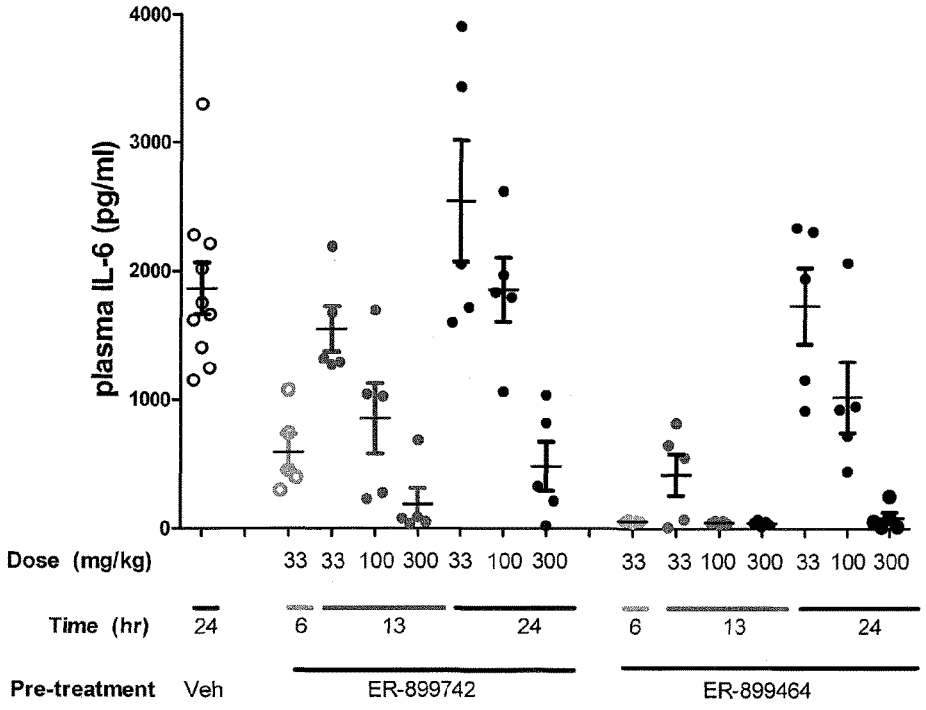
FIG. 1A and FIG. 1B show short-term in vivo suppression of the TLR7 pathway in mouse by compounds ER-899742 and ER-899464. Figure Legend: Female BALB/c mice were dosed by oral gavage with Vehicle alone (0.5% aqueous methyl-cellulose) or compound formulated in Vehicle at 33 mg/kg, 100 mg/kg or 300 mg/kg. At 6, 13 or 24 hours following oral dosing, mice were injected subcutaneously with 15 ug R848 to stimulate TLR7. Blood plasma was collected by cardiac puncture, and the IL-6 level at 1.5 hours after TLR7 stimulation was then assessed by standard ELISA procedure.

In addition to their role as innate immune receptors capable of detecting exogenous ("non-self") pathogen-associated molecular patterns (PAMPs—i.e., bacterial LPS detection by TLR4), mammalian Toll-like receptors (TLRs) are also capable of recognizing endogenous stimuli (DAMPs) released following host tissue damage or stress. Kono, H. and K. L. Rock, How dying cells alert the immune system to danger. Nat Rev Immunol, 2008. 8(4): p. 279-89. In the last decade an appreciation for the link between TLR activation by endogenous ("self") danger-associated molecular patterns (DAMPs) and the etiology of autoimmune disorders has emerged. Specifically, TLR7 can be activated by single-stranded RNA (ssRNA) derived from both mammalian and viral sources, whereas TLR9 can be activated by DNA derived from mammalian, viral, and bacterial sources.

Lupus is characterized by auto-antibodies reactive against double-stranded DNA (dsDNA) itself and associated proteins (histones) as well as against a broad array of RNA-associated proteins such as Ro, La, Smith (Sm), and U1 snRNP. Kirou, K. A., et al., Activation of the interferon-alpha pathway identifies a subgroup of systemic lupus erythematosus patients with distinct serologic features and active disease. Arthritis Rheum, 2005. 52(5): p. 1491-503. A second common hallmark of lupus, which was shown to correlate directly with disease severity, is dysregulated expression of type-1 interferons (IFNs), in particular IFNα, and the corresponding elevation of a large panel of IFNalpha-regulated genes in lupus patients' PBMC (the so called "type-1 IFN gene signature"). Kirou, K. A., et al., supra. A major source of IFN in the blood is a specialized immunocyte called a plasmacytoid dendritic cell (pDC), which constitutively expresses both TLR7 and TLR9.

A causal relationship between these two disease characteristics, auto-antibodies and IFN levels, was postulated when a number of research groups collectively demonstrated that antibody complexes isolated from lupus patients but not from healthy donors are capable of driving IFN production by pDC in a TLR7/9- and RNA/DNA-dependent manner. Means, T. K., et al., Human lupus autoantibody-DNA complexes activate DCs through cooperation of CD32 and TLR9. J Clin Invest, 2005. 115(2): p. 407-17; Vollmer, J., et al., Immune stimulation mediated by autoantigen binding sites within small nuclear RNAs involves Toll-like receptors 7 and 8. J Exp Med, 2005. 202(11): p. 1575-85; Savarese, E., et al., U1 small nuclear ribonucleoprotein immune complexes induce type I interferon in plasmacytoid dendritic cells through TLR7. Blood, 2006. 107(8): p. 3229-34. Moreover, IFN stimulates increased TLR7/9 expression on B-cells, thereby enhancing TLR/BCR (B-cell receptor) activation of auto-reactive B-cells to differentiate to antibody-producing plasma cells. Banchereau, J. and V. Pascual, Type I interferon in systemic lupus erythematosus and other autoimmune diseases. Immunity, 2006. 25(3): p. 383-92; In this fashion, levels of auto-antibody complexes containing nucleic acid TLR7/9 ligands drive the pro-inflammatory cycle and lupus disease progression. We believe it is likely that pharmacological antagonism of TLR7/8 will offer therapeutic benefit to lupus patients by disrupting this pro-inflammatory cycle, decreasing IFN levels, and dampening the autoimmune disease process mediated by pDC and B-cells.

Several other lines of evidence suggest a role for TLR7 in human lupus etiology and support the notion that TLR receptors are valid targets for disease intervention. Specific polymorphisms in the 3' UTR of TLR7 have been identified and shown to correlate with both elevated TLR7 expression and enhanced IFN gene signature. Shen, N., et al., Sex-specific association of X-linked Toll-like receptor 7 (TLR7) with male systemic lupus erythematosus. Proc Natl Acad Sci USA, 2010. 107(36): p. 15838-43. Deng, Y. et al., MicroRNA-3148 modulates allelic expression of toll-like receptor 7 variant associated with systemic lupus erythematosus. PLOS Genetics, 2013. e1003336. In addition, lupus standard-of-care (SOC) anti-malarial drugs such as chloroquine disrupt endosomal TLR7/9 signaling and inhibit PBMC and/or pDC IFNalpha production induced by ssRNA-ribonucleoprotein complexes or lupus patient serum. Moreover, myeloid DC and monocytes produce IL-12p40, TNF alpha, and IL-6 following self-RNA/TLR8 signaling, suggesting the additional contribution of TLR8-dependent pro-inflammatory cytokines to human lupus etiology in addition to TLR7-driven IFN by pDC. Vollmer, supra; Gorden, K. B., et al., Synthetic TLR agonists reveal functional differences between human TLR7 and TLR8. J Immunol, 2005. 174(3): p. 1259-68.

Mouse model evidence also exists for the role of TLR in lupus. Published studies have collectively demonstrated that both single TLR7 or dual TLR7/9 gene deletion or dual TLR7/9 pharmacologic inhibition reduces disease severity in four distinct lupus models. Nickerson, K. M., et al., TLR9 regulates TLR7-and MyD88-dependent autoantibody production and disease in a murine model of lupus. J Immunol, 2010. 184(4): p. 1840-8; Fairhurst, A. M., et al., Yaa autoimmune phenotypes are conferred by overexpression of TLR7. Eur J Immunol, 2008. 38(7): p. 1971-8; Deane, J. A., et al., Control of toll-like receptor 7 expression is essential to restrict autoimmunity and dendritic cell proliferation. Immunity, 2007. 27(5): p. 801-10; Savarese, E., et al., Requirement of Toll-like receptor 7 for pristane-induced production of autoantibodies and development of murine lupus nephritis. Arthritis Rheum, 2008. 58(4): p. 1107-15. Highlighting the role of TLR7 as a critical determinant of autoimmunity, transgenic overexpression of TLR7 alone leads to spontaneous anti-RNA auto-reactivity and nephritis in the normally disease-resistant C57BL/6 strain. Deane, supra.

From a safety perspective, there are no reports that TLR7, 8, or 9-single or 7/8- and 7/9-dual gene deficient mice are immune-compromised to the extent that infection by opportunistic pathogens is observed. Likewise, SOC anti-malarials are thought to be largely safe and effective for long-term use in humans to control lupus disease flare at doses predicted to at least partially inhibit TLR7/9 signaling. Lafyatis, R., M. York, and A. Marshak-Rothstein, Antimalarial agents: closing the gate on Toll-like receptors? Arthritis Rheum, 2006. 54(10): p. 3068-70; Costedoat-Chalumeau, N., et al., Low blood concentration of hydroxychloroquine is a marker for and predictor of disease exacerbations in patients with systemic lupus erythematosus. Arthritis Rheum, 2006. 54(10): p. 3284-90. In fact, save for increased susceptibility to Gram-positive bacterial infections in childhood and to a lesser extent in adulthood, humans with highly compromised TLR and IL-1R signaling pathways (MyD88- or IRAK-4-deficiency) are nonetheless healthy and maintain sufficient host defense mechanisms. Casanova, J. L., L. Abel, and L. Quintana-Murci, Human TLRs and IL-1Rs in Host Defense: Natural Insights from Evolutionary, Epidemiological, and Clinical Genetics. Annu Rev Immunol, 2010.

Based on this and other information, we believe that TLR7 in particular is a well-validated target in the context of mouse pre-clinical SLE models. Both genetic and functional human studies support the hypothesis that antagonism of the TLR7 and/or TLR8 pathways will afford therapeutic benefit to lupus patients. Moreover, both mouse TLR gene deletion studies and the long-term use of anti-malarials in humans suggest that pharmacological TLR7, 8 and/or 9 suppression can be undertaken without significantly compromising host defense.

A compound that suppresses TLR7, TLR8, or both TLR7 and TLR8 may therefore be expected to act as a therapeutic or prophylactic agent for SLE or lupus nephritis.

The present inventors have found compounds that suppress TLR 7 and/or 8 and are therefore expected to have a prophylactic or therapeutic effect on SLE or lupus nephritis. Compounds and methods of the disclosure are described herein.

II. Therapeutic Use

Dosage levels of active ingredients in the pharmaceutical compositions of the disclosure may be varied to obtain an amount of the active compound(s) that achieves the desired therapeutic response for a particular patient, composition, and mode of administration. The selected dosage level depends upon the activity of the particular compound, the route of administration, the severity of the condition being treated, and the condition and prior medical history of the patient being treated. Doses are determined for each particular case using standard methods in accordance with factors unique to the patient, including age, weight, general state of health, and other factors that can influence the efficacy of the compound(s) of the disclosure. In general, in the case of oral administration, the compound according to the present disclosure or a pharmaceutically acceptable salt thereof is administered at a dose of approximately 30 μg to 100 μg, a dose of 30 μg to 500 μg, a dose of 30 μg to 10 g, a dose of 100 μg to 5 g, ora dose of 100 μg to 1 g per adult per day. In the case of administration via injection, it is administered at a dose of approximately 30 μg to 1 g, a dose of 100 μg to 500 mg, or a dose of 100 μg to 300 mg per adult per day. In both cases, a dose is administered once or divided over several administrations. Dosage may be simulated, for example, using the Simcyp® program.

It is not intended that the administration of a compound of the disclosure to a mammal, including humans, be limited to a particular mode of administration, dosage, or frequency of dosing. The present disclosure contemplates all modes of administration, including oral, intraperitoneal, intramuscular, intravenous, intraarticular, intralesional, subcutaneous, or any other route sufficient to provide a dose adequate to prevent or treat SLE or lupus nephritis. One or more compounds of the disclosure may be administered to a mammal in a single dose or multiple doses. When multiple doses are administered, the doses may be separated from one another by, for example, several hours, one day, one week, one month, or one year. It is to be understood that, for any particular subject, specific dosage regimes should be adjusted over time according to the individual need and the professional judgment of the person administering or supervising the administration of a pharmaceutical composition that includes a compound of the disclosure.

For clinical applications, a compound of the present disclosure may generally be administered intravenously, subcutaneously, intramuscularly, colonically, nasally, intraperitoneally, rectally, buccally, or orally. Compositions containing at least one compound of the disclosure that is suitable for use in human or veterinary medicine may be presented in forms permitting administration by a suitable route. These compositions may be prepared according to the customary methods, using one or more pharmaceutically acceptable adjuvants or excipients. The adjuvants comprise, inter alia, diluents, sterile aqueous media, and various non-toxic organic solvents. Acceptable carriers or diluents for therapeutic use are well known in the pharmaceutical field, and are described, for example, in Remington: The Science and Practice of Pharmacy (20th ed.), ed. A. R. Gennaro, Lippincott Williams & Wilkins, 2000, Philadelphia, and Encyclopedia of Pharmaceutical Technology, eds. J. Swarbrick and J. C. Boylan, 1988, 1999, Marcel Dekker, New York. The compositions may be presented in the form of tablets, pills, granules, powders, aqueous solutions or suspensions, injectable solutions, elixirs, or syrups, and the compositions may optionally contain one or more agents chosen from the group comprising sweeteners, flavorings, colorings, and stabilizers to obtain pharmaceutically acceptable preparations.

The choice of vehicle and the content of active substance in the vehicle are generally determined in accordance with the solubility and chemical properties of the product, the particular mode of administration, and the provisions to be observed in pharmaceutical practice. For example, excipients such as lactose, sodium citrate, calcium carbonate, and dicalcium phosphate and disintegrating agents such as starch, alginic acids, and certain complex silicates combined with lubricants (e.g., magnesium stearate, sodium lauryl sulfate, and talc) may be used for preparing tablets. To prepare a capsule, it is advantageous to use lactose and high molecular weight polyethylene glycols. When aqueous suspensions are used, they may contain emulsifying agents that facilitate suspension. Diluents such as sucrose, ethanol, polyethylene glycol, propylene glycol, glycerol, chloroform, or mixtures thereof may also be used.

For parenteral administration, emulsions, suspensions, or solutions of the compositions of the disclosure in vegetable oil (e.g., sesame oil, groundnut oil, or olive oil), aqueous-organic solutions (e.g., water and propylene glycol), injectable organic esters (e.g., ethyl oleate), or sterile aqueous solutions of the pharmaceutically acceptable salts are used. The solutions of the salts of the compositions of the disclosure are especially useful for administration by intramuscular or subcutaneous injection. Aqueous solutions that include solutions of the salts in pure distilled water may be used for intravenous administration with the proviso that (i) their pH is adjusted suitably, (ii) they are appropriately buffered and rendered isotonic with a sufficient quantity of glucose or sodium chloride, and (iii) they are sterilized by heating, irradiation, or microfiltration. Suitable compositions containing a compound of the disclosure may be dissolved or suspended in a suitable carrier for use in a nebulizer or a suspension or solution aerosol, or may be absorbed or adsorbed onto a suitable solid carrier for use in a dry powder inhaler. Solid compositions for rectal administration include suppositories formulated in accordance with known methods and containing at least one compound of the disclosure.

Dosage formulations of a compound of the disclosure to be used for therapeutic administration should be sterile. Sterility is readily accomplished by filtration through sterile membranes (e.g., 0.2 micron membranes) or by other conventional methods. Formulations typically are stored in lyophilized form or as an aqueous solution. The pH of the compositions of this disclosure in some embodiments, for example, may be between 3 and 11, may be between 5 and 9, or may be between 7 and 8, inclusive.

While one route of administration is by oral dosage administration, other methods of administration may be used. For example, compositions may be administered subcutaneously, intravenously, intramuscularly, colonically, rectally, nasally, or intraperitoneally in a variety of dosage forms such as suppositories, implanted pellets or small cylinders, aerosols, oral dosage formulations, and topical formulations such as ointments, drops, and dermal patches. Compounds of embodiments of the disclosure may be incorporated into shaped articles such as implants, including but not limited to valves, stents, tubing, and prostheses, which may employ inert materials such as synthetic polymers or silicones, (e.g., Silastic® compositions, silicone rubber, or other commercially available polymers). Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, a compound of the disclosure may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates, and cross linked or amphipathic block copolymers of hydrogels.

A compound of the disclosure may also be administered in the form of liposome delivery systems, such as small unilamellar vesicles, large unilamellar vesicles, and multilamellar vesicles. Liposomes can be formed from a variety of lipids, such as cholesterol, stearylamine, or phosphatidylcholines. A compound of the disclosure may also be delivered using antibodies, antibody fragments, growth factors, hormones, or other targeting moieties to which the compound molecules are coupled (e.g., see Remington: The Science and Practice of Pharmacy, vide supra), including in vivo conjugation to blood components of a compound of an embodiment of the disclosure.

III. Synthesis

General and specific synthesis routes are provided that we found useful for preparation of embodiments of the disclosure. Those skilled in the art may recognize that certain variations or modifications of these procedures could also lead to synthesis of compounds according to the disclosure. In some situations the phrase "such as" is used to enumerate various alternatives for more generic compounds or structures. It will be understood that "such as" should not be construed to be limiting, and that its meaning is in accord with "including, for example, but not limited to."

Certain conditions were common to specific examples presented below. Microwave heating was done using a Biotage® Emrys Liberator or Initiator microwave reactor. Column chromatography was carried out using Biotage® SP4 flash chromatography system. Solvent removal was carried out using either a Büchii rotary evaporator or a Genevac® centrifugal evaporator. NMR spectra were recorded at 400 MHz on a Varian Unity® spectrometer using deuterated solvents. Chemical shifts are reported relative to residual protonated solvent.

Thin layer chromatography was performed on Whatman® glass plates precoated with a 0.25 mm layer of silica gel using various ratios of one or more of the following solvents: EtOAc, heptane, dichloromethane or MeOH.

Analytical LC/MS was performed for many examples on a Waters Acquity™ system using an XBridge™ C18 1.7 μm 2.1×50 mm column. Solvents A and B are Water w/0.1% formic acid and Acetonitrile w/0.1% formic acid, respectively. 5 minute total method time with 5% B to 99% B over 4 minutes with a flow rate of 0.3 ml/min. Mass spectral data were acquired on a Waters SQD from 100-2000 amu in electrospray positive mode.

Alternatively, purity and mass confirmation were carried out on a Waters Autopurification system using an XBridge™ C8 3.5 μm 4.6×50 mm column. Solvents A and B are water w/0.1% formic acid and acetonitrile w/0.1% formic acid, respectively. 6 minute total method time with 10% B to 95% B over 5 minutes with a flow rate of 2.5 ml/min. Mass spectral data were acquired on a Micromass ZQ™ from 130-1000 amu in electrospray positive mode.

Preparative reverse phase LC/MS was carried out for many examples on a Waters Autopurification system using an XBridge™ C8 5 μm, 19×100 mm column. Solvents A and B are water w/0.1% formic acid and Acetonitrile w/0.1% formic acid, respectively. 12 minute total method time with 30% B to 95% B over 10 minutes with a flow rate of 20 ml/min. Mass spectral data were acquired on a Micromass ZQ™ from 130-1000 amu in electrospray positive mode.

Preparative HPLC resolution of racemic compounds was carried out for many examples using one of the following chiral columns: Chiralpak® IA (5 cm×50 cm or 2 cm×25 cm), Chiralpak® AD (2 cm×25 cm) or Chiralcel® OD (2 cm×25 cm). Enantiomer ratios of purified compounds were determined by HPLC analysis on a 0.45 cm×25 cm column comprised of the same stationary phase (IA, AD or OD).

General methods and experimentals for preparing compounds of the present disclosure are set forth below. In certain cases, a particular compound is described by way of example. However, it will be appreciated that in each case a series of compounds of the present disclosure were prepared in accordance with the schemes and experimentals described below. For those compounds where NMR and/or mass spectrometry data are available, the data is presented in FIG. 6.

The following abbreviations are used herein:

Definitions: The following abbreviations have the indicated meanings:

AcOH: acetic acid
anhyd: anhydrous
aq.: aqueous
Bn: benzyl
Boc: tert-butoxycabonyl
CSA: Camphor sulfonic acid
d: day(s)
DAMP: Danger-Associated Molecular Pattern
DBU: 1,8-Diazobicyclo[5.4.0]undec-7-ene
DCE: 1,2-dichloroethane
DCM: dichloromethane
DIPEA: N,N-diisopropylethylamine
DMA: N,N-Dimethylacetamide
DMAP: 4-Dimethylaminopyridine
DMF: N,N-dimethylformamide
DMSO: Dimethyl sulfoxide
dsDNA: double-stranded DNA
EDC: 1-(3-dimethylaminopropyl)-3-ethylcarbodiimide hydrochloride
ee: enantiomeric excess
EtOAc: ethyl acetate
EtOH: ethanol
h: hour(s)
HATU: N,N,N,N'-Tetramethyl-O-(7-azabenzotriazol-1-yl)uronium hexafluorophosphate
HCl: hydrochloric acid
HCQ: hydroxychloroquine
hep: n-heptane
HEPES: 4-(2-hydroxyethyl)-1-piperazineethanesulfonic acid
HPLC: high performance liquid chromatography
IFN: interferon
IPA: isopropyl alcohol or isopropanol
$K_2CO_3$: potassium carbonate
MeOH: methanol
$MgSO_4$: magnesium sulfate (anhydrous)
min: minute(s)
MTBE: methyl tert-butyl ether
$Na_2CO_3$: sodium carbonate
$Na_2SO_4$: sodium sulfate (anhydrous)
$NaBH_4$: sodium borohydride
NaCl: sodium chloride
NaH: 60% sodium hydride dispersed in oil
NaHCO3: sodium bicarbonate
NaOH: sodium hydroxide
NBS: N-bromosuccinimide
$NH_4Cl$: ammonium chloride
$NH_4OH$: ammonium hydroxide
NMP: N-methylpyrrolidone
Ns: Nosyl or o-nitrobenzenesulfonyl
° C.: degrees Celsius
PAMP: Pathogen-Associated Molecular Pattern
PBMC: peripheral blood mononuclear cell
PBS: phosphate buffered saline
pDC: plasmacytoid dendritic cell
$PhNTf_2$: N-phenyltrifluoromethanesulfonimide
qPCR: quantitative polymerase chain reaction
R848: resiquimod
rt: room temperature
sat: saturated
SNAP: BIOTAGE® brand flash chromatography cartridge
SOC: standard-of-care
ssRNA: single-stranded RNA
T3P: Propylphosphonic anhydride tBuOK: potassium tert-butyloxide TEA: triethylamine TEMPO: 2,2,6,6-Tetramethylpiperidine 1-oxyl Tf: trifluoromethanesulfonate TFA: trifluoroacetic acid THF: tetrahydrofuran TLDA: Taqman® Low Density Array TLR: Toll-like receptor TSA: p-toluenesulfonic acid General Synthetic Methods:

Compounds were made according to the general synthetic methods shown in Schemes 1-31:

Scheme 1

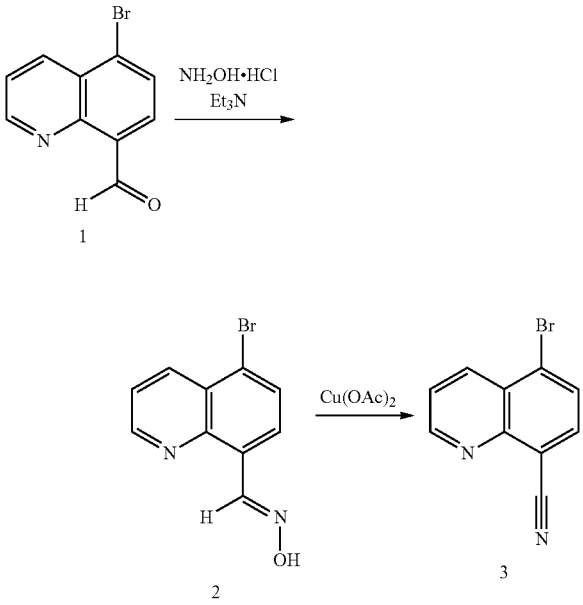

The preparation of several of the examples use key intermediate 3, which is can be prepared according to the route depicted in Scheme 1. The commercially available 5-bromoquinoline-8-carbaldehyde 1 (Frédérieric de Montigny, Gilles Argouarch, Claude Lapinte, "New Route to Unsymmetrical 9,10-Disubstituted Ethynylanthracene Derivatives," Synthesis, 2006, 293-298.) is treated with hydroxylamine hydrochloride to provide the oxime 2. 2 is subsequently converted to the corresponding nitrile 3 in the presence of catalytic amount of copper acetate to provide one of the key intermediates reported herein. Intermediate 3 is used for the generation of compounds reported herein by the displacement of the 5-position of 5-bromoquinoline-8-carbaldehyde with appropriate aromatic, heteroaromatic and saturated heterocyclic compounds such as piperidines, piperazines and morpholines using appropriate conditions described in detail below.

An alternative method for the generation of the key intermediate 3 is shown in Scheme 2 wherein triethylamine for the first step of the synthesis is replaced with sodium acetate.

Scheme 2

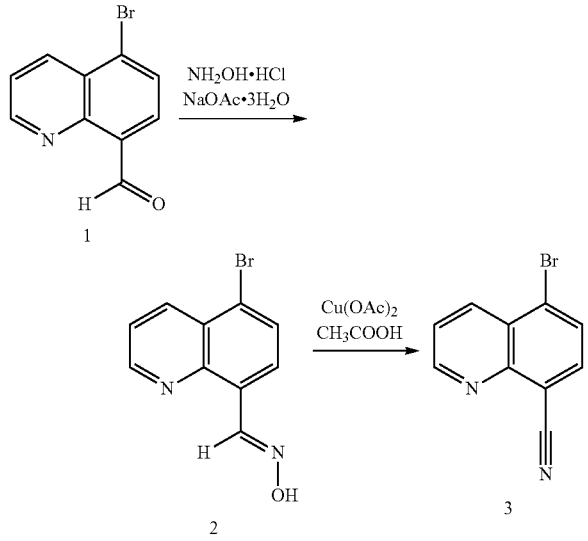

Several examples are produced by the general condensation process as depicted in Scheme 3, wherein bromoquinoline 3 is condensed with the appropriate nucleophile 4 to form 5 which may be either a key intermediate or a final compound described in more detailed below.

Scheme 3

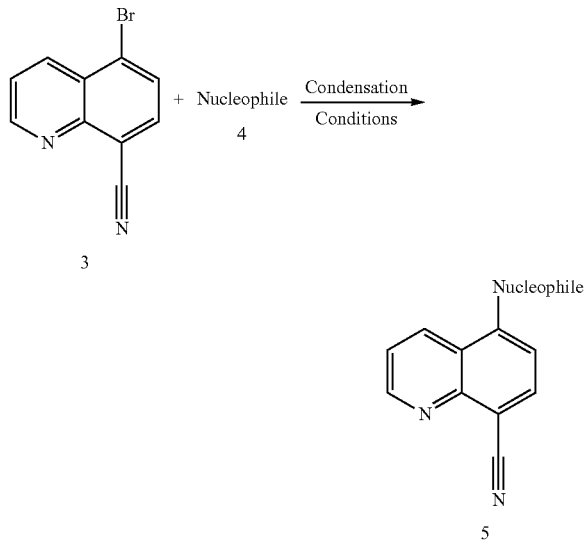

A number of the examples represented by compound 15 were prepared from the advanced intermediate 14 as depicted in the general method shown in Scheme 4. An appropriately protected chiral epoxide 6 is condensed with allyl amine to provide the chiral aminoalcohol 7. After protection of the secondary amine with a nesylate the resultant intermediate 8 is intermolecularly cyclized to form the unsaturated pyran 9. Reduction of the enamine double bond to form 10 was followed by deprotection of the nesyl group to provide 9. Condensation of 11 with the bromide 3 (Scheme 1 or 2) with or without the use of a palladium catalyst provides 12, after which deprotection of 13 followed by activation of the resulting alcohol provides the key intermediate 14. Activated 14 can be easily transformed to a number of the examples provided below by the use of the appropriately substituted amine and condensation reagents to provide compounds of general structure 15.

Scheme 4

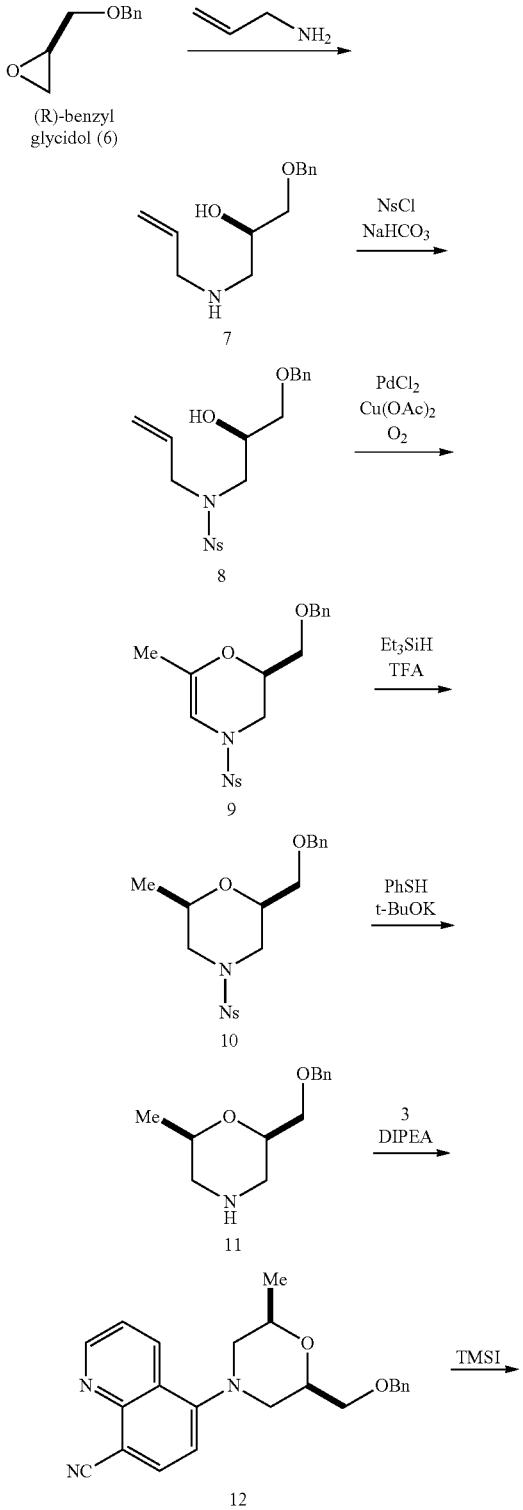

-continued

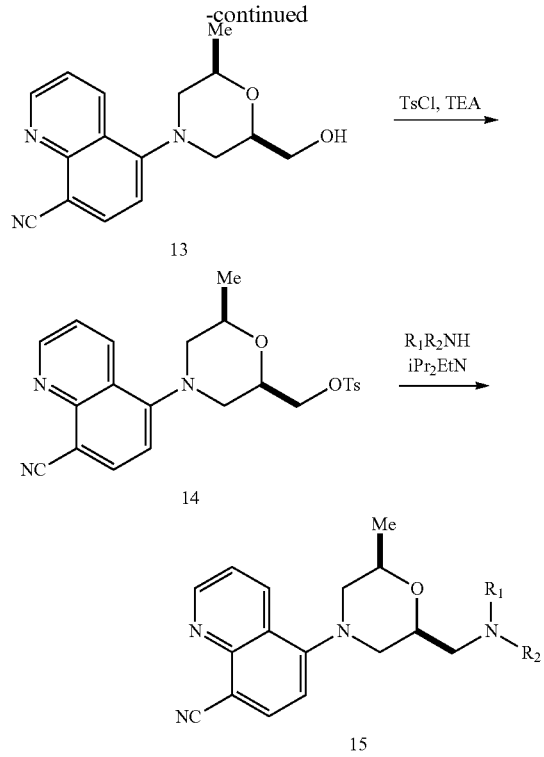

An alternative method for the preparation of general structure 10 is depicted in Scheme 5. Radical cyclization of the protected alcohol 8 can be obtain by treatment with N-bromosuccinimide to provide 16. Elimination of the bromo-group using base provides the enol 17, which is then reduced with a silane to provide intermediate 10.

Scheme 5

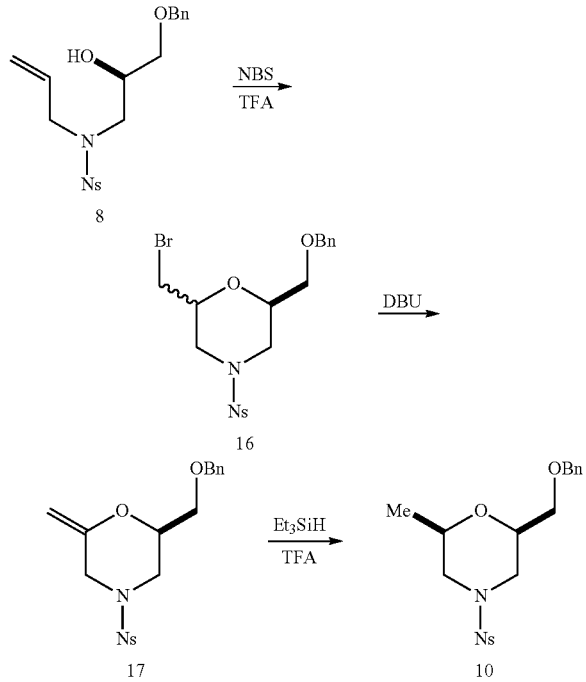

An alternative method for the preparation of general structure 11 is depicted in Scheme 6. Starting with the chiral epoxy starting material 6, one forms the alcohol 18 after protection of the secondary amine with a Boc-protecting group. Lactonation using water soluble DCC provides 19 which then can be subjected to alkylation using an alkyl lithium, such as methyl lithium to form a mixture of ketals, 20 and 21. The ketal mixture is subsequently reduced to form a diastereomeric mixture of morpholine compounds 22 (being the desired diastereomer isomer) and 23 which can be easily separated by silica gel column chromatography. The ratio of the methyl morpholine mixture was found to be from 4:1 to 9:1 in favor of structure 22. X-ray crystal structures were obtained of subsequent, advanced compounds to confirm the absolute stereochemistry of compound 22. Compound 22 is easily converted to 11 by deprotection with acid such as TFA followed by neutralization with a base.

Scheme 6

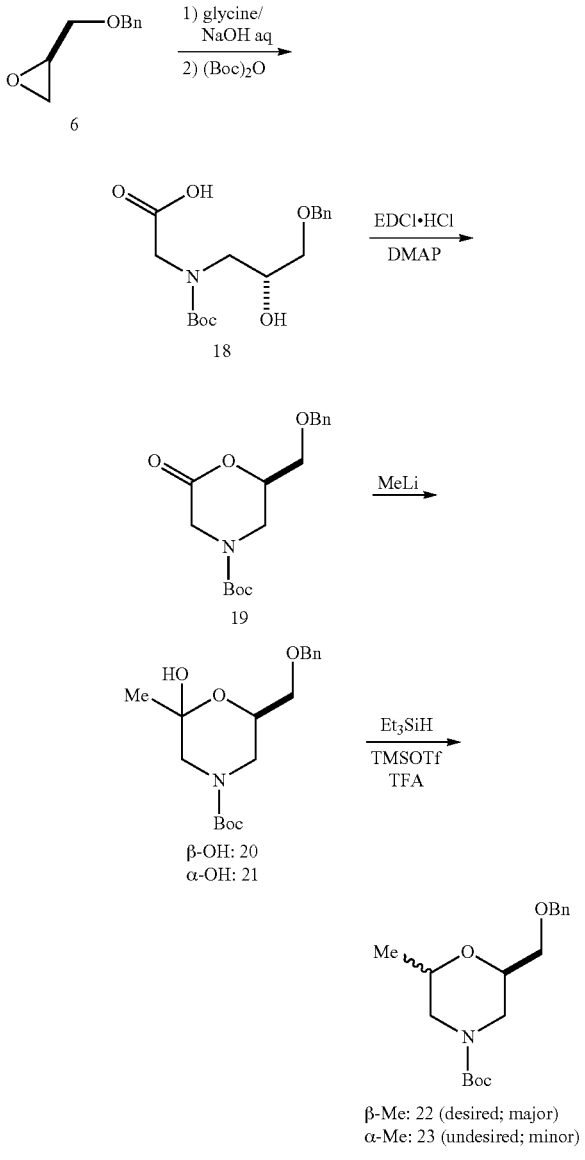

-continued

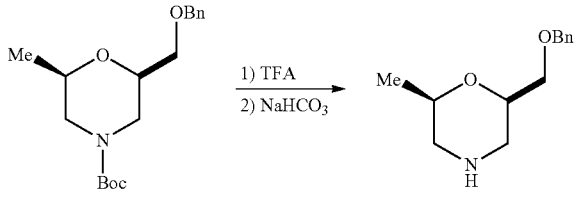

A third method for the preparation of key intermediate 11 is shown in Scheme 7. The commercially available protected epoxide 6 is condensed with aqueous ammonia to provide the amino alcohol 23 which in turn is condensed with the chiral chloropropinate 24 to form the enantiomerically pure amide 25. Ether formation using a strong base such as sodium hydride provides lactam 26, which can be converted to intermediate 11 by amide reduction to the cyclic amine.

Scheme 7

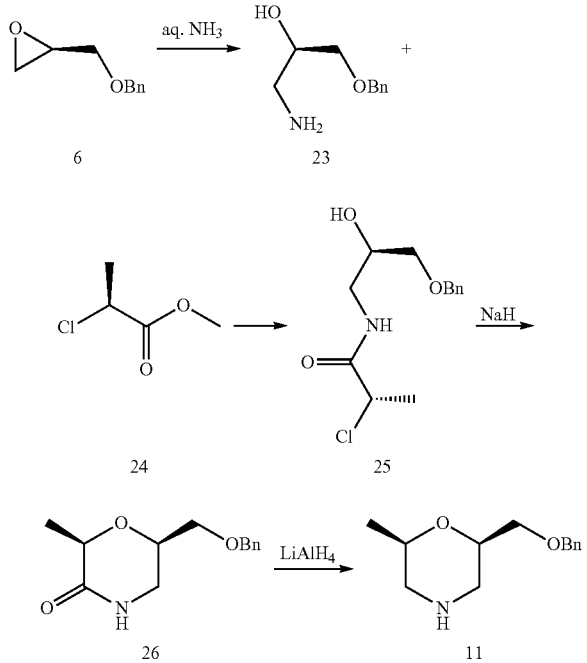

An alternative method for the production of examples encompassed in the generic structure 5 in Scheme 3 and compound 12 in Scheme 4 is illustrated in Scheme 8. The starting materials 28 and 30, prepared from commercially available sources (27 & 29), can be easily condensed in the presence of an inorganic base to form 31. The phenolic protecting group is removed via reductive hydrolysis to form 32, the acetal protecting group is hydrolized with acid to form the aldehyde 33, and then formation of the bicyclic heterocycle 34 under catalytic acidic, condensation conditions. The phenolic hydroxyl group on 34 is then activated to form 35, which subsequently can be condensed with 11 to form 12 as shown in Scheme 4. Compound 11 can be replaced by other nucleophiles as shown in the examples below.

Scheme 8

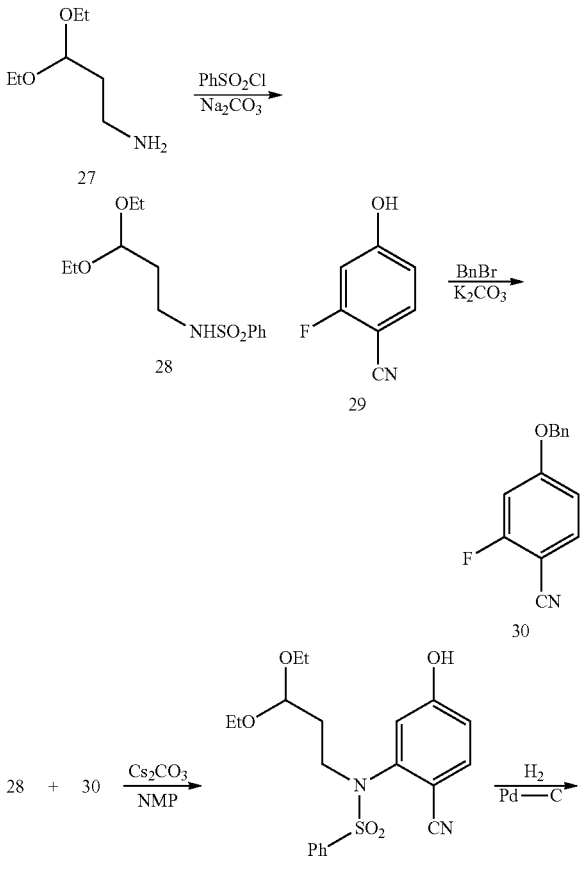

Two alternative methods for the preparation of compounds with general structure 15 use the processes depicted in Scheme 9 and 10. Intermediate 13 is activated by forming the triflate 36 followed by displacement with the appropriate amine in the presence of base such as potassium carbonate to form the desired target compound 15 as depicted in Scheme 9.

Scheme 9

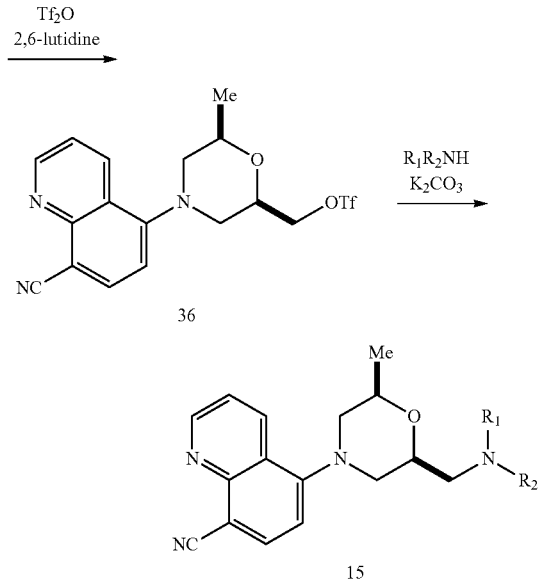

Starting with the Boc-protected chiral morpholine 22 from Scheme 6, one familiar in the art is able to produce additional examples of compounds with general structure 15 by the conversion of the protected alcohol to the azide intermediate 37 as shown in Scheme 10. 37 is easily converted to the primary amine ER-884884 after reduction of the azide, deprotection of the Boc-group, and condensation with 3. ER-884884 likewise can be converted to additional analogs depicted by general structure 15 by either alkylation or acylation processes.

Scheme 10

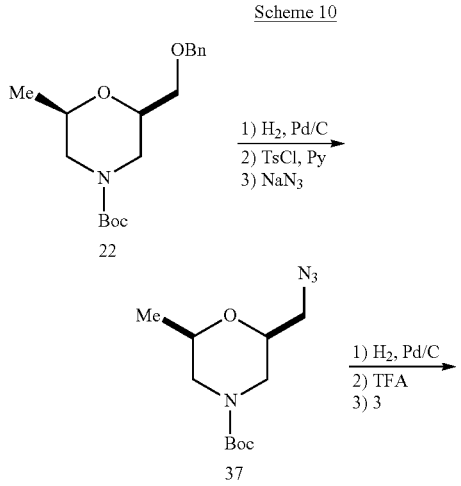

-continued

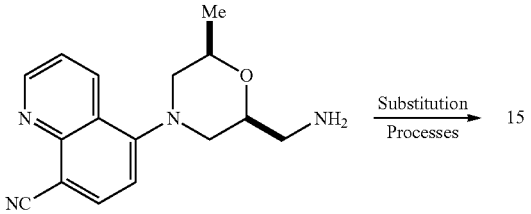

ER-884884
15 R1 = R2 = H

Preparation of alternative set of compound examples is by oxidation of the key intermediate 13 to form 38 followed by formation of the examples via amide coupling conditions to form 39 as shown in Scheme 11. The preparation of some of the examples using this general method will require one or two additional steps to provide the desired target compounds of general structure 40. Likewise various esters depicted by general structure 41 can be easily produced from 38 using various methods by those persons familiar with the art.

Likewise, ether examples are prepared by two possible methods: (1) the displacement of activated group on an alkyl, alkenyl or aryl functional group using base and compound 11 from Scheme 4; or using the activated alcohol 14 or 36 with phenols or alkyl alcohols in the presences of an appropriate base. Both methods to provide examples with the general chemical structure 42 are shown in Scheme 12.

Scheme 12

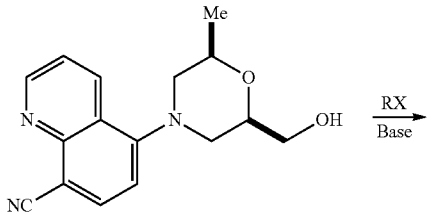

13

Scheme 11

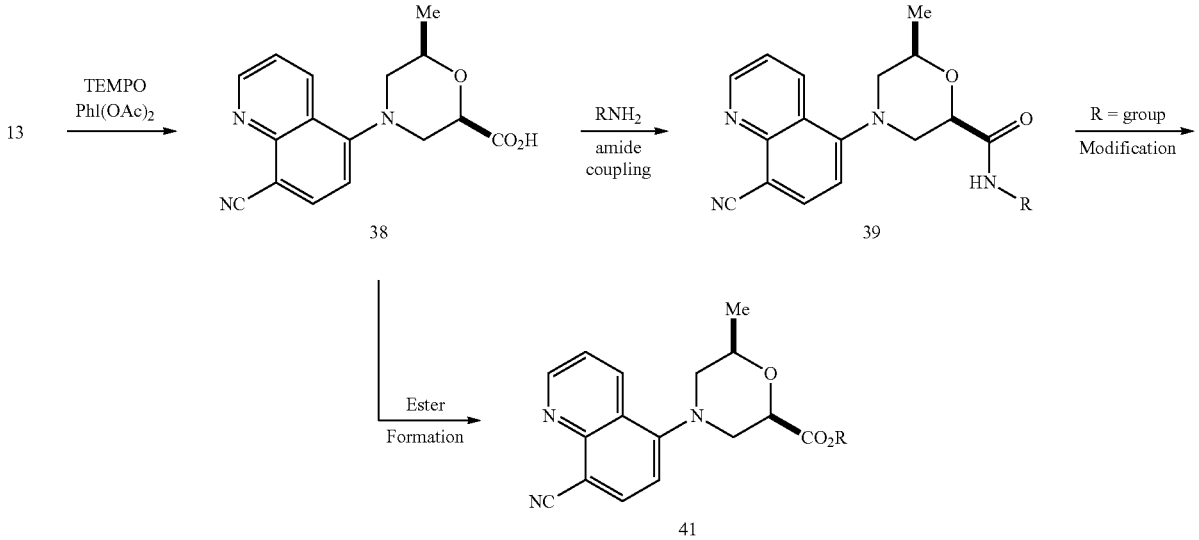

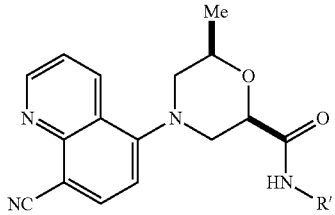

40

-continued

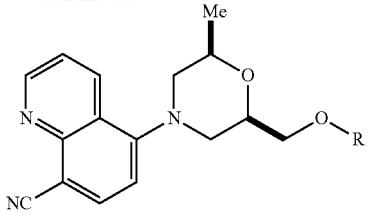

42

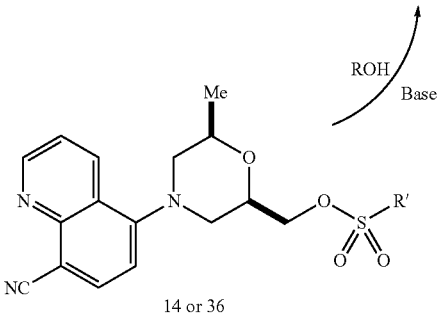

14 or 36

Key intermediate 13 may also be oxidized to form an aldehyde 43 followed by condensation with various alkyl and aryl coupling reagents to provide examples 44 or 46 as depicted in Scheme 13. The resultant products can then be transformed to additional examples by either oxidation of 44 to provide compounds of general structure 45 or reduction of 46 to provide compounds of general structure 47 where n=2. Likewise persons familiar with the art may generate the additional examples from intermediate 44 by activation of the hydroxyl group such as forming the triflate followed by reduction using several possible reducing reagents to provide examples that contains one less methylene group or 47 where n=1.

A final set of examples are prepared by the use of Scheme 14. Using the same synthetic methodology to prepare compound 13 in Scheme 4, one can prepare the desired seven-membered heterocycle 68 replacing allyl amine with 1-amino-3-butente 62. 68 can then be activated and then condensed with various substituted amines to generate additional analogs in a similar manner as shown in several the schemes depicted above.

Scheme 14

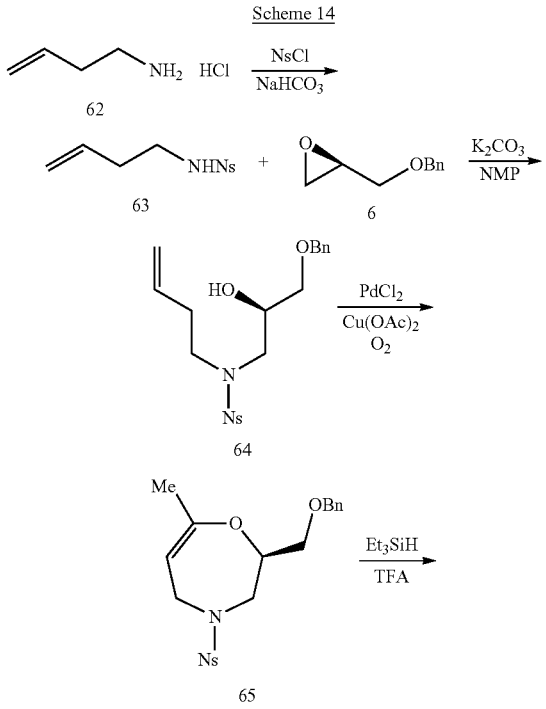

Scheme 13

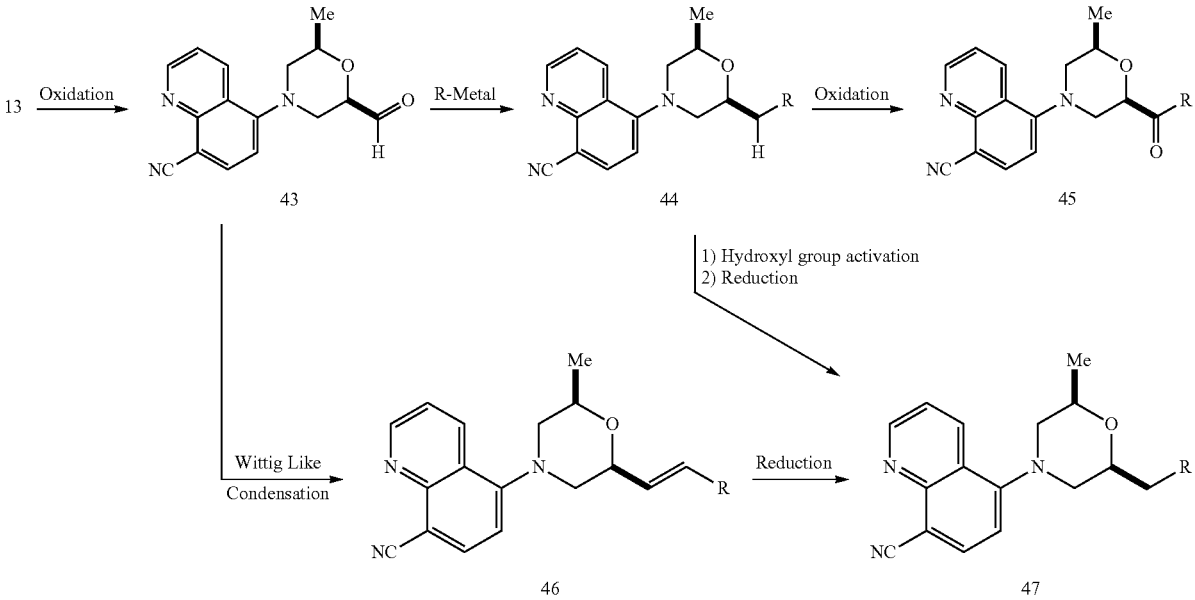

-continued

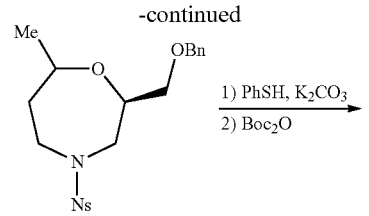

66

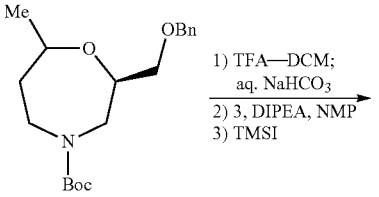

67

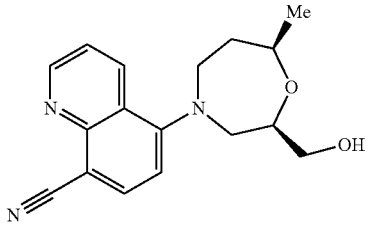

68 or ER-889363

Preparation of Examples

Compound 3—Scheme 1

To a suspension of 5-bromoquinoline-8-carbaldehyde 1 (1.00 g, 4.24 mmol) and hydroxylamine hydrochloride (1.177 g, 16.94 mmol) in acetonitrile (110 mL) was added TEA (2.362 mL, 16.94 mmol) followed by heating to reflux for 3 h to afford a yellow suspension. The completed reaction completion was cooled to rt, the precipitate was filtered, and the filter cake rinsed with acetonitrile (50 mL). The crude solid was purified over a short pad of silica gel (10 g) eluting with EtOAc (300 mL) providing the aldoxime 2 as a yellow solid.

Aldoxime 2 (1.001 g, 4.0 mmol) and copper (II) acetate monohydrate (84.6 mg, 0.424 mmol) in anhydrous acetonitrile (180 mL) were stirred at reflux for 12 h. The completed reaction was cooled to rt, filtered and the filter pad washed with $H_2O$ to afford a brown solid. The crude solid was purified over a short pad of silica gel (ca. 10 g) eluting with (DCM 100 mL) to provide 5-bromoquinoline-8-carbonitrile, 3 (0.783 g, 3.4 mmol, 79.3% yield over 2 steps) as a white-beige solid after concentration and drying in vacuo the eluted product. See: Frédérieric de Montigny, Gilles Argouarch, Claude Lapinte, Synthesis, 2006, 293.

Compound 3—scheme 2

To a stirred solution of sodium acetate trihydrate (31.6 g, 0.232 mol) in EtOH (0.498 L) at 15° C. was added 5-bromoquinoline-8-carbaldehyde (49.84 g, 0.211 mol) followed by hydroxylamine hydrochloride (15.55 g, 0.223 mol). The resultant mixture was heated to 70° C. for 3 h after which time the reaction was cooled to 35° C. and then diluted with water (250 mL). The mixture was partially concentrated to approximately 250 mL after which time water (250 mL), 2-methoxy-2-methylpropane (120 mL), and heptane (120 mL) were added followed by re-concentrated the mixture to approximately 250 mL. The resultant slurry was diluted with water (250 mL) and cooled to 0° C. after which time 1 M NaOH in water (211 mL) was added and the final mixture was stirred vigorously for 10 min. The suspension was filtered, rinsed with water (498 mL) and the filter cake dried at 30° C. for 18 h to afford aldoxime 2 (49.75 g, 0.198 mol, 93.9% yield) as tan powder.

To a stirred suspension of 2 (48.21 g, 0.192 mol) in acetonitrile (386 mL) at 15° C. was added copper (II) acetate (0.523 g, 2.9 mmol) followed by acetic acid (13.1 mL, 0.229 mol). The resultant mixture was heated to reflux for 21 h after which time the completed reaction was cooled to 50° C. Water (0.39 L) was added and the mixture was partially concentrated followed by dilution with water (290 mL) and cooled to 5° C. 1 M NaOH in water (230 mL) was added and vigorous stirring was continued for 10 min. The suspension was filtered, the filter cake rinsed with water (500 mL) and dried to afford compound 3 (42.80 g, 0.183 mol, 95.6% yield) as dark gray powder.

synthesis of ER-878952—scheme 3 & 15(Method 1)

Scheme 15

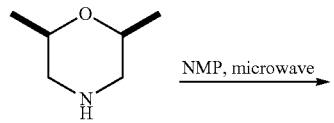

69

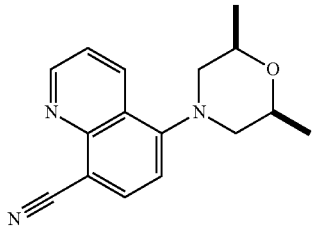

ER-878952

3 (200.2 mg, 0.86 mmol) in NMP (1 mL) and commercially available cis-2,6 dimethylmorpholine 69 (133.4 mg, 1.16 mmol—as a representative of compound 4 in Scheme 3) was microwaved at 150° C. for 1 h. The completed reaction was filtered and divided into several vials, diluted with NMP and purified by HPLC (C18 column, gradient 10/90-95/5 acetonitrile/water with 0.1% TFA, 15 min run, t=8.5-9 min) to yield ER-878952 (180 mg. 0.68 mmol, 79.1% yield) after concentration and drying in vacuo the desired combined fractions.

ER-880369 (8.2 mg, 0.031 mmol, 48.4% yield) was produced in a similar manner to ER-878952 using 3 (15 mg, 0.064 mmol) and 2-ethylmorpholine (22.2 mg, 0.191 mmol). The separation of the enantiomers was not performed.

ER-885618 (385.2 mg, 1.032 mmol, 60.7% yield) was produced in a similar manner to ER-878952 using 3 (400 mg, 1.716 mmol) and 11 (398.1 mg, 1.799 mmol) from Scheme 4.

synthesis of compound ER-878952(Method 2, Scheme 3 & 15)

To a stirred suspension of Compound 3 (12.00 g, 0.0515 mol) in NMP (30.0 mL) was added 69 (14.8 g, 0.129 mol) followed by heating at 120° C. for 4 h. The completed reaction was cooled to 50° C., diluted with IPA (30 mL), heptane (60 mL) and then further cooled to 0° C. After 30 min, the precipitates were collected by filtration, rinsed with pre-chilled (at 0° C.) IPA (18.0 mL)/heptane (36 mL) mixture and dried under $N_2$/vacuum for 2 h to afford ER-878952 (11.00 g) as a yellow powdered. The filtrate was concentrated, partitioned between EtOAc (120 mL) and saturated aqueous $NaHCO_3$ (60 mL). The organic layer was separated, washed with water (60 mL) and passed through pre-conditioned (heptane-EtOAc 1:1) silica gel, eluted with EtOAc (120 mL) then concentrated. Brownish solid thus obtained was suspended in EtOAc (10 mL) heptane (10 mL) and heated to 70° C. and then allowed to cool down to 20° C. Precipitates were collected by filtration, rinsed with a mixture of EtOAc (5.0 mL) and heptane (5.0 mL), then dried under $N_2$/vacuum for 1 h, affording the additional ER-878952 (0.649 g) as yellow powder. Overall the process provided ER-878952 (11.64 g, 43.6 mmol, 89.6% yield).

ER-879484(Method 3, Scheme 3 and 16)

Scheme 16

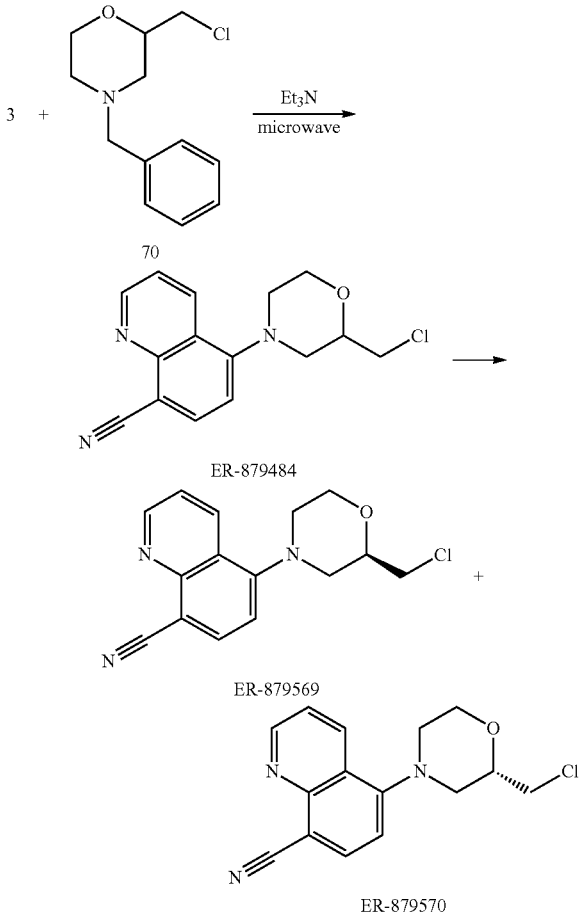

To a stirred solution of 3 (15 mg, 64.4 mmol) and 4-benzyl-2-(chloromethyl)morpholine, 70 (43.6 mg (0.193 mmol) in DMF (0.5 mL) was added TEA (0.27 uL, 0.194 mmol). The reaction mixture was microwaved at 160° C. for 1 h after which time the completed reaction was directly purified over a C-18 reverse phase preparative HPLC column (Water's X-Bridge C18 19×100 mm column; eluting with 0-40% gradient of acetonitrile in water with 0.05% TFA). The fractions containing the desired product were combined, concentrated and dried in vacuo to provide ER-879484 (4.2 mg, 0.015 mmol, 22.7% yield). The enantiomers of ER-879484 (3.0 mg, 0.010 mmol) were separated using a chiral HPLC column to providing ER-879569 (1.0 mg, 0.004 mmol) and ER-879570 (1.0 mg, 0.004 mmol) after concentration the desired fractions and drying in vacuo. The absolute stereochemistry is unknown, but arbitrarily assigned.

ER-879739 (12 mg, 0.047 mmol, 73.6% yield) was produced in a similar manner to ER-879484 starting using 3 (15 mg, 0.064 mmol) and 2-methylmorpholine (19.5 mg, 0.195 mmol). Separation of the enantiomers was not performed.

ER-880191 (9.5 mg, 0.036 mmol, 23.7% yield) was produced in a similar manner to ER-879484 starting using 3 (35 mg, 0.150 mmol) and (2S,6S)-2,6-dimethylmorpholine (741 mg, 6.434 mmol). The cis-isomer ER-878952 (15.2 mg, 0.057 mmol, 37.9% yield) was also isolated. TEA was not used in this preparation.

Additional Examples derived from ER-878952:

ER-885160: ER-878952 (85.6 mg, 0.320 mmol) was dissolved in 1,2-ethanediol (1 mL) followed by the addition of potassium hydroxide (60 mg, 1.069 mmol). The reaction mixture was microwaved at 120° C. for 10 h after which time, it was filtered then directly injected onto a C-18 reverse-phase preparative HPLC for purification (Water's X-Bridge C18 19×100 mm column, eluting with 10-100% acetonitrile in water with 0.05% TFA). The desired fractions were concentrated to dry, dissolved in MeOH (3 mL) and eluted over a carbonate impregnated silica gel column (Biotage Isolute SPE, Si—$CO_3$, 1 g), washed with MeOH (3 mL), concentrated and dried in vacuo to provide ER-885160 (56.2 mg, 0.197 mmol, 61.6% yield).

Preparation of Compound ER-890963 as an Example of Compound 15, Scheme 4

Compound 7: A 22 L reactor was charged with (2R)-benzyl 2-epoxypropyl ether (0.7692 kg, 4.684 mol) T-internal 18-19C. Allylamine (3800 mL, 51 mol) was added at 18-19° C. and resultant mixture was heated to 50° C. After 20 h, the mixture was concentrated, azeotroped with MTBE (4 L×3) to give (R)-1-(allylamino)-3-(benzyloxy)propan-2-ol, 7 (ca. 1037 g, 4.684 mol, 100% yield assumed) as colorless oil.

Compound 8: To a stirred suspension of sodium bicarbonate (1180 g, 14.0 mol) in water (7.2 L) at 10-11° C. was added a solution of o-nitrobenzenesulfonyl chloride (1038 g, 4.684 mol) in DCM (3100 mL) followed by warming the resultant biphasic mixture to 20° C. A solution of 7 (ca. 1037 g, 4.684 mol assumed) in DCM (4100 mL) was added over 3 h while maintaining-T-internal between 20-23° C. and vigorous stirring was continued overnight. The mixture was diluted with water (4100 mL) with stifling followed by separation of the layers. The aqueous layer was extracted with MTBE (4100 mL). The combined organic layers were diluted with n-heptane (4100 mL), sequentially washed with 1.0 M HCl (4700 mL), saturated $NaHCO_3$ (2.0 kg), water (4100 mL), concentrated, and azeotroped with MTBE (5200 mL×3) to dry to provide (R)—N-allyl-N-(3-(benzyloxy)-2-hydroxypropyl)-2-nitrobenzenesulfonamide, 8 (1.855 kg, 4.56 mol, 97% yield) as brownish green oil after drying for 3 days in vacuo.

Compound 9: A stirred suspension of 8 (1.80 kg, 4.429 mol) in DMA (5.40 L) was heated to 40° C. to achieve complete dissolution, then cooled down to 25° C. after which time the mixture was added to a separate reactor was containing Cu(II) acetate (0.145 kg, 0.797 mol) followed by rinsing the original vessel with DMA (5.40 L). Palladium(II) chloride (0.063 kg, 0.354 mol) was added followed by was replacing internal atmosphere with oxygen (1 bar) and warming up 28-32° C. for 3 days. The completed reaction mixture was split into equal 2 portions to facilitate work-up. Each portion was separately poured into a mixture of 0.1 M HCl (23 L) and MTBE (9.0 L) while controlling T-internal <25° C. The layers were separated and the aqueous layer was extracted with MTBE (9.0 L & 5.4 L). All organic layers were combined, sequentially washed with 0.1 M HCl (5.5 L), 8% $NaHCO_3$ (5.9 kg), 29% NaCl (6.3 kg). Celite 545 (270 g) was added to the organic layer, stirred for 30 min, filtered, and filter cake were rinsed with MTBE (2.7 L). All filtrates were combined and concentrated. The reddish oil was re-dissolved in DCM (3.6 L) and treated with 1,3,5-triazinane-2,4,6-trithione (79 g kg, 0.44 mol) at 25° C. for 1 h. The mixture was diluted with MTBE (18 L) and filtered through Celite 545 (270 g). The reactor and filter cake were rinsed with MTBE (3.6 L) and combined filtrate was concentrated to give (R)-2-((benzyloxy)methyl)-6-methyl-4-((2-nitrophenyl)sulfonyl)-3,4-dihydro-2H-1,4-oxazine, 9 (1748 g, 4.322 mol, 97.6% yield) as yellow oil.

Compound 10: To a stirred suspension of 9 (1748 g, 4.322 mol) in DCM (3.5 L) was heated to 33-35° C. until a free-flowing suspension was obtained after which time the mixture was cooled to 18-20° C. A separate reactor TFA (1.67 L, 21.6 mol) in DCM (2.62 L) was cooled to 5° C. with stirring after which time triethylsilane (1.04 L, 6.48 mol) was added maintaining the temperature at 5-6° C. followed by cooling to −5° C. The suspension of 9 in DCM was slowly added to the main reactor over 1.5 h while maintaining the temperature between −5 and −3° C. followed by stirring for 4 h continuing at −5 to −3° C. The completed reaction was diluted with pre-chilled n-heptane (8.74 L at −10° C.) then poured into pre-chilled NaOH solution (NaOH: 890 g, 22.3 mol in water: 8.7 L at 5° C.) while controlling T-internal <15° C. (over 1 h) followed by rinsing the reactor rinsed with MTBE (3.5 L). The mixture was diluted with MTBE (5.2 L) and the layers separated. The organic layer was sequentially washed with: water (8.7 L), 30 wt % NaCl (3.5 kg) in water, water (5.2 L), treated with Celite 545 (175 g) and filtered. The work-up vessel and filter cake were rinsed with MTBE (1.75 L) and the combined filtrates were concentrated under vacuum to approx. 3.5 L, azeotroped with n-heptane (8.7 L) and concentrated to approx. 5 L. The tan precipitates were collected by filtration, rinsed with n-heptane (3.5 L) and dried under $N_2$/vacuum for 1 h. 1.65 kg of the resultant solid was combined with 353 g solid obtained from a separate batch and suspended in n-heptane/EtOAc 1:1 (8.0 L). The mixture was heated to 61-63° C. to achieve complete dissolution, cooled down to 23-25° C. over 1 h, diluted with heptane (4 L) and further cooled down to 10-12° C. over 30 min. Stirring was continued at this temperature for 30 min. Light tan precipitates were collected by filtration, rinsed with n-heptane/EtOAc 6:1 (2 L) and then n-heptane (4 L) followed by drying under $N_2$/vacuum overnight, and then vacuum oven dried at 35° C. for 2 d to give (2R,6R)-2-((benzyloxy)methyl)-6-methyl-4-((2-nitrophenyl)sulfonyl)morpholine, 10 (1616 g, 3.98 mol, 74% yield in 2 steps from 8) as a tan solid.

71

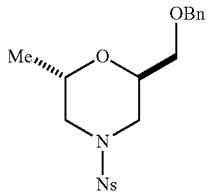

The minor product: (2R,65)-2-((benzyloxy)methyl)-6-methyl-4-((2-nitrophenyl)-sulfonyl)morpholine, 71 (diastereoisomer) isolated by purification of 10 mother liquor.

Compound 11: To a stirred solution of 1.0 M of t-BuOK in THF (0.650 L, 0.650 mol). In THF (0.310 L) cooled to 5° C. was added benzenethiol (63.66 mL, 0.620 mol) while maintaining at <10° C. The mixture was stirred at 10° C. for 30 min, then warmed up to 15° C. for 1 h after which time a solution of 10 (240.00 g, 590.5 mmol) in THF (0.60 L) was added while maintaining the temperature 15-20° C. followed by and stirring 2 h. The completed reaction was slowly quenched with mixture of 1.0 M HCl (1.30 L) in n-heptane (3.60 L, previously cooled to 10° C.) while maintaining the reaction mixture at <15° C. Resultant mixture was vigorously stirred for 10 min followed by separation of the layers. The organic layer was extracted with water (0.24 L) with rinsing with n-heptane (0.24 L). All aqueous layers were combined and washed with n-heptane (3.60 L) followed by the addition of NaCl (240 g) with stifling. The aqueous mixture was rendered basic with 5.0 M of NaOH (165 mL) followed by extraction two times with DCM (3.60 L & 2.40 L each). The combined organic layers were washed with 20 wt % NaCl in water (1400 g), concentrated, azeotroped with MTBE (1400 mL), re-diluted with MTBE (960 mL) and filtered through a glass filter. The filtrate was concentrated to give (2R,6R)-2-((benzyloxy)methyl)-6-methylmorpholine, 11 as brownish clear oil which was used for subsequent reaction without further purification.

Compound 12: To a stirred solution of 3 (137.6 g, 0.591 mol) in DMA (260 mL) was added DIPEA (308 mL, 1.77 mol) followed by a solution of 11 (130.67 g, 0.5905 mol) in DMA (260 ml) rinsing with DMA (130 mL). The reaction mixture was heated at 125-130° C. for 2 h. The completed reaction mixture was cooled to 30° C. and diluted with EtOAc (1.96 L) and water (0.65 L) after which time it was poured into water (2.61 L) with vigorous stifling. The resulting mixture was filtered through a pad of Celite 545 (260 g) and the layers separated. The aqueous layer was extracted with EtOAc (1.31 L) followed by combining the organic layers washing two times with 5% NaCl (1.0 kg, each) and concentrated to give black solid. The solid was dissolved in DCM (1 L), diluted with n-heptane (520 mL) followed by the addition of silica gel (196 g) and $MgSO_4$ (130 g). The resultant slurry was stirred at 20° C. for 30 min, filtered and eluted with isopropyl acetate (2.09 L). The combined filtrate was concentrated and resultant brownish solid was suspended in a mixture of EtOAc (196 mL) and n-heptane (523 mL). The mixture was heated to 70° C., followed by cooling to rt and stirred overnight. The precipitates were collected by filtration, washed with a mixture of EtOAc/n-heptane 3:8 (220 mL), and dried under vacuum to provide 5-((2R,6R)-2-((benzyloxy)methyl)-6-methylmorpholino)quinoline-8-carbonitrile, 12 (178.44 g, 0.478 mol, 80% yield) as tan powder.

Compound 13: To a stirred suspension of 12 (167.3 g, 0.45 mol) in acetonitrile (500 mL) was added trimethylsilyl iodide (82.9 mL, 0.582 mol) at rt. The resultant mixture was heated at 70° C. for 2 h after which time it was cooled to rt, slowly quenched with water (167 g) and stirred at 25-30° C. for 1 h. The reaction mixture was cooled to 15° C. followed by the addition 28% aqueous ammonium hydroxide (500 g) after which time the reaction was stirred at rt overnight. The mixture was partially concentrated and then diluted with water (0.5 L), MTBE (0.04 L) and n-heptane (0.3 L) followed by cooling to 0-5° C. Precipitates were collected by filtration and rinsed with pre-chilled water (500 ml), then n-heptane/MTBE 7:1 (400 ml) followed by drying under vacuum (40° C.) overnight to 5-((2R,6R)-2-(hydroxymethyl)-6-methylmorpholino)quinoline-8-carbonitrile, 13 or ER-885493 (127.2 g, 0.45 mol, 100% yield) as tan powder.

Compound 14: To a stirred solution of 13 (24.8 g, 0.0875 mol) in DCM (200 mL) was added portion wise p-toluenesulfonyl chloride (17.95 g, 94.17 mmol) followed by TEA (24.60 mL, 0.1765 mol) at rt. The reaction was stirred for 3 h after which time the completed reaction was quenched with water (200 mL). The separated organic layer was washed with brine (50 mL), dried over $Na_2SO_4$, filtered and concentrated to a brownish tar. The crude product was purified over silica gel (SNAP 340×2 g, eluting with heptane/EtOAc=5/1 to 3/1, TLC heptane/EtOAc=3/1, rf=0.6) to provide ((2R,6R)-4-(8-cyanoquinolin-5-yl)-6-methylmorpholin-2-yl)methyl 4-methylbenzenesulfonate, 14 (34.98 g. 79.95 mmol, 84.9% yield) as a yellow powder after concentration of the desired fractions and drying in vacuo.

Compound 15 as Boc-Protected ER-890963

To a solution of 14 (13.9 g, 31.77 mmol) and TEA (8.86 mL, 63.541 mmol) in DMA (89 mL) at rt was added dropwise commercially available (S)-tert-butyl 2-ethylpiperazine-1-carboxylate (7.49 g, 34.95 mmol) over 5-min period. The reaction mixture was stirred at 110° C. for 12 h to completion after which time the reaction was cooled to rt. The reaction was concentrated to remove DMA followed by dilution with DCM (30 mL). The resultant organic solution was washed two times with water (30 mL each), brine (30 mL), and dried over $MgSO_4$. The crude was filtered, concentrated in vacuo, and purified over silica gel (SNAP 340 g eluting 10% to 30% EtOAc in heptene, TLC heptane/EtOAc=3/1, rt=0.6) gave 5-((2S,6R)-2-(((S)-4-(3,3-dimethylbutanoyl)-3-ethylpiperazin-1-yl)methyl)-6-methylmorpholino)quinoline-8- carbonitrile or Boc-protected ER-890963 (12.27 g, 24.15 mmol, 76% yield) as yellow powder after concentration of the combined desired fractions and drying in vacuo.

ER-890963 or Compound 15:

Boc-protected ER-890963 (23.55 g, 49.10 mmol) was dissolved with stifling in DCM (50 mL) followed by TFA (50 mL) at rt. The reaction was stirred for 4 h at rt after which time the completed reaction was concentrated in vacuo. The crude dark orange material dissolved with stirring in DCM (50 mL) and neutralized with the addition of sat. aqueous $NaHCO_3$ at 20° C. until the solution became pH 5-6. The separated aqueous layer was extracted two times with DCM (50 mL each) after which time the combined organic layers were washed with brine (20 mL), dried over $Na_2SO_4$, filtered, concentrated to dry. The crude residue was crystallized from DCM/iPrOH/heptane/$Et_2O$=1/1/1/1 to provide ER-890963 (17.89 g, 47.14 mmol, 96% yield) as a yellow powder.

ER-886604 (7.8 mg, 0.021 mmol, 73% yield) was prepared by a similar method described for ER-886604 starting with 14 (12.5 mg, 0.029 mmol) and 1-amino-4-methylbenzene (0.030 mL, 0.290 mmol) using a microwave at 180° C. for 15 min. ER-886604 was purified by reverse-phase HPLC (Water's X-Bridge C18 19×100 mm column, eluting with 10% acetonitrile in water containing 0.05% TFA). The product fractions were combined and concentrated to dry followed by dilution in MeOH (1 mL), passed through as basic silica gel plug (Biotage $SiCO_3$, 1 g, eluting with MeOH (1 mL)), concentrated and dried in vacuo. Boc-deprotection was not required.

ER-886608 (8.2 mg, 0.019 mmol, 67% yield) was prepared by a similar method described for ER-886604 starting with 14 (12.5 mg, 0.029 mmol) and 5-Amino-1,2-dimethylbenzimidazole dihydrochloride (30 mg, 0.128 mmol) along with TEA (0.040 mL, 0.290 mmol).

ER-886609 (7.4 mg, 0.017 mmol, 59% yield) was prepared by a similar method described for ER-886604 starting with 14 (12.5 mg, 0.029 mmol) and 5-amino-1-ethyl-2-methylbenzimidazole (30 mg, 0.171 mmol).

ER-886611 (9.2 mg, 0.027 mmol, 88% yield) was prepared by a similar method described for ER-886604 starting with 14 (12.5 mg, 0.029 mmol) and 1-aminocyclohexane (30 mg, 0.171 mmol).

ER-886787 (4.5 mg, 0.012 mmol, 43.9% yield) was prepared by a similar method described for ER-886604 starting with 14 (12.5 mg, 0.029 mmol) and 2-aminopyrimidine (24.7 mg, 0.263 mmol).

ER-886788 (5.2 mg, 0.014 mmol, 51% yield) was prepared by a similar method described for ER-886604 starting with 14 (12.5 mg, 0.029 mmol) and 2-aminopyridine (24.4 mg, 0.263 mmol).

ER-886789 (4.5 mg, 0.012 mmol, 42% yield) was prepared by a similar method described for ER-886604 starting with 14 (12.5 mg, 0.029 mmol) and 2-amino-6-methylpyridine (28.1 mg, 0.263 mmol).

ER-886790 (4.6 mg, 0.012 mmol, 43% yield) was prepared by a similar method described for ER-886604 starting with 14 (12.5 mg, 0.029 mmol) and 2-amino-5-methylpyridine (28.1 mg, 0.263 mmol).

ER-886814 (4.2 mg, 0.012 mmol, 40.4% yield) was prepared by a similar method described for ER-886604 starting with 14 (12.5 mg, 0.029 mmol) and D-prolinol (26.2 mg, 0.263 mmol).

ER-886815 (4.0 mg, 0.011 mmol, 38.2% yield) was prepared by a similar method described for ER-886604 starting with 14 (12.5 mg, 0.029 mmol) and 2,2-dimetylpyrrolidine (14.2 mg, 0.145 mmol).

ER-886816 (6.0 mg, 0.016 mmol, 60% yield) was prepared by a similar method described for ER-886604 starting with 14 (12.5 mg, 0.029 mmol) and 2-isopropylpyrrolidine (29.4 mg, 0.263 mmol).

ER-886817 (4.2 mg, 0.012 mmol, 62% yield) was prepared by a similar method described for ER-886604 starting with 14 (12.5 mg, 0.029 mmol) and (R)-2-methylpyrrolidine (22.1 mg, 0.263 mmol).

ER-886818 (4.2 mg, 0.010 mmol, 35.2% yield) was prepared by a similar method described for ER-890604 starting with 14 (12.5 mg, 0.029 mmol) and (S) 3-phenylpyrrolidine (38.2 mg, 0.263 mmol).

ER-886819 (5.2 mg, 0.015 mmol, 52% yield) was prepared by a similar method described for ER-886604 starting with 14 (12.5 mg, 0.029 mmol) and (R)-3-methylpyrrolidine (22.1 mg, 0.263 mmol).

ER-886820 (6.2 mg, 0.018 mmol, 62% yield) was prepared by a similar method described for ER-886604 starting with 14 (12.5 mg, 0.029 mmol) and (S)-3-hydroxypyrrolidine (22.6 mg, 0.263 mmol).

ER-886853 (6.2 mg, 0.017 mmol, 58% yield) was prepared by a similar method described for ER-886604 starting with 14 (12.5 mg, 0.029 mmol) and 2-amino-4-methylpyridine (28.1 mg, 0.263 mmol).

ER-886854 (2.9 mg, 0.007 mmol, 25% yield) was prepared by a similar method described for ER-886604 starting with 14 (12.5 mg, 0.029 mmol) and 3-phenylpyrrolidine hydrochloride (47.7 mg, 0.263 mmol).

ER-886855 (4.9 mg, 0.013 mmol, 44% yield) was prepared by a similar method described for ER-886604 starting with 14 (12.5 mg, 0.029 mmol) and 2-amino-5-methoxypyridine (32.2 mg, 0.263 mmol).

ER-886856 (7.8 mg, 0.022 mmol, 78% yield) was prepared by a similar method described for ER-886604 starting with 14 (12.5 mg, 0.029 mmol) and (S)-2-methylpyrrolidine (22.1 mg, 0.263 mmol).

ER-886857 (5.6 mg, 0.015 mmol, 54% yield) was prepared by a similar method described for ER-886604 starting with 14 (12.5 mg, 0.029 mmol) and 2,5-dimethylpyrrolidine (25.7 mg, 0.263 mmol).

ER-886858 (3.6 mg, 0.009 mmol, 32% yield) was prepared by a similar method described for ER-886604 starting with 14 (12.5 mg, 0.029 mmol) and 2-amino-4-methoxypyridine (32.2 mg, 0.263 mmol).

ER-886859 (2 mg, 0.005 mmol, 20% yield) was prepared by a similar method described for ER-886604 starting with 14 (12.5 mg, 0.029 mmol) and 2-amino-6-methoxypyridine (32.2 mg, 0.263 mmol).

ER-886860 (2.5 mg, 0.006 mmol, 21% yield) was prepared by a similar method described for ER-886604 starting with 14 (12.5 mg, 0.029 mmol) and 5-amino-1-phenylpyrazole (41.3 mg, 0.263 mmol).

ER-886866 (8.2 mg, 0.022 mmol, 78% yield) was prepared by a similar method described for ER-886604 starting with 14 (12.5 mg, 0.029 mmol) and L-prolinol (22.1 mg, 0.263 mmol).

ER-886867 (4.5 mg, 0.013 mmol, 45% yield) was prepared by a similar method described for ER-886604 starting with 14 (12.5 mg, 0.029 mmol) and (R)-3-hydroxypyrrolidine (22.6 mg, 0.263 mmol).

ER-886868 (6.5 mg, 0.019 mmol, 65% yield) was prepared by a similar method described for ER-886604 starting with 14 (12.5 mg, 0.029 mmol) and (S)-3-methylpyrrolidine (22.1 mg, 0.263 mmol).

ER-886869 (5.3 mg, 0.015 mmol, 51% yield) was prepared by a similar method described for ER-886604 starting with 14 (12.5 mg, 0.029 mmol) and 3,3-dimethylpyrrolidine (25.7 mg, 0.263 mmol).

ER-886948 (6.2 mg, 0.016 mmol, 56% yield) was prepared by a similar method described for ER-886604 starting with 14 (12.5 mg, 0.029 mmol) and 2-amino-3-methoxypyridine (32.2 mg, 0.263 mmol).

ER-886949 (4.8 mg, 0.013 mmol, 46% yield) was prepared by a similar method described for ER-886604 starting with 14 (12.5 mg, 0.029 mmol) and (R)-3-hydroxypiperidine (26.2 mg, 0.263 mmol).

ER-886950 (5.0 mg, 0.013 mmol, 46% yield) was prepared by a similar method described for ER-886604 starting with 14 (12.5 mg, 0.029 mmol) and (R,S)-2,6-dimethylpiperidine (29.4 mg, 0.263 mmol).

ER-886951 (3.2 mg, 0.009 mmol, 31% yield) was prepared by a similar method described for ER-886604 starting with 14 (12.5 mg, 0.029 mmol) and (S)-3-hydroxypiperidine (26.2 mg, 0.263 mmol).

ER-886953 (5.8 mg, 0.016 mmol, 55% yield) was prepared by a similar method described for ER-886604 starting with 14 (12.5 mg, 0.029 mmol) and 4-hydroxypiperidine (26.2 mg, 0.263 mmol).

ER-886955 (7.5 mg, 0.020 mmol, 69% yield) was prepared by a similar method described for ER-886604 starting with 14 (12.5 mg, 0.029 mmol) and 2-hydroxymethylpiperidine (29.9 mg, 0.263 mmol).

ER-887137 (4.5 mg, 0.012 mmol, 42% yield) was prepared by a similar method described for ER-886604 starting with 14 (12.5 mg, 0.029 mmol) and 2,3 dimethylpiperazine (29.6 mg, 0.263 mmol).

ER-887138 (5.9 mg, 0.016 mmol, 57% yield) was prepared by a similar method described for ER-886604 starting with 14 (12.5 mg, 0.029 mmol) and 3-aminopyridine (24.4 mg, 0.263 mmol).

ER-887139 (6.5 mg, 0.018 mmol, 63% yield) was prepared by a similar method described for ER-886604 starting with 14 (12.5 mg, 0.029 mmol) and 3-aminopyridine (24.4 mg, 0.263 mmol).

ER-887141 (5.2 mg, 0.014 mmol, 50% yield) was prepared by a similar method described for ER-886604 starting with 14 (12.5 mg, 0.029 mmol) and 4-methylpiperidine (25.7 mg, 0.263 mmol).

ER-887142 (4.5 mg, 0.012 mmol, 41% yield) was prepared by a similar method described for ER-886604 starting with 14 (12.5 mg, 0.029 mmol) and 4,4-difluroropiperidine (31.4 mg, 0.263 mmol).

ER-887143 (4.7 mg, 0.011 mmol, 38% yield) was prepared by a similar method described for ER-886604 starting with 14 (12.5 mg, 0.029 mmol) and 4-phenylpiperidine (41.8 mg, 0.263 mmol).

ER-887144 (6.2 mg, 0.017 mmol, 59% yield) was prepared by a similar method described for ER-886604 starting with 14 (12.5 mg, 0.029 mmol) and 4-fluroropiperidine (26.8 mg, 0.263 mmol).

ER-887145 (6.5 mg, 0.019 mmol, 65% yield) was prepared by a similar method described for ER-886604 starting with 14 (12.5 mg, 0.029 mmol) and 1-aminocyclopentane (22.1 mg, 0.263 mmol).

ER-887146 (7 mg, 0.018 mmol, 60% yield) was prepared by a similar method described for ER-886604 starting with 14 (12.5 mg, 0.029 mmol) and 1-amino-3-methylcyclohexane (29.4 mg, 0.263 mmol).

ER-887177 (5.3 mg, 0.014 mmol, 49% yield) was prepared by a similar method described for ER-886604 starting with 14 (12.5 mg, 0.029 mmol) and 2-amino-3-methylpyridine (20 mg, 0.145 mmol).

ER-887253 (10.2 mg, 0.029 mmol, 60% yield) was prepared by a similar method described for ER-886604 starting with 14 (20 mg, 0.046 mmol) and piperazine (40 mg, 0.460 mmol).

ER-887442 (6.2 mg, 0.016 mmol, 59% yield) was prepared by a similar method described for ER-886604 starting with 14 (12.2 mg, 0.028 mmol) and 1-amino-4-methylcyclohexane (30 mg, 0.265 mmol).

ER-887443 (4.5 mg, 0.013 mmol, 47% yield) was prepared by a similar method described for ER-886604 starting with 14 (12.5 mg, 0.029 mmol) and 1-amino-cyclobutane (10 mg, 0.141 mmol).

ER-887444 (7.7 mg, 0.020 mmol, 70.7% yield) was prepared by a similar method described for ER-886604 starting with 14 (12.5 mg, 0.029 mmol) and 1-aminocycloheptane (20 mg, 0.177 mmol).

ER-887526 (6.2 mg, 0.016 mmol, 57% yield) was prepared by a similar method described for ER-886604 starting with 14 (12.5 mg, 0.029 mmol) and 1-amino-4-hydroxycyclohexane (30 mg, 0.260 mmol).

ER-887528 (5.4 mg, 0.015 mmol, 51.2% yield) was prepared by a similar method described for ER-886604 starting with 14 (12.5 mg, 0.029 mmol) and 1-amino-2-hydroxycyclopentane (30 mg, 0.297 mmol).

ER-887539 (5.3 mg, 0.014 mmol, 49% yield) was prepared by a similar method described for ER-886604 starting with 14 (12.5 mg, 0.029 mmol) and 1-amino-2-methylcyclohexane (30 mg, 0.265 mmol).

ER-887538 (6.5 mg, 0.014 mmol, 51.8% yield) was prepared by a similar method described for ER-886604 starting with 14 (12.5 mg, 0.029 mmol) and 2-amino-5-phenylpyridine (50 mg, 0.294 mmol).

ER-887540 (6.1 mg, 0.014 mmol, 49% yield) was prepared by a similar method described for ER-886604 starting with 14 (12.5 mg, 0.029 mmol) and 2-amino-3-phenylpyridine (50 mg, 0.294 mmol).

ER-887586 (6.2 mg, 0.017 mmol, 59% yield) was prepared by a similar method described for ER-886604 starting with 14 (12.5 mg, 0.029 mmol) and (S,R)-1-amino-2-hydroxypyrrolidine (10 mg, 0.099 mmol).

ER-887587 (7.5 mg, 0.019 mmol, 65% yield) was prepared by a similar method described for ER-886604 starting with 14 (12.5 mg, 0.029 mmol) and 2-amino-3-ethoxylpyridine (40 mg, 0.290 mmol).

ER-887588 (5.6 mg, 0.013 mmol, 45% yield) was prepared by a similar method described for ER-886604 starting with 14 (12.5 mg, 0.029 mmol) and 4-amino-2-phenylpyridine (20 mg, 0.118 mmol).

ER-887589 (2.4 mg, 0.006 mmol, 19% yield) was prepared by a similar method described for ER-886604 starting with 14 (12.5 mg, 0.029 mmol) and 2-amino-6-phenylpyridine (20 mg, 0.118 mmol).

ER-887722 (3.5 mg, 0.009 mmol, 32% yield) was prepared by a similar method described for ER-886604 starting with 14 (12.5 mg, 0.029 mmol) and 5-methylpiperazin-2-one (20 mg, 0.175 mmol).

ER-887723 (6.2 mg, 0.017 mmol, 59% yield) was prepared by a similar method described for ER-886604 starting with 14 (12.5 mg, 0.029 mmol) and 1-N-methylpiperazine (10 mg, 0.100 mmol).

ER-887724 (6.2 mg, 0.016 mmol, 55% yield) was prepared by a similar method described for ER-886604 starting with 14 (12.5 mg, 0.029 mmol) and 1-N-propylpiperazine (40 mg, 0.138 mmol).

ER-887725 (7.2 mg, 0.018 mmol, 64% yield) was prepared by a similar method described for ER-886604 starting with 14 (12.5 mg, 0.029 mmol) and 4-(dimethylamino)-piperidine (20 mg, 0.156 mmol).

ER-887927 (10.2 mg, 0.024 mmol, 82.3% yield) was prepared by a similar method described for ER-886604 starting with 14 (12.5 mg, 0.029 mmol) and 1,4'-bipiperidine (20 mg, 0.119 mmol).

ER-887928 (3.2 mg, 0.009 mmol, 31% yield) was prepared by a similar method described for ER-886604 starting with 14 (12.5 mg, 0.029 mmol) and (R)-tert-butyl piperidin-3-ylcarbamate (30 mg, 0.150 mmol).

ER-888070 (4.5 mg, 0.012 mmol, 43% yield) was prepared by a similar method described for ER-886604 starting with 14 (12.5 mg, 0.029 mmol) and tert-butyl piperidin-4-ylcarbamate (30 mg, 0.150 mmol).

ER-888202 (6.2 mg, 0.018 mmol, 62% yield) was prepared by a similar method described for ER-886604 starting with 14 (12.5 mg, 0.029 mmol) and piperidine (0.034 mL, 0.348 mmol).

ER-888203 (7.2 mg, 0.020 mmol, 58% yield) was prepared by a similar method described for ER-886604 starting with 14 (15.5 mg, 0.035 mmol) and morpholine (0.030 mL, 0.350 mmol).

ER-888204 (6.2 mg, 0.016 mmol, 57% yield) was prepared by a similar method described for ER-886604 starting with 14 (12.5 mg, 0.029 mmol) and (2S,6R)-2,6-dimethylmorpholine (0.070 mL, 0.580 mmol).

ER-888205 (4.6 mg, 0.012 mmol, 41% yield) was prepared by a similar method described for ER-886604 starting with 14 (12.5 mg, 0.029 mmol) and ((2R,6R)-6-methylmorpholin-2-yl)methanol or ER-885491 (40 mg, 0.305 mmol).

ER-885491: To a stirred suspension of 11 (890.2 mg, 4.023 mmol) in MeOH (8 mL) was added 5% palladium on carbon (270 mg) after which time the mixture was purged with $H_2$ gas three times with vacuum evacuation between charges. The reaction was stirred under a $H_2$ atm at 40° C. for 8 h. The incomplete reaction was degassed under vacuum with purging with $N_2$ gas, followed by 5% palladium on carbon (100 mg) and 2 drops conc. HCl after which time the reaction was placed under a $H_2$ atm as described above for 4 h at 40° C. The completed reaction was purged with $N_2$ gas, followed by filtering over Celite 545, eluting with MeOH (5 mL), concentrating and drying in vacuo. The crude product ER-885491 (378. 2 mg, 2.883 mmol, 71.7% yield) was used in the previous step without further purification.

ER-888285 (8.6 mg, 0.020 mmol, 59% yield) was prepared by a similar method described for ER-886604 starting with 14 (15 mg, 0.034 mmol) and N-(2-pyridyl)piperazine (30 mg, 0.184 mmol).

ER-888286 (10.2 mg, 0.020 mmol, 71.3% yield) was prepared by a similar method described for ER-886604 starting with 14 (14.6 mg, 0.033 mmol) and N-(4-pyridyl) piperazine (30 mg, 0.184 mmol).

ER-888288 (7.2 mg, 0.016 mmol, 52% yield) was prepared by a similar method described for ER-886604 starting with 14 (15 mg, 0.034 mmol) and N-(piperidin-4-yl)acetamide (20 mg, 0.141 mmol). The HCl salt is formed by procedures previously described.

ER-888289 (16.2 mg, 0.039 mmol, 21.6% yield) was prepared by a similar method described for ER-886604 starting with 14 (80 mg, 0.183 mmol) and 1,8-naphthyridin-2-amine (100 mg, 0.689 mmol).

ER-888320 (5.8 mg, 0.015 mmol, 42% yield) was prepared by a similar method described for ER-886604 starting with 14 (15.5 mg, 0.035 mmol) and piperidine-4-carboxamide (20 mg, 0.156 mmol).

ER-888321 (6.2 mg, 0.013 mmol, 37% yield) was prepared by a similar method described for ER-886604 starting with 14 (15.5 mg, 0.035 mmol) and N-(piperidin-4-yl) benzamide (40 mg, 0.196 mmol).

ER-888322 (10.5 mg, 0.027 mmol, 75.3% yield) was prepared by a similar method described for ER-886604 starting with 14 (15.5 mg, 0.035 mmol) and 1-isopropylpiperazine (20 mg, 0.156 mmol).

ER-888330 (4.2 mg, 0.011 mmol, 30% yield) was prepared by a similar method described for ER-886604 starting with 14 (15.5 mg, 0.035 mmol) and piperazine-1-carboxamide (20 mg, 0.155 mmol).

ER-888479 (7.6 mg, 0.018 mmol, 51% yield) was prepared by a similar method described for ER-886604 starting with 14 (15 mg, 0.034 mmol) and 4-cyclohexylpiperidine (30 mg, 0.179 mmol).

ER-888480 (8.3 mg, 0.020 mmol, 58% yield) was prepared by a similar method described for ER-886604 starting with 14 (15 mg, 0.034 mmol) and 4-(pyrrolidin-1-yl)piperidine (30 mg, 0.194 mmol).

ER-888838 (6.2 mg, 0.015 mmol, 45% yield) was prepared by a similar method described for ER-886604 starting with 14 (15 mg, 0.034 mmol) and 3,5-dimethylpyridine-2,6-diamine (20 mg, 0.146 mmol).

ER-888977 (1.2 mg, 0.003 mmol, 11% yield) was prepared by a similar method described for ER-886604 starting with 14 (12.5 mg, 0.029 mmol) and 1,3-dimethyl-1H-pyrazol-5-amine (28.8 mg, 0.259 mmol).

ER-889448 (8.2 mg, 0.022 mmol, 63% yield) was prepared by a similar method described for ER-886604 starting with 14 (15 mg, 0.034 mmol) and 1-ethylpiperazine (0.020 mL, 0.136 mmol).

ER-889469 (6.5 mg, 0.018 mmol, 52% yield) was prepared by a similar method described for ER-886604 starting with 14 (15 mg, 0.034 mmol) and 1-(azetidin-3-yl)pyrrolidine (20 mg, 0.158 mmol).

ER-889470 (7.2 mg, 0.017 mmol, 48% yield) was prepared by a similar method described for ER-886604 starting with 14 (15 mg, 0.034 mmol) and 1-(azetidin-3-yl)piperidine (20 mg, 0.158 mmol).

ER-889557 (7.7 mg, 0.020 mmol, 58.6% yield) was prepared by a similar method described for ER-886604 starting with 14 (15 mg, 0.034 mmol) and piperidin-4-ylmethanol (20 mg, 0.174 mmol).

ER-889571 (3.2 mg, 0.008 mmol, 23% yield) was prepared by a similar method described for ER-886604 starting with 14 (15 mg, 0.034 mmol) and (R)-1,3'-bipyrrolidine (20 mg, 0.143 mmol).

ER-889572 (1.1 mg, 0.003 mmol, 7.7% yield) was prepared by a similar method described for ER-886604 starting with 14 (15 mg, 0.034 mmol) and (R)-1-(pyrrolidin-3-yl) piperidine (20 mg, 0.130 mmol).

ER-889601 (6.7 mg, 0.018 mmol, 51% yield) was prepared by a similar method described for ER-886604 starting with 14 (15 mg, 0.034 mmol) and 1-methyl-1,4-diazepane (20 mg, 0.175 mmol).

ER-889602 (10.2 mg, 0.022 mmol, 65.3% yield) was prepared by a similar method described for ER-886604 starting with 14 (15 mg, 0.034 mmol) and phenyl(piperazin-1-yl)methanone (30 mg, 0.158 mmol).

ER-891084 (7.2 mg, 0.016 mmol, 47% yield) was prepared by a similar method described for ER-886608 starting with 14 (15 mg, 0.034 mmol) and 1-(piperidin-4-yl)azepane (30 mg, 0.165 mmol).

ER-890108 (15.2 mg, 0.036 mmol, 58.6% yield) was prepared by a similar method described for ER-886604 starting with 14 (27 mg, 0.062 mmol) and 1-(azetidin-3-yl)-4-methylpiperazine (90.2 mg, 0.581 mmol). Triethylamine (0.008 mL, 0.062 mmol) was also added to the reaction.

ER-890112 (296.5 mg, 0.683 mmol, 74.7% yield) was prepared by a similar method described for ER-886604 starting with 14 (400.6 mg, 0.916 mmol) and 4,4'-bipiperidine (290 mg, 1.723 mmol).

ER-894472 (53.9 mg, 0.143 mmol, 25% yield) and ER-894473 (51.2 mg, 0.135 mmol, 23.6% yield) was prepared by a similar method described for ER-886604 starting with 14 (250 mg, 0.571 mmol) and 5-methylpiperazin-2-one (78.3 mg, 0.686 mmol). The stereochemistry of each diastereomeric methyl group is arbitrarily assigned.

ER-886507 (4.2 mg, 0.013 mmol, 51.9% yield) was prepared by a similar method described for ER-886604 starting with 14 (10.6 mg, 0.024 mmol) and pyrrolidine (0.022 mL, 0.257 mmol) using toluene (1 mL) instead of DMA as solvent. Boc-deprotection was not required.

ER-886508 (3.3 mg, 0.010 mmol, 38.9% yield) was prepared by a similar method described for ER-890507 starting with 14 (10.8 mg, 0.025 mmol) and N,N-diethylamine (0.027 mL, 0.262 mmol).

ER-886509 (4.8 mg, 0.013 mmol, 44.9% yield) was prepared by a similar method described for ER-890507 starting with 14 (12.5 mg, 0.029 mmol) and benzylamine (0.028 mL, 0.263 mmol).

ER-886601 (6.6 mg, 0.018 mmol, 64.2% yield) was prepared by a similar method described for ER-890507 starting with 14 (12.5 mg, 0.029 mmol) and phenylamine (0.008 mL, 0.087 mmol).

ER-886602 (6.4 mg, 0.017 mmol, 60.1% yield) was prepared by a similar method described for ER-890507 starting with 14 (12.5 mg, 0.029 mmol) and 1-amino-3-methylbenzene (0.028 mL, 0.263 mmol).

ER-887104 (2.1 mg, 0.005 mmol, 17.9% yield) was prepared by a similar method described for ER-890507 starting with 14 (12.5 mg, 0.029 mmol) and (S)-2-(trifluoromethyl)pyrrolidine (36.1 mg, 0.260 mmol).

ER-886603 (7.6 mg, 0.020 mmol, 71% yield) was prepared by a similar method described for ER-890507 starting with 14 (12.5 mg, 0.029 mmol) and 1-amino-2-methylbenzene (0.030 mL, 0.290 mmol) using NMP(1 mL) instead of toluene as a solvent.

ER-886957 (4.7 mg, 0.013 mmol, 45% yield) was prepared by a similar method described for ER-886507 starting with 14 (12.5 mg, 0.029 mmol) and 2-methylpiperidine (25.7 mg, 0.263 mmol).

ER-886958 (6.2 mg, 0.016 mmol, 57% yield) was prepared by a similar method described for ER-886507 starting with 14 (12.5 mg, 0.029 mmol) and 2-ethylpiperidine (29.3 mg, 0.263 mmol).

ER-887139 (2.1 mg, 0.005 mmol, 18% yield) was prepared by a similar method described for ER-886507 starting with 14 (12.5 mg, 0.029 mmol) and (S)-2-trifluoromethypyrrolidine (36.1 mg, 0.263 mmol).

ER-887252 (2.6 mg, 0.006 mmol, 21% yield) was prepared by a similar method described for ER-886507 starting with 14 (12.5 mg, 0.029 mmol) and 2-amino-4-phenylpyridine (20 mg, 0.145 mmol).

ER-887258 (4.2 mg, 0.010 mmol, 34% yield) was prepared by a similar method described for ER-886507 starting with 14 (12.5 mg, 0.029 mmol) and N-phenyl piperazine (0.040 mL, 0.290 mmol) in toluene (0.5 mL).

ER-887259 (3.2 mg, 0.009 mmol, 30% yield) was prepared by a similar method described for ER-886507 starting with 14 (12.5 mg, 0.029 mmol) and 2,6-dimethylpyridine (30 mg, 0.290 mmol).

ER-887260 (3.3 mg, 0.009 mmol, 30.1% yield) was prepared by a similar method described for ER-886507 starting with 14 (12.5 mg, 0.029 mmol) and (S,S)-2,5-dimethylpiperazine (29.6 mg, 0.263 mmol).

ER-887261 (4.2 mg, 0.011 mmol, 39% yield) was prepared by a similar method described for ER-886507 starting with 14 (12 mg, 0.027 mmol) and N-acetyl piperazine (40 mg, 0.274 mmol).

ER-887262 (2.4 mg, 0.006 mmol, 22% yield) was prepared by a similar method described for ER-886507 starting with 14 (12.5 mg, 0.029 mmol) and 4-(R)-hydroxy-2-(S)-hydroxymethylpyrrolidine (30.4 mg, 0.263 mmol).

ER-887268 (9.3 mg, 0.017 mmol, 10% yield) was prepared by a similar method described for ER-886608 starting with 14 (50 mg, 0.114 mmol) and (R)-tert-butyl 3-methylpiperazine-1-carboxylate (100 mg, 0.570 mmol) using toluene (1 mL). Boc-deprotection was required as described for Boc-protected ER-890963 above. ER-887268 was purified by reverse-phase HPLC (Water's X-Bridge C18 19×100 mm column, eluting with 10-40% acetonitrile in water with 0.05% TFA) followed by neutralization as described for ER-886608.

ER-887269 (6.2 mg, 0.025 mmol, 21.4% yield) was prepared by a similar method described for ER-887268 starting with 14 (51.8 mg, 0.118 mmol) and (R)-tert-butyl 2-methylpiperazine-1-carboxylate (100 mg, 0.570 mmol).

ER-887270 (12.2 mg, 0.033 mmol, 30% yield) was prepared by a similar method described for ER-887268 starting with 14 (50 mg, 0.114 mmol) and (S)-tert-butyl 2-methylpiperazine-1-carboxylate (200 mg, 1.14 mmol).

ER-887271 (2.3 mg, 0.006 mmol, 5.5% yield) was prepared by a similar method described for ER-887268 starting with 14 (48.2 mg, 0.110 mmol) and (R,R)-tert-butyl 2,5-dimethylpiperazine-1-carboxylate hydrochloride (100 mg, 0.399 mmol) and DIPEA (0.10 mL, 0.55 mmol).

ER-887272 (3.2 mg, 0.008 mmol, 7.1% yield) was prepared by a similar method described for ER-887268 starting with 14 (52.7 mg, 0.120 mmol) and (S,R)-tert-butyl 2,5-dimethylpiperazine-1-carboxylate (100 mg, 0.467 mmol).

ER-890119 (256.2 mg, 0.630 mmol, 58.6% yield) was prepared by a similar method described for ER-890963 starting with 14 (450 mg, 1.029 mmol) and tert-butyl 4-(azetidin-3-yl)piperazine-1-carboxylate (314.2 mg, 1.302 mmol). Triethylamine (0.172 mL, 1.23 mmol) was also added to the reaction. Dioxane (2 mL) was used instead of DMA. Deprotection of a Boc-group with TFA was required followed by neutralization of the final product as described previously.

ER-892253 (152.3 mg, 0.362 mmol, 4.0% overall yield) was prepared by a similar method described for ER-890119 starting with 14 (4.0 g, 9.1 mmol) and tert-butyl(1-(azetidin-3-yl)piperidin-4-yl)carbamate (2.52 g, 9.9 mmol).

ER-888605 (7.6 mg, 0.017 mmol, 5.0% yield) was prepared by a similar method described for ER-890119 starting with 14 (150 mg, 0.343 mmol) and [1,4'-bipiperidin]-2-one hydrochloride (82.5 mg, 0.377 mmol). Boc-group deprotection was not required.

ER-888605 (7.6 mg, 0.017 mmol, 5.0% yield) was prepared by a similar method described for ER-890119 starting with 14 (150 mg, 0.343 mmol) and [1,4'-bipiperidin]-2-one hydrochloride (82.5 mg, 0.377 mmol). Boc-group deprotection was not required.

ER-890093 (15.2 mg, 0.035 mmol, 45.4% yield) was prepared by a similar method described for ER-890119 starting with 14 (33.6 mg, 0.077 mmol) and 4-(piperidin-4-yl)morpholine (52 mg, 0.305 mmol). Boc-group deprotection was not required.

ER-890104 (569 mg, 1.06 mmol, 42.6% yield) was prepared by a similar method described for ER-890119 starting with 14 (1.08 g, 2.5 mmol) and tert-butyl 4-(piperidin-4-yl) piperazine-1-carboxylate (1.00 g, 3.7 mmol). Boc-group deprotection of ER-890104 (21 mg, 0.039 mmol) was performed as described above to provide ER-890106 (12.4 mg, 0.029 mmol, 73.2% yield).

ER-890105 (65 mg, 0.122 mmol, 11.3% yield) was prepared by a similar method described for ER-890119 starting with 14 (1.08 g, 2.5 mmol) and tert-butyl 4-(piperidin-4-yl) piperazine-1-carboxylate (1.00 g, 3.7 mmol). DIPEA (0.65 mL, 3.7 mmol) was also added to the reaction mixture. Boc-group deprotection of ER-890105 (60 mg, 0.112 mmol) was performed as described above to provide ER-890107 (11.3 mg, 0.026 mmol, 23.2% yield).

ER-890311 (4.5 mg, 0.011 mmol, 31% yield) was prepared by a similar method described for ER-886608 starting with 14 (15 mg, 0.034 mmol) and (S)-1-(pyrrolidin-3-yl) piperidine dihydrochloride (30 mg, 0.108 mmol) replacing DMA with acetonitrile (1 mL). Triethylamine (0.014 mL, 0.102 mmol) was also added to the reaction. The dihydrochloride salt of the product was produced according to processes described previously.

ER-890342 (41.3 mg, 0.101 mmol, 11% yield) was prepared by a similar method described for ER-890311 starting with 14 (150.2 mg, 0.916 mmol) and 4-(azetidin-3-yl) morpholine (221.6 mg, 1.030 mmol).

ER-890343 (25.2 mg, 0.062 mmol, 77.2% yield yield) was prepared by a similar method described for ER-890311 starting with 14 (35.2 mg, 0.080 mmol) and 1-(azetidin-3-yl)-4-methylpiperazine (40.3 mg, 0.0201 mmol).

ER-890344 (21.4 mg, 0.059 mmol, 73.8%) was prepared by a similar method described for ER-890311 starting with 14 (35.2 mg, 0.080 mmol) and (S)-tert-butyl 3-methylpiperazine-1-carboxylate (28.2 mg, 0.201 mmol). Deprotection of the Boc-group with TFA followed by neutralization was performed.

ER-890963 (685.2 mg, 1.806 mmol, 86%) was prepared by a similar method described for ER-890344 starting with 14 (919 mg, 2.101 mmol) and (S)-tert-butyl 2-ethylpiperazine-1-carboxylate (500 mg, 2.333 mmol). The dihydrochloride salt of the product was produced according to processes described previously.

ER-891090 (54.2 mg, 0.133 mmol, 46.8% yield) was prepared by a similar method described for ER-890311 starting with 14 (137.5 mg, 0.314 mmol) and (S)-1,3'-bipyrrolidine dihydrochloride (30 mg, 0.165 mmol). Boc-group deprotection was not required.

ER-895204 (35.2 mg, 0.084 mmol, 73.1% yield) was prepared by a similar method described for ER-890311 starting with 14 (50 mg, 0.114 mmol) and N-ethylpiperidine-4-carboxamide (21.4 mg, 0.137 mmol). The hydrochloride salt of the product was produced according to processes described previously.

Preparation of ER-887612 as a Modified Example of Compound 15 from Scheme 4

A mixture of Compound 3 (201 mg, 0.862 mmol) and (R)-2-hydroxymethyl morpholine hydrochloride (132, 0.856 mmol) in NMP(3 mL) was heated to 170° C. for 16 h. The completed reaction was cooled, filtered, eluted with MeOH (2 mL) then purified directly by HPLC using a C-18 column eluting with a 10-100% acetonitrile in water containing 0.1% TFA. The desired product was collected and concentrated to dry. The resulting product was dissolved in MeOH (2 mL) and passed over a basic silica plug (Biotage, 1 g, $SiCO_3$) eluting with MeOH (5 mL) to provide (R)-5-(2-(hydroxymethyl)morpholino)quinoline-8-carbonitrile or ER-886849 (108 mg, 0.401 mmol, 46.9% yield).

To a stirred solution of ER-886849 (101 mg, 0.375 mmol) in DCM (2 mL) was added p-toluenesulfonyl chloride (78.5 mg, 0.412 mmol) followed by DIPEA (0.13 mL, 0.746 mmol) and DMAP (2.3 mg, 0.019 mmol). The reaction mixture was stirred at rt for 2 h after which time additional p-toluenesulfonyl chloride (78.7 mg, 0.413 mmol) was added followed by stirring at rt for 4 h. Water (1.2 mL) and DCM (5.9 mL) were added to the completed reaction with stirring followed separation of the layers. The organic layer was washed with brine (1.2 mL), dried over $MgSO_4$, filtered and concentrated to dry. The crude product was purified over silica gel (Biotage SP4, Interchim 25 g, eluting with 20-100% EtOAc in heptane gradient), the desired fractions collected, concentrated and dried in vacuo to provide (R)-(4-(8-cyanoquinolin-5-yl)morpholin-2-yl)methyl 4-methylbenzenesulfonate (85 mg, 0.201 mmol, 53.6% yield).

A solution of (R)-(4-(8-cyanoquinolin-5-yl)morpholin-2-yl)methyl 4-methylbenzene-sulfonate (27 mg, 0.064 mmol) and 2-aminopyridine (90 mg, 0.956 mmol) in NMP (1 mL) was microwaved at 150° C. for 15 min. The cooled reaction was diluted with NMP (3 mL) and purified directly by HPLC using a C-18 column eluting with a 10-100% acetonitrile in water containing 0.1% TFA. The desired product was collected and concentrated to dry. The resulting product was dissolved in MeOH (2 mL) and passed over a basic silica plug (Biotage, 1 g, $SiCO_3$) eluting with MeOH (5 mL) to provide ER-887612 (16 mg, 0.046 mmol, 71.9% yield).

ER-885211 (4 mg, 0.016 mmol, 24.7% yield) was prepared in a similar manner to ER-886849 starting with Compound 3 (15 mg, 0.064 mmol) and (R)-2-methylmorpholine (22 mg, 0.160 mmol). TEA (0.05 mL, 0.359 mmol) was added to the reaction.

Alternative Synthesis of Compound 10—scheme 5

Compound 16: To a stirred solution of compound 8 (2.869 g, 7.06 mmol) in acetonitrile (14.4 ml) cooled to 5-6° C. was added TFA (0.163 ml, 2.12 mmol) followed by NBS (1.385 g, 7.78 mmol). The reaction mixture was stirred for 1 h after which time 9% $NaHCO_3$ (6.6 g, 7.1 mmol) was added followed by sodium sulfite ($Na_2SO_3$; 0.27 g, 2.1 mmol) and then stirred for 5 min. The mixture was diluted with water (5.7 ml) and toluene (29 ml), stirred for an additional 5 min followed by separation of the layers. The aqueous layer was extracted with toluene (14.4 ml) after which time the combined organic layers were washed with 20% NaCl (7.20 ml), concentrated to approx. 5 ml, and then diluted with MTBE (29 ml). 2 M NaOH (7.1 ml) was added and resultant biphasic mixture was vigorously stirred for 10 min. The organic layer was separated and sequentially washed two times with 20% NaCl (14 ml each), water (5.7 ml), concentrated to approx. 5 ml, and diluted with toluene (14.4 ml). The resultant solution containing (2R)-2-((benzyloxy)methyl)-6-(bromomethyl)-4-((2-nitrophenyl)-sulfonyl)morpholine, 16, was used directly in the next reaction.

Compound 17: To the stirred solution of 16 (ca. 3.43 g, 7.06 mmol from above) in toluene was added DBU (2.66 ml, 17.648 mmol) followed by heating at 100° C. for 4 h. The completed reaction was cooled to 15° C. followed by the addition of MTBE (60 ml) and 1 M HCl (21.2 ml) with stirring. The layers were separated after which time the aqueous layer was extracted with MTBE (20 ml). The combined organic layers were washed with water (10 ml), 9 wt % $NaHCO_3$ in water (10 g, 10.713 mmol), 20 wt % NaCl (10 ml), concentrated to dry. The give crude yellow oil with salts was diluted with DCM (10 ml), filtered and concentrated to give crude (R)-2-((benzyloxy)methyl)-6-methylene-4-((2-nitrophenyl)sulfonyl)morpholine, 17 (3.2 g) as orange-colored oil.

Compound 10: To a stirred solution triethylsilane (1.69 ml, 10.6 mmol) in DCM (4 ml) at 0° C. was added TFA (2.72 ml, 35.3 mmol) followed by cooling to −15° C. Crude 17 (ca. 2.86 g, 7.06 mmol) in DCM (4 ml) was added while maintaining the temperature at −5° C. followed by adding the rinsed residuals with DCM (4 ml). The resultant mixture was stirred at −10 to −5° C. for 1 h then warmed to 2-3° C. for an additional 1 h. The completed reaction was cooled to −10° C., poured into pre-chilled (2° C.) 2 M NaOH (21.2 ml, 42.4 mmol) rinsing the reactor with DCM (2 ml). The final mixture was extracted with MTBE (50 ml) and the organic layer was washed with water (10 ml), 20 wt % NaCl (10 ml) and concentrated to give orange-colored oil. Crude product was purified over silica gel (n-heptane/MTBE 1:2) to provide (2R,6R)-2-((benzyloxy)methyl)-6-methyl-4-((2-nitrophenyl)sulfonyl)morpholine, 10 (1.437 g, 3.54 mmol, 50% yield in 3 steps from 8) as light yellow solid after combining and concentration of the desired fractions then drying in vacuo.

Alternative Synthesis of Compound 11—scheme 6

Compounds 18 & 19: To a stirred suspension of glycine (85.86 g, 1.144 mol) was in 1,4-dioxane (660 mL) was added 1.0 M aqueous NaOH (1144 mL, 1.114 mol) followed by heating to 80° C. after which time a solution of (2R)-benzyl 2-epoxypropyl ether 6 (93.90 g, 0.5718 mol) in 1,4-dioxane (94 mL) was added slowly while maintaining T-internal between 77-82° C. over a 2-h period. The completed reaction mixture was cooled to 18° C. followed by the addition of di-tert-butyl dicarbonate (262.1 g, 1.201 mol) maintaining the temperature between 18 and 21° C. The mixture was stirred at rt overnight after which time the completed mixture was washed two times with heptane (2000 mL). The aqueous layer was acidified with 20 wt % citric acid (270 g) and extracted three times with EtOAc (2000 mL & 2×1000 mL). The combined organic layers were washed twice with 20 wt % NaCl (460 g each), concentrated, dissolved in EtOAc (560 mL), filtered, concentrated and diluted with DCM (280 mL) to give (R)-2-((3-(benzyloxy)-2-hydroxypropyl)(tert-butoxycarbonyl)amino)acetic acid, 18 in a solution.

To a stirred solution of EDC (120.6 g, 0.6290 mol) and DMAP (2.10 g, 0.0172 mol) were suspended in DCM (380 mL) at 15° C. was added the above 18 solution over a 30-min period while maintaining the temperature below 20° C. The reaction mixture was stirred at 18-20° C. for 3 h after which time it was cooled to 10° C. and then quenched with of 20 wt % citric acid (820 g) with stifling. The layers were separated and the aqueous layer was extracted with MTBE (1.4 L). The combined organic layers were washed with saturated aqueous $NaHCO_3$ (480 g), 30% NaCl (470 g) and concentrated. The crude product thus obtained was purified over silica gel (eluting with n-heptane/EtOAc 4:1 to 3:1) to provide (R)-tert-butyl 2-((benzyloxy)methyl)-6-oxomorpholine-4-carboxylate, 19 (96 g, 0.298 mol, 26.1% yield in two steps) as clear yellow oil after combining the desired fractions, concentration and drying in vacuo.

Compounds 22 & 23: To a stirred solution of 19 (134.29 g, 0.418 mol) in THF (1100 mL) cooled to −75° C. was added 1.5 M of MeLi—LiBr complex in diethyl ether (334 mL, 0.501 mol)) was dropwise over 1 h while maintaining the temperature at <−65° C. The mixture was cooled to −75° C. and stirred for 1.5 h after which time the reaction was slowly quenched over a 10-min period with 20 wt % aqueous $NH_4Cl$ (270 g) while maintaining the temperature at <−55° C. The mixture was warmed to 0° C. over 1 h, partitioned between water (270 g) and MTBE (1340 mL. The aqueous layer was extracted with MTBE (1100 mL) followed by combining the organic layers and washing them with 20 wt % NaCl (270 g) and concentrated to dry. The residue was dissolved in toluene (1100 mL), filtered, concentrated, azeotroped to dry with toluene (1100 mL), and then dissolved in DCM (1200 ml). The mixture was cooled to −72° C. and triethylsilane (0.200 L, 1.25 mol) was added followed by trimethylsilyl trifluoromethanesulfonate (151 mL, 0.836 mol) over 45-min period while maintaining the temperature at <−68° C. TFA (129 mL, 1.67 mol) in DCM (336 mL, 5.24 mol) was added over 20-min period to the completed reaction while maintaining the temperature at <−65° C. The mixture was warmed up to −10° C. followed by the addition of saturated aqueous $NaHCO_3$ (0.70 kg) with stifling. The layers were separated and the aqueous layer was extracted two times with DCM (940 mL each). The combined organic layers were washed with saturated aqueous $NaHCO_3$ (0.70 kg), concentrated, dissolved in acetonitrile (400 mL), treated with di-tert-butyl dicarbonate (91.2 g, 0.418 mol) at 20-25° C., and stirred for 1 h. The completed reaction azeotroped to dry with toluene (800 ml) and purified over silica gel (eluted with n-heptane/EtOAc 9:1 to 4:1) to provide (2R,6R)-tert-butyl 2-((benzyloxy)methyl)-6-methylmorpholine-4-carboxylate, 22 (61.90 g, 0.193 mol, 46% yield from 19) as white solid after combining the desired fractions, concentration and drying in vacuo. The minor stereoisomer (2R,6S)-tert-butyl 2-((benzyloxy) methyl)-6-methylmorpholine-4-carboxylate, 23, was separable by silica gel column chromatography.

Compound 11: To a stirred solution of 22 (27 mg, 0.084 mol) in DCM (0.60 mL) was added TFA (0.30 mL, 0.0039 mol) at rt followed by stirring for 30 min. The completed reaction was concentrated, azeotroped twice to dryness with toluene (1.8 mL×2) and dissolved in DCM (3.0 mL). The organic solution was washed with saturated aqueous $NaHCO_3$ (0.50 g), concentrated, and dried in vacuo to provide (2R,6R)-2-((benzyloxy)methyl)-6-methylmorpholine, 11 (19 mg, 100% yield) as colorless film.

$2^{nd}$ Alternative Synthesis of Compound 11—scheme 7

Compound 23: A solution of (2R)-benzyl 2-epoxypropyl ether, 6 (21.0 g, 0.128 mol) in EtOH (100 mL) was added slowly to a solution of 7.0 M ammonia in MeOH (100 mL) and 28% aq. ammonium hydroxide (210 mL) at rt. The reaction vessel was tightly capped and stirred at rt for 23 h. The completed reaction was concentrated in vacuo, and the crude product was azeotroped to dry twice with toluene (100 mL) to provide (R)-1-amino-3-(benzyloxy)propan-2-ol, 23 (23 g) as waxy solid containing approximately 15% of dimer. The crude was used for next reaction without further purification.

Compound 25: To the solution of 23 (12.0 g, 49.7 mmol) in EtOH (15 mL) was added commercially available methyl (S)-(−)-2-chloropropionate, 24 (6.69 g, 54.6 mol). The mixture was heated to 70° C. and stirred for 14 h after which time the completed reaction was concentrated in vacuo. The crude product was diluted with EtOAc (50 mL), washed with 1N HCl (20 mL), brine (20 mL), and then the organic phase was dried over anhydrous $Na_2SO_4$, filtered and concentrated to dry. Purification over silica gel (SNAP 10 g, heptane/EtOAc=5/1 to 1/5, then EtOAc only, TLC hep/EtOAc=1/3, rf=0.45) provided the colorless syrup (S)—N—((R)-3-(benzyloxy)-2-hydroxypropyl)-2-chloropropanamide, 25 (9.86 g, 36.2 mmol, 73% yield) after the desired collected fractions were concentrated and dried in vacuo.

Compound 26: To the stirred suspension of 60% sodium hydride (5.82 g, 0.0728 mol) in THF (440 mL) cooled to 0° C. was added 25 (9.89 g, 36.4 mmol) in THF (100 mL) dropwise over a 15 min period. The reaction mixture was stirred at 0° C. an additional 30 min after which time it was allowed to warm to rt for 1 h. The completed reaction completion cooled to 0° C. upon which time isopropyl alcohol (100 mL) was added slowly. The crude solution was neutralized with Dowex $H^+$ followed by filtering off the resin, washing with isopropanol two times (20 mL each) and concentrating the filtrate to dry. The crude product was purified over silica gel (SNAP 100 g, hep/EtOAc=1/1 to EtOAc only, TLC hep/EtOAc=1/3, rf=0.4)) to provide (2R,6R)-6-((benzyloxy)methyl)-2-methylmorpholin-3-one, 26 (6.42 g, 27.3 mmol, 75% yield) after the desired collected fractions were collected, concentrated and dried in vacuo.

Compound 11

To a stirred solution of 26 (6.67 g, 28.3 mmol) in THF (20 mL) solution was added to 1 M of lithium tetrahydroaluminate in THF (40.0 mL) at rt dropwise. The reaction was stirred at rt for 2.5 h after which time the completed reaction was cooled to 0° C. followed by a slow dropwise addition of water (13 mL), then 1 M of NaOH in water (0.8 mL). The quenched reaction was stirred at rt until a free flowing white precipitate formed. The precipitate was filtered over a Celite 545 pad and washed with EtOAc, DCM, and $Et_2O$ (10 mL each). The filtrate was concentrated and purified over silica gel (SNAP 100 g, DCM only to DCM/MeOH=97/3, TLC $CHCl_3$/MeOH=9/1, $rf_{trans}$=0.5, $rf_{cis}$=0.4). Obtained the cis/trans diastereomer mixture of 11 (4.42 g, 20.0 mmol, 70.6% yield) of which pure 11 (0.93 g, 4.2 mmol, 15% yield) was obtained.

Alternative Preparation of Compound 12—scheme 8

Compound 28: To a suspension of sodium carbonate (31 g, 0.37 mol) in water (50 ml) was added a solution of 1-amino-3,3-diethoxypropane (10.00 mL, 61.81 mmol) in DCM (50 mL) followed by cooling to 0° C. benzenesulfonyl chloride (7.65 mL, 60.0 mmol) was added at 0° C. with vigorous stirring followed by warming to 20° C. and continued stirring for 2 h after which time MTBE (150 mL) was added. Organic layer was separated, washed with 1.0 M of HCl (50 mL), saturated $NaHCO_3$ (50 g), water (50 g), concentrated and azeotroped to dry two times with MTBE (150 mL×2) to provide N-(3,3-diethoxypropyl)benzenesulfonamide, 28 (17.34 g, 60.34 mmol, 97% yield) as light yellow clear oil.

Compound 30: To a stirred solution of 2-fluoro-4-hydroxybenzonitrile, 29 (15.00 g, 0.1094 mol) in DMF (45.0 mL) cooled to 0° C. was added potassium carbonate (37.8 g, 0.274 mol) followed by stifling at 0-5° C. for 30 min. Benzyl bromide (13.7 mL, 0.115 mol) was added to the reaction mixture at <5° C., stirred at 5° C. for 1 h followed by warming to 20° C. and stirring for additional 2.5 h. The completed reaction was partitioned between water (180 ml) and MTBE (220 mL), the layers separated and the organic layer was washed with water (90 mL), concentrated and azeotroped to dry two times with EtOAc (150 mL each) to provide 4-(benzyloxy)-2-fluorobenzonitrile, 30 (24.64 g, 0.1084 mol, 99% yield) as white solid.

Compounds 32: To a stirred solution of 28 (13.28 g, 46.21 mmol) in NMP (30.0 mL) was added 30 (10.00 g, 44.01 mmol) at rt followed by $Cs_2CO_3$ (21.5 g, 66.0 mmol). Resultant mixture was heated at 110° C. for 16 h followed cooling to rt. The mixture was partitioned between water (120 g) and MTBE (120 mL) and the aqueous layer was extracted with MTBE (120 mL). The combined organic layers were washed with water (60 g) concentrated and azeotroped to dry two times with EtOAc (100 mL each) to give N-(5-(benzyloxy)-2-cyanophenyl)-N-(3,3-diethoxypropyl)benzenesulfonamide, 31, as a brownish oil. The crude product was subjected to hydrogenolysis with 10 wt % Pd—C(1.40 g) in EtOAc (100 mL) under a hydrogen gas atmosphere (balloon pressure) for 3 h, after which time the purged reaction mixture was filtered through a pad of Celite, rinsed with EtOAc (100 mL) and concentrated. The crude product thus obtained was purified over silica gel (eluting with n-heptane/MTBE 2:3) to provide N-(2-cyano-5-hydroxyphenyl)-N-(3,3-diethoxypropyl)benzenesulfonamide, 32 (16.38 g, 40.50 mmol, 92% yield) as yellow viscous oil.

Compound 33: To a stirred solution of 32 (5.45 g, 13.5 mmol) in THF (40 mL) cooled to 0° C. was added water (5.4 mL) followed by TFA (11 mL, 0.14 mol). The resultant mixture was allowed to warm to 20° C. and stirred overnight. The completed reaction was azeotroped to dry two times with toluene (54 mL each) to provide N-(2-cyano-5-hydroxyphenyl)-N-(3-oxopropyl)benzenesulfonamide, 33 (4.55 g, 13.8 mmol, 100% yield. as viscous oil.

Compound 34: To a stirred suspension of 33 (1.64 g, 4.96 mmol) in a mixture of toluene (29.5 mL) and NMP (1.2 mL) heated at 70° C. was added D-(+)-10-camphorsulfonic acid (1.15 g, 4.96 mmol) followed by heating at 100° C. for 14 h. The completed reaction was cooled to rt, diluted with EtOAc (60 mL), washed with water (6.3 mL), and concentrated to give dark brownish oil. Crude product was purified over silica gel (eluting with n-heptane/EtOAc 1:1) to provide 5-hydroxy-1-(phenylsulfonyl)-1,2-dihydroquinoline-8-carbonitrile, 34 (685 mg, 2.19 mmol, 44% yield) as yellow solid.

Compounds 35 and 12: To a stirred suspension of 34 (0.393 g, 1.26 mmol) in DCM (3.0 ml) was added 2,6-lutidine (0.437 ml, 3.78 mmol) followed by cooling to 1-2° C. A solution of trifluoromethanesulfonic anhydride (0.275 ml, 1.64 mmol) in DCM (1.0 ml) was added while maintaining the temperature below 4° C. The reaction mixture was stirred at 2-3° C. for 1 h, poured into a pre-chilled (5° C.) mixture of MTBE (20 ml) and 1 M HCl (6.3 ml). The resultant, separated organic layer was washed with 9 wt % $NaHCO_3$ (3 g), 20 wt % NaCl (5 g), dried over $Na_2SO_4$ (2 g) for 1 h, filtered and concentrated to give crude 8-cyano-1-(phenylsulfonyl)-1,2-dihydroquinolin-5-yl trifluoromethane-sulfonate, 35 as a yellow oil. 35 was dissolved in NMP (2.5 ml) and DIPEA (1.75 ml, 10.1 mmol) followed by 11 (0.446 g, 2.02 mmol) and resultant mixture was heated at 125° C. overnight. The completed reaction was cooled to rt and partitioned between EtOAc (30 ml) and water (10 ml). The organic layer was washed with water (10 ml), concentrated and purified over a silica gel plug column (eluting with n-heptane/EtOAc 1:1) to provide 5-((2R,6R)-2-((benzyloxy)methyl)-6-methylmorpholino)-quinoline-8-carbonitrile, 12 (80.2 mg, 0.215 mmol, 17% yield) as brownish solid.

synthesis of Compound 36—scheme 9: To a stirred suspension of 13 (10.97 g, 38.72 mmol) in DCM (44 mL) was added 2,6-lutidine (5.38 mL, 46.5 mmol) followed by cooling to 0° C. A solution of trifluoromethanesulfonic anhydride (Tf2O; 6.84 mL, 40.7 mmol) in DCM (22 mL) was added while maintaining the temperature at <5° C. and stirring for 1 h. The completed reaction was quenched with saturated sodium bicarbonate (65 g) and the mixture was warmed up to 15° C. The layers were separated and the aqueous layer was extracted with DCM (55 mL). The combined organic layers were washed with 20 wt % NaCl (33 g) and stirred over Florisil (11 g) for 1.5 h after which time the mixture was filtered, eluted with MTBE (55 mL) and concentrated. The tan solid was suspended in DCM (11 ml), diluted with n-heptane (110 ml), filtered, rinsed with n-heptane/DCM 10:1 (121 ml), and dried under vacuum to provide ((2R,6R)-4-(8-cyanoquinolin-5-yl)-6-methylmorpholin-2-yl)methyl trifluoromethanesulfonate, 36 (15.20 g, 36.6 mmol, 94% yield) as light tan solid.

synthesis of ER-887927 using Schemes 9 and 17:

Scheme 17

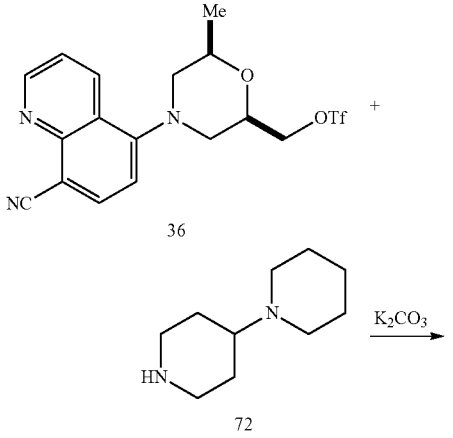

-continued

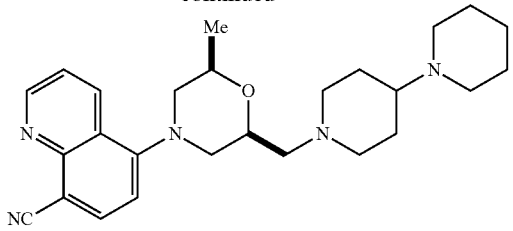

ER-887927

To a stirred suspension of 36 (1.002 g, 2.412 mmol) in acetonitrile (6.0 mL) was added potassium carbonate (1.33 g, 9.65 mmol) followed by commercially available 1,4'-bipiperidine, 72 (609 mg, 3.62 mmol). The reaction mixture was heated at reflux for 5 h after which time the completed reaction was cooled to rt, diluted with water (12 mL) and partially concentrated. N-Heptane (10 mL) and MTBE (10 mL) were added and the mixture was partially concentrated upon which time a brownish solid thus formed was collected by filtration, rinsed with: (1) water (15 mL) and (2) n-heptane (15 mL), and dried under vacuum overnight. The dried solid was dissolved in n-heptane (10 mL, 0.2 mol), diluted with acetonitrile (5.0 mL, 0.096 mol) then treated with Florisil (0.50 g) at rt for 10 min. The mixture was filtered, eluted with acetonitrile (10 mL) and concentrated to give tan solid, which was triturated with MTBE/n-heptane 1:2 (15 ml), filtered, rinsed with MTBE/n-heptane 1:3 (10 ml) and dried under $N_2$/vacuum to give ER-887927 as light tan powder (1.001 g, 2.31 mmol, 95% yield).

ER-893881 (15.2 mg, 0.037 mmol, 51.6% yield) was prepared by a similar method described for ER-887927 starting with 36 (30 mg, 0.072 mmol) and (S)-1,3'-bipyrrolidine dihydrochloride (20.5 mg, 0.144 mmol) using TEA (0.020 mL, 0.141 mmol) instead of $K_2CO_3$.

ER-894483 (30 mg, 0.079 mmol, 32.8% yield) was prepared by a similar method described for ER-893881 starting with 36 (100 mg, 0.241 mmol) and (R)-3-methylpiperazin-2-one (54.9 mg, 0.481 mmol).

ER-894484 (30 mg, 0.079 mmol, 32.8% yield) was prepared by a similar method described for ER-893881 starting with 36 (100 mg, 0.241 mmol) and (S)-3-methylpiperazin-2-one (54.9 mg, 0.481 mmol).

ER-894504 (30 mg, 0.076 mmol, 31.5% yield) was prepared by a similar method described for ER-893881 starting with 36 (100 mg, 0.241 mmol) and (2S,5R)-2,5-dimethylpiperazine (54.9 mg, 0.481 mmol).

ER-894505 (30 mg, 0.076 mmol, 31.5% yield) was prepared by a similar method described for ER-893881 starting with 36 (100 mg, 0.241 mmol) and 2,3-dimethylpiperazine (54.9 mg, 0.481 mmol).

ER-894655 (140 mg, 0.309 mmol, 64.2% yield) was prepared by a similar method described for ER-893881 starting with 36 (200 mg, 0.482 mmol) and tert-butyl 2,2-dimethylpiperazine-1-carboxylate (206 mg, 0.961 mmol). The Boc-protecting group was hydrolyzed using 4 N HCl dioxane followed by isolation of the desired product by azeotroping to dry with toluene and drying under vacuo.

ER-894151 (1.066 g, 3.16 mmol, 65.4% yield) was prepared by a similar method described for ER-893881 starting with 36 (2.0 g, 4.81 mmol) and tert-butyl azetidin-3-ylcarbamate (0.995 g, 5.78 mmol). The Boc-protected intermediate was deprotected using TFA (3 mL) in DCM (3 mL). The reaction was allowed to stir for 30 m, after which time the reaction was concentrated to dry with azeotroping three times with toluene (5 mL each). The residue was diluted with DCM (10 mL), washed two times with sat. $NaHCO_3$ (5 mL), water (5 mL), brine (5 mL), dried over $MgSO_4$, filtered, concentrated and dried in vacuo to provide the desired product.

ER-890250: To a cooled stirring solution of ER-887927 (50 mg, 0.115 mmol) in THF (1 mL) at −78° C. was added 1.6 M methyl lithium-lithium bromide complex in ethyl ether (0.15 mL, 0.24 mmol) whereupon the pale yellow solution was changed to bright red/orange. The reaction mixture was stirred for 1.5 h at −78° C. after which time it was quenched with aqueous ammonium hydroxide (2 mL) followed by slowly warming to rt. The reaction was extracted three times with DCM (5 mL) and the combined organic layers were dried over, filtered and concentrated to dry.

The crude intermediate was dissolved in acetone (1 mL) followed by a solution of ceric ammonium nitrate (300 mg, 0.547 mmol) in water (1.5 mL). The reaction mixture was stirred for 30 min after which time the reaction mixture was concentrated to a crude solid. The solid was suspended in acetone 5 mL, stirred for 5 min, filtered and the solid filter pad eluted three times with acetone (5 mL each). The combined filtrates were concentrated in then purified by reverse-phase HPLC (X-Bridge C18 19×100 mm column using a acetonitrile/water gradient containing 0.1% formic acid). The desired fractions were combined, concentrated, dissolved in MeOH (2 mL), passed over a $SiCO_3$ column, eluted two times with MeOH, concentrated and dried in vacuo to provide ER-890250 (4.4 mg, 0.010 mmol, 8.5% yield).

synthesis of ER-884884 from Scheme 10:

Compound 37: To a stirred solution of 22 from Scheme 6 (1.003 g, 3.121 mmol) in EtOH (5 mL) was added 5% Pd on carbon (100 mg) followed by charging the flask several times with hydrogen gas. The reaction was heated to 40° C. maintaining a hydrogen atmosphere (balloon pressure) and stirred overnight, after which time the reaction was purged with nitrogen gas several times while evacuating the system with house vacuum between purges. The completed reaction was filtered over Celite 545, the filter pad washed two times with EtOH (5 mL each), followed by concentration of the combined filtrates were concentrated and dried in vacuo. The crude product, (3R,5S)-tert-butyl 3-(hydroxymethyl)-5-methylpiperidine-1-carboxylate (0.720 g, 3.114 mmol, 99.8% yield) was used in the next step without further purification.

To a stirred solution of (3R,5S)-tert-butyl 3-(hydroxymethyl)-5-methylpiperidine-1-carboxylate (0.783 g, 3.385 mmol) in DCM (5 mL) was added p-toluenesulfonyl chloride (0.968 g, 5.078 mmol) followed by DMAP (40 mg, 0.33 mmol) and DIPEA (1.18 mL, 6.77 mmol) at rt. The reaction mixture was stirred at rt for 3 h after which time water (5 mL) was added followed by stifling an additional 15 min. The resultant organic layer was washed with 0.1 N HCl (5 mL), brine (3 mL), dried over $MgSO_4$, filtered and concentrated to dryness. The crude product was purified over silica gel (Biotage, eluting with 3:1 heptanes: EtOAc) to provide (3S,5R)-tert-butyl 3-methyl-5-((tosyloxy)methyl)piperidine-1-carboxylate (0.8602 g, 2.232 mmol, 65.9% yield).

To a stirred solution of (3S,5R)-tert-butyl 3-methyl-5-((tosyloxy)methyl)piperidine-1-carboxylate (0.860 g, 2.232 mmol) in DMF (7 mL) at rt was added sodium azide (0.218 g, 3.347 mmol) after which time the reaction was warmed to 80° C. and stirred an additional 3 h. The completed reaction was cooled to rt, diluted with EtOAc (25 mL) and washed three times with water (5 mL each). The resultant organic layer was dried over anhydrous $Na_2SO_4$, filtered, concentrated after which time the crude product was purified over silica gel (Biotage eluting with 0 to 15% EtOAc in heptane gradient) to provide (2R,6R)-tert-butyl 2-(azidomethyl)-6-methylmorpholine-4-carboxylate, 37 (0.545 g, 2.126 mmol, 95.3% yield) as a colorless crystalline solid after concentration of the desired combined fractions and drying in vacuo.

ER-884884: To a stirred solution of 37 (0.545 g, 2.126 mmol) in MeOH (5 mL) was added 5% palladium on activated carbon (250 mg) followed by charging the flask several times with hydrogen gas. The reaction was maintaining under a hydrogen atmosphere (balloon pressure) at rt and stirred for 12 h, after which time the reaction was purged with nitrogen gas several times while evacuating the system with house vacuum between purges. The completed reaction was filtered over Celite 545, the filter pad washed two times with EtOH (2 mL each), followed by concentration of the combined filtrates were concentrated and dried in vacuo. The crude product, (2S,6R)-tert-butyl 2-(aminomethyl)-6-methylmorpholine-4-carboxylate (0.489 g, 2.10 mmol, 99.9% yield) was used in the next step without further purification.

To a stirred solution of (2S,6R)-tert-butyl 2-(aminomethyl)-6-methylmorpholine-4-carboxylate (50.2 mg, 0.218 mmol) in DCM (0.5 mL) was added TFA (0.25 mL, 3.4 mmol) at rt. The reaction mixture was stirred for 1 h after which time it was concentrated and azeotroped to dry two times with toluene (2 mL each) and dried in vacuo. The crude deprotected morpholine was dissolved with stirring in DMA (1 mL) followed by TEA (2 mL) and compound 3 (50 mg, 0.214 mmol). The reaction mixture was warmed to 140° C. and stirred for 1 h after which time the completed reaction was cooled to rt and directly injected onto a preparative reverse-phase HPLC column (after filtering) to provide ER-884884 (12.1 mg, 0.043 mmol, 19.7% yield) after concentration of the desired combined fractions and drying under vacuo.

substituted Compound 15, Scheme 10 or ER-879713: To a stirred solution of ER-884884 (30.2 mg, 0.107 mmol) in DCM (0.5 mL) was added TEA (30 uL, 0.20 mmol) followed by 2,2-dimethylpropanoyl chloride (20 uL, 0.162 mmol). The reaction mixture was stirred at rt for 3 h after which time the completed reaction was concentrated, filtered, and purified directly via preparative reverse-phase HPLC (Water's X-Bridge C18 19×100 mm column; eluted with a gradient of acetonitrile in water containing 0.05% TFA) to provide ER-879713 (20.5 mg, 0.056 mmol, 52.3% yield) after concentration of the desired combined fractions and drying under vacuo.

ER-886432 (10.2 mg, 0.023 mmol, 52.7% yield) was obtained using a similar process to ER-879713 starting with ER-884884 (50 mg, 0.177 mmol) and 1-phenylcyclobutanecarbonyl chloride (8.5 mg, 0.044 mmol).

ER-886563 (3.6 mg, 0.023 mmol, 20.3% yield) was obtained using a similar process to ER-879713 starting with ER-884884 (12.4 mg, 0.044 mmol) and benzeneacetyl chloride (0.007 mL, 0.053 mmol).

ER-888137: To a stirred solution of ER-884884 (30.2 mg, 0.107 mmol) in NMP(0.5 mL) was added 2-chloro-5-fluoropyrimidine (140 mg, 1.056 mmol). The reaction mixture was microwaved at 150° C. for 5 min, after which time the cooled reaction was purified over a C-18 reverse-phase HPLC preparative column eluting with a 10 to 40% acetonitrile in water gradient. The desired fractions were concentrated and dried under vacuo to provide ER-888137 (6.5 mg, 0.017 mmol, 9.7% yield).

ER-888701 (12.2 mg, 0.031 mmol, 17.7% yield) was prepared in a similar manner to ER-888137 starting with ER-884884 (50 mg, 0.177 mmol) and 2-chloro-5-ethylpyrimidine (150 mg, 1.052 mmol).

ER-888896 (3.0 mg, 0.008 mmol, 23.1% yield) was prepared in a similar manner to ER-888137 starting with ER-884884 (10.1 mg, 0.036 mmol) and 2-chloropyrazine (30 mg, 0.261 mmol).

Scheme 18:
Alternative Route to Substituted Compound 15:

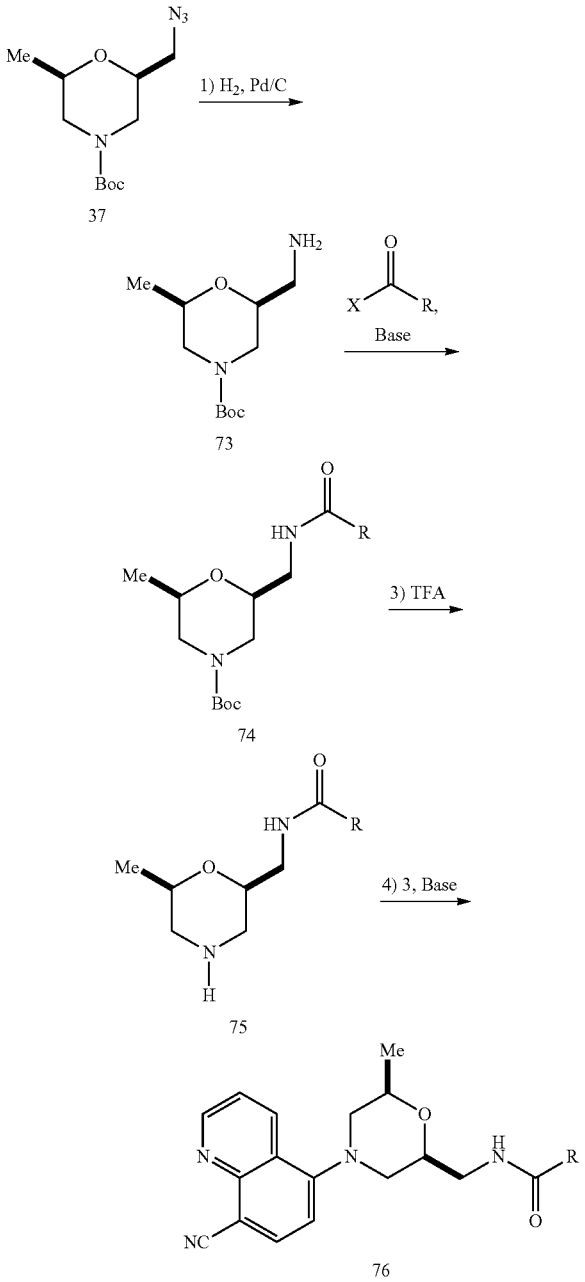

[15 R = H, R2 = —C(O)R]

ER-879713 or Compound 76 using Scheme 18:

Compound 73: To a stirred solution of 37 (0.545 g, 2.126 mmol) in MeOH (5 mL) was added 5% palladium on activated carbon (250 mg) followed by charging the flask several times with hydrogen gas. The reaction was maintaining under a hydrogen atmosphere (balloon pressure) at rt and stirred for 12 h, after which time the reaction was purged with nitrogen gas several times while evacuating the system with house vacuum between purges. The completed reaction was filtered over Celite 545, the filter pad washed two times with EtOH (2 mL each), followed by concentration of the combined filtrates were concentrated and dried in vacuo. The crude product, (2S,6R)-tert-butyl 2-(aminomethyl)-6-methylmorpholine-4-carboxylate, 73 (0.489 g, 2.10 mmol, 99.9% yield) was used in the next step without further purification.

Compound 74: To a stirred solution of 73 (50.2 mg, 0.218 mmol) in DCM (0.5 mL)) was added TEA (36.5 uL, 0.268 mmol) followed by 2,2-dimethylpropanoyl chloride (29.5 uL, 0.235 mmol). The reaction mixture was stirred at rt for 1 h after which time the completed reaction was poured over water, extract three times with DCM (3 mL each) and the combined organic layers were dried over $MgSO_4$, filtered, concentrated, and dried under vacuo to provide crude (2R, 6S)-tert-butyl 2-methyl-6-(pivalamidomethyl)morpholine-4-carboxylate, 74 (R=tBu).

ER-879713: To as stirred solution of crude 74 in DCM (5 mL) was added TFA (0.25 mL, 3.4 mmol) followed by stirring at rt for 1 h. The completed reaction was concentrated and azeotroped two times with toluene and then dried in vacuo for 30 min, after which time the crude, advanced intermediate, 75, was dissolved in DMA (1 mL) followed by TEA (2 mL) and compound 3 (50 mg, 0.214 mmol). The reaction mixture was warmed to 140° C. and stirred for 1 h after which time the completed reaction was cooled to rt and directly injected onto a preparative reverse-phase HPLC column (after filtering) to provide an example of 76 or ER-879713 (9.3 mg, 0.025 mmol, 11.6% yield, R=tBu) after concentration of the desired combined fractions and drying under vacuo.

ER-879689 (4.3 mg, 0.013 mmol, 6.0% yield, R=Me) was obtain using a similar process to ER-879713 starting with 73 (50.2 mg, 0.218 mmol, R=Me) and 3 (50 mg, 0.215 mmol).

ER-886360 (14.3 mg, 0.035 mmol, 15.8% yield, R═CH(Me)Ph) was obtain using a similar process to ER-879713 starting with 73 (50.2 mg, 0.218 mmol, R═CH(Me)Ph) and 3 (50 mg, 0.215 mmol).

Additional examples of substituted Compound 15:

ER-888603: To stirred solution of 37 (58.1 mg, 0.227 mmol) and cyclohexylacetylene (0.026 mL, 0.200 mmol) in tert-butyl alcohol (0.08 mL) and water (0.07 mL) was added sodium bicarbonate (2.5 mg, 0.030 mmol) followed by copper(II) sulfate pentahydrate (2.5 mg, 0.010 mmol) and sodium ascorbate (7.8 mg, 0.039 mmol). The reaction mixture was stirred at rt for 14 h after which time DCM (5 mL) and saturated sodium bicarbonate (5 mL) was added and stirred an additional 10 min. The layers were separated and the aqueous layer was extracted two times with DCM (3 mL each). The combined organic layers were dried over anhydrous $MgSO_4$, filtered and concentrated to dry. The crude Boc-protected intermediate was dissolved with stirring in DCM (3 mL) followed by TFA (0.8 mL). The reaction was stirred at rt for 1 h after which time the completed reaction was concentrated and azeotroped to dryness using toluene (2 times @ 5 mL each). The crude product was purified via HPLC (Water's X-Bridge C18 19×100 mm column; eluted with a gradient of acetonitrile in water containing 0.05% TFA) to provide (2R,6R)-2-((4-cyclohexyl-1H-1,2,3-triazol-1-yl)methyl)-6-methylmorpholine (8.9 mg, 0.034 mmol, 16.8% yield)

To a stirred solution of (2R,6R)-2-((4-cyclohexyl-1H-1,2,3-triazol-1-yl)methyl)-6-methylmorpholine (8.9 mg, 0.034 mmol) in DMA (0.3 mL) and TEA (0.005 mL, 0.036 mmol) was added 3 (7.85 mg, 0.034 mmol). The mixture was microwaved at 150° C. for 30 min after which time the cooled reaction was directly injected onto a preparative, C-18 reverse phase HPLC column (Water's X-Bridge C18 19×100 mm column; eluting with a gradient of 10-40% acetonitrile in water containing 0.05% TFA). The desired collected fractions were concentrated and dried in vacuo to provide ER-888603 (3.3 mg, 0.008 mmol, 23.3% yield or a 3.9% overall yield).

ER-888604 (5.2 mg, 0.013 mmol, 6.5% overall yield) was prepared in a similar manner to ER-888603 starting with 37 (58.1 mg, 0.227 mmol), phenylacetylene (0.022 mL, 0.200 mmol) and 3 (7.85 mg, 0.034 mmol).

ER-889556: To a stirred suspension of ER-887268 (140.3 mg, 0.384 mmol) in water (1.5 mL) was added formaldehyde (1 mL) and formic acid (0.55 mL) after which time the reaction mixture was microwaved at 110° C. for 1.5 h. The completed reaction was cooled and directly injected onto a preparative, C-18 reverse phase HPLC column eluting with a gradient of 10-40% acetonitrile in water containing 0.1% TFA. The desired collected fractions were concentrated, dissolved in MeOH (5 mL), passed over a plug of $SiCO_3$ eluting with MeOH (10 mL), concentrated and dried in vacuo to provide ER-889556 (75 mg, 0.197 mmol, 51.5% yield).

ER-890114 (75.9 mg, 0.170 mmol, 40.5% yield) was prepared in a similar manner to ER-889556 starting with ER-890112 (182 mg, 0.420 mmol).

ER-890108 (72.1 mg, 0.171 mmol, 40.7% yield) was prepared in a similar manner to ER-889556 starting with ER-890119 (170.6 mg, 0.420 mmol).

ER-890345 (43.5 mg, 0.115 mmol, 38% yield) was prepared in a similar manner to ER-889556 starting with ER-890344 (110.2 mg, 0.302 mmol).

ER-890346 (52.6 mg, 0.139 mmol, 73.3% yield) was prepared in a similar manner to ER-889556 starting with ER-887269 (69 mg, 0.189 mmol).

ER-890831 (85.2 mg, 0.225 mmol, 74.5% yield) was prepared in a similar manner to ER-889556 starting with ER-887270 (110.2 mg, 0.302 mmol).

ER-890964 (506.2 mg, 1.286 mmol, 71.2% yield) was prepared in a similar manner to ER-889556 starting with ER-890963 (685.2 mg, 1.806 mmol).

ER-890186 (10.2 mg, 0.023 mmol, 20.7% yield) was prepared in a similar manner to ER-889556 starting with ER-890107 (48 mg, 0.111 mmol).

ER-890223 (35 mg, 0.078 mmol, 42.9% yield) was prepared in a similar manner to ER-889556 starting with ER-890106 (100 mg, 0.182 mmol) as the TFA salt.

ER-894656 (31.7 mg, 0.068 mmol, 61.5% yield) was prepared in a similar manner to ER-889556 starting with ER-894655 (50 mg, 0.111 mmol) as the dihydrochloride salt.

ER-889728: To a stirred solution of ER-888070 (12.5 mg, 0.034 mmol) in DCM (0.5 mL) was added TEA (0.01 mL, 0.072 mmol) followed by nicotinoyl chloride (10 mg, 0.071 mmol). The reaction mixture was stirred at rt for 1 h after which time the reaction was diluted with DCM (5 mL), washed with water (2 mL), brine (2 mL), dried over $MgSO_4$, filtered and concentrated to dry. The crude product was purified over a preparative, C-18 reverse phase HPLC column eluting with a gradient of 10-25% acetonitrile in water containing 0.1% TFA. The desired collected fractions were concentrated, dissolved in MeOH (5 mL), passed over a plug of $SiCO_3$ eluting with MeOH (10 mL), concentrated and dried in vacuo to provide ER-889728 (7.2 mg, 0.015 mmol, 45% yield).

ER-889729 (8.2 mg, 0.017 mmol, 51.3% yield) was prepared in a similar manner to ER-889728 starting with ER-888070 (12.5 mg, 0.034 mmol) and isonicotinoyl chloride (10 mg, 0.071 mmol).

ER-889734 (8.6 mg, 0.018 mmol, 52.9% yield) was prepared in a similar manner to ER-889728 starting with ER-888070 (12.5 mg, 0.034 mmol) and picolinoyl chloride (10 mg, 0.071 mmol).

ER-889744 (12 mg, 0.028 mmol, 80.8% yield) was prepared in a similar manner to ER-889728 starting with ER-888070 (12.5 mg, 0.034 mmol) and hexanoyl chloride (9 mg, 0.067 mmol).

ER-889745 (8 mg, 0.018 mmol, 54% yield) was prepared in a similar manner to ER-889728 starting with ER-888070 (12.5 mg, 0.034 mmol) and isobutyryl chloride (7 mg, 0.066 mmol).

ER-889746 (7.6 mg, 0.017 mmol, 50% yield) was prepared in a similar manner to ER-889728 starting with ER-888070 (12.5 mg, 0.034 mmol) and 2,2-dimethylpropanoyl chloride (8 mg, 0.066 mmol).

ER-890113 (25.6 mg, 0.054 mmol, 66.7% yield) was prepared in a similar manner to ER-889728 starting with ER-890112 (35.2 mg, 0.081 mmol) and acetic anhydride (0.093 mL, 0.984 mmol).

ER-890120 (20.3 mg, 0.045 mmol, 54.2% yield) was prepared in a similar manner to ER-889728 starting with ER-890119 (33.7 mg, 0.083 mmol) and acetic anhydride (0.012 mL, 0.127 mmol).

ER-890122 (35.2 mg, 0.069 mmol, 43.1% yield) was prepared in a similar manner to ER-889728 starting with ER-890119 (65.2 mg, 0.160 mmol) and benzoyl chloride (0.037 mL, 0.318 mmol).

ER-890142 (45.2 mg, 0.084 mmol, 53.1% yield) was prepared in a similar manner to ER-889728 starting with ER-890112 (68.5 mg, 0.158 mmol) and benzoyl chloride (0.037 mL, 0.318 mmol).

ER-890187 (9.4 mg, 0.020 mmol, 18.0% yield) was prepared in a similar manner to ER-889728 starting with ER-890107 (48 mg, 0.111 mmol) and acetic anhydride (0.125 mL, 1.3 mmol).

ER-890188 (8.9 mg, 0.018 mmol, 16.0% yield) was prepared in a similar manner to ER-889728 starting with ER-890107 (48 mg, 0.111 mmol) and isobutyryl chloride (0.051 mL, 0.487 mmol).

ER-890189 (10 mg, 0.019 mmol, 16.7% yield) was prepared in a similar manner to ER-889728 starting with ER-890107 (48 mg, 0.111 mmol) and benzoyl chloride (0.056 mL, 0.482 mmol).

ER-890190 (6.5 mg, 0.014 mmol, 36.8% yield) was prepared in a similar manner to ER-889728 starting with ER-890119 (15.6 mg, 0.038 mmol) and isobutyryl chloride (0.006 mL, 0.058 mmol).

ER-890219 (32.0 mg, 0.067 mmol, 91.8% yield) was prepared in a similar manner to ER-889728 starting with ER-890106 (40.2 mg, 0.073 mmol) as the TFA salt, TEA (0.20 mL, 1.43 mmol) and acetic anhydride (0.10 mL, 1.06 mmol).

ER-890221 (28.2 mg, 0.056 mmol, 76.7% yield) was prepared in a similar manner to ER-890219 starting with ER-890106 (40.2 mg, 0.073 mmol) as the TFA salt and isobutyryl chloride (0.080 mL, 0.764 mmol).

ER-890222 (30.1 mg, 0.056 mmol, 76.7% yield) was prepared in a similar manner to ER-890219 starting with ER-890106 (40.5 mg, 0.074 mmol) as the TFA salt and benzoyl chloride (0.20 mL, 1.723 mmol).

ER-892254 (24.2 mg, 0.0.52 mmol, 67.5% yield) was prepared in a similar manner to ER-889728 starting with ER-892253 (32.2 mg, 0.077 mmol) and acetic anhydride (0.015 mL, 0.151 mmol). Acetonitrile (0.5 mL) was added to the reaction mixture.

ER-892256 (25.2 mg, 0.052 mmol, 41.9% yield) was prepared in a similar manner to ER-889728 starting with ER-890119 (50.2 mg, 0.124 mmol) and methanesulfonyl chloride (0.011 mL, 0.142 mmol).

ER-893926 (124.2 mg, 0.255 mmol, 51.7% yield) was prepared in a similar manner to ER-889728 starting with ER-888070 (180.2 mg, 0.493 mmol) and 1,3-dimethyl-1H-pyrazole-4-carbonyl chloride (93.8 mg, 0.592 mmol).

ER-893927 (45.2 mg, 0.0.83 mmol, 57.8% yield) was prepared in a similar manner to ER-889728 starting with ER-892253 (60.5 mg, 0.144 mmol) and 1,3-dimethyl-1H-pyrazole-4-carbonyl chloride (27.4 mg, 0.173 mmol).

ER-893948 (65.3 mg, 0.147 mmol, 29.9% yield) was prepared in a similar manner to ER-889728 starting with ER-888070 (180.2 mg, 0.493 mmol) and methanesulfonyl chloride (68 mg, 0.593 mmol).

ER-894149 (67.2 mg, 0.133 mmol, 80.6% yield) was prepared in a similar manner to ER-889728 starting with ER-888070 (60.2 mg, 0.165 mmol) and benzenesulfonyl chloride (0.023 mL, 0.180 mmol).

ER-894150 (58.2 mg, 0.111 mmol, 69.9% yield) was prepared in a similar manner to ER-889728 starting with ER-888070 (58.2 mg, 0.159 mmol) and 4-fluorobenzenesulfonyl chloride (0.025 mL, 0.188 mmol).

ER-894152 (36.2 mg, 0.095 mmol, 63.6% yield) was prepared in a similar manner to ER-889728 starting with ER-894151 (50.6 mg, 0.150 mmol) and acetic anhydride (0.014 mL, 0.135 mmol).

ER-894153 (5.4 mg, 0.012 mmol, 7.4% yield) was prepared in a similar manner to ER-889728 starting with ER-894151 (52.2 mg, 0.155 mmol) and 4-fluorobenzenzoyl chloride (25 mg, 0.158 mmol).

ER-894154 (38.5 mg, 0.093 mmol, 62.4% yield) was prepared in a similar manner to ER-889728 starting with ER-894151 (50.4 mg, 0.149 mmol) and methanesulfonyl chloride (0.012 mL, 0146 mmol).

ER-894155 (42.1 mg, 0.085 mmol, 57.1% yield) was prepared in a similar manner to ER-889728 starting with ER-894151 (50.3 mg, 0.149 mmol) and 4-fluorobenzenesulfonyl chloride (29 mg, 0.149 mmol).

ER-894159 (20.4 mg, 0.041 mmol, 27.4% yield) was prepared in a similar manner to ER-889728 starting with ER-894151 (50.5 mg, 0.150 mmol) and 1,3-dimethyl-1H-pyrazole-4-sulfonyl chloride (29 mg, 0.149 mmol).

ER-894160 (47.2 mg, 0.0.90 mmol, 65.8% yield) was prepared in a similar manner to ER-889728 starting with ER-888070 (50.1 mg, 0.137 mmol) and 1,3-dimethyl-1H-pyrazole-4-sulfonyl chloride (27 mg, 0.139 mmol).

ER-894206 (11.3 mg, 0.029 mmol, 19% yield) was prepared in a similar manner to ER-889728 starting with ER-894151 (50.6 mg, 0.150 mmol) and isobutyryl chloride (16. mg, 0.150 mmol).

ER-894594 (215 mg, 0.487 mmol, 46.4% yield) was prepared in a similar manner to ER-889728 starting with ER-894151 (354 mg, 1.049 mmol) and benzoic anhydride (407 mg, 1.81 mmol). Acetonitrile (2 mL) was used instead of DCM.

Preparation of ER-890252: To a stirred solution of 36 (2.0 g, 4.8 mmol) from Scheme 9 in acetonitrile (15 mL) was added (R)-tert-butyl pyrrolidin-2-ylcarbamate (1.10 g, 5.9 mmol) followed by TEA (1.6 mL, 11.5 mmol). The reaction was stirred at 70° C. for 3 h after which time the completed reaction was concentrated to a crude syrup, diluted with DCM (20 mL), washed with water (5 mL), dried over, filtered and concentrated to dryness. The crude product was purified over silica gel (Biotage SP4, 40+M, eluting with a gradient of 5% MeOH in 1:1 EtOAc:DCM to 10% MeOH in 1:1 EtOAc:DCM over a 10 column volume cycle. The product containing fractions were combined, concentrated and dried under vacuo to provide tert-butyl((R)-1-(((2S,6R)-4-(8-cyanoquinolin-5-yl)-6-methylmorpholin-2-yl)methyl) pyrrolidin-3-yl)carbamate (1.35 g, 3.0 mmol, 62% yield).

To a stirred solution of tert-butyl((R)-1-(((2S,6R)-4-(8-cyanoquinolin-5-yl)-6-methylmorpholin-2-yl)methyl)-pyrrolidin-3-yl)carbamate (1.35 g, 3.0 mmol) in DCM (10 mL) was added TFA (8.1 mL). The reaction was stirred at rt after which time it was concentrated and azeotroped to dryness three times with toluene (10 mL each) and then dried under vacuo to provide crude 5-((2S,6R)-2-(((R)-3-aminopyrrolidin-1-yl)methyl)-6-methylmorpholino)quinoline-8-carbonitrile (1.39 g, 3.0 mmol, 100% yield) as the TFA salt.

ER-890252 (120.3 mg, 0.306 mmol, 71.2% yield) was prepared in a similar manner to ER-890222 starting with 5-((2S,6R)-2-(((R)-3-aminopyrrolidin-1-yl)methyl)-6-methylmorpholino)-quinoline-8-carbonitrile (200 mg, 0.430 mmol) as the TFA salt and acetic anhydride (0.80 mL, 8.46 mmol).

ER-890253 (146.5 mg, 0.348 mmol, 80.8% yield) was prepared in a similar manner to ER-890122 starting with 5-((2S,6R)-2-(((R)-3-aminopyrrolidin-1-yl)methyl)-6-methylmorpholino)-quinoline-8-carbonitrile (200 mg, 0.430 mmol) as the TFA salt and isobutyryl chloride (0.50 mL, 4.77 mmol).

ER-894544 (103.6 mg, 0.227 mmol, 52.9% yield) was prepared in a similar manner to ER-890122 starting with 5-((2S,6R)-2-(((R)-3-aminopyrrolidin-1-yl)methyl)-6-methylmorpholino)-quinoline-8-carbonitrile (200 mg, 0.430 mmol) as the TFA salt and benzoyl chloride (0.50 mL, 4.31 mmol).

ER-894546 (96.7 mg, 0.214 mmol, 49.8% yield) was prepared in a similar manner to ER-890222 starting with 5-((2S,6R)-2-(((S)-3-aminopyrrolidin-1-yl)methyl)-6-methylmorpholino)-quinoline-8-carbonitrile (200 mg, 0.430 mmol) as the TFA salt and acetic anhydride (0.80 mL, 8.46 mmol). 5-((2S,6R)-2-(((S)-3-aminopyrrolidin-1-yl)methyl)-6-methylmorpholino)-quinoline-8-carbonitrile was prepared in a similar manner to 5-((2S,6R)-2-(((R)-3-aminopyrrolidin-1-yl)methyl)-6-methylmorpholino)quinoline-8-carbonitrile using (S)-tert-butyl pyrrolidin-2-ylcarbamate as the starting material in the first step described above for the preparation of ER-890252.

ER-894547 (120.8 mg, 0.287 mmol, 66.7% yield) was prepared in a similar manner to ER-894546 starting with 5-((2S,6R)-2-(((S)-3-aminopyrrolidin-1-yl)methyl)-6-methylmorpholino)-quinoline-8-carbonitrile (200 mg, 0.430 mmol) as the TFA salt and isobutyric anhydride (0.70 mL, 4.22 mmol).

ER-894548 (110.4 mg, 0.242 mmol, 56.4% yield) was prepared in a similar manner to ER-894546 starting with 5-((2S,6R)-2-(((S)-3-aminopyrrolidin-1-yl)methyl)-6-methylmorpholino)-quinoline-8-carbonitrile (200 mg, 0.430 mmol) as the TFA salt and benzoic anhydride (0.50 g, 2.21 mmol).

ER-894545 (32 mg, 0.084 mmol, 19.6% yield) was prepared in a similar manner to ER-889556 starting with 5-((2S,6R)-2-(((R)-3-aminopyrrolidin-1-yl)methyl)-6-methylmorpholino)-quinoline-8-carbonitrile (200 mg, 0.430 mmol) as the TFA.

ER-894549 (103.8 mg, 0.274 mmol, 63.6% yield) was prepared in a similar manner to ER-889556 starting with 5-((2S,6R)-2-(((S)-3-aminopyrrolidin-1-yl)methyl)-6-methylmorpholino)-quinoline-8-carbonitrile (200 mg, 0.430 mmol) as the TFA.

Preparation of 886355 using modifications to Scheme 7 and Scheme 4: To a stirred solution of (R)-1-amino-3-(benzyloxy)propan-2-ol, Compound 22 in Scheme 7 (8.0 g, 44.1 mmol) in DMF (60 mL) was added (S)-2-chlorobutanoic acid (5.0 g, 40.8 mmol) followed by TEA (10.5 g, 103.8 mmol), DMAP (0.4 g, 3.3 mmol) and finally EDC (9.52 g, 49.7 mmol). The reaction mixture was stirred at rt for 5 d after which time the completed reaction was concentrated to a crude syrup. Purification over silica gel (Biotage, eluting with a gradient of 20-100% EtOAc in heptanes) followed by collection of the desired fractions, concentration and drying in vacuo provided (S)—N—((R)-3-(benzyloxy)-2-hydroxypropyl)-2-chlorobutanamide (683.5 mg, 2.392 mmol, 5.9% yield).

To stirred suspension of sodium hydride (203.1 mg, 5.1 mmol as a 60% oil dispersion) in THF (18 mL) cooled to 0° C. was added dropwise (S)—N—((R)-3-(benzyloxy)-2-hydroxypropyl)-2-chlorobutanamide (362.8 mg, 1.270 mmol) in THF (3.8 mL) over a 5-min period after which the reaction was stirred at 0° C. for 30 min followed by stirring at rt for 5 h. The completed reaction was quenched with the slow addition of IPA (1 mL) followed by adding Dowex 50, H+ form, until a neutral to acidic pH was observed. The final suspension was filtered and the solid was rinsed two times with EtOAc. The combined filtrated were concentrated and the resultant crude product was purified over silica gel (Biotage, eluting with 1:1 EtOAc:heptane). The desired fractions were combined, concentrated and dried in vacuo to provide (2R,6R)-6-((benzyloxy)methyl)-2-ethylmorpholin-3-one (314 mg, 1.260 mmol, 99.2% yield).

To a stirred solution of (2R,6R)-6-((benzyloxy)methyl)-2-ethylmorpholin-3-one (362.2 mg, 1.453 mmol) in THF (2 mL) was added 1 M lithium tetrahydroaluminate in THF (2 mL, 2 mmol) dropwise at rt over a 2-min period. The reaction was stirred at rt for 2.5 h after which time it was cooled to 0° C. followed by a dropwise addition of water (0.6 mL) and then 1 M sodium hydroxide in water (0.04 mL). The quenched reaction was warmed to rt, stirred until a granular solid was formed and filtered over a Celite 545 pad rinsing with EtOAc (5 mL), DCM (5 mL) and ethyl ether (5 mL). The filtrate was concentrated and the resultant crude product was purified over silica gel (Biotage, eluting with a gradient of 5-10% MeOH in DCM) followed by combining the desired fractions, concentration and drying in vacuo to provide (2R,6R)-2-((benzyloxy)methyl)-6-ethylmorpholine (50.2 mg, 0.213 mmol, 14.6% yield).

To a stirred solution of (2R,6R)-2-((benzyloxy)methyl)-6-ethylmorpholine (12.4 mg, 0.053 mmol) and Compound 3 (10.2 mg, 0.044 mmol) in DMA (2 mL) was added DIPEA (0.015 mL, 0.086 mmol) followed by microwaving at 150° C. for 7 h. The cooled completed reaction was directly injected onto a C-18 reverse phase HPLC (Water's X-Bridge C18, 19×100 mm column, eluting with a linear gradient of 10%-90% acetonitrile in water with 0.1% formic acid) and concentrating the desired peak followed by high vacuum to dryness to provide ER-886355 (6.2 mg 0.016 mmol, 36.4% yield).

Preparation of ER-887199: To a stirred solution of (2R,6R)-2-((benzyloxy)methyl)-6-ethylmorpholine (552.2 mg, 2.347 mmol) in MeOH (10 mL) was cycled over 10% $Pd(OH)_2$ column with $H_2$ gas at 1 atmosphere over 16 h using a H-Qube hydrogenation instrument. The completed reaction solution was concentrated and dried in vacuo to provide crude product, ((2R,6R)-6-ethylmorpholin-2-yl)methanol (320 mg, 2.204 mmol, 93.9% yield) that was used in the next step without further purification.

((2R,6R)-6-ethylmorpholin-2-yl)methanol (145.2 mg, 1.00 mmol) and Compound 3 (266.4 mg, 1.143 mmol) in 1-methylpyrrolidin-2-one (2 mL) was microwaved at 180° C. for 15 minutes after which time it was cooled to room temperature and directly injected onto a C-18 reverse phase HPLC (Water's X-Bridge C18, 19×100 mm column, eluting with a linear gradient of 10%-90% acetonitrile in water with 0.1% formic acid) and concentrating the desired peak followed by high vacuum to dryness to provide ER-887199 (92.3 mg 0.313 mmol, 31.3% yield).

Preparation of example ER-899742 using Scheme 11 and 19

Scheme 19

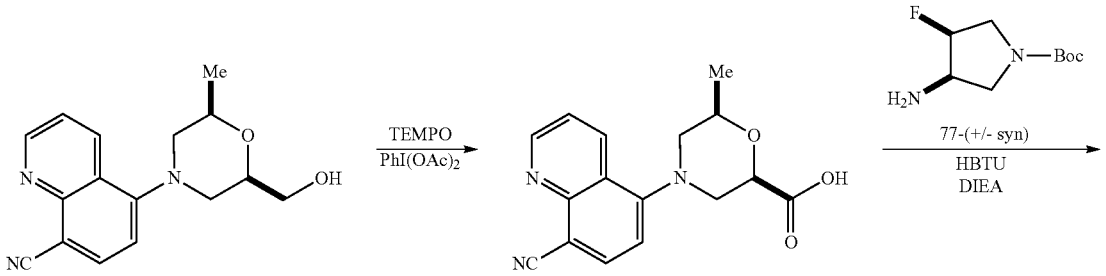

-continued

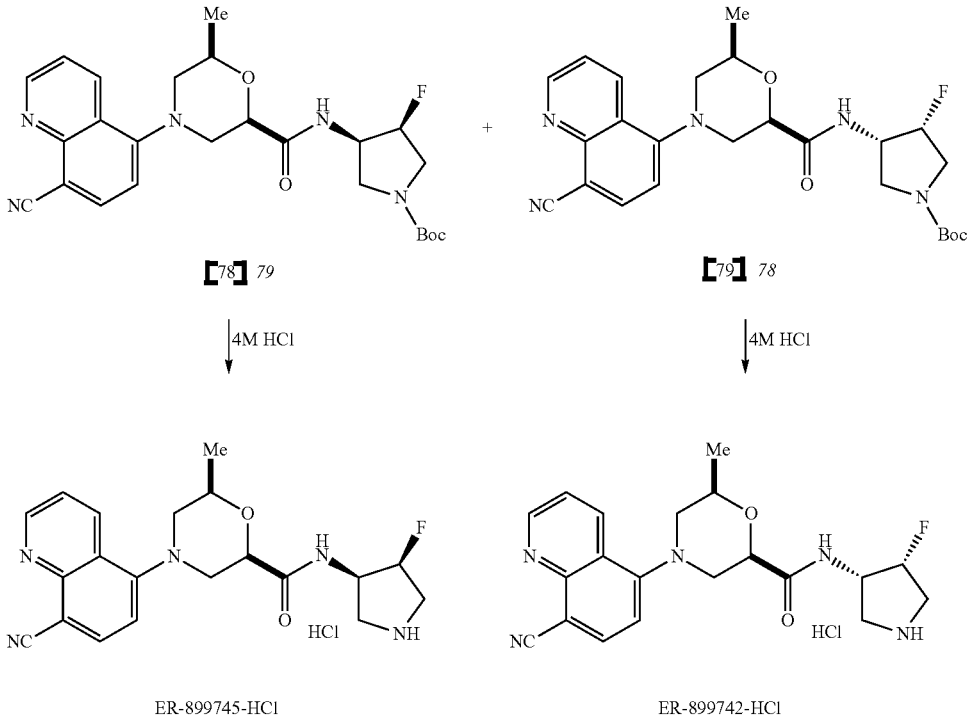

ER-895194 or 38: To a stirred solution of 13 (231.0 g, 815.3 mmol) in DCM (3.93 L) at 0-5° C. was added iodobenzene diacetate (525 g, 1630.6 mmol) while maintaining the temperature at <5° C. TEMPO (25.4 g, 162.8 mmol) was added followed by water (151 mL) after which time the resulting reaction mixture was warmed to 10° C., stirred for 30 minutes and then allowed to warm to rt and stirred for 15 h. The completed reaction was cooled to <15° C. and quenched by the slow addition of 1.34 L of a 10% (w/v) solution of sodium thiosulfate in water while maintaining the reaction temperature ≤15° C. followed by additional stifling at rt for 45 min. The pH of the quenched reaction was adjusted to pH 9 by the slow addition of 1M sodium hydroxide in water while maintaining the temperature at ≤25° C. The stirring layers were separated and the organic layer was washed with water (560 mL). 1-Butanol (2.31 L) was added to the combined aqueous layers after which time the mixture was cooled to 10-15° C. followed by the slow addition of 5 M sulfuric acid (231 mL) maintaining the temperature at ≤25° C. to obtain an approximate pH 5. The resultant layers were separated and the aqueous layer was extracted 3 times with 1-butanol (2.31 L) while maintaining the pH of the aqueous layer approximately pH 5 between extractions. The combined aqueous layers were concentrated while warming to 50-55° C. after which time the resultant yellow solid-slurry was concentrated via azeotroping three times with n-heptane (693 mL each) to a volume of 1.5 L followed by the addition of DCM (2.31 L). The yellow solid suspension was stirred at rt for 1 h followed by filtration, washing the filter pad two times with DCM (462 mL). The collected yellow cake was dried under vacuum) overnight at 40° C. followed by suspending in toluene (1.16 L) and concentrated to complete dryness at 45° C. in vacuo to provide 38 or ER-895194 (187 g, 629 mmol, 77% yield) as a yellow solid.

To a stirred solution of 38 (300 mg, 1.01 mmol) in DCM (2 mL) was added the mixture of (3S,4R)-tert-butyl 3-amino-4-fluoropyrrolidine-1-carboxylate and (3R,4S)-tert-butyl 3-amino-4-fluoropyrrolidine-1-carboxylate, 77 (205.3 mg, 1.005 mmol), HBTU (247 mg, 1.211 mmol) and DIEA (0.70 mL, 4.04 mmol) followed by stifling at rt for 16 h. The was found complete and concentrated to dryness followed by dissolving in EtOAc (20 mL), washed 1 time with water (10 mL), 2 N citric acid in water (10 mL), saturated $NaHCO_3$ (10 mL), and brine (10 mL). The combined aqueous layers were extracted 3 times with EtOAc (10 mL ea.) after which time the combined organic fractions were dried over MgSO4, filtered and concentrated to dry. The crude product was purified over a 25 g Biotage silica gel column eluting with 0-10% MeOH in DCM (200 mL total) to provide the diastereomeric mixture of 78 and 79.

78 and 79 were separated using Chiral Technologies' 5 uM Chiralpak IA column of appropriate size eluting with a Heptane:EtOH:MeOH:DEA (70:15:15:0.1) solvent system. Obtained after concentration and bringing to a dry solid via house vacuum: [72] *78* (95 mg, 0.196 mmol, 19.5% yield) as the first eluted fraction; and [73] *79* (75 mg, 0.155 mmol, 15.4% yield) as the second eluted fraction.

78 (95 mg, 0.196 mmol) was dissolved with stifling in dioxane (17 uL) followed by a dropwise addition of 4 N HCl in dioxane (0.49 mL 1.97 mmol, 10 equivalents) over a 3-minute period at rt. The reaction was stirred for an additional 4 h after which time the completed reaction was concentrated and azeotroped 3 times using toluene (10 mL each) to dryness and then high vacuumed dried to obtain ER-899742-HCl (69 mg, 0.164 mmol, 84% yield) as the HCl salt that did not require further purification.

Indirect determination of the absolute stereochemistry of ER-899742

Scheme 20

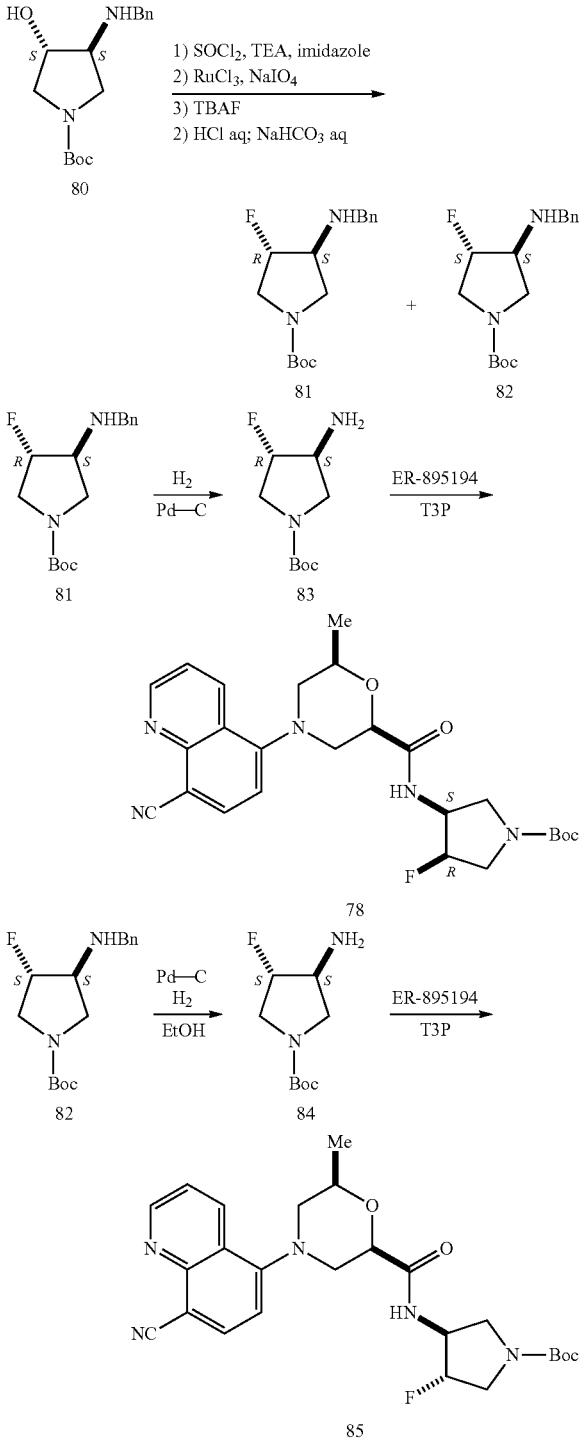

An indirect method was used to determine the absolute stereochemistry of ER-899742 using the confirmed chiral starting material that *was* described by Tsuzuki, et[.] al., in Tetrahedron Asymmetry 2001, 12, [29891] *2989* to provide the chiral compound 81 in Scheme 20.

To a stirred solution of (3S,4S)-tert-butyl 3-(benzylamino)-4-hydroxypyrrolidine-1-carboxylate, 80 (3.091 g, 10.57 mmol) and imidazole (3.60 g, 52.9 mmol) in DCM (185 ml) was added triethylamine (4.42 ml, 31.7 mmol). The resultant mixture was cooled to 1-2° C., and then a solution of thionyl chloride (1.16 ml, 15.9 mmol) in DCM (46 ml) was added dropwise over 30-min period. The mixture was stirred at 1-2° C. for 6 h, warm up to rt and stirred overnight after which time the reaction was quenched with water (46 ml). The organic layer was separated, concentrated to give crude product as white solid/foam, which was subjected to silica gel column chromatography (n-heptane/EtOAc 2:1) to give (3S,6S)-tert-butyl 3-benzyltetrahydropyrrolo[3,4-d][1,2,3]oxathiazole-5(3H)-carboxylate 2-oxide (2.10 g, 6.21 mmol, 58.7% yield) as white solid.

To stirred solution of (3S,6S)-tert-butyl 3-benzyltetrahydropyrrolo[3,4-d][1,2,3]oxathiazole-5(3H)-carboxylate 2-oxide (2.10 g, 6.21 mmol) in 1,2-dichloroethane (10 ml) diluted with acetonitrile (10 ml) and water (10 ml) cooled down to 2-3° C. was added ruthenium(III) chloride hydrate (14 mg) followed by sodium periodate (1.39 g, 6.50 mmol). The resultant mixture was stirred at 2-3° C. for 1 h, warmed up to 17-18° C. over 1 h, and stirred at this temperature for 16 h. 20 wt % $Na_2SO_4$ (5 g) was added followed by EtOAc (30 ml) after which time the resultant mixture was stirred vigorously for 10 min and filtered through a pad of Celite (2 g). Organic layer was separated, washed with 20 wt % sodium sulfite (5 g), 20 wt % NaCl (5 g) and concentrated to give light purple/gray oil. The crude oil was passed over silica gel plug (10 g) eluting with EtOAc (120 ml) and concentrated to dryness to provide (3S,6S)-tert-butyl 3-benzyltetrahydropyrrolo[3,4-d][1,2,3]oxathiazole-5(3 H)-carboxylate 2,2-dioxide (1.54 g, 4.35 mmol, 70.0% yield) as white solid.

(3S,6S)-tert-butyl 3 -benzyltetrahydropyrrolo[3,4-d][1,2,3]oxathiazole-5 (3H)-carboxylate 2,2-dioxide (20 mg, 0.056 mmol) was dissolved in TBAF (1 M solution in THF, 1.0 ml) and heated at reflux overnight, after which time the reaction was cooled to room temperature and acidified with HCl (1 M solution, 2 ml). After 2 h, the mixture was neutralized with $NaHCO_3$ (9% aqueous solution, 2.5 g) and extracted with EtOAc (10 ml). Organic layer was separated, concentrated and combined with two additional batches using 100 mg (0.282 mmol ea.) of starting oxathiazole for each batch. The combined crude products were purified over silica gel column chromatography (n-heptane/EtOAc 1:1) to provide (3S,4S)-tert-butyl 3-(benzylamino)-4-fluoropyrrolidine-1-carboxylate, 82 (29 mg, 0.099 mmol, 15.9% yield) as a light brown oil and being less polar via TLC (silica gel), and (3S,4R)-tert-butyl 3-(benzylamino)-4-fluoropyrrolidine-1-carboxylate, 81 (20 mg, 0.068 mmol, 11.0% yield) as a light brown oil and being more polar via TLC (silica gel).

(3S,4R)-tert-butyl 3-(benzylamino)-4-fluoropyrrolidine-1-carboxylate, 81 (16 mg, 0.054 mmol) was subjected to hydrogenolysis with 10 wt % Pd—C(10 mg) in ethanol (3 ml). The completed reaction mixture was filtered, concentrated and azeotroped with $CDCl_3$ to provide (3S,4R)-tert-butyl 3-amino-4-fluoropyrrolidine-1-carboxylate, 83 (8.3 mg, 0.041 mmol, 75.9% yield).

To a stirred solution of (3S,4R)-tert-butyl 3-amino-4-fluoropyrrolidine-1-carboxylate and 38 or ER-895194 (15 mg, 0.050 mmol) in DMF (0.2 ml) was added propylphosphonic anhydride (0.2 g of a 50% solution in EtOAc) at 40° C. for 2 h. The reaction mixture was passed over a silica gel plug (3 g, eluting with heptane-EtOAc 1:3), and then further purified by preparative TLC (n-heptane/EtOAc 1:4) to give corresponding amide, 78, as yellow/green oil (11.2 mg, 0.023 mmol, 56% yield in 2 steps). The 1H-NMR & HPLC matched with Compound 78 as described earlier thus the absolute stereochemistry of ER-899742 was confirmed indirectly.

Absolute stereochemistry of ER-899742 was also confirmed by X-Ray diffraction. Crystallization process: 5.3 mg of ER-899742-01 (lot. MC2-1130-120-1) was dissolved in 0.5 mL IPA and 0.3 mL $H_2O$. The vial containing the solution was capped and stored at room temperature for a day. The next day the cap was opened and IPA was evaporated slowly for a day at room temperature. The next day the cap was closed and the vial was stored at room temperature for 2 weeks, after which colorless needle crystals of ER-899742-01 appeared from which a single crystal was selected for X-ray analysis. X-ray diffraction analysis: Equipment: R-AXIS RAPID II (RIGAKU); X-ray source: CuKa (1=1.54187A); Temperature: 297 K; Measurement: oscillation method along the ω axis; Crystal size: 0.1×0.1×0.4 mm. The crystal structure was solved with a final R-factor of 0.0606 and a Flack parameter of −0.01. The structure of ER-899742-01 was determined as (2R,6R)-4-(8-cyanoquinolin-5-yl)-N-[(3S,4R)-4-fluoropyrrolidin-3-yl]-6-methylmorpholine-2-carboxamide hydrochloride. See FIG. 8 for ORTEP drawing.

(3S,4S)-tert-butyl 3-(benzylamino)-4-fluoropyrrolidine-1-carboxylate, 82 (24 mg, 0.082 mmol) was subjected to hydrogenolysis with 10 wt % Pd—C(10 mg) in ethanol (3 ml). The reaction mixture was filtered, concentrated and azeotroped dry with $CHCl_3$ to provide (3S,4S)-tert-butyl 3-amino-4-fluoropyrrolidine-1-carboxylate (16.6 mg, 0.081 mmol, 99.2% yield) that was used in the next step without purification.

To a stirred solution of (3S,4S)-tert-butyl 3-amino-4-fluoropyrrolidine-1-carboxylate (12.5 mg, 0.061 mmol) and 38, or ER-895194 (18 mg, 0.061 mmol) in DMF (0.2 ml) was treated with propylphosphonic anhydride (50% solution in EtOAc; 0.2 g,) at 40° C. for 2 h. The reaction mixture was passed over silica gel plug (3 g, eluting with heptane-EtOAc 1:3), and then further purified by preparative TLC (n-heptane/EtOAc 1:4) to provide (3S,4S)-tert-butyl 3-((2R,6R)-4-(8-cyanoquinolin-5-yl)-6-methylmorpholine-2-carboxamido)-4-fluoropyrrolidine-1-carboxylate, 85 (14.2 mg, 0.029 mmol, 47% yield in 2 steps) as yellow/green oil.

ER-899745-HCL (62.3 mg, 0.148 mmol, 96% yield) was obtained using the same equivalents of reagents as for ER-899742-HCl, starting with compound 79 (75 mg, 0.155 mmol). ER-894550 (5.3 mg, 0.016 mmol, 18.4% yield) was prepared in a similar manner to ER-899742 starting with 38 (25.9 mg, 0.087 mmol) and ethyl amine hydrochloride (206 mg, 0.962 mmol). DMF (0.5 mL) was used instead of DCM. The ER-894550 was purified by reverse-phase HPLC (X-Bridge C18 19×100 mm column; eluting with a gradient of increasing acetonitrile in water containing 0.1% formic acid) followed by combining the desired fractions, concentration and drying in vacuo. The product fractions were combined and concentrated to dry followed by dilution in MeOH (1 mL), passed through as basic silica gel plug (Biotage $SiCO_3$, 1 g, eluting with MeOH (1 mL)), concentrated and dried in vacuo.

ER-895473 (103 mg, 0.261 mmol, 27.1% yield) was prepared in a similar manner to ER-899742 starting with 38 (286 mg, 0.962 mmol) and (S)-tert-butyl 2-ethylpiperazine-1-carboxylate (206 mg, 0.962 mmol). DMF (3 mL) was used instead of DCM for the amide forming reaction and 2.0 M HCl in ethyl ether (1.3 mL, 2.6 mmol) was used in the Boc-deprotection process using acetonitrile (1 mL) as a solvent. ER-895473 was purified by reverse-phase HPLC (X-Bridge C18 19×100 mm column; eluting with a gradient of increasing acetonitrile in water containing 0.1% formic acid). The product fractions were combined and concentrated to dry followed by dilution in MeOH (1 mL), passed through as basic silica gel plug (Biotage $SiCO_3$, 1 g, eluting with MeOH (1 mL)), concentrated and dried in vacuo.

ER-895474 (6.3 mg, 0.015 mmol, 19.6% yield) was prepared in a similar manner to ER-899742 starting with 38 (22.5 mg, 0.076 mmol) and (3,4-difluorophenyl)methanamine (10.83 mg, 0.076 mmol). Boc-deprotection was not required.

ER-895475 (16.2 mg, 0.044 mmol, 71.5% yield) was prepared in a similar to ER-895473 starting with 38 (18.3 mg, 0.062 mmol) and (R)-tert-butyl pyrrolidin-3-ylcarbamate (11.46 mg, 0.062 mmol).

ER-895476 (14.0 mg, 0.042 mmol, 28.8% yield) was prepared in a similar manner to ER-895474 starting with 38 (43.0 mg, 0.145 mmol) and azetidine hydrochloride (13.53 mg, 0.145 mmol).

ER-895477 (26.1 mg, 0.058 mmol, 32.1% yield) was prepared in a similar manner to ER-895474 starting with 38 (54.0 mg, 0.182 mmol) and 1,4'-bipiperidine (30.6 mg, 0.182 mmol).

ER-895478 (15.9 mg, 0.047 mmol, 29.0% yield) was prepared in a similar manner to ER-895474 starting with 38 (48.4 mg, 0.163 mmol) and cyclopropanamine (11.42 μl, 0.163 mmol).

ER-895479 (14.9 mg, 0.042 mmol, 23.7% yield) was prepared in a similar manner to ER-895473 starting with 38 (53.2 mg, 0.179 mmol) and tert-butyl azetidin-3-ylcarbamate (30.8 mg, 0.179 mmol).

ER-897922 (15.1 mg, 0.041 mmol, 48.7% yield) was prepared in a similar manner to ER-895474 starting with 38 (25 mg, 0.084 mmol) and 1-aminobutan-2-ol (13.0 mg, 0.146 mmol).

ER-897923 (13.9 mg, 0.038 mmol, 44.9% yield) was prepared in a similar manner to ER-895474 starting with 38 (25 mg, 0.084 mmol) and 2-ethoxyethanamine (13.0 mg, 0.146 mmol).

ER-897924 (17.0 mg, 0.046 mmol, 54.9% yield) was prepared in a similar manner to ER-895474 starting with 38 (25 mg, 0.084 mmol) and (R)-2-aminobutan-1-ol (14.0 mg, 0.157 mmol).

ER-897925 (4.5 mg, 0.012 mmol, 14.5% yield) was prepared in a similar manner to ER-895474 starting with 38 (25 mg, 0.084 mmol) and 2-aminopropane-1,3-diol (14.0 mg, 0.154 mmol).

ER-897926 (7.6 mg, 0.021 mmol, 24.4% yield) was prepared in a similar manner to ER-895474 starting with 38 (25 mg, 0.084 mmol) and 3-aminopropane-1,2-diol (15.0 mg, 0.165 mmol).

ER-897927 (15.0 mg, 0.039 mmol, 46.9% yield) was prepared in a similar manner to ER-895474 starting with 38 (25 mg, 0.084 mmol) and (R)-(tetrahydrofuran-2-yl)methanamine (15.0 mg, 0.148 mmol).

ER-897928 (14.9 mg, 0.039 mmol, 46.6% yield) was prepared in a similar manner to ER-895474 starting with 38 (25 mg, 0.084 mmol) and (tetrahydrofuran-2-yl)methanamine (16.0 mg, 0.158 mmol).

ER-897929 (10.3 mg, 0.027 mmol, 32.0% yield) was prepared in a similar manner to ER-895474 starting with 38 (25 mg, 0.084 mmol) and 2-propoxyethanamine (16.0 mg, 0.155 mmol).

ER-897930 (12.8 mg, 0.033 mmol, 39.8% yield) was prepared in a similar manner to ER-895474 starting with 38 (25 mg, 0.084 mmol) and (R)-2-aminopentan-1-ol (16.0 mg, 0.155 mmol).

ER-897931 (11.1 mg, 0.029 mmol, 34.5% yield) was prepared in a similar manner to ER-895474 starting with 38 (25 mg, 0.084 mmol) and 2-isopropoxyethanamine (15.0 mg, 0.145 mmol).

ER-897932 (10.0 mg, 0.026 mmol, 31.1% yield) was prepared in a similar manner to ER-895474 starting with 38 (25 mg, 0.084 mmol) and 1-methoxybutan-2-amine (0.0160 g, 0.155 mmol).

ER-897933 (9.0 mg, 0.021 mmol, 24.6% yield) was prepared in a similar manner to ER-895474 starting with 38 (25 mg, 0.084 mmol) and 2-amino-1-(2-fluorophenyl)ethanol (23.0 mg, 0.148 mmol).

ER-897934 (13.3 mg, 0.035 mmol, 41.1% yield) was prepared in a similar manner to ER-895474 starting with 38 (25 mg, 0.084 mmol) and (S)-2-amino-3-methylbutan-1-ol (15.0 mg, 0.145 mmol).

ER-897935 (15.7 mg, 0.041 mmol, 48.6% yield) was prepared in a similar manner to ER-895474 starting with 38 (25 mg, 0.084 mmol) and 2,2-dimethoxyethanamine (15.0 mg, 0.143 mmol).

ER-897936 (10.4 mg, 0.027 mmol, 32.2% yield) was prepared in a similar manner to ER-895474 starting with 38 (25 mg, 0.084 mmol) and 2-(2-aminoethoxyl)ethanol (16.0 mg, 0.152 mmol).

ER-897937 (12.1 mg, 0.031 mmol, 36.5% yield) was prepared in a similar manner to ER-895474 starting with 38 (25 mg, 0.084 mmol) and (1S,2S)-2-aminocyclohexanol (23.0 mg, 0.200 mmol).

ER-897938 (8.5 mg, 0.022 mmol, 25.6% yield) was prepared in a similar manner to ER-895474 starting with 38 (25 mg, 0.084 mmol) and 2-aminocyclohexanol (17.0 mg, 0.148 mmol).

ER-897939 (10.1 mg, 0.025 mmol, 30.3% yield) was prepared in a similar manner to ER-895474 starting with 38 (25 mg, 0.084 mmol) and 2-aminohexan-1-ol (18.3 mg, 0.156 mmol).

ER-897940 (10.3 mg, 0.026 mmol, 30.9% yield) was prepared in a similar manner to ER-895474 starting with 38 (25 mg, 0.084 mmol) and (S)-2-amino-3,3-dimethylbutan-1-ol (19.0 mg, 0.162 mmol).

ER-897941 (14.0 mg, 0.035 mmol, 42.0% yield) was prepared in a similar manner to ER-895474 starting with 38 (25 mg, 0.084 mmol) and (S)-2-aminohexan-1-ol (19.0 mg, 0.162 mmol).

ER-897942 (9.9 mg, 0.025 mmol, 29.7% yield) was prepared in a similar manner to ER-895474 starting with 38 (25 mg, 0.084 mmol) and (2S,3S)-2-amino-3-methylpentan-1-ol (18.0 mg, 0.154 mmol).

ER-897943 (11.1 mg, 0.028 mmol, 33.3% yield) was prepared in a similar manner to ER-895474 starting with 38 (25 mg, 0.084 mmol) and (S)-2-amino-4-methylpentan-1-ol (18.0 mg, 0.154 mmol).

ER-897944 (10.9 mg, 0.027 mmol, 32.7% yield) was prepared in a similar manner to ER-895474 starting with 38 (25 mg, 0.084 mmol) and (R)-2-amino-4-methylpentan-1-ol (18.0 mg, 0.154 mmol).

ER-897945 (13.2 mg, 0.032 mmol, 38.3% yield) was prepared in a similar manner to ER-895474 starting with 38 (25 mg, 0.084 mmol) and (4-methylmorpholin-2-yl)methanamine (20.0 mg, 0.154 mmol).

ER-897946 (16.1 mg, 0.035 mmol, 42.0% yield) was prepared in a similar manner to ER-895474 starting with 38 (25 mg, 0.084 mmol) and (S)-2-amino-4-(methylthio)butan-1-ol (20.0 mg, 0.148 mmol).

ER-897947 (12.0 mg, 0.029 mmol, 34.3% yield) was prepared in a similar manner to ER-895474 starting with 38 (25 mg, 0.084 mmol) and 2-phenoxyethanamine (21.0 mg, 0.153 mmol).

ER-897948 (12.0 mg, 0.028 mmol, 33.1% yield) was prepared in a similar manner to ER-895474 starting with 38 (25 mg, 0.084 mmol) and (S)-2-amino-3-phenylpropan-1-ol (24.0 mg, 0.159 mmol).

ER-897949 (11.7 mg, 0.027 mmol, 32.3% yield) was prepared in a similar manner to ER-895474 starting with 38 (25 mg, 0.084 mmol) and 2-phenoxypropan-1-amine (29.0 mg, 0.192 mmol).

ER-897950 (11.7 mg, 0.027 mmol, 32.3% yield) was prepared in a similar manner to ER-895474 starting with 38 (25 mg, 0.084 mmol) and 1-amino-3-phenylpropan-2-ol (23.0 mg, 0.152 mmol).

ER-897952 (14.0 mg, 0.032 mmol, 38.6% yield) was prepared in a similar manner to ER-895474 starting with 38 (25 mg, 0.084 mmol) and 2-(pyridin-3-yloxy)propan-1-amine (24.0 mg, 0.158 mmol).

ER-897955 (8.2 mg, 0.019 mmol, 22.5% yield) was prepared in a similar manner to ER-895474 starting with 38 (25 mg, 0.084 mmol) and 2-(4-fluorophenoxyl)ethanamine (23.0 mg, 0.148 mmol).

ER-897956 (11.2 mg, 0.026 mmol, 26% yield) was prepared in a similar manner to ER-895474 starting with 38 (25 mg, 0.084 mmol) and 2-amino-1-(3-fluorophenyl)ethanol (24.0 mg, 0.155 mmol).

ER-897957 (9.8 mg, 0.022 mmol, 26.7% yield) was prepared in a similar manner to ER-895474 starting with 38 (25 mg, 0.084 mmol) and (S)-2-amino-3-cyclohexylpropan-1-ol (30.0 mg, 0.191 mmol).

ER-897958 (13.6 mg, 0.031 mmol, 36.5% yield) was prepared in a similar manner to ER-895474 starting with 38 (25 mg, 0.084 mmol) and isochroman-1 -ylmethanamine (24.0 mg, 0.147 mmol).

ER-897960 (13.0 mg, 0.029 mmol, 34.6% yield) was prepared in a similar manner to ER-895474 starting with 38 (25 mg, 0.084 mmol) and 1-amino-3-phenoxypropan-2-ol (25.0 mg, 0.150 mmol).

ER-897961 (9.7 mg, 0.022 mmol, 25.8% yield) was prepared in a similar manner to ER-895474 starting with 38 (25 mg, 0.084 mmol) and 4-((1S,2R)-2-amino-1-hydroxypropyl)phenol (32.0 mg, 0.191 mmol).

ER-897962 (17.8 mg, 0.040 mmol, 47.4% yield) was prepared in a similar manner to ER-895474 starting with 38 (25 mg, 0.084 mmol) and (1S,2S)-2-amino-1-phenylpropane-1,3-diol (26.0 mg, 0.155 mmol).

ER-897963 (3.1 mg, 0.007 mmol, 8.4% yield) was prepared in a similar manner to ER-895473 starting with 38 (25 mg, 0.084 mmol) and tert-butyl 4-(3-amino-2-hydroxypropyl)piperazine-1-carboxylate (40.0 mg, 0.154 mmol).

ER-897964 (12.7 mg, 0.036 mmol, 21.5% yield) was prepared in a similar manner to ER-895473 starting with 38 (25 mg, 0.084 mmol) and tert-butyl 3-aminoazetidine-1-carboxylate (27.0 mg, 0.157 mmol).

ER-897965 (0.4 mg, 0.001 mmol, 1.3% yield) was prepared in a similar manner to ER-895473 starting with 38 (25 mg, 0.084 mmol) and (S)-tert-butyl 3-aminopyrrolidine-1-carboxylate (29.0 mg, 0.156 mmol).

ER-897966 (0.4 mg, 0.001 mmol, 1.3% yield) was prepared in a similar manner to ER-895473 starting with 38 (25 mg, 0.084 mmol) and (R)-tert-butyl 3-aminopyrrolidine-1-carboxylate (29.0 mg, 0.156 mmol).

ER-897967 (0.3 mg, 0.001 mmol, 0.9% yield) was prepared in a similar manner to ER-895473 starting with 38 (25 mg, 0.084 mmol) and (S)-tert-butyl 3-aminopiperidine-1-carboxylate (30.0 mg, 0.150 mmol).

ER-897968 (0.4 mg, 0.001 mmol, 1.3% yield) was prepared in a similar manner to ER-895473 starting with 38 (25 mg, 0.084 mmol) and (R)-tert-butyl 3-aminopiperidine-1-carboxylate (30.0 mg, 0.150 mmol).

ER-897969 (0.2 mg, 0.001 mmol, 0.6% yield) was prepared in a similar manner to ER-895473 starting with 38 (25 mg, 0.084 mmol) and (S)-tert-butyl 2-(aminomethyl)pyrrolidine-1-carboxylate (30.0 mg, 0.150 mmol).

ER-897970 (3.4 mg, 0.008 mmol, 9.4% yield) was prepared in a similar manner to ER-895473 starting with 38 (25 mg, 0.084 mmol) and tert-butyl(2-aminoethyl)(benzyl)carbamate (38.0 mg, 0.152 mmol).

ER-898560 (11.2 mg, 0.030 mmol, 30.9% yield) was prepared in a similar manner to ER-895473 starting with 38 (28.8 mg, 0.097 mmol) and pyridin-2-amine (9.12 mg, 0.097 mmol).

ER-898561 (12.8 mg, 0.033 mmol, 44.6% yield) was prepared in a similar manner to ER-895474 starting with 38 (22.1 mg, 0.074 mmol) and 6-methylpyridin-2-amine (8.04 mg, 0.074 mmol).

ER-898562 (7.4 mg, 0.020 mmol, 18.7% yield) was prepared in a similar manner to ER-895474 starting with 38 (31.2 mg, 0.105 mmol) and 5-methylisoxazol-3-amine (10.30 mg, 0.105 mmol).

ER-898563 (6.5 mg, 0.017 mmol, 16.7% yield) was prepared in a similar manner to ER-895474 starting with 38 (30.7 mg, 0.103 mmol) and 2,2,2-trifluoroethanamine hydrochloride (13.99 mg, 0.103 mmol).

ER-898564 (1.4 mg, 0.004 mmol, 3.8% yield) was prepared in a similar manner to ER-895474 starting with 38 (30 mg, 0.101 mmol) and 2,2-difluoroethanamine (8.18 mg, 0.101 mmol).

ER-898565 (3.0 mg, 0.008 mmol, 7.5% yield) was prepared in a similar manner to ER-895474 starting with 38 (30.2 mg, 0.102 mmol) and 3,3,3-trifluoropropan-1-amine (11.49 mg, 0.102 mmol).

ER-898566 (14.6 mg, 0.037 mmol, 20.4% yield) was prepared in a similar manner to ER-895474 starting with 38 (53.7 mg, 0.181 mmol) and N2,N2,2-trimethylpropane-1,2-diamine (20.99 mg, 0.181 mmol).

ER-898914 (31.6 mg, 0.092 mmol, 28.8% yield) was prepared in a similar manner to ER-895474 starting with 38 (95.2 mg, 0.320 mmol) and 2-fluoroethanamine hydrochloride (31.9 mg, 0.32 mmol).

ER-898915 (19.1 mg, 0.054 mmol, 19.3% yield) was prepared in a similar manner to ER-895474 starting with 38 (82.3 mg, 0.277 mmol) and 3-fluoropropan-1-amine hydrochloride (31.4 mg, 0.277 mmol).

ER-898916 (14.6 mg, 0.037 mmol, 21.5% yield) was prepared in a similar manner to ER-895474 starting with 38 (51.4 mg, 0.173 mmol) and (R)-1,1,1-trifluoropropan-2-amine (20 mg, 0.177 mmol).

ER-898917 (27.6 mg, 0.066 mmol, 20.4% yield) was prepared in a similar manner to ER-895474 starting with 38 (95.7 mg, 0.322 mmol) and (R)-1,1,1-trifluoro-3-methylbutan-2-amine (45.4 mg, 0.322 mmol).

ER-898918 (15.0 mg, 0.038 mmol, 19.3% yield) was prepared in a similar manner to ER-895474 starting with 38 (59.2 mg, 0.199 mmol) and 1,3-dimethyl-1H-pyrazol-5-amine (22.13 mg, 0.199 mmol).

ER-898919 (13.1 mg, 0.035 mmol, 10.5% yield) was prepared in a similar manner to ER-895474 starting with 38 (98.1 mg, 0.33 mmol) and 1-methyl-1H-pyrazol-5-amine (32.0 mg, 0.33 mmol).

ER-898920 (20.1 mg, 0.060 mmol, 21.4% yield) was prepared in a similar manner to ER-895474 starting with 38 (83.3 mg, 0.280 mmol) and 2-aminoacetonitrile hydrochloride (25.9 mg, 0.28 mmol).

ER-898921 (11.4 mg, 0.032 mmol, 12.8% yield) was prepared in a similar manner to ER-895474 starting with 38 (73.1 mg, 0.246 mmol) and cyclopropanecarbonitrile hydrochloride (25.5 mg, 0.246 mmol).

ER-898922 (25.4 mg, 0.067 mmol, 33.7% yield) was prepared in a similar manner to ER-895474 starting with 38 (59.0 mg, 0.198 mmol) and 1,2,4-thiadiazol-5-amine (20.07 mg, 0.198 mmol).

ER-898923 (12.6 mg, 0.032 mmol, 16.5% yield) was prepared in a similar manner to ER-895474 starting with 38 (57.6 mg, 0.194 mmol) and 3-methyl-1,2,4-thiadiazol-5-amine (22.31 mg, 0.194 mmol).

ER-899017-HCl (328 mg, 0.769 mmol, 65.3% yield) was prepared in a similar manner to ER-899742-HCl starting with 38 (350 mg, 1.177 mmol) and tert-butyl 2,6-diazaspiro[3.4]octane-6-carboxylate (250 mg, 1.177 mmol).

ER-899019-HCl (26 mg, 0.059 mmol, 58.2% yield) was prepared in a similar manner to ER-899742-HCl starting with 38 (30 mg, 0.101 mmol) and tert-butyl 4-(aminomethyl)-4-fluoropiperidine-1-carboxylate (23.4 mg, 0.101 mmol).

ER-899020-HCl (25 mg, 0.062 mmol, 61.4% yield) was prepared in a similar manner to ER-899742-HCl starting with 38 (30 mg, 0.101 mmol) tert-butyl 3-(aminomethyl) azetidine-1-carboxylate (18.8 mg, 0.101 mmol).

ER-899023-HCl (25.5 mg, 0.060 mmol, 59.4% yield) was prepared in a similar manner to ER-899742-HCl starting with 38 (30 mg, 0.101 mmol) and tert-butyl 1,6-diazaspiro[3.4]octane-6-carboxylate (21.4 mg, 0.101 mmol).

ER-899024-HCl (30.1 mg, 0.068 mmol, 67.5% yield) was prepared in a similar manner to ER-899742-HCl starting with 38 (30 mg, 0.101 mmol) and tert-butyl 1,7-diazaspiro[4.4]nonane-1-carboxylate (22.8 mg, 0.101 mmol).

ER-899025-HCl (32.1 mg, 0.077 mmol, 76% yield) was prepared in a similar manner to ER-899742-HCl starting with 38 (30 mg, 0.101 mmol) and 4-amino-1 -methyl-1H-pyrazole-3-carboxamide (14.1 mg, 0.101 mmol). Boc-deprotection was not required.

ER-899031-HCl (30.1 mg, 0.079 mmol, 78% yield) was prepared in a similar manner to ER-899742-HCl starting with 38 (30 mg, 0.101 mmol) and (3-methyloxetan-3-yl) methanamine (10.2 mg, 0.101 mmol). Boc-deprotection was not required.

ER-899032-HCl (28.7 mg, 0.079 mmol, 78% yield) was prepared in a similar manner to ER-899742-HCl starting with 38 (30 mg, 0.101 mmol) and 2-oxo-6-azasprio[3.3] helptane (10.0 mg, 0.101 mmol). Boc-deprotection was not required.

ER-899033-HCl (32.8 mg, 0.093 mmol, 92% yield) was prepared in a similar manner to ER-899742-HCl starting with 38 (30 mg, 0.101 mmol) and oxetane-3-amine (7.4 mg, 0.101 mmol). Boc-deprotection was not required.

ER-899034-HCl (26.4 mg, 0.067 mmol, 66.2% yield) was prepared in a similar manner to ER-899742-HCl starting with 38 (30 mg, 0.101 mmol) and oxetane-3,3-diyldimethanamine dihydrochloride (19.1 mg, 0.101 mmol). Boc-deprotection was not required.

ER-899035-HCl (25.9 mg, 0.071 mmol, 70.1% yield) was prepared in a similar manner to ER-899742-HCl starting with 38 (30 mg, 0.101 mmol) and oxetan-2-ylmethanamine (8.8 mg, 0.101 mmol). Boc-deprotection was not required.

ER-899036-HCl (33.1 mg, 0.082 mmol, 82% yield) was prepared in a similar manner to ER-899742-HCl starting with 38 (30 mg, 0.101 mmol) and tert-butyl piperazine-1-carboxylate (18.8 mg, 0.101 mmol).

ER-899191-HCl (30.7 mg, 0.081 mmol, 80% yield) was prepared in a similar manner to ER-899742-HCl starting with 38 (30 mg, 0.101 mmol) and azetidine-3-carboxamide (10.1 mg, 0.101 mmol). Boc-deprotection was not required.

ER-899192-HCl (34.4 mg, 0.078 mmol, 77% yield) was prepared in a similar manner to ER-899742-HCl starting with 38 (30 mg, 0.101 mmol) and tert-butyl 2,7-diazaspiro[4.4]nonane-2-carboxylate (22.8 mg, 0.101 mmol).

ER-899193-HCl (38.1 mg, 0.081 mmol, 80% yield) was prepared in a similar manner to ER-899742-HCl starting with 38 (30 mg, 0.101 mmol) and tert-butyl 3,9-diazaspiro[5.5]undecane-3-carboxylate (25.7 mg, 0.101 mmol).

ER-899196-HCl (23.7 mg, 0.057 mmol, 56.4% yield) was prepared in a similar manner to ER-899742-HCl starting with 38 (30 mg, 0.101 mmol) and 4-aminonicotinamide (13.84 mg, 0.101 mmol). Boc-deprotection was not required.

ER-899282-HCl (29.6 mg, 0.079 mmol, 79% yield) was prepared in a similar manner to ER-899742-HCl starting with 38 (30 mg, 0.101 mmol) and pyridin-4-amine (9.5 mg, 0.101 mmol). Boc-deprotection was not required.

ER-899283-HCl (31.1 mg, 0.083 mmol, 83% yield) was prepared in a similar manner to ER-899742-HCl starting with 38 (30 mg, 0.101 mmol) and pyridin-3-amine (9.5 mg, 0.101 mmol). Boc-deprotection was not required.

ER-899285-HCl (28.5 mg, 0.059 mmol, 58.6% yield) was prepared in a similar manner to ER-899742-HCl starting with 38 (30 mg, 0.101 mmol) and tert-butyl 4-(4-amino-1H-pyrazol-1-yl)piperidine-1-carboxylate (26.9 mg, 0.101 mmol).

ER-899286-HCl (31.7 mg, 0.070 mmol, 69.2% yield) was prepared in a similar manner to ER-899742-HCl starting with 38 (30 mg, 0.101 mmol) and tert-butyl 3-(4-amino-1H-pyrazol-1-yl)azetidine-1-carboxylate (24.0 mg, 0.101 mmol).

ER-899287 (29.7 mg, 0.079 mmol, 78% yield) was prepared in a similar manner to ER-895474 starting with 38 (30 mg, 0.101 mmol) and (1H-pyrazol-5-yl)methanamine (9.80 mg, 0.101 mmol).

ER-899288 (20.7 mg, 0.057 mmol, 56.6% yield) was prepared in a similar manner to ER-895474 starting with 38 (30 mg, 0.101 mmol) and 1H-pyrazol-4-amine (8.38 mg, 0.101 mmol).

ER-899289 (35.5 mg, 0.078 mmol, 77% yield) was prepared in a similar manner to ER-895474 starting with 38 (30 mg, 0.101 mmol) and (3-(trifluoromethyl)pyridin-2-yl) methanamine (17.77 mg, 0.101 mmol).

ER-899290 (15.0 mg, 0.034 mmol, 33.9% yield) was prepared in a similar manner to ER-895474 starting with 38 (30 mg, 0.101 mmol) and 1-(pyridin-2-yl)ethanamine (12.33 mg, 0.101 mmol).

ER-899291 (26.1 mg, 0.067 mmol, 66.7% yield) was prepared in a similar manner to ER-895474 starting with 38 (30 mg, 0.101 mmol) and pyridin-2-ylmethanamine (10.91 mg, 0.101 mmol).

ER-899292 (31.0 mg, 0.077.2 mmol, 76.4% yield) was prepared in a similar manner to ER-895474 starting with 38 (30 mg, 0.101 mmol) and (6-methylpyridin-2-yl)methanamine (12.3 mg, 0.101 mmol).

ER-899293 (32.0 mg, 0.079 mmol, 77.7% yield) was prepared in a similar manner to ER-895474 starting with 38 (30 mg, 0.101 mmol) and (1-methylpiperidin-2-yl)methanamine (12.9 mg, 0.101 mmol).

ER-899294 (32.2 mg, 0.080 mmol, 79% yield) was prepared in a similar manner to ER-895474 starting with 38 (30 mg, 0.101 mmol) and (3-methylpyridin-2-yl)methanamine (12.3 mg, 0.101 mmol).

ER-899334 (51.3 mg, 0.140 mmol, 11.7% yield) was prepared in a similar manner to ER-895473 starting with 38 (357.2 mg, 1.201 mmol) and (R)-tert-butyl 2-(aminomethyl) pyrrolidine-1-carboxylate (224 mg, 1.201 mmol).

ER-899414-HCl (31.1 mg, 0.075 mmol, 74.1% yield) was prepared in a similar manner to ER-899742-HCl starting with 38 (30 mg, 0.101 mmol) and (R)-tert-butyl 2-(aminomethyl)pyrrolidine-1-carboxylate (20.2 mg, 0.101 mmol).

ER-899415-HCl (30.5 mg, 0.071 mmol, 70.3% yield) was prepared in a similar manner to ER-899742-HCl starting with 38 (30 mg, 0.101 mmol) and (S)-tert-butyl 2-(aminomethyl)piperidine-1-carboxylate (21.6 mg, 0.101 mmol).

ER-899416-HCl (24.2 mg, 0.055 mmol, 54.3% yield) was prepared in a similar manner to ER-899742-HCl starting with 38 (30 mg, 0.101 mmol) and tert-butyl 3-amino-8-azabicyclo[3.2.1]octane-8-carboxylate (22.84 mg, 0.101 mmol).

ER-899417-HCl (32.8 mg, 0.076 mmol, 76% yield) was prepared in a similar manner to ER-899742-HCl starting with 38 (30 mg, 0.101 mmol) and tert-butyl 4-amino-azepane-1-carboxylate (21.62 mg, 0.101 mmol).

ER-899418-HCl (29.6 mg, 0.072 mmol, 70.9% yield) was prepared in a similar manner to ER-899742-HCl starting with 38 (30 mg, 0.101 mmol) and (1R,5S,6S)-tert-butyl 6-amino -3-azabicyclo[3.1.0]hexane-3-carboxylate (20.0 mg, 0.101 mmol).

ER-899476-HCl (31.0 mg, 0.068 mmol, 67.4% yield) or the diastereomeric mixture of ER-899742 and ER-899745 was prepared in a similar manner to ER-899742-HCl starting with 38 (30 mg, 0.101 mmol) and a 1:1 mixture of (3R,4S)-tert-butyl 3-amino-4-fluoropyrrolidine-1-carboxylate and (3S,4R)-tert-butyl 3-amino-4-fluoropyrrolidine-1-carboxylate (20.6 mg, 0.101 mmol).

ER-899477-HCl (25.5 mg, 0.059 mmol, 58.2% yield) as a diastereomer mixture was prepared in a similar manner to ER-899742-HCl starting with 38 (30 mg, 0.101 mmol) and a 1:1 mixture of (3R,4S)-tert-butyl 3-amino-4-fluoropiperidine-1-carboxylate and (3S,4R)-tert-butyl 3-amino-4-fluoropiperidine-1-carboxylate (22.02 mg, 0.101 mmol).

ER-899479-HCl (30.5 mg, 0.071 mmol, 70.6% yield) was prepared in a similar manner to ER-899742-HCl starting with 38 (30 mg, 0.101 mmol) and tert-butyl 6-amino-2-azaspiro[3.3]heptane-2-carboxylate (21.42 mg, 0.101 mmol).

ER-897383 (14.2 mg, 0.017 mmol, 14.1% yield) was prepared in a similar manner to ER-895474 starting with 38 (35.2 mg, 0.118 mmol) and 2-aminoethanol (10.9 mg, 0.178 mmol). DMF (1 mL) was used instead of DMAC.

ER-897385 (14.2 mg, 0.017 mmol, 14.1% yield) was prepared in a similar manner to ER-897383 starting with 38 (35 mg, 0.118 mmol) and 2-methoxyethanamine (13.7 mg, 0.178 mmol).

ER-897445 (87 mg, 0.245 mmol, 72.9% overall yield) was prepared in a similar manner to ER-897383 starting with 38 (100 mg, 0.336 mmol) and (R)-2-((tert-butyldiphenylsilyl)oxy)propan-1-amine (158 mg, 0.505 mmol) followed by the removal of the tert-butyldiphenylsilyl-protecting group using 1 M TBAF in THF (0.43 mL, 0.43 mmol) in DCM (1.1 mL) stirring for 1 h at rt. The desired product was purified over silica gel (eluted with 80-100% EtOAc in heptane).

ER-897446 (67 mg, 0.189 mmol, 75% overall yield) was prepared in a similar manner to ER-897445 starting with 38

(75 mg, 0.252 mmol) and (S)-1-((tert-butyldiphenylsilyl) oxy)propan-2-amine (103 mg, 0.329 mmol).

ER-897447 (78 mg, 0.220 mmol, 65.5% overall yield) was prepared in a similar manner to ER-897445 starting with 38 (100 mg, 0.336 mmol) and (R)-1-((tert-butyldiphenylsilyl)oxy)propan-2-amine (158 mg, 0.505 mmol).

ER-897827 (48.2 mg, 0.131 mmol, 64.9% overall yield) was prepared in a similar manner to ER-897445 starting with 38 (60 mg, 0.202 mmol) and (S)-1-((tert-butyldiphenylsilyl)oxy)butan-2-amine (90 mg, 0.303 mmol).

ER-897828 (49.4 mg, 0.129 mmol, 64% overall yield) was prepared in a similar manner to ER-897445 starting with 38 (60 mg, 0.202 mmol) and (S)-1-((tert-butyldiphenylsilyl)oxy)-3-methylbutan-2-amine (103 mg, 0.303 mmol).

ER-897829 (65.2 mg, 0.157 mmol, 77.7% overall yield) was prepared in a similar manner to ER-897445 starting with 38 (60 mg, 0.202 mmol) and (S)-2-((tert-butyldiphenylsilyl)oxy)-1-phenylethanamine (114 mg, 0.303 mmol).

ER-897830 (60.2 mg, 0.145 mmol, 71.8% overall yield) was prepared in a similar manner to ER-897445 starting with 38 (60 mg, 0.202 mmol) and (R)-2-((tert-butyldiphenylsilyl)oxy)-1-phenylethanamine (114 mg, 0.303 mmol).

ER-899722 (79 mg, 0.215 mmol, 25.6% yield) was prepared in a similar manner to ER-895474 starting with 38 (250 mg, 0.841 mmol) and 2-methylpropane-1,2-diamine (0.09 mL, 0.841 mmol). DCM (2 mL) was used instead of DMAC.

ER-899295 (27.5 mg, 0.0.71 mmol, 70.4% yield) was prepared in a similar manner to ER-899722 starting with 38 (30 mg, 0.101 mmol) and 3-amino-1H-pyrazole-4-carbonitrile (10.9 mg, 0.101 mmol).

ER-898946: 38 (50 mg, 0.168 mmol), HATU (128 mg, 0.336 mmol) and DIEA (0.176 ml, 1.009 mmol) was dissolved in DCM:DMF (5 mL: 2 mL) followed by tert-butyl 4-aminopiperidine-1-carboxylate (67.4 mg, 0.336 mmol). The resulting reaction mixture was stirred at rt for 16 h after which time additional HATU (128 mg, 0.336 mmol), and by tert-butyl 4-aminopiperidine-1-carboxylate (67.4 mg, 0.336 mmol) was added followed by stifling for an additional 3 h. The completed reaction was concentrated to dry and the crude product was purified by chromatography (25 g Silica gel) eluting with 10% acetonitrile in DCM to give pure Boc protected product. The Boc-protected product was dissolved in DCM(4 ml)/TFA (0.5 ml) and stirred at rt for 3 h after which time the solvent was removed under reduced pressure, the residue was dissolved in MeOH (10 mL) and 0.3 g of MP-carbonate was added (pH>7). The resulting suspension was stirred at rt for 30 min after which time the polymer beads were filtered, washed with MeOH (10 mL) and the solvent was concentrated and high vacuum to dry to give ER-898946 (12 mg, 0.027 mmol, 16.0% yield).

ER-898694-2 HCl (67 mg, 0.155 mmol, 46.1% yield) was prepared in a similar manner to ER-898946 starting with 38 (100 mg, 0.336 mmol) and (S)-tert-butyl 2-(aminomethyl) morpholine-4-carboxylate (95 mg, 0.437 mmol) followed by the addition of 3N HCl in dioxane (31 uL) to provide the dihydrochloride salt after concentration and high vacuum to dryness.

Alternative method for the preparation of ER-899742 & ER-899745: To a stirred solution 38 (2.91 g, 9.79 mmol and TEA (1.706 ml, 12.24 mmol) in DCM (50.0 ml) was added 77 (2.000 g, 9.792 mmol) and HOBT (2.65 g, 19.59 mmol). The reaction mixture was cooled to 0° C. followed by the portion wise addition of EDC (3.75 g, 19.59 mmol) after which time mixture was warmed to 40° C. and stirred for 3 hours. DCM (50 mL) was added, the layers separated after which time the organic layer was washed with sat. ammonium chloride (20 mL), sat. $NaHCO_3$ (20 mL), brine (20 mL), dried over $Na_2SO_4$, filtered and concentrated to dry. The crude product was purified over silica gel (Biotage SP4, eluting with 10% MeOH:DCM). The diastereomers were separated as described above to obtain 78 (1.65 g, 3.41 mmol, 34.8% yield) and 79 (1.49 g, 3.08 mmol, 31.5% yield).

78 (470 mg, 0.97 mmol) was dissolved in a stifling solution of DCM (5.0 mL) followed by the addition of TFA (2.5 mL, 32.45 mmol) after which time the reaction was warmed to 49° C. and stirred for 2 h. The completed reaction was azeotroped to dryness three times with toluene (2 mL each) and then dried in vacuo to provide ER-899742-TFA (543 mg, 0.97 mmol, 100% yield—the product contained 1.5 molecules of TFA to one molecule of ER-899742 via mass spectrum) as an orange solid.

ER-899742 free base can be obtained by dissolving the TFA salt in MeOH and adding Amberlite IRA 400 hydroxide form and stifling for 10 min or once a neutral pH is obtained. The resultant suspension is filtered, washed with MeOH two times with MeOH of equal volumes, and concentration of the combined filtrates to paste. The paste is azeotroped two times with toluene to provide ER-899742 in the free base form in quantitative yield. The HCl salt form can be then be generated as described above.

ER-899742-HCl salt may be obtained directly from 78 by treatment with 5.5 N HCL in isopropanol to provide desired product in quantitative yield after stifling for 2 h at rt followed by azeotroping to dry 3 times with toluene and high vacuum drying as 1.5 molecules of HCl to one molecule of ER-899742 demonstrated by mass spectra analyses.

ER-899464-HC1: To a stirred solution of 38 (50 g, 168.2 mmol) in DMF (250 mL) was added TEA (29.3 mL, 210.2 mmol) followed by 4-amino-1-methylpiperidine (28.8 g, 252.3 mmol) and HOBT (45.4 g, 336.4 mmol). The reaction mixture was cooled to 0° C. followed by a portion wise addition of EDC (64.5 g, 336.4 mmol). The reaction mixture was warmed to 40° C. and stirred for an additional 6 h. The completed reaction was slowly poured into a flask containing water (1.5 L) with stifling after which time DCM (1.5 L) was added, stirred an additional 10 min. The two layers were separated and the aqueous layer was extracted three times with DCM (600 mL each). The combined organic layers were concentrated to a DMF solution followed by concentration at 50° C. under vacuum. The resultant yellow slurry was diluted with ethyl ether (1 L) and stirred for 15 min, after which time the solid was collected by filtration followed by rinsing the filter pad with ethyl ether (0.5 L) and dried in vacuo to provide ER-899464 (44.9 g, 114 mmol, 67.9% yield). The HCl salt is obtained by dissolving ER-899464 (22.8 g, 57.9 mmol) in 10 volumes of isopropanol and 1 volume of water followed by the addition of 1 equivalent of 5.5 N HCl in isopropanol to provide a white precipitate. The solid is filtered and washed with isopropanol (2 vol) followed by drying in a vacuo to provide ER-899464.HCl (20.3 g, 47.2 mmol, 81.5%).

ER-899477 (78 mg, 0.196 mmol, 58.3% yield) was prepared in a similar manner to ER-899464 starting with 38 (100 mg, 0.336 mmol) and (3S,4R)-tert-butyl 3-amino-4-fluoropiperidine-1-carboxylate (220 mg, 1.009 mmol).

ER-897968 (475 mg, 1.252 mmol, 37.2% yield) was prepared in a similar manner to ER-899464 starting with 38 (1.00 g, 3.364 mmol) and (R)-tert-butyl 3-aminopiperidine-1-carboxylate (2.021 g, 10.091 mmol).

ER-899018 (370 mg, 0.975 mmol, 58.0% yield) was prepared in a similar manner to ER-899464 starting with 38

(500 mg, 1.682 mmol) and tert-butyl(azetidin-3-ylmethyl)(methyl)carbamate (500 mg, 2.497 mmol).

ER-899819 (62 mg, 0.158 mmol, 31.3% yield) was prepared in a similar manner to ER-899464 starting with 38 (150 mg, 0.505 mmol) and tert-butyl 3-aminoazepane-1-carboxylate (324 mg, 1.514 mmol).

ER-899416-HCl (53 mg, 0.120 mmol, 35.7% yield) was prepared in a similar manner to ER-899464-HCl starting with 38 (100 mg, 0.336 mmol) and (1R,3S,5S)-tert-butyl 3-amino-8-azabicyclo[3.2.1]octane-8-carboxylate (76 mg, 0.336 mmol).

ER-899417-HCl (56 mg, 0.130 mmol, 38.7% yield) was prepared in a similar manner to ER-899464-HCl starting with 38 (100 mg, 0.336 mmol) and tert-butyl 4-amino-azepane-1-carboxylate (144 mg, 0.673 mmol).

ER-899285-HCl (52 mg, 0.108 mmol, 32.1% yield) was prepared in a similar manner to ER-899464-HCl starting with 38 (100 mg, 0.336 mmol) and tert-butyl 4-(4-amino-1H-pyrazol-1-yl)piperidine-1-carboxylate (179 mg, 0.673 mmol)

ER-899021-HCl (62 mg, 0.140 mmol, 41.7% yield) was prepared in a similar manner to ER-899464-HCl starting with 38 (100 mg, 0.336 mmol) and tert-butyl 2,6-diazaspiro[3.5]nonane-6-carboxylate (152 mg, 0.673 mmol).

ER-899619-HCl (36 mg, 0.084 mmol, % yield) was in a similar manner to ER-899464-HCl starting with 38 (100 mg, 0.336 mmol) and (S)-tert-butyl 3-(methylamino)piperidine-1-carboxylate (216 mg, 1.009 mmol).

ER-899616-HCl (21 mg, 0.049 mmol, % yield) was prepared in a similar manner to ER-899464-HCl starting with 38 (100 mg, 0.336 mmol) and (R)-tert-butyl 3-(methylamino)piperidine-1-carboxylate (216 mg, 1.009 mmol).

ER-898566-HCl (272 mg, 0.630 mmol, 37.5% yield) was prepared in a similar manner to ER-899464-HCl starting with 38 (500 mg, 1.682 mmol) and N2,N2,2-trimethylpropane-1,2-diamine (586 mg, 5.045 mmol).

ER-899618-HCl (4.8 mg, 0.011 mmol, 3.2% yield) was prepared in a similar manner to ER-899464-HCl starting with 38 (500 mg, 1.682 mmol) and 4-aminopicolinamide (138 mg, 1.009 mmol).

ER-899477 (78 mg, 0.196 mmol, 58.3% yield as a diastereomeric mixture) was prepared in a similar manner to ER-899464 starting with 38 (100 mg, 0.336 mmol) and a racemic mixture of (3S,4R)-tert-butyl 3-amino-4-fluoropiperidine-1-carboxylate and (3R,4S)-tert-butyl 3-amino-4-fluoropiperidine-1-carboxylate (220 mg, 1.009 mmol).

ER-895415 as an example for Compound 41 in Scheme 11: To a stirred solution of 38 (1.10 g, 3.70 mmol) in DCM (5 mL) at 0° C. was added oxalyl chloride (1.0 mL, 11.42 mmol) dropwise over 2 min. The reaction mixture was allowed to warm to rt and stir for 1 h after which time the reaction was concentrated and dried in vacuo. The dried syrup was cooled to 0° C. followed by the slow addition of MeOH (5 mL) with stirring. The completed reaction was concentrated to dry, diluted with DCM (10 mL), washed with saturated sodium sulfite (3 mL), brine (3 mL) and then dried over $Na_2SO_4$, filtered and concentrated to dry. The crude product was purified over silica gel (eluting w a 0-50% EtOAc in heptane gradient) to provide ER-895415 (894 mg, 2.81 mmol, 76% yield) after combining the desired fractions, concentrating and drying in vacuo.

Preparation of Example ER-899332 Following Scheme 21:

Scheme 21

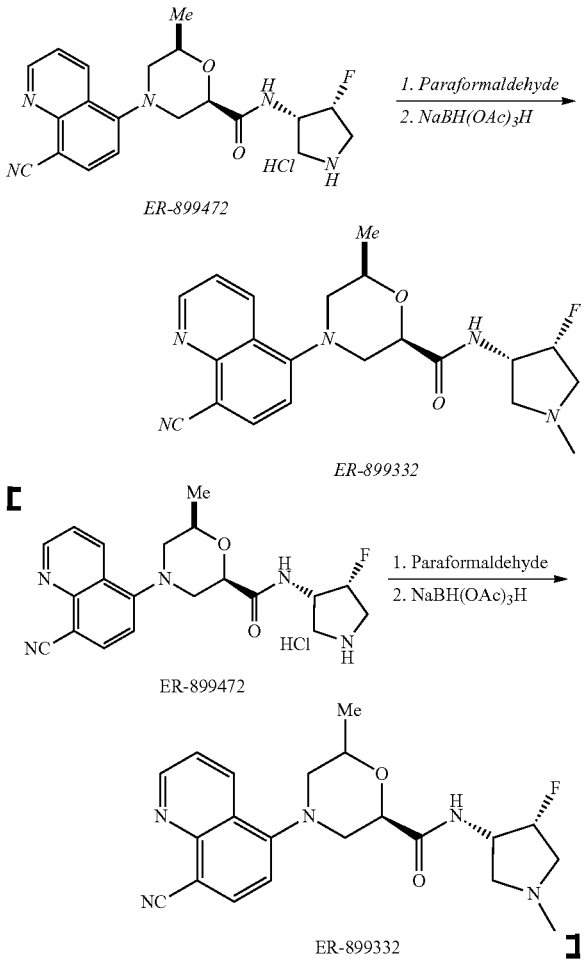

The solution of ER-899472-HCl (49.8 mg, 0.119 mmol) and paraformaldehyde (8.90 mg, 0.297 mmol) in DCM (0.5 mL) was stirred at room for 1 hr. Sodium triacetoxyborohydride (62.8 mg, 0.297 mmol) was added and resulting solution was stirred at rt for 2 days. After the solvents were removed, the crude was chromatographed on silica (15% MeOH in DCM) to give ER-899332 (8.16 mg, 0.021 mmol, 18.3% yield).

ER-899457 (50 mg, 0.117 mmol, 97% yield) was prepared in a similar manner to ER-899332 starting with ER-899336 (50 mg, 0.122 mmol).

ER-899836: A stirred solution of ER-899477 (76 mg, 0.191 mmol) in solution of 37% formaldehyde in water (0.5 g, 16.652 mmol) and formic acid (0.5 ml, 13.036 mmol) was warmed to 80° C. for 3 h after which time the completed reaction is cooled to rt. The mixture was azeotroped to dryness four times with toluene (2 mL each) and the resultant residue was dissolved in MeOH (5 mL) followed by the addition of Amberlite IRA400 hydroxide form (2 g) and stirred for 10 min. Additional Amberlite IRA400 is added with stifling until a neutral pH is obtained after which time the suspension was filtered, concentrated, and azeotroped two times with toluene (2 mL each). The crude material was then purified over silica gel (Biotage SNAP Ultra, 25 g, eluting with a 1-40% MeOH in DCM) to provide ER-899836 (55 mg, 0.134 mmol, 69.9% yield) after combining the desired fractions, concentrating and drying in vacuo.

ER-899836 (50 mg, 0.124 mmol) was dissolved in acetonitrile (1 mL) followed by the addition of 2 M HCl in diethyl ether (0.062 ml, 0.124 mmol) and stirred at rt for 30 min. The resultant orange solution was concentrated to dryness and placed under high vacuum overnight to provide ER-899836-HCl in quantitative yield.

ER-899688-HCl (381 mg, 0.886 mmol, 88.4% yield) was prepared in a similar manner to ER-899836-HCl starting with ER-897968 (600 mg, 1.58 mmol).

ER-899820-HCl (45 mg, 0.110 mmol, 69.9% yield) was prepared in a similar manner to ER-899836-HCl starting with ER-899819 (62 mg, 0.158 mmol).

ER-899337 (35.6 mg, 0.087 mmol, 24. % yield) was similarly prepared in a similar manner to ER-899836 starting with ER-897968 (142 mg, 0.361 mmol) as a free base.

ER-899835 (29 mg, 0.071 mmol, 81. % yield) was similarly prepared in a similar manner to ER-899836 starting with ER-899718 (34 mg, 0.086 mmol) as a free base.

ER-899837 (35.6 mg, 0.087 mmol, 24.2% yield) was similarly prepared in a similar manner to ER-899836 starting with ER-899417 (142 mg, 0.361 mmol) as a free base.

ER-898707-formate (17 mg, 0.0.36 mmol, 78. % yield) was prepared in a similar manner to ER-899836 starting with ER-898694 (20 mg, 0.046 mmol) maintaining as the formate salt instead of conversion to the HCl salt as above.

Other Examples Depicted by General Structure 39 or 40 in Scheme 11

ER-895472: To a cooled solution of 38 (22.7 mg, 0.076 mmol) and TEA (12.8 μl, 0.092 mmol) in THF at −15° C. was added ethyl chloroformate (8.1 μl, 0.084 mmol). After stifling 1.5 hr, ammonium hydroxide (6.0 μl, 0.153 mmol) was added after which time stifling continued for an additional 2 hr at −10° C. The reaction was allowed to warm to rt and stirred an additional 2 h. The completed reaction was quenched by addition of sat. $NaHCO_3$ (5 mL) followed by the extraction of the aqueous phase 3 times with EtOAc (5 mL each). The combined organic layers were dried over anhydrous $Na_2SO_4$, filtered and concentrated to give a pale yellow oil. The crude product was purified using reverse phase HPLC C-18 (Water's X-Bridge C18 19×100 mm column; gradient using acetonitrile/water containing 0.1% formic acid) to provide ER-895472 (6.2 mg, 0.021 mmol, 27.5% yield).

ER-899122: To a cooled solution of 38 (80 mg, 0.24 mmol) and 4-methylmorpholine (32 μl, 0.288 mmol) in THF (4 mL) at 0° C. was added isopropyl chloroformate (38 μl, 0.084 mmol). After stifling 30 min, Tetrahydro-pyran-4-ylamine (29.1 mg, 0.288 mmol) was added after which time stifling continued for an additional 2 hr at −10° C. The reaction was allowed to warm to rt and stirred an additional 16 h. The completed reaction was quenched by addition of sat. $NaHCO_3$ (5 mL) followed by the extraction of the aqueous phase 3 times with EtOAc (5 mL each). The combined organic layers were dried over anhydrous $Na_2SO_4$, filtered and concentrated to give a pale yellow oil. The crude product was purified over silica gel (25 g) eluting with a linear gradient of 80-100% EtOAc in heptane to provide ER-899122 (40 mg, 0.100 mmol, 41.7% yield) after concentration of the desired fractions to dry and placing the product under high vacuum.

ER-899121 (40 mg, 0.104 mmol, 43.3% yield) was prepared in a similar manner to ER-899122 starting with 38 (80 mg, 0.24 mmol) and 3-aminomethyl-oxetane (25.06 mg, 0.288 mmol).

ER-899123 (40 mg, 0.109 mmol, 45.5% yield) was prepared in a similar manner to ER-899122 starting with 38 (80 mg, 0.24 mmol) and 3-aminotetrahydrofuran (25.06 mg, 0.288 mmol).

ER-899140 (20 mg, 0.051 mmol, 21.3% yield) was prepared in a similar manner to ER-899122 starting with 38 (80 mg, 0.24 mmol) and tert-butyl(2-aminoethyl)(methyl)carbamate (50.1 mg, 0.288 mmol) after removal of the Boc group using TFA and neutralizing with MP-carbonate as described.

ER-899151 (15 mg, 0.035 mmol, 14.6% yield) and ER-899152 (15 mg, 0.035 mmol, 14.6% yield) were prepared in a similar manner to ER-899122 starting with 38 (80 mg, 0.24 mmol) and 3-Amino-1,1,1-trifluoro-2-propanol (37.1 mg, 0.288 mmol) as a mixture of stereoisomers. The two products were separated using the chromatography method described for ER-899122. The stereocenters were arbitrarily assigned and have not been definitively determined.

ER-899153 (32 mg, 0.083 mmol, 34.4% yield) was prepared in a similar manner to ER-899122 starting with 38 (80 mg, 0.24 mmol) and glycine methyl ester hydrochloride (36.1 mg, 0.288 mmol).

ER-899154 (16 mg, 0.041 mmol, 17.3% yield) was prepared in a similar manner to ER-899122 starting with 38 (80 mg, 0.24 mmol) and dimethylethylenediamine (31.6 μl, 0.288 mmol).

ER-899159 (14 mg, 0.033 mmol, 13.8% yield) and ER-899160 (13 mg, 0.031 mmol, 12.8% yield) were prepared in a similar manner to ER-899122 starting with 38 (80 mg, 0.24 mmol) and 4-amino-1,1,1-trifluorobutan-2-ol hydrochloride (51.6 mg, 0.288 mmol) as a mixture of stereoisomers. The two products were separated using the chromatography method described for ER-899122. The stereocenters were arbitrarily assigned and have not been definitively determined.

ER-899161 (13 mg, 0.031 mmol, 12.9% yield) was prepared in a similar manner to ER-899122 starting with 38 (80 mg, 0.24 mmol) and 4,4,4-trifluorobutane-1,3-diamine dihydrochloride (61.9 mg, 0.288 mmol) as a diastereomeric mixture.

ER-899152 (9 mg, 0.024 mmol, 37.0% yield) was prepared by dissolving ER-899153 (24 mg, 0.65 mmol) in MeOH (2 mL) and water (0.5 mL) followed by the addition of lithium hydroxide (3.12 mg, 13.0 mmol). The reaction was stirred for 16 h at rt after which time the completed reaction was acidified with 3 N HCl to pH 3 followed by extraction 3 times with EtOAc (10 mL each), combining the organic layers, drying over anhydrous $Na_2SO_4$, filtering and concentrating to dryness. The crude product was purified over a C-18 reverse phase HPLC column eluting with a linear gradient of 10%-90% acetonitrile in water with 0.1% formic acid and concentrating the desired peak followed by high vacuum to dryness.

ER-899278 (20 mg, 0.051 mmol, 33.8% yield) was prepared in a similar manner to ER-899140 starting with 38 (50 mg, 0.15 mmol) and (R)-tert-butyl 2-(aminomethyl)morpholine-4-carboxylate (48.6 mg, 0.225 mmol).

ER-899366 (70 mg, 0.171 mmol, 42.4% yield) was prepared in a similar manner to ER-899140 starting with 38 (120 mg, 0.404 mmol) and (2S,6R)-tert-butyl 2-(aminomethyl)-6-methylmorpholine-4-carboxylate (112 mg, 0.484 mmol).

ER-899367 (40 mg, 0.102 mmol, 38% yield) was prepared in a similar manner to ER-899140 starting with 38 (80 mg, 0.269 mmol) and tert-butyl hexahydropyrrolo[3,4-c]pyrrole-2(M)-carboxylate (68.5 mg, 0.373 mmol).

ER-899459 (30 mg, 0.074 mmol, 31.3% yield) was prepared in a similar manner to ER-899122 starting with 38 (70 mg, 0.235 mmol) and N,N-dimethylpiperidin-4-amine (36.2 mg, 0.283 mmol).

ER-899464 (20 mg, 0.051 mmol, 18.9% yield) was prepared in a similar manner to ER-899122 starting with 38 (80 mg, 0.269 mmol) and 1-methylpiperidin-4-amine (36.9 mg, 0.323 mmol).

ER-899588 (40 mg, 0.105 mmol, 44.8% yield) was prepared in a similar manner to ER-899140 starting with 38 (70 mg, 0.235 mmol) and tert-butyl piperidin-4-ylcarbamate (56.6 mg, 0.283 mmol).

ER-899608 (40 mg, 0.102 mmol, 37.8% yield) was prepared in a similar manner to ER-899140 starting with 38 (70 mg, 0.235 mmol) and tert-butyl(4-methylpiperidin-4-yl)carbamate (63.4 mg, 0.296 mmol).

ER-899680 (40 mg, 0.098 mmol, 19.2% yield) was prepared in a similar manner to ER-899122 starting with 38 (100 mg, 0.336 mmol) and 1-ethylpiperidin-3-amine (43.1 mg, 0.336 mmol).

ER-899431 (53 mg, 0.103 mmol, 51.3% yield) was prepared in a similar manner to ER-899122 starting with 38 (99 mg, 0.333 mmol) and methylamine (2M in THF) (1.50 mL, 3.00 mmol).

ER-899626 (29 mg, 0.071 mmol, 35.3% yield) was prepared in a similar manner to ER-899122 starting with 38 (60 mg, 0.202 mmol) and 4-amino-1-ethyl piperidine (25.9 mg, 0.202 mmol).

ER-899718 (32 mg, 0.081 mmol, 40.1% yield) was prepared in a similar manner to ER-899140 starting with 38 (60 mg, 0.202 mmol) and tert-butyl 4-amino-4-methylpiperidine-1-carboxylate (47.6 mg, 0.222 mmol).

Additional Examples: Modification of general structure 39, Scheme 11:

Scheme 22

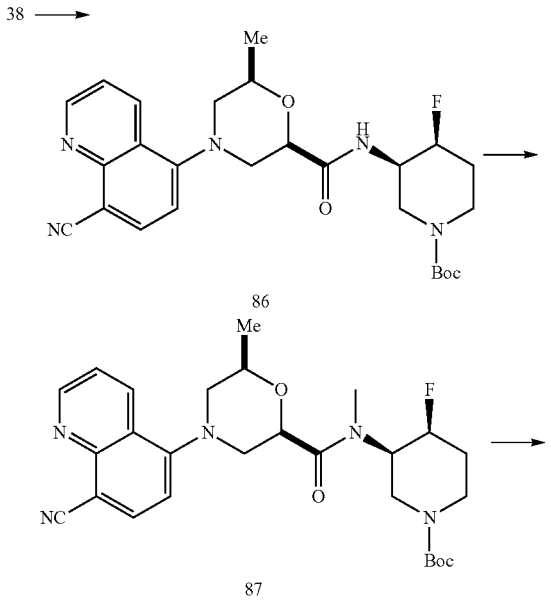

-continued

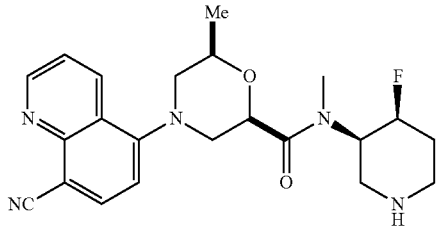

ER-899333-HCl

ER-899333-HCl: To a stirred solution of 38 (58.2 mg, 0.196 mmol) and HBTU (89 mg, 0.235 mmol) in DCM (1.94 mL) was added DIEA (137 μl, 0.783 mmol) followed by (3R,4S)-tert-butyl 3-amino-4-fluoropiperidine-1-carboxylate (42.7 mg, 0.196 mmol). The reaction was stirred overnight after which time the completed reaction was concentrated and diluted with EtOAc (10 mL). The organic solution was washed with 2N aqueous citric acid, saturated $NaHCO_3$, dried over anhydrous $Na_2SO_4$, filtered and concentrated to dryness. The crude product was purified over silica gel (50 g, eluting with a 40-100% EtOAc in heptane, 20 column volumes) to provide 86 (58.5 mg, 0.118 mmol, 56.2% yield) as a pale yellow solid.

To a stirred solution of 86 (58.8 mg, 0.118 mmol) and methyl iodide (7.39 μL, 0.118 mmol) in DMF (1 mL) cooled to 0° C. was added NaH (5.20 mg, 0.13 mmol, oil dispersion). The reaction was warmed to rt and stirred for 3.5 h. The completed reaction was cooled with ice/water bath and quenched by the slow addition of saturated ammonium chloride (5 mL) followed by water (5 mL) and extraction two times with EtOAc (10 mL each). The combined organic phases were dried over anhydrous $Na_2SO_4$, filtered and concentrated to dryness. The crude product was purified over silica gel (25 g, eluting with a 40-100% gradient of EtOAc in heptane, 20 column volumes) to provide 87 (42.9 mg, 0.084 mmol, 71.0%) as a pale yellow solid.

To a stirred solution of 87 (42.9 mg, 0.084 mmol) in EtOAc (1 mL) was added 4.0 N HCl in 1,4-Dioxane (0.419 mL, 1.677 mmol) followed by stifling at rt for 1 hr, after which time the completed reaction was concentrated and dried in vacuo to provide ER-89933-HCL (23.4 mg, 0.054 mmol, 62.3%).

Scheme 23

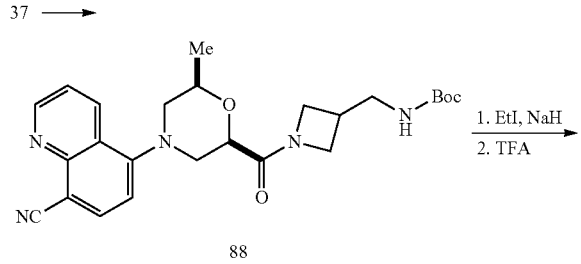

-continued

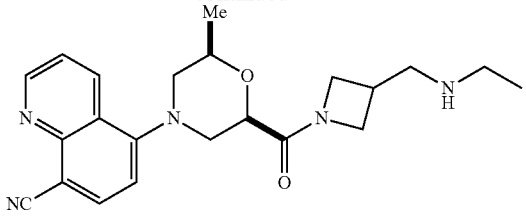

ER-899335

ER-8999335: To a stirred solution 38 (357.2 mg, 1.201 mmol) and HBTU (547 mg, 1.442 mmol) in DCM (10 mL) was added DIEA (0.84 mL, 4.806 mmol) and tert-butyl (azetidin-3-ylmethyl)carbamate (224 mg, 1.201 mmol). The reaction mixture was stirred for 3 h after which time the completed reaction concentrated, dissolved in EtOAc (25 mL) and washed with 2N aqueous citric acid (20 mL), saturated $NaHCO_3$ (20 mL), and dried over anhydrous $Na_2SO_4$, filtered and concentrated to dry. The crude product was purified over silica gel (40 g, eluting with a 50-100% EtOAc/heptane, 20 column volumes) to provide 88 (181.6 mg, 0.390 mmol, 32.5% yield) of pale yellow solid.

To a stirred solution 88 (52.6 mg, 0.113 mmol) and ethyl iodide (10.50 μL, 0.13 mmol) in DMF (1.0 mL, 12.915 mmol) at 0° C. was added 60% sodium hydride (5.87 mg, 0.147 mmol) after which time the reaction was allowed to warm to rt and stirred for 6 h. The completed reaction was cooled to 0° C. and quenched by the slow addition of saturated $NH_4Cl$ (5 mL) followed by dilution with water (5 mL) and extraction two times with EtOAc (10 mL each). The combined organic phases were dried over anhydrous $Na_2SO_4$, filtered and concentrated to dryness. The crude product was purified over silica gel (25 g, eluting with 70-100% EtOAc in heptane, 20 column volumes) to provide the Boc-protected intermediate which was used in the next step. The Boc was removed by dissolving the intermediate in EtOAc (1 mL) and adding TFA (0.5 mL) followed by stifling for 1 h. The completed reaction was concentrated to dry, dissolved in DCM (10 mL), washed 2 times with saturated $NaHCO_3$, dried over anhydrous $Na_2SO_4$, filtered, concentrated, and high vacuum to dry to provide ER-899335 (4.1 mg, 0.010, mmol, 9.3%) as a pale yellow solid.

Scheme 24

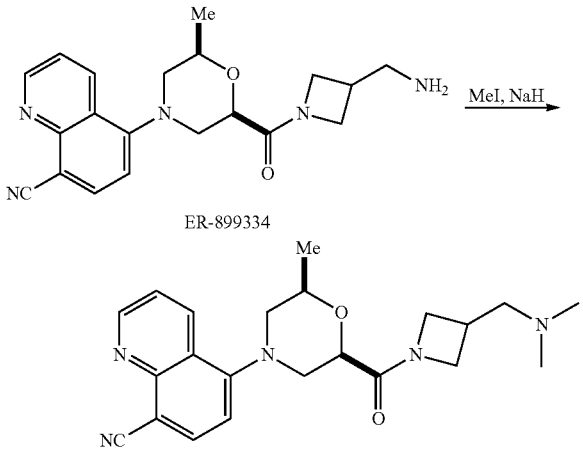

ER-899334

ER-899336

ER-899336: To a stirred solution of ER-899334 (35.4 mg, 0.097 mmol) and iodomethane (0.013 mL, 0.213 mmol) in DMF (1 mL) at 0° C. was added 60% sodium hydride (9.69 mg, 0.242 mmol) after which time the reaction was warmed to rt and stirred overnight. The completed reaction was cooled to 0° C. and quenched by the slow addition of saturated $NH_4Cl$ (5 mL) followed by dilution with water (5 mL) and extraction two times with EtOAc (10 mL each). The combined organic phases were dried over anhydrous $Na_2SO_4$, filtered and concentrated to dryness. The crude product was purified over silica gel (25 g, eluting with 70-100% EtOAc in heptane, 20 column volumes) to provide ER-899336 (5.2 mg, 0.013 mmol, 13.6% yield) after collection of the desired material, concentration and high vacuo.

Scheme 25

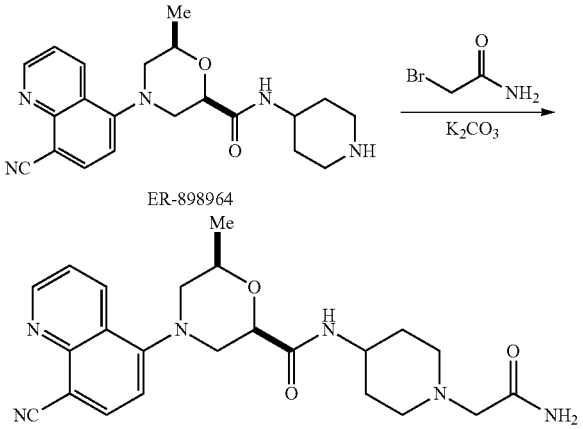

ER-898964

ER-899481

ER-899481: To a stirred solution of ER-898946 (60 mg, 0.158 mmol) in acetonitrile (10 mL) was added $K_2CO_3$ (87 mg, 0.632 mmol) and 2-bromoacetamide (43.6 mg, 0.316 mmol). The reaction mixture was warmed to 60° C. and stirred for 16 h, after which time the completed reaction was filtered. The resultant solution was concentrated and the crude product was purified over a C-18 HPLC column (eluting with 10% to 50% acetonitrile in water with 0.1% formic acid) to provide ER-899481 (43 mg, 0.099 mmol, 62.3% yield) after collection of the desired material, concentration and high vacuo.

ER-885612 as an Example of Compound 42, Scheme 12: To a cooled, stirred solution of 13 (25 mg, 0.088 mmol) in DMF (0.5 mL) at 0° C. was added NaH (3.5 mg, 0.088 mmol, 60% oil dispersion) followed by methyl iodide (16.5 uL, 0.265 mmol). The reaction was stirred an additional 20 min after which time water (1 mL) was slowly added. The quenched reaction was extracted two times with DCM (2 mL each), dried over $MgSO_4$, filtered and concentrated to dry. Purification over a reverse-phase preparative HPLC column (X-Bridge C18 19×100 mm column; eluting with 0-50% acetonitrile in water containing 0.05% TFA) provided ER-885612 (16.9 mg, 0.057 mmol, 64.6% yield) after combining the desired collected fractions, concentration and drying in vacuo.

ER-885807 (15.2 mg, 0.049 mmol, 55.7% yield) was prepared in a similar manner to ER-885612 starting with 13 (25 mg, 0.088 mmol) and iodoethane (20.6 mg, 0.132 mmol).

ER-885808 (8.2 mg, 0.025 mmol, 28.6% yield) was prepared in a similar manner to ER-885612 starting with 13 (25 mg, 0.088 mmol) and isopropyl iodide (22.5 mg, 0.132 mmol).

ER-885892 (3.1 mg, 0.009 mmol, 10.4% yield) was prepared in a similar manner to ER-885612 starting with 13 (25 mg, 0.088 mmol) and 1-iodo-2-methylpropane (15.2 uL, 0.132 mmol).

ER-885929 (17.5 mg, 0.048 mmol, 54.6% yield) was prepared in a similar manner to ER-885612 starting with 13 (25 mg, 0.088 mmol) and 1-iodohexane (37.4 mg, 0.176 mmol).

ER-885930 (7.9 mg, 0.021 mmol, 23.7% yield) was prepared in a similar manner to ER-885612 starting with 13 (25 mg, 0.088 mmol) and cyclohexylmethyl bromide (31.3 mg, 0.177 mmol).

ER-895324 (35.2 mg, 0.098 mmol, 54.7% yield) was prepared in a similar manner to ER-885612 starting with 13 (50.6 mg, 0.179 mmol) and 2-bromopyridine (20.4 uL, 0.214 mmol). THF (1 mL) was used instead of DMF.

ER-895325 (54.2 mg, 0.150 mmol, 83.8% yield) was prepared in a similar manner to ER-893324 starting with 13 (50.6 mg, 0.179 mmol) and 2-bromopyrimidine (57 mg, 0.359 mmol).

ER-894552 (5 mg, 0.014 mmol, 19.2% yield) was prepared in a similar manner to ER-893324 starting with 13 (20.4 mg, 0.072 mmol) and 2-chloropyrazine (8.3 mg, 0.0.072 mmol).

ER-886137: In a dry microwave reaction vessel was added cesium carbonate (172.5 mg, 0.529 mmol), copper (I) iodide (33.6 mg, 0.176 mmol), 1,1'-binaphthyl-2,2'-diamine (50.2 mg, 0.177 mmol, 2-iodo-1,3-dimethylbenzene (123 mg, 0.53 mmol) in DMSO (0.3 mL) followed by 13 (50 mg, 0.177 mmol). The reaction mixture was microwaved at 110° C. for 12 h after which time the mixture was directly injected on a reverse-phase preparative HPLC column (Water's X-Bridge C18 19×100 mm column; gradient using 0-50% acetonitrile in water containing 0.05% TFA) for purification eluting with, providing a crude product. The crude product was purified over silica gel (Biotage eluting with a gradient from 25% EtOAc in heptane to 100% EtOAc) to provide ER-886137 (12.1 mg, 0.031 mmol, 17.6% yield) after combining the desired collected fractions, concentration and drying in vacuo.

ER-886514: To a stirred suspension of 14 (10.5 mg, 0.024 mmol) and potassium carbonate (30 mg, 0.217 mmol) in toluene (1 mL) was added phenol (24.4 mg, 0.259 mmol). The reaction mixture was microwaved at 150° C. for 5 h after which time the crude mixture was filtered and directly injected on a reverse-phase preparative HPLC column (Water's X-Bridge C18 19×100 mm column; gradient using 0-50% acetonitrile in water containing 0.05% TFA) to provide ER-886514 (4.5 mg, 0.013 mmol, 54.1% yield) after combining the desired collected fractions, concentration and drying in vacuo.

ER-886515 (3.2 mg, 0.009 mmol, 37.6% yield) was prepared in a similar manner to ER-886514 starting with 14 (10.6 mg, 0.024 mmol) and 3-methylphenol (28.1 mg, 0.260 mmol).

ER-886516 (4.7 mg, 0.013 mmol, 52.4% yield) was prepared in a similar manner to ER-886514 starting with 14 (10.6 mg, 0.024 mmol) and 4-methylphenol (28.1 mg, 0.260 mmol).

ER-886605 (7.9 mg, 0.020 mmol, 85.1% yield) was prepared in a similar manner to ER-886514 starting with 14 (10.3 mg, 0.024 mmol) and 3,4-diflurorphenol (20 mg, 0.154 mmol). 1-Methylpyrrolidinone (1 mL) was used instead of toluene in this preparation.

ER-886606 (7.2 mg, 0.019 mmol, 81.2% yield) was prepared in a similar manner to ER-886605 starting with 14 (10.3 mg, 0.024 mmol) and 3-flurorphenol (13.2 mg, 0.118 mmol).

ER-886624 (5.1 mg, 0.014 mmol, 59% yield) was prepared in a similar manner to ER-886605 starting with 14 (10 mg, 0.023 mmol) and 2-flurorphenol (10 mg, 0.089 mmol).

ER-886786 (8.2 mg, 0.022 mmol, 76.9% yield) was prepared in a similar manner to ER-886605 starting with 14 (12.5 mg, 0.029 mmol) and 2-methylphenol (28.1 mg, 0.260 mmol).

Other Examples using Compound 13 or ER-885493 as a starting material:

ER-885621: To a stirred solution of bis(2-methoxyethyl) aminosulfur trifluoride (24.4 uL, 0.132 mmol) in DCM (0.1 mL) cooled to −78° C. under a $N_2$ atmosphere was added 13 (25 mg, 0.088 mmol) in DCM (0.1 mL). The reaction mixture was allowed to warm to −50° C. and stirred for 0.5 h, warmed to 0° C., and stirred for 1.5 h. The reaction mixture was warmed to 5° C. and stirred for 2 h after which time saturated $NaHCO_3$ in water was added dropwise until reach pH 10. The layers were separated and the organic layer was washed two times with water (1 mL), dried over $MgSO_4$, filtered and concentrated to dry. Purification over a reverse-phase preparative HPLC column eluting with 0-50% acetonitrile in water, provided ER-885621 (12.5 mg, 0.044 mmol, 49.8% yield) after combining the desired collected fractions, concentration and drying in vacuo.

ER-885906: A stirred solution of 13 (85.5 mg, 0.302 mmol) in thionyl chloride (2 mL) was warmed to 85° C. for 24 h, after which time the excess thionyl chloride was removed and the crude product was purified over a reverse-phase preparative HPLC column eluting with 0-50% acetonitrile in water, provided ER-885906 (4.3 mg, 0.014 mmol, 4.7% yield) after combining the desired collected fractions, concentration and drying in vacuo.

Preparation of ER-886431 & ER-886480 as examples of Compound 44, Scheme 13

Compound 43 or ER-886250: To a stirred solution of 13 (200 mg, 0.706 mmol) in DCM (5 mL) and pyridine (0.114 mL, 1.4 mmol) at 0° C. under a nitrogen atmosphere was added Dess-Martin periodinane (359 mg, 0.846 mmol) after which time the reaction was warmed to rt and stirred for 1 h. The reaction was found to be incomplete thus additional Dess-Martin periodinane (359 mg, 0.846 mmol) and pyridine (0.114 mL, 1.4 mmol) were added followed by stirring for an additional 30 min. The completed reaction was poured over saturated aqueous $NaHCO_3$ (4 mL) with 10% aqueous sodium thiosulfate (2 mL). The mixture was stirred for 30 min after which time the mixture was extracted three times with DCM (4 mL each). The combined organic layers were washed with brine (4 mL), dried over $Na_2SO_4$, filtered and concentrated. The crude product was purified over silica gel (Biotage SP4, 25 g, eluting with 10-100% EtOAc in heptane) to provide 5-((2R,6R)-2-formyl-6-methylmorpholino) quinoline-8-carbonitrile, 43 or ER-886250 (110 mg, 0.391 mmol, 55.4% yield) as a yellow syrup after combining the desired fractions, concentration and drying in vacuo.

To stirred solution of 43 (25 mg, 0.089 mmol) in THF (0.5 mL) at 0° C. under a nitrogen atmosphere was added 1 M vinyl magnesium bromide (0.098 mL, 0.098 mmol) in THF dropwise over a 2-min period. The reaction was stirred at 0° C. for 2 h after which time saturated ammonium chloride (0.5 mL) was added slowly followed by water (0.25 mL).

The quenched reaction was warmed to rt, stirred for an additional 10 min, and extracted two times with EtOAc (2 mL each). The combined organic layers were washed with brine (1 mL), dried over $Na_2SO_4$, filtered and concentrated. The crude product was purified on preparative TLC plates (Merck Silica Gel 60 F254, 2 20×20 cm plates, eluting with EtOAc) to provide ER-886431 (3 mg, 0.010 mmol, 11.2% yield, Rf=0.75, EtOAc) and ER-886480 (3 mg, 0.0.10 mmol, 11.2% yield, Rf=0.80. EtOAc) as a yellow syrup after the desired fractions were eluted separately from the silica gel, concentration and drying in vacuo. The stereochemistry for the free alcohol functionality for both examples was arbitrarily assigned.

ER-886530 (11 mg, 0.032 mmol, 36.4% yield, Rf=0.80, EtOAc) and ER-886531 (3 mg, 0.0.10 mmol, 11.2% yield, Rf=0.75, EtOAc) were prepared in a similar manner to ER-886431 and ER-886480 starting with 43 (25 mg, 0.089 mmol) and 2 M butylmagnesium chloride in THF (0.131 mL, 0.262 mmol). The crude product was purified over silica gel (Biotage SP4, 25 g, eluting with 20-100% EtOAc in heptane. The stereochemistry for the free alcohol functionality for both examples was arbitrarily assigned.

ER-886532 (4 mg, 0.011 mmol, 6.3% yield, Rf=0.80, EtOAc) and ER-886533 (4 mg, 0.011 mmol, 6.3% yield, Rf=0.75, EtOAc) were prepared in a similar manner to ER-886530 and ER-886531 starting with 43 (49 mg, 0.174 mmol) and 1.3 M cyclohexylmagnesium chloride in THF (0.20 mL, 0.260 mmol). The stereochemistry for the free alcohol functionality for both examples was arbitrarily assigned.

ER-886567 (3.6 mg, 0.009 mmol, 5.3% yield, Rf=0.80, EtOAc) and ER-886568 (8.6 mg, 0.022 mmol, 12.8% yield, Rf=0.75, EtOAc) were prepared in a similar manner to ER-886530 and ER-886531 starting with 43 (49 mg, 0.174 mmol) and 1 M phenethylmagnesium chloride in THF (0.26 mL, 0.260 mmol). The stereochemistry for the free alcohol functionality for both examples was arbitrarily assigned.

ER-886520 (26 mg, 0.084 mmol, 49.1% yield, Rf=0.80, EtOAc) was prepared in a similar manner to ER-886530 and ER-886531 starting with 43 (48 mg, 0.171 mmol) and 2 M ethylmagnesium chloride in THF (0.128 mL, 0.256 mmol). The diastereomeric mixture was used for additional studies.

ER-886564 and ER-886565 via Scheme 26

Scheme 26

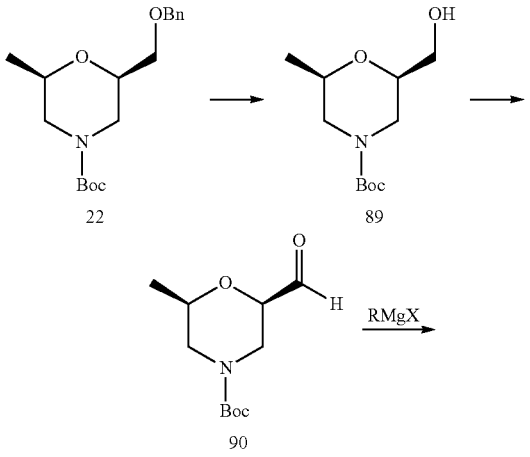

-continued

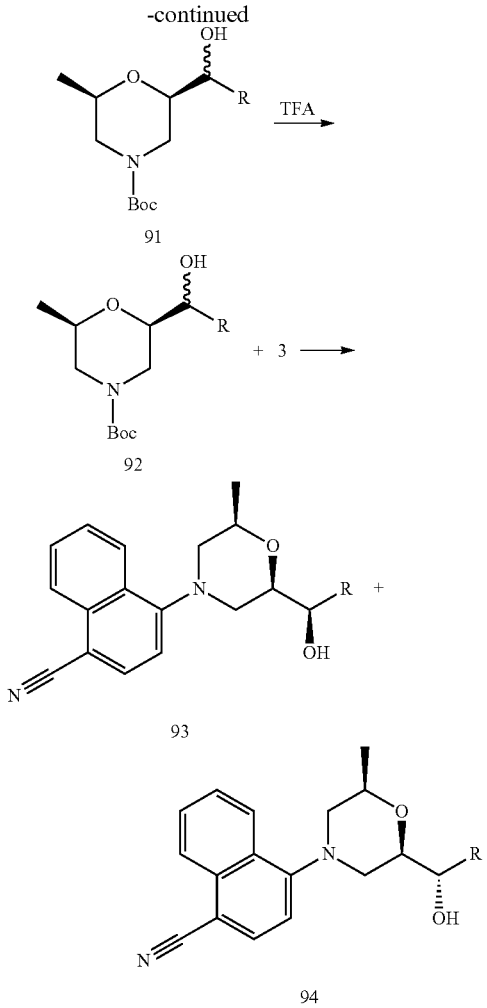

To a stirred solution of 22 (2.51 g, 7.8 mmol) in EtOH (40 mL) was added 10% palladium on activated carbon in 50% water (1.66 g) followed by charging the flask several times with hydrogen gas. The reaction was maintaining under a hydrogen atmosphere (balloon pressure) at 40° C. and stirred for 16 h, after which time the reaction was purged with nitrogen gas several times while evacuating the system with house vacuum between purges. The completed reaction was filtered over Celite 545, the filter pad washed two times with EtOH (85 mL each), followed by concentration of the combined filtrates were concentrated and dried in vacuo. The crude product, (2R,6R)-tert-butyl 2-(hydroxymethyl)-6-methylmorpholine-4-carboxylate, 89 (1.56 g, 6.7 mmol, 86.5% yield) was used in the next step without further purification.

To a stirred solution of 89 (1.501 g, 6.5 mmol) in DCM (30 mL) and pyridine (1.05 mL, 13.0 mmol) at 0° C. under a nitrogen atmosphere was added Dess-Martin periodinane (3.3 g, 7.8 mmol) after which time the reaction was warmed to rt and stirred for 1 h. The reaction was found to be incomplete thus additional Dess-Martin periodinane (1.4 g, 3.3 mmol) and pyridine (0.52 mL, 6.4 mmol) were added followed by stirring for an additional 2 h. The completed reaction was poured over saturated aqueous $NaHCO_3$ (37 mL) with 10% aqueous sodium thio sulfate (18 mL). The mixture was stirred for 30 min after which time the mixture was extracted three times with DCM (40 mL each). The combined organic layers were washed with brine (37 mL), dried over $Na_2SO_4$, filtered and concentrated. The crude product was purified over silica gel (Biotage 40+S, 40 g, eluting with 10-100% EtOAc in heptane) to provide (2R, 6R)-tert-butyl 2-formyl-6-methylmorpholine-4-carboxylate, 90 (1.285 g, 5.6 mmol, 86.2% yield) as a colorless syrup after combining the desired fractions, concentration and drying in vacuo.

To stirred solution of 90 (208 mg, 0.907 mmol) in THF (5 mL) at 0° C. under a nitrogen atmosphere was added 1 M benzylmagnesium bromide (2.3 mL, 2.3 mmol) in THF dropwise over a 2-min period. The reaction was stirred at 0° C. for 2.5 h after which time saturated ammonium chloride (4.8 mL) was added slowly followed by water (2.5 mL). The quenched reaction was warmed to rt, stirred for an additional 10 min, and extracted two times with EtOAc (20 mL each). The combined organic layers were washed with brine (9.5 mL), dried over $Na_2SO_4$, filtered and concentrated. The crude product over silica gel (Biotage SP4, 25 g, eluting with 25-100% EtOAc in heptane) to provide (2R,6R)-tert-butyl 2-((R,S)-1-hydroxy-2-phenylethyl)-6-methylmorpholine-4-carboxylate, 91 (172 mg, 0.539 mmol, 59.4% yield, R═—$CH_2C_6H_5$) as a colorless oil after the desired fractions were combined, concentration and drying in vacuo.

To a stirred solution of 91 (172 mg, 0.539 mmol) in DCM (1.2 mL) was added TFA (1.2 mL). The reaction was stirred for 30 min at rt after which time the completed reaction was diluted with toluene (4.6 mL), concentrated and azeotroped to dry two times with toluene (4.6 mL each) to dryness to provide 1-((2R,6R)-6-methylmorpholin-2-yl)-2-phenylethanol, 92 (179 mg, 0.534 mmol, 99.0% yield, R═—$CH_2C_6H_5$) as the TFA salt without further purification.

Crude 92 (179 mg, 0.534 mmol), was dissolved in N-methylpyrrolidone (3 mL) followed by 3 (187 mg, 0.802 mmol) and DIPEA (0.2 mL, 1.1 mmol). The mixture was microwaved at 170° C. for 5 h after which time the cooled mixture was directly injected onto a C-18 reverse-phase preparative HPLC column eluting with 10-60% acetonitrile in water with 0.1% TFA. The two eluted fractions were separately concentrated to dry, azeotroped two times with MeOH (5 mL each). Each isomer was dissolved in MeOH (2 mL) and passed over a basic plug of silica gel (silica gel—$CO_2$) eluting two times with MeOH (2 mL each) followed by concentration and drying in vacuo to provide separately 93 or ER-886564 (19 mg, 0.051 mmol, 9.5% yield, first fraction, R═—$CH_2C_6H_5$) and 94 or ER-886565 (23 mg, 0.062 mmol, 11.5% yield, second fraction, R═—$CH_2C_6H_5$). The stereochemistry of the alcohol position was arbitrarily assigned.

ER-895200 (22.2 mg, 0.075 mmol, 32.1% yield, first fraction) and ER-895310 (15.2 mg, 0.051 mmol, 21.8% yield, second fraction) were prepared in a similar fashion to ER-886564 and ER-886564 starting with 3 (54.6 mg, 0.234 mmol) and 1-((2R,6R)-6-methylmorpholin-2-yl)ethanol (68.2 mg, 0.470 mmol). The stereochemistry of the alcohol position was arbitrarily assigned.

ER-895326: To a stirred solution ER-895200 (17.9 mg, 0.060 mmol) in THF (0.3 mL) was added sodium hydride (4.8 mg, 0.120 mmol, 60% oil dispersion) followed by 2-bromopyrimidine (19 mg, 0.120 mmol). The reaction was warmed to 60° C. and stirred for 30 min after which time it was cooled to rt and slowly quenched with a dropwise addition of water (0.5 mL). The mixture was extracted three times with DCM (3 mL each) and the combined organic layers were washed with brine (3 mL), dried over $Na_2SO_4$, filtered and concentrated to dry. The crude product was purified over silica gel (Biotage, eluting with a gradient of 0-10% EtOAc in heptane) to provide ER-895326 (20.3 mg, 0.054 mmol, 90.1% yield) after collection of the desired fractions, concentration and drying in vacuo.

ER-895327 (6.4 mg, 0.017 mmol, 63% yield) was prepared in a similar manner to ER-895326 starting with ER-895310 (7.9 mg, 0.027 mmol) and 2-bromopyrimidine (8 mg, 0.0.50 mmol).

ER-895412: To a stirred solution of 1.6 M n-butyl lithium in THF (1.36 mL, 2.18 mmol) at −40° C. was added dropwise 2-bromopyridine (0.21 mL, 2.20 mmol) in diethylether (2 mL) followed by stifling for 30 min at −40° C. 90 (500 mg, 2.18 mmol) in THF (2 mL) was added dropwise over a 3-min period after which time the reaction mixture was stirred at −40° C. for 2 h and then at 0° C. for 1 h. The completed reaction was slowly quenched with saturated ammonium chloride in water (2 mL) followed warming to rt, separation of the layers and extracting the aqueous layer two times with EtOAc (2 mL each). The combined organic layers were washed with brine (2 mL), dried over $Na_2SO_4$, filtered and concentrated to dry. The crude product was purified first by passing over a silica gel (Biotage, eluting with 30% EtOAc in heptane followed by crystallization from 3:1 DCM:MeOH to provide after filtering and drying in vacuo (2R,6R)-tert-butyl 2-((S)-hydroxy(pyridin-2-yl)methyl)-6-methylmorpholine-4-carboxylate (150 mg, 0.486 mmol, 22.3% yield)

To a stirred solution of (2R,6R)-tert-butyl 2-((S)-hydroxy (pyridin-2-yl)methyl)-6-methylmorpholine-4-carboxylate (150 mg, 0.486 mmol) in DCM (5 mL) was added TFA (1 mL) followed by stifling at rt for 1 h. The completed reaction was concentrated and azeotroped to dry three times with toluene (5 mL each) followed by diluting with DCM (10 ml) washing two times with saturated $NaHCO_3$ in water (2 mL), brine (2 mL), drying over $MgSO_4$, filtering and concentration and drying in vacuo to provide crude (S)-((2R,6R)-6-methylmorpholin-2-yl)(pyridin-2-yl)methanol (97.8 mg, 0.469, 96.4% yield).

To a stirred solution of (S)-((2R,6R)-6-methylmorpholin-2-yl)(pyridin-2-yl)methanol (97.8 mg, 0.469 mmol) and Compound 3 (54.6 mg, 0.234 mmol) in DMAC (1 mL) was added TEA (0.132 mL, 0.947 mmol). The reaction was microwaved at 105° C. for 3 h after which time the cooled reaction was directly purified over a reverse-phase preparative HPLC column (Water's X-Bridge C18 19×100 mm column; gradient using 0-50% acetonitrile in water containing 0.1% formic acid) to provided ER-895296 (15.2 mg, 0.042 mmol, 18.0% yield, R=2-pyridyl) after combining the desired collected fractions, concentration and drying in vacuo.

Preparation of ER-886625 as an example of Compound 45, Scheme 13

To a stirred solution of ER-886520 (19 mg, 0.061 mmol) in DCM (0.5 mL) and pyridine (0.010 mL, 0124 mmol) at 0° C. under a nitrogen atmosphere was added Dess-Martin periodinane (31.1 mg, 0.073 mmol) after which time the reaction was warmed to rt and stirred for 1 h. The reaction was found to be incomplete thus additional Dess-Martin periodinane (31.1 mg, 0.073 mmol) and pyridine (0.010 mL, 0124 mmol) were added followed by stirring for an additional 30 min. The completed reaction was poured over saturated aqueous $NaHCO_3$ (0.4 mL) with 10% aqueous sodium thiosulfate (0.2 mL). The mixture was stirred for 30 min after which time the mixture was extracted three times with DCM (0.3 mL each). The combined organic layers were washed with brine (0.35 mL), dried over $Na_2SO_4$, filtered and concentrated. The crude product was purified over silica gel (Biotage SP4, 25 g, eluting with 10-80% EtOAc in heptane) to provide 45 or ER-886625 (7 mg, 0.023 mmol, 37.1% yield) as a yellow solid after combining the desired fractions, concentration and drying in vacuo.

ER-886626 (10.8 mg, 0.030 mmol, 90.9% yield) was prepared in a similar manner to ER-886625 starting with the mixture of ER-886532 and ER-886533 (12 mg, 0.033 mmol).

ER-886629 (6.6 mg, 0.017 mmol, 81% yield) was prepared in a similar manner to ER-886625 starting with the mixture of ER-886567 and ER-886568 (8 mg, 0.021 mmol).

Preparation of ER-886912 and ER-886913:

To a stirred solution of ER-886568 (124 mg, 0.32 mmol) in DCM (1.3 mL) at rt was added methanesulfonyl chloride (37 uL, 0.478 mmol) followed by DMAP (7.8 mg, 0.064 mmol) and DIPEA (0.17 mL, 0.959 mmol). The reaction was stirred at rt for 2 h after which time water (1 mL) and DCM (5 mL) were added followed by stirring an additional 5 min and separation of the layers. The organic layer was washed with brine (1 mL), dried over $Na_2SO_4$, filtered and concentrated. The crude product was purified over silica gel (Biotage SP4, 25 g, eluting with 20-100% EtOAc in heptane) to provide (R)-1-((2R,6R)-4-(8-cyanoquinolin-5-yl)-6-methylmorpholin-2-yl)-3-phenylpropylmethane-sulfonate (136 mg, 0.292 mmol, 93.5% yield) as a yellow solid after combining the desired fractions, concentration and drying in vacuo.

A solution of (R)-1-((2R,6R)-4-(8-cyanoquinolin-5-yl)-6-methylmorpholin-2-yl)-3-phenylpropyl methanesulfonate (38 mg, 0.082 mmol) in NMP (2 mL) and pyrrolidine (0.10 mL, 1.21 mmol) was microwaved at 150° C. for 15 min followed by cooling, filtering and direct injection onto a C-18 HPLC (Water's X-Bridge C18 19×100 mm column; gradient using 0-50% acetonitrile in water containing 0.05% TFA). ER-886912 and ER-886913 fractions were separately concentrated to dry, dissolved in MeOH (3 mL) and eluted over a carbonate impregnated silica gel column (Biotage Isolute SPE, Si—$CO_3$, 1 g), washed with MeOH (3 mL), concentrated and dried in vacuo to provide ER-886912 (1.4 mg, 0.003 mmol, 3.9% yield) as the first eluted peak and ER-886913 (0.6 mg, 0.001 mmol, 1.5% yield) as the second eluted. The stereochemistry for the amine functionality for both examples was arbitrarily assigned.

Preparation of ER-886131: A modification of Scheme 7 via Scheme 27:

Scheme 27

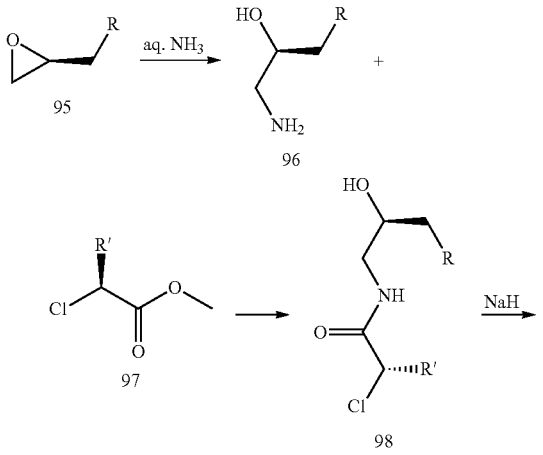

-continued

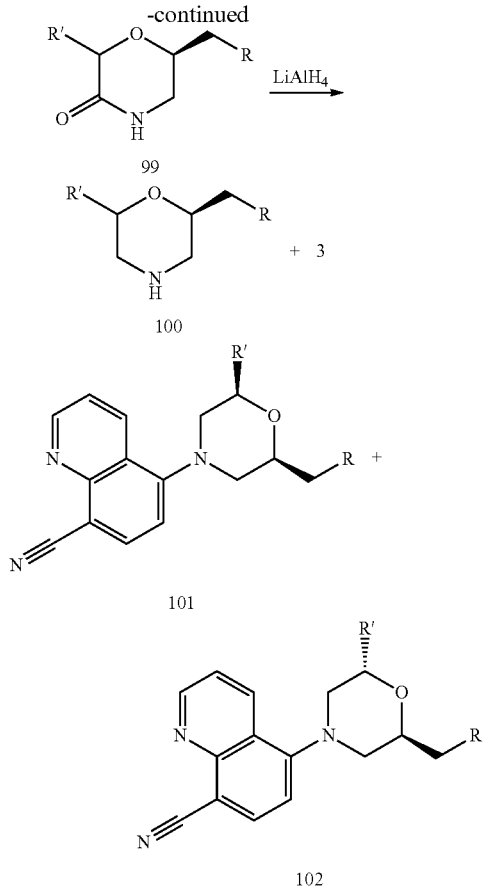

A stirred solution of commercially available (S)-2-propyloxirane, 95 (3.0 g, 34.8 mmol, R=ethyl) in ammonium hydroxide (100 mL) was sealed and stirred for 24 h followed azeotroping to dryness three times with toluene (100 mL each). The crude, colorless product (S)-1-aminopentan-2-ol, 96 (R=ethyl), was used in the next reaction without purification.

To a stirred solution of crude 96 (0.987 mg, 9.57 mmol) in EtOH (20 mL) was added (S)-methyl 2-chloropropanoate, 97 (1.568 g, 11.5 mmol, R'=methyl) followed by warming to 70° C. and stifling for 24 h. The complete reaction was cooled to rt, concentrated to dry and the residue dissolved in EtOAc (20 mL). The organic solution was washed three times with 1 N aqueous HCL (5 mL each), brine (5 mL), dried over $MgSO_4$, filtered and concentrated to dry. The crude product was purified over silica gel (Biotage, eluted with a gradient of 20-100% EtOAc in heptanes) to provide (S)-2-chloro-N—((S)-2-hydroxypentyl)propanamide, 98 (0.356 g, 1.839 mmol, 19.2% yield, R=ethyl; R'=methyl).

To a stirred solution of 98 (0.356 g, 1.839 mmol) in THF (22 mL) at 0° C. was added sodium hydride (294.2 mg, 7.277 mmol, 60% oil dispersion). The reaction was stirred at 0° C. for 30 min then warmed to rt and stirred for an additional 5 h. The completed reaction was slowly quenched with IPA (1 mL) followed by adding Dowex 50, H+ form until a neutral pH is demonstrated. The suspension was filtered and washed two times with IPA (5 mL each). The filtrate was concentrated followed by purification over silica gel (Biotage 25 g, eluting with EtOAc). Obtained a mixture of (2S,6S)-2-methyl-6-propylmorpholin-3-one and (2R,6S)-2-methyl-6-propylmorpholin-3-one, 99 (168.2 mg, 1.07 mmol, 58.2% yield, R=ethyl; R'=methyl) in a 2:1, cis to trans, ratio after collection of the desired fractions, concentration and drying in vacuo.

To a stirred solution of 99 (168.2 mg, 1.07 mmol) in THF (0.8 mL) at rt was added 1 M lithium tetrhydroaluminate (1 mL, 1 mmol) dropwise over a 2-minute period. The reaction was stirred for an additional 2.5 h after which time the completed reaction was cooled to 0° C. followed by the addition of water (0.43 mL) and 1 M sodium hydroxide in water (0.03 mL) and then stirring for 30 min. The resultant precipitate was filtered over Celite 454 and eluted with EtOAc (2 mL), DCM (2 mL), and diethyl ether (2 mL). The combined filtrates were concentrated and dried in vacuo to provide crude (2R,S;6S)-2-methyl-6-propylmorpholine, 100 (R=ethyl; R'=methyl) that will be used directly in the next reaction.

Crude 100 was dissolved in NMP (5 mL) followed by 3 (150 mg, 0.636 mmol) and DIPEA (0.2 mL, 1.1 mmol). The mixture was microwaved at 145° C. for 7 h after which time the cooled mixture was directly injected onto a C-18 reverse-phase preparative HPLC column eluting with 10-60% acetonitrile in water with 0.1% TFA. The two eluted fractions were separately concentrated to dry, azeotroped two times with MeOH (5 mL each). Each isomer was dissolved in MeOH (2 mL) and passed over a basic plug of silica gel (silica gel—$CO_2$) eluting two times with MeOH (2 mL each) followed by concentration and drying in vacuo to provide separately ER-886131, 101 (64.2 mg, 0.217 mmol, 34.2% yield, cis-isomer, R=ethyl; R'=methyl), and ER-886132, 102 (25.2 mg, 0.85 mmol, 13.4% yield, trans-isomer, R=ethyl; R'=methyl).

ER-886212 (315.2 mg, 0.975 mmol, 8.5% overall yield) was prepared in a similar manner to ER-886131 starting with commercially available (S)-1-aminoheptan-2-ol, 90 (3.08 g, 23.5 mmol, R=n-butyl) and (S)-methyl 2-chloropropanoate, 97 (1.568 g, 11.5 mmol, R'=methyl).

Alternative examples of 101 using Scheme 28:

Scheme 28

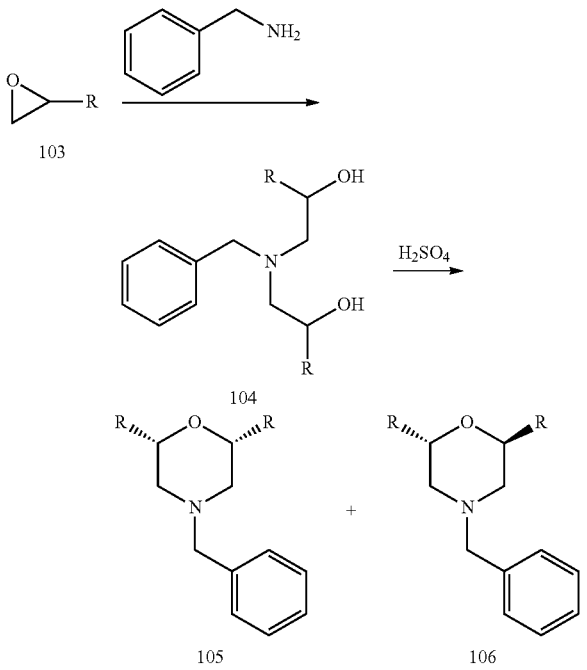

-continued

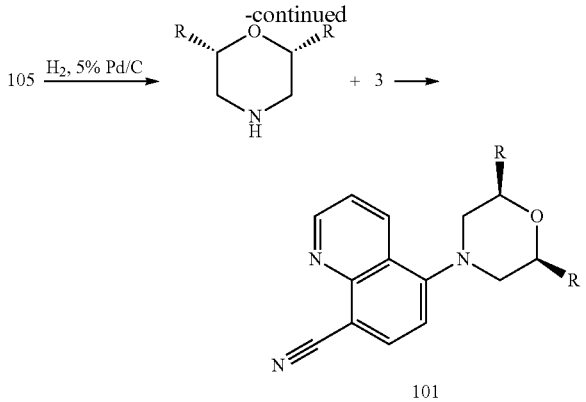

Preparation of ER-886211:

To a stirred solution of 2-ethyloxirane, 103 (621 mg, 8.61 mmol, R=ethyl) in DCM (60 mL) was added benzylamine (996 mg, 9.30 mmol) followed by scandium triflate (341 mg, 0.693 mmol) under a nitrogen atmosphere. The reaction mixture was stirred at rt for 20 h after which time the completed reaction was quenched with saturated $NaHCO_3$ (20 mL), extracted three times with DCM (10 mL each), and the combined organic layers was dried over $MgSO_4$, filtered and concentrated to dry. The crude product was purified over silica gel (Biotage 25 g, eluting with a 10:10:0.1 ratio of heptanes:EtOAc:TEA) to provide 1,1'-(benzylazanediyl)bis (butan-2-ol), 104 (658 mg, 2.628 mmol, 30.4% yield, R=ethyl) after concentration of the combined desired fractions and drying in vacuo.

To a stirred solution of 104 (584 mg, 2.323 mmol) in water (0.3 mL) was slowly added concentrated sulfuric acid (2 mL) over a 5-minute period after which time the reaction was heated at 150° C. for 2 h. The completed reaction was cooled to rt and slowly poured over saturated $NaHCO_3$ (20 mL) with stifling. The mixture was extracted two times with DCM (10 mL each) and the combined organic layers was washed with water (5 mL), brine (5 mL), dried over $MgSO_4$, filtered and concentrated to dry. The crude product was purified over silica gel (Biotage 25 g, eluting with a 2:1 ratio of heptanes:EtOAc) to provide (3S,5R)-1-benzyl-3,5-diethylpiperidine, 105 (234.2 mg, 1.003 mmol, 43.2% yield, R=ethyl) and (3R,5R)-1-benzyl-3,5-diethylpiperidine, 106 (190.2 mg, 0.815 mmol, 35.1% yield, R=ethyl) after separately concentration of the combined desired fractions and drying in vacuo.

To a stirred solution 105 (107.1 mg, 0.462 mmol) in MeOH (5 mL) was added 5% palladium on activated carbon (250 mg) followed by charging the flask several times with hydrogen gas. The reaction was maintaining under a hydrogen atmosphere (balloon pressure) at rt and stirred for 12 h, after which time the reaction was purged with nitrogen gas several times while evacuating the system with house vacuum between purges. The completed reaction was filtered over Celite 545, the filter pad washed two times with MeOH (2 mL each), followed by concentration of the combined filtrates were concentrated and dried in vacuo. The crude product, (3S,5R)-3,5-diethylpiperidine, 107 (0.066 g, 0.462 mmol, 99.9% yield, R=ethyl) was used in the next step without further purification.

To a stirred solution 107 (0.066 g, 0.462 mmol, R=ethyl) in NMP (2 mL) was added DIPEA (0.13 mL, 0.728 mmol) and 3 (86.3 mg, 0.370 mmol). The reaction mixture was microwaved at 150° C. for 1 h after which time it was directly purified over a reverse-phase preparative HPLC column (Water's X-Bridge C18 19×100 mm column; gradient using 0-50% acetonitrile in water containing 0.05% TFA) to provide an analog of 101 or ER-886211 (45.2 mg, 0.153 mmol, 41.4% yield, R=ethyl) after combining the desired collected fractions, concentration and drying in vacuo.

Other Examples:

ER-885113: To a stirred solution of 2-(di-tert-butylphosphino)biphenyl (20 mg, 0.067 mmol) and tris(dibenzylideneacetone)dipalladium(0) (20 mg, 0.022 mmol) in toluene (0.8 mL) under an nitrogen atmosphere was added commercially available 5-bromo-8-methoxyquinoline (201 mg, 0.844 mmol), sodium t-butoxide (122 mg, 1.27 mmol) and cis-2,6-dimethylmorpholine (125 mg, 1.085 mmol) at rt followed by toluene (0.8 mL). The reaction mixture was warmed to reflux and stirred for 3 h, after which time the completed reaction was cooled to rt followed by addition of water (5 mL). The resultant mixture was extracted two times with EtOAc(5 mL each) and the combined organic layers were washed with brine (2 mL), dried over $Na_2SO_4$, filtered and concentrated to dryness. The crude product was purified over silica gel twice (Biotage SP4, 25+S eluting with 12-100% EtOAc in heptane) to provide ER-885113 (49 mg, 0.180 mmol, 21.3% yield) after collection of the desired fractions, concentration and drying in vacuo.

ER-887960 (13.7 mg, 0.049 mmol, 23.5% yield) was prepared in a similar manner to ER-885113 starting with 5-bromo-8-chloro-1,7-naphthyridine (51 mg, 0.210 mmol) and cis-2,6-dimethylmorpholine (31.4 mg, 0.273 mmol)

ER-886133 and ER-886134: A solution of (S)-2-((benzyloxy)methyl)oxirane (65 g, 0.396 mol) and 28% $NH_4OH$ in water was stirred at rt for 14 h after which time the completed reaction was concentrated and azeotroped two times with toluene (150 mL each) to obtained (S)-1-amino-3-(benzyloxy)propan-2-ol (70.6 g, 0.390 mol, 98% yield) as a crude white solid.

To a stirred solution of crude (S)-1-amino-3-(benzyloxy) propan-2-ol (54.4 g, 0.300 mol) in ethanol (400 mL) was added methyl(R)-(+)-2-chloropropionate (40.44 g, 0.330 mol) dropwise over a 30-min period. The reaction was heated to 75° C. and stirred for 16 h after which time the completed reaction was concentrated to dryness. The crude mixture was diluted with EtOAc (200 mL), washed with aq. 1 N HCl (100 mL), brine (100 mL), dried over $Na_2SO_4$, filtered and concentrated to dry. The crude product was purified over silica gel (Biotage, eluting with a linear gradient of 30-80% EtOAc in heptane) to provide (R)—N—((R)-1-(benzyloxy)propan-2 -yl)-2 -chloropropanamide (65.7 g, 0.239 mol, 79.7% yield) after combining the desired fractions, concentration and drying in vacuo.

To a cooled stirred solution of (R)13 N—((R)-1-(benzyloxy)propan-2-yl)-2-chloropropanamide (8.8 g, 0.032 mol) in THF (440 mL) at 0° C. was added portion wise NaH (5.181 g, 0.130 mol, as a 60% oil dispersion) over a 10-min period. The reaction mixture was stirred at 0° C. then allowed to warm slowly to rt and stirred an additional 6 h. The completed reaction was slowly quenched with IPA (20 mL) followed by Dowex 50, H+ resin (30 g) followed by stifling until an acidic pH was registered. The quenched suspension was filtered, washed with EtOAc (50 mL) and concentrated to dryness. The crude product was purified over silica gel (200 g, eluting with a 30-50% gradient of EtOAc in heptane) to provide (2S,6S)-6-((benzyloxy) methyl)-2-methylmorpholin-3-one (6.12 g, 0.026 mol, 81.3% yield) after combining the desired fractions, concentration and drying in vacuo.

To a stirred solution of (2S,6S)-6-((benzyloxy)methyl)-2-methylmorpholin-3-one (6.12 g, 0.026 mol) in THF (20 mL) under a nitrogen atmosphere at rt was added 1 M tetrahydroaluminate in THF (30 mL, 0.030 mol) dropwise over a 15-min period. The reaction mixture was stirred for 2.5 h after which time it was cooled to 0° C. followed by the slow addition of water (13 mL) and then 1 N aq. NaOH (0.9 mL). The quenched reaction was stirred until the precipitate became granular after which time Celite 545 (10 g) was added followed by filtering over a Celite pad and rinsing three times with DCM (30 mL) and ethyl ether (30 mL). The combined filtrates were concentrated and purified over silica gel (Biotage, eluting with a gradient of 0-5% MeOH in DCM) to provide (2S,6S)-2-((benzyloxy)methyl)-6-methylmorpholine (2.7 g, 0.012 mol, 46.2% yield) after combining the desired fractions, concentration and drying in vacuo.

To a stirred solution of (2S,6S)-2-((benzyloxy)methyl)-6-methylmorpholine (2.7 g, 0.012 mol) in DCM (50 mL) was added di-tert-butyldicaarbonate (6.807 g, 0.031 mol) followed by TEA (4.35 mL, 0.031 mol) and DMAP (100 mg, 0.82 mmol). The reaction was stirred at rt for 3 h after which time the completed reaction was washed with 0.1 N HCl (50 mL) and brine (50 mL). The organic phase was concentrated followed by purification over silica gel (Biotage, eluting with a 10-20% gradient of EtOAc in heptane) to provide to provide (2S,6S)-tert-butyl 2-((benzyloxy)methyl)-6-methylmorpholine-4-carboxylate (3.68 g, 11.4 mmol, 95.4% yield) after combining the desired fractions, concentration and drying in vacuo.

To a stirred solution of (2S,6S)-tert-butyl 2-((benzyloxy) methyl)-6-methylmorpholine-4-carboxylate (3.102 g, 9.7 mmol) in ethanol (15 mL) was added 5% Pd on carbon (300 mg) followed by evacuation and charging of the reaction vessel three times with hydrogen gas. The reaction was heated to 40° C. maintaining under a hydrogen atmosphere (balloon pressure) and stirred overnight, after which time the reaction was purged with nitrogen gas several times while evacuating the system with house vacuum between purges. The completed reaction was filtered over Celite 545, the filter pad washed two times with ethanol (10 mL each), followed by concentration of the combined filtrates were concentrated and dried in vacuo. The crude product, (2S, 6S)-tert-butyl 2-(hydroxymethyl)-6-methylmorpholine-4-carboxylate (2.15 g, 9.3 mmol, 95.8% yield) was used in the next step without further purification.

To a stirred solution of (2S,6S)-tert-butyl 2-(hydroxymethyl)-6-methylmorpholine-4-carboxylate (200 mg, 0.865 mmol) in DCM (5 mL) was added TFA (0.5 mL, 6.7 mmol) at rt. The reaction mixture was stirred for 1 h after which time it was concentrated and azeotroped to dry two times with toluene (5 mL each) and dried in vacuo. The crude deprotected morpholine was dissolved with stirring in DMAC (1 mL) followed by DIPEA (0.23 mL, 1.3 mmol) and compound 3 (152.4 mg, 0.654 mmol). The reaction mixture was microwaved at 140° C. and stirred for 3 h after which time the completed reaction was cooled to rt, concentrated and purified over silica gel (Biotage, eluting with 30-80% EtOAc in heptane) to provide 5-((2S,6S)-2-(hydroxymethyl)-6-methylmorpholino)quinoline-8-carbonitrile or ER-885477 (165.2 mg, 0.583 mmol, 89.2% yield) after concentration of the desired combined fractions and drying under vacuo.

To a cooled, stirred solution of bis(2-methoxyethyl) aminosulfur trifluoride (Deoxo-Fluor®) (0.044 mL, 0.239 mmol) in DCM (2 mL) under a nitrogen atmosphere at −78° C. was added dropwise ER-885477 (50.4 mg, 0.178 mmol) in DCM (2 mL) over a 3-min period. The reaction mixture was warmed to −50° C. and stirred for 30 min after which time it was warmed to 0° C. and stirred for 1.5 h. The completed reaction was slowly quenched with a dropwise addition of saturated $NaHCO_3$ until a basic pH was observed (~5 mL). The mixture was diluted with DCM (10 mL), the layers separated after which time the organic layer was washed two times with water (5 mL each), dried over $MgSO_4$, filtered and concentrated. The crude product was purified over a reverse phase HPLC column (X-Bridge C18 19×100 mm column; eluting with a linear gradient of 10%-90% acetonitrile in water with 0.1% formic acid) and concentrating the desired peak followed by high vacuum to dryness to provide ER-886133 (35.2 mg 0.123 mmol, 69.3% yield).

To ER-885477 (25.2 mg, 0.089 mmol) was added thionyl chloride (2 mL) followed by warming to 85° C. and stifling for 24 h. The completed reaction was concentrated to dry with azeotroping two times with toluene (5 mL each). The crude product was purified over a reverse phase HPLC column (X-Bridge C18 19×100 mm column; eluting with a linear gradient of 10%-90% acetonitrile in water with 0.1% formic acid) and concentrating the desired peak followed by high vacuum to dryness to provide ER-886134 (2.1 mg 0.007 mmol, 7.8% yield).

Preparation of ER-889363 using Scheme 14 : To a stirred suspension of 3-butenylamine hydrochloride, 62 (5.45 g, 50.6 mmol) was in DCM (33 mL) was added $NaHCO_3$ (110 g) followed by o-nitrobenzenesulfonyl chloride (13.5 g, 60.8 mmol). Resultant mixture was vigorously stirred at rt for 2 h after which time phenylhydrazine hydrochloride (2.9 g, 20 mmol) was added and stifling was continued for additional 1 h. The completed reaction mixture was extracted with MTBE (70 mL) and then sequentially washed with 20% aq. citric acid (35 mL), water (35 mL) and concentrated. Resultant purple solid (13.32 g) was dissolved in NMP (70 mL) and potassium carbonate (21 g, 0.15 mol) was added followed by (R)-glycidol-benzyl ether, 6 (9.98 g, 60.8 mmol). The mixture was heated to 50° C. and stirred for 22 h after which time it was diluted with water (300 mL) and extracted two times with MTBE (200 mL each). All organic layers were combined and concentrated to give orange-colored oil, which was subjected to silica gel column chromatography (n-heptane/MTBE 1:1) to give 64, (7.90 g, 18.8 mmol, 37% yield in 2 steps) as orange colored oil.

To a stirred solution of 64 (7.90 g, 18.8 mmol) in DMAC (94.8 mL) was added copper (II) acetate (0.853 g, 4.70 mmol) followed by $PdCl_2$ (0.416 g, 2.35 mmol) at rt. Resultant mixture was stirred under $O_2$ (balloon) at rt for 16 h after which time additional $PdCl_2$ (0.200 g, 1.13 mmol) was added and the mixture was heated to 40° C. and stirred for 6 h. The completed reaction was quenched with pyridine (4.5 mL, 56 mmol), stirred for 5 min followed by diluting with MTBE (400 mL). The mixture was washed with water (250 mL) and the organic layer was separated, concentrated. The crude yellow oil was purified by silica gel column chromatography (n-heptane/MTBE 1:1) to give 65 (0.740 g, 1.77 mmol, 9.4% yield, 31% yield based on recovered substrate).

To a cooled, stirred solution of 65 (1.480 g, 3.54 mmol) in DCM (14.8 mL) at to 0° C. was added triethylsilane (2.96 mL, 18.6 mmol) followed by TFA (4.44 mL, 57.6 mmol). The reaction mixture was stirred at 0° C. for 1 h after which time the mixture was warmed to rt and stirred for an additional 1 h. The completed reaction mixture was azeotroped two times with toluene (60 mL each) and then purified by silica gel column chromatography (n-heptane/MTBE 1:1) to give 66 (1.382 g, 3.29 mmol, 92% yield) as yellow oil.

To a stirred solution of 66 (1.382 g, 3.29 mmol) in DMF (8.3 mL, 0.11 mol) was added potassium carbonate (1.45 g, 10.5 mmol) followed by benzenethiol (0.360 mL, 3.50 mmol). The resultant mixture was heated at 40° C. for 2 h after which time the completed reaction was diluted with water (12 mL). Di-tert-butyl dicarbonate (0.897 g, 4.11 mmol) was added followed by stirring at rt for 1 h. The completed reaction was diluted with water (29 mL) and extracted two times with MTBE (40 mL each) and the combined organic layers were concentrated to give yellow oil. Crude product was purified by silica gel column chromatography (n-heptane/MTBE 4:1) to provide 67 (847 mg, 2.52 mmol, 77% yield) as a colorless oil and its stereoisomer (8.3 mg, 0.25 mmol, 7.5% yield) as a colorless oil.

To a stirred solution of 67 (0.847 g, 2.52 mmol) in DCM (4.2 mL) was added TFA (4.2 mL, 0.055 mol) at rt and stirred for 30 min. The completed reaction mixture was concentrated, azeotroped with toluene (20 mL) and partitioned between saturated $NaHCO_3$ (8.5 mL) and DCM (20 mL). Organic layer was separated, dried over $MgSO_4$ (2.0 g), filtered, and concentrated to dry. The crude intermediate was dissolved in NMP (2.12 mL) followed by DIPEA (0.66 mL, 3.8 mmol) and then 3 (0.706 g, 3.03 mmol). The resultant mixture was heated to 140° C. and stirred for 2 h after which time the completed reaction was cooled to rt and partitioned between EtOAc(40 mL) and water (20 mL). Aqueous layer was extracted with EtOAc (20 mL) and the combined organic layers were washed with water (10 ml) and concentrated to give crude product as brownish solid/oil. The crude product was purified over silica gel (eluting with n-heptane/EtOAc1:1) to give a 4:1 mixture of the desired intermediate:3 (0.684 mg).

The crude intermediate mixture (0.684 mg) was suspended in acetonitrile (6.0 ml) followed by iodotrimethylsilane (0.377 mL, 2.65 mmol) followed by heating to 60° C. and stirring for 2 h. The completed reaction was cooled to 40° C. followed by the addition of water (3.0 ml) and the reaction was cooled to rt with stifling for an additional 1 h. 28% aq. ammonium hydroxide (1.0 mL) was added and the resultant mixture was extracted two times with EtOAc(20 mL each) after which time the combined organic layers were concentrated followed by purification over silica gel (eluting with EtOAc100%) to give 68 or ER-889363 (404 mg, 1.36 mmol, 53% yield) as yellow solid.

To a stirred solution of ER-889363 (355 mg, 1.194 mmol) in DCM (4 mL) was added p-toluenesulfonyl chloride (350 mg, 1.836 mmol) followed by DIPEA (0.32 mL, 1.837 mmol) and DMAP (10 mg, 0.082 mmol). The reaction mixture was stirred at rt for 16 h after which time the completed reaction was washed with water (2 mL) and brine (2 mL) followed by drying over $Na_2SO_4$, filtering and concentrating to dryness. The crude product was purified over silica gel (Biotage, SP4, 25+M eluting with 10-60% EtOAc in heptane over 20 column volumes. The desired fractions were combined, concentrated and dried in vacuo to provide ((2R,7R)-4-(8-cyanoquinolin-5-yl)-7-methyl-1,4-oxazepan-2-yl)methyl 4-methylbenzenesulfonate (476.6 mg, 1.056 mmol, 88.4% yield)

((2R,7R)-4-(8-cyanoquinolin-5-yl)-7-methyl-1,4-oxazepan-2-yl)methyl-4-methyl-benzenesulfonate (19.4 mg, 0.043 mmol) and 1,4'-bipiperidine (30 mg, 0.178 mmol) were dissolved in DMAC (0.5 mL) and then microwaved at 150° C. for 10 min. The cooled reaction was diluted with acetonitrile (0.5 mL), filtered and purified by reverse-phase HPLC (Xbridge C18 column, eluting with a gradient of 10-40% acetonitrile in water containing 0.1% formic acid). The combined desired fractions were concentrated, diluted with MeOH (1 mL) and passed over a basic $SiCO_3$ column eluting with MeOH (2 mL) followed by concentrations and drying in vacuo to provide ER-889822 (11 mg, 0.025 mmol, 57.2% yield).

Other Examples:

ER-890094: A solution of (3-(bromomethyl)phenyl)boronic acid (129.5 mg, 0.603 mmol) and 1,4'-bipiperidine (190 mg, 1.129 mmol) in DMAC (1 mL) was microwaved at 150° C. for 10 min after which time the reaction was cooled and concentrated to dryness to be used in the next step as crude (3-([1,4'-bipiperidin]-1'-ylmethyl)phenyl)boronic acid.

A stirred solution containing 3 (44.5 mg, 0.191 mmol), crude (3-([1,4'-bipiperidin]-1'-ylmethyl)phenyl)boronic acid (86.5 mg, 0.286 mmol), palladium(II) acetate (6 mg, 0.027 mmol), 2-dicyclohexylphosphino-2',6'-dimethoxybiphenyl (12 mg, 0.029 mmol) and 1 M sodium carbonate in water (0.029 ml, 0.029 mmol) in EtOH (0.6 mL) and toluene (0.6 mL) was heated to 70° C. for 16 h. The completed reaction was cooled, diluted with DCM (10 mL), washed with water (3 mL), dried over $Na_2SO_4$, filtered and concentrated to dryness. The crude product was diluted with 1:1 DMSO: acetonitrile (2 mL) and directly purified by HPLC (Xbridge C18, eluting with a 10-40% acetonitrile in water containing 0.1% formic acid). The desired product was collected and concentrated to dry. The resulting product was dissolved in MeOH (2 mL) and passed over a basic silica plug (Biotage, 1 g, $SiCO_3$) eluting with MeOH (5 mL) to provide after concentration and drying in vacuo ER-890094 (5 mg, 0.012 mmol, 6.3% yield).

ER-890244 (63.2 mg, 0.153 mmol, 27.3% overall yield) was prepared in a similar manner to ER-890094 starting with (4-(bromomethyl)phenyl)boronic acid (134.2 mg, 0.625 mmol) and 1,4'-bipiperidine (125 mg, 0.564 mmol).

ER-888200: A stirred solution containing 3 (251 mg, 1.077 mmol), (3-formyl-5-methylphenyl)boronic acid (350 mg, 2.135 mmol), bis(triphenylphosphine)palladium(II) chloride (150 mg, 0.214 mmol), lithium chloride (91 mg, 2.147 mmol), sodium carbonate (230 mg, 2.17 mmol) and 10% sodium carbonate in water (2.3 ml) in DMF (11 mL) was heated to 90° C. for 3 h. The cooled reaction was diluted with EtOAc (48 mL) and water (12 mL) with stifling followed by filtering through Celite 545 (1.2 g) eluting with EtOAc (10 ml). The separated aqueous layer was extracted two times with EtOAc (12 mL each) and the combined organic layers was washed with water (24 mL) and brine (24 mL) followed by drying over $Na_2SO_4$, filtering and concentrating to dry. The crude product was purified over silica gel (Biotage SP4, Interchim 25 g, eluting with 20-100% EtOAc in heptane) after which time the desired product fractions were combined, concentrated and dried in vacuo to provide ER-888200 (163 mg, 0.599 mmol, 55.6% yield).

ER-888201: To a stirred solution of ER-888200 (21 mg, 0.077 mmol) in MeOH (2.1 mL) cooled to 0° C. was added sodium tetrahydroborate (3.2 mg, 0.085 mmol). The reaction mixture was stirred for 1 h after which time water (2.1 mL) was added, the mixture concentrated to half volume, followed by extraction with EtOAc (19 mL). The organic layer was washed with brine (3.9 ml), dried over $Na_2SO_4$, filtered and concentrated to dry to provide ER-888201 (17.4 mg, 0.63 mmol, 82.4% yield).

ER-888644: To a stirred solution of ER-888201 (91 mg, 0.332 mmol) in DCM (1.8 mL) was added p-toluenesulfonyl chloride (101 mg, 0.530 mmol) followed by DMAP (2 mg, 0.016 mmol) and DIPEA (1.8 mL, 1.03 mmol). The reaction mixture was stirred at rt for 3 h after which time additional p-toluenesulfonyl chloride (101 mg, 0.530 mmol) was added followed by stifling for 2 h. The completed reaction was diluted with stirring with water (1 mL) and DCM (5.2 mL). The layers were separated and the organic layer was washed with brine (1 mL), dried over $Na_2SO_4$, filtered and concentrated to dry. The crude product was purified over silica gel (Biotage SP4, Interchim 25 g, eluting with 20-100% EtOAc in heptane) after which time the desired product fractions were combined, concentrated and dried in vacuo to provide ER-888644 (63 mg, 0.212 mmol, 65% yield).

ER-888645: A solution of ER-888644 (20 mg, 0.068 mmol) and 4-hydroxypiperidine (70 mg, 0.692 mmol) in N-methylpyrrolidone (2 mL) was microwaved at 150° C. for 15 min. The cooled reaction was diluted with NMP (4 mL) and directly purified by HPLC using a C-18 column (Xbridge C18, eluting with a 10-40% acetonitrile in water containing 0.1% TFA). The desired product was collected and concentrated to dry. The resulting product was dissolved in MeOH (2 mL) and passed over a basic silica plug (Biotage, 1 g, $SiCO_3$) eluting with MeOH (5 mL) to provide after concentration and drying in vacuo ER-888645 (19.9 mg, 0.056 mmol, 81.5% yield).

ER-888646 (17.9 mg, 0.047 mmol, 68.1% yield) was prepared in a similar manner to ER-888645 starting with ER-888644 (20 mg, 0.068 mmol) and 4-dimethylaminopiperidine (87.6 mg, 0.683 mmol).

ER-888647 (15.3 mg, 0.043 mmol, 62.8% yield) was prepared in a similar manner to ER-888645 starting with ER-888644 (20 mg, 0.068 mmol) and 1-methylpiperazine (68.4 mg, 0.683 mmol).

ER-889504 (46 mg, 0.108 mmol, 62% yield) was prepared in a similar manner to ER-888645 starting with ER-888644 (51 mg, 0.174 mmol) and 1,4'-bipiperidine (102 mg, 0.606 mmol).

General Screening Assay and Pharmacology Strategy.

To identify potent and selective TLR7/8 compounds, analogs were initially screened across a cell-based panel of human TLR4, TLR7, and TLR9 reporter lines (see Pharmacology Materials and Methods for more details). A subset of compounds that were potent and selective for TLR7 were also tested for TLR8 activity (see Table 3 below) and for TLR7/8 potency in the primary human PBMC assay (see Pharmacology Materials and Methods for more details). Certain compounds were advanced into the short-term in vivo (STIV) assay to determine dose-dependent activity and duration-of-action against mouse TLR7 (see Pharmacology Materials and Methods for more details). Select compounds were then evaluated for impact in one or more of the following mouse lupus disease models: BXSB-Yaa, NZBxNZW, and Pristane DBA/1.

Many compounds reported as embodiments herein demonstrate nanomolar potency against both human and mouse TLR7 and human TLR8 when these receptors, expressed on either cell lines or primary cells, are stimulated by synthetic, small molecule (CL097, R848) or nucleic-acid (RNA) ligands. Conversely, most compounds reported as embodiments herein are inactive against the TLR9 pathway.

Current lupus SOC drugs include anti-malarials such as chloroquine and hydroxychloroquine (HCQ) which have been shown to inhibit TLR7/9 activation in vitro. This may at least partially explain their effectiveness in controlling lupus flare. Embodiments of the disclosure, however, have been shown to offer significantly more potent inhibition. For example, compound ER-899742 (shown and discussed above) was found to be approximately 1000-fold more potent against the RNA-Ig TLR7/8 stimulus versus HCQ ($IC_{50}$=0.0009 uM, HCQ $IC_{50}$~1.5 uM). This suggests that ER-899742 would offer much more effective TLR7/8 pathway inhibition versus current lupus treatments. This is demonstrated by results shown in Table 1 below.

TABLE 1

Potency and selectivity of compound ER-899742 as compared to hydroxychloroquine (Plaquenil).

| Cell Format: | Ligand: | Receptor(s): | Analyte: | ER-899742 IC50 (uM) | HCQ[2] IC50 (uM) |
|---|---|---|---|---|---|
| HEK-293 | LPS | Human TLR4 | NFkB-luciferase | >10 | N.D. |
| HEK-293 | CL097 | Human TLR7 | NFkB-luciferase | 0.006 | N.D. |
| HEK-293 | CpG-ODN | Human TLR9 | NFkB-luciferase | >10 | N.D. |
| Hu PBMC | [1]RNA-Ig | Human TLR7/8 | IL-6 | 0.0009 | 1-2 |
| Hu PBMC | LPS | Human TLR4 | IL-6 | | >10 |
| Hu PBMC | CpG-ODN | Human TLR9 | IL-6 | | 0.15-0.30 |

TABLE KEY:

[1]RNA-Ig = ssRNA derived from U1snRNA stem loop IV sequence in complex with antibody (see Materials and Methods for more details)

[2]HCQ = Hydroxychloroquine

The comparative potency of ER-899742 versus hydroxychloroquine was further explored using cloned TLR7 and 8 in the HEK 293 cell line as described below in In Vitro Pharmacology. Effects on mouse TLR7 were also compared. Cells were stimulated overnight with TLR7/8 agonist CL097 at pre-determined $ED_{70-80}$: 3 ug/ml for HEK-hTLR7, 1.5 ug/ml for HEK-mTLR7 and 12 ug/ml for HEK-hTLR8, before reading luminescence intensity. Three tests were performed and IC50 value was determined using Graphpad Prism 6 nonlinear regression curve fit. Individual test results and their average are shown in Table 2. The data show that in this assay, ER-899742 had an average IC50 of 0.024 uM in the HEK/TLR7 cell line, and an average IC50 of 0.0024 uM in the HEK/TLR8 cell line.

TABLE 2

ER-899742 effects on TLR7 and TLR8 response compared to hydroxychloroquine.

| | | IC50 (uM) | |
|---|---|---|---|
| Cell Format: | Test | ER-899742 | HCQ |
| HEK-mTLR7[1] | 1 | 0.066 | 13.85 |
| | 2 | 0.071 | 13.53 |
| | 3 | 0.076 | 15 |
| | average | 0.071 | 14.13 |
| HEK-hTLR7 | 1 | 0.024 | 6.8 |
| | 2 | 0.023 | 14.55 |
| | 3 | 0.026 | 5.95 |
| | average | 0.024 | 9.10 |
| HEK-hTLR8 | 1 | 0.002 | >>10 |
| | 2 | 0.0025 | >>10 |
| | 3 | 0.0026 | >>10 |
| | average | 0.0024 | >>10 |

[1]mTLRV, mouse TLR7; hTLRV, human TLR7; hTLR8, human TLR8

TABLE 3

Potency of select compounds against human TLR8 in the HEK-293 assay format (see Materials and Methods for more details).

| Compound Number | HEK/hTLR8 IC50 (μM) |
|---|---|
| ER-878952 | 0.0060 |
| ER-878952 | 0.0195 |
| ER-879484 | 0.0180 |
| ER-879713 | 0.0800 |
| ER-880191 | 0.0100 |
| ER-880639 | 0.0500 |
| ER-885047 | 0.0940 |
| ER-885113 | 0.0110 |
| ER-885493 | 0.1007 |
| ER-885612 | 0.0550 |
| ER-885618 | 0.0050 |
| ER-885621 | 0.0250 |
| ER-885892 | 0.0370 |
| ER-885906 | 0.0200 |
| ER-885930 | 0.1470 |
| ER-886355 | 0.0660 |
| ER-886431 | 0.0310 |
| ER-886507 | 0.1820 |
| ER-886508 | 0.1860 |
| ER-886509 | 0.1190 |
| ER-886514 | 0.0050 |
| ER-886530 | 0.0050 |
| ER-886532 | 0.0300 |
| ER-886533 | 0.0140 |
| ER-886565 | 0.0290 |
| ER-886567 | 0.0050 |
| ER-886568 | 0.0050 |
| ER-886624 | 0.0860 |
| ER-886625 | 0.0100 |
| ER-886626 | 0.0050 |
| ER-886629 | 0.0050 |
| ER-886814 | 0.0600 |
| ER-886816 | 0.1070 |
| ER-886818 | 0.0810 |
| ER-886820 | 0.0780 |
| ER-886854 | 0.0460 |
| ER-886857 | 0.0720 |
| ER-886858 | 0.0020 |
| ER-886869 | 0.1610 |
| ER-886949 | 0.0780 |
| ER-886953 | 0.0660 |
| ER-886955 | 0.0830 |
| ER-887138 | 0.0130 |
| ER-887139 | 0.0080 |
| ER-887142 | 0.1150 |
| ER-887143 | 0.1480 |
| ER-887144 | 0.0480 |
| ER-887145 | 0.1050 |
| ER-887199 | 0.0770 |
| ER-887253 | 0.0020 |
| ER-887258 | 0.1750 |
| ER-887259 | 0.0005 |
| ER-887261 | 0.0770 |
| ER-887269 | 0.0032 |
| ER-887271 | 0.0016 |
| ER-887272 | 0.0029 |
| ER-887443 | 0.1380 |
| ER-887444 | 0.1930 |
| ER-887526 | 0.1220 |
| ER-887528 | 0.1350 |
| ER-887538 | 0.0850 |
| ER-887539 | 0.0005 |
| ER-887540 | 0.0030 |
| ER-887586 | 0.1265 |
| ER-887587 | 0.0018 |
| ER-887588 | 0.0005 |
| ER-887722 | 0.0210 |
| ER-887723 | 0.0090 |
| ER-887724 | 0.0060 |
| ER-887725 | 0.0010 |
| ER-887927 | 0.0005 |
| ER-887928 | 0.0110 |

TABLE 3-continued

Potency of select compounds against human TLR8 in the HEK-293 assay format (see Materials and Methods for more details).

| Compound Number | HEK/hTLR8 IC50 (μM) |
|---|---|
| ER-890963 | 0.0028 |
| ER-894594 | 0.1160 |

Figure 1B:
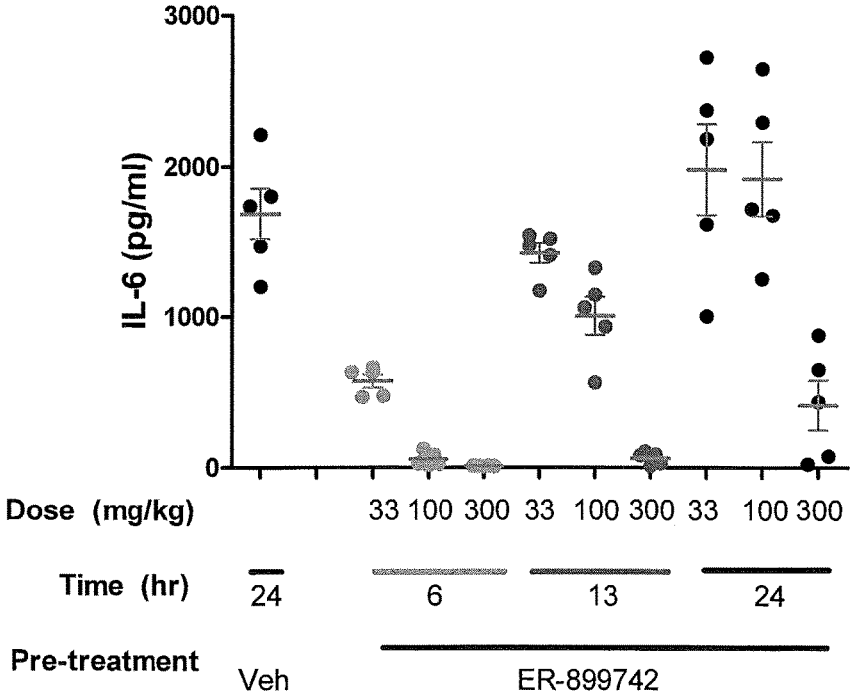

Short-term in vivo (STIV) assay: To assess compound potency in vivo against mouse TLR7, a short-term in vivo (STIV) assay was utilized. Briefly, mice were orally dosed with compounds and at various time points afterwards were injected subcutaneously with agonist R848 to stimulate TLR7. The plasma IL-6 level following R848 stimulation was then measured by ELISA to assess compound potency and duration-of-action. Importantly, cytokine production following in vitro or in vivo stimulation with R848 was shown to be completely TLR7-dependent utilizing TLR7-deficient mice. Therefore, the activity of compounds in the STIV assay can be confidently attributed to their modulation of the TLR7 pathway. A single oral dose of ER-899742 at 300 mg/kg fully suppresses the R848/TLR7/IL-6 pathway in vivo for at least 24 hours (see FIG. 1A and FIG. 1B). A summary of STIV assay potency for a panel of compounds appears in Table 4 below.

TABLE 4

Short-term in vivo (STIV) assay data summary for select compounds.

| | Dose | % Suppression vs. Vehicle | | | | | | | |
|---|---|---|---|---|---|---|---|---|---|
| Time | (mg/kg) | ER-878419 | ER-878629 | ER-878952 | ER-885493 | ER-886611 | ER-886788 | ER-886814 | ER-886820 |
| 3 h | 11 | | | | | 53 | | | |
| | 22 | | | | *39* [3] | | | | |
| | 33 | | | | | 90 | 0 | 93 | 93 |
| | 67 | | | | *86* [8] | | | | |
| | 100 | | | | | *100* [10] | 0 | *100* [10] | *100* [10] |
| | 200 | | | | *88* [8] | | | | |
| | 300 | *90* [9] | *60* [6] | | | X | *24* [2] | *100* [10] | *100* [10] |
| 5 h | 22 | | | | *26* [2] | | | | |
| | 67 | | | | *99* [9] | | | | |
| | 200 | | | | *94* [9] | | | | |
| 6 h | 11 | | | | | 0 | | | |
| | 33 | | | | | 90 | 0 | 57 | 68 |
| | 100 | | | | | *100* [10] | *27* [2] | *100* [10] | 96 |
| | 300 | *60* [6] | *54* [5] | | | X | *26* [2] | *100* [10] | *100* [10] |
| 12 h | 200 | | | *93* [9] | | | | | |
| | 400 | | | | *76* [7] | | | | |
| | 600 | | | *95* [9] | | | | | |
| 13 h | 33 | | | | | | | | |
| | 100 | | | | | | | | |
| | 300 | | | | | | | | |
| 18 h | 22 | | | | 0 | | | | |
| | 67 | | | | 5 | | | | |
| | 200 | | | *90* [9] | *29* [2] | | | | |
| | 600 | | | *96* [9] | | | | | |
| 19 h | 11 | | | | | 19 | | | |
| | 33 | | | | | 0 | 0 | 14 | 43 |
| | 100 | | | | | *100* [10] | *17* [1] | 19 | 35 |
| | 300 | *30* [3] | *14* [1] | | | X | 2 | *100* [10] | 39 |
| 24 h | 33 | | | | | | | | |
| | 100 | | | | | | | | |
| | 300 | | | | | | | | |

TABLE 4-continued

| Time | Dose (mg/kg) | % Suppression vs. Vehicle | | | | | | | |
|---|---|---|---|---|---|---|---|---|---|
| | | ER-886948 | ER-886953 | ER-887137 | ER-887145 | ER-887259 | ER-887268 | ER-887269 | ER-887270 |
| 3 h | 11 | | | | *67* [6] | | | | |
| | 22 | | | | | | | | |
| | 33 | 46 | *99* [9] | *100* [10] | *97* [9] | | | | |
| | 67 | | | | | | | | |
| | 100 | 89 | *99* [9] | *100* [10] | *99* [9] | | | | |
| | 200 | | | | | | | | |
| | 300 | *100* [10] | *99* [9] | *100* [10] | X | | | | |
| 5 h | 22 | | | | | | | | |
| | 67 | | | | | | | | |
| | 200 | | | | | | | | |
| 6 h | 11 | | | | *32* [3] | | *80* [8] | | |
| | 33 | 35 | *99* [9] | 99 | *91* [9] | 84 | *98* [9] | 95 | 98 |
| | 100 | 44 | *99* [9] | *100* [10] | *99* [9] | 99 | *99* [9] | *100* [10] | |
| | 300 | 81 | *99* [9] | *100* [10] | X | 99 | | 98 | |
| 12 h | 200 | | | | | | | | |
| | 400 | | | | | | | | |
| | 600 | | | | | | | | |
| 13 h | 33 | | | | | | | | 37 |
| | 100 | | | | | | | | 81 |
| | 300 | | | | | | | | *99* |
| 18 h | 22 | | | | | | | | |
| | 67 | | | | | | | | |
| | 200 | | | | | | | | |
| | 600 | | | | | | | | |
| 19 h | 11 | | | | 0 | | *25* [2] | | |
| | 33 | 0 | *23* [2] | 38 | 0 | 15 | *63* [6] | 9 | |
| | 100 | 5 | *45* [4] | 63 | *96* [9] | 62 | *95* [9] | 58 | |
| | 300 | 49 | *99* [9] | *100* [10] | X | 99 | | 95 | |
| 24 h | 33 | | | | | | | | 25 |
| | 100 | | | | | | | | 26 |
| | 300 | | | | | | | | *100* [10] |

| Time | Dose (mg/kg) | ER-887586 | ER-887723 | ER-887724 | ER-887725 | ER-887927 | ER-888070 | ER-888201 | ER-888281 |
|---|---|---|---|---|---|---|---|---|---|
| 3 h | 33 | | | 99 | *99* [9] | | | | *78* [7] |
| | 100 | | | 99 | *99* [9] | | | | *92* [9] |
| | 200 | | | | | | | | |
| | 300 | | | 99 | *99* [9] | | | | |
| 6 h | 11 | | | | | | | | |
| | 33 | 62 | *100* [10] | 99 | *99* [9] | 100 | 88 | *35* [3] | *45* [4] |
| | 100 | 99 | *100* [10] | 99 | *99* [9] | 100 | *100* [10] | *50* [5] | *75* [7] |
| | 300 | *100* [10] | *100* [10] | 99 | *99* [9] | 100 | *100* [10] | *40* [4] | |
| 13 hr | 11 | | | | | | | | |
| | 33 | | | | | | | | |
| | 100 | | | | | | | | |
| | 300 | | | | | | | | |
| 19 hr | 1.22 | | | | | 56 | | | |
| | 3.67 | | | | | 70 | | | |
| | 11 | | | | | 94 | | | |
| | 33 | 15 | 77 | 83 | *90* [9] | 98 | 70 | *45* [4] | 0 |
| | 100 | 45 | 97 | 91 | *91* [9] | 100 | 90 | *71* [7] | *61* [6] |
| | 300 | 95 | *100* [10] | *99** [99] | *99* [9] | 100 | 99 | *79* [7] | |

TABLE 4-continued

| | | | | | | | |
|---|---|---|---|---|---|---|---|
| 24 hr | 11 | | | | | | |
| | 33 | | | | | | |
| | 100 | | | | | | |
| | 300 | | | | | | |

| Time | Dose (mg/kg) | ER-888288 | ER-888320 | ER-888321 | ER-888322 | ER-888480 | ER-889469 |
|---|---|---|---|---|---|---|---|
| 3 h | 33 | *100* [10] | | 98 | | | 100 |
| | 100 | 98 | *100* [10] | *100* [10] | | | 100 |
| | 200 | | | | | | |
| | 300 | | | | | | |
| 6 h | 11 | | | | | 85 | |
| | 33 | 78 | 78 | 86 | 99 | *100* [10] | 100 |
| | 100 | 99 | 94 | *100* [10] | *100* [10] | *100* [10] | 100 |
| | 300 | 97 | | | *100* [10] | | |
| 13 hr | 11 | | | | | | |
| | 33 | | 9 | 87 | | | |
| | 100 | | 31 | *100* [10] | | | |
| | 300 | | | | | | |
| 19 hr | 1.22 | | | | | | |
| | 3.67 | | | | | | |
| | 11 | | | | | 63 | |
| | 33 | 50 | | 59 | 24 | 89 | |
| | 100 | 53 | | 59 | 82 | 98 | 73 |
| | 300 | | | | *100* [10] | | |
| 24 hr | 11 | | | | | | |
| | 33 | 14 | | | | | |
| | 100 | 0 | | | | | |
| | 300 | 55 | | | | | |

| Time | Dose (mg/kg) | ER-889470 | ER-889556 | ER-889601 | ER-889745 | ER-890093 | ER-890223 | ER-890311 | ER-890345 |
|---|---|---|---|---|---|---|---|---|---|
| 3 h | 33 | *100* [10] | *100* [10] | | | | 93 | *88* [8] | *100* [10] |
| | 67 | | | | | | | | |
| | 100 | 98 | *100* [10] | 96 | 93 | 92 | 99 | | |
| 6 h | 11 | | | | | | | | |
| | 33 | 96 | *100* [10] | 95 | 94 | 92 | 82 | | |
| | 100 | *100* [10] | *100* [10] | 90 | 84 | 95 | 99 | | |
| | 300 | | | | | | | | |
| 13 hr | 33 | | | | 0 | 98 | | | |
| | 100 | | | | 99 | *100* [10] | | | |
| | 300 | | | | 95 | | | | |
| 19 hr | 1.22 | | 44 | | | | | | |
| | 3.67 | | 89 | | | | | 0 | |
| | 11 | | 29 | | | | | 0 | 48 |
| | 33 | | 47 | | 0 | | | 0 | 52 |
| | 100 | 78 | 98 | 96 | 52 | | 88 | | |
| 24 hr | 33 | | | | 0 | | | | |
| | 100 | | | | 64 | | | | |
| | 300 | | | | *100* [10] | | | | |

| Time | Dose (mg/kg) | ER-890346 | ER-890931 | ER-890963 | ER-890964 | ER-893881 | ER-894206 | ER-894550 |
|---|---|---|---|---|---|---|---|---|
| 3 h | 33 | *99* [9] | *100* [10] | 90 | 96 | 95 | *96* [9] | |
| | 67 | | | | | | | |
| | 100 | | | | | | | |
| 6 h | 11 | | | | | | | |
| | 33 | | | 98 | | 82 | *85* [8] | 98 |
| | 100 | | | 99 | | 99 | *98* [9] | |
| | 300 | | | *100* [10] | | | | |

TABLE 4-continued

| | | | | | | | | | | | | | |
|---|---|---|---|---|---|---|---|---|---|---|---|---|---|
| 13 hr | 33 | | | | | 31 | | | 0 | | *42* [4] | | 72 |
| | 100 | | | | | 80 | | | 19 | | *77* [7] | | 97 |
| | 300 | | | | | *100* [10] | | | | | | | 99 |
| 19 hr | 1.22 | | | | | | | | | | | | |
| | 3.67 | | | | | | | | | | | | |
| | 11 | | 0 | | 0 | | | | | | | | |
| | 33 | | *20* [2] | | 53 | 45 | | 0 | | | | | |
| | 100 | | | | | | | | | | | | |
| 24 hr | 33 | | | | | | | | | | | | 48 |
| | 100 | | | | | 50 | | | | | | | 71 |
| | 300 | | | | | *100* [10] | | | | | | | 99 |

| Time | (mg/kg) | ER-894551 | ER-895204 | ER897968 | ER-897969 | ER-898566 | ER-898694 | ER-898946 | ER-899017 | ER-899018 | ER-899122 | ER-899193 | ER-899285 |
|---|---|---|---|---|---|---|---|---|---|---|---|---|---|
| 6 h | 11 | 98 | | | | | | | | | 98 | | |
| | 33 | | 98 | 81 | 0 | *100* [10] | *93* [9] | 61 | *34* [3] | | | | |
| | 100 | | | | | 99 | | | | 73 | | *43* [4] | 75 |
| | 300 | | | | | | | | | | | | |
| 13 h | 11 | 52 | | | | | | | | | 37 | | |
| | 33 | 56 | 22 | 3 | 29 | 73 | 2 | 2 | 0 | | 90 | | |
| | 100 | 98 | 43 | 35 | 54 | 86 | *36* [3] | *16* | *0* | *12* | *100* [10] | *52* [5] | 0 |
| | 300 | X | 99 | 85 | 71 | 98 | *53* [5] | 55 | *10* [1] | | X | | |
| 24 h | 11 | | | | | | | | | | 0 | | |
| | 33 | 53 | 39 | 0 | 0 | 0 | 0 | 28 | | | 15 | | |
| | 100 | 91 | 39 | 8 | 4 | 30 | 0 | 0 | 0 | | 89 | | |
| | 300 | X | 78 | 80 | 29 | *100* [10] | *35* [3] | 34 | 0 | | X | | |

| Time | Dose (mg/kg) | ER-899322 | ER-899337 | ER-899369 | ER-899417 | ER-899418 | ER-899457 | ER-899464 | ER-899476 | ER-899477 | ER-899481 | ER-899616 |
|---|---|---|---|---|---|---|---|---|---|---|---|---|
| 6 h | 100 | 95 | 99 | 98 | 71 | 19 | *100* [10] | *99* [9] | 99 | 96 | *54* [5] | 79 |
| 13 h | 100 | 70 | 30 | 62 | 0 | 10 | 74 | *96* [9] | 65 | 68 | 5 | 27 |

| Time | Dose (mg/kg) | ER-899619 | ER-899688 | ER-899718 | ER-899722 | ER-899742 | ER-899745 | ER-899820 | ER-899835 | ER-899836 |
|---|---|---|---|---|---|---|---|---|---|---|
| 6 h | 100 | 79 | 10 | 74 | 89 | *100* [10] | *100* [10] | *97* [9] | 99 | *99* [9] |
| 13 h | 100 | 35 | 96 | 51 | 33 | 61 | 5 | *20* [2] | 79 | *88* [8] |

X = Mice did not tolerate this dose.
*4/12 mice found the compound incompatible

Mouse Lupus Disease Models. Two distinct lupus disease models (NZB/W and Pristane) were chosen for compound POC evaluation because (1) the NZB/W strain develops spontaneous disease with polygenic etiology, demonstrating many hallmarks of human lupus such as DNA-associated autoreactivity, proteinuria, and immune-complex mediated nephritis, and (2) positive TLR7 and/or TLR9 target validation results have been reported for both disease models.

Key findings for ER-899742 in the SLE disease models are as follows (see FIG. 2A-FIG. 2C, FIGS. 3A-3E, and FIGS. 7A-7G, and Table 7):

1) ER-899742 at several doses between 33 and 300 mg/kg afforded pronounced survival benefit in the NZB/W model, corresponding to significantly reduced proteinuria and histological signs of glomerulonephritis.
2) ER-899742 suppressed various auto-antibody specificities in the Pristane model, with particularly robust impact on RNA-related reactivity such as anti-RiboP titers. Decreased expression of some IFN-modulated genes in whole blood resulted from treatment with ER-899742 in this model. Control of arthritis by ER-899742 in this model was also observed.

Figure 4A:
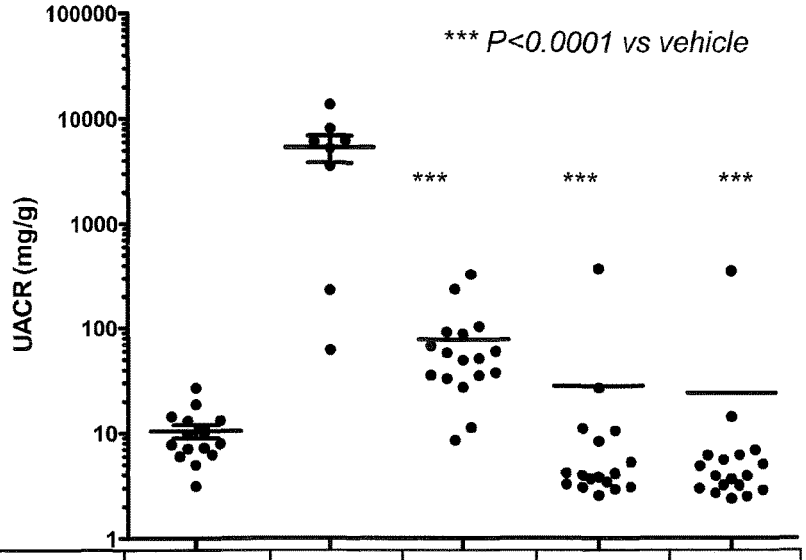
Figure 4C:
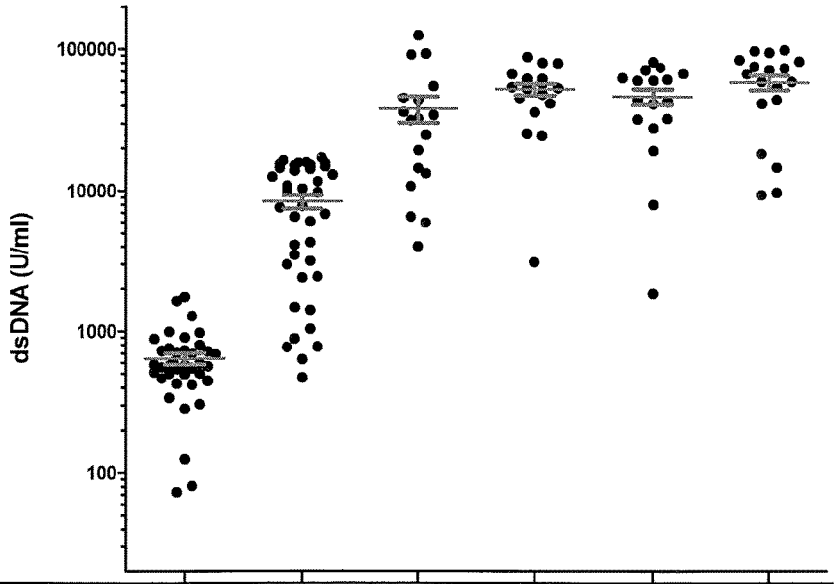
Figure 5A:
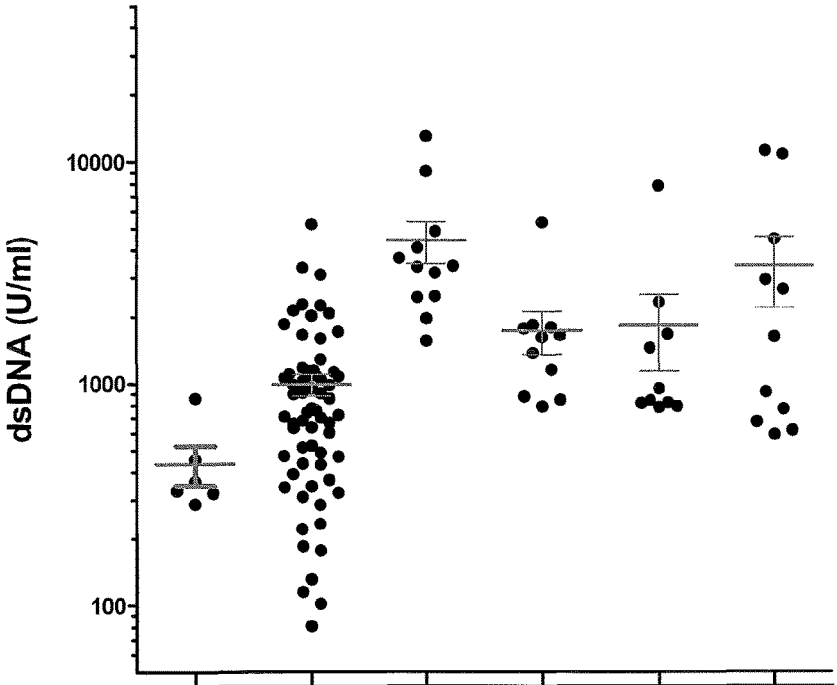
Figure 5B:
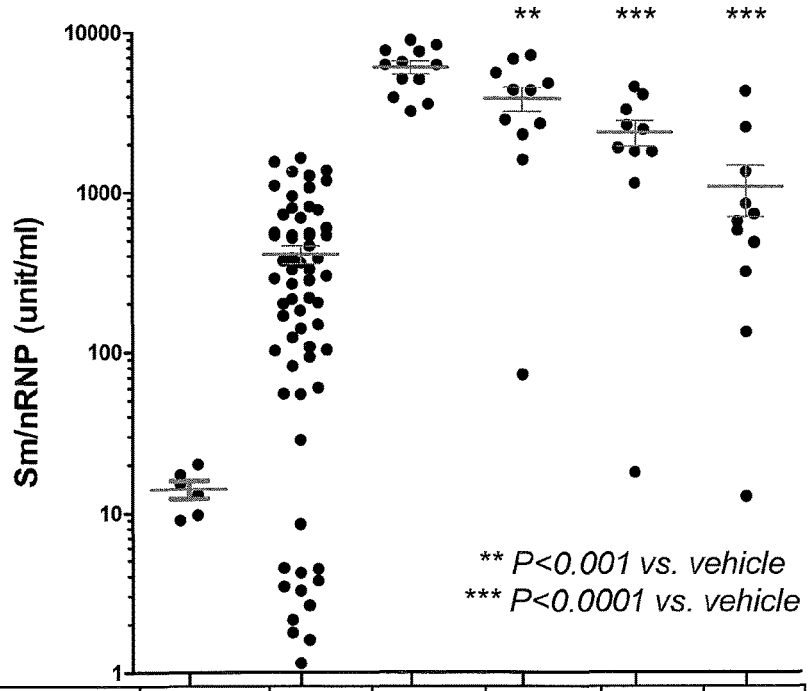
Figure 5C:
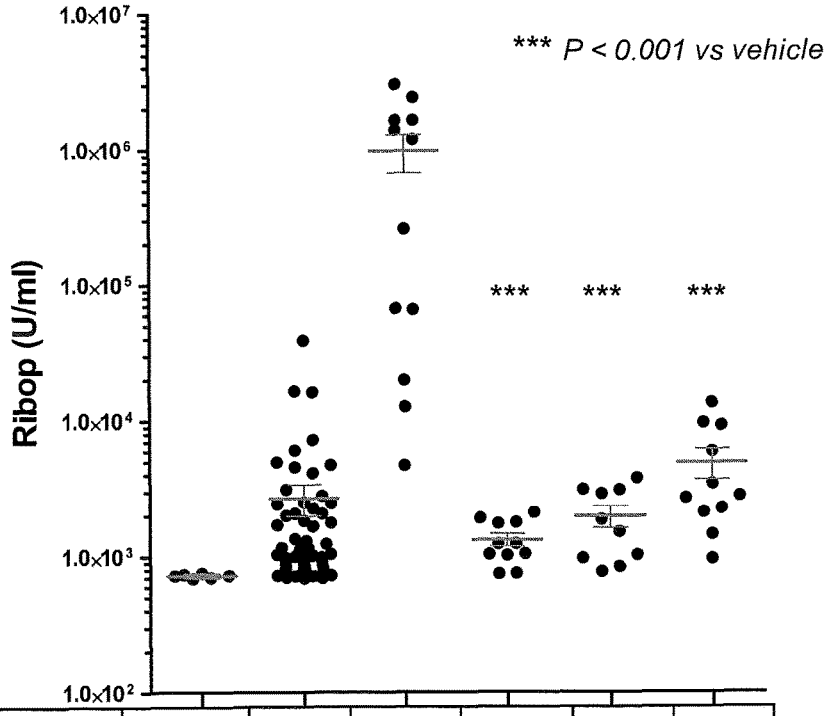
(FIG. 5C) Impact of treatment on anti-dsDNA titers after 17 weeks of dosing, at 46 weeks of age. No statistically significant effect was observed.
Figure 5D:
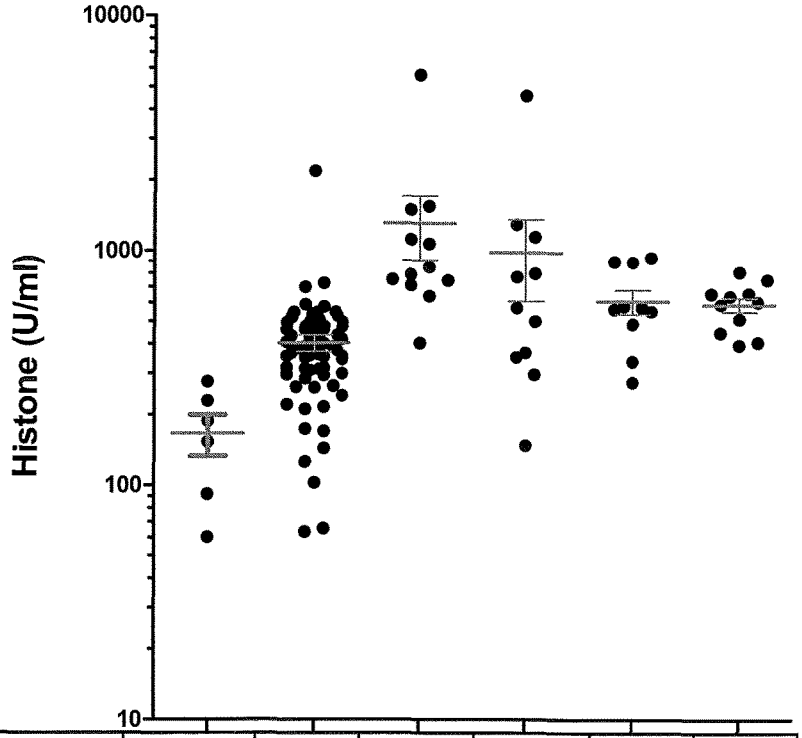
Figure 7A:
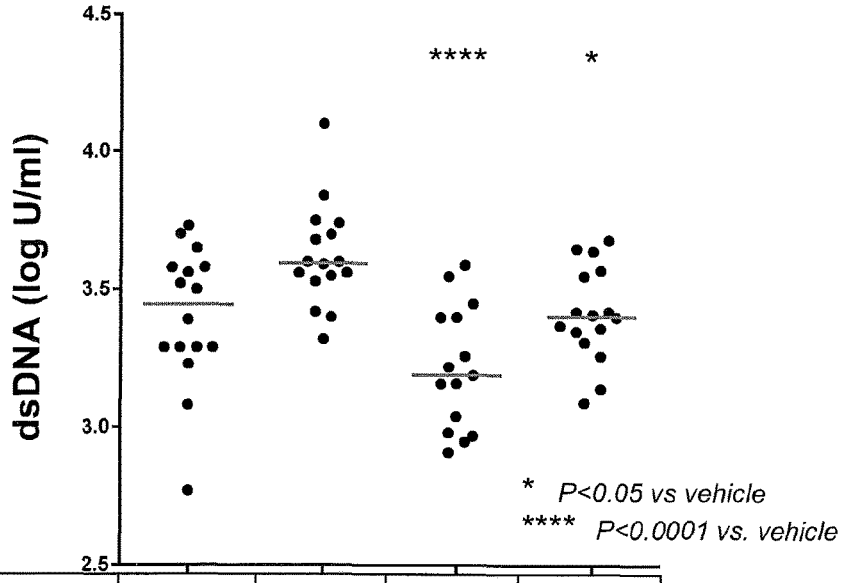
Figure 7B:
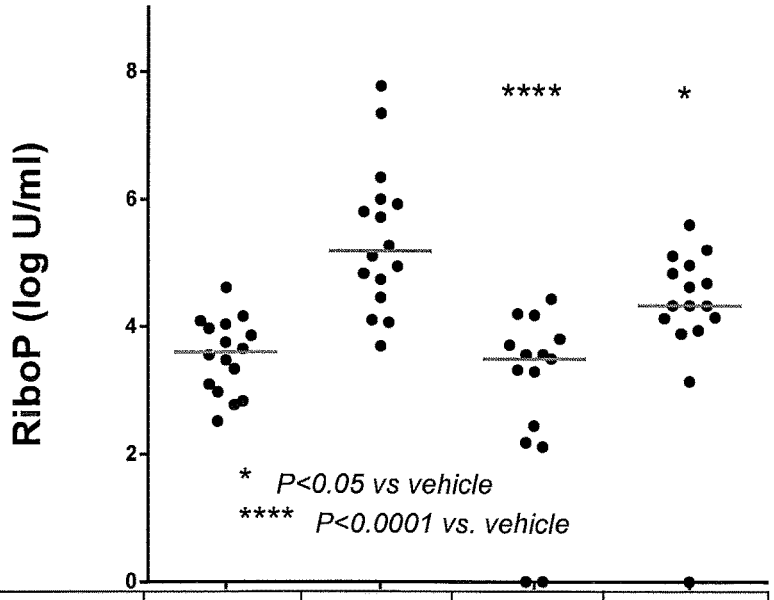
Figure 7C:
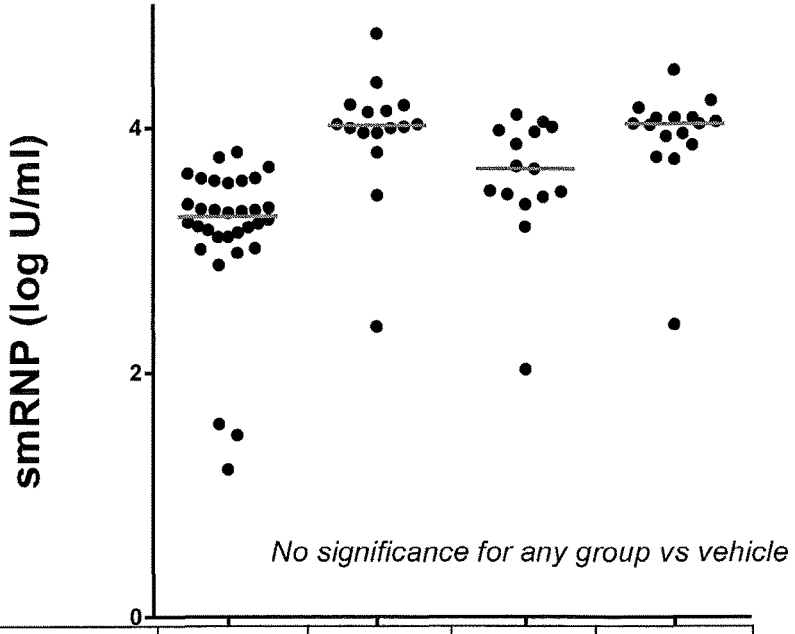
Figure 7D:
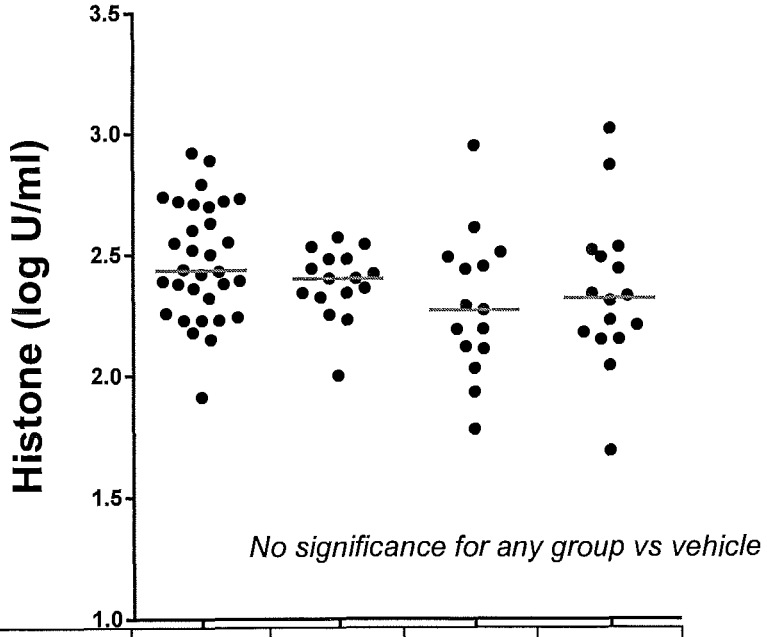
Figure 7E:
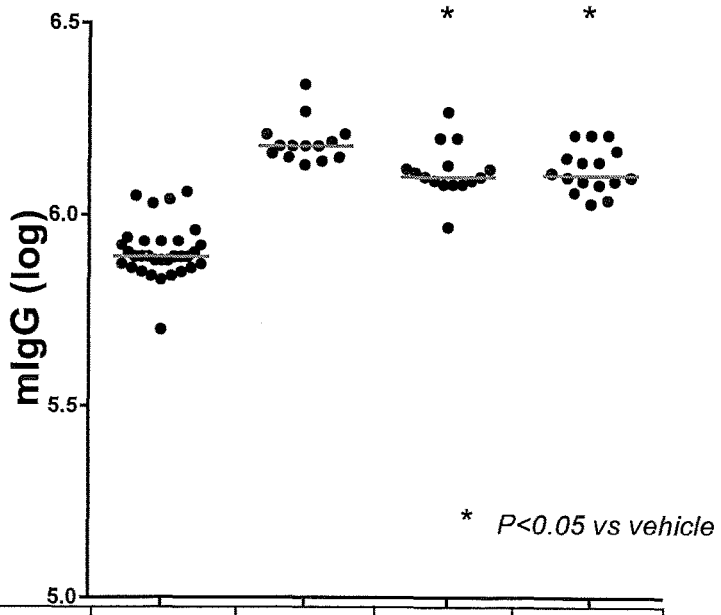
Figure 7F:
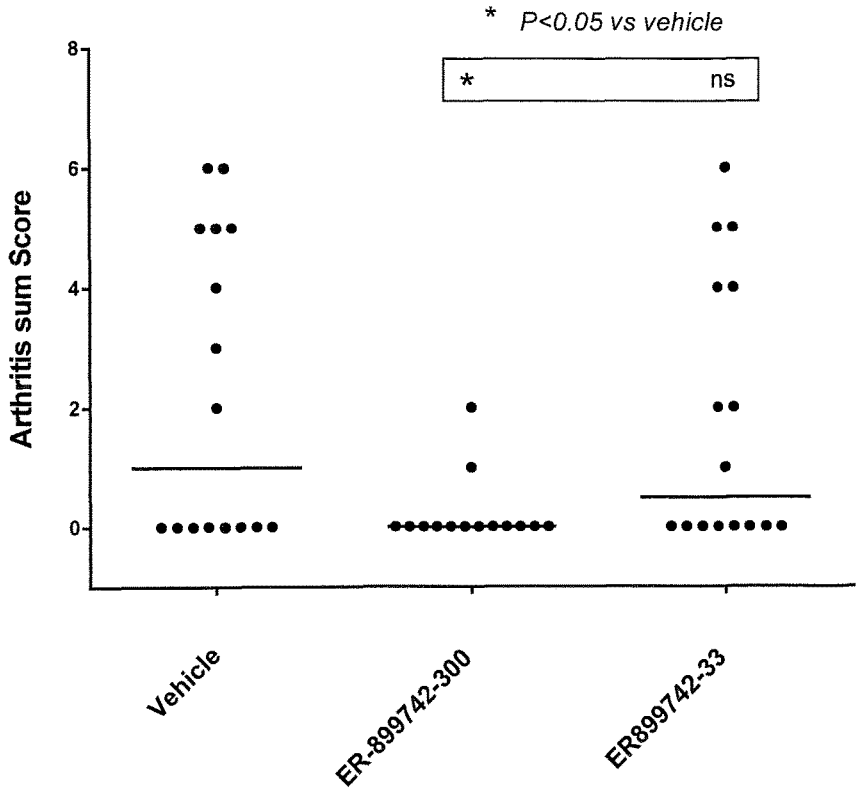

Key findings for ER-899464 in the SLE disease models are as follows (see FIGS. 4-5):

1) ER-899464 at several doses between 33 and 300 mg/kg afforded significant survival benefit in the NZB/W model, accompanied by significantly reduced proteinuria.
2) ER-899464 suppressed various auto-antibody specificities in the Pristane model, with particularly robust impact on RNA-related reactivity such as anti-RiboP titers.

PHARMACOLOGY MATERIALS & METHODS:

In vitro pharmacology:

HEK-293 cells (ATCC) were engineered to stably express a NF-kappaB transcription factor inducible E-selectin (ELAM-1) luciferase reporter derived from the plasmid pGL3 (Promega) containing base pairs −2241 bp to −254 bp from the promoter of the human E-selectin gene (Accession No. NM_000450). These cells were then subsequently engineered to stably and individually express human TLR4, TLR7 or TLR9 full-length ORF cDNAs. Human TLR4 cDNA (Accession No. NM_138554) was cloned into pcDNA 3.0 expression vector (Invitrogen). TLR4 transfected cells were also engineered to express human MD-2 co-receptor [MD-2 cDNA (Accession No. NM_015364) was cloned into the pEF-BOS vector] and were supplemented with 10 nM soluble CD14 (R&D Systems) in the media to optimize LPS responsiveness. Human TLR9 cDNA (Accession No. NM_017442) was cloned into the pBluescript II KS vector (Agilent). Human TLR7 cDNA (Accession No. NM_016562) was obtained from OriGene. HEK-293 cells stably expressing human TLR8 (Accession No. NM_138636) or mouse TLR7 (Accession No. NM_133211) were purchased from InvivoGen and were then stably transfected with pNiFty2(NF-kappaB)-luciferase reporter plasmid (InvivoGen). Each cell type was plated in Dulbecco's modified Eagle's medium (DMEM) containing 10% fetal bovine serum (FBS) at a density of $2.22\times10^5$ cells/ml into a 384-well plate and incubated for 2 days at 37° C., 5% $CO_2$. Varying concentrations of antagonist compounds were then added. Cells were then incubated for another 30 minutes before adding the appropriate TLR agonist as follows (final concentrations indicated): lipopolysaccharide (LPS; Sigma) at 10 ng/ml for TLR4, CL097 (InvivoGen) at 3 ug/ml for human TLR7 and TLR8 and mouse TLR7, and CvG-2006-2A [sequence: TCGTCGTTAAGTCGTTAAGTCGTT (SEQ ID NO: 1) with phosphorothioate backbone, synthesized by Sigma-Aldrich] at 0.6 uM for TLR9. The cells were then incubated overnight, and NF-kappaB dependent luciferase reporter activation was quantified by measuring luminescence with SteadyGlo® (Promega) or Steadylite™ (Perkin Elmer) reagent as per the manufacturer's suggested protocol.

Human PBMC Cell-Based Assay. Human peripheral blood mononuclear cells (PBMC) were isolated from freshly-drawn heparinized (10 USP units/ml, Hospira, Lakeforest, Ill.) healthy donor whole blood by density gradient (Histopaque® 1077, Sigma, Inc., St. Louis, Mo.). Briefly, 25 ml blood was diluted with 15 ml PBS (without $Ca^{2+}$, $Mg^{2+}$) in a 50 ml conical tube, and 12 ml Histopaque was underlaid using a spinal needle. Tubes were centrifuged for 45 minutes at 1200 rpm (350×g), and PBMC were collected from the buffy coat. Cells were then washed twice in PBS, and red blood cells were lysed by suspension in 5 ml ammonium chloride solution (1× Red Blood Cell Lysis Buffer, eBioscience) for 5 minutes at room temperature. After a final wash in PBS, PBMC were resuspended at a final concentration of $2\times10^6$/ml in RPMI-1640 media with L-glutamine (Invitrogen) and supplemented with 25 mM HEPES (Mediatech, Inc, Manassas Va.), 10% fetal bovine serum (HyClone, Logan, Utah), and Penicillin-Streptomycin-Glutamine (Mediatech) and plated at 100 ul/well ($2\times10^5$ cells/well) in tissue culture treated 96-well plates (Falcon).

Antagonist compounds solubilized and serial diluted in 100% DMSO were added in triplicate to cells to yield a final concentration of 0.1% DMSO (v/v). Hydroxychloroquine (Acros Organics) solubilized and serial diluted in PBS was added in triplicate to cells. PBMC were incubated with antagonist compounds or HCQ for 30 minutes at 37° C., 5% $CO_2$ before adding various TLR agonist reagents in 100 ul complete media per well as follows (final concentrations indicated): R848 (Resiquimod; GLSynthesis, Worcester, Mass.) at 1 uM for TLR7 and TLR8, LPS (Sigma) at 10 ng/ml for TLR4, and CpG-2216 (InvivoGen) at 5 ug/ml for TLR9. To prepare a TLR7/8 agonist that mimics RNA-containing auto-antibody immune complexes in lupus patients, a 26-mer RNA with a sequence derived from human U1 snRNA stem loop IV [(sequence: GGGGGACUGCGU-UCGCGCUUUCCC (SEQ ID NO: 2) with phosphorothioate backbone] was synthesized (Dharmacon, Inc., Lafayette, Colo.), which has been shown previously to be a potent TLR7 and TLR8 agonist. This RNA molecule was diluted to 2.5 μM in serum-free RPMI, and mouse anti-human single stranded DNA monoclonal antibody (MAB3034, Millipore, Inc., Billerica, Mass.), which also cross-reacts with RNA, was added at a 1:25 dilution or at 1 ug/ml. The resulting "RNA-Ig" stimulus was incubated at room temperature for 15-30 minutes before adding to cells. PBMC were incubated with the various TLR agonists for 20 hours at 37° C., 5% $CO_2$. Cell culture supernatants were collected, and levels of various human cytokines were assessed as indicated by standard ELISA procedure according to the manufacturer's recommended protocol (BD Biosciences, Inc., San Diego, Calif.). Results are shown in Table 5. In a subsequent assay (Table 6) the ability of ER-899742 to block stimulation of normal PBMC by various TLR7/8 ligands, but not DNA-mediated activation of TLR9, was examined. In this assay cells were plated at $1\times10^5$ cells/well in 100 ul in 96-well plates.

TABLE 5

PBMC Assay Data Summary for Selected Compounds

| Compound Number | Human PBMCs $IC_{50}$ (μM) |
|---|---|
| ER-878952 | 0.151 |
| ER-878952 | 0.151 |
| ER-879570 | 0.113 |
| ER-879689 | 1.240 |
| ER-880639 | 0.169 |
| ER-884884 | 0.204 |
| ER-885493 | 0.180 |
| ER-885612 | 0.614 |
| ER-885618 | 0.023 |
| ER-885807 | 0.331 |
| ER-885906 | 0.033 |
| ER-886131 | 0.098 |
| ER-886133 | 0.127 |
| ER-886134 | 0.277 |
| ER-886211 | 0.175 |
| ER-886355 | 0.177 |
| ER-886360 | 0.486 |
| ER-886516 | 0.056 |
| ER-886564 | 0.108 |
| ER-886565 | 0.095 |
| ER-886567 | 0.022 |
| ER-886568 | 0.079 |
| ER-886605 | 0.021 |
| ER-886606 | 0.015 |
| ER-886608 | 0.001 |
| ER-886609 | 0.004 |
| ER-886624 | 0.023 |
| ER-886625 | 0.091 |
| ER-886626 | 0.080 |
| ER-886787 | 0.076 |
| ER-886820 | 0.062 |
| ER-886853 | 0.004 |
| ER-886854 | 0.020 |
| ER-886855 | 0.034 |

TABLE 5-continued

PBMC Assay Data Summary for Selected Compounds

| Compound Number | Human PBMCs $IC_{50}$ (μM) |
|---|---|
| ER-886856 | 0.111 |
| ER-886857 | 0.098 |
| ER-887270 | 0.001 |
| ER-887271 | 0.002 |
| ER-887272 | 0.002 |
| ER-887442 | 0.047 |
| ER-887443 | 0.032 |
| ER-887526 | 0.050 |
| ER-887528 | 0.056 |
| ER-887538 | 0.048 |
| ER-887539 | 0.000 |
| ER-887540 | 0.001 |
| ER-887586 | 0.098 |
| ER-887587 | 0.001 |
| ER-887588 | 0.001 |
| ER-887589 | 0.036 |
| ER-887612 | 0.053 |
| ER-887722 | 0.065 |
| ER-887723 | 0.007 |
| ER-887724 | 0.006 |
| ER-887725 | 0.002 |
| ER-887927 | 0.000 |
| ER-887960 | 0.041 |
| ER-888070 | 0.003 |
| ER-888200 | 0.016 |
| ER-888201 | 0.004 |
| ER-888202 | 0.008 |
| ER-888203 | 0.105 |
| ER-888204 | 0.022 |
| ER-888205 | 0.040 |
| ER-888285 | 0.014 |
| ER-888286 | 0.223 |
| ER-888288 | 0.015 |
| ER-888288 | 0.015 |
| ER-888289 | 0.011 |
| ER-888321 | 0.022 |
| ER-888322 | 0.018 |
| ER-888330 | 0.154 |
| ER-888479 | 0.091 |
| ER-888480 | 0.001 |
| ER-890345 | 0.001 |
| ER-890346 | 0.006 |
| ER-890831 | 0.001 |
| ER-890963 | 0.002 |
| ER-890964 | 0.001 |
| ER-892253 | 0.066 |
| ER-893881 | 0.009 |
| ER-893926 | 0.008 |
| ER-893948 | 0.150 |
| ER-894149 | 0.031 |
| ER-894150 | 0.004 |
| ER-894152 | 0.175 |
| ER-894154 | 0.143 |
| ER-894155 | 0.042 |
| ER-894159 | 0.042 |
| ER-894160 | 0.011 |
| ER-894483 | 0.209 |
| ER-894484 | 0.174 |
| ER-894504 | 0.005 |
| ER-894545 | 0.005 |
| ER-894546 | 0.069 |
| ER-894547 | 0.012 |
| ER-894548 | 0.028 |
| ER-894549 | 0.014 |
| ER-894550 | 0.097 |
| ER-894551 | 0.003 |
| ER-894552 | 0.017 |
| ER-894594 | 0.087 |
| ER-894655 | 0.005 |
| ER-894656 | 0.007 |
| ER-895200 | 0.026 |
| ER-895204 | 0.023 |
| ER-895310 | 0.034 |
| ER-895324 | 0.001 |
| ER-895325 | 0.026 |

TABLE 5-continued

PBMC Assay Data Summary for Selected Compounds

| Compound Number | Human PBMCs $IC_{50}$ (μM) |
|---|---|
| ER-895326 | 0.002 |
| ER-895327 | 0.026 |
| ER-898563 | 0.122 |
| ER-898565 | 0.198 |
| ER-898566 | 0.011 |
| ER-898694 | 0.002 |
| ER-898707 | 0.002 |
| ER-898914 | 0.168 |
| ER-898919 | 0.055 |
| ER-898921 | 0.302 |
| ER-898922 | >1.00 |
| ER-898923 | 0.631 |
| ER-898946 | 0.002 |
| ER-899017 | 0.004 |
| ER-899018 | 0.009 |
| ER-899019 | 0.014 |
| ER-899020 | 0.035 |
| ER-899021 | 0.005 |
| ER-899121 | 0.142 |
| ER-899122 | 0.080 |
| ER-886858 | 0.015 |
| ER-886859 | 0.107 |
| ER-886860 | 0.240 |
| ER-886866 | 0.050 |
| ER-886867 | 0.034 |
| ER-886868 | 0.050 |
| ER-886869 | 0.112 |
| ER-886912 | 0.383 |
| ER-886913 | 0.520 |
| ER-886949 | 0.032 |
| ER-886950 | 0.114 |
| ER-886951 | 0.079 |
| ER-886953 | 0.026 |
| ER-886955 | 0.129 |
| ER-886957 | 0.017 |
| ER-886958 | 0.034 |
| ER-887137 | 0.002 |
| ER-887138 | 0.004 |
| ER-887139 | 0.005 |
| ER-887140 | 0.110 |
| ER-887141 | 0.049 |
| ER-887142 | 0.147 |
| ER-887143 | 0.013 |
| ER-887144 | 0.063 |
| ER-887145 | 0.015 |
| ER-887146 | 0.038 |
| ER-887177 | 0.000 |
| ER-887199 | 0.117 |
| ER-887252 | 0.002 |
| ER-887253 | 0.001 |
| ER-887258 | 0.055 |
| ER-887259 | 0.001 |
| ER-887260 | 0.004 |
| ER-887261 | 0.120 |
| ER-887262 | 0.103 |
| ER-887268 | 0.005 |
| ER-887269 | 0.001 |
| ER-888603 | 0.007 |
| ER-888604 | 0.006 |
| ER-888644 | 0.019 |
| ER-888645 | 0.047 |
| ER-888646 | 0.003 |
| ER-888647 | 0.012 |
| ER-888701 | 0.018 |
| ER-888896 | 0.050 |
| ER-888977 | 0.217 |
| ER-889469 | 0.013 |
| ER-889470 | 0.012 |
| ER-889504 | 0.002 |
| ER-889556 | 0.010 |
| ER-889557 | 0.085 |
| ER-889571 | 1.000 |
| ER-889728 | 0.021 |
| ER-889744 | 0.008 |
| ER-889745 | 0.046 |

TABLE 5-continued

PBMC Assay Data Summary for Selected Compounds

| Compound Number | Human PBMCs $IC_{50}$ (μM) |
|---|---|
| ER-889745 | 0.046 |
| ER-889746 | 0.073 |
| ER-889822 | 0.025 |
| ER-890093 | 0.022 |
| ER-890108 | 0.009 |
| ER-890113 | 0.022 |
| ER-890119 | 0.008 |
| ER-890120 | 0.005 |
| ER-890121 | 0.011 |
| ER-890186 | 0.001 |
| ER-890187 | 0.079 |
| ER-890188 | 0.087 |
| ER-890189 | 0.114 |
| ER-890250 | 0.116 |
| ER-890252 | 0.042 |
| ER-890253 | 0.064 |
| ER-890342 | 0.121 |
| ER-890344 | 0.002 |
| ER-895472 | 0.161 |
| ER-895477 | 0.013 |
| ER-897385 | 0.142 |
| ER-897445 | 0.104 |
| ER-897446 | 0.053 |
| ER-897447 | 0.100 |
| ER-897827 | 0.039 |
| ER-897828 | 0.021 |
| ER-897922 | 0.064 |
| ER-897938 | 0.016 |
| ER-897940 | 0.021 |
| ER-897945 | 0.002 |
| ER-897964 | 0.020 |
| ER-897965 | 0.010 |
| ER-897967 | 0.013 |
| ER-897968 | 0.001 |
| ER-897969 | 0.007 |
| ER-7982 | 0.009 |
| ER-899285 | 0.007 |

TABLE 5-continued

PBMC Assay Data Summary for Selected Compounds

| Compound Number | Human PBMCs $IC_{50}$ (μM) |
|---|---|
| ER-899287 | 0.120 |
| ER-899293 | 0.013 |
| ER-899295 | 0.032 |
| ER-899332 | 0.014 |
| ER-899337 | 0.002 |
| ER-899366 | 0.001 |
| ER-899367 | 0.012 |
| ER-899414 | 0.025 |
| ER-899415 | 0.013 |
| ER-899416 | 0.431 |
| ER-899417 | 0.001 |
| ER-899418 | 0.005 |
| ER-899431 | 0.347 |
| ER-899457 | 0.003 |
| ER-899459 | 0.016 |
| ER-899464 | 0.001 |
| ER-899476 | 0.003 |
| ER-899477 | 0.006 |
| ER-899479 | 0.002 |
| ER-899481 | 0.008 |
| ER-899588 | 0.007 |
| ER-899688 | 0.011 |
| ER-899742 | 0.001 |
| ER-899745 | 0.004 |
| ER-899134 | 0.010 |
| ER-899140 | 0.011 |
| ER-899152 | 0.036 |
| ER-899154 | 0.014 |
| ER-899160 | 0.252 |
| ER-899161 | 0.125 |
| ER-899193 | 0.009 |
| ER-899278 | 0.001 |
| ER-899282 | 0.034 |
| ER-899616 | 0.054 |
| ER-899619 | 0.033 |
| ER-899626 | 0.001 |

TABLE 6

IL-6 and IFN-α blockade by ER-899742 in human PBMC across multiple ligands compared to hydroxychloroquine

| | | IC50 (μM) | | | | | | | | | |
|---|---|---|---|---|---|---|---|---|---|---|---|
| | | SL4-Ig | | RNA40-DOTAP | | R848 | | ODN2006-DOTAP | | ODN2216-Ig | |
| Compound | Donor # | IL-6 | IFN-α | IL-6 | IFN-α | IL-6 | IFN-α | IL-6 | IFN-α | IL-6 | IFN-α |
| ER-899742 | 1 | 0.0077 | NA[1] | 0.035 | 0.017 | 0.0034 | 0.01 | >10 | >10 | NA | NA |
| | 2 | 0.0032 | NA | 0.023 | NA | 0.0065 | NA | >10 | NA | >10 | NA |
| | 3 | 0.0043 | NA | 0.054 | 0.0096 | 0.007 | NA | >10 | >10 | >10 | NA |
| | 4 | 0.0043 | 0.0022 | 0.033 | 0.018 | 0.0049 | 0.012 | >10 | >10 | >10 | >10 |
| | 5 | 0.0025 | NA | 0.029 | NA | 0.0055 | NA | >10 | NA | NA | NA |
| | 6 | 0.0033 | 0.0005 | 0.014 | 0.011 | 0.0081 | 0.011 | >10 | >10 | >10 | >10 |
| | Ave. | 0.0042 | 0.0014 | 0.0313 | 0.0139 | 0.0059 | 0.011 | >10 | >10 | >10 | >10 |
| HCQ | 1 | 5.2 | NA | 10 | 0.49 | >10 | 1.25 | 1.2 | 0.91 | NA | NA |
| | 2 | 3.7 | NA | 10.75 | NA | >10 | NA | 1.24 | NA | 0.6 | NA |
| | 3 | 3.2 | NA | >10 | 0.41 | >10 | NA | 1.54 | 4.1 | 7.3 | NA |
| | 4 | 3.6 | 0.459 | 15.5 | 0.99 | >10 | 2.57 | 2.4 | 3.1 | 1.24 | 0.28 |
| | 5 | 4.3 | NA | 18 | NA | >10 | NA | 1.58 | NA | NA | NA |
| | 6 | 4.6 | 0.324 | 6.1 | 0.502 | >10 | 2.03 | 2.37 | 3.96 | 0.38 | 0.29 |
| | Ave. | 4.10 | 0.3915 | 12.07 | 0.598 | >10 | 1.95 | 1.72 | 3.02 | 2.38 | 0.29 |

[1]NA, data not presented because values below detection limit, or replicates showed high variability Mouse Spleen cell-based assay. Spleens were harvested from female BALB/c mice (Jackson Labs, Bar Harbor, Me.) euthanized by $CO_2$. A single cell suspension was obtained by passing spleens through a 40 μm an nylon cell strainer. Cells were washed twice with 50 ml PBS (Mediatech, Inc., Manassas, Va.) and red blood cells were lysed in 5 ml RBC Lysis buffer (eBioscience, Inc., San Diego, Calif.) for 5 minutes at room temperature. Cells were washed twice more in PBS and finally resuspended in supplemented RPMI-1640 at $2.5\times10^6$ cells/ml. Cells were plated at 100 μl/well ($2.5\times10^5$ cells/well) in 96-well tissue culture treated plates (Falcon). Serial dilutions of compounds solubilized in 100% DMSO were added in triplicate to cells to yield a final concentration of 0.1% DMSO. Cells were incubated with compound for 30 minutes at 37° C., 5% $CO_2$ before adding 100 μl/well of 740 nM R848 (Resiquimod; GLSynthesis, Worcester, Mass.) in complete media for a final concentration of 370 nM R848. Cells were incubated for 20 hours at 37° C., 5% $CO_2$. Culture supernatants were collected, and levels of IL-6 were assessed by standard ELISA procedure according to the manufacturer's recommended protocol (BD Biosciences, Inc., San Diego, Calif.). Data is presented below in Table 7.

TABLE 7

Mouse Splenocyte Results

| Compound Number | Mouse Splenocytes $IC_{50}$ (μM) |
|---|---|
| ER-878952 | 1.611 |
| ER-885493 | 0.517 |
| ER-887253 | 0.049 |
| ER-887268 | 2.124 |
| ER-887722 | 0.463 |
| ER-887723 | 0.047 |
| ER-887724 | 0.070 |
| ER-887927 | 0.026 |
| ER-888070 | 0.076 |
| ER-888288 | 0.135 |
| ER-888480 | 0.087 |
| ER-889469 | 0.097 |
| ER-889470 | 0.152 |
| ER-889556 | 0.432 |
| ER-889601 | 0.179 |
| ER-889745 | 0.090 |
| ER-890093 | 0.088 |
| ER-890311 | 0.428 |
| ER-890831 | 0.170 |
| ER-890963 | 0.250 |
| ER-893881 | 0.270 |
| ER-893948 | 0.420 |
| ER-894152 | 0.660 |
| ER-894655 | 0.084 |
| ER-894656 | 0.023 |
| ER-895204 | 0.051 |
| ER-895325 | 0.120 |
| ER-895326 | 0.090 |

In vivo pharmacology:

Short-term in vivo (STIV) assay. Six to eight week old female BALB/c mice (Jackson Labs, Bar Harbor, Me.) were dosed by oral gavage in 200 ul volume with antagonist compounds formulated in 0.5% aqueous methyl-cellulose (Sigma, St. Louis, Mo.). At various time points afterwards, mice were injected subcutaneously (s.c.) in 100 ul volume with 15 ug R848 (Resiquimod; GLSynthesis, Worcester, Mass.) to stimulate TLR7. Blood plasma was collected by cardiac puncture, and levels of IL-6 at 1.5 hours after TLR7 stimulation were then assessed by standard ELISA procedure according to the manufacturer's recommended protocol (R&D Systems).

Mouse lupus disease model strains. Female NZBWF1/J mice were purchased from Jackson Labs (Bar Harbor, Me.), both of which manifest with spontaneous lupus disease. Female DBA/1 mice were purchased from Harlan Laboratories (Indianapolis, Ind.) and at the indicated ages given an intraperitoneal injection of 0.5 ml pristane (2,6,10,14-Tetramethylpentadecane; Sigma, St. Louis, Mo.) to chemically induce lupus disease or of 0.5 ml PBS to generate age-matched, non-diseased control mice.

Figure 2A:
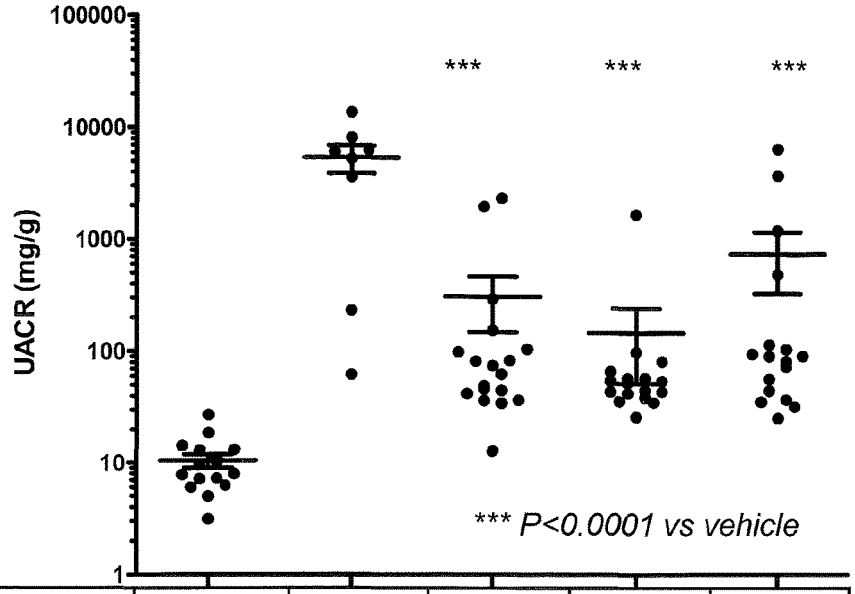
Figure 2C:
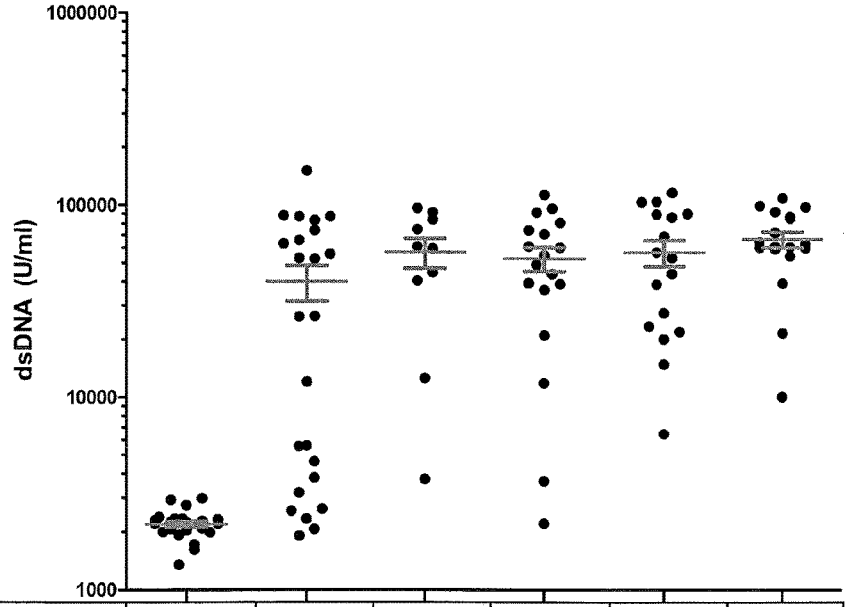
Figure 3A:
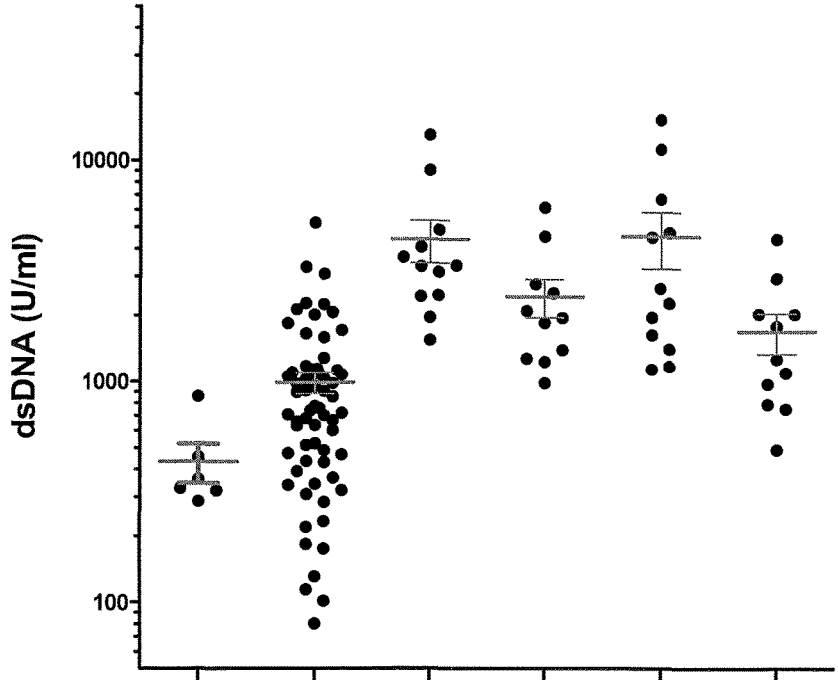
Figure 3B:
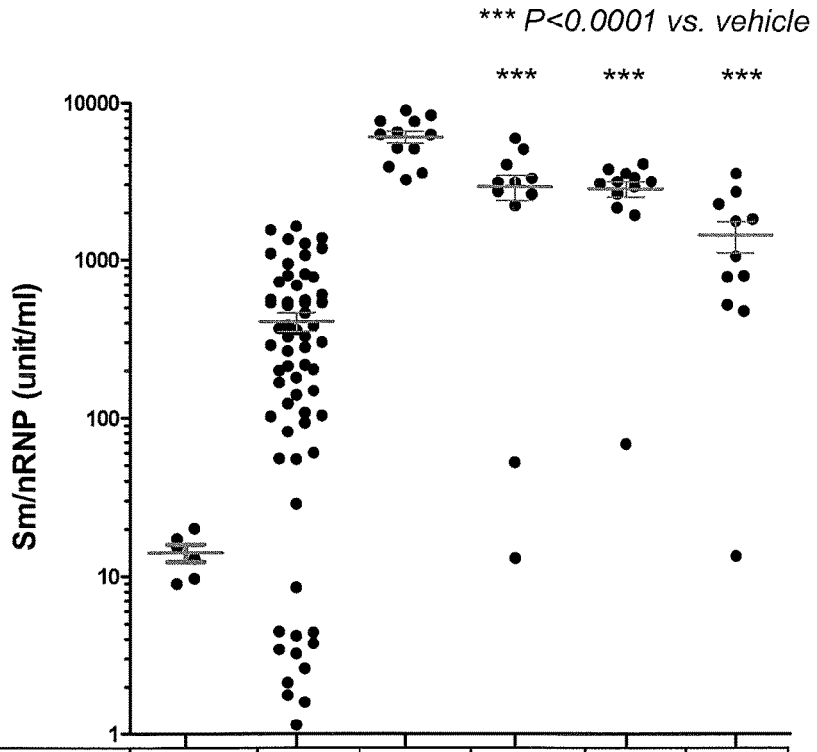
Figure 3C:
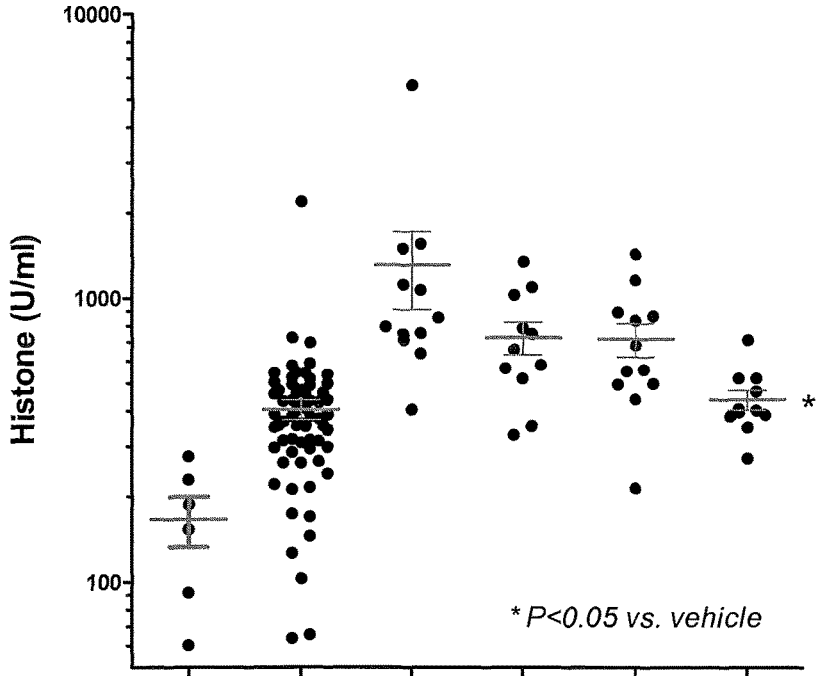
Figure 3D:
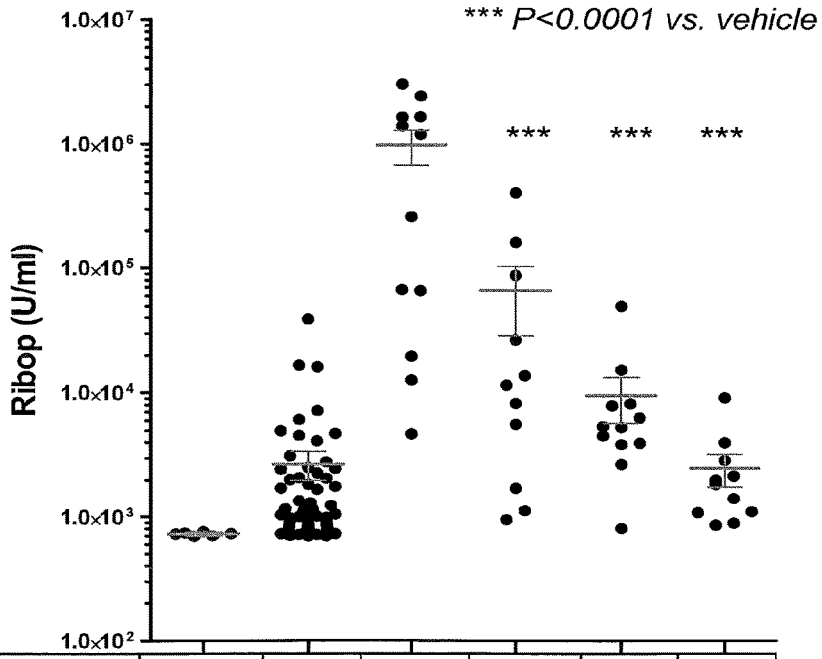

Further testing of an embodiment is shown in FIG. 2A through FIG. 2C, which demonstrates testing of ER-899742 in the NZBxNZW strain (abreviated hereafter as NZBWF1/J or NZB/W) lupus disease model. Female NZBWF1/J mice were received at 5 weeks of age, baseline bleeds were performed, and mice were monitored for disease progression by following anti-dsDNA titers. At 27 weeks of age, mice were randomized into groups with equivalent median anti-dsDNA titers and treated at 29 weeks of age with Vehicle (Veh; 0.5% methyl-cellulose) alone or 33, 100, or 300 mg/kg once-a-day orally (QD PO). At 46 weeks of age after 17 weeks of treatment, mice were bled and tested for anti-dsDNA titers. All mice were sacrificed at 50 weeks of age (21 weeks of compound treatment). FIG. 2(A) shows that just prior to termination at 50 weeks of age (following 21 weeks of treatment), urine was collected from individual mice, and the Urinary Albumin Creatinine Ratio (UACR, proteinuria) was determined for each animal as an indirect measure of kidney function. FIG. 2(B) shows a timecourse of mortality observed in this study for the highest and lowest dose groups. No mortality was seen with compound treatment. Further, no mortality was observed in the middle dose group (not shown). FIG. 2(C) shows impact of treatment on anti-dsDNA titers after 17 weeks of dosing, at 46 weeks of age. No statistically significant effect was observed.

At the end of the experiment kidneys were collected from the animals tested in FIG. 2A through 2C, fixed in 10% formalin for 24 hours, embedded in paraffin, and H&E stained sections were generated for histopathology assessment in a blinded fashion (Grade 0/1+: WNL to minimal; Grade 2: Mild; Grade 3: Moderate to Marked; Grade 4: Severe). Results are shown in Table 8.

TABLE 8

| | Vehicle | ER-899742, 33 mpk | ER-899742, 100 mpk | ER-899742, 300 mpk |
|---|---|---|---|---|
| Total # Mice Examined | 19 | 18 | 17 | 18 |
| GN Score | | | | |
| 0 | 0 | 11 | 15 | 9 |
| 2+ | 1 | 5 | 1 | 7 |
| 3+ | 4 | 1 | 1 | 0 |
| 4+ | 14 | 1 | 0 | 2 |
| % combined incidence of Grade 3 and 4 | 74% | 11% | 6% | 11% |

Assessment of auto-antibody titers by ELISA. Anti-dsDNA, -Sm/nRNP, -RiboP, and -Histone titers were evaluated by standard ELISA approach. Briefly, 96-well EIA/RIA ELISA plates (Corning) were coated with 100 ul of diluted antigen in PBS for 90 minutes at room temperature as follows (final concentrations indicated): 10 U/ml Sm/nRNP complex (Immunovision), 10 ug/ml calf thymus dsDNA (Sigma), 5 U/ml RiboP (Immunovision), and 5 ug/ml Histone (Immunovision). Plates were washed with PBS/0.05% Tween20 (washing buffer) and blocked overnight with PBS/1% BSA (blocking buffer) at 4° C. Plates were washed, mouse plasma samples diluted in blocking buffer (ranging from 1:25-1:10,000 depending on the model and the antigen) were added to wells in 100 ul volume per well, and plates were incubated for 90 minutes at room temperature. Plates were then washed, 100 ul anti-mouse-IgG-HRPO (Southern Biotech) diluted 1:50,000 in PBS/1% BSA/0.05% Tween was added to each well, and plates were incubated for 90 minutes at room temperature. Plates were washed, and 100 ul of a 1:1 mix of substrate components from the OptEIA TMB substrate kit (BD Biosciences) was added to the wells. Plates were incubated at room temperature, and after sufficient color development the reaction was stopped by adding 100 ul of 0.18M sulfuric acid solution. Plates were read by spectrophotometry at 450 nm.

Assessment of proteinuria. Urine was collected manually from individual mice or by housing 1-2 mice per metabolic cage for 18 hours, and the Urinary Albumin Creatinine Ratio (UACR) was determined for each animal as an indirect measure of kidney function (UACR calculated as the ratio of mg of albumin/g of creatinine per dL of urine). Albumin levels in the urine samples were determined using a custom sandwich ELISA protocol using an anti-mouse albumin antibody set (Bethyl Labs), which included a coating antibody and a secondary antibody tagged with an HRP conjugate for detection. Creatinine levels were determined using a commercial creatinine assay kit (Cayman).

Histological assessment of nephritis. Kidneys were collected from individual mice, fixed in 10% formalin for 24 hours, embedded in paraffin, and H&E stained sections were generated for histopathology assessment in a blinded fashion. Features of Nephritis Disease Scores are as follows: Grade 0—normal limits; Grade 1—ribbon-like capillary wall thickening; Grade 2—hypercellularity, segmentation, crescent formation; Grade 3—see Grade 2, increased severity and extent (% glomeruli affected) of glomerular lesions; Grade 4—sclerosis; severe glomerular disease (non-functional organ).

Assessment of interferon gene expression in whole blood. The expression of IFN-regulated genes in whole blood was measured by qPCR. Briefly, mice were euthanized, blood was collected via the vena cava, and 100 ul was preserved in tubes containing RNAlater (Ambion, Austin Tex.). Total RNA was isolated using the Mouse RiboPure Blood RNA Isolation Kit (Ambion). RNA concentrations were determined using a NanoDrop ND-1000 spectrophotometer (Thermo Scientific, Waltham Mass.). First strand cDNA was synthesized from 100 ng total RNA using SuperScript® VILO™ Master Mix (Life Technologies, Grand Island, N.Y.). After reverse transcription, cDNA was diluted with nuclease-free water and mixed with TaqMan® Fast Advanced Master Mix (Applied Biosystems). The mixture was then applied to a custom TaqMan® Low Density Array (TLDA) manufactured by Applied Biosystems, and qPCR was performed on the ABI 7900HT Fast Real-time PCR System (Applied Biosystems). Raw data was collected using RQ Manager 1.2.1 (Applied Biosystems) and analyzed using GeneData Analyst 2.2 software (GeneData).

The TLDA panel contained as many as 45 target genes chosen from Table 9 below, and 3 housekeeping genes for normalization. The housekeeping gene Hprt1 was chosen for normalization based on coefficient-of-variation. Relative quantities were determined for the target genes and used to calculate a fold change for each diseased mouse relative to the non-diseased control group receiving intraperitoneal PBS injection only. A standard Student's t-test was performed to determine which target genes were significantly increased between the non-diseased group (PBS treated) and the vehicle-treated diseased group (pristane treated), thereby representing the disease-regulated gene set. For FIG. 7G a false discovery rate (FDR) correction was done using the p.adjust command in package "base" with default option. Holm, S. A simple sequentially rejective multiple test procedure. Scandinavian Journal of Statistics, 1979. 6(2): p. 65-70. An "IFN score" was subsequently calculated for each mouse as the median fold change of all disease-regulated genes identified in the t-test.

TABLE 9

| Gene symbol | Taqman ID | Gene name |
|---|---|---|
| 18S | Hs99999901_s1 | Eukaryotic 18S rRNA |
| Bst2 | Mm01609165_g1 | bone marrow stromal cell antigen 2 |
| C1qa | Mm00432142_m1 | complement component 1, q subcomponent, alpha polypeptide |
| C3 | Mm00437858_m1 | complement component 3 |
| C3ar1 | Mm02620006_s1 | complement component 3a receptor 1 |
| Ccl2 | Mm00441243_g1 | chemokine (C-C motif) ligand 2 |
| Ccl5 | Mm01302427_m1 | chemokine (C-C motif) ligand 5 |
| Ccr2 | Mm00438270_m1 | chemokine (C-C motif) receptor 2 |
| Cd274 | Mm00452054_m1 | CD274 antigen |
| Cd300e | Mm00468131_m1 | CD300e antigen |
| Cd38 | Mm01220906_m1 | CD38 antigen |
| Cd40 | Mm00441891_m1 | CD40 antigen |
| Cdkn2c | Mm00483243_m1 | cyclin-dependent kinase inhibitor 2C (p18, inhibits CDK4) |
| Cmpk2 | Mm00469582_m1 | cytidine monophosphate (UMP-CMP) kinase 2 |
| Cxcl10 | Mm00445235_m1 | chemokine (C-X-C motif) ligand 10 |
| Cxcl11 | Mm00444662_m1 | chemokine (C-X-C motif) ligand 11 |
| Ddx60 | Mm00460708_m1 | DEAD (Asp-Glu-Ala-Asp) box polypeptide 60 |
| Elane | Mm00469310_m1 | elastase, neutrophil expressed |
| Epsti1 | Mm00712734_m1 | epithelial stromal interaction 1 (breast) |
| Fcgr1 | Mm00438874_m1 | Fc receptor, IgG, high affinity I |
| Fpr1 | Mm00442803_s1 | formyl peptide receptor 1 |
| Gapdh | Mm99999915_g1 | glyceraldehyde-3-phosphate dehydrogenase |
| Herc6 | Mm01341950_m1 | hect domain and RLD 6 |
| Hprt | Mm00446968_m1 | hypoxanthine guanine phosphoribosyl transferase |
| Ifi202b | Mm00839397_m1 | interferon activated gene 202B |
| Ifi204 | Mm00492602_m1 | interferon activated gene 204 |
| Ifi2712a | Mm01329883_gH | interferon, alpha-inducible protein 27 like 2A |
| Ifi35 | Mm00510329_m1 | interferon-induced protein 35 |
| Ifi44 | Mm00505670_m1 | interferon-induced protein 44 |
| Ifih1 | Mm00459183_m1 | interferon induced with helicase C domain 1 |
| Ifit1 | Mm00515153_m1 | interferon-induced protein with tetratricopeptide repeats 1 |
| Ifit2 | Mm00492606_m1 | interferon-induced protein with tetratricopeptide repeats 2 |
| Ifit3 | Mm01704846_s1 | interferon-induced protein with tetratricopeptide repeats 3 |
| Il3ra | Mm00434273_m1 | interleukin 3 receptor, alpha chain |
| Il6 | Mm00446190_m1 | interleukin 6 |
| Il6ra | Mm00439653_m1 | interleukin 6 receptor, alpha |
| Irf5 | Mm00496477_m1 | interferon regulatory factor 5 |
| Irf7 | Mm00516788_m1 | interferon regulatory factor 7 |
| Isg15 | Mm01705338_s1 | ISG15 ubiquitin-like modifier |
| Isg20 | Mm00469585_m1 | interferon-stimulated protein |
| Lta | Mm00440228_gH | lymphotoxin A |
| Ly6e | Mm01200460_g1 | lymphocyte antigen 6 complex, locus E |
| Mmp8 | Mm00439509_m1 | matrix metallopeptidase 8 |
| Mmp9 | Mm00442991_m1 | matrix metallopeptidase 9 |
| Mpo | Mm00447886_m1 | myeloperoxidase |
| Ms4a6c | Mm00459296_m1 | membrane-spanning 4-domains, subfamily A, member 6C |
| Mx1 | Mm00487796_m1 | myxovirus (influenza virus) resistance 1 |
| Oas3 | Mm00460944_m1 | 2-5 oligoadenylate synthetase 3 |
| Oasl2 | Mm00496187_m1 | 2-5 oligoadenylate synthetase-like 2 |
| Ppia | Mm02342430_g1 | peptidylprolyl isomerase A (cyclophilin A) |

TABLE 9-continued

| Gene symbol | Taqman ID | Gene name |
|---|---|---|
| Prf1 | Mm00812512_m1 | perforin 1 (pore forming protein) |
| Rsad2 | Mm00491265_m1 | radical S-adenosyl methionine domain containing 2 |
| Siglec1 | Mm00488332_m1 | sialic acid binding Ig-like lectin 1, sialoadhesin |
| Stat1 | Mm00439531_m1 | signal transducer and activator of transcription 1 |
| Tlr7 | Mm00446590_m1 | toll-like receptor 7 |
| Tlr9 | Mm00446193_m1 | toll-like receptor 9 |
| Tnf | Mm00443258_m1 | tumor necrosis factor |
| Tnfsf10 | Mm01283606_m1 | tumor necrosis factor (ligand) superfamily, member 10 |
| Tnfsf13b | Mm00446347_m1 | tumor necrosis factor (ligand) superfamily, member 13b |
| Treml4 | Mm00553947_m1 | triggering receptor expressed on myeloid cells-like 4 |
| Trex1 | Mm00810120_s1 | three prime repair exonuclease 1 |
| Usp18 | Mm00449455_m1 | ubiquitin specific peptidase 18 |
| Xaf1 | Mm01248390_m1 | XIAP associated factor 1 |

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: synthetic construct

<400> SEQUENCE: 1

tcgtcgttaa gtcgttaagt cgtt                                          24


<210> SEQ ID NO 2
<211> LENGTH: 24
<212> TYPE: RNA
<213> ORGANISM: Artificial Sequence
<220> FEATURE:
<223> OTHER INFORMATION: synthetic construct

<400> SEQUENCE: 2

gggggacugc guucgcgcuu uccc                                          24
```

We claim:

1. A compound of formula (I) or pharmaceutically acceptable salt thereof:

(I)

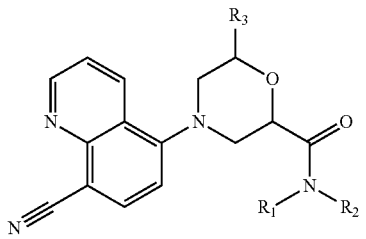

wherein at least one of $R_1$ and $R_2$ is [H] —*H*, methyl, or ethyl, and the other is —H; or the other is $C_1$-$C_6$ alkyl that is optionally substituted with:

—OH, methoxy, ethoxy, —$OCH(CH_3)_2$, —$O(CH_2)_2CH_3$, phenyl, furanyl, —$O(CH_2)_2OH$, phenoxy, methylthio, —F, —$N(CH_3)_2$, cyano, pyridinyloxy, fluorophenoxy, isochromanyl, phenol, benzylamino, —$NHCH_3$, oxo-, amino, carboxyl, 7-member spiroaminyl, a three to six member cycloalkyl, saturated or unsaturated and optionally including one or more heteroatoms selected from O and N, and optionally substituted at one or more C or N atoms by methyl, cyano, fluoro, methylamino, or trifluoromethyl; or the other is $C_3$-$C_7$ cycloalkane, saturated or unsaturated, optionally bridged, optionally including one or more heteroatoms selected from O, S, and N, and optionally substituted at one or more C or N atoms by methyl, ethyl, pyridinyl, azetidinyl, acetamidyl, carboxamidyl, cyano, fluoro, methylamino, or trifluoromethyl; or $R_1$ and $R_2$, together with the nitrogen atom to which they are attached, form an 8 to 11 member spirodiamine, an 8 member bicyclodiamine, a 7 member spiroxamine, a piperidinyl optionally substituted with ethyl, or a four to six member cycloalkyl, optionally substituted with at least one of carboxamidyl, aminomethyl, methyl, (ethylamino)methyl, (dimethylamino)methyl, dimethylamino, (methylamino)methyl, and amino; and wherein $R_3$ is —H or methyl.

2. The compound or pharmaceutically acceptable salt of claim 1, wherein said compound or salt has a stereochemical configuration selected from one of those shown in the group consisting of Formula (Ia), Formula (Ib), Formula (1c), and Formula (1d):

(Ia)

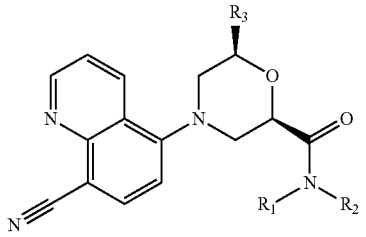

-continued (Ib)

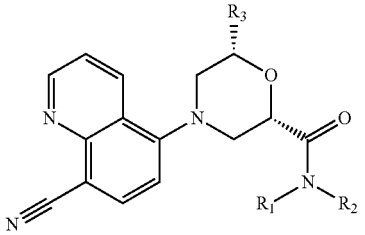

(Ic)

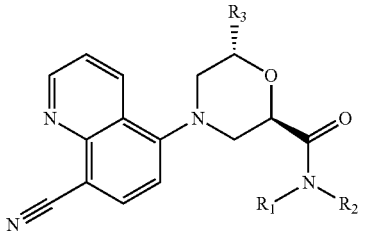

(Id)

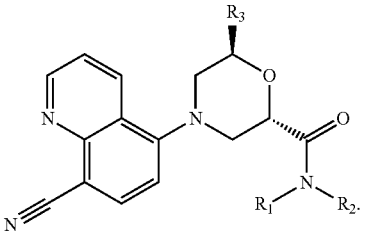

3. The compound or pharmaceutically acceptable salt of claim 1, wherein said compound or salt is selected from the group consisting of:

[5-((2R,6R)-2-formyl-6-methylmorpholino)quinoline-8-carbonitrile;]

(2R,6R)-4-(8-cyanoquinolin-5-yl)-N-ethyl-6-methylmorpholine-2-carboxamide;

(2R,6R)-4-(8-cyanoquinolin-5-yl)-N-isopropyl-6-methylmorpholine-2-carboxamide;

[5-((2R,6R)-2-formyl-6-methylmorpholino)quinoline-8-carbonitrile;

(2R,6R)-methyl 4-(8-cyanoquinolin-5-yl)-6-methylmorpholine-2-carboxylate;]

(6R)-4-(8-cyanoquinolin-5-yl)-6-methylmorpholine-2-carboxamide;

5-((2R,6R)-2((S)-3-ethylpiperazine-1-carbonyl)-6-methylmorpholino)quinoline-8-carbonitrile;

(2R,6R)-4-(8-cyanoquinolin-5-yl)-N-(3,4-difluorobenzyl)-6-methylmorpholine-2-carboxamide;

5-((2R,6R)-2-((S)-3-aminopyrrolidine-1-carbonyl)-6-methylmorpholino)quinoline-8-carbonitrile;

5-((2R,6R)-2-(azetidine-1-carbonyl)-6-methylmorpholino)quinoline-8-carbonitrile;

5-((2R,6R)-2-([1,4'-bipiperidine]-1'-carbonyl)-6-methylmorpholino)quinoline-8-carbonitrile;

(2R,6R)-4-(8-cyanoquinolin-5-yl)-N-cyclopropyl-6-methylmorpholine-2-carboxamide;

5-((2R,6R)-2-(3-aminoazetidine-1-carbonyl)-6-methylmorpholino)quinoline-8-carbonitrile;

(2R,6R)-4-(8-cyanoquinolin-5-yl)-N-(2-hydroxyethyl)-6-methylmorpholine-2-carboxamide;

(2R,6R)-4-(8-cyanoquinolin-5-yl)-N-(2-methoxyethyl)-6-methylmorpholine-2-carboxamide;

(2R,6R)-4-(8-cyanoquinolin-5-yl)-N-((R)-2-hydroxypropyl)-6-methylmorpholine-2-carboxamide;

(2R,6R)-4-(8-cyanoquinolin-5-yl)-N-((S)-1-hydroxypropan-2-yl)-6-methylmorpholine-2-carboxamide;

(2R,6R)-4-(8-cyanoquinolin-5-yl)-N-((R)-1-hydroxypropan-2-yl)-6-methylmorpholine-2-carboxamide;

(2R,6R)-4-(8-cyanoquinolin-5-yl)-N-((S)-1-hydroxybutan-2-yl)-6-methylmorpholine-2-carboxamide;

(2R,6R)-4-(8-cyanoquinolin-5-yl)-N-((S)-1-hydroxy-3-methylbutan-2-yl)-6-methylmorpholine-2-carboxamide;

(2R,6R)-4-(8-cyanoquinolin-5-yl)-N-((S)-2-hydroxy-1-phenylethyl)-6-methylmorpholine-2-carboxamide;

(2R,6R)-4-(8-cyanoquinolin-5-yl)-N-((R)-2-hydroxy-1-phenylethyl)-6-methylmorpholine-2-carboxamide;

(2R,6R)-4-(8-cyanoquinolin-5-yl)-N-(2-hydroxybutyl)-6-methylmorpholine-2-carboxamide;

(2R,6R)-4-(8-cyanoquinolin-5-yl)-N-(2-ethoxyethyl)-6-methylmorpholine-2-carboxamide;

(2R,6R)-4-(8-cyanoquinolin-5-yl)-N-((R)-1-hydroxybutan-2-yl)-6-methylmorpholine-2-carboxamide;

(2R,6R)-4-(8-cyanoquinolin-5-yl)-N-(1,3-dihydroxypropan-2-yl)-6-methylmorpholine-2-carboxamide;

(2R,6R)-4-(8-cyanoquinolin-5-yl)-N-(2,3-dihydroxypropyl)-6-methylmorpholine-2-carboxamide;

(2R,6R)-4-(8-cyanoquinolin-5-yl)-6-methyl-N-(((R)-tetrahydrofuran-2-yl)methyl)morpholine-2-carboxamide;

(2R,6R)-4-(8-cyanoquinolin-5-yl)-6-methyl-N-((tetrahydrofuran-2-yl)methyl)morpholine-2-carboxamide;

(2R,6R)-4-(8-cyanoquinolin-5-yl)-6-methyl-N-(2-propoxyethyl)morpholine-2-carboxamide;

(2R,6R)-4-(8-cyanoquinolin-5-yl)-N-((R)-1-hydroxypentan-2-yl)-6-methylmorpholine-2-carboxamide;

(2R,6R)-4-(8-cyanoquinolin-5-yl)-N-(2-isopropoxyethyl)-6-methylmorpholine-2-carboxamide;

(2R,6R)-4-(8-cyanoquinolin-5-yl)-N-(1-methoxybutan-2-yl)-6-methylmorpholine-2-carboxamide;

(2R,6R)-4-(8-cyanoquinolin-5-yl)-N-(2-(2-fluorophenyl)-2-hydroxyethyl)-6-methylmorpholine-2-carboxamide;

(2R,6R)-4-(8-cyanoquinolin-5-yl)-N-((R)-1-hydroxy-3-methylbutan-2-yl)-6-methylmorpholine-2-carboxamide;

(2R,6R)-4-(8-cyanoquinolin-5-yl)-N-(2,2-dimethoxyethyl)-6-methylmorpholine-2-carboxamide;

(2R,6R)-4-(8-cyanoquinolin-5-yl)-N-(2-(2-hydroxyethoxy)ethyl)-6-methylmorpholine-2-carboxamide;

(2R,6R)-4-(8-cyanoquinolin-5-yl)-N-((1S,2S)-2-hydroxycyclohexyl)-6-methylmorpholine-2-carboxamide;

(2R,6R)-4-(8-cyanoquinolin-5-yl)-N-(2-hydroxycyclohexyl)-6-methylmorpholine-2-carboxamide;

(2R,6R)-4-(8-cyanoquinolin-5-yl)-N-(1-hydroxyhexan-2-yl)-6-methylmorpholine-2-carboxamide;

(2R,6R)-4-(8-cyanoquinolin-5-yl)-N-((S)-1-hydroxy-3,3-dimethylbutan-2-yl)-6-methylmorpholine-2-carboxamide;

(2R,6R)-4-(8-cyanoquinolin-5-yl)-N-((S)-1-hydroxyhexan-2-yl)-6-methylmorpholine-2-carboxannide;

(2R,6R)-4-(8-cyanoquinolin-5-yl)-N-((2S,3S)-1-hydroxy-3-methylpentan-2-yl)-6-methylmorpholine-2-carboxamide;

(2R,6R)-4-(8-cyanoquinolin-5-yl)-N-((S)-1-hydroxy-4-methylpentan-2-yl)-6-methylmorpholine-2-carboxamide;

(2R,6R)-4-(8-cyanoquinolin-5-yl)-N-((R)-1-hydroxy-4-methylpentan-2-yl)-6-methylmorpholine-2-carboxamide;

(2R,6R)-4-(8-cyanoquinolin-5-yl)-6-methyl-N-((4-methylmorpholin-2-yl)methyl)morpholine-2-carboxamide;
(2R,6R)-4-(8-cyanoquinolin-5-yl)-N-((S)-1-hydroxy-4-(methylthio)butan-2-yl)-6-methylmorpholine-2-carboxamide;
(2R,6R)-4-(8-cyanoquinolin-5-yl)-6-methyl-N-(2-phenoxyethyl)morpholine-2-carboxamide;
(2R,6R)-4-(8-cyanoquinolin-5-yl)-N-((S)-1-hydroxy-3-phenylpropan-2-yl)-6-methylmorpholine-2-carboxamide;
(2R,6R)-4-(8-cyanoquinolin-5-yl)-6-methyl-N-(2-phenoxypropyl)morpholine-2-carboxamide;
(2R,6R)-4-(8-cyanoquinolin-5-yl)-N-(2-hydroxy-3-phenylpropyl)-6-methylmorpholine-2-carboxamide;
(2R,6R)-4-(8-cyanoquinolin-5-yl)-6-methyl-N-(2-(pyridin-3-yloxy)propyl)morpholine-2-carboxamide;
(2R,6R)-4-(8-cyanoquinolin-5-yl)-N-(2-(4-fluorophenoxy)ethyl)-6-methylmorpholine-2-carboxamide;
(2R,6R)-4-(8-cyanoquinolin-5-yl)-N-(2-(3-fluorophenyl)-2-hydroxyethyl)-6-methylmorpholine-2-carboxamide;
(2R,6R)-4-(8-cyanoquinolin-5-yl)-N-((S)-1-cyclohexyl-3-hydroxypropan-2-yl)-6-methylmorpholine-2-carboxamide;
(2R,6R)-4-(8-cyanoquinolin-5-yl)-N-(isochroman-1-ylmethyl)-6-methylmorpholine-2-carboxamide;
(2R,6R)-4-(8-cyanoquinolin-5-yl)-N-(2-hydroxy-3-phenoxypropyl)-6-methylmorpholine-2-carboxamide;
(2R,6R)-4-(8-cyanoquinolin-5-yl)-N-((1S,2R)-1-hydroxy-1-(4-hydroxyphenyl)propan-2-yl)-6-methylmorpholine-2- carboxamide;
(2R,6R)-4-(8-cyanoquinolin-5-yl)-N-((1S)-1,3-dihydroxy-1-phenylpropan-2-yl)-6-methylmorpholine-2-carboxamide,
(2R,6R)-4-(8-cyanoquinolin-5-yl)-N-(2-hydroxy-3-(piperazin-1-yl)propyl)-6-methylmorpholine-2-carboxamide;
(2R,6R)-N-(azetidin-3-yl)-4-(8-cyanoquinolin-5-yl)-6-methylmorpholine-2-carboxamide;
(2R,6R)-4-(8-cyanoquinolin-5-yl)-6-methyl-N-((S)-pyrrolidin-3-yl)morpholine-2-carboxamide;
(2R,6R)-4-(8-cyanoquinolin-5-yl)-6-methyl-N-((R)-pyrrolidin-3-yl)morpholine-2-carboxamide;
(2R,6R)-4-(8-cyanoquinolin-5-yl)-6-methyl-N-((S)-piperidin-3-yl)morpholine-2-carboxamide;
(2R,6R)-4-(8-cyanoquinolin-5-yl)-6-methyl-N-((R)-piperidin-3-yl)morpholine-2-carboxamide;
(2R,6R)-4-(8-cyanoquinolin-5-yl)-6-methyl-N-((S)-pyrrolidin-2-ylmethyl)morpholine-2-carboxamide;
(2R,6R)-N-(2-(benzylamino)ethyl)-4-(8-cyanoquinolin-5-yl)-6-methylmorpholine-2-carboxamide;
(2R,6R)-4-(8-cyanoquinolin-5-yl)-6-methyl-N-(pyridin-2-yl)morpholine-2-carboxamide;
(2R,6R)-4-(8-cyanoquinolin-5-yl)-6-methyl-N-(6-methylpyridin-2-yl)morpholine-2-carboxamide;
(2R,6R)-4-(8-cyanoquinolin-5-yl)-6-methyl-N-(5-methylisoxazol-3-morpholine-2-carboxamide;
(2R,6R)-4-(8-cyanoquinolin-5-yl)-6-methyl-N-(2,2,2-trifluoroethyl)morpholine-2-carboxamide;
(2R,6R)-4-(8-cyanoquinolin-5-yl)-N-(2,2-difluoroethyl)-6-methylmorpholine-2-carboxamide;
(2R,6R)-4-(8-cyanoquinolin-5-yl)-6-methyl-N-(3,3,3-trifluoropropyl)morpholine-2-carboxamide;
(2R,6R)-4-(8-cyanoquinolin-5-yl)-N-(2-(dimethylamino)-2-methylpropyl)-6-methylmorpholine-2-carboxamide;
(2R,6R)-4-(8-cyanoquinolin-5-yl)-6-methyl-N-((S)-morpholin-2-ylmethyl)morpholine-2-carboxamide hydrochloride;
(2R,6R)-4-(8-cyanoquinolin-5-yl)-6-methyl-N-(((S)-4-methylmorpholin-2-yl)methyl)morpholine-2-carboxamide acetic acetate;
(2R,6R)-4-(8-cyanoquinolin-5-yl)-N-(2-fluoroethyl)-6-methylmorpholine-2-carboxamide;
(2R,6R)-4-(8-cyanoquinolin-5-yl)-N-(3-fluoropropyl)-6-methylmorpholine-2-carboxamide;
(2R,6R)-4-(8-cyanoquinolin-5-yl)-6-methyl-N-((S)-1,1,1-trifluoropropan-2-yl)morpholine-2-carboxamide;
(2R,6R)-4-(8-cyanoquinolin-5-yl)-6-methyl-N-((R)-1,1,1-trifluoropropan-2-yl)morpholine-2-carboxamide;
(2R,6R)-4-(8-cyanoquinolin-5-yl)-N-(1,3-dimethyl-1H-pyrazol-5-yl)-6-methylmorpholine-2-carboxamide;
(2R,6R)-4-(8-cyanoquinolin-5-yl)-6-methyl-N-(1-methyl-1H-pyrazol-5-yl)morpholine-2-carboxamide;
(2R,6R)-N-(cyanomethyl)-4-(8-cyanoquinolin-5-yl)-6-methylmorpholine-2-carboxamide;
(2R,6R)-N-(1-cyanocyclopropyl)-4-(8-cyanoquinolin-5-yl)-6-methylmorpholine-2-carboxamide;
(2R,6R)-4-(8-cyanoquinolin-5-yl)-6-methyl-N-(1,2,4-thiadiazol-5-yl)morpholine-2-carboxamide;
(2R,6R)-4-(8-cyanoquinolin-5-yl)-6-methyl-N-(3-methyl-1,2,4-thiadiazol-5-yl)morpholine-2-carboxamide;
(2R,6R)-4-(8-cyanoquinolin-5-yl)-6-methyl-N-(piperidin-4-yl)morpholine-2-carboxamide;
5-((2R,6R)-2-methyl-6-(2,6-diazaspiro[3.4]octane-2-carbonyl)morpholino)quinoline-8-carbonitrile hydrochloride;
5-((2R,6R)-2-methyl-6-(3-((methylamino)methyl)azetidine-1-carbonyl)morpholino)quinoline-8-carbonitrile hydrochloride;
(2R,6R)-4-(8-cyanoquinolin-5-yl)-N-((4-fluoropiperidin-4-yl)methyl)-6-methylmorpholine-2-carboxamide hydrochloride;
(2R,6R)-N-(azetidin-3-ylmethyl)-4-(8-cyanoquinolin-5-yl)-6-methylmorpholine-2-carboxamide hydrochloride;
5-((2R,6R)-2-methyl-6-(2,6-diazaspiro[3.5]nonane-2-carbonyl)morpholino) quinoline-8-carbonitrile hydrochloride;
5-((2R,6R)-2-methyl-6-(1,6-diazaspiro[3.4]octane-1-carbonyl)morpholino) quinoline-8-carbonitrile hydrochloride;
5-((2R,6R)-2-methyl-6-(1,7-diazaspiro[4.4]nonane-7-carbonyl)morpholino quinoline-8-carbonitrile hydrochloride;
(2R,6R)-N-(3-carbamoyl-1-methyl-1H-pyrazol-4-yl)-4-(8-cyanoquinolin-5-yl)-6-methylmorpholine-2-carboxamide;
(2R,6R)-4-(8-cyanoquinolin-5-yl)-6-methyl-N-(oxetan-3-ylmethyl)morpholine-2-carboxamide;
(2R,6R)-4-(8-cyanoquinolin-5-yl)-6-methyl-N-(tetrahydro-2H-pyran-4-yl)morpholine-2-carboxamide;
(2R,6R)-4-(8-cyanoquinolin-5-yl)-6-methyl-N-(tetrahydrofuran-3-yl)morpholine-2-carboxamide;
(2R,6R)-4-(8-cyanoquinolin-5-yl)-6-methyl-N-((3-methyloxetan-3-yl)methyl)morpholine-2-carboxamide;
5-((2R,6R)-2-methyl-6-(2-oxa-6-azaspiro[3.3]heptane-6-carbonyl)morpholino) quinoline-8-carbonitrile;
(2R,6R)-4-(8-cyanoquinolin-5-yl)-6-methyl-N-(oxetan-3-yl)morpholine-2-carboxamide;

(2R,6R)-N-((3-(aminomethyl)oxetan-3-yl)methyl)-4-(8-cyanoquinolin-5-yl)-6-methylmorpholine-2-carboxamide;

(2R,6R)-4-(8-cyanoquinolin-5-yl)-6-methyl-N-(oxetan-2-ylmethyl)morpholine-2-carboxamide;

5-((2R,6R)-2-methyl-6-(piperazine-1carbonyl)morpholino)quinoline-8-carbonitrile hydrochloride;

(2R,6R)-4-(8-cyanoquinolin-5-yl)-6-methyl-N-(2-(methylamino)ethyl)morpholine-2-carboxamide;

(2R,6R)-4-(8-cyanoquinolin-5-yl)-6-methyl-N-((S)-3,3,3-trifluoro-2-hydroxypropyl) morpholine-2-carboxamide;

(2R,6R)-4-(8-cyanoquinolin-5-yl)-6-methyl-N-((R)-3,3,3-trifluoro-2-hydroxypropyl) morpholine-2-carboxamide;

Methyl 2-((2R,6R)-4-(8-cyanoquinolin-5-yl)-6-methylmorpholine-2-carboxamido) acetate;

(2R,6R)-4-(8-cyanoquinolin-5-yl)-N-(2-(dimethylamino)ethyl)-6-methylmorpholine-2-carboxamide;

(2R,6R)-4-(8-cyanoquinolin-5-yl)-6-methyl-N-((S)-4,4,4-trifluoro-3-hydroxybutyl) morpholine-2-carboxamide;

(2R,6R)-4-(8-cyanoquinolin-5-yl)-6-methyl-N-((R)-4,4,4-trifluoro-3-hydroxybutyl) morpholine-2-carboxamide;

(2R,6R)-N-(3-amino-4,4,4-trifluorobutyl)-4-(8-cyanoquinolin-5-yl)-6-methyl morpholine-2-carboxamide;

2-((2R,6R)-4-(8-cyanoquinolin-5-yl)-6-methylmorpholine-2-carboxamido)acetic acid;

1-((2R,6R)-4-(8-cyanoquinolin-5-yl)-6-methylmorpholine-2-carbonyl)azetidine-3-carboxamide;

5-((2R,6R)-2-methyl-6-(2,7-diazaspiro[4.4]nonane-2-carbonyl)morpholino) quinoline-8-carbonitrile hydrochloride;

5-((2R,6R)-2-methyl-6-(3,9-diazaspiro[5.5]undecane-3-carbonyl)morpholino) quinoline-8-carbonitrile hydrochloride;

(2R,6R)-N-(3-carbamoylpyridin-4-yl)-4-(8-cyanoquinolin-5-yl)-6-methyl morpholine-2-carboxamide;

(2R,6R)-4-(8-cyanoquinolin-5-yl)-6-methyl-N-((R)-morpholin-2-ylmethyl) morpholine-2-carboxamide;

(2R,6R)-4-(8-cyanoquinolin-5-yl)-6-methyl-N-(pyridin-4-yl)morpholine-2-carboxamide;

(2R,6R)-4-(8-cyanoquinolin-5-yl)-6-methyl-N-(pyridin-3-yl)morpholine-2-carboxamide;

(2R,6R)-4-(8-cyanoquinolin-5-yl)-6-methyl-N-(1-(piperidin-4-yl)-1H-pyrazol-4-yl)morpholine-2-carboxamide hydrochloride;

(2R,6R)-N-(1-(azetidin-3-yl)-1H-pyrazol-4-yl)-4-(8-cyanoquinolin-5-yl)-6-methylmorpholine-2-carboxamide hydrochloride;

(2R,6R)-N-((1H-pyrazol-5-yl)methyl)-4-(8-cyanoquinolin-5-yl)-6-methyl morpholine-2-carboxamide;

(2R,6R)-N-((1H-pyrazol-4-yl)methyl)-4-(8-cyanoquinolin-5-yl)-6-methyl morpholine-2-carboxamide;

(2R,6R)-4-(8-cyanoquinolin-5-yl)-6-methyl-N-((3-(trifluoromethyl)pyridin-2-yl)methyl)morpholine-2-carboxamide;

(2R,6R)-4-(8-cyanoquinolin-5-yl)-6-methyl-N-(1-(pyridin-2-yl)ethyl)morpholine-2-carboxamide;

(2R,6R)-4-(8-cyanoquinolin-5-yl)-6-methyl-N-(pyridin-2-ylmethyl)morpholine-2-carboxamide;

(2R,6R)-4-(8-cyanoquinolin-5-yl)-6-methyl-N-((6-methylpyridin-2-yl)methyl) morpholine-2-carboxamide;

(2R,6R)-4-(8-cyanoquinolin-5-yl)-6-methyl-N-((1-methylpiperidin-2-yl)methyl) morpholine-2-carboxamide;

(2R,6R)-4-(8-cyanoquinolin-5-yl)-6-methyl-N-((3-methylpyridin-2-yl)methyl) morpholine-2-carboxamide;

(2R,6R)-N-(4-cyano-1H-pyrazol-3-yl)-4-(8-cyanoquinolin-5-yl)-6-methyl morpholine-2-carboxamide;

(2R,6R)-4-(8-cyanoquinolin-5-yl)-N-((3S,4R)-4-fluoro-1-methylpyrrolidin-3-yl)-6-methylmorpholine-2-carboxamide;

(2R,6R)-4-(8-cyanoquinolin-5-yl)-N-((3S,4R)-4-fluoropiperidin-3-yl)-N,6-dimethylmorpholine-2-carboxamide hydrochloride;

5-((2R,6R)-2-(3-(aminomethyl)azetidine-1-carbonyl)-6-methylmorpholino) quinoline-8-carbonitrile;

5-((2R,6R)-2-(3-((ethylamino)methyl)azetidine-1-carbonyl)-6-methylmorpholino) quinoline-8-carbonitrile;

5-((2R,6R)-2-(3-((dimethylamino)methyl)azetidine-1-carbonyl)-6-methyl morpholino)quinoline-8-carbonitrile;

(2R,6R)-4-(8-cyanoquinolin-5-yl)-6-methyl-N-(1-methylazepan-4-yl)morpholine-2-carboxamide;

(2R,6R)-4-(8-cyanoquinolin-5-yl)-6-methyl-N-(((2R,6R)-6-methylmorpholin-2-yl)methyl)morpholine-2-carboxamide;

5-((2R,6R)-2-methyl-6-(octahydropyrrolo[3,4-c]pyrrole-2-carbonyl)morpholino) quinoline-8-carbonitrile;

(2R,6R)-4-(8-cyanoquinolin-5-yl)-6-methyl-N-((R)-pyrrolidin-2-ylmethyl) morpholine-2-carboxamide hydrochloride;

(2R,6R)-4-(8-cyanoquinolin-5-yl)-6-methyl-N-((S)-piperidin-2-ylmethyl) morpholine-2-carboxamide hydrochloride;

(2R,6R)-N-((1R,3R,5S)-8-azabicyclo[3.2.1]octan-3-yl)-4-(8-cyanoquinolin-5-yl)-6-methylmorpholine-2-carboxamide hydrochloride;

(2R,6R)-N-(azepan-4-yl)-4-(8-cyanoquinolin-5-yl)-6-methylmorpholine-2-carboxamide hydrochloride;

(2R,6R)-N-((1R,5S,6S)-3-azabicyclo[3.1.0]hexan-6-yl)-4-(8-cyanoquinolin-5-yl)-6-methylmorpholine-2-carboxamide hydrochloride;

(2R,6R)-4-(8-cyanoquinolin-5-yl)-N-6-dimethylmorpholine-2-carboxamide;

(2R,6R)-4-(8-cyanoquinolin-5-yl)-N-(((2S,6R)-4,6-dimethylmorpholin-2-yl)methyl)-6-methylmorpholine-2-carboxamide;

5-((2R,6R)-2-(4-(dimethylamino)piperidine-1-carbonyl)-6-methylmorpholino) quinoline-8-carbonitrile;

(2R,6R)-4-(8-cyanoquinolin-5-yl)-6-methyl-N-(1-methylpiperidin-4-yl)morpholine-2-carboxamide;

(2R,6R)-4-(8-cyanoquinolin-5-yl)-N-((3S,4R)-4-fluoropyrrolidin-3-yl)-6-methyl morpholine-2-carboxamide hydrochloride;

(2R,6R)-4-(8-cyanoquinolin-5-yl)-N-((3S, 4R)-4-fluoropiperidin-3-yl)-6-methyl morpholine-2-carboxamide hydrochloride;

(2R,6R)-4-(8-cyanoquinolin-5-yl)-6-methyl-N-(2-azaspiro[3.3]heptan-6-yl)morpholine-2-carboxamide hydrochloride;

(2R,6R)-N-(1-(2-amino-2-oxoethyl)piperidin-4-yl)-4-(8-cyanoquinolin-5-yl)-6-methylmorpholine-2-carboxarnide;

5-((2R,6R)-2-(4-aminopiperidine-1-carbonyl)-6-methylmorpholino)quinoline-8-carbonitrile;

5-((2R,6R)-2-(4-amino-4-methylpiperidine-1carbonyl)-6-methylmorpholino) quinoline-8-carbonitrile;

(2R,6R)-4-(8-cyanoquinolin-5-yl)-N,6-dimethyl-N-((R)-piperidin-3-yl)morpholine-2-carboxamide hydrochloride;

(2R,6R)-N-(2-carbamoylpyridin-4-yl)-4-(8-cyanoquinolin-5-yl)-6-methylmorpholine-2-carboxamide hydrochloride;

(2R,6R)-4-(8-cyanoquinolin-5-yl)-N-6-dimethyl-N-((S)-piperidin-3-yl)morpholine-2-carboxamide hydrochloride;

(2R,6R)-4-(8-cyanoquinolin-5-yl)-N-(1-ethylpiperidin-4-yl)-6-methylmorpholine-2-carboxamide;

(2R,6R)-4-(8-cyanoquinolin-5-yl)-N-(1-ethylpiperidin-3-yl)-6-methylmorpholine-2-carboxamide;

(2R,6R)-4-(8-cyanoquinolin-5-yl)-6-methyl-N-((R)-1-methylpiperidin-3-yl)morpholine-2-carboxamide hydrochloride;

(2R,6R)-4-(8-cyanoquinolin-5-yl)-6-methyl-N-(4-methylpiperidin-4-yl)morpholine-2-carboxamide;

(2R,6R)-N-(2-amino-2-methylpropyl)-4-(8-cyanoquinolin-5-yl)-6-methyl morpholine-2-carboxamide;

rel-(2R,6R)-4-(8-cyanoquinolin-5-yl)-N-((3R,4S)-4-fluoropyrrolidin-3-yl)-6-methylmorpholine-2-carboxamide hydrochloride;

rel-(2R,6R)-4-(8-cyanoquinolin-5-yl)-N-((3S,4R)-4-fluoropyrrolidin-3-yl)-6-methylmorpholine-2-carboxamide hydrochloride;

(2R,6R)-N-(azepan-3-yl)-4-(8-cyanoquinolin-5-yl)-6-methylmorpholine-2-carboxamide hydrochloride;

(2R,6R)-4-(8-cyanoquinolin-5-yl)-6-methyl-N-(1-methylazepan-3-yl)morpholine-2-carboxamide hydrochloride;

(2R,6R)-4-(8-cyanoquinolin-5-yl)-N-(1,4-dimethylpiperidin-4-yl)-6-methylmorpholine-2-carboxamide; and (2R,6R)-4-(8-cyanoquinolin-5-yl)-N-(4-fluoro-l-methylpiperidin-3-yl)-6-methylmorpholine-2-carboxamide hydrochloride.

4. The compound or pharmaceutically acceptable salt of claim 3, wherein said compound or salt is selected from the group consisting of rel-(2R,6R)-4-(8-cyanoquinolin-5-yl)-N-((3R,4S)-4-fluoropyrrolidin-3-yl)-6-methylmorpholine-2-carboxamide hydrochloride and (2R,6R)-4-(8-cyanoquinolin-5-yl)-6-methyl-N-(1-methylpiperidin-4-yl) morpholine-2-carboxamide.

5. A compound of [Formula (1e)] *the following formula* or pharmaceutically acceptable salt thereof[, with relative stereochemistry indicated]:

[

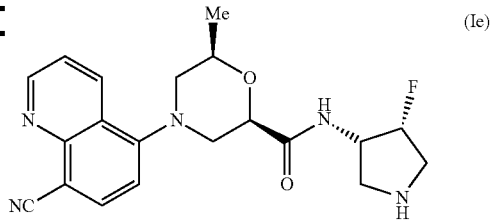

(Ie)

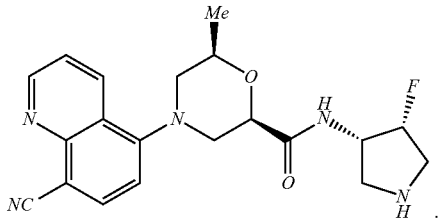

].

6. A compound of Formula (II) or pharmaceutically acceptable salt thereof:

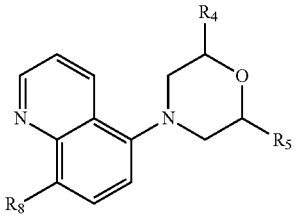

(II)

wherein $R_4$ is methyl;

$R_5$ is $C_1$-$C_5$ alkyl that is saturated, [partially saturated,] or unsaturated, and that is optionally substituted with:

—H, [—cl] —*Cl*, —F, —OH, —$NH_2$, oxo-, —$N(CH_2CH_3)_2$, phenyl, cyclohexyl, phenyltriazolyl, cyclohexyltriazolyl, pyridinyl, pyrrolidinyl, morpholinyl optionally substituted with methyl or hydroxymethyl, —O—, substituted with:

$C_1$-$C_6$ alkyl, methylphenyl, methylcyclohexyl, pyridinyl, diazinyl, or phenyl optionally substituted with —F or methyl, —NH—, substituted with:

$C_2$-$C_7$ alkyl that is linear, branched, or cyclic, saturated or unsaturated, and optionally substituted with oxo-, phenyl, methyl, or —OH, pyridinyl optionally substituted with methyl, methoxy, phenyl, or amino, diazinyl optionally substituted with ethyl, benzoimidazolyl, methylphenyl, phenylpyrazolyl, naphthyridyl, phenyl optionally substituted with —F, methyl, ethyl, or ethoxy, imidazolidinyl optionally substituted with methyl or $R_5$ is

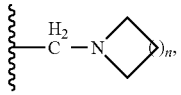

wherein n is 1-3, and wherein the cyclic amine is optionally substituted with $C_1$-$C_3$ alkyl optionally substituted with —OH, —F, phenyl, —$NH_2$, cyclohexyl, —$N(CH_3)_2$, [—c(O)$NH_2$] —*C(O)NH*$_2$, methylsulfonamidyl, benzenesulfonamidyl, methylbenzenesulfonamidyl, or pyrrolidinyl optionally substituted with methyl or hydroxyl, or —NHC(O)$R_6$, wherein $R_6$ is $C_1$-$C_5$ alkyl, phenyl, pyridinyl, fluorophenyl, methylsulfonyl, fluorobenzenesulfonyl, dimethyl pyrazole sulfonyl, or pyrazolyl optionally substituted with methyl;

piperidinyl optionally substituted with —C(O)$CH_3$, —C(O)$CH_2CH_3$, methyl, oxo-, C(O)Ph, —$NH_2$, —NH—C(O)$CH_3$, or

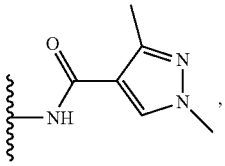

piperazinyl optionally substituted with —C(O)OC$(CH_3)_3$, methyl, —C(O)$CH_3$, —C(O)Ph, C(O)CH$(CH_3)_2$, —C(O)$CH_3$, or methylsulfonyl; or $R_5$ is

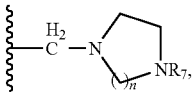

where n is 1 or 2, and wherein the cyclic diamine is optionally substituted on at least one carbon atom with methyl, oxo-, —N$(CH_3)_2$, amino, —$CH_2CH_3$, or piperidinyl optionally substituted with methyl, —C(O)$CH_3$, —C(O)CH$(CH_3)_2$, —C(O)Ph, or —C(O)OC$(CH_3)_3$, and wherein $R_7$ is —H, phenyl, —C(O)$CH_3$, $C_1$-$C_3$ alkyl, —C(O)$NH_2$, or —C(O)Ph; and $R_8$ is methoxy or cyano.

7. The compound or pharmaceutically acceptable salt of claim 6, wherein said compound or salt is selected from the group consisting of:

5-((2R,6S)-2,6-dimethylmorpholino)quinoline-8-carbonitrile;

(*2R,6R*)-*methyl 4-(8-cyanoquinolin-5-yl)-6-methylmorpholine-2-carboxylate;*

5-((2R,6S)-2,6-dimethylmorpholino)quinoline-8-carbonitrile dihydrochloride;

5-((2R,6S)-2,6-dimethylmorpholino)quinoline-8-carbonitrile methanesulfonate;

5-((2R,6S)-2,6-dimethylmorpholino)quinoline-8-carbonitrile bis(2,2,2-trifluoro-acetate);

5-((2R,6S)-2,6-dimethylmorpholino)quinoline-8-carbonitrile bis(sulfonate);

5-((2R,6S)-2,6-dimethylmorpholino)quinoline-8-carbonitrile sulfonate;

5-((2S,6R)-2,6-dimethylmorpholino)quinoline-8-carbonitrile 2,3-dihydroxy-succinate;

5-((2S,6R)-2,6-dimethylmorpholino)quinoline-8-carbonitrile dimethanesulfonate;

N-(((2S,6R)-4-(8-cyanoquinolin-5-yl)-6-[methylniorpholin]*methylmorpholin*-2-yl)[methy]*methyl* )acetamide;

N-(((2S,6R)-4-(8-cyanoquinolin-5-yl)-6-methylmorpholin-2-yl)methyl)pivalamide;

5-((2S,6S)-2,6-dimethylmorpholino)quinoline-8-carbonitrile;

5-((2S,6R)-2-(aminomethyl)-6-methylmorpholino)quinoline-8-carbonitrile;

5-(2-(hydroxymethyl)-6-methylmorpholino)quinoline-8-carbonitrile;

(2R,6S)-4-(8-methoxyquinolin-5-yl)-2,6-dimethylmorpholine;

5-((2R,6S)-2,6-dimethylmorpholino)quinoline-8-carboxamide;

5-((2R,6R)-2-(hydroxymethyl)-6-methylmorpholino)quinoline-8-carbonitrile;

5-((2R,6R)-2-(methoxymethyl)-6-methylmorpholino)quinoline-8-carbonitrile;

5-((2R,6R)-2-((benzyloxy)methyl)-6-methylmorpholino)quinoline-8-carbonitrile;

5-((2R,6R)-2-(fluoromethyl)-6-methylmorpholino)quinoline-8-carbonitrile;

5-((2R,6R)-2-(ethoxymethyl)-6-methylmorpholino)quinoline-8-carbonitrile;

5-((2R,6R)-2-(isopropoxymethyl)-6-methylmorpholino)quinoline-8-carbonitrile;

5-((2R,6R)-2-(isobutoxymethyl)-6-methylmorpholino)quinoline-8- carbonitrile, 5-((2R,6R)-2-(chloromethyl)-6-methylmorpholino)quinoline-8-carbonitrile;

5-((2R,6R)-2-((hexyloxy)methyl)-6-methylmorpholino)quinoline-8-carbonitrile;

5-((2R,6R)-2-((cyclohexylmethoxy)methyl)-6-methylmorpholino)quinoline-8-carbonitrile;

5-((2R,6S)-2-methyl-6-propylmorpholino)quinoline-8-carbonitrile;

5-((2S,6S)-2-(fluoromethyl)-6-methylmorpholino)quinoline-8-carbonitrile;

5-((2S,6S)-2-(chloromethyl)-6-methylmorpholino)quinoline-8-carbonitrile;

5-((2R,6R)-2-((2,6-dimethylphenoxy)methyl)-6-methylmorpholino)quinoline-8-carbonitrile;

[5-((2R,6S)-2,6-diethylmorpholino)quinoline-8-carbonitrile;]

5-((2R,6S)-2-methyl-6-pentylmorpholino)quinoline-8-carbonitrile;

5-((2R,6R)-2-formyl-6-methylmorpholino)quinoline-8-carbonitrile;

[5-((2R,6R)-2-((benzyloxy)methyl)-6-ethylmorpholino)quinoline-8-carbonitrile;]

N-(((2S,6R)-4-(8-cyanoquinolin-5-yl)-6-methylmorpholin-2-yl)methyl)-2-phenylpropanamide;

5-((2R,6R)-2-(1-hydroxyallyl)-6-methylmorpholino)quinoline-8-carbonitrile;

5-((2R,6R)-2-((S)-1-hydroxyallyl)-6-[nnethylmorpholino]*methylmorpholino*)quinoline-8-carbonitrile;

N-(((2S,6R)-4-(8-cyanoquinolin-5-yl)-6-methylmorpholin-2-yl)methyl)-1-phenylcyclobutanecarboxamide;

5-((2R,6R)-2-((R)-1-hydroxyallyl)-6-methylmorpholino)quinoline-8-carbonitrile;

5-((2R,6S)-2-methyl-6-(pyrrolidin-1-ylmethyl)morpholino)quinoline-8-carbonitrile;

5-((2S,6R)-2-((diethylamino)methyl)-6-methylmorpholino)quinoline-8-carbonitrile;

5-((2S,6R)-2-((benzylamino)methyl)-6-methylmorpholino)quinoline-8-carbonitrile;

5-((2R,6R)-2-methyl-6-(phenoxymethyl)morpholino)quinoline-8-carbonitrile;

5-((2R,6R)-2-methyl-6-((m-tolyloxy)methyl)morpholino)quinoline-8-carbonitrile;

5-((2R,6R)-2-methyl-6-((p-tolyloxy)methyl)morpholino)quinoline-8-carbonitrile;

5-((2R,6R)-2-(1-hydroxypropyl)-6-methylmorpholino)quinoline-8-carbonitrile;

5-((2R,6R)-2-((R)-1-hydroxypentyl)-6-methylmorpholino)quinoline-8-carbonitrile;

5-((2R,6R)-2-((S)-1-hydroxypentyl)-6-methylmorpholino)quinoline-8-carbonitrile;

5-((2R,6R)-2-((R)-cyclohexyl(hydroxy)methyl)-6-methylmorpholino)quinoline-8-carbonitrile;

5-((2R,6R)-2-((S)-cyclohexyl(hydroxy)methyl)-6-methylmorpholino)quinoline-8-carbonitrile;

N-(((2S,6R)-4-(8-cyanoquinolin-5-yl)-6-methylmorpholin-2-yl)methyl)-2-phenylacetamide;
5-((2R,6R)-2-((R)-1-hydroxy-2-phenylethyl)-6-methylmorpholino)quinoline-8-carbonitrile;
5-((2R,6R)-2-((S)-1-hydroxy-2-phenylethyl)-6-methylmorpholino)quinoline-8-carbonitrile;
5-((2R,6R)-2-((R)-1-hydroxy-3-phenylpropyl)-6-methylmorpholino)quinoline-8-carbonitrile;
5-((2R,6R)-2-((S)-1-hydroxy-3-phenylpropyl)-6-nnethylmorpholino)quinoline-8-carbonitrile;
5-((2R,6S)-2-methyl-6-((phenylamino)methyl)morpholino)quinoline-8-carbonitrile;
5-((2R,6S)-2-methyl-6-((m-tolylamino)methyl)morpholino)quinoline-8-carbonitrile;
5-((2R,6S)-2-methyl-6-((o-tolylamino)methyl)morpholino)quinoline-8-carbonitrile;
5-((2R,6S)-2-methyl-6-((p-tolylamino)methyl)morpholino)quinoline-8-carbonitrile;
5-((2R,6R)-2-((3,4-difluorophenoxy)nnethyl)-6-methylmorpholino)quinoline-8-carbonitrile;
5-((2R,6R)-2-((3-fluorophenoxy)methyl)-6-methylmorpholino)quinoline-8-carbonitrile;
5-((2S,6R)-2-(((1,2-dimethyl-1H-benzo[d]imidazol-5-yl)amino)methyl)-6-methylmorpholino)quinoline-8-carbonitrile;
5-((2S,6R)-2-(((1-ethyl-2-methyl-1H-benzo[d]imidazol-5-yl)amino)methyl)-6-methylmorpholino)quinoline-8-carbonitrile;
5-((2S,6R)-2-((cyclohexylamino)methyl)-6methylmorpholino)quinoline-8-carbonitrile;
5-((2R,6R)-2-((2-fluorophenoxy)methyl)-6-methylmorpholino)quinoline-8-carbonitrile;
5-((2R,6R)-2-methyl-6-propionylmorpholino)quinoline-8-carbonitrile;
5-((2R,6R)-2-(cyclohexanecarbonyl)-6-methylmorpholino)quinoline-8-carbonitrile;
5-((2R,6R)-2-methyl-6-(3-phenylpropanoyl)morpholino) quinoline-8-carbonitrile;
5-((2R,6R)-2-methyl-6-((o-tolyloxy)methyl)morpholino) quinoline-8-carbonitrile;
5-((2R,6S)-2-methyl-6-((pyrimidin-2-ylamino)methyl) morpholino)quinoline-8-carbonitrile;
5-((2R,6S)-2-methyl-6-((pyridin-2-ylamino)methyl)morpholino)quinoline-8-carbonitrile;
5-((2R,6S)-2-methyl-6-(((6-methylpyridin-2-yl)amino) methyl)morpholino) quinoline-8-carbonitrile;
5-((2R,6S)-2-methyl-6-(((5-methylpyridin-2-yl)amino) methyl)morpholino) quinoline-8-carbonitrile;
5-((2S,6R)-2-(((R)-2-(hydroxymethyl)pyrrolidin-1-yl) methyl)-6-methylmorpholino) quinoline-8-carbonitrile;
5-((2R,6R)-2((2,2-dimethylpyrrolidin-1-yl)methyl)-6-methylmorpholino)quinoline-8-carbonitrile;
5-((2S,6R)-2-((2-isopropylpyrrolidin-1-yl)methyl)-6-methylmorpholino)quinoline-8-carbonitrile;
5-((2R,6S)-2-methyl-6-(((S)-2-methylpyrrolidin-1-yl) methyl)morpholino)quinoline-8-carbonitrile;
5-((2R,6S)-2-methyl-6-(((S)-3-phenylpyrrolidin-1-yl) methyl)morpholino)quinoline-8-carbonitrile,
5-((2R,6S)-2-methyl-6-(((R)-3-methylpyrrolidin-1-yl) methyl)morpholino)quinoline-8-carbonitrile;
5-((2S,6R)-2-(((S)-3-hydroxypyrrolidin-1-yl)methyl)-6-methylmorpholino) quinoline-8-carbonitrile;
5-((2R,6S)-2-methyl-6-(((4-methylpyridin-2-yl)amino) methyl)morpholino) quinoline-8-carbonitrile;
5-((2R,6S)-2-methyl-6-((3-phenylpyrrolidin-1-yl) methyl)morpholino)quinoline-8-carbonitrile;
5-((2S,6R)-2-(((6-methoxypyridin-3-yl)amino)methyl)-6-methylmorpholino) quinoline-8-carbonitrile;
5-((2R,6S)-2-methyl-6-(((R)-2-methylpyrrolidin-1-yl) methyl)morpholino)quinoline-8-carbonitrile;
5-((2S,6R)-2-((2,5-dimethylpyrrolidin-1-yl)methyl)-6-methylmorpholino)quinoline-8-carbonitrile;
5-((2S,6R)-2-(((4-methoxypyridin-2-yl)amino)methyl)-6-methylmorpholino) quinoline-8-carbonitrile;
5-((2S,6R)-2-(((6-methoxypyridin-2-yl)amino)methyl)-6-methylmorpholino) quinoline-8-carbonitrile;
5-((2R,6S)-2-methyl-6-(((1-phenyl-1H-pyrazol-5-yl) amino)methyl)morpholino) quinoline-8-carbonitrile;
5-((2S,6R)-2-(((S)-2-(hydroxymethyl)pyrrolidin-1-yl) methyl)-6-methylmorpholino) quinoline-8-carbonitrile;
5-((2S,6R)-2-(((R)-3-hydroxypyrrolidin-1-yl)methyl)-6-methylmorpholino) quinoline-8-carbonitrile;
5-((2R,6S)-2-methyl-6-(((S)-3-methylpyrrolidin-1-yl) methyl)morpholino)quinoline-8-carbonitrile;
5-((2S,6R)-2-((3,3-dimethylpyrrolidin-1-yl)methyl)-6-methylmorpholino)quinoline-8-carbonitrile;
5-((2R,6R)-2-methyl-6-((R)-3-phenyl-1-(pyrrolidin-1-yl) propyl)morpholino) quinoline-8-carbonitrile;
5-((2R,6R)-2-methyl-6-((S)-3-phenyl-1-(pyrrolidin-1-yl) propyl)morpholino) quinoline-8-carbonitrile;
5-((2S,6R)-2-(((3-methoxypyridin-2-yl)amino)methyl)-6-methylmorpholino) quinoline-8-carbonitrile;
5-((2S,6R)-2-(((R)-3-hydroxypiperidin-1-yl)methyl)-6-methylmorpholino)quinoline-8-carbonitrile,
5-((2S,6R)-2-(((2R,6S)-2,6-dimethylpiperidin-1-yl) methyl)-6-methylmorpholino) quinoline-8-carbonitrile;
5-((2S,6R)-2-(((S)-3-hydroxypiperidin-1-yl)methyl)-6-methylmorpholino)quinoline-8-carbonitrile;
5-((2S,6R)-2-((4-hydroxypiperidin-1-yl)methyl)-6-methylmorpholino)quinoline-8-carbonitrile;
5-((2S,6R)-2-((2-(hydroxymethyl)piperidin-1-yl) methyl)-6-methylmorpholino) quinoline-8-carbonitrile;
5-(2R,6S)-2-methyl-6-((2-methylpiperidin-1-yl)methyl) morpholino)quinoline-8-carbonitrile;
5-((2S,6R)-2-((2-ethylpiperidin-1-yl)methyl)-6-methylmorpholino)quinoline-8-carbonitrile;
5-((2S,6R)-2-((2,3-dimethylpiperazin-1-yl)methyl)-6-methylmorpholino)quinoline-8-carbonitrile;
5-((2R,6S)-2-methyl-6-((pyridin-3-ylamino) [nnethyl]*methyl*)morpholino)quinoline-8-carbonitrile;
5-((2R,6S)-2-methyl-6-((pyridin-4-ylamino)methyl)morpholino)quinoline-8-carbonitrile;
5-((2R,6S)-2-methyl-6-(((S)-2-(trifluoromethyl)pyrrolidin-1-yl)methyl)morpholino) quinoline-8-carbonitrile;
5-((2R,6S)-2-methyl-6-((4-methylpiperidin-1-yl)methyl) morpholino)quinoline-8-carbonitrile;
5-((2S,6R)-2-((4,4-difluoropiperidin-1-yl)methyl)-6-methylmorpholino)quinoline-8-carbonitrile;
5-((2R,6S)-2-methyl-6-((4-phenylpiperidin-1-yl)methyl) morpholino)quinoline-8-carbonitrile;
5-((2S,6R)-2-((4-fluoropiperidin-1-yl)methyl)-6-methylmorpholino)quinoline-8-carbonitrile;
5-((2S,6R)-2-((cyclopentylamino)methyl)-6-methylmorpholino)quinoline-8-carbonitrile;
5-(2R,6S)-2-methyl-6-(((3-methylcyclohexyl)amino) methyl)morpholino)quinoline-8-carbonitrile;
5-((2R,6S)-2-methyl-6-(((3-methylpyridin-2-yl)amino) methyl)morpholino) quinoline-8-carbonitrile;
5-((2R,6R)-2-ethyl-6-(hydroxymethyl)morpholino)quinoline-8-carbonitrile;

5-((2R,6S)-2-methyl-6-(((4-phenylpyridin-2-yl)amino) methyl)morpholino) quinoline-8-carbonitrile;
5-((2R,6S)-2-methyl-6-(piperazin-1-ylmethyl)morpholino)quinoline-8-carbonitrile;
5-((2R,6S)-2-methyl-6-((4-phenylpiperazin-1-yl)methyl) morpholino)quinoline-8-carbonitrile;
5-((2S,6R)-2-(((6-aminopyridin-2-yl)amino)methyl)-6-methylmorpholino)quinoline-8-carbonitrile;
5-((2S,6R)-2-((2,5-dimethylpiperazin-1-yl)methyl)-6-methylmorpholino)quinoline-8-carbonitrile;
5-((2S,6R)-2-((4-acetylpiperazin-1-yl)methyl)-6-methylmorpholino)quinoline-8-carbonitrile;
5-((2S,6R)-2-(((2S,4R)-4-hydroxy-2-(hydroxymethyl) pyrrolidin-1-yl)methyl)-6-methylmorpholino)quinoline-8-carbonitrile;
5-((2R,6S)-2-methyl-6-(((R)-2-methylpiperazin-1-yl) methyl)morpholino)quinoline-8-carbonitrile;
5-((2R,6S)-2-methyl-6-(((R)-3-methylpiperazin-1-yl) methyl)morpholino)quinoline-8-carbonitrile;
5-((2R,6S)-2-methyl-6-(((S)-3-methylpiperazin-1-yl) methyl)morpholino)quinoline-8-carbonitrile;
5-((2S,6R)-2-(((2R,5R)-2,5-dimethylpiperazin-1-yl) methyl)-6-methylmorpholino) quinoline-8-carbonitrile;
5-((2S,6R)-2-(((2R,5S)-2,5-dimethylpiperazin-1-yl) methyl)-6-methylmorpholino) quinoline-8-carbonitrile;
5-((2R,6S)-2-methyl-6-(((4-methylcyclohexyl)amino) methyl)morpholino)quinoline-8-carbonitrile;
5-((2S,6R)-2-((cyclobutylamino)methyl)-6-methylmorpholino)quinoline-8-carbonitrile;
5-((2S,6R)-2-((cycloheptylamino)methyl)-6-methylmorpholino)quinoline-8-carbonitrile;
5-((2S,6R)-2-(((4-hydroxycyclohexyl)amino)methyl)-6-methylmorpholino) quinoline-8-carbonitrile;
5-((2S,6R)-2-(((2-hydroxycyclopentyl)amino)methyl)-6-methylmorpholino) quinoline-8-carbonitrile;
5-((2R,6S)-2-methyl-6-(((2-methylcyclohexyl)amino) methyl)morpholino)quinoline-8-carbonitrile;
5-((2R,6S)-2-methyl-6-(((5-phenylpyridin-2-yl)amino) methyl)morpholino) quinoline-8-carbonitrile;
5-((2R,6S)-2-methyl-6-(((3-phenylpyridin-2-yl)amino) methyl)morpholino) quinoline-8-carbonitrile;
5-((2S,6R)-2-((((1S,3R)-3-hydroxycyclopentyl)amino) methyl)-6-methyl-morpholino)quinoline-8-carbonitrile;
5-([-](2S, 6R)-2-(((3-ethoxypyridin-2-yl)amino)methyl)-6-methylmorpholino) quinoline-8-carbonitrile;
5-((2R,6S)-2-methyl-6-(((2-phenylpyridin-4-yl)amino) methyl)morpholino) quinoline-8-carbonitrile;
5-((2R,6S)-2-methyl-6-(((6-phenylpyridin-2-yl)amino) methyl)morpholino) quinoline-8-carbonitrile;
5-((2R,6S)-2-methyl-6-((2-methyl-5-oxopiperazin-1-yl) methyl)morpholino) quinoline-8-carbonitrile;
5-((2R,6S)-2-methyl-6-((4-methylpiperazin-1-yl)methyl) morpholino)quinoline-8-carbonitrile;
5-((2R,6S)-2-methyl-6-((4-propylpiperazin-1-yl)methyl) morpholino)quinoline-8-carbonitrile;
5-((2S,6R)-2-((4-(dimethylamino)piperidin-1-yl) methyl)-6-methylmorpholino) quinoline-8-carbonitrile;
5-((2S,6R)-2-([1,4'-bipiperidin]-1'-ylmethyl)-6-methylmorpholino)quinoline-8-carbonitrile;
5-((2S,6R)-2-([1,4'-bipiperidin]-1'-ylmethyl)-6-methylmorpholino)quinoline-8-carbonitrile dihydrochloride;
5-((2S,6R)-2-(((R)-3-aminopiperidin-1-yl)methyl)-6-methylmorpholino)quinoline-8-carbonitrile;
[(2R,6S)-4-(8-chloro-1,7-naphthyridin-5-yl)-2,6-dimethylmorpholine;]
5-((2S,6R)-2-((4-aminopiperidin-1-yl)methyl)-6-methylmorpholino)quinoline-8-carbonitrile,
5-((2S,6R)-2-(((5-fluoropyrimidin-2-yl)amino)methyl)-6-methylmorpholino) quinoline-8-carbonitrile;
5-((2R,6S)-2-methyl-6-(piperidin-1-ylmethyl)morpholino)quinoline-8-carbonitrile;
5-((2R,6S)-2-methyl-6-(morpholinomethyl)morpholino) quinoline-8-carbonitrile;
5-((2S,6R)-2-(((2S,6R)-2,6-dimethylmorpholino) methyl)-6-methylmorpholino) quinoline-8-carbonitrile;
5-((2S,6R)-2-(((2R,6R)-2-(hydroxymethyl)-6-methylmorpholino)methyl)-6-methylmorpholino)quinoline-8-carbonitrile;
5-((2R,6S)-2-methyl-6-((4-(pyridin-2-yl)piperazin-1-yl) methyl)morpholino) quinoline-8-carbonitrile;
5-((2R,6S)-2-methyl-6-((4-(pyridin-4-yl)piperazin-1-yl) methyl)morpholino) quinoline-8-carbonitrile;
N-(1-(((2S,6R)-4-(8-cyanoquinolin-5-yl)-6-methylmorpholin-2-yl)methyl)piperidin-4-yl)acetamide;
N-(1-(((2S,6R)-4-(8-cyanoquinolin-5-yl)-6-methylmorpholin-2-yl)methyl)piperidin-4-yl)acetamide hydrochloride;
[5-((2S,6R)-2-(((1,8-naphthyridin-2-yl)amino)methyl)-6-methylmorpholino) quinoline-8-carbonitrile;]
1-(((2S,6R)-4-(8-cyanoquinolin-5-yl)-6-methylmorpholin-2-yl)methyl)piperidine-4-carboxamide;
N-(1-(((2S,6R)-4-(8-cyanoquinolin-5-yl)-6-methylmorpholin-2-yl)methyl)piperidin-4-yl)benzamide;
5-((2S,6R)-2-((4-isopropylpiperazin-1-yl)methyl)-6-methylmorpholino)quinoline-8-carbonitrile;
4-(((2S,6R)-4-(8-cyanoquinolin-5-yl)-6-methylmorpholin-2-yl)methyl)piperazine-1-carboxamide;
5-((2S,6R)-2-((4-cyclohexylpiperidin-1-yl)methyl)-6-methylmorpholino)quinoline-8-carbonitrile;
5-((2R,6S)-2-methyl-6-((4-(pyrrolidin-1-yl)piperidin-1-yl)methyl)morpholino) quinoline-8-carbonitrile;
5-((2R,6R)-2-((4-cyclohexyl-1H-1,2,3-triazol-1-yl) methyl)-6-methylmorpholino) quinoline-8-carbonitrile;
5-((2R,6R)-2-methyl-6-((4-phenyl-1H-1,2,3-triazol-1-yl) methyl)morpholino) quinoline-8-carbonitrile;
5-((2R,6S)-2-methyl-6-((2-oxo-[1,4'-bipiperidin]-1'-yl) methyl)morpholino)quinoline-8-carbonitrile;
5-((2S,6R)-2-(((5-ethylpyrimidin-2-yl)amino)methyl)-6-methylmorpholino) quinoline-8-carbonitrile;
5-((2S,6R)-2-(((6-amino-3,5-dimethylpyridin-2-yl) amino)methyl)-6-methyl-morpholino)quinoline-8-carbonitrile;
5-((2R,6S)-2-methyl-6-((pyrazin-2-ylamino)methyl)morpholino)quinoline-8-carbonitrile;
5-((2S,6R)-2-(((1,3-dimethyl-1H-pyrazol-5-yl)amino) methyl)-6-methylmorpholino) quinoline-8-carbonitrile;
[5-((2R,7R)-2-(hydroxyrnethyl)-7-methyl-1,4-oxazepan-4-yl)quinoline-8-carbonitrile;]
5-((2S,6R)-2-((4-ethylpiperazin-1-yl)methyl)-6-methylmorpholino)quinoline-8-carbonitrile;
5-((2R,6S)-2-methyl-6-((3-(pyrrolidin-1-yl)azetidin-1-yl) methyl)morpholino) quinoline-8-carbonitrile;
5-((2R,6 S)-2-methyl-6-((3-(piperidin-1-yl)azetidin-1-yl) methyl)morpholino) quinoline-8-carbonitrile;
5-((2S,6R)-2-(((R)-2,4-dimethylpiperazin-1-yl)methyl)-6-methylmorpholino) quinoline-8-carbonitrile;

5-((2S,6R)-2-((4-(hydroxymethyl)piperidin-1-yl) methyl)-6-methylmorpholino) quinoline-8-carbonitrile;

5-((2S,6R)-2-((R)-[1,3'-bipyrrolidin]-1'-ylmethyl)-6-methylmorpholino)quinoline-8-carbonitrile;

5-((2R,6S)-2-methyl-6-(((R)-3-(piperidin-1-yl)pyrrolidin-1-yl)methyl)morpholino) quinoline-8-carbonitrile;

5-((2R,6S)-2-methyl-6-((4-methyl-1,4-diazepan-1-yl) methyl)morpholino)quinoline-8-carbonitrile;

5-((2S,6R)-2-((4-benzoylpiperazin-1-yl)methyl)-6-methylmorpholino)quinoline-8-carbonitrile;

N-(1-(((2S,6R)-4-(8-cyanoquinolin-5-yl)-6-methylmorpholin-2-yl)methyl)piperidin-4-yl)nicotinamide;

N-(1-(((2S,6R)-4-(8-cyanoquinolin-5-yl)-6-methylmorpholin-2-yl)methyl)piperidin-4-yl)isonicotinamide;

N-(1-(((2S,6R)-4-(8-cyanoquinolin-5-yl)-6-methylmorpholin-2-yl)methyl)piperidin-4-yl)picolinamide;

N-(1-(((2S,6R)-4-(8-cyanoquinolin-5-yl)-6-methylmorpholin-2-yl)methyl)piperidin-4-yl)hexanamide;

N-(1-(((2S,6R)-4-(8-cyanoquinolin-5-yl)-6-methylmorpholin-2-yl)methyl)piperidin-4-yl)isobutyramide;

N-(1-(((2S,6R)-4-(8-cyanoquinolin-5-yl)-6-methylmorpholin-2-yl)methyl)piperidin-4-yl)isobutyramide hydrochloride;

N-(1-(((2S,6R)-4-(8-cyanoquinolin-5-yl)-6-methylmorpholin-2-yl)methyl)piperidin-4-yl)pivalamide;

[5-((2S, 7R)-2-([1,4'-bipiperidin]-1'-ylmethyl)-7-methyl-1,4-oxazepan-4-yl)quinoline-8-carbonitrile;]

5-((2R,6S)-2-methyl-6-((4-morpholinopiperidin-1-yl) methyl)morpholino)quinoline-8-carbonitrile;

tert-butyl 4-(1-(((2S,6R)-4-(8-cyanoquinolin-5-yl)-6-methylmorpholin-2-yl)methyl) piperidin-4-yl)piperazine-1-carboxylate;

tert-butyl 4-(4-(((2S,6R)-4-(8-cyanoquinolin-5-yl)-6-methylmorpholin-2-yl)methyl) piperazin-1-yl)piperidine-1-carboxylate;

5-((2R,6S)-2-methyl-6-((4-(piperazin-1-yl)piperidin-1-yl)methyl)morpholino) quinoline-8-carbonitrile;

5-((2R,6S)-2-methyl-6-((4-(piperidin-4-yl)piperazin-1-yl)methyl)morpholino) quinoline-8-carbonitrile;

5-((2R,6S)-2-methyl-6-((3-(4-methylpiperazin-1yl)azetidin-1-yl)methyl) morpholino)quinoline-8-carbonitrile;

5-((2S,6R)-2-([4,4'-bipiperidin]-1-ylmethyl)-6-methylmorpholino)quinoline-8-carbonitrile;

5-((2S,6R)-2-(1'-acetyl-[4,4'-bipiperidin]-1-yl)methyl)-6-methylmorpholino) quinoline-8-carbonitrile;

5-((2R,6S)-2-methyl-6-((1'-methyl-[4,4'-bipiperidin]-1-yl)methyl)morpholino) quinoline-8-carbonitrile;

5-((2R,6S)-2-methyl-6-((3-(piperazin-1-yl)azetidin-1-yl) ethyl)morpholino) quinoline-8-carbonitrile;

5-((2S,6R)-2-((3-(4-acetylpiperazin-1-yl)azetidin-1-yl) methyl)-6-methyl-morpholino)quinoline-8-carbonitrile;

5-((2S,6R)-2-((1'-isobutyryl-[4,4'-bipiperidin]-1-yl) methyl)-6-methylmorpholino) quinoline-8-carbonitrile;

5-((2S,6R)-2-((3-(4-benzoylpiperazin-1-yl)azetidin-1-yl) methyl)-6-methylmorpholino) quinoline-8-carbonitrile;

5-((2S,6R)-2-((1'-benzoyl-[4,4'-bipiperidin]-1-yl) methyl)-6-methylmorpholino) quinoline-8-carbonitrile;

5-((2R,6S)-2-methyl-6-((4-(1-methylpiperidin-4-yl)piperazin-1-yl)methyl)-morpholino)quinoline-8-carbonitrile;

5-((2S,6R)-2-((4-(1-acetylpiperidin-4-yl)piperazin-1-yl) methyl)-6-methyl-morpholino)quinoline-8-carbonitrile;

5-((2S,6R)-2-(4-(1-isobutyrylpiperidin-4-yl)piperazin-1-yl)methyl)-6-methyl-morpholino)quinoline-8-carbonitrile;

5-((2S,6R)-2-((4-(1-benzoylpiperidin-4-yl)piperazin-1-yl)methyl)-6-methyl-morpholino)quinoline-8-carbonitrile;

5-((2S,6R)-2-((3-(4-isobutyrylpiperazin-1-yl)azetidin-1-yl)methyl)-6-methyl-morpholino)quinoline-8-carbonitrile;

5-((2S,6R)-2-((4-(4-acetylpiperazin-1-yl)piperidin-1-yl) methyl)-6-methyl-morpholino)quinoline-8-carbonitrile;

5-((2S,6R)-2-((4-(4-isobutyrylpiperazin-1-yl)piperidin-1-yl)methyl)-6-methylmorpholino)quinoline-8-carbonitrile;

5-((2S,6R)-2-((4-(4-benzoylpiperazin-1-yl)piperidin-1-yl)methyl)-6-methyl-morpholino)quinoline-8-carbonitrile;

5-((2R,6S)-2-methyl-6-((4-(4-methylpiperazin-1-yl)piperidin-1-yl)methyl)-morpholino)quinoline-8-carbonitrile;

5-((2R,6S)-2-methyl-6-((4-(4-methylpiperazin-1-yl)piperidin-1-yl)methyl)-morpholino)quinoline-8-carbonitrile trihydrochloride;

5-((2S,6R)-2-([1,4'-bipiperidin]-1'-ylmethyl)-6-methylmorpholino)-2-methyl-quinoline-8-carbonitrile;

N-((R)-1-(((2S,6R)-4-(8-cyanoquinolin-5-yl)-6-methylmorpholin-2-yl)methyl)-pyrrolidin-3-yl)acetamide;

N-((R)-1-(((-(2S, 6R)-4-(8-cyanoquinolin-5-yl)-6-methylmorpholin-2-yl)methyl)-pyrrolidin-3-yl)isobutyramide, 5-((2R,6S)-2-methyl-6-(((S)-3-(piperidin-1-yl)pyrrolidin-1-yl)methyl)morpholino) quinoline-8-carbonitrile;

5-((2R,6S)-2-methyl-6-(((S)-3-(piperidin-1-yl)pyrrolidin-1-yl)methyl)morpholino)-quinoline-8-carbonitrile dihydrochloride;

5-((2R,6S)-2-methyl-6-((3-morpholinoazetidin-1-yl) methyl)morpholino)quinoline-8-carbonitrile;

5-((2R,6S)-2-methyl-6-((3-((S)-2-methylpyrrolidin-1-yl) azetidin-1-yl)methyl)-morpholino)quinoline-8-carbonitrile;

5-((2R,6S)-2-methyl-6-(((S)-2-methylpiperazin-1-yl) methyl)morpholino)quinoline-8-carbonitrile;

5-((2S,6R)-2-(((S)-2,4-dimethylpiperazin-1-yl)methyl)-6-methylmorpholino) quinoline-8-carbonitrile;

5-((2S,6R)-2-(((R)-3,4-dimethylpiperazin-1-yl)methyl)-6-methylmorpholino) quinoline-8-carbonitrile;

5-((2S,6R)-2-(((S)-3,4-dimethylpiperazin-1-yl)methyl)-6-methylmorpholino) quinoline-8-carbonitrile;

5-((2S,6R)-2-(((S)-3-ethylpiperazin-1-yl)methyl)-6-methylmorpholino)quinoline-8-carbonitrile;

5-((2S,6R)-2-(((S)-3-ethylpiperazin-1-yl)methyl)-6-methylmorpholino)quinoline-8-carbonitrile dihydrochloride;

5-((2S,6R)-2-(((S)-3-ethyl-4-methylpiperazin-1-yl) methyl)-6-methylmorpholino) quinoline-8-carbonitrile;

5-((2S,6R)-2-(4-(azepan-1-yl)piperidin-1-yl)methyl)-6-methylmorpholino) quinoline-8-carbonitrile;

5-((2S,6R)-2-((S)-[1,3'-bipyrrolidin]-1'-ylmethyl)-6-methylmorpholino)quinoline-8-carbonitrile;

5-((2S,6R)-2-((3-(4-aminopiperidin-1-yl)azetidin-1-yl) methyl)-6-methylmorpholino) quinoline-8-carbonitrile;

N-(1-(1-(((2S,6R)-4-(8-cyanoquinolin-5-yl)-6-methylmorpholin-2-yl)methyl)-azetidin-3-yl)piperidin-4-yl) acetamide;

5-((2R,6S)-2-methyl-6-((3-(4-(methylsulfonyl)piperazin-1-yl)azetidin-1-yl)methyl)-morpholino)quinoline-8-carbonitrile;

5-((2S,6R)-2-((3-((S)-3-hydroxypyrrolidin-1-yl)azetidin-1-yl)methyl)-6-methyl-morpholino)quinoline-8-carbonitrile;

N-(1-(((2S,6R)-4-(8-cyanoquinolin-5-yl)-6-methylmorpholin-2-yl)methyl)piperidin-4-yl)-1,3-dimethyl-1H-pyrazole-4- carboxamide;

N-(1-(1-(((2S,6R)-4-(8-cyanoquinolin-5-yl)-6-methylmorpholin-2-yl)methyl)-azetidin-3-yl)piperidin-4-yl)-1,3-dimethyl-1H-pyrazole-4-carboxamide;

N-(1-(((2S,6R)-4-(8-cyanoquinolin-5-yl)-6-methylmorpholin-2-yl)methyl)piperidin-4-yl)methanesulfonamide;

N-(1-(((2S,6R)-4-(8-cyanoquinolin-5-yl)-6-methylmorpholin-2-yl)methyl)piperidin-4-yl)benzenesulfonamide;

N-(1-(((2S,6R)-4-(8-cyanoquinolin-5-yl)-6-methylmorpholin-2-yl)methyppiperidin-4-yl)-4-fluorobenzenesulfonamide;

5-((2S,6R)-2-((3-aminoazetidin-1-yl)methyl)-6-methylmorpholino)quinoline-8-carbonitrile;

N-(1-(((2S,6R)-4-(8-cyanoquinolin-5-yl)-6-methylmorpholin-2-yl)methyl)azetidin-3-yl)acetamide;

N-(1-(((2S,6R)-4-(8-cyanoquinolin-5-yl)-6-methylmorpholin-2-yl)methyl)azetidin-3-yl)-4-fluorobenzamide;

N-(1-(((2S,6R)-4-(8-cyanoquinolin-5-yl)-6-methylmorpholin-2-yl)methyl)azetidin-3-yl)methanesulfonamide;

N-(1-(((2S,6R)-4-(8-cyanoquinolin-5-yl)-6-methylmorpholin-2-yl)methyl)azetidin-3-yl)-4-fluorobenzenesulfonamide;

N-(1-(((2S,6R)-4-(8-cyanoquinolin-5-yl)-6-methylmorpholin-2-yl)methyl)azetidin-3-yl)-1,3-dimethyl-1H-pyrazole-4- sulfonamide;

N-(1-(((2S,6R)-4-(8-cyanoquinolin-5-yl)-6-methylmorpholin-2-yl)methyl)piperidin-4-yl)-1,3-dimethyl-1H-pyrazole-4- sulfonamide;

N-(1-(((2S,6R)-4-(8-cyanoquinolin-5-yl)-6-methylmorpholin-2-yl)[methypazetidin]*methyl)azetidin*-3-yl)isobutyramide;

5-((2R,6S)-2-methyl-6-(((S)-2-methyl-5-oxopiperazin-1-yl)methyl)morpholino) quinoline-8-carbonitrile;

5-((2R,6S)-2-methyl-6-(((R)-2-methyl-5-oxopiperazin-1-yl)methyl)morpholino) quinoline-8-carbonitrile;

5-((2R,6S)-2-methyl-6-(((R)-2-methyl-3-oxopiperazin-1-yl)methyl)morpholino) quinoline-8-carbonitrile;

5-((2R,6S)-2-methyl-6-(((S)-2-methyl-3-oxopiperazin-1-yl)methyl)morpholino) quinoline-8-carbonitrile;

5-((2R,6S)-2-methyl-6-((2,4,5-trimethylpiperazin-1-yl) methyl)morpholino) quinoline-8-carbonitrile;

5-((2R,6S)-2-methyl-6-((2,3,4-trimethylpiperazin-1-yl) methyl)morpholino) quinoline-8-carbonitrile;

N-((R)-1-(((2S,6R)-4-(8-cyanoquinolin-5-yl)-6-methylmorpholin-2-yl)methyl)pyrrolidin-3-yl)benzamide;

5-((2S,6R)-2-(((R)-3-(dimethylamino)pyrrolidin-1-yl) methyl)-6-methylmorpholino) quinoline-8-carbonitrile;

N-((S)-1-(((2S,6R)-4-(8-cyanoquinolin-5-yl)-6-methylmorpholin-2-yl)methyl)-pyrrolidin-3-yl)acetamide;

N-((S)-1-(((2S,6R)-4-(8-cyanoquinolin-5-yl)-6-methylmorpholin-2-yl)methyl)-pyrrolidin-3-yl)isobutyramide;

N-((S)-1-(((2S,6R)-4-(8-cyanoquinolin-5-yl)-6-methylmorpholin-2-yl)methyl)-pyrrolidin-3-yl)benzarnide;

5-((2S,6R)-2-(((S)-3-(dimethylamino)pyrrolidin-1-yl) methyl)-6-methylmorpholino) quinoline-8-carbonitrile;

5-((2R,6R)-2-methyl-6-((pyrazin-2-yloxy)methyl)morpholino)quinoline-8-carbonitrile, N-(1-(((2S,6R)-4-(8-cyanoquinolin-5-yl)-6-methylmorpholin-2-yl)methyl)azetidin-3-yl)benzamide;

5-((2S,6R)-2-((3,3-dimethylpiperazin-1-yl)methyl)-6-methylmorpholino)quinoline-8-carbonitrile dihydrochloride;

5-((2R,6S)-2-methyl-6-((3,3,4-trimethylpiperazin-1-yl) methyl)morpholino) quinoline-8-carbonitrile dihydrochloride;

5-((2R,6R)-2-((R)-1-hydroxyethyl)-6-methylmorpholino)quinoline-8-carbonitrile;

1-(((2S,6R)-4-(8-cyanoquinolin-5-yl)-6-methylmorpholin-2-yl)methyl)-N-ethylpiperidine-4-carboxamide;

1-(((2S,6R)-4-(8-cyanoquinolin-5-yl)-6-methylmorpholin-2-yl)methyl)-N-ethylpiperidine-4-carboxamide hydrochloride;

5-((2R,6R)-2-((S)-1-hydroxyethyl)-6-methylmorpholino) quinoline-8-carbonitrile;

5-((2R,6R)-2-methyl-6-((pyridin-2-yloxy)methyl)morpholino)quinoline-8-carbonitrile;

5-((2R,6R)-2-methyl-6-((pyrimidin-2-yloxy)methyl)morpholino)quinoline-8-carbonitrile;

5-((2R,6R)-2-methyl-6-((R)-1-(pyrimidin-2-yloxy)ethyl) morpholino)quinoline-8-carbonitrile;

5-((2R,6R)-2-methyl-6-((S)-1-(pyrimidin-2-yloxy)ethyl) morpholino)quinoline-8-carbonitrile; and 5-((2R,6R)-2-((S)-hydroxy(pyridin-2-yl)methyl)-6-methylmorpholino)quinoline-8-carbonitrile.

8. [The compound or pharmaceutically acceptable salt of claim 6, wherein said] *A* compound or *pharmaceutically acceptable* salt [is] selected from the group consisting of 5-((2S,6R)-2-([1,4'-bipiperidin]-1'-ylmethyl)-6-methylmorpholino)quinoline-8-carbonitrile [and] ; 5-((2R,7R)-2-(hydroxymethyl)-7-methyl-1,4-oxazepan-4-yl)quinoline-8-carbonitrile*; 5-((2S,7R)-2([1,4'-bipiperidin]-1'-ylmethyl)-7-methyl-1,4-oxazepan-4-yl)quinoline-8-carbonitrile; 5-((2S,6R)-2-(((1,8-naphthyridin-2-yl)amino)methyl)-6-methylmorpholino) quinoline-8-carbonitrile; 5-((2R,6S)-2,6-diethylmorpholino)quinoline-8-carbonitrile; (2R,6S)-4-(8-chloro-1,7-naphthyridin-5-yl)-2,6-dimethylmorpholine; and 5-((2R,6R)-2-((benzyloxy)methyl-6-ethylmorpholino) quinoline-8-carbonitrile; 5-(3-methyl-5-((4-methylpiperazin-1-yl)methyl)phenyl)quinoline-8-carbonitrile; 5-(3-(chloromethyl)-5-methylphenyl)quinoline-8-carbonitrile; or a pharmaceutically acceptable salt thereof.*

9. A compound of Formula (III) or pharmaceutically acceptable salt thereof:

(III)

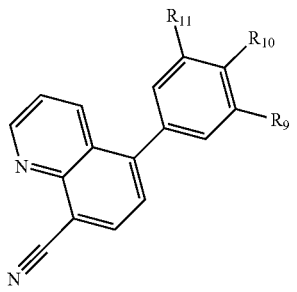

wherein $R_{11}$ is H or methyl;

$R_{10}$ is H or, when both $R_{11}$ and $R_9$ are H, is methyl-1,4'-bipiperidinyl;

$R_9$ is —H or is —$CH_2$- substituted by 1,4'-bipiperidinyl, oxo-, hydroxyl, methylpyridinyl, or piperidinyl optionally substituted with hydroxyl, —$N(CH_3)_2$, or piperidinyl.

10. The compound or pharmaceutically acceptable salt of claim 9, wherein said compound or salt is selected from the group consisting of:

5-(3-([1,4'-bipiperidin]-1'-ylmethyl)pheny)quinoline-8-carbonitrile;

5-(4-([1,4'-bipiperidin]-1'-ylmethyl)pheny)quinoline-8-carbonitrile;

5-(3-formyl-5-methylphenyl)quinoline-8-carbonitrile;

5-(3-(hydroxymethyl)-5-methylphenyl)quinoline-8-carbonitrile;

[5-(3-(chloromethyl)-5-methylphenyl)quinoline-8-carbonitrile;]

5-(3-((4-hydroxypiperidin-1-yl)methyl)-5-methylphenyl) quinoline-8-carbonitrile;

5-(3-((4-(dimethylamino)piperidin-1-yl)methyl)-5-methylphenyl)quinoline-8-carbonitrile;

[5-(3-methyl-5-((4-methylpiperazin-1-yl)methyl)phenyl) quinoline-8-carbonitrile;] and 5-(3-([1,4'-bipiperidin]-1'-ylmethyl)-5-methylphenyl)quinoline-8-carbonitrile.

11. A method for treatment of lupus, *in a subject in need thereof,* comprising administering *to said subject* a pharmaceutically effective amount of a compound or pharmaceutically acceptable salt of claim 1.

12. The method of claim 11, wherein said compound is administered as a pharmaceutically acceptable salt.

13. A method for antagonizing TLR7, *in a subject in need thereof,* comprising administering *to said subject* a pharmaceutically effective amount of a compound or pharmaceutically acceptable salt of claim 1.

14. A method for antagonizing TLR8, *in a subject in need thereof,* comprising administering *to said subject* a pharmaceutically effective amount of a compound or pharmaceutically acceptable salt of claim 1.

15. A pharmaceutical composition comprising at least one compound or pharmaceutically acceptable salt of claim 1 and at least one pharmaceutically acceptable carrier.

16. The pharmaceutical composition of claim 15, wherein said compound or pharmaceutically acceptable salt thereof has an IC50 less than or equal to 100 nM against human TLR7 receptors in a HEK-293 cell line.

17. The pharmaceutical composition of claim 15, wherein said compound or pharmaceutically acceptable salt thereof has an IC50 less than or equal to 20 nM against human TLR7 receptors expressed in a HEK-293 cell line.

18. The pharmaceutical composition of claim 15, wherein said compound or pharmaceutically acceptable salt thereof has an IC50 less than or equal to 5 nM against human TLR7 receptors expressed in a HEK-293 cell line.

19. The pharmaceutical composition of claim 16, wherein the IC50 against human TLR7 receptors expressed in a HEK-293 cell line is measured by (1) plating cells of the HEK-293 cell line stably expressing TLR7 in a Dulbecco's modified Eagle's medium containing 10% fetal bovine serum at a density of 2.22×105 cells/ml into a 384-well plate and incubating for 2 days at 37° C., 5% [CO2] $CO_2$; (2) adding the compound or pharmaceutically acceptable salt thereof and incubating the cells for 30 minutes; (3) adding [CL097 (InvivoGen)] *2-(ethoxymethyl)-1H-imidazo[4,5-c] quinolin-4-amine* at 3 ug/ml and incubating the cells for approximately 20 hours; and (4) quantifying NF-kappaB dependent reporter activation by measuring luminescence.

20. A method for treatment of a [systematic] *systemic* lupus erythematosus, cutaneous lupus, or neuropsychiatric lupus, *in a subject in need thereof,* comprising administering *to said subject* a pharmaceutically effective amount of a compound or pharmaceutically acceptable salt of claim 1.

21. The method of claim 20, wherein said compound is administered as a pharmaceutically acceptable salt.

22. A pharmaceutically acceptable salt of claim 5, wherein the pharmaceutically acceptable salt[, with relative stereochemistry indicated,] is [Rel-(2R,6R)-4-(8-cyanoquinolin-5-yl)-N-((3S,4R)-4-fluoropyrrolidin-3-yl)-6-methylmorpholine-2- carboxamide] *(2R,6R)-4-(8-cyanoquinolin-5-yl)-N-((3S,4R)-4-fluoropyrrolidin-3-yl)-6-methylmorpholine-2-carboxamide* hydrochloride.

23. A method for treatment of lupus, *in a subject in need thereof,* comprising administering *to said subject* a pharmaceutically effective amount of the pharmaceutically acceptable salt of claim 22.

24. A pharmaceutical composition comprising the pharmaceutically acceptable salt of claim 22 and at least one pharmaceutically acceptable carrier.

25. A method for treatment of [systematic] *systemic* lupus erythematosus, cutaneous lupus, or neutopsychiatric lupus, *in a subject in need thereof,* comprising administering *to said subject* a pharmaceutically effective amount of the pharmaceutically acceptable salt of claim 22.

26. A method for antagonizing TLR7, *in a subject in need thereof,* comprising administering *to said subject* a pharmaceutically effective amount of the pharmaceutically acceptable salt of claim 22.

27. A method for antagonizing TLR8, *in a subject in need thereof,* comprising administering *to said subject* a pharmaceutically effective amount of the pharmaceutically acceptable salt of claim 22.

28. A method for treatment of lupus, *in a subject in need thereof,* comprising administering *to said subject* a pharmaceutically effective amount of the pharmaceutically acceptable salt of claim 5.

29. A pharmaceutical composition comprising the pharmaceutically acceptable salt of claim 5 and at least one pharmaceutically acceptable carrier.

30. A method for treatment of [systematic] *systemic* lupus erythematosus, cutaneous lupus, or neutopsychiatric lupus, *in a subject in need thereof,* comprising administering *to said subject* a pharmaceutically effective amount of the pharmaceutically acceptable salt of claim 5.

31. A method for antagonizing TLR7, *in a subject in need thereof,* comprising administering *to said subject* a pharmaceutically effective amount of the pharmaceutically acceptable salt of claim 5.

32. A method for antagonizing TLR8, *in a subject in need thereof,* comprising administering *to said subject* a pharmaceutically effective amount of the pharmaceutically acceptable salt of claim 5.

* * * * *